US008951982B2

(12) United States Patent
Jiménez et al.

(10) Patent No.: US 8,951,982 B2
(45) Date of Patent: Feb. 10, 2015

(54) METHODS AND COMPOSITIONS FOR THE TREATMENT OF EYE DISORDERS WITH INCREASED INTRAOCULAR PRESSURE

(71) Applicant: Sylentis S.A.U., Madrid (ES)

(72) Inventors: Ana I. Jiménez, Madrid (ES); Ángela Sesto, Madrid (ES); Irene Gascón, Madrid (ES); José P. Román, Vitoria (ES); Gonzalo González de Buitrago, Madrid (ES)

(73) Assignee: Sylentis S.A.U., Madrid (ES)

( * ) Notice: Subject to any disclaimer, the term of this patent is extended or adjusted under 35 U.S.C. 154(b) by 0 days.

(21) Appl. No.: 13/744,881

(22) Filed: Jan. 18, 2013

(65) Prior Publication Data

US 2014/0018527 A1 Jan. 16, 2014

Related U.S. Application Data

(63) Continuation of application No. 12/874,928, filed on Sep. 2, 2010, now Pat. No. 8,389,490, which is a continuation of application No. 12/563,530, filed on Sep. 21, 2009, now Pat. No. 7,902,169, which is a continuation of application No. 11/360,305, filed on Feb. 22, 2006, now Pat. No. 7,592,325, which is a continuation-in-part of application No. PCT/GB2005/050134, filed on Aug. 23, 2005.

(30) Foreign Application Priority Data

Aug. 23, 2004 (GB) .................................. 0418762.1
Feb. 18, 2005 (GB) .................................. 0503412.9

(51) Int. Cl.
*C12N 15/11* (2006.01)
*C12N 15/113* (2010.01)

(52) U.S. Cl.
CPC .......... *C12N 15/113* (2013.01); *C12N 15/1137* (2013.01); *C12N 15/1138* (2013.01); *C12N 2310/14* (2013.01)
USPC ....................................................... 514/44 A

(58) Field of Classification Search
USPC ....................................................... 514/44 A
See application file for complete search history.

(56) References Cited

U.S. PATENT DOCUMENTS

| | | | |
|---|---|---|---|
| 4,343,794 | A | 8/1982 | Podos et al. |
| 4,617,299 | A | 10/1986 | Knepper |
| 4,652,586 | A | 3/1987 | Nathanson |
| 4,757,089 | A | 7/1988 | Epstein |
| 4,812,448 | A | 3/1989 | Knepper |
| 5,075,323 | A | 12/1991 | Fain et al. |
| 5,242,943 | A | 9/1993 | Louis et al. |
| 5,260,059 | A | 11/1993 | Acott et al. |
| 5,464,866 | A | 11/1995 | Clark et al. |
| 5,545,626 | A | 8/1996 | Stein et al. |
| 5,585,401 | A | 12/1996 | Brandt et al. |
| 6,365,576 | B1 | 4/2002 | Carr |
| 6,372,249 | B1 | 4/2002 | Smith et al. |
| 6,489,307 | B1 | 12/2002 | Phillips et al. |
| 7,176,304 | B2 | 2/2007 | McSwiggen et al. |
| 7,294,504 | B1 | 11/2007 | Wang |
| 7,462,602 | B2 | 12/2008 | Schultz et al. |
| 7,521,431 | B2 | 4/2009 | Reich et al. |
| 7,579,457 | B2 | 8/2009 | Khvorova et al. |
| 7,592,324 | B2 | 9/2009 | Shepard et al. |
| 7,592,325 | B2 | 9/2009 | Jimenez et al. |
| 7,618,814 | B2 | 11/2009 | Bentwich |
| 7,655,789 | B2 | 2/2010 | Khvorova et al. |
| 7,687,665 | B2 | 3/2010 | Yao et al. |
| 7,691,997 | B2 | 4/2010 | Khvorova et al. |
| 7,700,575 | B2 | 4/2010 | Andrew et al. |
| 7,902,169 | B2 | 3/2011 | Jimenez et al. |
| 8,030,284 | B2 | 10/2011 | Jimenez et al. |
| 8,090,542 | B2 | 1/2012 | Khvorova et al. |
| 8,198,250 | B2 | 6/2012 | Jimenez et al. |
| 8,247,386 | B2 | 8/2012 | Jimenez et al. |

(Continued)

FOREIGN PATENT DOCUMENTS

| | | |
|---|---|---|
| AU | 2005276245 | 3/2006 |
| EP | 1 527 176 | 1/2007 |

(Continued)

OTHER PUBLICATIONS

Dykxhoorn et al. (Nature Reviews 4, 2003, 457-467).*
Tuschl et al. (The siRNA user guide, 2001, pp. 1-5).*
Abrams et al., "Comparison of Three Tonometers for Measuring Intraocular Pressure in Rabbits," Invest Ophthalmol Vis Sci. Apr. 1996, 37(5):940-944.
Achenbach et al., Oligonucleotide-Based Knockdown Technologies: Antisense Versus RNA Interference, ChemBioChem., 4, pp. 928-935, 2003.
"Acuity has New Approach to AMD, Its Drug is Designed to Shut Down VEGF Production" Ophthalmology Management, Apr. 1, 2004, pp. 1-4—cited in AU opposition.
The Agis Investigators, "The Advanced Glaucoma Intervention Study (AGIS): 7. The Relationship Between Control of Intraocular Pressure and Visual Field Deterioration," Am. J. Ophthalmol., 130, pp. 429-440, 2000—Cited in AU Opposition.
Akashi et al., "Suppression of Gene Expression by RNA Interference in Cultured Plant Cells," Antisense Nucleic Acid Drug Dev, 2001, 11(6):359-367.

(Continued)

*Primary Examiner* — Brian Whiteman
(74) *Attorney, Agent, or Firm* — Margaret B. Brivanlou; Leslie A. Serunian; King & Spalding LLP

(57) ABSTRACT

The present invention relates to methods and compositions that decrease intraocular pressure (IOP) of the eye. The compositions of the invention comprise short interfering nucleic acid molecules (siNA) including, but not limited to, siRNA that decrease expression of genes associated with production or drainage of intraocular fluid. The compositions of the invention can be used in the preparation of a medicament for the treatment of eye conditions displaying increased IOP such as glaucoma, infection, inflammation, uveitis, and diabetic retinopathy. The methods of the invention comprise the administration to a patient in need thereof of an effective amount of one or more siNAs of the invention.

13 Claims, 54 Drawing Sheets

(56) References Cited

U.S. PATENT DOCUMENTS

Figure 4:
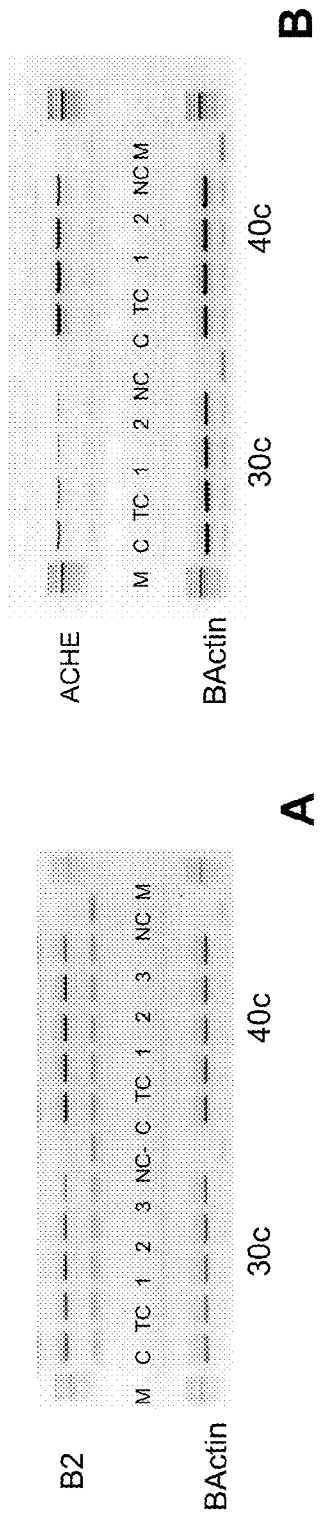

| | | | |
|---|---|---|---|
| 8,247,387 | B2 | 8/2012 | Jimenez et al. |
| 8,252,758 | B2 | 8/2012 | Jimenez et al. |
| 8,252,759 | B2 | 8/2012 | Jimenez et al. |
| 8,258,110 | B2 | 9/2012 | Jimenez et al. |
| 8,389,490 | B2 | 3/2013 | Jimenez et al. |
| 2002/0055536 | A1 | 5/2002 | DeWitte et al. |
| 2002/0114784 | A1 | 8/2002 | Li et al. |
| 2002/0165158 | A1 | 11/2002 | King |
| 2004/0029275 | A1 | 2/2004 | Brown et al. |
| 2004/0115641 | A1 | 6/2004 | Cowsert et al. |
| 2004/0167090 | A1 | 8/2004 | Monahan et al. |
| 2004/0198640 | A1 | 10/2004 | Leake et al. |
| 2004/0209832 | A1 | 10/2004 | McSwiggen et al. |
| 2004/0224405 | A1 | 11/2004 | Leake et al. |
| 2004/0235031 | A1 | 11/2004 | Schultz et al. |
| 2004/0259247 | A1 | 12/2004 | Tuschl et al. |
| 2004/0266707 | A1 | 12/2004 | Leake et al. |
| 2005/0020521 | A1 | 1/2005 | Rana |
| 2005/0171039 | A1 | 8/2005 | McSwiggen et al. |
| 2005/0208658 | A1 | 9/2005 | Castonguay |
| 2005/0255487 | A1 | 11/2005 | Khvorova et al. |
| 2006/0058266 | A1 | 3/2006 | Manoharan et al. |
| 2006/0094032 | A1 | 5/2006 | Fougerolles et al. |
| 2006/0122136 | A1 | 6/2006 | Schubert |
| 2006/0172963 | A1 | 8/2006 | Shepard et al. |
| 2006/0172965 | A1 | 8/2006 | Shepard et al. |
| 2006/0257851 | A1 | 11/2006 | Bentwich |
| 2007/0049543 | A1 | 3/2007 | McSwiggen et al. |
| 2007/0050146 | A1 | 3/2007 | Bentwich et al. |
| 2007/0093435 | A1 | 4/2007 | Andrews et al. |
| 2007/0167384 | A1 | 7/2007 | Leake et al. |
| 2009/0326044 | A1 | 12/2009 | Shepard et al. |
| 2012/0094374 | A1 | 4/2012 | Bentwich et al. |

FOREIGN PATENT DOCUMENTS

| | | |
|---|---|---|
| GB | 2406568 | 4/2005 |
| WO | WO 03/057840 | 7/2003 |
| WO | WO 03/059267 | 7/2003 |
| WO | WO 03/070744 | 8/2003 |
| WO | WO 03/087367 | 10/2003 |
| WO | WO 03/092584 | 11/2003 |
| WO | WO 2004/009794 | 1/2004 |
| WO | WO 2004/009796 | 1/2004 |
| WO | WO 2004/029212 | 4/2004 |
| WO | WO 2004/042024 | 5/2004 |
| WO | WO 2005/032493 | 4/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/083945 | 8/2006 |
| WO | WO 2006/084217 | 8/2006 |
| WO | WO 2006/099353 | 9/2006 |

OTHER PUBLICATIONS

Amaratunga et al., "Inhibition of Kinesin Synthesis and Rapid Anterograde Axonal Transport in Vivo by an Antisense Oligonucleotide," The Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191 , Apr. 2000.

Ambion, "The Basics: RNase Control," printout from website <<http://web.archive.org/web/20041207234247>>, dated 2004, retrieved on Sep. 17, 2009.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.

Amended Statement of Grounds and Particulars filed on Jun. 5, 2012 (amending original Grounds filed on Dec. 2, 2010), from opponents in Opposition by Alcon Research, Ltd. against Australian Patent Application No. 2005276245 in the name of Sylentis SAU.

Andrieu-Soler C., et al "Ocular gene therapy: A review of nonviral strategies," Molecular Vision, 12:1334-47, 2006.

Aravin et al., "Role of Double-Stranded RNA in Eukaryotic Gene Silencing," Mol. Biol. (Mosk.), 36(2), pp. 240-251, Mar.-Apr. 2002, Abstract Only.

Banan et al., "The Ins and Outs of RNAi in Mammalian Cells," Current Pharmaceutical Biotechnology, 5, pp. 441-450, 2004.

Banerjee et al., "Control of Developmental Timing by Small Temporal RNAs: a Paradigm for RNA-mediated Regulation of Gene Expression," Bioessays, 2002, 24(2):119-129.

Barar J. et al., "Ocular novel drug delivery impacts of membranes and barriers," *Expert Opin. Drug Deliv.*, 5(5): 567-81, 2008.

Bass, "The Short Answer," Nature, vol. 411, pp. 428-429, 2001.

Bhattacharya et al., "Cochlin Deposits in the Trabecular Meshwork of the Glaucomatous DBA/2J mouse," Exp Eye Res., May 2005 80(5):741-744.

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec. 3, 2004.

Bill, "Movement of Albumin and Dextran," Arch. Opthal., vol. 74, pp. 248-252, Aug. 1965.

Borrás, "Gene Expression in the Trabecular Meshwork and the Influence of Intraocular Pressure," *Progress in Retinal and Eye Research*, 22, 435-463, 2003.

Bosher et al., "RNA Interference: Genetic Wand and Genetic Watchdog." Nat Cell Biol, 2000, 2(2):E31-6.

Braasch et al., "Novel Antisense and Peptide Nucleic Acid Strategies for Controlling Gene Expression," Biochemistry, 2002, 41(14):4503-4510.

Brummelkamp et al., "A System for Stable Expression of Short Interfering RNAs in Mammalian Cells," Science, American Association for the Advancement of Science, 2002, 296(5567):550-553.

Busch et al., "Adenylyl Cyclase in Human and Bovine Trabecular Meshwork," Investigative Ophthalmology & Visual Science, 34(10), pp. 3028-3034, Sep. 1993.

Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.

Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.

Caplen et al., "Specific inhibition of Gene Expression by Small Double Stranded RNAs in Invertebrate and Vertebrate Systems," Proc. Natl. Acad. Sci. USA, 2001,98: 9742-9747.

Cho et al., "Small Interfering RNA-Induced TLR3 Activation Inhibits Blood and Lymphatic Vessel Growth," PNAS, pp. 1-6, Dec. 5, 2008.

Chudgar et al., "Elevated Intraocular Pressure and Mechanical Stress Increase Connective Tissue Growth Factos Expression in the Trabecular Meshwork," Invest Ophthalmol Vis Sci, 45, E-Abstract 4433, 2004.

Clark et al., "Opthalamic Drug Discovery," Nature Reviews Drug Discover, pp. 448-459, 2003.

Comes N. and Borrás T, "Functional delivery of synthetic naked siRNA to the human trabecular meshwork in perfused organ cultures," *Molec. Vision*, 13: 1363-74, 2007.

Costagliola et al., "Effect of Oral Losartan Potassium Administration on Intraocular Pressure in Normotensive and Glaucomatous Human Subjects," Exp Eye Res., Aug. 2000, 71(2):167-171.

Costagliola et al., "Effect of Oral Captopril (SQ 14225) on Intraocular Pressure in Man," Eur. J. Opthalmol, Jan. 1995, 5(1):19-25.

Crooke et al., "Nucleotides in Ocular Secretions: Their Role in Ocular Physiology," Pharmacology & Therapeutics, 119, pp. 55-73, 2008.

Cullinane et al., "Renin-angiotensin System Expression and Secretory Function in Cultured human Ciliary Cody Nonpigmented Epithelium," Br J Ophthalmol. Jun. 2002, 86(6):676-83.

Davson H, "The Aqueous Humour and the Intraocular Pressure," Dayson's Physiology of the Eye, 5th edition, Pergamon Press, pp. 3-95, 1990.

(56) References Cited

OTHER PUBLICATIONS

Dejneka NS., et al., "Ocular Biodistribution of Bevasiranib Following a Single Intravitreal Injection to Rabbit Eyes," Molecular Vision, 14:997-1005, 2008.
Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.
Diffen, DNA vs. RNA—Difference and Comparison, retrieved from <<http://www.diffen.com/difference/Dna_vs_Rna>> on May 21, 2009.
Dinslage et al., "Intraocular Pressure in Rabbits by Telemetry II: Effects of Animal Handling and Drugs," Invest. Ophthalmol Vis Sci., vol. 39(12), pp. 2485-2489, 1998.
Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.
Dos Santos ALG., et al "Intraocular Delivery of Oligonucleotides," Current Pharmaceutical Biotechnology, 6:7-15, 2005.
Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in *Drosophila melanogaster* Embryo Lysate," EMBO Journal, vol. 20, No. 23, pp. 6877-6888, 2001.
Elbashir et al., "RNA Interference is Mediated by 21- and 22-Nucleotide RNAs," Genes Dev, 2001, 15(2):188-200.
Elena et al., "Autoradiographic Localization of Beta-Adrenergic Receptors in Rabbit Eye," Investigative Ophthalmology & Visual Science, 28, pp. 1436-1441, Aug. 1987.
Epstein et al., "*Effect of Iodoacetamide Perfusion on Outflow Facility and Metabolism of the Trabecular Meshwork*," Invest. Ophthalmol. Vis. Sci., 625-631, May 1981.
Fattal et al., "Ocular Delivery of Nucleic Acids: Antisense Oligonucleotides, Aptamers and siRNA," Advanced Drug Delivery Reviews, 2006, 58:1203-1223.
Fire et al., "Potent and Specific Genetic Interference by Double Stranded RNA in a *Caenorhabditis elegans*," Nature, 1998, 391(6669):806-11.
Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.
Fuchshofer et al., "The Effect of TGF-β2 on Human Trabecular Meshwork Extracellular Proteolytic System," Experimental Eye Research, 77, pp. 757-765, 2003.
Ganesh Prasanna, Ph.D., Resume, 12 pages, May 18, 2012.
Statutory Declaration of Ganesh Prasanna, 19 pages, Jun. 1, 2012.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.
Ghate D. and Edelhauser H.F., "Barriers to glaucoma drug delivery," *J. Glaucoma*, 17(2), 147-56, 2008.
Gil et al., "Induction of Apoptosis by the dsRNA-dependent Protein Kinase (PKR): Mechanism of Action," Apoptosis, 2000, 5(2):107-114.
Gonzalez et al., "Genes Upregulated in the Human Trabecular Meshwork in Response to Elevated Intraocular Pressure," Investigative Opthalmology & Visual Science, Feb. 2000, 41(2):352-361.
Grosshans et al., "Micro-RNAs: Small is Plentiful," J Cell Bioi, 2002, 156(1):17-21.
Hammond et al., "Post-Transcriptional Gene Silencing by Double-Standed RNA," Nature, 2001, 2:110-119.
Hare et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.
Hart WM, "Intraocular Pressure," Chapter 8, Adler's Physiology of the Eye: Clinical Application, Mosby-Year Book Inc., 9th edition, pp. 248-267, 1992.
Herkel et al., "Update on Topical Carbonic Anhydrase Inhibitors," Current Opinion in Ophthamology, Apr. 2001, 12(2):88-93.
Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.
Horinouchi et al., "Pharmacological Evaluation of Ocular β-Adrenoceptors in Rabbit by Tissue Segment Binding Method," Life Sciences, 84, pp. 181-187, 2009.
Jens Kurreck, "Antisense Technologies," Eur. J. Biochem., 270, pp. 1628-1644, 2003.
Jens Kurreck, "Antisense and RNA Interference Approaches to Target Validation in Pain Research," Current Opinion in Drug Discovery & Development, 7(2), pp. 179-187, 2004.
Jiménez et al., "Efficacy of Topically Administered siRNAs in Glaucoma Treatment: In vivo Results in Hypertensive Model," Investigative Ophthalmology & Visual Science, 50, E-Abstract 4054, 2009.
Jiménez et al., "$Na^+/K^+$ ATPase: A New Target for Treating Ocular Hypertension by RNAi," Investigative Ophthalmology & Visual Science, 48, E-Abstract 4809 2007.
Jiménez et al., "SYL04003: A New Therapeutic Candidate for Treating Ocular Hypertension using RNAi Technology," Investigative Ophthalmology & Visual Science, 49, E-Abstract 1643, 2008.
Jiménez et al., "SYL040012 A New siRNA-Based Treatment for Glaucoma: Pharmacokinetics and Mechanism of Action," Investigative Ophthalmology & Visual Science, 51, E-Abstract 176, 2010.
Kaplan et al., "Aqueous Humor Flow in Unilateral Carotid Stenosis," Journal of Glaucoma, 5, pp. 237-240, 1996.
Khaw et al., "Glaucoma-1: Diagnosis," BMJ, 2004a, 328:97-99.
Khaw et al., "Glaucoma-2: Treatment," BMJ, 2004, 328:156-158.
Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.
Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.
Krutzfeldt et al., "Silencing of microRNAs in vivo with 'Antagomirs'," Nature, 2005, 438(7068):685-689.
Kwon et al., "Primary Open-Angle Glaucoma," The New England Journal of Medicine, 360(11), pp. 1113-1124, Mar. 12, 2009.
Liao et al., "Expression of Cell Surface Transmembrane Carbonic Anhydrase Genes CA9 and CA12 in the Human Eye: Overexpression of CA12 (CAXII) in Glaucoma," J. Med. Genet, 40, 257-262, 2003.
Lograno et al., "Receptor-Responses in Fresh Human Ciliary Muscle," Br. J. Pharmac., 87, pp. 379-385, 1986.
Madsen, "Ocular Finding in 123 Patients with Proliferative Diabetic Retinopathy," Documenta Ophthalmologica, Advances in ophthalmology, May 14, 1971, 29(2):345-349.
Mahato et al., "Modulation of Gene Expression by Antisense and Antigene Oligodeoxynucleotides and Small Interfering RNA," Expert Opinion on Drug Delivery, Jan. 2005, 2(1):3-28.
Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.
Miller et al., "Allele-specific Silencing of Dominant Disease Genes," Proceedings of the National Academy of Sciences of USA, Jun. 10, 2003, 100(12):7195-7200.
Mirshahi et al., "The Mineralocorticoid Hormone Receptor and Action in the Eye," Biochem Biophys Res Commun, vol. 219, pp. 150-156, 1996.
Muratovska et al., "Conjugate for Efficient Delivery of Short Interfering RNA (siRNA) into Mammalian Cells," FEBS Letters, 558, pp. 63-68, 2004.
Nakamura et al., "RNA Interference Targeting Transforming Growth Factor-β type II Receptor Suppresses Ocular Inflammation and Fibrosis," Molecular Vision, 10, pp. 703-711, 2004.

(56) References Cited

OTHER PUBLICATIONS

Nie Y., et al., "The potential therapeutic of siRNA eye drops in ocular diseases," *Bioscience Hypotheses*, 2, 223-25, 2009.
Okabe et al., "Effect of Benzalkonium Chloride on Transscleral Drug Delivery," Investigative Ophthalmology & Visual Science, vol. 46, No. 2, pp. 703-708 , Feb. 2005.
Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.
Osborne et al., "Some Current Ideas on the Pathogenesis and the Role of Neuroprotection in Glaucomatous Optic Neuropathy," Eur J Ophthalmol., Apr. 2003, 13Suppl. 3:519-26.
Paddison et al., "Short hairpin RNAs (shRNAs) Induce Sequence-Specific Silencing in Mammalian Cells," Genes Dev, 2002, 16(8):948-958.
Papers filed on Mar. 2, 2012, from opponents in Opposition by Alcon Research, Ltd. against Australian Patent Application No. 2005276245 in the name of Sylentis SAU.
Peral et al., "Effect of Several siRNA in the Treatment of Ocular Hypertension and Glaucoma," Invest. Ophthalmol. Vis. Sci., 48, E-Abstract 4808, 2007.
Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.
Pintor et al., "SiRNA in the Treatment of Ocular Hypertension Targeting Alpha and Beta Adrenoceptors," Invest. Ophthalmol. Vis. Sci., 47, E-Abstract 403, 2006.
Rao et al., "Modulation of Aqueous Humor Outflow Facility by the Rho Kinase-Specific Inhibitor Y-27632," Investigative Opthalmology & Visual Science, Apr. 2001, 42(5): 1029-1037.
Reich et al., "Small Interfering RNA (siRNA) Targeting *VEGF* effectively Inhibits Ocular Neovascularization in a Mouse Model," Molecular Vision, 2003, 9:210-216.
Ruz et al., "Phase I Study With a New siRNA: SYL040012. Tolerance and Effect on Intraocular Pressure," Investigative Ophthalmology Visual Science, 52, E-Abstract 223, 2011.
Sakaguchi et al., "Chymase and Angiotensin Converting Enzyme Activities in a Hamster Model of Glaucoma Filtering Surgery," Curr Eye Res., May 2002, 24(5):325-331.
Scherer et al., "Approaches for the Sequence-Specific Knockdown of mRNA," Nat. Biotechnology, 2003, 21(12):1457-1465.
Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.
Stamer et al., "Isolation and Culture of Human Trabecular Meshwork Cells by Extracellular Matrix Digestion," Current Eye Research, pp. 611-617, Jan. 10, 1995.
Studies conducted in the Biochemistry Department of the School of Optics at the Universidad Complutense de Madrid, as filed in the Information Disclosure Statement of Oct. 30, 2008 (in U.S. Appl. No. 11/574,169).
Supuran et al., "Carbonic Anhydrase Inhibitors," Medicinal Research Reviews, 23(2):146-189, 2003.
Tan et al., "Recent Developments in Understanding the Pathophysiology of Elevated Intraocular Pressure," Current Opinion in Opthalmology, vol. 17, pp. 168-174, 2006.
Tolentino et al., "Intravitreal Injection of Vascular Endothelial Growth Factor Small Interfering RNA Inhibits Growth and Leakage in a Nonhuman Primate, Laser-Induced Model of Chorodial Neovascularization," Retina, The Journal of Retinal and Vitreous Diseases, vol. 24, No. 1, 2004, pp. 132-138.
Tuschl et al., "Targeted mRNA degradation by double-stranded RNA in vitro," Genes Dev., 1999, 13(24):3191-3197.
Uprichard et al., The Therapeutic Potential of RNA Interference, FEBS Letters, Oct. 31, 2005 579(26):5996-6007.
Valls et al., "Validation of a Device for Transcorneal Drug Permeation Measure," Journal of Pharmaceutical and Biomedical Analysis, 48, pp. 657-663, 2008.
Vittal et al., "Changes in Gene Expression by Trabecular Meshword Cells in Response to Mechanical Stretching," Investigative Opthalmology & Visual Science, Aug. 2005, 46(8):2857-2868.
Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan. 4, 2005.
Wax et al., "Vacuolar $H^+$ -ATPase in Ocular Ciliary Epithelium," Proc. Natl. Acad. Sci., vol. 94, pp. 6752-6757, Jun. 1997.
Wetering et al., "Specific Inhibition of Gene Expression Using a Stably Integrated, Inducible Small-Interfering-RNA Vector," EMBO Reports, Jun. 2003, 4(6):609-615.
Wianny et al., "Specific Interference with Gene Function by Double-Stranded RNA in Early Mouse Development," Nat Cell Biol, 2000, 2(2):70-75.
Williams BR, "Role of the Double-Stranded RNA-activated Protein kinase (PKR) in Cell Regulation," Biochem Soc Trans, 1997, 25(2):509-513.
Wirtz et al., "The Genetic Loci of Open-Angle Glaucoma," Ophthalmol. Clin. North Am. 2003 16:505-514.
Wiznerowicz et al., "Conditional Suppression of Cellular Genes: Lentivirus Vector-Mediated Drug-Inducible RNA Interference," Journal of Virology, Aug. 2003, 77(16):8957-8961.
Woodward et al., "The Inflow and Outflow of Anti-Glaucoma Drugs," Trends in Pharmacological Sciences, May 2004, 25(5):238-241.
Xie et al., "Harnessing in vivo siRNA Delivery for Drug Discovery and Therapeutic Development," Drug Discovery Today, Jan. 2006, 11(1-2):67-73.
Yang-Feng et al., " Chromosomal Organization of Adrenergic Receptor Genes," PNAS, 1990, 87:1516-1520.
Yang et al., "Early Growth Response Gene 1 Modulates Androgen Receptor Signaling in Prostate Carcinoma Cells," The Journal of Biological Chemistry, 278(41), pp. 39906-39911, 2003.
Yan et al., "Requirement of NeuroD for Photoreceptor Formation in the Chick Retina," Invest Ophthalmol Vis. Sci., 45(1), pp. 48-58, Jan. 2004.
Office Action dated Jul. 14, 2008 in corresponding U.S. Appl. No. 11/360,305.
Office Action dated Jan. 29, 2009 in corresponding U.S. Appl. No. 11/360,305.
Office Action dated Nov. 12, 2008 in corresponding U.S. Appl. No. 11/574,169.
Final Office Action dated May 8, 2009 in corresponding U.S. Appl. No. 11/574,169.
Office Action dated Nov. 3, 2009 in corresponding U.S. Appl. No. 12/170,078.
Office Action dated Oct. 15, 2009 in corresponding U.S. Appl. No. 12/170,104.
Office Action dated Oct. 15, 2009 in corresponding U.S. Appl. No. 12/170,157.
Office Action dated Oct. 30, 2009 in corresponding U.S. Appl. No. 12/170,116.
Office Action dated Oct. 30, 2009 in corresponding U.S. Appl. No. 12/170,132.
Office Action dated Oct. 19, 2009 in corresponding U.S. Appl. No. 12/170,148.
Office Action dated Dec. 4, 2009 in corresponding U.S. Appl. No. 11/574,169.
Office Action dated Mar. 19, 2010 in corresponding U.S. Appl. No. 12/170,078.
Office Action dated Mar. 22, 2010 in corresponding U.S. Appl. No. 12/170,104.
Office Action dated Mar. 19, 2010 in corresponding U.S. Appl. No. 12/170,116.
Office Action dated Mar. 22, 2010 in corresponding U.S. Appl. No. 12/170,132.
Office Action dated Mar. 22, 2010 in corresponding U.S. Appl. No. 12/170,148.
Office Action dated Mar. 22, 2010 in corresponding U.S. Appl. No. 12/170,157.
Office Action dated Mar. 25, 2010 in corresponding U.S. Appl. No. 12/563,530.
Final Office Action dated Jul. 22, 2010 in corresponding U.S. Appl. No. 11/574,169.

(56) References Cited

OTHER PUBLICATIONS

Office Action dated Sep. 7, 2010 in corresponding U.S. Appl. No. 11/574,169.
Office Action dated Sep. 23, 2010 in corresponding U.S. Appl. No. 12/170,078.
Office Action dated Sep. 23, 2010 in corresponding U.S. Appl. No. 12/170,104.
Office Action dated Sep. 23, 2010 in corresponding U.S. Appl. No. 12/170,116.
Office Action dated Sep. 23, 2010 in corresponding U.S. Appl. No. 12/170,132.
Office Action dated Sep. 23, 2010 in corresponding U.S. Appl. No. 12/170,148.
Office Action dated Sep. 23, 2010 in corresponding U.S. Appl. No. 12/170,157.
Office Action dated Aug. 10, 2011 in corresponding U.S. Appl. No. 12/091,498.
Office Action dated Mar. 19, 2012 in corresponding U.S. Appl. No. 12/170,104.
Office Action dated Mar. 19, 2012 in corresponding U.S. Appl. No. 12/170,116.
Office Action dated Mar. 19, 2012 in corresponding U.S. Appl. No. 12/170,132.
Office Action dated Mar. 19, 2012 in corresponding U.S. Appl. No. 12/170,148.
Office Action dated Mar. 19, 2012 in corresponding U.S. Appl. No. 12/170,157.

* cited by examiner

Figure 1

| Gene name | Transcript accession numbers |
|---|---|
| Carbonic anhydrase IV (CA4) | NM_000717 |
| Carbonic anhydrase II (CA2) | NM_000067 |
| Carbonic anhydrase XII (CA12) | NM_001218, NM_206925 |
| Adrenergic, beta-1-, receptor (ADRB1) | NM_000684 |
| Adrenergic, beta-2-, receptor (ADRB2) | NM_000024 |
| Acetylcholinesterase (ACHE) | NM_000665, NM_015831 |
| Selectin E (endothelial adhesion molecule 1) (SELE) | NM_000450 |
| Prostaglandin-endoperoxide synthase 1 (prostaglandin G/H synthase and cyclooxygenase) (PTGS1) | NM_000962, NM_080591 |
| Prostaglandin-endoperoxide synthase 2 (prostaglandin G/H synthase and cyclooxygenase) (PTGS2) | NM_000963 |
| Adrenergic, alpha-1A-, receptor (ADRA1A) | NM_033302, NM_033303, NM_033304, NM_000680 |
| Adrenergic, alpha-1B-, receptor (ADRA1B) | NM_000679 |
| Adrenergic, alpha-1D-, receptor (ADRA1D) | NM_000678 |
| Angiotensinogen (AGT) | NM_000029 |
| Angiotensin II receptor, type 1 (AGTR1) | NM_000685, NM_009585, NM_004835, NM_031850, NM_032049 |
| Angiotensin II receptor, type 2 (AGTR2) | NM_000686 |
| Angiotensin I converting enzyme 1 (ACE1) | NM_000789, NM_152830, NM_152831 |
| Angiotensin I converting enzyme 2 (ACE2) | NM_021804 |
| Renin (REN) | NM_000537 |
| Coagulation factor C homolog, cochlin (COCH) | NM_004086 |
| ATPase, Na+/K+ transporting, alpha 1 polypeptide (ATP1A1) | NM_000701, NM_001001586 |
| ATPase, Na+/K+ transporting, alpha 2 (+) polypeptide (ATP1A2) | NM_000702 |
| ATPase, Na+/K+ transporting, alpha 3 polypeptide (ATP1A3) | NM_152296 |
| ATPase, Na+/K+ transporting, beta 1 polypeptide (ATP1B1) | NM_001677, NM_001001787 |
| ATPase, Na+/K+ transporting, beta 2 polypeptide (ATP1B2) | NM_001678 |

Figure 2A

| CA4 | |
|---|---|
| SEQ ID 1 | 5' GCCGAGUCCUCCAACUACC 3'<br>3' CGGCUCAGGAGGUUGAUGG 5' |
| SEQ ID 2 | 5' CUACCCCUGCUUGGUGCCA 3'<br>3' GAUGGGGACGAACCACGGU 5' |
| SEQ ID 3 | 5' GUGGGGUGGAAACUGCCAG 3'<br>3' CACCCCACCUUUGACGGUC 5' |
| SEQ ID 4 | 5' ACUGCCAGAAGGACCGCCA 3'<br>3' UGACGGUCUUCCUGGCGGU 5' |
| SEQ ID 5 | 5' CAUCGUCACCACCAAGGCA 3'<br>3' GUAGCAGUGGUGGUUCCGU 5' |
| SEQ ID 6 | 5' GGCAAAGGUGGACAAAAAA 3'<br>3' CCGUUUCCACCUGUUUUUU 5' |
| SEQ ID 7 | 5' AGGUGGACAAAAAACUGGG 3'<br>3' UCCACCUGUUUUUUGACCC 5' |
| SEQ ID 8 | 5' GGUGGACAAAAAACUGGGA 3'<br>3' CCACCUGUUUUUUGACCCU 5' |
| SEQ ID 9 | 5' AAAACUGGGACGCUUCUUC 3'<br>3' UUUUGACCCUGCGAAGAAG 5' |
| SEQ ID 10 | 5' AAACUGGGACGCUUCUUCU 3'<br>3' UUUGACCCUGCGAAGAAGA 5' |
| SEQ ID 11 | 5' AACUGGGACGCUUCUUCUU 3'<br>3' UUGACCCUGCGAAGAAGAA 5' |
| SEQ ID 12 | 5' ACUGGGACGCUUCUUCUUC 3'<br>3' UGACCCUGCGAAGAAGAAG 5' |
| SEQ ID 13 | 5' CUGGGACGCUUCUUCUUCU 3'<br>3' GACCCUGCGAAGAAGAAGA 5' |
| SEQ ID 14 | 5' GAAGCAAACGUGGACUGUC 3'<br>3' CUUCGUUUGCACCUGACAG 5' |

Figure 2B

| | |
|---|---|
| SEQ ID 15 | 5' GCAAACGUGGACUGUCCAA 3'<br>3' CGUUUGCACCUGACAGGUU 5' |
| SEQ ID 16 | 5' ACGUGGACUGUCCAAAAUA 3'<br>3' UGCACCUGACAGGUUUUAU 5' |
| SEQ ID 17 | 5' CGUGGACUGUCCAAAAUAA 3'<br>3' GCACCUGACAGGUUUUAUU 5' |
| SEQ ID 18 | 5' AAUAACGGGCACUCAGUGA 3'<br>3' UUAUUGCCCGUGAGUCACU 5' |
| SEQ ID 19 | 5' AUAACGGGCACUCAGUGAU 3'<br>3' UAUUGCCCGUGAGUCACUA 5' |
| SEQ ID 20 | 5' UAACGGGCACUCAGUGAUG 3'<br>3' AUUGCCCGUGAGUCACUAC 5' |
| SEQ ID 21 | 5' CGGGCACUCAGUGAUGAUG 3'<br>3' GCCCGUGAGUCACUACUAC 5' |
| SEQ ID 22 | 5' CAAGGCCAGCAUUUCUGGA 3'<br>3' GUUCCGGUCGUAAAGACCU 5' |
| SEQ ID 23 | 5' GGCCAGCAUUUCUGGAGGA 3'<br>3' CCGGUCGUAAAGACCUCCU 5' |
| SEQ ID 24 | 5' ACAGUUGCACCUGCACUGG 3'<br>3' UGUCAACGUGGACGUGACC 5' |
| SEQ ID 25 | 5' CAGUUGCACCUGCACUGGU 3'<br>3' GUCAACGUGGACGUGACCA 5' |
| SEQ ID 26 | 5' AGAGAAGGGGACAUCGAGG 3'<br>3' UCUCUUCCCCUGUAGCUCC 5' |
| SEQ ID 27 | 5' GAGAAGGGGACAUCGAGGA 3'<br>3' CUCUUCCCCUGUAGCUCCU 5' |
| SEQ ID 28 | 5' GGGGACAUCGAGGAAUGUG 3'<br>3' CCCCUGUAGCUCCUUACAC 5' |
| SEQ ID 29 | 5' UGUGAAAGAGGCCCAGGAC 3'<br>3' ACACUUUCUCCGGGUCCUG 5' |

Figure 2C

| | |
|---|---|
| SEQ ID 30 | 5' AGAGGCCCAGGACCCUGAA 3'<br>3' UCUCCGGGUCCUGGGACUU 5' |
| SEQ ID 31 | 5' GACGAAAUUGCGGUGCUGG 3'<br>3' CUGCUUUAACGCCACGACC 5' |
| SEQ ID 32 | 5' AUUGCGGUGCUGGCCUUUC 3'<br>3' UAACGCCACGACCGGAAAG 5' |
| SEQ ID 33 | 5' UUGCGGUGCUGGCCUUUCU 3'<br>3' AACGCCACGACCGGAAAGA 5' |
| SEQ ID 34 | 5' CCCAGGUGAACGAGGGCUU 3'<br>3' GGGUCCACUUGCUCCCGAA 5' |
| SEQ ID 35 | 5' UAUCCCCAAACCUGAGAUG 3'<br>3' AUAGGGGUUUGGACUCUAC 5' |
| SEQ ID 36 | 5' ACCUGAGAUGAGCACUACG 3'<br>3' UGGACUCUACUCGUGAUGC 5' |
| SEQ ID 37 | 5' CCUGAGAUGAGCACUACGA 3'<br>3' GGACUCUACUCGUGAUGCU 5' |
| SEQ ID 38 | 5' GGAGGAGAAACUGAGGCAC 3'<br>3' CCUCCUCUUUGACUCCGUG 5' |
| SEQ ID 39 | 5' ACUGAGGCACUACUUCCGC 3'<br>3' UGACUCCGUGAUGAAGGCG 5' |
| SEQ ID 40 | 5' CUGAGGCACUACUUCCGCU 3'<br>3' GACUCCGUGAUGAAGGCGA 5' |
| SEQ ID 41 | 5' GGUCGUCUGGACUGUGUUC 3'<br>3' CCAGCAGACCUGACACAAG 5' |
| SEQ ID 42 | 5' CAGAUCCUGGCAUUCUCUC 3'<br>3' GUCUAGGACCGUAAGAGAG 5' |
| SEQ ID 43 | 5' GCUGUACUACGACAAGGAA 3'<br>3' CGACAUGAUGCUGUUCCUU 5' |
| SEQ ID 44 | 5' GGAACAGACAGUGAGCAUG 3'<br>3' CCUUGUCUGUCACUCGUAC 5' |

Figure 2D

| | |
|---|---|
| SEQ ID 45 | 5' CAGACAGUGAGCAUGAAGG 3'<br>3' GUCUGUCACUCGUACUUCC 5' |
| SEQ ID 46 | 5' GGACAAUGUCAGGCCCCUG 3'<br>3' CCUGUUACAGUCCGGGGAC 5' |
| **CA2** | |
| SEQ ID 47 | 5' ACACAACGGACCUGAGCAC 3'<br>3' UGUGUUGCCUGGACUCGUG 5' |
| SEQ ID 48 | 5' CACAACGGACCUGAGCACU 3'<br>3' GUGUUGCCUGGACUCGUGA 5' |
| SEQ ID 49 | 5' CGGACCUGAGCACUGGCAU 3'<br>3' GCCUGGACUCGUGACCGUA 5' |
| SEQ ID 50 | 5' GGACUUCCCCAUUGCCAAG 3'<br>3' CCUGAAGGGGUAACGGUUC 5' |
| SEQ ID 51 | 5' GUAUGACCCUUCCCUGAAG 3'<br>3' CAUACUGGGAAGGGACUUC 5' |
| SEQ ID 52 | 5' GCCCCUGUCUGUUUCCUAU 3'<br>3' CGGGGACAGACAAAGGAUA 5' |
| SEQ ID 53 | 5' GCAACUUCCCUGAGGAUCC 3'<br>3' CGUUGAAGGGACUCCUAGG 5' |
| SEQ ID 54 | 5' CUUCCCUGAGGAUCCUCAA 3'<br>3' GAAGGGACUCCUAGGAGUU 5' |
| SEQ ID 55 | 5' CAAUGGUCAUGCUUUCAAC 3'<br>3' GUUACCAGUACGAAAGUUG 5' |
| SEQ ID 56 | 5' UGGUCAUGCUUUCAACGUG 3'<br>3' ACCAGUACGAAAGUUGCAC 5' |
| SEQ ID 57 | 5' CGUGGAGUUUGAUGACUCU 3'<br>3' GCACCUCAAACUACUGAGA 5' |
| SEQ ID 58 | 5' AGCAGUGCUCAAGGGAGGA 3'<br>3' UCGUCACGAGUUCCCUCCU 5' |

Figure 2E

| | |
|---|---|
| SEQ ID 59 | 5' GCAGUGCUCAAGGGAGGAC 3'<br>3' CGUCACGAGUUCCCUCCUG 5' |
| SEQ ID 60 | 5' GGUUCAGAGCAUACUGUGG 3'<br>3' CCAAGUCUCGUAUGACACC 5' |
| SEQ ID 61 | 5' AAGAAAUAUGCUGCAGAAC 3'<br>3' UUCUUUAUACGACGUCUUG 5' |
| SEQ ID 62 | 5' AGAAAUAUGCUGCAGAACU 3'<br>3' UCUUUAUACGACGUCUUGA 5' |
| SEQ ID 63 | 5' GAAAUAUGCUGCAGAACUU 3'<br>3' CUUUAUACGACGUCUUGAA 5' |
| SEQ ID 64 | 5' AUAUGCUGCAGAACUUCAC 3'<br>3' UAUACGACGUCUUGAAGUG 5' |
| SEQ ID 65 | 5' UAUGCUGCAGAACUUCACU 3'<br>3' AUACGACGUCUUGAAGUGA 5' |
| SEQ ID 66 | 5' CUUCACUUGGUUCACUGGA 3'<br>3' GAAGUGAACCAAGUGACCU 5' |
| SEQ ID 67 | 5' CACCAAAUAUGGGGAUUUU 3'<br>3' GUGGUUUAUACCCCUAAAA 5' |
| SEQ ID 68 | 5' AUAUGGGGAUUUUGGGAAA 3'<br>3' UAUACCCCUAAAACCCUUU 5' |
| SEQ ID 69 | 5' UAUGGGGAUUUUGGGAAAG 3'<br>3' AUACCCCUAAAACCCUUUC 5' |
| SEQ ID 70 | 5' AGCUGUGCAGCAACCUGAU 3'<br>3' UCGACACGUCGUUGGACUA 5' |
| SEQ ID 71 | 5' GCUGUGCAGCAACCUGAUG 3'<br>3' CGACACGUCGUUGGACUAC 5' |
| SEQ ID 72 | 5' CCUGAUGGACUGGCCGUUC 3'<br>3' GGACUACCUGACCGGCAAG 5' |
| SEQ ID 73 | 5' GGUUGGCAGCGCUAAACCG 3'<br>3' CCAACCGUCGCGAUUUGGC 5' |
| SEQ ID 74 | 5' ACCGGGCCUUCAGAAAGUU 3'<br>3' UGGCCCGGAAGUCUUUCAA 5' |

Figure 2F

| | |
|---|---|
| SEQ ID 75 | 5' CCGGGCCUUCAGAAAGUUG 3'<br>3' GGCCCGGAAGUCUUUCAAC 5' |
| SEQ ID 76 | 5' AGUUGUUGAUGUGCUGGAU 3'<br>3' UCAACAACUACACGACCUA 5' |
| SEQ ID 77 | 5' GUUGUUGAUGUGCUGGAUU 3'<br>3' CAACAACUACACGACCUAA 5' |
| SEQ ID 78 | 5' AACAAAGGGCAAGAGUGCU 3'<br>3' UUGUUUCCCGUUCUCACGA 5' |
| SEQ ID 79 | 5' ACAAAGGGCAAGAGUGCUG 3'<br>3' UGUUUCCCGUUCUCACGAC 5' |
| SEQ ID 80 | 5' CAAAGGGCAAGAGUGCUGA 3'<br>3' GUUUCCCGUUCUCACGACU 5' |
| SEQ ID 81 | 5' AGGGCAAGAGUGCUGACUU 3'<br>3' UCCCGUUCUCACGACUGAA 5' |
| SEQ ID 82 | 5' GGGCAAGAGUGCUGACUUC 3'<br>3' CCCGUUCUCACGACUGAAG 5' |
| SEQ ID 83 | 5' GAGUGCUGACUUCACUAAC 3'<br>3' CUCACGACUGAAGUGAUUG 5' |
| SEQ ID 84 | 5' GAGUGCUGACUUCACAAAC 3'<br>3' CUCACGACUGAAGUGUUUG 5' |
| SEQ ID 85 | 5' ACUUUGCAGCUCGUGGCCU 3'<br>3' UGAAACGUCGAGCACCGGA 5' |
| SEQ ID 86 | 5' CUUCGAUCCUCGUGGCCUC 3'<br>3' GAAGCUAGGAGCACCGGAG 5' |
| SEQ ID 87 | 5' UCCCUGGAUUACUGGACCU 3'<br>3' AGGGACCUAAUGACCUGGA 5' |
| SEQ ID 88 | 5' UGUGUGACCUGGAUUGUGC 3'<br>3' ACACACUGGACCUAACACG 5' |
| SEQ ID 89 | 5' GGAACCCAUCAGCGUCAGC 3'<br>3' CCUUGGGUAGUCGCAGUCG 5' |
| SEQ ID 90 | 5' ACUUAACUUCAAUGGGGAG 3'<br>3' UGAAUUGAAGUUACCCCUC 5' |

Figure 2G

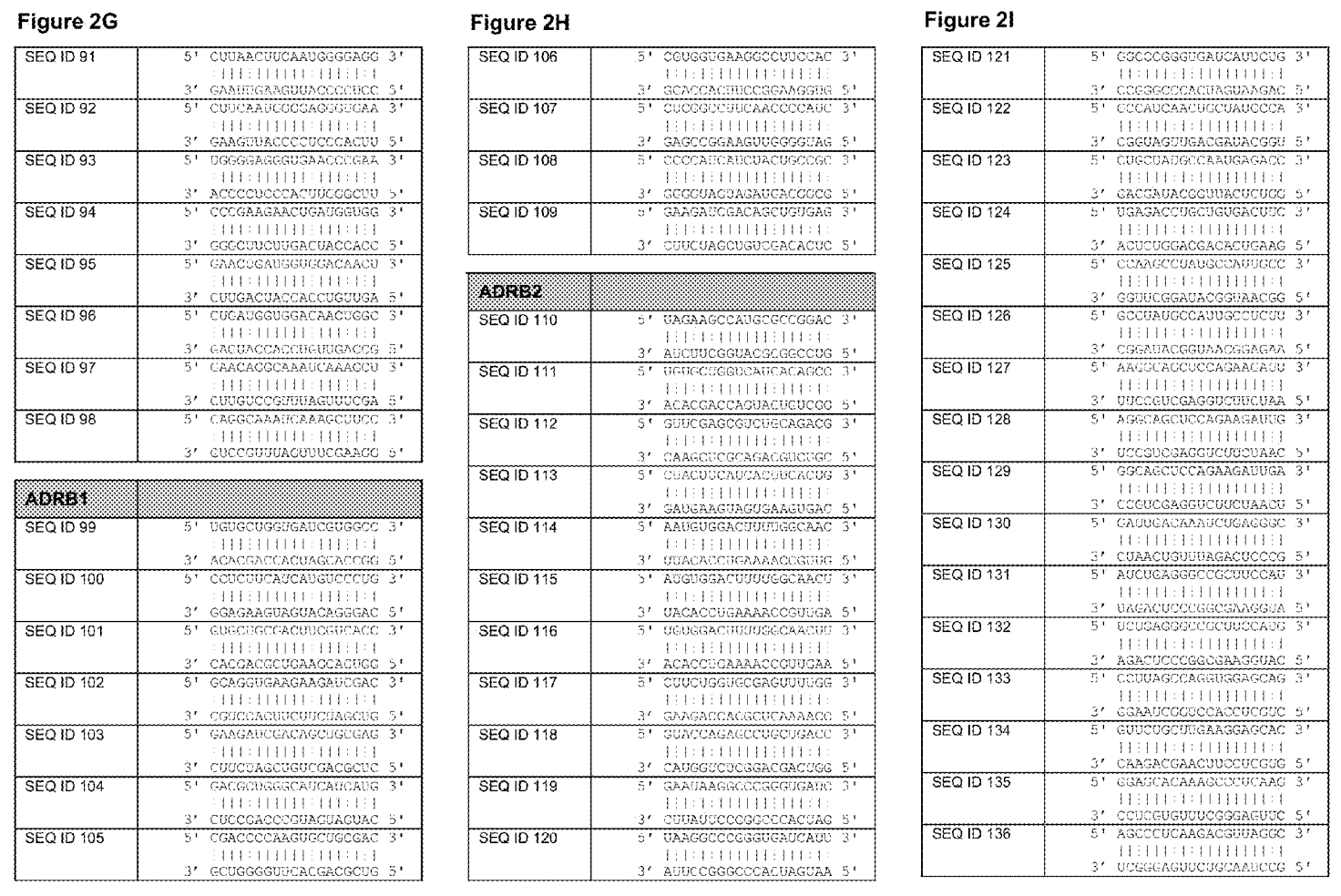

| | |
|---|---|
| SEQ ID 91 | 5' CUUAACUUCAAUGGGGAGG 3'<br>3' GAAUUGAAGUUACCCCUCC 5' |
| SEQ ID 92 | 5' CUUCAAUCGGGAGGGUGAA 3'<br>3' GAAGUUACCCCUCCCACUU 5' |
| SEQ ID 93 | 5' UGGGGAGGGUGAACCCGAA 3'<br>3' ACCCCUCCCACUUGGGCUU 5' |
| SEQ ID 94 | 5' CCCGAAGAACUGAUGGUGG 3'<br>3' GGGCUUCUUGACUACCACC 5' |
| SEQ ID 95 | 5' GAACUGAUGGUGGACAACU 3'<br>3' CUUGACUACCACCUGUUGA 5' |
| SEQ ID 96 | 5' CUGAUGGUGGACAACUGGC 3'<br>3' GACUACCACCUGUUGACCG 5' |
| SEQ ID 97 | 5' GAACAGGCAAAUCAAAGCU 3'<br>3' CUUGUCCGUUUAGUUUCGA 5' |
| SEQ ID 98 | 5' CAGGCAAAUCAAAGCUUCC 3'<br>3' GUCCGUUUAGUUUCGAAGG 5' |

| ADRB1 | |
|---|---|
| SEQ ID 99 | 5' UGUGCUGGUGAUCGUGGCC 3'<br>3' ACACGACCACUAGCACCGG 5' |
| SEQ ID 100 | 5' CCUCUUCAUCAUGUCCCUG 3'<br>3' GGAGAAGUAGUACAGGGAC 5' |
| SEQ ID 101 | 5' GUGCUGCGACUUCGUCACC 3'<br>3' CACGACGCUGAAGCAGUGG 5' |
| SEQ ID 102 | 5' GCAGGUGAAGAAGAUCGAC 3'<br>3' CGUCCACUUCUUCUAGCUG 5' |
| SEQ ID 103 | 5' GAAGAUCGACAGCUGCGAG 3'<br>3' CUUCUAGCUGUCGACGCUC 5' |
| SEQ ID 104 | 5' GACGCUGGGCAUCAUCAUG 3'<br>3' CUCCGACCCGUAGUAGUAC 5' |
| SEQ ID 105 | 5' CGACCCCAAGUGCUGCGAC 3'<br>3' GCUGGGGUUCACGACGCUG 5' |

Figure 2H

| | |
|---|---|
| SEQ ID 106 | 5' CGUGGUGAAGGCCUUCCAC 3'<br>3' GCACCACUUCCGGAAGGUG 5' |
| SEQ ID 107 | 5' CUCGGCCUUCAACCCCAUC 3'<br>3' GAGCCGGAAGUUGGGGUAG 5' |
| SEQ ID 108 | 5' CCCCAUCAUCUACUGCCGC 3'<br>3' GGGGUAGUAGAUGACGGCG 5' |
| SEQ ID 109 | 5' GAAGAUCGACAGCUGUGAG 3'<br>3' CUUCUAGCUGUCGACACUC 5' |

| ADRB2 | |
|---|---|
| SEQ ID 110 | 5' UAGAAGCCAUGCGCCGGAC 3'<br>3' AUCUUCGGUACGCGGCCUG 5' |
| SEQ ID 111 | 5' UGUGCUGGUCAUCACAGCC 3'<br>3' ACACGACCAGUAGUGUCGG 5' |
| SEQ ID 112 | 5' GUUCGAGCGUCUGCAGACG 3'<br>3' CAAGCUCGCAGACGUCUGC 5' |
| SEQ ID 113 | 5' CUACUUCAUCACUUCACUG 3'<br>3' GAUGAAGUAGUGAAGUGAC 5' |
| SEQ ID 114 | 5' AAUGUGGACUUUUGGCAAC 3'<br>3' UUACACCUGAAAACCGUUG 5' |
| SEQ ID 115 | 5' AUGUGGACUUUUGGCAACU 3'<br>3' UACACCUGAAAACCGUUGA 5' |
| SEQ ID 116 | 5' UGUGGACUUUUGGCAACUU 3'<br>3' ACACCUGAAAACCGUUGAA 5' |
| SEQ ID 117 | 5' CUUCUGGUGCGAGUUUUGG 3'<br>3' GAAGACCACGCUCAAAACC 5' |
| SEQ ID 118 | 5' GUACCAGAGCCUGCUGACC 3'<br>3' CAUGGUCUCGGACGACUGG 5' |
| SEQ ID 119 | 5' GAAUAAGGCCCGGGUGAUC 3'<br>3' CUUAUUCCGGGCCCACUAG 5' |
| SEQ ID 120 | 5' UAAGGCCCGGGUGAUCAUU 3'<br>3' AUUCCGGGCCCACUAGUAA 5' |

Figure 2I

| | |
|---|---|
| SEQ ID 121 | 5' GGCCCGGGUGAUCAUUCUG 3'<br>3' CCGGGCCCACUAGUAAGAC 5' |
| SEQ ID 122 | 5' GCCAUCAACUGCUAUGCCA 3'<br>3' CGGUAGUUGACGAUACGGU 5' |
| SEQ ID 123 | 5' CUGCUAUGCCAAUGAGACC 3'<br>3' GACGAUACGGUUACUCUGG 5' |
| SEQ ID 124 | 5' UGAGACCUGCUGUGACUUC 3'<br>3' ACUCUGGACGACACUGAAG 5' |
| SEQ ID 125 | 5' CCAAGCCUAUGCCAUUGCC 3'<br>3' GGUUCGGAUACGGUAACGG 5' |
| SEQ ID 126 | 5' GCCUAUGCCAUUGCCUCUU 3'<br>3' CGGAUACGGUAACGGAGAA 5' |
| SEQ ID 127 | 5' AAGGCAGCUCCAGAACAUU 3'<br>3' UUCCGUCGAGGUCUUCUAA 5' |
| SEQ ID 128 | 5' AGGCAGCUCCAGAAGAUUG 3'<br>3' UCCGUCGAGGUCUUCUAAC 5' |
| SEQ ID 129 | 5' GGCAGCUCCAGAAGAUUGA 3'<br>3' CCGUCGAGGUCUUCUAACU 5' |
| SEQ ID 130 | 5' GAUUGACAAAUCUGAGGGC 3'<br>3' CUAACUGUUUAGACUCCCG 5' |
| SEQ ID 131 | 5' AUCUGAGGGCCGCUUCCAU 3'<br>3' UAGACUCCCGGCGAAGGUA 5' |
| SEQ ID 132 | 5' UCUGAGGGCCGCUUCCAUG 3'<br>3' AGACUCCCGGCGAAGGUAC 5' |
| SEQ ID 133 | 5' CCUUAGCCAGGUGGAGCAG 3'<br>3' GGAAUCGGUCCACCUCGUC 5' |
| SEQ ID 134 | 5' GUUCUGCUUGAAGGAGCAC 3'<br>3' CAAGACGAACUUCCUCGUG 5' |
| SEQ ID 135 | 5' GGAGCACAAAGCCCUCAAG 3'<br>3' CCUCGUGUUUCGGGAGUUC 5' |
| SEQ ID 136 | 5' AGCCCUCAAGACGUUAGGC 3'<br>3' UCGGGAGUUCUGCAAUCCG 5' |

Figure 2J

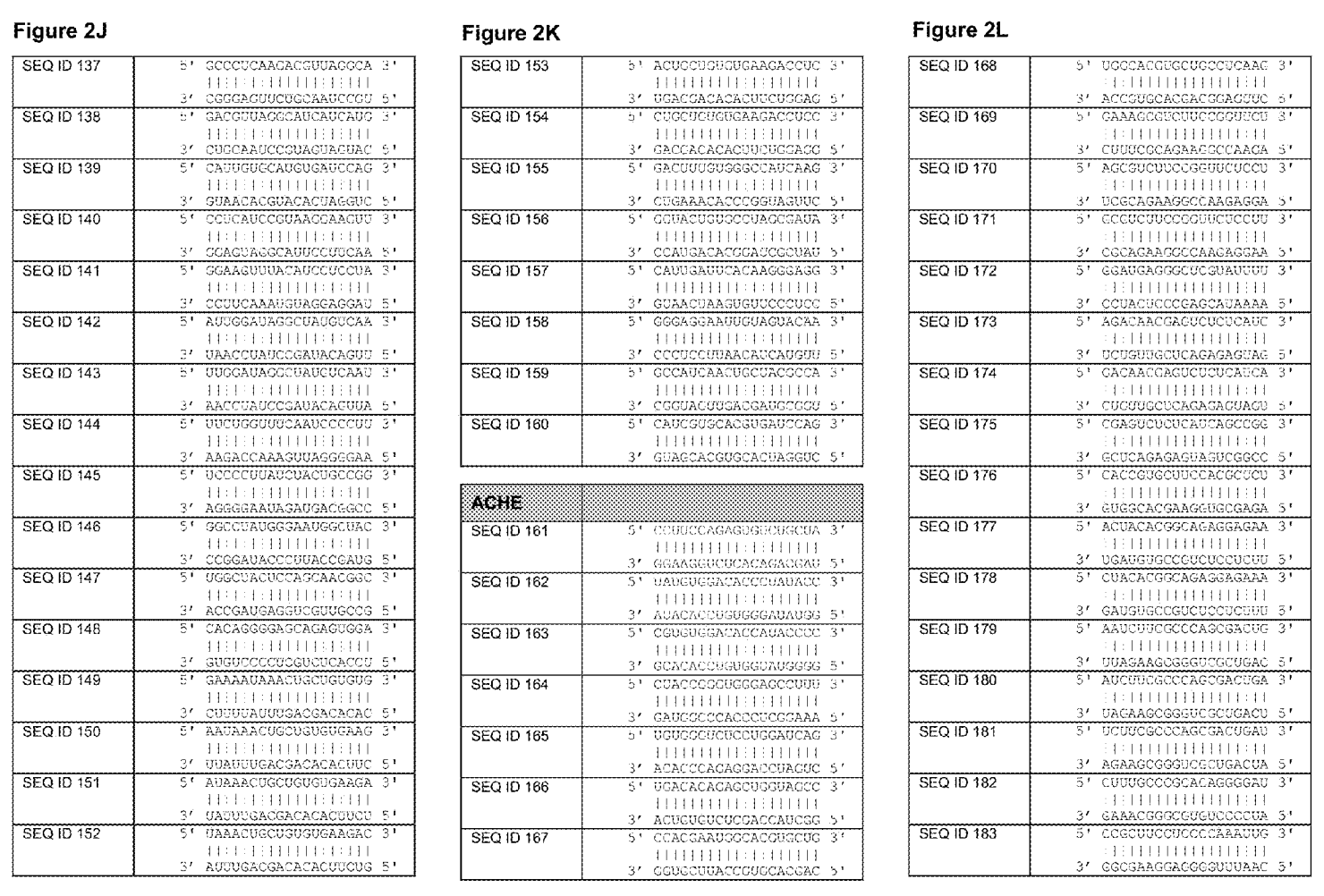

| | |
|---|---|
| SEQ ID 137 | 5' GCCCUCAAGACGUUAGGCA 3'<br>3' CGGGAGUUCUGCAAUCCGU 5' |
| SEQ ID 138 | 5' GACGUUAGGCAUCAUCAUG 3'<br>3' CUGCAAUCCGUAGUAGUAC 5' |
| SEQ ID 139 | 5' CAUUGUGCAUGUGAUCCAG 3'<br>3' GUAACACGUACACUAGGUC 5' |
| SEQ ID 140 | 5' CCUCAUCCGUAAGGAACUU 3'<br>3' GGAGUAGGCAUUCCUUCAA 5' |
| SEQ ID 141 | 5' GGAAGUUUACAUCCUCCUA 3'<br>3' CCUUCAAAUGUAGGAGGAU 5' |
| SEQ ID 142 | 5' AUUGGAUAGGCUAUGUCAA 3'<br>3' UAACCUAUCCGAUACAGUU 5' |
| SEQ ID 143 | 5' UUGGAUAGGCUAUGUCAAU 3'<br>3' AACCUAUCCGAUACAGUUA 5' |
| SEQ ID 144 | 5' UUCUGGUUUCAAUCCCCUU 3'<br>3' AAGACCAAAGUUAGGGGAA 5' |
| SEQ ID 145 | 5' UCCCCUUAUCUACUGCCGG 3'<br>3' AGGGGAAUAGAUGACGGCC 5' |
| SEQ ID 146 | 5' GGCCUAUGGGAAUGGCUAC 3'<br>3' CCGGAUACCCUUACCGAUG 5' |
| SEQ ID 147 | 5' UGGCUACUCCAGCAACGGC 3'<br>3' ACCGAUGAGGUCGUUGCCG 5' |
| SEQ ID 148 | 5' CACAGGGGAGCAGAGUGGA 3'<br>3' GUGUCCCCUCGUCUCACCU 5' |
| SEQ ID 149 | 5' GAAAAUAAACUGCUGUGUG 3'<br>3' CUUUUAUUUGACGACACAC 5' |
| SEQ ID 150 | 5' AAUAAACUGCUGUGUGAAG 3'<br>3' UUAUUUGACGACACACUUC 5' |
| SEQ ID 151 | 5' AUAAACUGCUGUGUGAAGA 3'<br>3' UAUUUGACGACACACUUCU 5' |
| SEQ ID 152 | 5' UAAACUGCUGUGUGAAGAC 3'<br>3' AUUUGACGACACACUUCUG 5' |

Figure 2K

| | |
|---|---|
| SEQ ID 153 | 5' ACUGCUGUGUGAAGACCUC 3'<br>3' UGACGACACACUUCUGGAG 5' |
| SEQ ID 154 | 5' CUGCUGUGUGAAGACCUCC 3'<br>3' GACGACACACUUCUGGAGG 5' |
| SEQ ID 155 | 5' GACUUUGUGGGCCAUCAAG 3'<br>3' CUGAAACACCCGGUAGUUC 5' |
| SEQ ID 156 | 5' GGUACUGUGCCUAGCGAUA 3'<br>3' CCAUGACACGGAUCGCUAU 5' |
| SEQ ID 157 | 5' CAUUGAUUCACAAGGGAGG 3'<br>3' GUAACUAAGUGUUCCCUCC 5' |
| SEQ ID 158 | 5' GGGAGGAAUUGUAGUACAA 3'<br>3' CCCUCCUUAACAUCAUGUU 5' |
| SEQ ID 159 | 5' GCCAUCAACUGCUACGCCA 3'<br>3' CGGUAGUUGACGAUGCGGU 5' |
| SEQ ID 160 | 5' CAUCGUGCACGUGAUCCAG 3'<br>3' GUAGCACGUGCACUAGGUC 5' |

| ACHE | |
|---|---|
| SEQ ID 161 | 5' CCUUCCAGAGUGUCUGCUA 3'<br>3' GGAAGGUCUCACAGACGAU 5' |
| SEQ ID 162 | 5' UAUGUGGACACCCUAUACC 3'<br>3' AUACACCUGUGGGAUAUGG 5' |
| SEQ ID 163 | 5' CGUGUGGACACCAUACCCC 3'<br>3' GCACACCUGUGGUAUGGGG 5' |
| SEQ ID 164 | 5' CUACCGGGUGGGAGCCUUU 3'<br>3' GAUGGCCCACCCUCGGAAA 5' |
| SEQ ID 165 | 5' UGUGGGUCUCCUGGAUCAG 3'<br>3' ACACCCAGAGGACCUAGUC 5' |
| SEQ ID 166 | 5' UGACACAGAGCUGGUAGCC 3'<br>3' ACUGUGUCUCGACCAUCGG 5' |
| SEQ ID 167 | 5' CCACGAAUGGCACGUGCUG 3'<br>3' GGUGCUUACCGUGCACGAC 5' |

Figure 2L

| | |
|---|---|
| SEQ ID 168 | 5' UGGCACGUGCUGCCUCAAG 3'<br>3' ACCGUGCACGACGGAGUUC 5' |
| SEQ ID 169 | 5' GAAAGCGUCUUCCGGUUCU 3'<br>3' CUUUCGCAGAAGGCCAAGA 5' |
| SEQ ID 170 | 5' AGCGUCUUCCGGUUCUCCU 3'<br>3' UCGCAGAAGGCCAAGAGGA 5' |
| SEQ ID 171 | 5' GCGUCUUCCGGUUCUCCUU 3'<br>3' CGCAGAAGGCCAAGAGGAA 5' |
| SEQ ID 172 | 5' GGAUGAGGGCUCGUAUUUU 3'<br>3' CCUACUCCCGAGCAUAAAA 5' |
| SEQ ID 173 | 5' AGACAACGAGUCUCUCAUC 3'<br>3' UCUGUUGCUCAGAGAGUAG 5' |
| SEQ ID 174 | 5' GACAACGAGUCUCUCAUCA 3'<br>3' CUGUUGCUCAGAGAGUAGU 5' |
| SEQ ID 175 | 5' CGAGUCUCUCAUCAGCCGG 3'<br>3' GCUCAGAGAGUAGUCGGCC 5' |
| SEQ ID 176 | 5' CACCGUGCUUCCACGCUCU 3'<br>3' GUGGCACGAAGGUGCGAGA 5' |
| SEQ ID 177 | 5' ACUACACGGCAGAGGAGAA 3'<br>3' UGAUGUGCCGUCUCCUCUU 5' |
| SEQ ID 178 | 5' CUACACGGCAGAGGAGAAA 3'<br>3' GAUGUGCCGUCUCCUCUUU 5' |
| SEQ ID 179 | 5' AAUCUUCGCCCAGCGACUG 3'<br>3' UUAGAAGCGGGUCGCUGAC 5' |
| SEQ ID 180 | 5' AUCUUCGCCCAGCGACUGA 3'<br>3' UAGAAGCGGGUCGCUGACU 5' |
| SEQ ID 181 | 5' UCUUCGCCCAGCGACUGAU 3'<br>3' AGAAGCGGGUCGCUGACUA 5' |
| SEQ ID 182 | 5' CUUUGCCCGCACAGGGGAU 3'<br>3' GAAACGGGCGUGUCCCCUA 5' |
| SEQ ID 183 | 5' CCGCUUCCUCCCCAAAUUG 3'<br>3' GGCGAAGGAGGGGUUUAAC 5' |

Figure 2M

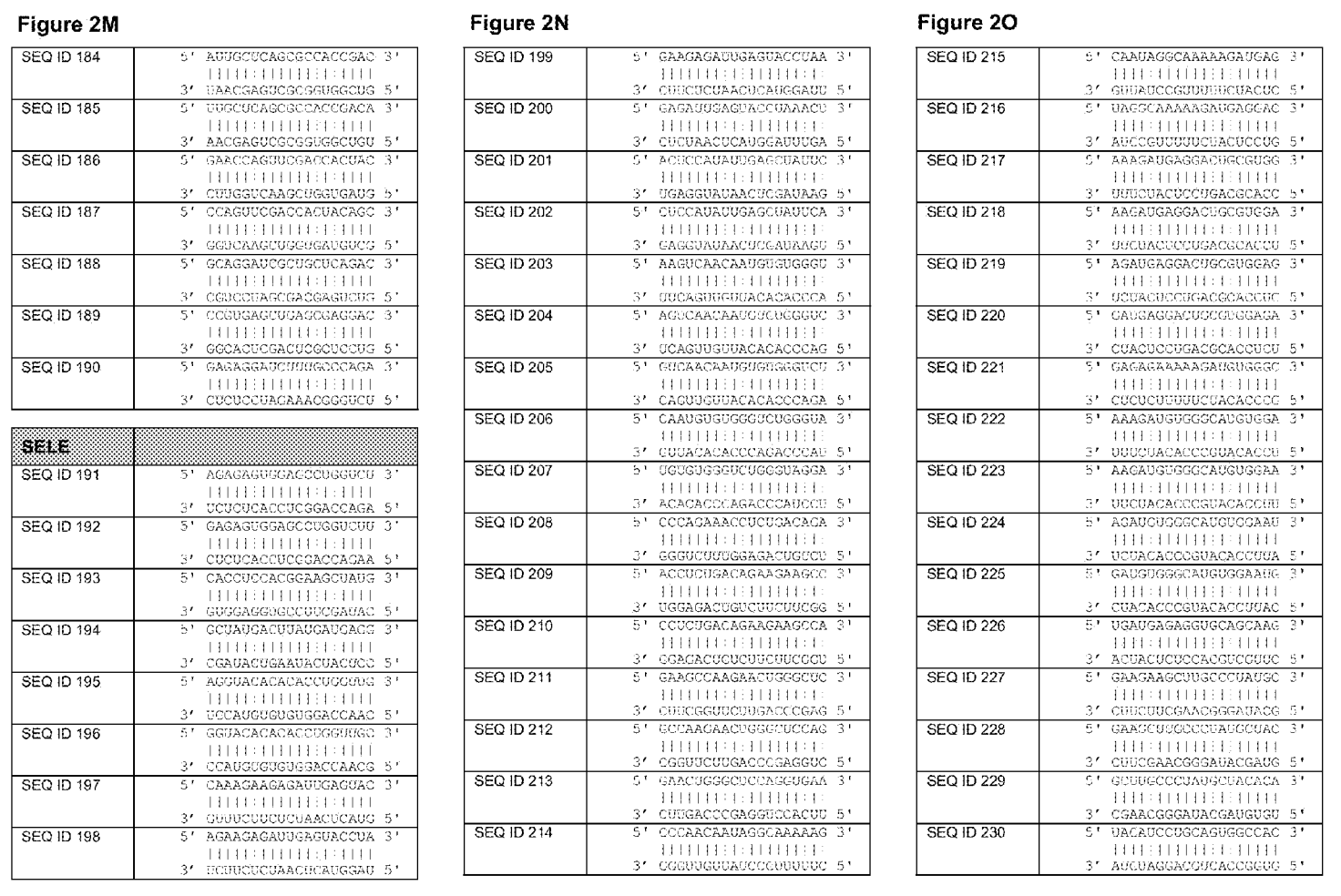

| | |
|---|---|
| SEQ ID 184 | 5' AUUGCUCAGCGCCACCGAC 3'<br>3' UAACGAGUCGCGGUGGCUG 5' |
| SEQ ID 185 | 5' UUGCUCAGCGCCACCGACA 3'<br>3' AACGAGUCGCGGUGGCUGU 5' |
| SEQ ID 186 | 5' GAACCAGUUCGACCACUAC 3'<br>3' CUUGGUCAAGCUGGUGAUG 5' |
| SEQ ID 187 | 5' CCAGUUCGACCACUACAGC 3'<br>3' GGUCAAGCUGGUGAUGUCG 5' |
| SEQ ID 188 | 5' GCAGGAUCGCUGCUCAGAC 3'<br>3' CGUCCUAGCGACGAGUCUG 5' |
| SEQ ID 189 | 5' CCGUGAGCUGAGCGAGGAC 3'<br>3' GGCACUCGACUCGCUCCUG 5' |
| SEQ ID 190 | 5' GAGAGGAUCUUUGCCCAGA 3'<br>3' CUCUCCUAGAAACGGGUCU 5' |

| SELE | |
|---|---|
| SEQ ID 191 | 5' AGAGAGUGGAGCCUGGUCU 3'<br>3' UCUCUCACCUCGGACCAGA 5' |
| SEQ ID 192 | 5' GAGAGUGGAGCCUGGUCUU 3'<br>3' CUCUCACCUCGGACCAGAA 5' |
| SEQ ID 193 | 5' CACCUCCACGGAAGCUAUG 3'<br>3' GUGGAGGUGCCUUCGAUAC 5' |
| SEQ ID 194 | 5' GCUAUGACUUAUGAUCAGG 3'<br>3' CGAUACUGAAUACUACUCC 5' |
| SEQ ID 195 | 5' AGGUACACACACCUGGUUG 3'<br>3' UCCAUGUGUGUGGACCAAC 5' |
| SEQ ID 196 | 5' GGUACACACACCUGGUUGC 3'<br>3' CCAUGUGUGUGGACCAACG 5' |
| SEQ ID 197 | 5' CAAAGAAGAGAUUGAGUAC 3'<br>3' GUUUCUUCUCUAACUCAUG 5' |
| SEQ ID 198 | 5' AGAAGAGAUUGAGUACCUA 3'<br>3' UCUUCUCUAACUCAUGGAU 5' |

Figure 2N

| | |
|---|---|
| SEQ ID 199 | 5' GAAGAGAUUGAGUACCUAA 3'<br>3' CUUCUCUAACUCAUGGAUU 5' |
| SEQ ID 200 | 5' GAGAUUGAGUACCUAAACU 3'<br>3' CUCUAACUCAUGGAUUUGA 5' |
| SEQ ID 201 | 5' ACUCCAUAUUGAGCUAUUC 3'<br>3' UGAGGUAUAACUCGAUAAG 5' |
| SEQ ID 202 | 5' CUCCAUAUUGAGCUAUUCA 3'<br>3' GAGGUAUAACUCGAUAAGU 5' |
| SEQ ID 203 | 5' AAGUCAACAAUGUGUGGGU 3'<br>3' UUCAGUUGUUACACACCCA 5' |
| SEQ ID 204 | 5' AGUCAACAAUGUGUGGGUC 3'<br>3' UCAGUUGUUACACACCCAG 5' |
| SEQ ID 205 | 5' GUCAACAAUGUGUGGGUCU 3'<br>3' CAGUUGUUACACACCCAGA 5' |
| SEQ ID 206 | 5' CAAUGUGUGGGUCUGGGUA 3'<br>3' GUUACACACCCAGACCCAU 5' |
| SEQ ID 207 | 5' UGUGUGGGUCUGGGUAGGA 3'<br>3' ACACACCCAGACCCAUCCU 5' |
| SEQ ID 208 | 5' CCCAGAAACCUCUGACAGA 3'<br>3' GGGUCUUUGGAGACUGUCU 5' |
| SEQ ID 209 | 5' ACCUCUGACAGAAGAAGCC 3'<br>3' UGGAGACUGUCUUCUUCGG 5' |
| SEQ ID 210 | 5' CCUCUGACAGAAGAAGCCA 3'<br>3' GGAGACUGUCUUCUUCGGU 5' |
| SEQ ID 211 | 5' GAAGCCAAGAACUGGGCUC 3'<br>3' CUUCGGUUCUUGACCCGAG 5' |
| SEQ ID 212 | 5' GCCAAGAACUGGGCUCCAG 3'<br>3' CGGUUCUUGACCCGAGGUC 5' |
| SEQ ID 213 | 5' GAACUGGGCUCCAGGUGAA 3'<br>3' CUUGACCCGAGGUCCACUU 5' |
| SEQ ID 214 | 5' CCCAACAAUAGGCAAAAAG 3'<br>3' GGGUUGUUAUCCGUUUUUC 5' |

Figure 2O

| | |
|---|---|
| SEQ ID 215 | 5' CAAUAGGCAAAAAGAUGAG 3'<br>3' GUUAUCCGUUUUUCUACUC 5' |
| SEQ ID 216 | 5' UAGGCAAAAAGAUGAGGAC 3'<br>3' AUCCGUUUUUCUACUCCUG 5' |
| SEQ ID 217 | 5' AAAGAUGAGGACUGCGUGG 3'<br>3' UUUCUACUCCUGACGCACC 5' |
| SEQ ID 218 | 5' AAGAUGAGGACUGCGUGGA 3'<br>3' UUCUACUCCUGACGCACCU 5' |
| SEQ ID 219 | 5' AGAUGAGGACUGCGUGGAG 3'<br>3' UCUACUCCUGACGCACCUC 5' |
| SEQ ID 220 | 5' GAUGAGGACUGCGUGGAGA 3'<br>3' CUACUCCUGACGCACCUCU 5' |
| SEQ ID 221 | 5' GAGAGAAAAAGAUGUGGGC 3'<br>3' CUCUCUUUUUCUACACCCG 5' |
| SEQ ID 222 | 5' AAAGAUGUGGGCAUGUGGA 3'<br>3' UUUCUACACCCGUACACCU 5' |
| SEQ ID 223 | 5' AAGAUGUGGGCAUGUGGAA 3'<br>3' UUCUACACCCGUACACCUU 5' |
| SEQ ID 224 | 5' AGAUGUGGGCAUGUGGAAU 3'<br>3' UCUACACCCGUACACCUUA 5' |
| SEQ ID 225 | 5' GAUGUGGGCAUGUGGAAUG 3'<br>3' CUACACCCGUACACCUUAC 5' |
| SEQ ID 226 | 5' UGAUGAGAGGUGCAGCAAG 3'<br>3' ACUACUCUCCACGUCGUUC 5' |
| SEQ ID 227 | 5' GAAGAAGCUUGCCCUAUGC 3'<br>3' CUUCUUCGAACGGGAUACG 5' |
| SEQ ID 228 | 5' GAAGCUUGCCCUAUGCUAC 3'<br>3' CUUCGAACGGGAUACGAUG 5' |
| SEQ ID 229 | 5' GCUUGCCCUAUGCUACACA 3'<br>3' CGAACGGGAUACGAUGUGU 5' |
| SEQ ID 230 | 5' UACAUCCUGCAGUGGCCAC 3'<br>3' AUGUAGGACGUCACCGGUG 5' |

Figure 2P

<table>
<tr><td>SEQ ID 231</td><td>5' UGUGUAGAGACCAUCAAUA 3'<br>|||:||||||:||||||:|<br>3' ACACAUCUCUGGUAGUUAU 5'</td></tr>
<tr><td>SEQ ID 232</td><td>5' UUACACUUGCAAGUGUGAC 3'<br>|||:||||||:||||||:|<br>3' AAUGUGAACGUUCACACUG 5'</td></tr>
<tr><td>SEQ ID 233</td><td>5' GUGUGACCCUGGCUUCAGU 3'<br>|||:||||||:||||||:|<br>3' CACACUGGGACCGAAGUCA 5'</td></tr>
<tr><td>SEQ ID 234</td><td>5' GUGUGAGCAAAUUGUGAAC 3'<br>|||:||||||:||||||:|<br>3' CACACUCGUUUAACACUUG 5'</td></tr>
<tr><td>SEQ ID 235</td><td>5' AUUGUGAACUGUACAGCCC 3'<br>|||:||||||:||||||:|<br>3' UAACACUUGACAUGUCGGG 5'</td></tr>
<tr><td>SEQ ID 236</td><td>5' UUGUGAACUGUACAGCCCU 3'<br>|||:||||||:||||||:|<br>3' AACACUUGACAUGUCGGGA 5'</td></tr>
<tr><td>SEQ ID 237</td><td>5' CUGUACAGCCCUGGAAUCC 3'<br>|||:||||||:||||||:|<br>3' GACAUGUCGGGACCUUAGG 5'</td></tr>
<tr><td>SEQ ID 238</td><td>5' UCCCCUGAGCAUGGAAGCC 3'<br>|||:||||||:||||||:|<br>3' AGGGGACUCGUACCUUCGG 5'</td></tr>
<tr><td>SEQ ID 239</td><td>5' GCCUGGUUUGCAGUCACCC 3'<br>|||:||||||:||||||:|<br>3' CGGACCAAACGUCAGUGGG 5'</td></tr>
<tr><td>SEQ ID 240</td><td>5' ACUUCAGCUACAAUUCUUC 3'<br>|||:||||||:||||||:|<br>3' UGAAGUCGAUGUUAAGAAG 5'</td></tr>
<tr><td>SEQ ID 241</td><td>5' CUUCAGCUACAAUUCUUCC 3'<br>|||:||||||:||||||:|<br>3' GAAGUCGAUGUUAAGAAGG 5'</td></tr>
<tr><td>SEQ ID 242</td><td>5' UUCUUCCUGCUCUAUCAGC 3'<br>|||:||||||:||||||:|<br>3' AAGAAGGACGAGAUAGUCG 5'</td></tr>
<tr><td>SEQ ID 243</td><td>5' GCAGCAUGGAGACCAUGCA 3'<br>|||:||||||:||||||:|<br>3' CGUCGUACCUCUGGUACGU 5'</td></tr>
<tr><td>SEQ ID 244</td><td>5' UGGAGUGCUCCUAUUCCAG 3'<br>|||:||||||:||||||:|<br>3' ACCUCACGAGGAUAAGGUC 5'</td></tr>
<tr><td>SEQ ID 245</td><td>5' UGUGGUUGAGUGUGAUGCU 3'<br>|||:||||||:||||||:|<br>3' ACACCAACUCACACUACGA 5'</td></tr>
<tr><td>SEQ ID 246</td><td>5' AUCCAGCCAAUGGGUUCGU 3'<br>|||:||||||:||||||:|<br>3' UAGGUCGGUUACCCAAGCA 5'</td></tr>
</table>

Figure 2Q

<table>
<tr><td>SEQ ID 247</td><td>5' UCCAGCCAAUGGGUUCGUG 3'<br>||||:||:||||||:||::<br>3' AGGUCGGUUACCCAAGCAC 5'</td></tr>
<tr><td>SEQ ID 248</td><td>5' UGGGUUCGUGGAAUGUUUC 3'<br>||||:||:||||||:||::<br>3' ACCCAAGCACCUUACAAAG 5'</td></tr>
<tr><td>SEQ ID 249</td><td>5' UGUUUCCAAAACCCUGGAA 3'<br>||||:||:||||||:||::<br>3' ACAAAGGUUUUGGGACCUU 5'</td></tr>
<tr><td>SEQ ID 250</td><td>5' AACCCUGGAAGCUUCCCAU 3'<br>||||:||:||||||:||::<br>3' UUGGGACCUUCGAAGGGUA 5'</td></tr>
<tr><td>SEQ ID 251</td><td>5' ACCCUGGAAGCUUCCCAUG 3'<br>||||:||:||||||:||::<br>3' UGGGACCUUCGAAGGGUAC 5'</td></tr>
<tr><td>SEQ ID 252</td><td>5' CCCUGGAAGCUUCCCAUGG 3'<br>||||:||:||||||:||::<br>3' GGGACCUUCGAAGGGUACC 5'</td></tr>
<tr><td>SEQ ID 253</td><td>5' GCUUCCCAUGGAACACAAC 3'<br>||||:||:||||||:||::<br>3' CGAAGGGUACCUUGUGUUG 5'</td></tr>
<tr><td>SEQ ID 254</td><td>5' CACAACCUGUACAUUUGAC 3'<br>||||:||:||||||:||::<br>3' GUGUUGGACAUGUAAACUG 5'</td></tr>
<tr><td>SEQ ID 255</td><td>5' CCUGUACAUUUGACUGUGA 3'<br>||||:||:||||||:||::<br>3' GGACAUGUAAACUGACACU 5'</td></tr>
<tr><td>SEQ ID 256</td><td>5' GAAGGAUUUGAACUAAUGG 3'<br>||||:||:||||||:||::<br>3' CUUCCUAAACUUGAUUACC 5'</td></tr>
<tr><td>SEQ ID 257</td><td>5' GGAUUUGAACUAAUGGAG 3'<br>||||:||:||||||:||::<br>3' CCUAAACUUGAUUACCCUC 5'</td></tr>
<tr><td>SEQ ID 258</td><td>5' CUAAUGGCAGCCCAGAGCC 3'<br>||||:||:||||||:||::<br>3' GAUUACCCUCGGGUCUCGG 5'</td></tr>
<tr><td>SEQ ID 259</td><td>5' UGGGAGCCCAGAGCCUUCA 3'<br>||||:||:||||||:||::<br>3' ACCCUCGGGUCUCGGAAGU 5'</td></tr>
<tr><td>SEQ ID 260</td><td>5' UUGGGACAACGAGAAGCCA 3'<br>||||:||:||||||:||::<br>3' AACCCUGUUGCUCUUCGGU 5'</td></tr>
<tr><td>SEQ ID 261</td><td>5' CGAGAAGCCAACGUGUAAA 3'<br>||||:||:||||||:||::<br>3' GCUCUUCGGUUGCACAUUU 5'</td></tr>
<tr><td>SEQ ID 262</td><td>5' GCCAACGUGUAAAGCUGUG 3'<br>||||:||:||||||:||::<br>3' CGGUUGCACAUUUCGACAC 5'</td></tr>
</table>

Figure 2R

<table>
<tr><td>SEQ ID 263</td><td>5' CGUGUAAAGCUGUGACAUG 3'<br>|:|||:|||||||||:|||<br>3' GCACAUUUCGACACUGUAC 5'</td></tr>
<tr><td>SEQ ID 264</td><td>5' AGCUGUGACAUGCAGGGCC 3'<br>|:|||:|||||||||:|||<br>3' UCGACACUGUACGUCCCGG 5'</td></tr>
<tr><td>SEQ ID 265</td><td>5' UGGCUCUGUGAGGUGCAGC 3'<br>|:|||:|||||||||:|||<br>3' ACCGAGACACUCCACGUCG 5'</td></tr>
<tr><td>SEQ ID 266</td><td>5' AUCAUCCUGCAACUUCACC 3'<br>|:|||:|||||||||:|||<br>3' UAGUAGGACGUUGAAGUGG 5'</td></tr>
<tr><td>SEQ ID 267</td><td>5' UCAUCCUGCAACUUCACCU 3'<br>|:|||:|||||||||:|||<br>3' AGUAGGACGUUGAAGUGGA 5'</td></tr>
<tr><td>SEQ ID 268</td><td>5' CUUCACCUGUGAGGAAGGC 3'<br>|:|||:|||||||||:|||<br>3' GAAGUGGACACUCCUUCCG 5'</td></tr>
<tr><td>SEQ ID 269</td><td>5' GGCUUCAUGUUGCAGGGAC 3'<br>|:|||:|||||||||:|||<br>3' CCGAAGUACAACGUCCCUG 5'</td></tr>
<tr><td>SEQ ID 270</td><td>5' UGCACCACUCAAGGGCAGU 3'<br>|:|||:|||||||||:|||<br>3' ACGUGGUGAGUUCCCGUCA 5'</td></tr>
<tr><td>SEQ ID 271</td><td>5' GGGCAGUGGACACAGCAAA 3'<br>|:|||:|||||||||:|||<br>3' CCCGUCACCUGUGUCGUUU 5'</td></tr>
<tr><td>SEQ ID 272</td><td>5' AUCCCAGUUUGUGAAGCUU 3'<br>|:|||:|||||||||:|||<br>3' UAGGGUCAAACACUUCGAA 5'</td></tr>
<tr><td>SEQ ID 273</td><td>5' UCCCAGUUUGUGAAGCUUU 3'<br>|:|||:|||||||||:|||<br>3' AGGGUCAAACACUUCGAAA 5'</td></tr>
<tr><td>SEQ ID 274</td><td>5' GCUUUCCAGUGCACACCCU 3'<br>|:|||:|||||||||:|||<br>3' CGAAAGGUCACGUGUCGGA 5'</td></tr>
<tr><td>SEQ ID 275</td><td>5' UUGUCUUCCUAGUGCUUCU 3'<br>|:|||:|||||||||:|||<br>3' AACAGAAGGAUCACGAAGA 5'</td></tr>
<tr><td>SEQ ID 276</td><td>5' GGGAUCCAAAAGGCUCCAA 3'<br>|:|||:|||||||||:|||<br>3' CCCUAGGUUUUCCGAGGUU 5'</td></tr>
<tr><td>SEQ ID 277</td><td>5' AAGGCUCCAAUGUGGCCCC 3'<br>|:|||:|||||||||:|||<br>3' UUCCGAGGUUACACCGGGG 5'</td></tr>
<tr><td>SEQ ID 278</td><td>5' AGGCUCCAAUGUGGCCCCA 3'<br>|:|||:|||||||||:|||<br>3' UCCGAGGUUACACCGGGGU 5'</td></tr>
</table>

Figure 2S

| | |
|---|---|
| SEQ ID 279 | 5' CGAGAAGCCCACAUGUGAA 3'<br>\|::\|\|\|\|::\|\|\|\|\|:\|\|\|\|<br>3' GCUCUUCGGGUGUACACUU 5' |
| SEQ ID 280 | 5' GCCCACAUGUGAAGCUGUG 3'<br>\|::\|\|\|\|::\|\|\|\|\|:\|\|\|\|<br>3' CGGGUGUACACUUCGACAC 5' |
| SEQ ID 281 | 5' GCUGUGAGAUGCGAUGCUG 3'<br>\|::\|\|\|\|::\|\|\|\|\|:\|\|\|\|<br>3' CGACACUCUACGCUACGAC 5' |
| SEQ ID 282 | 5' GGGUUUGGUGAGGUGUGGU 3'<br>\|::\|\|\|\|::\|\|\|\|\|:\|\|\|\|<br>3' CCCAAACCACUCCACACCA 5' |
| SEQ ID 283 | 5' UUCACCUACAAGUCCUCUU 3'<br>\|::\|\|\|\|::\|\|\|\|\|:\|\|\|\|<br>3' AAGUGGAUGUUCAGGAGAA 5' |
| SEQ ID 284 | 5' GUCCUCUUGUGCCUUCAGC 3'<br>\|::\|\|\|\|::\|\|\|\|\|:\|\|\|\|<br>3' CAGGAGAACACGGAAGUCG 5' |
| SEQ ID 285 | 5' CUCAACUUGAGUGCACAUC 3'<br>\|::\|\|\|\|::\|\|\|\|\|:\|\|\|\|<br>3' GAGUUGAACUCACGUGUAG 5' |
| SEQ ID 286 | 5' CUUGAGUGCACAUCUCAGG 3'<br>\|::\|\|\|\|::\|\|\|\|\|:\|\|\|\|<br>3' GAACUCACGUGUAGAGUCC 5' |
| SEQ ID 287 | 5' UGGACAGAAGAGGUUCCUU 3'<br>\|::\|\|\|\|::\|\|\|\|\|:\|\|\|\|<br>3' ACCUGUCUUCUCCAAGGAA 5' |
| SEQ ID 288 | 5' GAGGUUCCUUCCUGCCAAG 3'<br>\|::\|\|\|\|::\|\|\|\|\|:\|\|\|\|<br>3' CUCCAAGGAAGGACGGUUC 5' |
| SEQ ID 289 | 5' GUGGUAAAAUGUUCAAGCC 3'<br>\|::\|\|\|\|::\|\|\|\|\|:\|\|\|\|<br>3' CACCAUUUUACAAGUUCGG 5' |
| SEQ ID 290 | 5' AAUGUUCAAGCCUGGCAGU 3'<br>\|::\|\|\|\|::\|\|\|\|\|:\|\|\|\|<br>3' UUACAAGUUCGGACCGUCA 5' |
| SEQ ID 291 | 5' AUGUUCAAGCCUGGCAGUU 3'<br>\|::\|\|\|\|::\|\|\|\|\|:\|\|\|\|<br>3' UACAAGUUCGGACCGUCAA 5' |
| SEQ ID 292 | 5' UGUUCAAGCCUGGCAGUUC 3'<br>\|::\|\|\|\|::\|\|\|\|\|:\|\|\|\|<br>3' ACAAGUUCGGACCGUCAAG 5' |
| SEQ ID 293 | 5' GCCUGGCAGUUCCGGGAAA 3'<br>\|::\|\|\|\|::\|\|\|\|\|:\|\|\|\|<br>3' CGGACCGUCAAGGCCCUUU 5' |
| SEQ ID 294 | 5' AGAUCAACAUGAGCUGCAG 3'<br>\|::\|\|\|\|::\|\|\|\|\|:\|\|\|\|<br>3' UCUAGUUGUACUCGACGUC 5' |

Figure 2T

| | |
|---|---|
| SEQ ID 295 | 5' GAUCAACAUGAGCUGCAGU 3'<br>\|\|\|\|\|\|\|\|\|\|\|\|\|\|\|\|\|\|\|<br>3' CUAGUUGUACUCGACGUCA 5' |
| SEQ ID 296 | 5' CAUGAGCUGCAGUGGGGAG 3'<br>\|\|\|\|\|\|\|\|\|\|\|\|\|\|\|\|\|\|\|<br>3' GUACUCGACGUCACCCCUC 5' |
| SEQ ID 297 | 5' GUUCGCCUGUCCUGAAGGA 3'<br>\|\|\|\|\|\|\|\|\|\|\|\|\|\|\|\|\|\|\|<br>3' CAAGCGGACAGGACUUCCU 5' |
| SEQ ID 298 | 5' GGAUGGACGCUCAAUGGCU 3'<br>\|\|\|\|\|\|\|\|\|\|\|\|\|\|\|\|\|\|\|<br>3' CCUACCUGCGAGUUACCGA 5' |
| SEQ ID 299 | 5' UGGCUCUGCAGCUCGGACA 3'<br>\|\|\|\|\|\|\|\|\|\|\|\|\|\|\|\|\|\|\|<br>3' ACCGAGACGUCGAGCCUGU 5' |
| SEQ ID 300 | 5' GCUCCCACUGAGUCCAACA 3'<br>\|\|\|\|\|\|\|\|\|\|\|\|\|\|\|\|\|\|\|<br>3' CGAGGGUGACUCAGGUUGU 5' |
| SEQ ID 301 | 5' CAUUCCCUUGGUAGCUGGA 3'<br>\|\|\|\|\|\|\|\|\|\|\|\|\|\|\|\|\|\|\|<br>3' GUAAGGGAACCAUCGACCU 5' |
| SEQ ID 302 | 5' AUGCUUACGGAAAGCAAAG 3'<br>\|\|\|\|\|\|\|\|\|\|\|\|\|\|\|\|\|\|\|<br>3' UACGAAUGCCUUUCGUUUC 5' |
| SEQ ID 303 | 5' UGCUUACGGAAAGCAAAGA 3'<br>\|\|\|\|\|\|\|\|\|\|\|\|\|\|\|\|\|\|\|<br>3' ACGAAUGCCUUUCGUUUCU 5' |
| SEQ ID 304 | 5' GCAAAGAAAUUUGUUCCUG 3'<br>\|\|\|\|\|\|\|\|\|\|\|\|\|\|\|\|\|\|\|<br>3' CGUUUCUUUAAACAAGGAC 5' |
| SEQ ID 305 | 5' AGAAAUUUGUUCCUGCCAG 3'<br>\|\|\|\|\|\|\|\|\|\|\|\|\|\|\|\|\|\|\|<br>3' UCUUUAAACAAGGACGGUC 5' |
| SEQ ID 306 | 5' GAAAUUUGUUCCUGCCAGC 3'<br>\|\|\|\|\|\|\|\|\|\|\|\|\|\|\|\|\|\|\|<br>3' CUUUAAACAAGGACGGUCG 5' |
| SEQ ID 307 | 5' AUUUGUUCCUGCCAGCAGC 3'<br>\|\|\|\|\|\|\|\|\|\|\|\|\|\|\|\|\|\|\|<br>3' UAAACAAGGACGGUCGUCG 5' |
| SEQ ID 308 | 5' UUUGUUCCUGCCAGCAGCU 3'<br>\|\|\|\|\|\|\|\|\|\|\|\|\|\|\|\|\|\|\|<br>3' AAACAAGGACGGUCGUCGA 5' |
| SEQ ID 309 | 5' AGCCUUGAAUCAGACGGAA 3'<br>\|\|\|\|\|\|\|\|\|\|\|\|\|\|\|\|\|\|\|<br>3' UCGGAACUUAGUCUGCCUU 5' |
| SEQ ID 310 | 5' GCCUUGAAUCAGACGGAAG 3'<br>\|\|\|\|\|\|\|\|\|\|\|\|\|\|\|\|\|\|\|<br>3' CGGAACUUAGUCUGCCUUC 5' |

Figure 2U

| | |
|---|---|
| SEQ ID 311 | 5' UCAGACGGAAGCUACCAAA 3'<br>:\|\|\|\|\|:\|\|\|\|\|::\|\|\|\|\|<br>3' AGUCUGCCUUCGAUGGUUU 5' |
| SEQ ID 312 | 5' GCUACCAAAAGCCUUCUUA 3'<br>:\|\|\|\|\|:\|\|\|\|\|::\|\|\|\|\|<br>3' CGAUGGUUUUCGGAAGAAU 5' |
| SEQ ID 313 | 5' AAGCCUUCUUACAUCCUUU 3'<br>:\|\|\|\|\|:\|\|\|\|\|::\|\|\|\|\|<br>3' UUCGGAAGAAUGUAGGAAA 5' |
| SEQ ID 314 | 5' AGCCUUCUUACAUCCUUUA 3'<br>:\|\|\|\|\|:\|\|\|\|\|::\|\|\|\|\|<br>3' UCGGAAGAAUGUAGGAAAU 5' |
| SEQ ID 315 | 5' GCCUUCUUACAUCCUUUAA 3'<br>:\|\|\|\|\|:\|\|\|\|\|::\|\|\|\|\|<br>3' CGGAAGAAUGUAGGAAAUU 5' |
| SEQ ID 316 | 5' AGCCUUGAAUCAGAUGGAA 3'<br>:\|\|\|\|\|:\|\|\|\|\|::\|\|\|\|\|<br>3' UCGGAACUUAGUCUACCUU 5' |
| SEQ ID 317 | 5' GCCUUGAAUCAGAUGGAAG 3'<br>:\|\|\|\|\|:\|\|\|\|\|::\|\|\|\|\|<br>3' CGGAACUUAGUCUACCUUC 5' |
| SEQ ID 318 | 5' UCAGAUGGAAGCUACCAAA 3'<br>:\|\|\|\|\|:\|\|\|\|\|::\|\|\|\|\|<br>3' AGUCUACCUUCGAUGGUUU 5' |

| PTGS1 | |
|---|---|
| SEQ ID 319 | 5' UCCCUGUUGUUACUAUCCA 3'<br>:\|\|\|\|\|:\|\|\|\|\|::\|\|\|\|\|<br>3' AGGGACAACAAUGAUAGGU 5' |
| SEQ ID 320 | 5' UGCCACCUUCAUCCGAGAG 3'<br>:\|\|\|\|\|:\|\|\|\|\|::\|\|\|\|\|<br>3' ACGGUGGAAGUAGGCUCUC 5' |
| SEQ ID 321 | 5' CUCAGCACAUGACUACAUC 3'<br>:\|\|\|\|\|:\|\|\|\|\|::\|\|\|\|\|<br>3' GAGUCGUGUACUGAUGUAG 5' |
| SEQ ID 322 | 5' CGUGAGCUAUUACACUCGU 3'<br>:\|\|\|\|\|:\|\|\|\|\|::\|\|\|\|\|<br>3' GCACUCGAUAAUGUGAGCA 5' |
| SEQ ID 323 | 5' AGAUUGCCCCACACCCAUG 3'<br>:\|\|\|\|\|:\|\|\|\|\|::\|\|\|\|\|<br>3' UCUAACGGGGUGUGGGUAC 5' |
| SEQ ID 324 | 5' GAUUGCCCCACACCCAUGG 3'<br>:\|\|\|\|\|:\|\|\|\|\|::\|\|\|\|\|<br>3' CUAACGGGGUGUGGGUACC 5' |
| SEQ ID 325 | 5' CCAAAGGGAAGAAGCAGUU 3'<br>:\|\|\|\|\|:\|\|\|\|\|::\|\|\|\|\|<br>3' GGUUUCCCUUCUUCGUCAA 5' |

Figure 2V

| | |
|---|---|
| SEQ ID 326 | 5' AGGGAAGAAGCAGUUGCCA 3'<br>\|\|\|:\|\|\|\|\|\|\|:\|\|\|:\|\|\|<br>3' UCCCUUCUUCGUCAACGGU 5' |
| SEQ ID 327 | 5' GGGAAGAAGCAGUUGCCAG 3'<br>\|\|\|:\|\|\|\|\|\|\|:\|\|\|:\|\|\|<br>3' CCCUUCUUCGUCAACGGUC 5' |
| SEQ ID 328 | 5' GAAGCAGUUGCCAGAUGCC 3'<br>\|\|\|:\|\|\|\|\|\|\|:\|\|\|:\|\|\|<br>3' CUUCGUCAACGGUCUACGG 5' |
| SEQ ID 329 | 5' GCAGUUGCCAGAUGCCCAG 3'<br>\|\|\|:\|\|\|\|\|\|\|:\|\|\|:\|\|\|<br>3' CGUCAACGGUCUACGGGUC 5' |
| SEQ ID 330 | 5' GUUCAUACCUGACCCCCAA 3'<br>\|\|\|:\|\|\|\|\|\|\|:\|\|\|:\|\|\|<br>3' CAAGUAUGGACUGGGGGUU 5' |
| SEQ ID 331 | 5' GGCACCAACCUCAUGUUUG 3'<br>\|\|\|:\|\|\|\|\|\|\|:\|\|\|:\|\|\|<br>3' CCGUGGUUGGAGUACAAAC 5' |
| SEQ ID 332 | 5' CCUCAUGUUUGCCUUCUUU 3'<br>\|\|\|:\|\|\|\|\|\|\|:\|\|\|:\|\|\|<br>3' GGAGUACAAACGGAAGAAA 5' |
| SEQ ID 333 | 5' CACUUCACCCACCAGUUCU 3'<br>\|\|\|:\|\|\|\|\|\|\|:\|\|\|:\|\|\|<br>3' GUGAAGUGGGUGGUCAAGA 5' |
| SEQ ID 334 | 5' AACUUCUGGCAAGAUGGGU 3'<br>\|\|\|:\|\|\|\|\|\|\|:\|\|\|:\|\|\|<br>3' UUGAAGACCGUUCUACCCA 5' |
| SEQ ID 335 | 5' ACUUCUGGCAAGAUGGGUC 3'<br>\|\|\|:\|\|\|\|\|\|\|:\|\|\|:\|\|\|<br>3' UGAAGACCGUUCUACCCAG 5' |
| SEQ ID 336 | 5' CUUCUGGCAAGAUGCCUCC 3'<br>\|\|\|:\|\|\|\|\|\|\|:\|\|\|:\|\|\|<br>3' GAAGACCGUUCUACCCAGG 5' |
| SEQ ID 337 | 5' GAUGGGUCCUGGCUUCACC 3'<br>\|\|\|:\|\|\|\|\|\|\|:\|\|\|:\|\|\|<br>3' CUACCCAGGACCGAAGUGG 5' |
| SEQ ID 338 | 5' UCUGGAGCGUCAGUAUCAA 3'<br>\|\|\|:\|\|\|\|\|\|\|:\|\|\|:\|\|\|<br>3' AGACCUCGCAGUCAUAGUU 5' |
| SEQ ID 339 | 5' CUGCGGCUCUUUAAGGAUG 3'<br>\|\|\|:\|\|\|\|\|\|\|:\|\|\|:\|\|\|<br>3' GACGCCGAGAAAUUCCUAC 5' |
| SEQ ID 340 | 5' GGAUGGGAAACUCAAGUAC 3'<br>\|\|\|:\|\|\|\|\|\|\|:\|\|\|:\|\|\|<br>3' CCUACCCUUUGAGUUCAUG 5' |
| SEQ ID 341 | 5' ACUCAAGUACCAGGUGCUG 3'<br>\|\|\|:\|\|\|\|\|\|\|:\|\|\|:\|\|\|<br>3' UGAGUUCAUGGUCCACGAC 5' |

Figure 2W

| | |
|---|---|
| SEQ ID 342 | 5' CUCAAGUACCAGGUGCUGG 3'<br>\|\|\|:\|\|\|:\|\|\|:\|\|\|\|\|\|\|<br>3' GAGUUCAUGGUCCACGACC 5' |
| SEQ ID 343 | 5' GUACCAGGUGCUGGAUGGA 3'<br>\|\|\|:\|\|\|:\|\|\|:\|\|\|\|\|\|\|<br>3' CAUGGUCCACGACCUACCU 5' |
| SEQ ID 344 | 5' AUGUACCCGCCCUCGGUAG 3'<br>\|\|\|:\|\|\|:\|\|\|:\|\|\|\|\|\|\|<br>3' UACAUGGGCGGGAGCCAUC 5' |
| SEQ ID 345 | 5' UGUACCCGCCCUCGGUAGA 3'<br>\|\|\|:\|\|\|:\|\|\|:\|\|\|\|\|\|\|<br>3' ACAUGGGCGGGAGCCAUCU 5' |
| SEQ ID 346 | 5' GAGGCGCCUGUGUUGAUGC 3'<br>\|\|\|:\|\|\|:\|\|\|:\|\|\|\|\|\|\|<br>3' CUCCGCGGACACAACUACG 5' |
| SEQ ID 347 | 5' CCGUGUGUGACCUGCUG 3'<br>\|\|\|:\|\|\|:\|\|\|:\|\|\|\|\|\|\|<br>3' GGCACACACACUGGACGAC 5' |
| SEQ ID 348 | 5' GAUUGUCAUCGAGGAGUAC 3'<br>\|\|\|:\|\|\|:\|\|\|:\|\|\|\|\|\|\|<br>3' CUAACAGUAGCUCCUCAUG 5' |
| SEQ ID 349 | 5' AUUUGACCCAGAGCUGCUG 3'<br>\|\|\|:\|\|\|:\|\|\|:\|\|\|\|\|\|\|<br>3' UAAACUGGGUCUCGACGAC 5' |
| SEQ ID 350 | 5' UUUGACCCAGAGCUGCUGU 3'<br>\|\|\|:\|\|\|:\|\|\|:\|\|\|\|\|\|\|<br>3' AAACUGGGUCUCGACGACA 5' |
| SEQ ID 351 | 5' UACCGCAACCGCAUUGCCA 3'<br>\|\|\|:\|\|\|:\|\|\|:\|\|\|\|\|\|\|<br>3' AUGGCGUUGGCGUAACGGU 5' |
| SEQ ID 352 | 5' CCCCAUUGCCAUGGACUUC 3'<br>\|\|\|:\|\|\|:\|\|\|:\|\|\|\|\|\|\|<br>3' GGCGUAACGGUACCUCAAG 5' |
| SEQ ID 353 | 5' CCAUCUCUACCACUGGCAC 3'<br>\|\|\|:\|\|\|:\|\|\|:\|\|\|\|\|\|\|<br>3' GGUAGAGAUGGUGACCGUG 5' |
| SEQ ID 354 | 5' CACCUCCAUGUUGGUGGAC 3'<br>\|\|\|:\|\|\|:\|\|\|:\|\|\|\|\|\|\|<br>3' GUCCAGGUACAACCACCUG 5' |
| SEQ ID 355 | 5' CAUGGACCACCACAUCCUG 3'<br>\|\|\|:\|\|\|:\|\|\|:\|\|\|\|\|\|\|<br>3' GUACCUGGUGGUGUAGGAC 5' |
| SEQ ID 356 | 5' UGAGUACCGCAAGAGGUUU 3'<br>\|\|\|:\|\|\|:\|\|\|:\|\|\|\|\|\|\|<br>3' ACUCAUGGCGUUCUCCAAA 5' |
| SEQ ID 357 | 5' GAGGUUUGGCAUGAAACCC 3'<br>\|\|\|:\|\|\|:\|\|\|:\|\|\|\|\|\|\|<br>3' CUCCAAACCGUACUUUGGG 5' |

Figure 2X

| | |
|---|---|
| SEQ ID 358 | 5' ACCCUACACCUCCUUCCAG 3'<br>\|\|\|:\|\|\|:\|\|\|:\|\|\|\|\|\|\|<br>3' UGGGAUGUGGAGGAAGGUC 5' |
| SEQ ID 359 | 5' CCCUACACCUCCUUCCAGG 3'<br>\|\|\|:\|\|\|:\|\|\|:\|\|\|\|\|\|\|<br>3' GGGAUGUGGAGGAAGGUCC 5' |
| SEQ ID 360 | 5' GGAGAUGGCAGCAGAGUUG 3'<br>\|\|\|:\|\|\|:\|\|\|:\|\|\|\|\|\|\|<br>3' CCUCUACCGUCGUCUCAAC 5' |
| SEQ ID 361 | 5' UUGUAUGGAGACAUUGAUG 3'<br>\|\|\|:\|\|\|:\|\|\|:\|\|\|\|\|\|\|<br>3' AACAUACCUCUGUAACUAC 5' |
| SEQ ID 362 | 5' AAGUGCCAUCCAAACUCUA 3'<br>\|\|\|:\|\|\|:\|\|\|:\|\|\|\|\|\|\|<br>3' UUCACGGUAGGUUUGAGAU 5' |
| SEQ ID 363 | 5' AGUGCCAUCCAAACUCUAU 3'<br>\|\|\|:\|\|\|:\|\|\|:\|\|\|\|\|\|\|<br>3' UCACGGUAGGUUUGAGAUA 5' |
| SEQ ID 364 | 5' GUGCCAUCCAAACUCUAUC 3'<br>\|\|\|:\|\|\|:\|\|\|:\|\|\|\|\|\|\|<br>3' CACGGUAGGUUUGAGAUAG 5' |
| SEQ ID 365 | 5' ACUCUAUCUUUGGGGAGAG 3'<br>\|\|\|:\|\|\|:\|\|\|:\|\|\|\|\|\|\|<br>3' UGAGAUAGAAACCCCUCUC 5' |
| SEQ ID 366 | 5' CUCUAUCUUUGGGGAGAGU 3'<br>\|\|\|:\|\|\|:\|\|\|:\|\|\|\|\|\|\|<br>3' GAGAUAGAAACCCCUCUCA 5' |
| SEQ ID 367 | 5' GGGUCUCCUAGGGAAUCCC 3'<br>\|\|\|:\|\|\|:\|\|\|:\|\|\|\|\|\|\|<br>3' CCCAGAGGAUCCCUUAGGG 5' |
| SEQ ID 368 | 5' UCCCAUCUGUUCUCCGGAG 3'<br>\|\|\|:\|\|\|:\|\|\|:\|\|\|\|\|\|\|<br>3' AGGGUAGACAAGAGGCCUC 5' |
| SEQ ID 369 | 5' CAUUGUCAAGACGGCCACA 3'<br>\|\|\|:\|\|\|:\|\|\|:\|\|\|\|\|\|\|<br>3' GUAACAGUUCUGCCGGUGU 5' |
| SEQ ID 370 | 5' GACGGCCACACUGAAGAAG 3'<br>\|\|\|:\|\|\|:\|\|\|:\|\|\|\|\|\|\|<br>3' CUGCCGGUGUGACUUCUUC 5' |
| SEQ ID 371 | 5' GAAGCUGGUCUGCCUCAAC 3'<br>\|\|\|:\|\|\|:\|\|\|:\|\|\|\|\|\|\|<br>3' CUUCGACCAGACGGAGUUG 5' |
| SEQ ID 372 | 5' GCUGGUCUGCCUCAACACC 3'<br>\|\|\|:\|\|\|:\|\|\|:\|\|\|\|\|\|\|<br>3' CGACCAGACGGAGUUGUGG 5' |
| SEQ ID 373 | 5' CACCAAGACCUGUCCCUAC 3'<br>\|\|\|:\|\|\|:\|\|\|:\|\|\|\|\|\|\|<br>3' GUGGUUCUGGACAGGGAUG 5' |

Figure 2Y

| | |
|---|---|
| SEQ ID 374 | 5' GACCUGUCCCUACGUUUCC 3'<br>\|\|\|\|\|\|\|\|\|::\|\|\|\|\|\|\|\|<br>3' CUGGACAGGGAUGCAAAGG 5' |
| **PTGS2** | |
| SEQ ID 375 | 5' AUCCUUGCUGUUCCCACCC 3'<br>\|\|\|\|\|\|\|\|\|::\|\|\|\|\|\|\|\|<br>3' UAGGAACGACAAGGGUGGG 5' |
| SEQ ID 376 | 5' UCCUUGCUGUUCCCACCCA 3'<br>\|\|\|\|\|\|\|\|\|::\|\|\|\|\|\|\|\|<br>3' AGGAACGACAAGGGUGGGU 5' |
| SEQ ID 377 | 5' AACCGAGGUGUAUGUAUGA 3'<br>\|\|\|\|\|\|\|\|\|::\|\|\|\|\|\|\|\|<br>3' UUGGCUCCACAUACAUACU 5' |
| SEQ ID 378 | 5' ACCGAGGUGUAUGUAUGAG 3'<br>\|\|\|\|\|\|\|\|\|::\|\|\|\|\|\|\|\|<br>3' UGGCUCCACAUACAUACUC 5' |
| SEQ ID 379 | 5' CCGAGGUGUAUGUAUGAGU 3'<br>\|\|\|\|\|\|\|\|\|::\|\|\|\|\|\|\|\|<br>3' GGCUCCACAUACAUACUCA 5' |
| SEQ ID 380 | 5' GUGCGAUUGUACCCGGACA 3'<br>\|\|\|\|\|\|\|\|\|::\|\|\|\|\|\|\|\|<br>3' CACGCUAACAUGGGCCUGU 5' |
| SEQ ID 381 | 5' AACUGCUCAACACCGGAAU 3'<br>\|\|\|\|\|\|\|\|\|::\|\|\|\|\|\|\|\|<br>3' UUGACGAGUUGUGGCCUUA 5' |
| SEQ ID 382 | 5' ACUGCUCAACACCGGAAUU 3'<br>\|\|\|\|\|\|\|\|\|::\|\|\|\|\|\|\|\|<br>3' UGACGAGUUGUGGCCUUAA 5' |
| SEQ ID 383 | 5' CUGCUCAACACCGGAAUUU 3'<br>\|\|\|\|\|\|\|\|\|::\|\|\|\|\|\|\|\|<br>3' GACGAGUUGUGGCCUUAAA 5' |
| SEQ ID 384 | 5' CACCGGAAUUUUUGACAAG 3'<br>\|\|\|\|\|\|\|\|\|::\|\|\|\|\|\|\|\|<br>3' GUGGCCUUAAAAACUGUUC 5' |
| SEQ ID 385 | 5' UUAUUUCUGAAACCCACUC 3'<br>\|\|\|\|\|\|\|\|\|::\|\|\|\|\|\|\|\|<br>3' AAUAAAGACUUUGGGUGAG 5' |
| SEQ ID 386 | 5' ACCCACUCCAAACACAGUG 3'<br>\|\|\|\|\|\|\|\|\|::\|\|\|\|\|\|\|\|<br>3' UGGGUGAGGUUUGUGUCAC 5' |
| SEQ ID 387 | 5' CCCACUCCAAACACAGUGC 3'<br>\|\|\|\|\|\|\|\|\|::\|\|\|\|\|\|\|\|<br>3' GGGUGAGGUUUGUGUCACG 5' |
| SEQ ID 388 | 5' ACACAGUGCACUACAUACU 3'<br>\|\|\|\|\|\|\|\|\|::\|\|\|\|\|\|\|\|<br>3' UGUGUCACGUGAUGUAUGA 5' |

Figure 2Z

| | |
|---|---|
| SEQ ID 389 | 5' CACAGUGCACUACAUACUU 3'<br>\|\|\|\|\|\|\|:\|:\|\|\|\|\|\|\|\|\|<br>3' GUGUCACGUGAUGUAUGAA 5' |
| SEQ ID 390 | 5' GGGAUUUUGGAACGUUGUG 3'<br>\|\|\|\|\|\|\|:\|:\|\|\|\|\|\|\|\|\|<br>3' CCCUAAAACCUUGCAACAC 5' |
| SEQ ID 391 | 5' CGUUGUGAAUAACAUUCCC 3'<br>\|\|\|\|\|\|\|:\|:\|\|\|\|\|\|\|\|\|<br>3' GCAACACUUAUUGUAAGGG 5' |
| SEQ ID 392 | 5' UAACAUUCCCUUCCUUCGA 3'<br>\|\|\|\|\|\|\|:\|:\|\|\|\|\|\|\|\|\|<br>3' AUUGUAAGGGAAGGAAGCU 5' |
| SEQ ID 393 | 5' CAUUCCCUUCCUUCGAAAU 3'<br>\|\|\|\|\|\|\|:\|:\|\|\|\|\|\|\|\|\|<br>3' GUAAGGGAAGGAAGCUUUA 5' |
| SEQ ID 394 | 5' CUUACAAUGCUGACUAUGG 3'<br>\|\|\|\|\|\|\|:\|:\|\|\|\|\|\|\|\|\|<br>3' GAAUGUUACGACUGAUACC 5' |
| SEQ ID 395 | 5' UGCUGACUAUGGCUACAAA 3'<br>\|\|\|\|\|\|\|:\|:\|\|\|\|\|\|\|\|\|<br>3' ACGACUGAUACCGAUGUUU 5' |
| SEQ ID 396 | 5' AAGCUGGGAAGCCUUCUCU 3'<br>\|\|\|\|\|\|\|:\|:\|\|\|\|\|\|\|\|\|<br>3' UUCGACCCUUCGGAAGAGA 5' |
| SEQ ID 397 | 5' AGCUGGGAAGCCUUCUCUA 3'<br>\|\|\|\|\|\|\|:\|:\|\|\|\|\|\|\|\|\|<br>3' UCGACCCUUCGGAAGAGAU 5' |
| SEQ ID 398 | 5' GCUGGGAAGCCUUCUCUAA 3'<br>\|\|\|\|\|\|\|:\|:\|\|\|\|\|\|\|\|\|<br>3' CGACCCUUCGGAAGAGAUU 5' |
| SEQ ID 399 | 5' GCCUUCUCUAACCUCUCCU 3'<br>\|\|\|\|\|\|\|:\|:\|\|\|\|\|\|\|\|\|<br>3' CGGAAGAGAUUGGAGAGGA 5' |
| SEQ ID 400 | 5' CCUCUCCUAUUAUACUAGA 3'<br>\|\|\|\|\|\|\|:\|:\|\|\|\|\|\|\|\|\|<br>3' GGAGAGGAUAAUAUGAUCU 5' |
| SEQ ID 401 | 5' AGGUAAAAAGCAGCUUCCU 3'<br>\|\|\|\|\|\|\|:\|:\|\|\|\|\|\|\|\|\|<br>3' UCCAUUUUUCGUCGAAGGA 5' |
| SEQ ID 402 | 5' GGUAAAAAGCAGCUUCCUG 3'<br>\|\|\|\|\|\|\|:\|:\|\|\|\|\|\|\|\|\|<br>3' CCAUUUUUCGUCGAAGGAC 5' |
| SEQ ID 403 | 5' AAAGCAGCUUCCUGAUUCA 3'<br>\|\|\|\|\|\|\|:\|:\|\|\|\|\|\|\|\|\|<br>3' UUUCGUCGAAGGACUAAGU 5' |
| SEQ ID 404 | 5' AAGCAGCUUCCUGAUUCAA 3'<br>\|\|\|\|\|\|\|:\|:\|\|\|\|\|\|\|\|\|<br>3' UUCGUCGAAGGACUAAGUU 5' |

Figure 2AA

| | |
|---|---|
| SEQ ID 405 | 5' AGCAGCUUCCUGAUUCAAA 3'<br>\|\|\|\|\|::\|\|\|\|\|\|\|\|\|\|::<br>3' UCGUCGAAGGACUAAGUUU 5' |
| SEQ ID 406 | 5' GCAGCUUCCUGAUUCAAAU 3'<br>\|\|\|\|\|::\|\|\|\|\|\|\|\|\|\|::<br>3' CGUCGAAGGACUAAGUUUA 5' |
| SEQ ID 407 | 5' GAAGAAAGUUCAUCCCUGA 3'<br>\|\|\|\|\|::\|\|\|\|\|\|\|\|\|\|::<br>3' CUUCUUUCAAGUAGGGACU 5' |
| SEQ ID 408 | 5' GAAAGUUCAUCCCUGAUCC 3'<br>\|\|\|\|\|::\|\|\|\|\|\|\|\|\|\|::<br>3' CUUUCAAGUAGGGACUAGG 5' |
| SEQ ID 409 | 5' AGUUCAUCCCUGAUCCCCA 3'<br>\|\|\|\|\|::\|\|\|\|\|\|\|\|\|\|::<br>3' UCAAGUAGGGACUAGGGGU 5' |
| SEQ ID 410 | 5' GUUCAUCCCUGAUCCCCAG 3'<br>\|\|\|\|\|::\|\|\|\|\|\|\|\|\|\|::<br>3' CAAGUAGGGACUAGGGGUC 5' |
| SEQ ID 411 | 5' GACAGAUCAUAAGCGAGGG 3'<br>\|\|\|\|\|::\|\|\|\|\|\|\|\|\|\|::<br>3' CUGUCUAGUAUUCGCUCCC 5' |
| SEQ ID 412 | 5' ACUCUGGCUAGACAGCGUA 3'<br>\|\|\|\|\|::\|\|\|\|\|\|\|\|\|\|::<br>3' UGAGACCGAUCUGUCGCAU 5' |
| SEQ ID 413 | 5' CUCUGGCUAGACAGCGUAA 3'<br>\|\|\|\|\|::\|\|\|\|\|\|\|\|\|\|::<br>3' GAGACCGAUCUGUCGCAUU 5' |
| SEQ ID 414 | 5' ACUGCGCCUUUUCAAGGAU 3'<br>\|\|\|\|\|::\|\|\|\|\|\|\|\|\|\|::<br>3' UGACGCGGAAAAGUUCCUA 5' |
| SEQ ID 415 | 5' CUGCGCCUUUUCAAGGAUG 3'<br>\|\|\|\|\|::\|\|\|\|\|\|\|\|\|\|::<br>3' GACGCGGAAAAGUUCCUAC 5' |
| SEQ ID 416 | 5' UUGAUGCAGAGAUGUAUCC 3'<br>\|\|\|\|\|::\|\|\|\|\|\|\|\|\|\|::<br>3' AACUACGUCUCUACAUAGG 5' |
| SEQ ID 417 | 5' AGAUACUCAGGCAGAGAUG 3'<br>\|\|\|\|\|::\|\|\|\|\|\|\|\|\|\|::<br>3' UCUAUGAGUCCGUCUCUAC 5' |
| SEQ ID 418 | 5' GAUACUCAGGCAGAGAUGA 3'<br>\|\|\|\|\|::\|\|\|\|\|\|\|\|\|\|::<br>3' CUAUGAGUCCGUCUCUACU 5' |
| SEQ ID 419 | 5' GUCCCUGAGCAUCUACGGU 3'<br>\|\|\|\|\|::\|\|\|\|\|\|\|\|\|\|::<br>3' CAGGGACUCGUAGAUGCCA 5' |
| SEQ ID 420 | 5' UCUGGCUGCGGGAACACAA 3'<br>\|\|\|\|\|::\|\|\|\|\|\|\|\|\|\|::<br>3' AGACCGACGCCCUUGUGUU 5' |

Figure 2BB

| | |
|---|---|
| SEQ ID 421 | 5' CACAACAGAGUAUGCGAUG 3'<br>:||:|||||||||||||:||<br>3' GUGUUGUCUCAUACGCUAC 5' |
| SEQ ID 422 | 5' CAGAGUAUGCGAUGUGCUU 3'<br>:||:|||||||||||||:||<br>3' GUCUCAUACGCUACACGAA 5' |
| SEQ ID 423 | 5' ACAGGAGCAUCCUGAAUGG 3'<br>:||:|||||||||||||:||<br>3' UGUCCUCGUAGGACUUACC 5' |
| SEQ ID 424 | 5' CAGGAGCAUCCUGAAUGGG 3'<br>:||:|||||||||||||:||<br>3' GUCCUCGUAGGACUUACCC 5' |
| SEQ ID 425 | 5' UGGGGUGAUGAGCAGUUGU 3'<br>:||:|||||||||||||:||<br>3' ACCCCACUACUCGUCAACA 5' |
| SEQ ID 426 | 5' GCAGGCUAAUACUCAUAGG 3'<br>:||:|||||||||||||:||<br>3' CGUCCGAUUAUGACUAUCC 5' |
| SEQ ID 427 | 5' UACUGAUAGGAGAGACUAU 3'<br>:||:|||||||||||||:||<br>3' AUGACUAUCCUCUCUGAUA 5' |
| SEQ ID 428 | 5' GAUUAUGUGCAACACUUGA 3'<br>:||:|||||||||||||:||<br>3' CUAAUACACGUUGUGAACU 5' |
| SEQ ID 429 | 5' CACUUGAGUGGCUAUCACU 3'<br>:||:|||||||||||||:||<br>3' GUGAACUCACCGAUAGUGA 5' |
| SEQ ID 430 | 5' ACUGAAAUUUGACCCAGAA 3'<br>:||:|||||||||||||:||<br>3' UGACUUUAAACUGGGUCUU 5' |
| SEQ ID 431 | 5' CUGAAAUUUGACCCAGAAC 3'<br>:||:|||||||||||||:||<br>3' GACUUUAAACUGGGUCUUG 5' |
| SEQ ID 432 | 5' AUUUGACCCAGAACUACUU 3'<br>:||:|||||||||||||:||<br>3' UAAACUGGGUCUUGAUGAA 5' |
| SEQ ID 433 | 5' UUUGACCCAGAACUACUUU 3'<br>:||:|||||||||||||:||<br>3' AAACUGGGUCUUGAUGAAA 5' |
| SEQ ID 434 | 5' CAAACAAUUCCAGUACCAA 3'<br>:||:|||||||||||||:||<br>3' GUUUGUUAAGGUCAUGGUU 5' |
| SEQ ID 435 | 5' CAAUUCCAGUACCAAAAUC 3'<br>:||:|||||||||||||:||<br>3' GUUAAGGUCAUGGUUUUAG 5' |
| SEQ ID 436 | 5' UUCCAGUACCAAAAUCGUA 3'<br>:||:|||||||||||||:||<br>3' AAGGUCAUGGUUUUAGCAU 5' |

Figure 2CC

| | |
|---|---|
| SEQ ID 437 | 5' AAUCGUAUUGCUGCUGAAU 3'<br>|:||:||||||||:||||:|<br>3' UUAGCAUAACGACGACUUA 5' |
| SEQ ID 438 | 5' AUCGUAUUGCUGCUGAAUU 3'<br>|:||:||||||||:||||:|<br>3' UAGCAUAACGACGACUUAA 5' |
| SEQ ID 439 | 5' UCGUAUUGCUGCUGAAUUU 3'<br>|:||:||||||||:||||:|<br>3' AGCAUAACGACGACUUAAA 5' |
| SEQ ID 440 | 5' UUUAACACCCUCUAUCACU 3'<br>|:||:||||||||:||||:|<br>3' AAAUUGUGGGAGAUAGUGA 5' |
| SEQ ID 441 | 5' CACCCUCUAUCACUGGCAU 3'<br>|:||:||||||||:||||:|<br>3' GUGGGAGAUAGUGACCGUA 5' |
| SEQ ID 442 | 5' CAACUCUAUAUUGCUGGAA 3'<br>|:||:||||||||:||||:|<br>3' GUUGAGAUAUAACGACCUU 5' |
| SEQ ID 443 | 5' CUCUAUAUUGCUGGAACAU 3'<br>|:||:||||||||:||||:|<br>3' GAGAUAUAACGACCUUGUA 5' |
| SEQ ID 444 | 5' CAUGGAAUUACCCAGUUUG 3'<br>|:||:||||||||:||||:|<br>3' GUACCUUAAUGGGUCAAAC 5' |
| SEQ ID 445 | 5' UUACCCAGUUUGUUGAAUC 3'<br>|:||:||||||||:||||:|<br>3' AAUGGGUCAAACAACUUAG 5' |
| SEQ ID 446 | 5' UCAUUCACCAGGCAAAUUG 3'<br>|:||:||||||||:||||:|<br>3' AGUAAGUGGUCCGUUUAAC 5' |
| SEQ ID 447 | 5' AUUGCUGGCAGGGUUGCUG 3'<br>|:||:||||||||:||||:|<br>3' UAACGACCGUCCCAACGAC 5' |
| SEQ ID 448 | 5' UUGCUGGCAGGGUUGCUGG 3'<br>|:||:||||||||:||||:|<br>3' AACGACCGUCCCAACGACC 5' |
| SEQ ID 449 | 5' UGUUCCACCCGCAGUACAG 3'<br>|:||:||||||||:||||:|<br>3' ACAAGGUGGGCGUCAUGUC 5' |
| SEQ ID 450 | 5' AGUAUCACAGGCUUCCAUU 3'<br>|:||:||||||||:||||:|<br>3' UCAUAGUGUCCGAAGGUAA 5' |
| SEQ ID 451 | 5' GUAUCACAGGCUUCCAUUG 3'<br>|:||:||||||||:||||:|<br>3' CAUAGUGUCCGAAGGUAAC 5' |
| SEQ ID 452 | 5' UCAGUACCGCAAACGCUUU 3'<br>|:||:||||||||:||||:|<br>3' ACUCAUGGCGUUUGCGAAA 5' |

Figure 2DD

| | |
|---|---|
| SEQ ID 453 | 5' ACGCUUUAUGCUGAAGCCC 3'<br>||:||:||:||||||||:||<br>3' UGCGAAAUACGACUUCGGG 5' |
| SEQ ID 454 | 5' CGCUUUAUGCUGAAGCCCU 3'<br>||:||:||:||||||||:||<br>3' GCGAAAUACGACUUCGGGA 5' |
| SEQ ID 455 | 5' GCCCUAUGAAUCAUUUGAA 3'<br>||:||:||:||||||||:||<br>3' CGGGAUACUUAGUAAACUU 5' |
| SEQ ID 456 | 5' GAACUUACAGGAGAAAAGG 3'<br>||:||:||:||||||||:||<br>3' CUUGAAUGUCCUCUUUUCC 5' |
| SEQ ID 457 | 5' CUUACAGGAGAAAAGGAAA 3'<br>||:||:||:||||||||:||<br>3' GAAUGUCCUCUUUUCCUUU 5' |
| SEQ ID 458 | 5' AAGGAAAUGUCUGCAGAGU 3'<br>||:||:||:||||||||:||<br>3' UUCCUUUACAGACGUCUCA 5' |
| SEQ ID 459 | 5' AGGAAAUGUCUGCAGAGUU 3'<br>||:||:||:||||||||:||<br>3' UCCUUUACAGACGUCUCAA 5' |
| SEQ ID 460 | 5' GGAAAUGUCUGCAGAGUUG 3'<br>||:||:||:||||||||:||<br>3' CCUUUACAGACGUCUCAAC 5' |
| SEQ ID 461 | 5' AUGUCUGCAGAGUUGGAAG 3'<br>||:||:||:||||||||:||<br>3' UACAGACGUCUCAACCUUC 5' |
| SEQ ID 462 | 5' UGUCUGCAGAGUUGGAAGC 3'<br>||:||:||:||||||||:||<br>3' ACAGACGUCUCAACCUUCG 5' |
| SEQ ID 463 | 5' GCACUCUAUGGUGACAUCG 3'<br>||:||:||:||||||||:||<br>3' CGUGAGAUACCACUGUAGC 5' |
| SEQ ID 464 | 5' AAGCCUCGGCCAGAUGCCA 3'<br>||:||:||:||||||||:||<br>3' UUCGGAGCCGGUCUACGGU 5' |
| SEQ ID 465 | 5' AGCCUCGGCCAGAUGCCAU 3'<br>||:||:||:||||||||:||<br>3' UCGGAGCCGGUCUACGGUA 5' |
| SEQ ID 466 | 5' ACCAUGGUAGAAGUUGGAG 3'<br>||:||:||:||||||||:||<br>3' UGGUACCAUCUUCAACCUC 5' |
| SEQ ID 467 | 5' CCAUGGUAGAAGUUGGAGC 3'<br>||:||:||:||||||||:||<br>3' GGUACCAUCUUCAACCUCG 5' |
| SEQ ID 468 | 5' GUUGGACCACCAUUCUCCU 3'<br>||:||:||:||||||||:||<br>3' CAACCUGGUGGUAAGAGGA 5' |

Figure 2EE

| | |
|---|---|
| SEQ ID 469 | 5' AGGACUUAUGGGUAAUGUU 3'<br>\|\|:\|\|:\|\|\|\|\|\|\|\|\|\|:\|\|\|<br>3' UCCUGAAUACCCAUUACAA 5' |
| SEQ ID 470 | 5' GGACUUAUGGGUAAUGUUA 3'<br>\|\|:\|\|:\|\|\|\|\|\|\|\|\|\|:\|\|\|<br>3' CCUGAAUACCCAUUACAAU 5' |
| SEQ ID 471 | 5' UGUUAUAUGUUCUCCUGCC 3'<br>\|\|:\|\|:\|\|\|\|\|\|\|\|\|\|:\|\|\|<br>3' ACAAUAUACAAGAGGACGG 5' |
| SEQ ID 472 | 5' GCCAAGCACUUUUGGUGGA 3'<br>\|\|:\|\|:\|\|\|\|\|\|\|\|\|\|:\|\|\|<br>3' CCGUUCGUGAAAACCACCU 5' |
| SEQ ID 473 | 5' GCACUUUUGGUGGAGAAGU 3'<br>\|\|:\|\|:\|\|\|\|\|\|\|\|\|\|:\|\|\|<br>3' CGUGAAAACCACCUCUUCA 5' |
| SEQ ID 474 | 5' GUGGGUUUUCAAAUCAUCA 3'<br>\|\|:\|\|:\|\|\|\|\|\|\|\|\|\|:\|\|\|<br>3' CACCCAAAAGUUUAGUAGU 5' |
| SEQ ID 475 | 5' AUCAUCAACACUGCCUCAA 3'<br>\|\|:\|\|:\|\|\|\|\|\|\|\|\|\|:\|\|\|<br>3' UAGUAGUUGUGACGGAGUU 5' |
| SEQ ID 476 | 5' UCAUCAACACUGCCUCAAU 3'<br>\|\|:\|\|:\|\|\|\|\|\|\|\|\|\|:\|\|\|<br>3' AGUAGUUGUGACGGAGUUA 5' |
| SEQ ID 477 | 5' CACUGCCUCAAUUCAGUCU 3'<br>\|\|:\|\|:\|\|\|\|\|\|\|\|\|\|:\|\|\|<br>3' GUGACGGAGUUAAGUCAGA 5' |
| SEQ ID 478 | 5' UUCAGUCUCUCAUCUGCAA 3'<br>\|\|:\|\|:\|\|\|\|\|\|\|\|\|\|:\|\|\|<br>3' AAGUCAGAGAGUAGACGUU 5' |
| SEQ ID 479 | 5' UAACGUGAAGGGCUGUCCC 3'<br>\|\|:\|\|:\|\|\|\|\|\|\|\|\|\|:\|\|\|<br>3' AUUGCACUUCCCGACAGGG 5' |
| SEQ ID 480 | 5' CGUGAAGGGCUGUCCCUUU 3'<br>\|\|:\|\|:\|\|\|\|\|\|\|\|\|\|:\|\|\|<br>3' GCACUUCCCGACAGGGAAA 5' |
| SEQ ID 481 | 5' GGGCUGUCCCUUUACUUCA 3'<br>\|\|:\|\|:\|\|\|\|\|\|\|\|\|\|:\|\|\|<br>3' CCCGACAGGGAAAUGAAGU 5' |
| SEQ ID 482 | 5' AACAGUCACCAUCAAUGCA 3'<br>\|\|:\|\|:\|\|\|\|\|\|\|\|\|\|:\|\|\|<br>3' UUGUCAGUGGUAGUUACGU 5' |
| SEQ ID 483 | 5' ACAGUCACCAUCAAUGCAA 3'<br>\|\|:\|\|:\|\|\|\|\|\|\|\|\|\|:\|\|\|<br>3' UGUCAGUGGUAGUUACGUU 5' |
| SEQ ID 484 | 5' CAGUCACCAUCAAUGCAAG 3'<br>\|\|:\|\|:\|\|\|\|\|\|\|\|\|\|:\|\|\|<br>3' GUCAGUGGUAGUUACGUUC 5' |

Figure 2FF

| | |
|---|---|
| SEQ ID 485 | 5' UGCAAGUUCUUCCCGCUCC 3'<br>\|\|:\|\|\|\|\|\|:\|\|:\|\|\|:\|\|<br>3' ACGUUCAAGAAGGGCGAGG 5' |
| SEQ ID 486 | 5' GUUCUUCCCGCUCCGGACU 3'<br>\|\|:\|\|\|\|\|\|:\|\|:\|\|\|:\|\|<br>3' CAAGAAGGGCGAGGCCUGA 5' |
| SEQ ID 487 | 5' UCCCACAGUACUACUAAAA 3'<br>\|\|:\|\|\|\|\|\|:\|\|:\|\|\|:\|\|<br>3' AGGGUGUCAUGAUGAUUUU 5' |
| SEQ ID 488 | 5' AAGAACGUUCGACUGAACU 3'<br>\|\|:\|\|\|\|\|\|:\|\|:\|\|\|:\|\|<br>3' UUCUUGCAAGCUGACUUGA 5' |
| SEQ ID 489 | 5' AGAACGUUCGACUGAACUG 3'<br>\|\|:\|\|\|\|\|\|:\|\|:\|\|\|:\|\|<br>3' UCUUGCAAGCUGACUUGAC 5' |
| SEQ ID 490 | 5' GAACGUUCGACUGAACUGU 3'<br>\|\|:\|\|\|\|\|\|:\|\|:\|\|\|:\|\|<br>3' CUUGCAAGCUGACUUGACA 5' |
| SEQ ID 491 | 5' CACAACAGAGUAUGCGACG 3'<br>\|\|:\|\|\|\|\|\|:\|\|:\|\|\|:\|\|<br>3' GUGUUGUCUCAUACGCUGC 5' |

| CA12 | |
|---|---|
| SEQ ID 492 | 5' AGGAACAGCCUUCCAGCCC 3'<br>\|\|:\|\|\|\|\|\|:\|\|:\|\|\|:\|\|<br>3' UCCUUGUCGGAAGGUCGGG 5' |
| SEQ ID 493 | 5' CGGUUCCAAGUGGACUUAU 3'<br>\|\|:\|\|\|\|\|\|:\|\|:\|\|\|:\|\|<br>3' GCCAAGGUUCACCUGAAUA 5' |
| SEQ ID 494 | 5' GUGGACUUAUUUUGGUCCU 3'<br>\|\|:\|\|\|\|\|\|:\|\|:\|\|\|:\|\|<br>3' CACCUGAAUAAAACCAGGA 5' |
| SEQ ID 495 | 5' UAGCUGGUCCAAGAAGUAC 3'<br>\|\|:\|\|\|\|\|\|:\|\|:\|\|\|:\|\|<br>3' AUCGACCAGGUUCUUCAUG 5' |
| SEQ ID 496 | 5' GAAGUACCCGUCGUGUGGG 3'<br>\|\|:\|\|\|\|\|\|:\|\|:\|\|\|:\|\|<br>3' CUUCAUGGGCAGCACACCC 5' |
| SEQ ID 497 | 5' GGCUACAAUCUGUCUGCCA 3'<br>\|\|:\|\|\|\|\|\|:\|\|:\|\|\|:\|\|<br>3' CCGAUGUUAGACAGACGGU 5' |
| SEQ ID 498 | 5' UCUGUCUGCCAACAAGCAG 3'<br>\|\|:\|\|\|\|\|\|:\|\|:\|\|\|:\|\|<br>3' AGACAGACGGUUGUUCGUC 5' |
| SEQ ID 499 | 5' CAAGCAGUUUCUCCUGACC 3'<br>\|\|:\|\|\|\|\|\|:\|\|:\|\|\|:\|\|<br>3' GUUCGUCAAAGAGGACUGG 5' |

Figure 2GG

| | |
|---|---|
| SEQ ID 500 | 5' GCAGUUUCUCCUGACCAAC 3'<br>:\|\|\|\|\|\|\|\|\|:\|\|\|\|\|\|\|\|<br>3' CGUCAAAGAGGACUGGUUG 5' |
| SEQ ID 501 | 5' CAAUGGCCAUUCAGUGAAG 3'<br>:\|\|\|\|\|\|\|\|\|:\|\|\|\|\|\|\|\|<br>3' GUUACCGGUAAGUCACUUC 5' |
| SEQ ID 502 | 5' UGGCCAUUCAGUGAAGCUG 3'<br>:\|\|\|\|\|\|\|\|\|:\|\|\|\|\|\|\|\|<br>3' ACCGGUAAGUCACUUCGAC 5' |
| SEQ ID 503 | 5' CUCAGACCUUUAUCCUGAC 3'<br>:\|\|\|\|\|\|\|\|\|:\|\|\|\|\|\|\|\|<br>3' GAGUCUGGAAAUAGGACUG 5' |
| SEQ ID 504 | 5' CAAGUCAGAAGGCCUCGCU 3'<br>:\|\|\|\|\|\|\|\|\|:\|\|\|\|\|\|\|\|<br>3' GUUCAGUCUUCCGGAGCGA 5' |
| SEQ ID 505 | 5' GUCAGAAGGCCUCGCUGUC 3'<br>:\|\|\|\|\|\|\|\|\|:\|\|\|\|\|\|\|\|<br>3' CAGUCUUCCGGAGCGACAG 5' |
| SEQ ID 506 | 5' UCCGUCCUAUGACAAGAUC 3'<br>:\|\|\|\|\|\|\|\|\|:\|\|\|\|\|\|\|\|<br>3' AGGCAGGAUACUGUUCUAG 5' |
| SEQ ID 507 | 5' GAUCUUCAGUCACCUUCAA 3'<br>:\|\|\|\|\|\|\|\|\|:\|\|\|\|\|\|\|\|<br>3' CUAGAAGUCAGUGGAAGUU 5' |
| SEQ ID 508 | 5' CAUGUAAAGUACAAAGGCC 3'<br>:\|\|\|\|\|\|\|\|\|:\|\|\|\|\|\|\|\|<br>3' GUACAUUUCAUGUUUCCGG 5' |
| SEQ ID 509 | 5' AGUACAAAGGCCAGGAAGC 3'<br>:\|\|\|\|\|\|\|\|\|:\|\|\|\|\|\|\|\|<br>3' UCAUGUUUCCGGUCCUUCG 5' |
| SEQ ID 510 | 5' GUACAAAGGCCAGGAAGCA 3'<br>:\|\|\|\|\|\|\|\|\|:\|\|\|\|\|\|\|\|<br>3' CAUGUUUCCGGUCCUUCGU 5' |
| SEQ ID 511 | 5' AGGCCAGGAAGCAUUCGUC 3'<br>:\|\|\|\|\|\|\|\|\|:\|\|\|\|\|\|\|\|<br>3' UCCGGUCCUUCGUAAGCAG 5' |
| SEQ ID 512 | 5' GGCCAGGAAGCAUUCGUCC 3'<br>:\|\|\|\|\|\|\|\|\|:\|\|\|\|\|\|\|\|<br>3' CCGGUCCUUCGUAAGCAGG 5' |
| SEQ ID 513 | 5' GCAUUCGUCCCGGGAUUCA 3'<br>:\|\|\|\|\|\|\|\|\|:\|\|\|\|\|\|\|\|<br>3' CGUAAGCAGGGCCCUAAGU 5' |
| SEQ ID 514 | 5' CAUUGAAGAGCUGCUUCCG 3'<br>:\|\|\|\|\|\|\|\|\|:\|\|\|\|\|\|\|\|<br>3' GUAACUUCUCGACGAAGGC 5' |
| SEQ ID 515 | 5' GAGCUGCUUCCGGAGAGGA 3'<br>:\|\|\|\|\|\|\|\|\|:\|\|\|\|\|\|\|\|<br>3' CUCGACGAAGGCCUCUCCU 5' |

Figure 2HH

<table>
<tr><td>SEQ ID 516</td><td>5' UAUUACCGCUACCGGGGU 3'<br>: | | : | | | : | | : | | | | | | : |<br>3' AUAAUGGCGAUGGCCCCA 5'</td></tr>
<tr><td>SEQ ID 517</td><td>5' CCCCACUGUGCUCUGGACA 3'<br>: | | : | | | : | | : | | | | | | : |<br>3' GGGGUGACACGAGACCUGU 5'</td></tr>
<tr><td>SEQ ID 518</td><td>5' ACCCCGUGCAAAUUUCCCA 3'<br>: | | : | | | : | | : | | | | | | : |<br>3' UGGGGCACGUUUAAAGGGU 5'</td></tr>
<tr><td>SEQ ID 519</td><td>5' CCCCGUGCAAAUUUCCCAG 3'<br>: | | : | | | : | | : | | | | | | : |<br>3' GGGGCACGUUUAAAGGGUC 5'</td></tr>
<tr><td>SEQ ID 520</td><td>5' AUUUCCCAGGAGCAGCUGC 3'<br>: | | : | | | : | | : | | | | | | : |<br>3' UAAAGGGUCCUCGUCGACG 5'</td></tr>
<tr><td>SEQ ID 521</td><td>5' UUUCCCAGGAGCAGCUGCU 3'<br>: | | : | | | : | | : | | | | | | : |<br>3' AAAGGGUCCUCGUCGACGA 5'</td></tr>
<tr><td>SEQ ID 522</td><td>5' AUGAUCAACAACUUCCGGC 3'<br>: | | : | | | : | | : | | | | | | : |<br>3' UACUAGUUGUUGAAGGCCG 5'</td></tr>
<tr><td>SEQ ID 523</td><td>5' UGAUCAACAACUUCCGGCA 3'<br>: | | : | | | : | | : | | | | | | : |<br>3' ACUAGUUGUUGAAGGCCGU 5'</td></tr>
<tr><td>SEQ ID 524</td><td>5' CAACUUCCGGCAGGUCCAG 3'<br>: | | : | | | : | | : | | | | | | : |<br>3' GUUGAAGGCCGUCCAGGUC 5'</td></tr>
<tr><td>SEQ ID 525</td><td>5' CUUCCGGCAGGUCCAGAAC 3'<br>: | | : | | | : | | : | | | | | | : |<br>3' GAAGGCCGUCCAGGUCUUC 5'</td></tr>
<tr><td>SEQ ID 526</td><td>5' GUUCGAUGAGAGGCUGGUA 3'<br>: | | : | | | : | | : | | | | | | : |<br>3' CAAGCUACUCUCCGACCAU 5'</td></tr>
<tr><td>SEQ ID 527</td><td>5' GUGCAAGUCUGUACUGCGG 3'<br>: | | : | | | : | | : | | | | | | : |<br>3' CACGUUCAGACAUGACGCC 5'</td></tr>
<tr><td>SEQ ID 528</td><td>5' GUCUGUACUGCGGCAGGAC 3'<br>: | | : | | | : | | : | | | | | | : |<br>3' CAGACAUGACGCCGUCCUG 5'</td></tr>
<tr><td>SEQ ID 529</td><td>5' GGAAGAGUAUCAAAAAAGG 3'<br>: | | : | | | : | | : | | | | | | : |<br>3' CCUUCUCAUAGUUUUUUCC 5'</td></tr>
<tr><td>SEQ ID 530</td><td>5' AAAACGUGAUAACAAGGGA 3'<br>: | | : | | | : | | : | | | | | | : |<br>3' UUUUCCACUAUUGUUCCCU 5'</td></tr>
<tr><td>SEQ ID 531</td><td>5' AAAGGUGAUAACAAGGGAG 3'<br>: | | : | | | : | | : | | | | | | : |<br>3' UUUCCACUAUUGUUCCCUC 5'</td></tr>
</table>

Figure 2II

<table>
<tr><td>SEQ ID 532</td><td>5' AAGGUGAUAACAAGGGAGU 3'<br>: | | | | | | | | | | | : | | : | | | |<br>3' UUCCACUAUUGUUCCCUCA 5'</td></tr>
<tr><td>SEQ ID 533</td><td>5' AGGUGAUAACAAGGGAGUC 3'<br>: | | | | | | | | | | | : | | : | | | |<br>3' UCCACUAUUGUUCCCUCAG 5'</td></tr>
<tr><td>SEQ ID 534</td><td>5' GGUGAUAACAAGGGAGUCA 3'<br>: | | | | | | | | | | | : | | : | | | |<br>3' CCACUAUUGUUCCCUCAGU 5'</td></tr>
<tr><td>SEQ ID 535</td><td>5' CAAGGGAGUCAUUUACAAG 3'<br>: | | | | | | | | | | | : | | : | | | |<br>3' GUUCCCUCAGUAAAUGUUC 5'</td></tr>
<tr><td>SEQ ID 536</td><td>5' GGGAGUCAUUUACAAGCCA 3'<br>: | | | | | | | | | | | : | | : | | | |<br>3' CCCUCAGUAAAUGUUCGGU 5'</td></tr>
<tr><td>SEQ ID 537</td><td>5' GCCAGCCACCAAGAUGGAG 3'<br>: | | | | | | | | | | | : | | : | | | |<br>3' CGGUCGGUGGUUCUACCUC 5'</td></tr>
<tr><td>SEQ ID 538</td><td>5' GAUGGAGACUGAGGCCCAC 3'<br>: | | | | | | | | | | | : | | : | | | |<br>3' CUACCUCUGACUCCGGGUG 5'</td></tr>
</table>

<table>
<tr><td>**ADRA1A**</td><td></td></tr>
<tr><td>SEQ ID 539</td><td>5' AUGCUUCCGACAGCUCCAA 3'<br>: | | | | | | | | | | | : | | : | | | |<br>3' UACGAAGGCUGUCGAGGUU 5'</td></tr>
<tr><td>SEQ ID 540</td><td>5' UGCUUCCGACAGCUCCAAC 3'<br>: | | | | | | | | | | | : | | : | | | |<br>3' ACGAAGGCUGUCGAGGUUG 5'</td></tr>
<tr><td>SEQ ID 541</td><td>5' CAUUUCCAAGGCCAUUCUG 3'<br>: | | | | | | | | | | | : | | : | | | |<br>3' GUAAAGGUUCCGGUAAGAC 5'</td></tr>
<tr><td>SEQ ID 542</td><td>5' CAUCCUAGUGAUCCUCUCC 3'<br>: | | | | | | | | | | | : | | : | | | |<br>3' GUAGGAUCACUAGGAGAGG 5'</td></tr>
<tr><td>SEQ ID 543</td><td>5' CAUCUGGGCGGCAGUGGAU 3'<br>: | | | | | | | | | | | : | | : | | | |<br>3' GUAGACCCGCCGUCACCUA 5'</td></tr>
<tr><td>SEQ ID 544</td><td>5' CCAUCGUCACCCAGACGAG 3'<br>: | | | | | | | | | | | : | | : | | | |<br>3' GGUACCAGUGGGUCUCCUC 5'</td></tr>
<tr><td>SEQ ID 545</td><td>5' GUCUGGCCUCAAGACCGAC 3'<br>: | | | | | | | | | | | : | | : | | | |<br>3' CAGACCGGAGUUCUGGCUG 5'</td></tr>
<tr><td>SEQ ID 546</td><td>5' GACCGACAAGUCGGACUCG 3'<br>: | | | | | | | | | | | : | | : | | | |<br>3' CUGGCUGUUCAGCCUGAGC 5'</td></tr>
</table>

Figure 2JJ

<table>
<tr><td>SEQ ID 547</td><td>5' GUCGGACUCGGAGCAAGUG 3'<br>| : | | : | | | | | | | : | | : | | | :<br>3' CAGCCUGAGCCUCGUUCAC 5'</td></tr>
<tr><td>SEQ ID 548</td><td>5' GUGACGCUCCGCAUCCAUC 3'<br>| : | | : | | | | | | | : | | : | | | :<br>3' CACUGCGAGGCGUAGGUAG 5'</td></tr>
<tr><td>SEQ ID 549</td><td>5' GACCAAGACGCACUUCUCA 3'<br>| : | | : | | | | | | | : | | : | | | :<br>3' CUGGUUCUGCGUGAAGAGU 5'</td></tr>
<tr><td>SEQ ID 550</td><td>5' GACGCACUUCUCAGUGAGG 3'<br>| : | | : | | | | | | | : | | : | | | :<br>3' CUGCGUGAAGAGUCACUCC 5'</td></tr>
<tr><td>SEQ ID 551</td><td>5' GUUCUCCCGGGACAAGAAA 3'<br>| : | | : | | | | | | | : | | : | | | :<br>3' CAAGAGGGCCCUGUUCUUU 5'</td></tr>
<tr><td>SEQ ID 552</td><td>5' GAAAGCGGCCAAAACGCUG 3'<br>| : | | : | | | | | | | : | | : | | | :<br>3' CUUUCGCCGGUUUUGCGAC 5'</td></tr>
<tr><td>SEQ ID 553</td><td>5' AACGCUGGCCAUCGUGGUC 3'<br>| : | | : | | | | | | | : | | : | | | :<br>3' UUGCGACCGGUAGCACCAG 5'</td></tr>
<tr><td>SEQ ID 554</td><td>5' GCCCUCUGAAACAGUUUUU 3'<br>| : | | : | | | | | | | : | | : | | | :<br>3' CGGGAGACUUUGUCAAAAA 5'</td></tr>
<tr><td>SEQ ID 555</td><td>5' AAUAGUAUUUUGGCUCGGA 3'<br>| : | | : | | | | | | | : | | : | | | :<br>3' UUAUCAUAAAACCGAGCCU 5'</td></tr>
<tr><td>SEQ ID 556</td><td>5' AUAGUAUUUUGGCUCGGAU 3'<br>| : | | : | | | | | | | : | | : | | | :<br>3' UAUCAUAAAACCGAGCCUA 5'</td></tr>
<tr><td>SEQ ID 557</td><td>5' UAGUAUUUUGGCUCGGAUA 3'<br>| : | | : | | | | | | | : | | : | | | :<br>3' AUCAUAAAACCGAGCCUAU 5'</td></tr>
<tr><td>SEQ ID 558</td><td>5' ACAGCUGCAUCAACCCCAU 3'<br>| : | | : | | | | | | | : | | : | | | :<br>3' UGUCGACGUAGUUGGGGUA 5'</td></tr>
<tr><td>SEQ ID 559</td><td>5' CAGCUGCAUCAACCCCAUC 3'<br>| : | | : | | | | | | | : | | : | | | :<br>3' GUCGACGUAGUUGGGGUAG 5'</td></tr>
<tr><td>SEQ ID 560</td><td>5' CCCCAUCAUAUACCCAUGC 3'<br>| : | | : | | | | | | | : | | : | | | :<br>3' GGGGUAGUAUAUGGGUACG 5'</td></tr>
<tr><td>SEQ ID 561</td><td>5' GAGUUCAAAAAGCCCUUUC 3'<br>| : | | : | | | | | | | : | | : | | | :<br>3' CUCAAGUUUUUCGGGAAAG 5'</td></tr>
<tr><td>SEQ ID 562</td><td>5' AAAGGCCUUUCAGAAUGUC 3'<br>| : | | : | | | | | | | : | | : | | | :<br>3' UUUCCGGAAAGUCUUACAG 5'</td></tr>
</table>

Figure 2KK

| | |
|---|---|
| SEQ ID 563 | 5' AAGGCCUUUCAGAAUGUCU 3'<br>\|\|\|\|\|\|\|:\|\|\|:\|\|\|:\|\|\|<br>3' UUCCGGAAAGUCUUACAGA 5' |
| SEQ ID 564 | 5' AGGCCUUUCAGAAUGUCUU 3'<br>\|\|\|\|\|\|\|:\|\|\|:\|\|\|:\|\|\|<br>3' UCCGGAAAGUCUUACAGAA 5' |
| SEQ ID 565 | 5' GGCCUUUCAGAAUGUCUUG 3'<br>\|\|\|\|\|\|\|:\|\|\|:\|\|\|:\|\|\|<br>3' CCGGAAAGUCUUACAGAAC 5' |
| SEQ ID 566 | 5' UGUCUUGAGAAUCCAGUGU 3'<br>\|\|\|\|\|\|\|:\|\|\|:\|\|\|:\|\|\|<br>3' ACAGAACUCUUAGGUCACA 5' |
| SEQ ID 567 | 5' UCCAGUGUCUCUGCAGAAA 3'<br>\|\|\|\|\|\|\|:\|\|\|:\|\|\|:\|\|\|<br>3' AGGUCACAGAGACGUCUUU 5' |
| SEQ ID 568 | 5' UCCAGUGUCUCCGCAGAAA 3'<br>\|\|\|\|\|\|\|:\|\|\|:\|\|\|:\|\|\|<br>3' AGGUCACAGAGGCGUCUUU 5' |
| SEQ ID 569 | 5' AGCAGUCUUCCAAACAUGC 3'<br>\|\|\|\|\|\|\|:\|\|\|:\|\|\|:\|\|\|<br>3' UCGUCAGAAGGUUUGUACG 5' |
| SEQ ID 570 | 5' GCAGUCUUCCAAACAUGCC 3'<br>\|\|\|\|\|\|\|:\|\|\|:\|\|\|:\|\|\|<br>3' CGUCAGAAGGUUUGUACGG 5' |
| SEQ ID 571 | 5' ACAUGCCCUGGGCUACACC 3'<br>\|\|\|\|\|\|\|:\|\|\|:\|\|\|:\|\|\|<br>3' UGUACGGGACCCGAUGUGG 5' |
| SEQ ID 572 | 5' GGGCAACACAAGGACAUGG 3'<br>\|\|\|\|\|\|\|:\|\|\|:\|\|\|:\|\|\|<br>3' CCCGUUGUGUUCCUGUACC 5' |
| SEQ ID 573 | 5' CACAAGGACAUGGUGCGCA 3'<br>\|\|\|\|\|\|\|:\|\|\|:\|\|\|:\|\|\|<br>3' GUGUUCCUGUACCACGCGU 5' |
| SEQ ID 574 | 5' GAGAGACCUUCUACAGGAU 3'<br>\|\|\|\|\|\|\|:\|\|\|:\|\|\|:\|\|\|<br>3' CUCUCUGGAAGAUGUCCUA 5' |
| SEQ ID 575 | 5' GACGGAUGGCGUUUGUGAA 3'<br>\|\|\|\|\|\|\|:\|\|\|:\|\|\|:\|\|\|<br>3' CUGCCUACCGCAAACACUU 5' |
| SEQ ID 576 | 5' AUUUUUCUCUUCCAUGCCC 3'<br>\|\|\|\|\|\|\|:\|\|\|:\|\|\|:\|\|\|<br>3' UAAAAAGAGAAGGUACGGG 5' |
| SEQ ID 577 | 5' UUUUUCUCUUCCAUGCCCC 3'<br>\|\|\|\|\|\|\|:\|\|\|:\|\|\|:\|\|\|<br>3' AAAAAGAGAAGGUACGGGG 5' |
| SEQ ID 578 | 5' AGACCAAUCCUCCUGUACC 3'<br>\|\|\|\|\|\|\|:\|\|\|:\|\|\|:\|\|\|<br>3' UCUGGUUAGGAGGACAUGG 5' |

Figure 2LL

| | |
|---|---|
| SEQ ID 579 | 5' GACCAAUCCUCCUGUACCA 3'<br>\|\|:\|\|\|:\|\|\|\|\|\|:\|\|\|:\|<br>3' CUGGUUAGGAGGACAUGGU 5' |
| SEQ ID 580 | 5' UCCUCCUGUACCACAGCCC 3'<br>\|\|:\|\|\|:\|\|\|\|\|\|:\|\|\|:\|<br>3' AGGAGGACAUGGUGUCGGG 5' |
| SEQ ID 581 | 5' GUCUCGCUCUGUCACCAGG 3'<br>\|\|:\|\|\|:\|\|\|\|\|\|:\|\|\|:\|<br>3' CAGAGCGAGACAGUGGUCC 5' |
| SEQ ID 582 | 5' GAGAUUCUCCUGCCUCAGC 3'<br>\|\|:\|\|\|:\|\|\|\|\|\|:\|\|\|:\|<br>3' CUCUAAGAGGACGGAGUCG 5' |
| SEQ ID 583 | 5' GAAUUGCAGAGAGCAUAUC 3'<br>\|\|:\|\|\|:\|\|\|\|\|\|:\|\|\|:\|<br>3' CUUAACGUCUCUCGUAUAG 5' |
| SEQ ID 584 | 5' UUGCAGAGAGCAUAUCAAG 3'<br>\|\|:\|\|\|:\|\|\|\|\|\|:\|\|\|:\|<br>3' AACGUCUCUCGUAUAGUUC 5' |
| SEQ ID 585 | 5' UUUUAUGAUGCCACCGUGG 3'<br>\|\|:\|\|\|:\|\|\|\|\|\|:\|\|\|:\|<br>3' AAAAUACUACGGUGGCACC 5' |
| SEQ ID 586 | 5' AGGGUCUAGAAUGCUGAUC 3'<br>\|\|:\|\|\|:\|\|\|\|\|\|:\|\|\|:\|<br>3' UCCCAGAUCUUACGACUAG 5' |
| SEQ ID 587 | 5' GGGUCUAGAAUGCUGAUCU 3'<br>\|\|:\|\|\|:\|\|\|\|\|\|:\|\|\|:\|<br>3' CCCAGAUCUUACGACUAGA 5' |
| SEQ ID 588 | 5' GUAAAAGCUUUUUGGAGGU 3'<br>\|\|:\|\|\|:\|\|\|\|\|\|:\|\|\|:\|<br>3' CAUUUUCGAAAAACCUCCA 5' |
| SEQ ID 589 | 5' AAGCUUUUUGGAGGUCUGC 3'<br>\|\|:\|\|\|:\|\|\|\|\|\|:\|\|\|:\|<br>3' UUCGAAAAACCUCCAGACG 5' |
| SEQ ID 590 | 5' AGCUUUUUGGAGGUCUGCU 3'<br>\|\|:\|\|\|:\|\|\|\|\|\|:\|\|\|:\|<br>3' UCGAAAAACCUCCAGACGA 5' |
| SEQ ID 591 | 5' GCUUUUUGGAGGUCUGCUG 3'<br>\|\|:\|\|\|:\|\|\|\|\|\|:\|\|\|:\|<br>3' CGAAAAACCUCCAGACGAC 5' |
| SEQ ID 592 | 5' CCCCCAGCCUUGACAAGAA 3'<br>\|\|:\|\|\|:\|\|\|\|\|\|:\|\|\|:\|<br>3' GGGGGUCGGAACUGUUCUU 5' |
| SEQ ID 593 | 5' GAACCAUCAAGUUCCAACC 3'<br>\|\|:\|\|\|:\|\|\|\|\|\|:\|\|\|:\|<br>3' CUUGGUAGUUCAAGGUUGG 5' |
| SEQ ID 594 | 5' CCAUCAAGUUCCAACCAUU 3'<br>\|\|:\|\|\|:\|\|\|\|\|\|:\|\|\|:\|<br>3' GGUAGUUCAAGGUUGGUAA 5' |

Figure 2MM

| | |
|---|---|
| SEQ ID 595 | 5' GUUCCAACCAUUAAGGUCC 3'<br>\|\|\|\|\|\|\|\|\|\|\|\|:\|\|\|:\|\|<br>3' CAAGGUUGGUAAUUCCAGG 5' |
| SEQ ID 596 | 5' CCAUUAAGGUCCACACCAU 3'<br>\|\|\|\|\|\|\|\|\|\|\|\|:\|\|\|:\|\|<br>3' GGUAAUUCCAGGUGUGGUA 5' |
| SEQ ID 597 | 5' GGUCCACACCAUCUCCCUC 3'<br>\|\|\|\|\|\|\|\|\|\|\|\|:\|\|\|:\|\|<br>3' CCAGGUGUGGUAGAGGGAG 5' |
| SEQ ID 598 | 5' CGGGGAGGAAGUCUAGGAC 3'<br>\|\|\|\|\|\|\|\|\|\|\|\|:\|\|\|:\|\|<br>3' GCCCCUCCUUCAGAUCCUG 5' |

| **ADRA1B** | |
|---|---|
| SEQ ID 599 | 5' GAUGAAUCCCGACCUGGAC 3'<br>\|\|\|\|\|\|\|\|\|\|\|\|:\|\|\|:\|\|<br>3' CUACUUAGGGCUGGACCUG 5' |
| SEQ ID 600 | 5' CACAUCAGCACCUGCCCAC 3'<br>\|\|\|\|\|\|\|\|\|\|\|\|:\|\|\|:\|\|<br>3' GUGUAGUCGUGGACGGGUG 5' |
| SEQ ID 601 | 5' AAAUGCCAACUUCACUGGC 3'<br>\|\|\|\|\|\|\|\|\|\|\|\|:\|\|\|:\|\|<br>3' UUUACGGUUGAAGUGACCG 5' |
| SEQ ID 602 | 5' AAUGCCAACUUCACUGGCC 3'<br>\|\|\|\|\|\|\|\|\|\|\|\|:\|\|\|:\|\|<br>3' UUACGGUUGAAGUGACCGG 5' |
| SEQ ID 603 | 5' AUGCCAACUUCACUGGCCC 3'<br>\|\|\|\|\|\|\|\|\|\|\|\|:\|\|\|:\|\|<br>3' UACGGUUGAAGUGACCGGG 5' |
| SEQ ID 604 | 5' UGCCAACUUCACUGGCCCC 3'<br>\|\|\|\|\|\|\|\|\|\|\|\|:\|\|\|:\|\|<br>3' ACGGUUGAAGUGACCGGGG 5' |
| SEQ ID 605 | 5' CUUCACUGGCCCCAACCAG 3'<br>\|\|\|\|\|\|\|\|\|\|\|\|:\|\|\|:\|\|<br>3' GAAGUGACCGGGGUUGGUC 5' |
| SEQ ID 606 | 5' CCAGACCUCGAGCAACUCC 3'<br>\|\|\|\|\|\|\|\|\|\|\|\|:\|\|\|:\|\|<br>3' GGUCUGGAGCUCGUUGAGG 5' |
| SEQ ID 607 | 5' CAUCCUAGUCAUCUUGUCU 3'<br>\|\|\|\|\|\|\|\|\|\|\|\|:\|\|\|:\|\|<br>3' GUAGGAUCAGUAGAACAGA 5' |
| SEQ ID 608 | 5' CUACUUCAUUGUCAACCUG 3'<br>\|\|\|\|\|\|\|\|\|\|\|\|:\|\|\|:\|\|<br>3' GAUGAAGUAACAGUUGGAC 5' |
| SEQ ID 609 | 5' CGAUGACAAGGAGUGCGGG 3'<br>\|\|\|\|\|\|\|\|\|\|\|\|:\|\|\|:\|\|<br>3' GCUACUGUUCCUCACGCCC 5' |

Figure 2NN

| | |
|---|---|
| SEQ ID 610 | 5' GAACCCUUCUAUGCCCUCU 3'<br>\|\|:\|\|\|\|\|\|::\|\|\|\|\|:\|\|<br>3' CUUGGGAAGAUACGGGAGA 5' |
| SEQ ID 611 | 5' CCCUUCUAUGCCCUCUUCU 3'<br>\|\|:\|\|\|\|\|\|::\|\|\|\|\|:\|\|<br>3' GGGAAGAUACGGGAGAAGA 5' |
| SEQ ID 612 | 5' GAGAACCACCAAGAACCUA 3'<br>\|\|:\|\|\|\|\|\|::\|\|\|\|\|:\|\|<br>3' CUCUUGGUGGUUCUUGGAU 5' |
| SEQ ID 613 | 5' CCACCAAGAACCUAGAGGC 3'<br>\|\|:\|\|\|\|\|\|::\|\|\|\|\|:\|\|<br>3' GGUGGUUCUUGGAUCUCCG 5' |
| SEQ ID 614 | 5' GAACCUAGAGGCAGGAGUC 3'<br>\|\|:\|\|\|\|\|\|::\|\|\|\|\|:\|\|<br>3' CUUGGAUCUCCGUCCUCAG 5' |
| SEQ ID 615 | 5' CCUAGAGGCAGGAGUCAUG 3'<br>\|\|:\|\|\|\|\|\|::\|\|\|\|\|:\|\|<br>3' GGAUCUCCGUCCUCAGUAC 5' |
| SEQ ID 616 | 5' GGAGAUGUCCAACUCCAAG 3'<br>\|\|:\|\|\|\|\|\|::\|\|\|\|\|:\|\|<br>3' CCUCUACAGGUUGAGGUUC 5' |
| SEQ ID 617 | 5' CUCCAAGGAGCUGACCCUG 3'<br>\|\|:\|\|\|\|\|\|::\|\|\|\|\|:\|\|<br>3' GAGGUUCCUCGACUGGGAC 5' |
| SEQ ID 618 | 5' GGAGCUGACCCUGAGGAUC 3'<br>\|\|:\|\|\|\|\|\|::\|\|\|\|\|:\|\|<br>3' CCUCGACUGGGACUCCUAG 5' |
| SEQ ID 619 | 5' GAACUUUCACGAGGACACC 3'<br>\|\|:\|\|\|\|\|\|::\|\|\|\|\|:\|\|<br>3' CUUGAAAGUGCUCCUGUGG 5' |
| SEQ ID 620 | 5' CUUUCACGAGGACACCCUU 3'<br>\|\|:\|\|\|\|\|\|::\|\|\|\|\|:\|\|<br>3' GAAAGUGCUCCUGUGGGAA 5' |
| SEQ ID 621 | 5' CCCCAGGAGUUCCAUAGCU 3'<br>\|\|:\|\|\|\|\|\|::\|\|\|\|\|:\|\|<br>3' GGGGUCCUCAAGGUAUCGA 5' |
| SEQ ID 622 | 5' ACUUUUUAAGUUCUCCAGG 3'<br>\|\|:\|\|\|\|\|\|::\|\|\|\|\|:\|\|<br>3' UGAAAAAUUCAAGAGGUCC 5' |
| SEQ ID 623 | 5' CUUUUUAAGUUCUCCAGGG 3'<br>\|\|:\|\|\|\|\|\|::\|\|\|\|\|:\|\|<br>3' GAAAAAUUCAAGAGGUCCC 5' |
| SEQ ID 624 | 5' GUUCUCCAGGGAAAAGAAA 3'<br>\|\|:\|\|\|\|\|\|::\|\|\|\|\|:\|\|<br>3' CAAGAGGUCCCUUUUCUUU 5' |
| SEQ ID 625 | 5' AAGAAAGCAGCUAAGACGU 3'<br>\|\|:\|\|\|\|\|\|::\|\|\|\|\|:\|\|<br>3' UUCUUUCGUCGAUUCUGCA 5' |

Figure 2OO

| | |
|---|---|
| SEQ ID 626 | 5' AGAAAGCAGCUAAGACGUU 3'<br>\|\|\|\|::\|\|\|\|\|\|::\|\|\|\|:<br>3' UCUUUCGUCGAUUCUGCAA 5' |
| SEQ ID 627 | 5' GAAAGCAGCUAAGACGUUG 3'<br>\|\|\|\|::\|\|\|\|\|\|::\|\|\|\|:<br>3' CUUUCGUCGAUUCUGCAAC 5' |
| SEQ ID 628 | 5' AGCAGCUAAGACGUUGGGC 3'<br>\|\|\|\|::\|\|\|\|\|\|::\|\|\|\|:<br>3' UCGUCGAUUCUGCAACCCG 5' |
| SEQ ID 629 | 5' GCAGCUAAGACGUUGGGCA 3'<br>\|\|\|\|::\|\|\|\|\|\|::\|\|\|\|:<br>3' CGUCGAUUCUGCAACCCGU 5' |
| SEQ ID 630 | 5' GACGUUGGGCAUUGUGGUC 3'<br>\|\|\|\|::\|\|\|\|\|\|::\|\|\|\|:<br>3' CUGCAACCCGUAACACCAG 5' |
| SEQ ID 631 | 5' CAGCUGCCUCAACCCCAUC 3'<br>\|\|\|\|::\|\|\|\|\|\|::\|\|\|\|:<br>3' GUCGACGGAGUUGGGGUAG 5' |
| SEQ ID 632 | 5' CCCCAUCAUCUACCCAUGC 3'<br>\|\|\|\|::\|\|\|\|\|\|::\|\|\|\|:<br>3' GGGGUAGUAGAUGGGUACG 5' |
| SEQ ID 633 | 5' GGAGUUCAAGCGCGCUUUC 3'<br>\|\|\|\|::\|\|\|\|\|\|::\|\|\|\|:<br>3' CCUCAAGUUCGCGCGAAAG 5' |
| SEQ ID 634 | 5' AAGCAACAUGCCCCUGGCG 3'<br>\|\|\|\|::\|\|\|\|\|\|::\|\|\|\|:<br>3' UUCGUUGUACGGGGACCGC 5' |

| ADRA1D | |
|---|---|
| SEQ ID 635 | 5' CCUGCUUGUCAUCCUCUCA 3'<br>\|\|\|\|::\|\|\|\|\|\|::\|\|\|\|:<br>3' GGACGAACAGUAGGAGAGU 5' |
| SEQ ID 636 | 5' CUAUUUCAUCGUGAACCUG 3'<br>\|\|\|\|::\|\|\|\|\|\|::\|\|\|\|:<br>3' GAUAAAGUAGCACUUGGAC 5' |
| SEQ ID 637 | 5' GUACCCAGCCAUCAUGACC 3'<br>\|\|\|\|::\|\|\|\|\|\|::\|\|\|\|:<br>3' CAUGGGUCGGUAGUACUGG 5' |
| SEQ ID 638 | 5' GUUCUCCCGUGAGAAGAAA 3'<br>\|\|\|\|::\|\|\|\|\|\|::\|\|\|\|:<br>3' CAAGAGGGCACUCUUCUUU 5' |
| SEQ ID 639 | 5' GAAAGCGGCCAAGACUCUG 3'<br>\|\|\|\|::\|\|\|\|\|\|::\|\|\|\|:<br>3' CUUUCGCCGGUUCUGAGAC 5' |
| SEQ ID 640 | 5' GACUCUGGCCAUCGUCGUG 3'<br>\|\|\|\|::\|\|\|\|\|\|::\|\|\|\|:<br>3' CUGAGACCGGUAGCAGCAC 5' |

Figure 2PP

| | |
|---|---|
| SEQ ID 641 | 5' GGUCAUCUUCUGGCUCGGC 3'<br>:\|\|\|\|\|\|:\|\|\|\|\|:\|\|\|\|\|<br>3' CCAGUAGAAGACCGAGCCG 5' |
| SEQ ID 642 | 5' CCCGCUCAUCUACCCCUGU 3'<br>:\|\|\|\|\|\|:\|\|\|\|\|:\|\|\|\|\|<br>3' GGGCGAGUAGAUGGGGACA 5' |
| SEQ ID 643 | 5' AGUCUCCAGCCUGUCGCAC 3'<br>:\|\|\|\|\|\|:\|\|\|\|\|:\|\|\|\|\|<br>3' UCAGAGGUCGGACAGCGUG 5' |
| SEQ ID 644 | 5' GUCUCCAGCCUGUCGCACA 3'<br>:\|\|\|\|\|\|:\|\|\|\|\|:\|\|\|\|\|<br>3' CAGAGGUCGGACAGCGUGU 5' |
| SEQ ID 645 | 5' UUGGCUGACUACAGCAACC 3'<br>:\|\|\|\|\|\|:\|\|\|\|\|:\|\|\|\|\|<br>3' AACCGGCUGAUGUCGUUGG 5' |
| SEQ ID 646 | 5' CCUACGGGAGACCGAUAUU 3'<br>:\|\|\|\|\|\|:\|\|\|\|\|:\|\|\|\|\|<br>3' GGAUGCCCUCUGGCUAUAA 5' |

| AGT | |
|---|---|
| SEQ ID 647 | 5' UGAGAGUACCUGUGAGCAG 3'<br>:\|\|\|\|\|\|:\|\|\|\|\|:\|\|\|\|\|<br>3' ACUCUCAUGGACACUCGUC 5' |
| SEQ ID 648 | 5' UGCCGGGAAGCCCAAAGAC 3'<br>:\|\|\|\|\|\|:\|\|\|\|\|:\|\|\|\|\|<br>3' ACGGCCCUUCGGGUUUCUG 5' |
| SEQ ID 649 | 5' GCCCAAAGACCCCACCUUC 3'<br>:\|\|\|\|\|\|:\|\|\|\|\|:\|\|\|\|\|<br>3' CGGGUUUCUGGGGUGGAAG 5' |
| SEQ ID 650 | 5' AGACCCCACCUUCAUACCU 3'<br>:\|\|\|\|\|\|:\|\|\|\|\|:\|\|\|\|\|<br>3' UCUGGGGUGGAAGUAUGGA 5' |
| SEQ ID 651 | 5' GACCCCACCUUCAUACCUG 3'<br>:\|\|\|\|\|\|:\|\|\|\|\|:\|\|\|\|\|<br>3' CUGGGGUGGAAGUAUGGAC 5' |
| SEQ ID 652 | 5' UUCAGGCCAAGACAUCCCC 3'<br>:\|\|\|\|\|\|:\|\|\|\|\|:\|\|\|\|\|<br>3' AAGUCCGGUUCUGUAGGGG 5' |
| SEQ ID 653 | 5' GACAUCCCCUGUGGAUGAA 3'<br>:\|\|\|\|\|\|:\|\|\|\|\|:\|\|\|\|\|<br>3' CUGUAGGGGACACCUACUU 5' |
| SEQ ID 654 | 5' AAGGCCCUACAGGACCAGC 3'<br>:\|\|\|\|\|\|:\|\|\|\|\|:\|\|\|\|\|<br>3' UUCCGGGAUGUCCUGGUCG 5' |
| SEQ ID 655 | 5' AGGCCCUACAGGACCAGCU 3'<br>:\|\|\|\|\|\|:\|\|\|\|\|:\|\|\|\|\|<br>3' UCCGGGAUGUCCUGGUCGA 5' |

Figure 2QQ

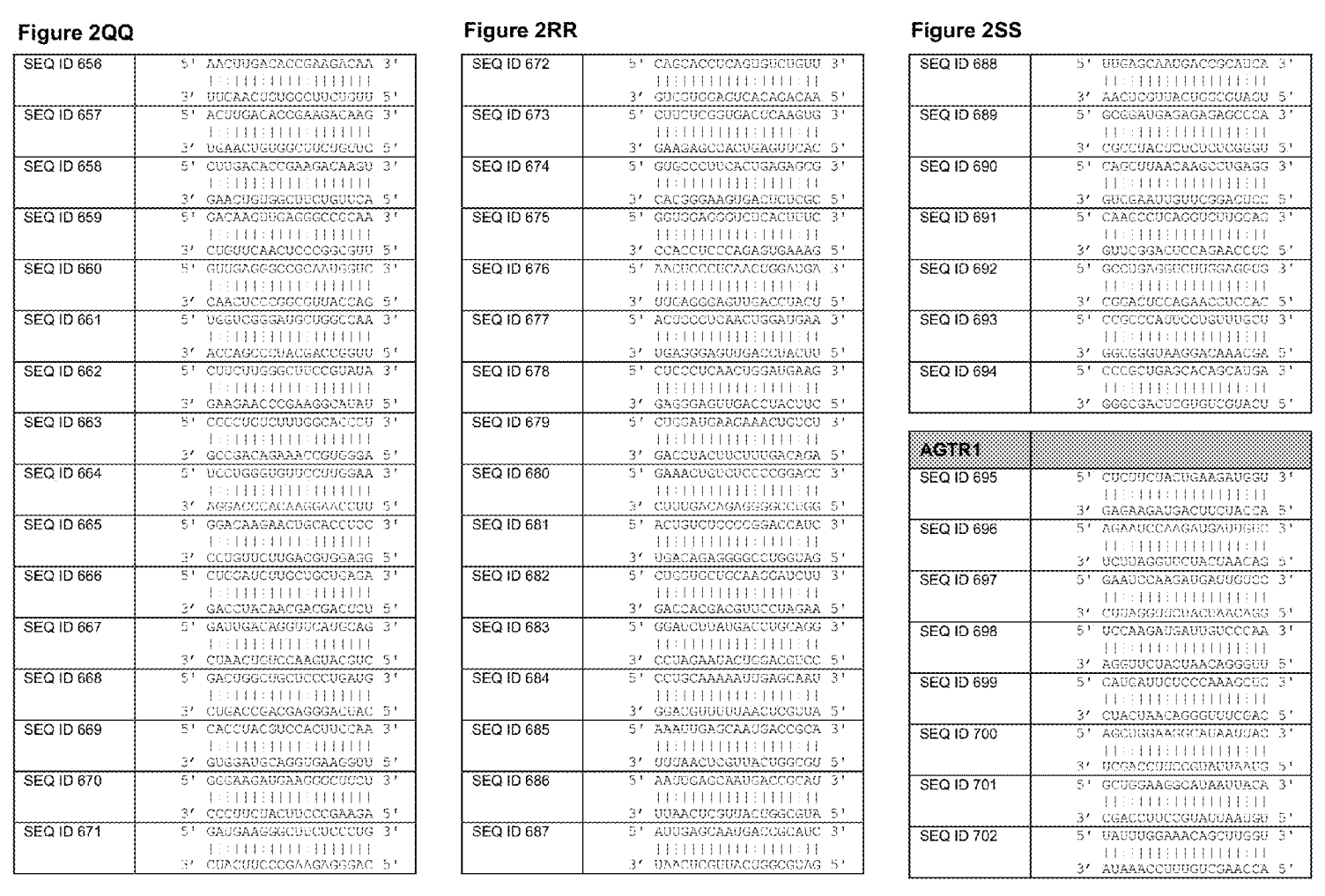

| | |
|---|---|
| SEQ ID 656 | 5' AACUUGACACCGAAGACAA 3'<br>\|::\|\|\|:\|\|\|\|:\|\|\|\|\|\|\|<br>3' UUGAACUGUGGCUUCUGUU 5' |
| SEQ ID 657 | 5' ACUUGACACCGAAGACAAG 3'<br>\|::\|\|\|:\|\|\|\|:\|\|\|\|\|\|\|<br>3' UGAACUGUGGCUUCUGUUC 5' |
| SEQ ID 658 | 5' CUUGACACCGAAGACAAGU 3'<br>\|::\|\|\|:\|\|\|\|:\|\|\|\|\|\|\|<br>3' GAACUGUGGCUUCUGUUCA 5' |
| SEQ ID 659 | 5' GACAAGUUGAGGGCCGCAA 3'<br>\|::\|\|\|:\|\|\|\|:\|\|\|\|\|\|\|<br>3' CUGUUCAACUCCCGGCGUU 5' |
| SEQ ID 660 | 5' GUUGAGGGCCGCAAUGGUC 3'<br>\|::\|\|\|:\|\|\|\|:\|\|\|\|\|\|\|<br>3' CAACUCCCGGCGUUACCAG 5' |
| SEQ ID 661 | 5' UGGUCGGGAUGCUGGCCAA 3'<br>\|::\|\|\|:\|\|\|\|:\|\|\|\|\|\|\|<br>3' ACCAGCCCUACGACCGGUU 5' |
| SEQ ID 662 | 5' CUUCUUGGGCUUCCGUAUA 3'<br>\|::\|\|\|:\|\|\|\|:\|\|\|\|\|\|\|<br>3' GAAGAACCCGAAGGCAUAU 5' |
| SEQ ID 663 | 5' CGGCUGUCUUUGGCACCCU 3'<br>\|::\|\|\|:\|\|\|\|:\|\|\|\|\|\|\|<br>3' GCCGACAGAAACCGUGGGA 5' |
| SEQ ID 664 | 5' UCCUGGGUGUUCCUUGGAA 3'<br>\|::\|\|\|:\|\|\|\|:\|\|\|\|\|\|\|<br>3' AGGACCCACAAGGAACCUU 5' |
| SEQ ID 665 | 5' GGACAAGAACUGCACCUCC 3'<br>\|::\|\|\|:\|\|\|\|:\|\|\|\|\|\|\|<br>3' CCUGUUCUUGACGUGGAGG 5' |
| SEQ ID 666 | 5' CUGGAUGUUGCUGCUGAGA 3'<br>\|::\|\|\|:\|\|\|\|:\|\|\|\|\|\|\|<br>3' GACCUACAACGACGACUCU 5' |
| SEQ ID 667 | 5' GAUUGACAGGUUCAUGCAG 3'<br>\|::\|\|\|:\|\|\|\|:\|\|\|\|\|\|\|<br>3' CUAACUGUCCAAGUACGUC 5' |
| SEQ ID 668 | 5' GACUGGCUGCUCCCUGAUG 3'<br>\|::\|\|\|:\|\|\|\|:\|\|\|\|\|\|\|<br>3' CUGACCGACGAGGGACUAC 5' |
| SEQ ID 669 | 5' CACCUACGUCCACUUCCAA 3'<br>\|::\|\|\|:\|\|\|\|:\|\|\|\|\|\|\|<br>3' GUGGAUGCAGGUGAAGGUU 5' |
| SEQ ID 670 | 5' GGGAAGAUGAAGGGCUUCU 3'<br>\|::\|\|\|:\|\|\|\|:\|\|\|\|\|\|\|<br>3' CCCUUCUACUUCCCGAAGA 5' |
| SEQ ID 671 | 5' GAUGAAGGGCUUCUCCCUG 3'<br>\|::\|\|\|:\|\|\|\|:\|\|\|\|\|\|\|<br>3' CUACUUCCCGAAGAGGGAC 5' |

Figure 2RR

| | |
|---|---|
| SEQ ID 672 | 5' CAGCACCUCAGUGUCUGUU 3'<br>\|\|:\|\|\|\|\|\|\|\|:\|\|\|\|:\|\|<br>3' GUCGUGGAGUCACAGACAA 5' |
| SEQ ID 673 | 5' CUUCUCGGUGACUCAAGUG 3'<br>\|\|:\|\|\|\|\|\|\|\|:\|\|\|\|:\|\|<br>3' GAAGAGCCACUGAGUUCAC 5' |
| SEQ ID 674 | 5' GUGCCCUUCACUGAGAGCG 3'<br>\|\|:\|\|\|\|\|\|\|\|:\|\|\|\|:\|\|<br>3' CACGGGAAGUGACUCUCGC 5' |
| SEQ ID 675 | 5' GGUGGAGGGUCUCACUUUC 3'<br>\|\|:\|\|\|\|\|\|\|\|:\|\|\|\|:\|\|<br>3' CCACCUCCCAGAGUGAAAG 5' |
| SEQ ID 676 | 5' AACUCCCUCAACUGGAUGA 3'<br>\|\|:\|\|\|\|\|\|\|\|:\|\|\|\|:\|\|<br>3' UUGAGGGAGUUGACCUACU 5' |
| SEQ ID 677 | 5' ACUCCCUCAACUGGAUGAA 3'<br>\|\|:\|\|\|\|\|\|\|\|:\|\|\|\|:\|\|<br>3' UGAGGGAGUUGACCUACUU 5' |
| SEQ ID 678 | 5' CUCCCUCAACUGGAUGAAG 3'<br>\|\|:\|\|\|\|\|\|\|\|:\|\|\|\|:\|\|<br>3' GAGGGAGUUGACCUACUUC 5' |
| SEQ ID 679 | 5' CUGGAUGAAGAAACUGUCU 3'<br>\|\|:\|\|\|\|\|\|\|\|:\|\|\|\|:\|\|<br>3' GACCUACUUCUUUGACAGA 5' |
| SEQ ID 680 | 5' GAAACUGUCUCCCCGGACC 3'<br>\|\|:\|\|\|\|\|\|\|\|:\|\|\|\|:\|\|<br>3' CUUUGACAGAGGGGCCUGG 5' |
| SEQ ID 681 | 5' ACUGUCUCCCCGGACCAUC 3'<br>\|\|:\|\|\|\|\|\|\|\|:\|\|\|\|:\|\|<br>3' UGACAGAGGGGCCUGGUAG 5' |
| SEQ ID 682 | 5' CUGGUGCUCCAAGGAUCUU 3'<br>\|\|:\|\|\|\|\|\|\|\|:\|\|\|\|:\|\|<br>3' GACCACGAGGUUCCUAGAA 5' |
| SEQ ID 683 | 5' GGAUCUUAUGACCUGCAGG 3'<br>\|\|:\|\|\|\|\|\|\|\|:\|\|\|\|:\|\|<br>3' CCUAGAAUACUGGACGUCC 5' |
| SEQ ID 684 | 5' CCUGCAAAAAUUGAGCAAU 3'<br>\|\|:\|\|\|\|\|\|\|\|:\|\|\|\|:\|\|<br>3' GGACGUUUUUAACUCGUUA 5' |
| SEQ ID 685 | 5' AAAUUGAGCAAUGACCGCA 3'<br>\|\|:\|\|\|\|\|\|\|\|:\|\|\|\|:\|\|<br>3' UUUAACUCGUUACUGGCGU 5' |
| SEQ ID 686 | 5' AAUUGAGCAAUGACCGCAU 3'<br>\|\|:\|\|\|\|\|\|\|\|:\|\|\|\|:\|\|<br>3' UUAACUCGUUACUGGCGUA 5' |
| SEQ ID 687 | 5' AUUGAGCAAUGACCGCAUC 3'<br>\|\|:\|\|\|\|\|\|\|\|:\|\|\|\|:\|\|<br>3' UAACUCGUUACUGGCGUAG 5' |

Figure 2SS

| | |
|---|---|
| SEQ ID 688 | 5' UUGAGCAAUGACCGCAUCA 3'<br>\|\|::\|\|\|:\|\|\|\|\|\|\|\|:\|\|<br>3' AACUCGUUACUGGCGUAGU 5' |
| SEQ ID 689 | 5' GCGGAUGAGAGAGAGCCCA 3'<br>\|\|::\|\|\|:\|\|\|\|\|\|\|\|:\|\|<br>3' CGCCUACUCUCUCUCGGGU 5' |
| SEQ ID 690 | 5' CAGCUUAACAAGCCUGAGG 3'<br>\|\|::\|\|\|:\|\|\|\|\|\|\|\|:\|\|<br>3' GUCGAAUUGUUCGGACUCC 5' |
| SEQ ID 691 | 5' CAAGCCUGAGGUCUUGGAG 3'<br>\|\|::\|\|\|:\|\|\|\|\|\|\|\|:\|\|<br>3' GUUCGGACUCCAGAACCUC 5' |
| SEQ ID 692 | 5' GCCUGAGGUCUUGGAGGUG 3'<br>\|\|::\|\|\|:\|\|\|\|\|\|\|\|:\|\|<br>3' CGGACUCCAGAACCUCCAC 5' |
| SEQ ID 693 | 5' CCGCCCAUUCCUGUUUGCU 3'<br>\|\|::\|\|\|:\|\|\|\|\|\|\|\|:\|\|<br>3' GGCGGGUAAGGACAAACGA 5' |
| SEQ ID 694 | 5' CCCGCUGAGCACAGCAUGA 3'<br>\|\|::\|\|\|:\|\|\|\|\|\|\|\|:\|\|<br>3' GGGCGACUCGUGUCGUACU 5' |

| AGTR1 | |
|---|---|
| SEQ ID 695 | 5' CUCUUCUACUGAAGAUGGU 3'<br>\|\|::\|\|\|:\|\|\|\|\|\|\|\|:\|\|<br>3' GAGAAGAUGACUUCUACCA 5' |
| SEQ ID 696 | 5' AGAAUCCAAGAUGAUUGUC 3'<br>\|\|::\|\|\|:\|\|\|\|\|\|\|\|:\|\|<br>3' UCUUAGGUUCUACUAACAG 5' |
| SEQ ID 697 | 5' GAAUCCAAGAUGAUUGUCC 3'<br>\|\|::\|\|\|:\|\|\|\|\|\|\|\|:\|\|<br>3' CUUAGGUUCUACUAACAGG 5' |
| SEQ ID 698 | 5' UCCAAGAUGAUUGUCCCAA 3'<br>\|\|::\|\|\|:\|\|\|\|\|\|\|\|:\|\|<br>3' AGGUUCUACUAACAGGGUU 5' |
| SEQ ID 699 | 5' GAUGAUUGUCCCAAAGCUG 3'<br>\|\|::\|\|\|:\|\|\|\|\|\|\|\|:\|\|<br>3' CUACUAACAGGGUUUCGAC 5' |
| SEQ ID 700 | 5' AGCUGGAAGGCAUAAUUAC 3'<br>\|\|::\|\|\|:\|\|\|\|\|\|\|\|:\|\|<br>3' UCGACCUUCCGUAUUAAUG 5' |
| SEQ ID 701 | 5' GCUGGAAGGCAUAAUUACA 3'<br>\|\|::\|\|\|:\|\|\|\|\|\|\|\|:\|\|<br>3' CGACCUUCCGUAUUAAUGU 5' |
| SEQ ID 702 | 5' UAUUUGGAAACAGCUUGGU 3'<br>\|\|::\|\|\|:\|\|\|\|\|\|\|\|:\|\|<br>3' AUAAACCUUUGUCGAACCA 5' |

Figure 2TT

| | |
|---|---|
| SEQ ID 703 | 5' ACAGCUUGGUGGUGAUAGU 3'<br>\|\|\|:\|\|\|:\|\|\|:\|\|\|\|\|\|\|<br>3' UGUCGAACCACCACUAUCA 5' |
| SEQ ID 704 | 5' CAGCUUGGUGGUGAUAGUC 3'<br>\|\|\|:\|\|\|:\|\|\|:\|\|\|\|\|\|\|<br>3' GUCGAACCACCACUAUCAG 5' |
| SEQ ID 705 | 5' GCUGAAGACUGUGGCCAGU 3'<br>\|\|\|:\|\|\|:\|\|\|:\|\|\|\|\|\|\|<br>3' CGACUUCUGACACCGGUCA 5' |
| SEQ ID 706 | 5' GACUGUGGCCAGUGUUUUU 3'<br>\|\|\|:\|\|\|:\|\|\|:\|\|\|\|\|\|\|<br>3' CUGACACCGGUCACAAAAA 5' |
| SEQ ID 707 | 5' UUUAGCACUGGCUGACUUA 3'<br>\|\|\|:\|\|\|:\|\|\|:\|\|\|\|\|\|\|<br>3' AAAUCGUGACCGACUGAAU 5' |
| SEQ ID 708 | 5' UACCGCUGGCCCUUUGGCA 3'<br>\|\|\|:\|\|\|:\|\|\|:\|\|\|\|\|\|\|<br>3' AUGGCGACCGGGAAACCGU 5' |
| SEQ ID 709 | 5' GAUUGCUUCAGCCAGCGUC 3'<br>\|\|\|:\|\|\|:\|\|\|:\|\|\|\|\|\|\|<br>3' CUAACGAAGUCGGUCGCAG 5' |
| SEQ ID 710 | 5' CCUGUACGCUAGUGUGUUU 3'<br>\|\|\|:\|\|\|:\|\|\|:\|\|\|\|\|\|\|<br>3' GGACAUGCGAUCACACAAA 5' |
| SEQ ID 711 | 5' UGAAGUCCCGCCUUCGACG 3'<br>\|\|\|:\|\|\|:\|\|\|:\|\|\|\|\|\|\|<br>3' ACUUCAGGGCGGAAGCUGC 5' |
| SEQ ID 712 | 5' UGCUUGUAGCCAAAGUCAC 3'<br>\|\|\|:\|\|\|:\|\|\|:\|\|\|\|\|\|\|<br>3' ACGAACAUCGGUUUCAGUG 5' |
| SEQ ID 713 | 5' AGUCACCUGCAUCAUCAUU 3'<br>\|\|\|:\|\|\|:\|\|\|:\|\|\|\|\|\|\|<br>3' UCAGUGGACGUAGUAGUAA 5' |
| SEQ ID 714 | 5' GUCACCUGCAUCAUCAUUU 3'<br>\|\|\|:\|\|\|:\|\|\|:\|\|\|\|\|\|\|<br>3' CAGUGGACGUAGUAGUAAA 5' |
| SEQ ID 715 | 5' AAUUCAACCCUUCCGAUAG 3'<br>\|\|\|:\|\|\|:\|\|\|:\|\|\|\|\|\|\|<br>3' UUAAGUUGGGAAGGCUAUC 5' |
| SEQ ID 716 | 5' AUUCAACCCUUCCGAUAGG 3'<br>\|\|\|:\|\|\|:\|\|\|:\|\|\|\|\|\|\|<br>3' UAAGUUGGGAAGGCUAUCC 5' |
| SEQ ID 717 | 5' UUCAACCCUUCCGAUAGGG 3'<br>\|\|\|:\|\|\|:\|\|\|:\|\|\|\|\|\|\|<br>3' AAGUUGGGAAGGCUAUCCC 5' |
| SEQ ID 718 | 5' AAAUAUACUGGGUUUCCUG 3'<br>\|\|\|:\|\|\|:\|\|\|:\|\|\|\|\|\|\|<br>3' UUUAUAUGACCCAAAGGAC 5' |

Figure 2UU

| | |
|---|---|
| SEQ ID 719 | 5' AAUAUACUGGGUUUCCUGU 3'<br>\|\|\|\|\|\|\|:\|\|\|\|\|\|\|\|:\|\|<br>3' UUAUAUGACCCAAAGGACA 5' |
| SEQ ID 720 | 5' AUAUACUGGGUUUCCUGUU 3'<br>\|\|\|\|\|\|\|:\|\|\|\|\|\|\|\|:\|\|<br>3' UAUAUGACCCAAAGGACAA 5' |
| SEQ ID 721 | 5' UAUACUGGGUUUCCUGUUU 3'<br>\|\|\|\|\|\|\|:\|\|\|\|\|\|\|\|:\|\|<br>3' AUAUGACCCAAAGGACAAA 5' |
| SEQ ID 722 | 5' GGCCCUAAAGAAGGCUUAU 3'<br>\|\|\|\|\|\|\|:\|\|\|\|\|\|\|\|:\|\|<br>3' CCGGGAUUUCUUCCGAAUA 5' |
| SEQ ID 723 | 5' GAAGGCUUAUGAAAUUCAG 3'<br>\|\|\|\|\|\|\|:\|\|\|\|\|\|\|\|:\|\|<br>3' CUUCCGAAUACUUUAAGUC 5' |
| SEQ ID 724 | 5' GGCUUAUGAAAUUCAGAAG 3'<br>\|\|\|\|\|\|\|:\|\|\|\|\|\|\|\|:\|\|<br>3' CCGAAUACUUUAAGUCUUC 5' |
| SEQ ID 725 | 5' UUCAGAAGAACAAACCAAG 3'<br>\|\|\|\|\|\|\|:\|\|\|\|\|\|\|\|:\|\|<br>3' AAGUCUUCUUGUUUGGUUC 5' |
| SEQ ID 726 | 5' CUAGGCAUCAUACGUGACU 3'<br>\|\|\|\|\|\|\|:\|\|\|\|\|\|\|\|:\|\|<br>3' GAUCCGUAGUAUGCACUGA 5' |
| SEQ ID 727 | 5' UUGCAGAUAUUGUGGACAC 3'<br>\|\|\|\|\|\|\|:\|\|\|\|\|\|\|\|:\|\|<br>3' AACGUCUAUAACACCUGUG 5' |
| SEQ ID 728 | 5' CAAUUGCCUGAAUCCUCUU 3'<br>\|\|\|\|\|\|\|:\|\|\|\|\|\|\|\|:\|\|<br>3' GUUAACGGACUUAGGAGAA 5' |
| SEQ ID 729 | 5' UUGCCUGAAUCCUCUUUUU 3'<br>\|\|\|\|\|\|\|:\|\|\|\|\|\|\|\|:\|\|<br>3' AACGGACUUAGGAGAAAAA 5' |
| SEQ ID 730 | 5' AGAUAUUUUCUCCAGCUUC 3'<br>\|\|\|\|\|\|\|:\|\|\|\|\|\|\|\|:\|\|<br>3' UCUAUAAAAGAGGUCGAAG 5' |
| SEQ ID 731 | 5' GAUAUUUUCUCCAGCUUCU 3'<br>\|\|\|\|\|\|\|:\|\|\|\|\|\|\|\|:\|\|<br>3' CUAUAAAAGAGGUCGAAGA 5' |
| SEQ ID 732 | 5' AAUAUAUUCCCCCAAAAGC 3'<br>\|\|\|\|\|\|\|:\|\|\|\|\|\|\|\|:\|\|<br>3' UUAUAUAAGGGGGUUUUCG 5' |
| SEQ ID 733 | 5' AUAUAUUCCCCCAAAAGCC 3'<br>\|\|\|\|\|\|\|:\|\|\|\|\|\|\|\|:\|\|<br>3' UAUAUAAGGGGGUUUUCGG 5' |
| SEQ ID 734 | 5' UAUAUUCCCCCAAAAGCCA 3'<br>\|\|\|\|\|\|\|:\|\|\|\|\|\|\|\|:\|\|<br>3' AUAUAAGGGGGUUUUCGGU 5' |

Figure 2VV

| | |
|---|---|
| SEQ ID 735 | 5' AAGCCAAAUCCCACUCAAA 3'<br>\|\|\|\|\|\|\|::\|\|\|\|\|\|\|:\|\|<br>3' UUCGGUUUAGGGUGAGUUU 5' |
| SEQ ID 736 | 5' AGCCAAAUCCCACUCAAAC 3'<br>\|\|\|\|\|\|\|::\|\|\|\|\|\|\|:\|\|<br>3' UCGGUUUAGGGUGAGUUUG 5' |
| SEQ ID 737 | 5' GCCAAAUCCCACUCAAACC 3'<br>\|\|\|\|\|\|\|::\|\|\|\|\|\|\|:\|\|<br>3' CGGUUUAGGGUGAGUUUGG 5' |
| SEQ ID 738 | 5' AUCCCACUCAAACCUUUCA 3'<br>\|\|\|\|\|\|\|::\|\|\|\|\|\|\|:\|\|<br>3' UAGGGUGAGUUUGGAAAGU 5' |
| SEQ ID 739 | 5' UCCCACUCAAACCUUUCAA 3'<br>\|\|\|\|\|\|\|::\|\|\|\|\|\|\|:\|\|<br>3' AGGGUGAGUUUGGAAAGUU 5' |
| SEQ ID 740 | 5' CCUUUCAACAAAAAUGAGC 3'<br>\|\|\|\|\|\|\|::\|\|\|\|\|\|\|:\|\|<br>3' GGAAAGUUGUUUUUACUCG 5' |
| SEQ ID 741 | 5' CAAAAAUGAGCACGCUUUC 3'<br>\|\|\|\|\|\|\|::\|\|\|\|\|\|\|:\|\|<br>3' GUUUUUACUCGUGCGAAAG 5' |
| SEQ ID 742 | 5' AAAUGAGCACGCUUUCCUA 3'<br>\|\|\|\|\|\|\|::\|\|\|\|\|\|\|:\|\|<br>3' UUUACUCGUGCGAAAGGAU 5' |
| SEQ ID 743 | 5' AAUGAGCACGCUUUCCUAC 3'<br>\|\|\|\|\|\|\|::\|\|\|\|\|\|\|:\|\|<br>3' UUACUCGUGCGAAAGGAUG 5' |
| SEQ ID 744 | 5' AUGAGCACGCUUUCCUACC 3'<br>\|\|\|\|\|\|\|::\|\|\|\|\|\|\|:\|\|<br>3' UACUCGUGCGAAAGGAUGG 5' |
| SEQ ID 745 | 5' UGAGCACGCUUUCCUACCG 3'<br>\|\|\|\|\|\|\|::\|\|\|\|\|\|\|:\|\|<br>3' ACUCGUGCGAAAGGAUGGC 5' |
| SEQ ID 746 | 5' UGUAAGCUCAUCCACCAAG 3'<br>\|\|\|\|\|\|\|::\|\|\|\|\|\|\|:\|\|<br>3' ACAUUCGAGUAGGUGGUUC 5' |
| SEQ ID 747 | 5' GCUCAUCCACCAAGAAGCC 3'<br>\|\|\|\|\|\|\|::\|\|\|\|\|\|\|:\|\|<br>3' CGAGUAGGUGGUUCUUCGG 5' |
| SEQ ID 748 | 5' GAAGCCUGCACCAUGUUUU 3'<br>\|\|\|\|\|\|\|::\|\|\|\|\|\|\|:\|\|<br>3' CUUCGGACGUGGUACAAAA 5' |
| SEQ ID 749 | 5' GCCUGCACCAUGUUUUGAG 3'<br>\|\|\|\|\|\|\|::\|\|\|\|\|\|\|:\|\|<br>3' CGGACGUGGUACAAAACUC 5' |

| | |
|---|---|
| AGTR2 | |

Figure 2WW

| | |
|---|---|
| SEQ ID 750 | 5' UAUGAAGGGCAACUCCACC 3'<br>\|\|\|\|\|\|:\|\|\|\|\|\|\|\|\|\|\|\|<br>3' AUACUUCCCGUUGAGGUGG 5' |
| SEQ ID 751 | 5' CUCCACCCUUGCCACUACU 3'<br>\|\|\|\|\|\|:\|\|\|\|\|\|\|\|\|\|\|\|<br>3' GAGGUGGGAACGGUGAUGA 5' |
| SEQ ID 752 | 5' AAACAUUACCAGCGGUCUU 3'<br>\|\|\|\|\|\|:\|\|\|\|\|\|\|\|\|\|\|\|<br>3' UUUGUAAUGGUCGCCAGAA 5' |
| SEQ ID 753 | 5' AACAUUACCAGCGGUCUUC 3'<br>\|\|\|\|\|\|:\|\|\|\|\|\|\|\|\|\|\|\|<br>3' UUGUAAUGGUCGCCAGAAG 5' |
| SEQ ID 754 | 5' ACAUUACCAGCGGUCUUCA 3'<br>\|\|\|\|\|\|:\|\|\|\|\|\|\|\|\|\|\|\|<br>3' UGUAAUGGUCGCCAGAAGU 5' |
| SEQ ID 755 | 5' CAUUACCAGCGGUCUUCAC 3'<br>\|\|\|\|\|\|:\|\|\|\|\|\|\|\|\|\|\|\|<br>3' GUAAUCCUCGCCAGAAGUG 5' |
| SEQ ID 756 | 5' CAUCUCUGGCAACAAUGAG 3'<br>\|\|\|\|\|\|:\|\|\|\|\|\|\|\|\|\|\|\|<br>3' GUAGAGACCGUUGUUACUC 5' |
| SEQ ID 757 | 5' CAAUGAGUCUACCUUGAAC 3'<br>\|\|\|\|\|\|:\|\|\|\|\|\|\|\|\|\|\|\|<br>3' GUUACUCAGAUGGAACUUG 5' |
| SEQ ID 758 | 5' UGAGUCUACCUUGAACUGU 3'<br>\|\|\|\|\|\|:\|\|\|\|\|\|\|\|\|\|\|\|<br>3' ACUCAGAUGGAACUUGACA 5' |
| SEQ ID 759 | 5' CUGUUCACAGAAACCAUCA 3'<br>\|\|\|\|\|\|:\|\|\|\|\|\|\|\|\|\|\|\|<br>3' GACAAGUGUCUUUGGUAGU 5' |
| SEQ ID 760 | 5' CCAUCAGAUAAGCAUUUAG 3'<br>\|\|\|\|\|\|:\|\|\|\|\|\|\|\|\|\|\|\|<br>3' GGUAGUCUAUUCGUAAAUC 5' |
| SEQ ID 761 | 5' GCAUUUAGAUGCAAUUCCU 3'<br>\|\|\|\|\|\|:\|\|\|\|\|\|\|\|\|\|\|\|<br>3' CGUAAAUCUACGUUAAGGA 5' |
| SEQ ID 762 | 5' UAUUGUCGUGGUUACACUG 3'<br>\|\|\|\|\|\|:\|\|\|\|\|\|\|\|\|\|\|\|<br>3' AUAACAGCACCAAUGUGAC 5' |
| SEQ ID 763 | 5' AAGGGUCCUAAAAAGGUUU 3'<br>\|\|\|\|\|\|:\|\|\|\|\|\|\|\|\|\|\|\|<br>3' UUCCCAGGAUUUUUCCAAA 5' |
| SEQ ID 764 | 5' AGGGUCCUAAAAAGGUUUC 3'<br>\|\|\|\|\|\|:\|\|\|\|\|\|\|\|\|\|\|\|<br>3' UCCCAGGAUUUUUCCAAAG 5' |
| SEQ ID 765 | 5' GGGUCCUAAAAAGGUUUCU 3'<br>\|\|\|\|\|\|:\|\|\|\|\|\|\|\|\|\|\|\|<br>3' CCCAGGAUUUUUCCAAAGA 5' |

Figure 2XX

| | |
|---|---|
| SEQ ID 766 | 5' GGUUUCUAGCAUAUACAUC 3'<br>\|\|:\|\|\|:\|\|\|\|\|\|\|\|:\|\|\|<br>3' CCAAAGAUCGUAUAUGUAG 5' |
| SEQ ID 767 | 5' CCUCGCUGUGGCUGAUUUA 3'<br>\|\|:\|\|\|:\|\|\|\|\|\|\|\|:\|\|\|<br>3' GGAGCGACACCGACUAAAU 5' |
| SEQ ID 768 | 5' UCUGUCAUCUACCCCUUUC 3'<br>\|\|:\|\|\|:\|\|\|\|\|\|\|\|:\|\|\|<br>3' AGACAGUAGAUGGGGAAAG 5' |
| SEQ ID 769 | 5' AGAAGAAAUCCCUGGCAAG 3'<br>\|\|:\|\|\|:\|\|\|\|\|\|\|\|:\|\|\|<br>3' UCUUCUUUAGGGACCGUUC 5' |
| SEQ ID 770 | 5' GAAGAAAUCCCUGGCAAGC 3'<br>\|\|:\|\|\|:\|\|\|\|\|\|\|\|:\|\|\|<br>3' CUUCUUUAGGGACCGUUCG 5' |
| SEQ ID 771 | 5' GAAAUCCCUGGCAAGCAUC 3'<br>\|\|:\|\|\|:\|\|\|\|\|\|\|\|:\|\|\|<br>3' CUUUAGGGACCGUUCGUAG 5' |
| SEQ ID 772 | 5' AUCCCUGGCAAGCAUCUUA 3'<br>\|\|:\|\|\|:\|\|\|\|\|\|\|\|:\|\|\|<br>3' UAGGGACCGUUCGUAGAAU 5' |
| SEQ ID 773 | 5' UCCCUGGCAAGCAUCUUAU 3'<br>\|\|:\|\|\|:\|\|\|\|\|\|\|\|:\|\|\|<br>3' AGGGACCGUUCGUAGAAUA 5' |
| SEQ ID 774 | 5' GCAUCUUAUAUAGUUCCCC 3'<br>\|\|:\|\|\|:\|\|\|\|\|\|\|\|:\|\|\|<br>3' CGUAGAAUAUAUCAAGGGG 5' |
| SEQ ID 775 | 5' CCAUUGAAUACUUAGGAGU 3'<br>\|\|:\|\|\|:\|\|\|\|\|\|\|\|:\|\|\|<br>3' GGUAACUUAUGAAUCCUCA 5' |
| SEQ ID 776 | 5' UACUUAGGAGUGAAUCCUU 3'<br>\|\|:\|\|\|:\|\|\|\|\|\|\|\|:\|\|\|<br>3' AUGAAUCCUCACUUAGGAA 5' |
| SEQ ID 777 | 5' UGCUUGCAUUAUGGCUUUC 3'<br>\|\|:\|\|\|:\|\|\|\|\|\|\|\|:\|\|\|<br>3' ACGAACGUAAUACCGAAAG 5' |
| SEQ ID 778 | 5' AUAUGCCCAAUGGUCAGCU 3'<br>\|\|:\|\|\|:\|\|\|\|\|\|\|\|:\|\|\|<br>3' UAUACGGGUUACCAGUCGA 5' |
| SEQ ID 779 | 5' UAUGCCCAAUGGUCAGCUG 3'<br>\|\|:\|\|\|:\|\|\|\|\|\|\|\|:\|\|\|<br>3' AUACGGGUUACCAGUCGAC 5' |
| SEQ ID 780 | 5' UGGUCAGCUGGGAUUGCCU 3'<br>\|\|:\|\|\|:\|\|\|\|\|\|\|\|:\|\|\|<br>3' ACCAGUCGACCCUAACGGA 5' |
| SEQ ID 781 | 5' AACACUUACUGAAGACGAA 3'<br>\|\|:\|\|\|:\|\|\|\|\|\|\|\|:\|\|\|<br>3' UUGUGAAUGACUUCUGCUU 5' |

Figure 2YY

| | |
|---|---|
| SEQ ID 782 | 5' ACACUUACUGAAGACGAAU 3'<br>\|\|::\|\|\|\|\|\|\|:\|\|\|:\|\|\|<br>3' UGUGAAUGACUUCUGCUUA 5' |
| SEQ ID 783 | 5' CACUUACUGAAGACGAAUA 3'<br>\|\|::\|\|\|\|\|\|\|:\|\|\|:\|\|\|<br>3' GUGAAUGACUUCUGCUUAU 5' |
| SEQ ID 784 | 5' GACGAAUAGCUAUGGGAAG 3'<br>\|\|::\|\|\|\|\|\|\|:\|\|\|:\|\|\|<br>3' CUGCUUAUCGAUACCCUUC 5' |
| SEQ ID 785 | 5' UAGCUAUGGGAAGAACAGG 3'<br>\|\|::\|\|\|\|\|\|\|:\|\|\|:\|\|\|<br>3' AUCGAUACCCUUCUUGUCC 5' |
| SEQ ID 786 | 5' GAACAGGAUAACCCGUGAC 3'<br>\|\|::\|\|\|\|\|\|\|:\|\|\|:\|\|\|<br>3' CUUGUCCUAUUGGGCACUG 5' |
| SEQ ID 787 | 5' CAGGAUAACCCGUGACCAA 3'<br>\|\|::\|\|\|\|\|\|\|:\|\|\|:\|\|\|<br>3' GUCCUAUUGGGCACUGGUU 5' |
| SEQ ID 788 | 5' CCCGUGACCAAGUCCUGAA 3'<br>\|\|::\|\|\|\|\|\|\|:\|\|\|:\|\|\|<br>3' GGGCACUGGUUCAGGACUU 5' |
| SEQ ID 789 | 5' GUCCUGAAGAUGGCAGCUG 3'<br>\|\|::\|\|\|\|\|\|\|:\|\|\|:\|\|\|<br>3' CAGGACUUCUACCGUCGAC 5' |
| SEQ ID 790 | 5' GAUGGCAGCUGCUGUUGUU 3'<br>\|\|::\|\|\|\|\|\|\|:\|\|\|:\|\|\|<br>3' CUACCGUCGACGACAACAA 5' |
| SEQ ID 791 | 5' UAGCUGCGAAGUUAUAGCA 3'<br>\|\|::\|\|\|\|\|\|\|:\|\|\|:\|\|\|<br>3' AUCGACGCUUCAAUAUCGU 5' |
| SEQ ID 792 | 5' GUUAUAGCAGUCAUUGACC 3'<br>\|\|::\|\|\|\|\|\|\|:\|\|\|:\|\|\|<br>3' CAAUAUCGUCAGUAACUGG 5' |
| SEQ ID 793 | 5' CAGCUGCGUUAAUCCGUUU 3'<br>\|\|::\|\|\|\|\|\|\|:\|\|\|:\|\|\|<br>3' GUCGACGCAAUUAGGCAAA 5' |
| SEQ ID 794 | 5' ACCGGUUCCAACAGAAGCU 3'<br>\|\|::\|\|\|\|\|\|\|:\|\|\|:\|\|\|<br>3' UGGCCAAGGUUGUCUUCGA 5' |
| SEQ ID 795 | 5' CCGGUUCCAACAGAAGCUC 3'<br>\|\|::\|\|\|\|\|\|\|:\|\|\|:\|\|\|<br>3' GGCCAAGGUUGUCUUCGAG 5' |
| SEQ ID 796 | 5' CAGAAGCUCCGCAGUGUGU 3'<br>\|\|::\|\|\|\|\|\|\|:\|\|\|:\|\|\|<br>3' GUCUUCGAGGCGUCACACA 5' |
| SEQ ID 797 | 5' GCUCCGCAGUGUGUUUAGG 3'<br>\|\|::\|\|\|\|\|\|\|:\|\|\|:\|\|\|<br>3' CGAGGCGUCACACAAAUCC 5' |

Figure 2ZZ

| | |
|---|---|
| SEQ ID 798 | 5' UUACUUGGCUCCAAGGGAA 3'<br>\|\|:\|\|\|\|\|\|\|:\|\|\|\|:\|\|\|<br>3' AAUGAACCGAGGUUCCCUU 5' |
| SEQ ID 799 | 5' GGCAAAAGAGAGACUAUGU 3'<br>\|\|:\|\|\|\|\|\|\|:\|\|\|\|:\|\|\|<br>3' CCCUUUUCUCUCUCAUACA 5' |
| SEQ ID 800 | 5' AAGAGAGAGUAUGUCUUGC 3'<br>\|\|:\|\|\|\|\|\|\|:\|\|\|\|:\|\|\|<br>3' UUCUCUCUCAUACAGAACG 5' |
| SEQ ID 801 | 5' ACAGAGAGUAUGUCUUGCC 3'<br>\|\|:\|\|\|\|\|\|\|:\|\|\|\|:\|\|\|<br>3' UCUCUCUCAUACAGAACGG 5' |
| SEQ ID 802 | 5' GAGAGAGUAUGUCUUGCCG 3'<br>\|\|:\|\|\|\|\|\|\|:\|\|\|\|:\|\|\|<br>3' CUCUCUCAUACAGAACGGC 5' |
| SEQ ID 803 | 5' AAGCAGUUCUCUUAGAGAA 3'<br>\|\|:\|\|\|\|\|\|\|:\|\|\|\|:\|\|\|<br>3' UUCGUCAAGAGAAUCUCUU 5' |
| SEQ ID 804 | 5' AGCAGUUCUCUUAGAGAAA 3'<br>\|\|:\|\|\|\|\|\|\|:\|\|\|\|:\|\|\|<br>3' UCGUCAAGAGAAUCUCUUU 5' |
| SEQ ID 805 | 5' GCAGUUCUCUUAGAGAAAU 3'<br>\|\|:\|\|\|\|\|\|\|:\|\|\|\|:\|\|\|<br>3' CGUCAAGAGAAUCUCUUUA 5' |
| SEQ ID 806 | 5' AUGGAGACCUUUGUGUCUU 3'<br>\|\|:\|\|\|\|\|\|\|:\|\|\|\|:\|\|\|<br>3' UACCUCUGGAAACACAGAA 5' |
| SEQ ID 807 | 5' UGGAGACCUUUGUGUCUUA 3'<br>\|\|:\|\|\|\|\|\|\|:\|\|\|\|:\|\|\|<br>3' ACCUCUGGAAACACAGAAU 5' |

| ACE1 | |
|---|---|
| SEQ ID 808 | 5' CUUUUCUGCUGACGAGGCC 3'<br>\|\|:\|\|\|\|\|\|\|:\|\|\|\|:\|\|\|<br>3' GAAAAGACGACUGCUCCGG 5' |
| SEQ ID 809 | 5' CAGGUGCUGUUCCAGAGCC 3'<br>\|\|:\|\|\|\|\|\|\|:\|\|\|\|:\|\|\|<br>3' GUCCACGACAAGGUCUCGG 5' |
| SEQ ID 810 | 5' CAUCACCGCGCAGAAUGCA 3'<br>\|\|:\|\|\|\|\|\|\|:\|\|\|\|:\|\|\|<br>3' GUAGUGGCGCCUCUUACGU 5' |
| SEQ ID 811 | 5' UGCAAGGCGCCAGGAGGAA 3'<br>\|\|:\|\|\|\|\|\|\|:\|\|\|\|:\|\|\|<br>3' ACGUUCCGCGGUCCUCCUU 5' |
| SEQ ID 812 | 5' GGCCAAGGAGCUGUAUGAA 3'<br>\|\|:\|\|\|\|\|\|\|:\|\|\|\|:\|\|\|<br>3' CCGGUUCCUCGACAUACUU 5' |

Figure 2AAA

| | |
|---|---|
| SEQ ID 813 | 5' CGAGCUGUAUGAACCGAUC 3'<br>:\|\|\|\|:\|\|:\|:\|\|:\|\|\|\|\|<br>3' GCUCGACAUACUUGGCUAG 5' |
| SEQ ID 814 | 5' CCGAUCUGGCAGAACUUCA 3'<br>:\|\|\|\|:\|\|:\|:\|\|:\|\|\|\|\|<br>3' GGCUAGACCGUCUUGAAGU 5' |
| SEQ ID 815 | 5' CGCCCUGCUAAGCAACAUG 3'<br>:\|\|\|\|:\|\|:\|:\|\|:\|\|\|\|\|<br>3' GCGGGACGAUUCGUUGUAC 5' |
| SEQ ID 816 | 5' GCAACAUGAGCAGGAUCUA 3'<br>:\|\|\|\|:\|\|:\|:\|\|:\|\|\|\|\|<br>3' CGUUGUACUCGUCCUAGAU 5' |
| SEQ ID 817 | 5' CAUGAGCAGGAUCUACUCC 3'<br>:\|\|\|\|:\|\|:\|:\|\|:\|\|\|\|\|<br>3' GUACUCGUCCUAGAUGAGG 5' |
| SEQ ID 818 | 5' GGUCUGCCUCCCCAACAAG 3'<br>:\|\|\|\|:\|\|:\|:\|\|:\|\|\|\|\|<br>3' CCAGACGGAGGGGUUGUUC 5' |
| SEQ ID 819 | 5' CAAGACUGCCACCUGCUGG 3'<br>:\|\|\|\|:\|\|:\|:\|\|:\|\|\|\|\|<br>3' GUUCUGACGGUGGACGACC 5' |
| SEQ ID 820 | 5' CAUCCUGGCUUCCUCGCGA 3'<br>:\|\|\|\|:\|\|:\|:\|\|:\|\|\|\|\|<br>3' GUAGGACCGAAGGAGCGCU 5' |
| SEQ ID 821 | 5' GCUACGCCAUGCUCCUGUU 3'<br>:\|\|\|\|:\|\|:\|:\|\|:\|\|\|\|\|<br>3' CGAUGCGGUACGAGGACAA 5' |
| SEQ ID 822 | 5' ACCGCUGUACGAGGAUUUC 3'<br>:\|\|\|\|:\|\|:\|:\|\|:\|\|\|\|\|<br>3' UGGCGACAUGCUCCUAAAG 5' |
| SEQ ID 823 | 5' CCGCUGUACGAGGAUUUCA 3'<br>:\|\|\|\|:\|\|:\|:\|\|:\|\|\|\|\|<br>3' GGCGACAUGCUCCUAAAGU 5' |
| SEQ ID 824 | 5' UGAAGCCUACAAGCAGGAC 3'<br>:\|\|\|\|:\|\|:\|:\|\|:\|\|\|\|\|<br>3' ACUUCGGAUGUUCGUCCUG 5' |
| SEQ ID 825 | 5' GCCUACAAGCAGGACGGCU 3'<br>:\|\|\|\|:\|\|:\|:\|\|:\|\|\|\|\|<br>3' CGGAUGUUCGUCCUGCCGA 5' |
| SEQ ID 826 | 5' GCAGGACGGCUUCACAGAC 3'<br>:\|\|\|\|:\|\|:\|:\|\|:\|\|\|\|\|<br>3' CGUCCUGCCGAAGUGUCUG 5' |
| SEQ ID 827 | 5' CACCUCUACCAACAGCUAG 3'<br>:\|\|\|\|:\|\|:\|:\|\|:\|\|\|\|\|<br>3' GUGGAGAUGGUUGUCGAUC 5' |
| SEQ ID 828 | 5' CAGCUAGAGCCCCUCUACC 3'<br>:\|\|\|\|:\|\|:\|:\|\|:\|\|\|\|\|<br>3' GUCGAUCUCGGGGAGAUGG 5' |

Figure 2BBB

| | |
|---|---|
| SEQ ID 829 | 5' AACAUCUACCACAUGGUGG 3'<br>:\|\|\|\|\|\|\|\|\|\|\|\|:\|\|:\|:<br>3' UUGUAGAUGCUGUACCACC 5' |
| SEQ ID 830 | 5' ACAUCUACCACAUGGUGGU 3'<br>:\|\|\|\|\|\|\|\|\|\|\|\|:\|\|:\|:<br>3' UGUAGAUGCUGUACCACCA 5' |
| SEQ ID 831 | 5' CAUCUACGACAUGGUGGUG 3'<br>:\|\|\|\|\|\|\|\|\|\|\|\|:\|\|:\|:<br>3' GUAGAUGCUGUACCACCAC 5' |
| SEQ ID 832 | 5' GCCCAACCUCGAUGUCACC 3'<br>:\|\|\|\|\|\|\|\|\|\|\|\|:\|\|:\|:<br>3' CGGGUUGGAGCUACAGUGG 5' |
| SEQ ID 833 | 5' CCUCGAUGUCACCAGUACU 3'<br>:\|\|\|\|\|\|\|\|\|\|\|\|:\|\|:\|:<br>3' GGAGCUACAGUGGUCAUGA 5' |
| SEQ ID 834 | 5' GGGUCGAUGCUGGAGAAGC 3'<br>:\|\|\|\|\|\|\|\|\|\|\|\|:\|\|:\|:<br>3' CCCAGCUACGACCUCUUCG 5' |
| SEQ ID 835 | 5' CAGCAAAGACUUCAGGAUC 3'<br>:\|\|\|\|\|\|\|\|\|\|\|\|:\|\|:\|:<br>3' GUCCUUUCUGAAGUCCUAG 5' |
| SEQ ID 836 | 5' AGACUUCAGGAUCAAGCAG 3'<br>:\|\|\|\|\|\|\|\|\|\|\|\|:\|\|:\|:<br>3' UCUGAAGUCCUAGUUCGUC 5' |
| SEQ ID 837 | 5' GACUUCAGGAUCAAGCAGU 3'<br>:\|\|\|\|\|\|\|\|\|\|\|\|:\|\|:\|:<br>3' CUGAAGUCCUAGUUCGUCA 5' |
| SEQ ID 838 | 5' CAUCUGCACAAAAUCGGCC 3'<br>:\|\|\|\|\|\|\|\|\|\|\|\|:\|\|:\|:<br>3' GUAGACGUGUUUUAGCCGG 5' |
| SEQ ID 839 | 5' AAUCGGCCUGCUGGACCGU 3'<br>:\|\|\|\|\|\|\|\|\|\|\|\|:\|\|:\|:<br>3' UUAGCCGGACGACCUGGCA 5' |
| SEQ ID 840 | 5' UGACACGGAAAGUGACAUC 3'<br>:\|\|\|\|\|\|\|\|\|\|\|\|:\|\|:\|:<br>3' ACUGUGCCUUUCACUGUAG 5' |
| SEQ ID 841 | 5' AGUGACAUCAAUUACUUGC 3'<br>:\|\|\|\|\|\|\|\|\|\|\|\|:\|\|:\|:<br>3' UCACUGUAGUUAAUGAACG 5' |
| SEQ ID 842 | 5' GUGACAUCAAUUACUUGCU 3'<br>:\|\|\|\|\|\|\|\|\|\|\|\|:\|\|:\|:<br>3' CACUGUAGUUAAUGAACGA 5' |
| SEQ ID 843 | 5' AUGGCACUGGAAAAAAUUG 3'<br>:\|\|\|\|\|\|\|\|\|\|\|\|:\|\|:\|:<br>3' UACCGUGACCUUUUUUAAC 5' |
| SEQ ID 844 | 5' UGGCACUGGAAAAAAUUGC 3'<br>:\|\|\|\|\|\|\|\|\|\|\|\|:\|\|:\|:<br>3' ACCGUGACCUUUUUUAACG 5' |

Figure 2CCC

| | |
|---|---|
| SEQ ID 845 | 5' AAAAUUGCCUUCCUGCCCU 3'<br>3' UUUUAACGGAACCACGGGA 5' |
| SEQ ID 846 | 5' AAAUUGCCUUCCUGCCCUU 3'<br>3' UUUAACGGAAGGACGGGAA 5' |
| SEQ ID 847 | 5' AAUUGCCUUCCUGCCCUUU 3'<br>3' UUAACGGAAGGACGGGAAA 5' |
| SEQ ID 848 | 5' AUUGCCUUCCUGCCCUUUG 3'<br>3' UAACGGAAGGACGGGAAAC 5' |
| SEQ ID 849 | 5' UUGCCUUCCUGCCCUUUGG 3'<br>3' AACGGAAGGACGGGAAACC 5' |
| SEQ ID 850 | 5' CUUCGACUGGUCGUAUCUU 3'<br>3' GAAGCUGACCACCAUAGAA 5' |
| SEQ ID 851 | 5' CCAAGUAUCAGGGGAUCUG 3'<br>3' GGUUCAUAGUCCCCUAGAC 5' |
| SEQ ID 852 | 5' GUAUCAGGGGAUCUGUCCU 3'<br>3' CAUAGUCCCCUAGACAGGA 5' |
| SEQ ID 853 | 5' ACGAAACCCACUUUGAUGC 3'<br>3' UGCUUUGGGUGAAACUACG 5' |
| SEQ ID 854 | 5' CGAAACCCACUUUGAUGCU 3'<br>3' GCUUUGGGUGAAACUACGA 5' |
| SEQ ID 855 | 5' ACCCACUUUGAUGCUGGAG 3'<br>3' UGGGUGAAACUACUACCUC 5' |
| SEQ ID 856 | 5' CCCACUUUGAUGCUGGAGC 3'<br>3' GGGUGAAACUACGACCUCG 5' |
| SEQ ID 857 | 5' GUUUCAUGUUCCAAAUGUG 3'<br>3' CAAAGUACAAGGUUUACAC 5' |
| SEQ ID 858 | 5' AUGUGACACCAUACAUCAG 3'<br>3' UACACUGUGGUAUGUAGUC 5' |
| SEQ ID 859 | 5' UGUGACACCAUACAUCAGG 3'<br>3' ACACUGUGGUAUGUAGUCC 5' |
| SEQ ID 860 | 5' GGACAUGGUCGGCUUAGAU 3'<br>3' CCUGUACCAGCCGAAUCUA 5' |

Figure 2DDD

| | |
|---|---|
| SEQ ID 861 | 5' GUACUUCCAGCCAGUCACC 3'<br>3' CAUGAAGGUCGGUCAGUGG 5' |
| SEQ ID 862 | 5' CUACCCGGAGGGCAUAGAC 3'<br>3' GAUGGGCCUCCCGUAUCUG 5' |
| SEQ ID 863 | 5' GUUUGUGGAGGAAUAUGAC 3'<br>3' CAAACACCUCCUUAUACUG 5' |
| SEQ ID 864 | 5' UAUGACCGGACAUCCCAGG 3'<br>3' AUACUGGCCUGUAGGGUCC 5' |
| SEQ ID 865 | 5' CGAGUAUGCCGAGGCCAAC 3'<br>3' GCUCAUACGGCUCCGGUUG 5' |
| SEQ ID 866 | 5' CUGGAACUACAACACCAAC 3'<br>3' GACCUUGAUGUUGUGGUUG 5' |
| SEQ ID 867 | 5' CUACAACACCAACAUCACC 3'<br>3' GAUGUUGUGGUUGUAGUGG 5' |
| SEQ ID 868 | 5' CACCAACAUCACCACAGAG 3'<br>3' GUGGUUGUAGUGGUGUCUC 5' |
| SEQ ID 869 | 5' CAUCACCACAGAGACCAGC 3'<br>3' GUAGUGGUGUCUCUGGUCG 5' |
| SEQ ID 870 | 5' GAUUCUGCUGCAGAAGAAC 3'<br>3' CUAAGACGACGUCUUCUUG 5' |
| SEQ ID 871 | 5' GAACAUGCAAAUAGCCAAC 3'<br>3' CUUGUACGUUUAUCGGUUG 5' |
| SEQ ID 872 | 5' CAUGCAAAUAGCCAACCAC 3'<br>3' GUACGUUUAUCGGUUGGUG 5' |
| SEQ ID 873 | 5' AUAGCCAACCACACCCUGA 3'<br>3' UAUCGGUUGGUGUGGGACU 5' |
| SEQ ID 874 | 5' UAGCCAACCACACCCUGAA 3'<br>3' AUCGGUUGGUGUGGGACUU 5' |
| SEQ ID 875 | 5' CCACACCCUGAAGUACGGC 3'<br>3' GGUGUGGGACUUCAUGCCG 5' |
| SEQ ID 876 | 5' GUUUGAUCUGAACCAGUUG 3'<br>3' CAAACUACACUUGGUCAAC 5' |

Figure 2EEE

| | |
|---|---|
| SEQ ID 877 | 5' CCAGUUGCAGAACACCACU 3'<br>3' GGUCAACGUCUUGUGGUGA 5' |
| SEQ ID 878 | 5' CACCACUAUCAAGCGGAUC 3'<br>3' GUGGUGAUAGUUCGCCUAG 5' |
| SEQ ID 879 | 5' GCGGAUCAUAAAGAAGGUU 3'<br>3' CGCCUAGUAUUUCUUCCAA 5' |
| SEQ ID 880 | 5' AGAAGGUUCAGGACCUAGA 3'<br>3' UCUUCCAAGUCCUGGAUCU 5' |
| SEQ ID 881 | 5' GAAGGUUCAGGACCUAGAA 3'<br>3' CUUCCAAGUCCUGGAUCUU 5' |
| SEQ ID 882 | 5' GGUUCAGGACCUAGAACGG 3'<br>3' CCAAGUCCUGGAUCUUGCC 5' |
| SEQ ID 883 | 5' CAAGAUCCUGUUGGAUAUG 3'<br>3' GUUCUAGGACAACCUAUAC 5' |
| SEQ ID 884 | 5' GAUCCUGUUGGAUAUGGAA 3'<br>3' CUAGGACAACCUAUACCUU 5' |
| SEQ ID 885 | 5' ACCACCUACAGCGUGGCCA 3'<br>3' UGGUGGAUGUCGCACCGGU 5' |
| SEQ ID 886 | 5' AUAUGAAGACCUGUUAUGG 3'<br>3' UAUACUUCUGGACAAUACC 5' |
| SEQ ID 887 | 5' UAUGAAGACCUGUUAUGGG 3'<br>3' AUACUUCUGGACAAUACCC 5' |
| SEQ ID 888 | 5' GACCUGUUAUGGGCAUGGG 3'<br>3' CUGGACAAUACCCGUACCC 5' |
| SEQ ID 889 | 5' AUACGUGGAACUCAUCAAC 3'<br>3' UAUGCACCUUGAGUAGUUG 5' |
| SEQ ID 890 | 5' UACGUGGAACUCAUCAACC 3'<br>3' AUGCACCUUGAGUAGUUGG 5' |
| SEQ ID 891 | 5' CUCAUCAACCAGGCUGCCC 3'<br>3' GAGUAGUUGGUCCGACGGG 5' |
| SEQ ID 892 | 5' UGGCUAUGUAGAUGCAGGG 3'<br>3' ACCGAUACAUCUACGUCCC 5' |

Figure 2FFF

| | |
|---|---|
| SEQ ID 893 | 5' CAUCUAUGACUUGGUGGUG 3'<br>\|\|\|\|\|\|:\|\|\|\|\|\|\|\|\|\|\|\|<br>3' GUAGAUACUGAACCACCAC 5' |
| SEQ ID 894 | 5' GGAGGCUGAUGAUUUCUUC 3'<br>\|\|\|\|\|\|:\|\|\|\|\|\|\|\|\|\|\|\|<br>3' CCUCCGACUACUAAAGAAG 5' |
| SEQ ID 895 | 5' CAAGUCGAUGCUGGAGAAG 3'<br>\|\|\|\|\|\|:\|\|\|\|\|\|\|\|\|\|\|\|<br>3' GUUCAGCUACGACCUCUUC 5' |
| SEQ ID 896 | 5' GUCGAUGCUGGAGAAGCCA 3'<br>\|\|\|\|\|\|:\|\|\|\|\|\|\|\|\|\|\|\|<br>3' CAGCUACGACCUCUUCGGU 5' |
| SEQ ID 897 | 5' CGGCAAGGACUUCCGGAUC 3'<br>\|\|\|\|\|\|:\|\|\|\|\|\|\|\|\|\|\|\|<br>3' GCCGUUCCUGAAGGCCUAG 5' |
| SEQ ID 898 | 5' GGACUUCCGGAUCAAGCAG 3'<br>\|\|\|\|\|\|:\|\|\|\|\|\|\|\|\|\|\|\|<br>3' CCUGAAGGCCUAGUUCGUC 5' |
| SEQ ID 899 | 5' GCAGUGCACCACCGUGAAC 3'<br>\|\|\|\|\|\|:\|\|\|\|\|\|\|\|\|\|\|\|<br>3' CGUCACGUGGUGGCACUUG 5' |
| SEQ ID 900 | 5' CUUGGAGGACCUGGUGGUG 3'<br>\|\|\|\|\|\|:\|\|\|\|\|\|\|\|\|\|\|\|<br>3' GAACCUCCUGGACCACCAC 5' |
| SEQ ID 901 | 5' AUGGGCCACAUCCAGUAUU 3'<br>\|\|\|\|\|\|:\|\|\|\|\|\|\|\|\|\|\|\|<br>3' UACCCGGUGUAGGUCAUAA 5' |
| SEQ ID 902 | 5' UGGGCCACAUCCAGUAUUU 3'<br>\|\|\|\|\|\|:\|\|\|\|\|\|\|\|\|\|\|\|<br>3' ACCCGGUGUAGGUCAUAAA 5' |
| SEQ ID 903 | 5' AGACUUACCUGUGGCCUUG 3'<br>\|\|\|\|\|\|:\|\|\|\|\|\|\|\|\|\|\|\|<br>3' UCUGAAUGGACACCGGAAC 5' |
| SEQ ID 904 | 5' GACUUACCUGUGGCCUUGA 3'<br>\|\|\|\|\|\|:\|\|\|\|\|\|\|\|\|\|\|\|<br>3' CUGAAUGGACACCGGAACU 5' |
| SEQ ID 905 | 5' GCACCUGCACAGUCUCAAC 3'<br>\|\|\|\|\|\|:\|\|\|\|\|\|\|\|\|\|\|\|<br>3' CGUGGACGUGUCAGAGUUG 5' |
| SEQ ID 906 | 5' CCUGCUGAGCAGUGAGGGU 3'<br>\|\|\|\|\|\|:\|\|\|\|\|\|\|\|\|\|\|\|<br>3' GGACGACUCGUCACUCCCA 5' |
| SEQ ID 907 | 5' CUUUCUGAUGAAGAUGGCC 3'<br>\|\|\|\|\|\|:\|\|\|\|\|\|\|\|\|\|\|\|<br>3' GAAAGACUACUUCUACCGG 5' |
| SEQ ID 908 | 5' GAUGGCCCUUGACAAGAUC 3'<br>\|\|\|\|\|\|:\|\|\|\|\|\|\|\|\|\|\|\|<br>3' CUACCGGGAACUGUUCUAG 5' |

Figure 2GGG

| | |
|---|---|
| SEQ ID 909 | 5' GAUCGCCUUUAUCCCCUUC 3'<br>\|\|\|\|\|\|\|\|:\|\|\|:\|\|\|:\|\|<br>3' CUAGCGGAAAUAGGGGAAG 5' |
| SEQ ID 910 | 5' GCAUCACCAAGGAGAACUA 3'<br>\|\|\|\|\|\|\|\|:\|\|\|:\|\|\|:\|\|<br>3' CGUAGUGGUUCCUCUUGAU 5' |
| SEQ ID 911 | 5' GGAGAACUAUAACCAGGAG 3'<br>\|\|\|\|\|\|\|\|:\|\|\|:\|\|\|:\|\|<br>3' CCUCUUGAUAUUGGUCCUC 5' |
| SEQ ID 912 | 5' CUAUAACCAGGAGUGGUGG 3'<br>\|\|\|\|\|\|\|\|:\|\|\|:\|\|\|:\|\|<br>3' GAUAUUGGUCCUCACCACC 5' |
| SEQ ID 913 | 5' GGUGACUUUGACCCAGGGG 3'<br>\|\|\|\|\|\|\|\|:\|\|\|:\|\|\|:\|\|<br>3' CCACUGAAACUGGGUCCCC 5' |
| SEQ ID 914 | 5' GUUCCACAUUCCUUCUAGC 3'<br>\|\|\|\|\|\|\|\|:\|\|\|:\|\|\|:\|\|<br>3' CAAGGUGUAAGGAAGAUCG 5' |
| SEQ ID 915 | 5' GUGUGACAUCUACCAGUCC 3'<br>\|\|\|\|\|\|\|\|:\|\|\|:\|\|\|:\|\|<br>3' CACACUGUAGAUGGUCAGG 5' |
| SEQ ID 916 | 5' GCCAUGCACCUGAUCACGG 3'<br>\|\|\|\|\|\|\|\|:\|\|\|:\|\|\|:\|\|<br>3' CGGUACGUCGACUAGUGCC 5' |
| SEQ ID 917 | 5' CGAGCUGCAUGGGGAGAAG 3'<br>\|\|\|\|\|\|\|\|:\|\|\|:\|\|\|:\|\|<br>3' GCUCGACGUACCCCUCUUC 5' |
| SEQ ID 918 | 5' CAGGUGACAGUCACCCAUG 3'<br>\|\|\|\|\|\|\|\|:\|\|\|:\|\|\|:\|\|<br>3' GUCCACUGUCAGUGGGUAC 5' |
| SEQ ID 919 | 5' GCAGCCAGGCAACAACCAG 3'<br>\|\|\|\|\|\|\|\|:\|\|\|:\|\|\|:\|\|<br>3' CGUCGGUCCGUUGUUGGUC 5' |
| SEQ ID 920 | 5' CAACCAGCAGCCAGACAAC 3'<br>\|\|\|\|\|\|\|\|:\|\|\|:\|\|\|:\|\|<br>3' GUUGGUCGUCGGUCUGUUG 5' |
| SEQ ID 921 | 5' CCAGCAGCCAGACAACCAC 3'<br>\|\|\|\|\|\|\|\|:\|\|\|:\|\|\|:\|\|<br>3' GGUCGUCGGUCUGUUGGUG 5' |
| SEQ ID 922 | 5' ACCUGGUGACUGAUGAGGC 3'<br>\|\|\|\|\|\|\|\|:\|\|\|:\|\|\|:\|\|<br>3' UGGACCACUGACUACUCCG 5' |
| SEQ ID 923 | 5' CCUGGUGACUGAUGAGGCU 3'<br>\|\|\|\|\|\|\|\|:\|\|\|:\|\|\|:\|\|<br>3' GGACCACUGACUACUCCGA 5' |
| SEQ ID 924 | 5' CUGGACGCCGAACUCCGAU 3'<br>\|\|\|\|\|\|\|\|:\|\|\|:\|\|\|:\|\|<br>3' GACCUGCGGCUUGAGGCUA 5' |

Figure 2HHH

| | |
|---|---|
| SEQ ID 925 | 5' CUCCGAUGACUUCUACAAU 3'<br>\|\|\|\|\|\|\|:\|\|\|\|\|\|\|\|\|\|\|<br>3' GAGGCUACUGAAGAUGUUA 5' |
| SEQ ID 926 | 5' UGAGACCGAGACCAAGAUC 3'<br>\|\|\|\|\|\|\|:\|\|\|\|\|\|\|\|\|\|\|<br>3' ACUCUGGCUCUGGUUCUAG 5' |
| SEQ ID 927 | 5' GAUCUUCCUGCAGUUUUAU 3'<br>\|\|\|\|\|\|\|:\|\|\|\|\|\|\|\|\|\|\|<br>3' CUAGAAGGACGUCAAAAUA 5' |
| SEQ ID 928 | 5' ACAGGGAUUUGGGACCAUG 3'<br>\|\|\|\|\|\|\|:\|\|\|\|\|\|\|\|\|\|\|<br>3' UGUCCCUAAACCCUGGUAC 5' |
| SEQ ID 929 | 5' CAGGGAUUUGGGACCAUGG 3'<br>\|\|\|\|\|\|\|:\|\|\|\|\|\|\|\|\|\|\|<br>3' GUCCCUAAACCCUGGUACC 5' |
| SEQ ID 930 | 5' GCAAGAGGAACAAGGGAAG 3'<br>\|\|\|\|\|\|\|:\|\|\|\|\|\|\|\|\|\|\|<br>3' CGUUCUCCUUGUUCCCUUC 5' |
| SEQ ID 931 | 5' GAGGAACAAGGGAAGCCCC 3'<br>\|\|\|\|\|\|\|:\|\|\|\|\|\|\|\|\|\|\|<br>3' CUCCUUGUUCCCUUCGGGG 5' |
| SEQ ID 932 | 5' CAAGGGAAGCCCCAGUGUA 3'<br>\|\|\|\|\|\|\|:\|\|\|\|\|\|\|\|\|\|\|<br>3' GUUCCCUUCGGGGUCACAU 5' |
| SEQ ID 933 | 5' GGGAAGCCCCAGUGUACAU 3'<br>\|\|\|\|\|\|\|:\|\|\|\|\|\|\|\|\|\|\|<br>3' CCCUUCGGGGUCACAUGUA 5' |
| SEQ ID 934 | 5' GCCCCAGUGUACAUGUCAA 3'<br>\|\|\|\|\|\|\|:\|\|\|\|\|\|\|\|\|\|\|<br>3' CGGGGUCACAUGUACAGUU 5' |
| SEQ ID 935 | 5' AGAGGGCUGCAAGCUCUGG 3'<br>\|\|\|\|\|\|\|:\|\|\|\|\|\|\|\|\|\|\|<br>3' UCUCCCGACGUUCGAGACC 5' |
| SEQ ID 936 | 5' GCCCUAAACUUCCUCCAGC 3'<br>\|\|\|\|\|\|\|:\|\|\|\|\|\|\|\|\|\|\|<br>3' CGGGAUUUGAAGGAGGUCG 5' |
| SEQ ID 937 | 5' ACUUCCUCCAGCUGCACAA 3'<br>\|\|\|\|\|\|\|:\|\|\|\|\|\|\|\|\|\|\|<br>3' UGAAGGAGGUCGACGUGUU 5' |
| SEQ ID 938 | 5' CUUCCUCCAGCUGCACAAG 3'<br>\|\|\|\|\|\|\|:\|\|\|\|\|\|\|\|\|\|\|<br>3' GAAGGAGGUCGACGUGUUC 5' |
| SEQ ID 939 | 5' GGACAUGGAGAGGUCCCAG 3'<br>\|\|\|\|\|\|\|:\|\|\|\|\|\|\|\|\|\|\|<br>3' CCUGUACCUCUCCAGGGUC 5' |

| | |
|---|---|
| ACE2 | |

Figure 2III

SEQ ID 940
5' GCUCUUCCUGGCUCCUUCU 3'
||||||:||||||||||||
3' CGAGAAGGACCGAGGAAGA 5'

SEQ ID 941
5' CUGCUGCUCAGUCCACCAU 3'
||||||:||||||||||||
3' GACGACGAGUCAGGUGGUA 5'

SEQ ID 942
5' CAGGCCAAGACAUUUUUGG 3'
||||||:||||||||||||
3' GUCCGGUUCUGUAAAAACC 5'

SEQ ID 943
5' GUUUAACCACGAAGCCGAA 3'
||||||:||||||||||||
3' CAAAUUGGUGCUUCGGCUU 5'

SEQ ID 944
5' CCACGAAGCCCAAGACCUG 3'
||||||:||||||||||||
3' GGUGCUUCGGCUUCUGGAC 5'

SEQ ID 945
5' GCCGAAGACCUGUUCUAUC 3'
||||||:||||||||||||
3' CGGCUUCUGGACAAGAUAG 5'

SEQ ID 946
5' GACCUGUUCUAUCAAAGUU 3'
||||||:||||||||||||
3' CUGGACAAGAUAGUUUCAA 5'

SEQ ID 947
5' AGUUCACUUGCUUCUUGGA 3'
||||||:||||||||||||
3' UCAAGUGAACGAAGAACCU 5'

SEQ ID 948
5' GUUCACUUGCUUCUUGGAA 3'
||||||:||||||||||||
3' CAAGUGAACGAAGAACCUU 5'

SEQ ID 949
5' CACCAAUAUUACUGAAGAG 3'
||||||:||||||||||||
3' GUGGUUAUAAUGACUUCUC 5'

SEQ ID 950
5' GAGAAUGUCCAAAACAUGA 3'
||||||:||||||||||||
3' CUCUUACAGGUUUUGUACU 5'

SEQ ID 951
5' AACAUGAAUAAUGCUGGGG 3'
||||||:||||||||||||
3' UUGUACUUAUUACGACCCC 5'

SEQ ID 952
5' ACAUGAAUAAUGCUGGGGA 3'
||||||:||||||||||||
3' UGUACUUAUUACGACCCCU 5'

SEQ ID 953
5' CAUGAAUAAUGCUGGGGAC 3'
||||||:||||||||||||
3' GUACUUAUUACGACCCCUG 5'

SEQ ID 954
5' UAAUGCUGGGGACAAAUGG 3'
||||||:||||||||||||
3' AUUACGACCCCUGUUUACC 5'

SEQ ID 955
5' UGCUGGGGACAAAUGGUCU 3'
||||||:||||||||||||
3' ACGACCCCUGUUUACCAGA 5'

Figure 2JJJ

SEQ ID 956
5' AUGGUCUGCCUUUUUAAAG 3'
||:|||:||||||||:|||
3' UACCAGACGGAAAAAUUUC 5'

SEQ ID 957
5' UGGUCUGCCUUUUUAAAGG 3'
||:|||:||||||||:|||
3' ACCAGACGGAAAAAUUUCC 5'

SEQ ID 958
5' AGGAACAGUCCACACUUGC 3'
||:|||:||||||||:|||
3' UCCUUGUCAGGUGUGAACG 5'

SEQ ID 959
5' GGAACAGUCCACACUUGCC 3'
||:|||:||||||||:|||
3' CCUUGUCAGGUGUGAACGG 5'

SEQ ID 960
5' CAGUCCACACUUGCCCAAA 3'
||:|||:||||||||:|||
3' GUCAGGUGUGAACGGGUUU 5'

SEQ ID 961
5' GAAAUUCAGAAUCUCACAG 3'
||:|||:||||||||:|||
3' CUUUAAGUCUUAGAGUGUC 5'

SEQ ID 962
5' AUUCAGAAUCUCACAGUCA 3'
||:|||:||||||||:|||
3' UAAGUCUUAGAGUGUCAGU 5'

SEQ ID 963
5' UUCAGAAUCUCACAGUCAA 3'
||:|||:||||||||:|||
3' AAGUCUUAGAGUGUCAGUU 5'

SEQ ID 964
5' UCUCACAGUCAAGCUUCAG 3'
||:|||:||||||||:|||
3' AGAGUGUCAGUUCGAAGUC 5'

SEQ ID 965
5' GCUUCAGCUGCAGGCUCUU 3'
||:|||:||||||||:|||
3' CGAAGUCGACGUCCGAGAA 5'

SEQ ID 966
5' AAUGGGUCUUCAGUGCUCU 3'
||:|||:||||||||:|||
3' UUACCCAGAAGUCACGAGA 5'

SEQ ID 967
5' AUGGGUCUUCAGUGCUCUC 3'
||:|||:||||||||:|||
3' UACCCACAAGUCACGAGAG 5'

SEQ ID 968
5' UGGGUCUUCAGUGCUCUCA 3'
||:|||:||||||||:|||
3' ACCCAGAAGUCACGAGAGU 5'

SEQ ID 969
5' GACAAGAGCAAACGGUUGA 3'
||:|||:||||||||:|||
3' CUGUUCUCGUUUGCCAACU 5'

SEQ ID 970
5' GAGCAAACGGUUGAACACA 3'
||:|||:||||||||:|||
3' CUCGUUUGCCAACUUGUGU 5'

SEQ ID 971
5' ACGGUUCAACACAAUUCUA 3'
||:|||:||||||||:|||
3' UGCCAACUUGUGUUAAGAU 5'

Figure 2KKK

SEQ ID 972
5' CGGUUGAACACAAUUCUAA 3'
||::|||||||:|||:|||
3' GCCAACUUGUGUUAAGAUU 5'

SEQ ID 973
5' AUACAAUGAGCACCAUCUA 3'
||::|||||||:|||:|||
3' UAUGUUACUCGUGGUAGAU 5'

SEQ ID 974
5' UACAAUGAGCACCAUCUAC 3'
||::|||||||:|||:|||
3' AUGUUACUCGUGGUAGAUG 5'

SEQ ID 975
5' UGAGCACCAUCUACAGUAC 3'
||::|||||||:|||:|||
3' ACUCGUGGUAGAUGUCAUG 5'

SEQ ID 976
5' GUUUGUAACCCAGAUAAUC 3'
||::|||||||:|||:|||
3' CAAACAUUGGGUCUAUUAG 5'

SEQ ID 977
5' CCCAGAUAAUCCACAAGAA 3'
||::|||||||:|||:|||
3' GGGUCUAUUAGGUGUUCUU 5'

SEQ ID 978
5' UGCUUAUUACUUGAACCAG 3'
||::|||||||:|||:|||
3' ACGAAUAAUGAACUUGGUC 5'

SEQ ID 979
5' UGGCAAACAGUUUAGACUA 3'
||::|||||||:|||:|||
3' ACCGUUUGUCAAAUCUGAU 5'

SEQ ID 980
5' CAGUUUAGACUACAAUGAG 3'
||::|||||||:|||:|||
3' GUCAAAUCUGAUGUUACUC 5'

SEQ ID 981
5' UGAGAGGCUCUGGGCUUGG 3'
||::|||||||:|||:|||
3' ACUCUCCGAGACCCGAACC 5'

SEQ ID 982
5' AGCUGGAGAUCUGAGGUCG 3'
||::|||||||:|||:|||
3' UCGACCUCUAGACUCCAGC 5'

SEQ ID 983
5' GCUGGAGAUCUGAGGUCGG 3'
||::|||||||:|||:|||
3' CGACCUCUAGACUCCAGCC 5'

SEQ ID 984
5' GCAGCUGAGGCCAUUAUAU 3'
||::|||||||:|||:|||
3' CGUCGACUCCGGUAAUAUA 5'

SEQ ID 985
5' GAGUAUGUGGUCUUGAAAA 3'
||::|||||||:|||:|||
3' CUCAUACACCAGAACUUUU 5'

SEQ ID 986
5' AAAUGAGAUGGCAAGAGCA 3'
||::|||||||:|||:|||
3' UUUACUCUACCGUUCUCGU 5'

SEQ ID 987
5' AAUGAGAUGGCAAGAGCAA 3'
||::|||||||:|||:|||
3' UUACUCUACCGUUCUCGUU 5'

Figure 2:
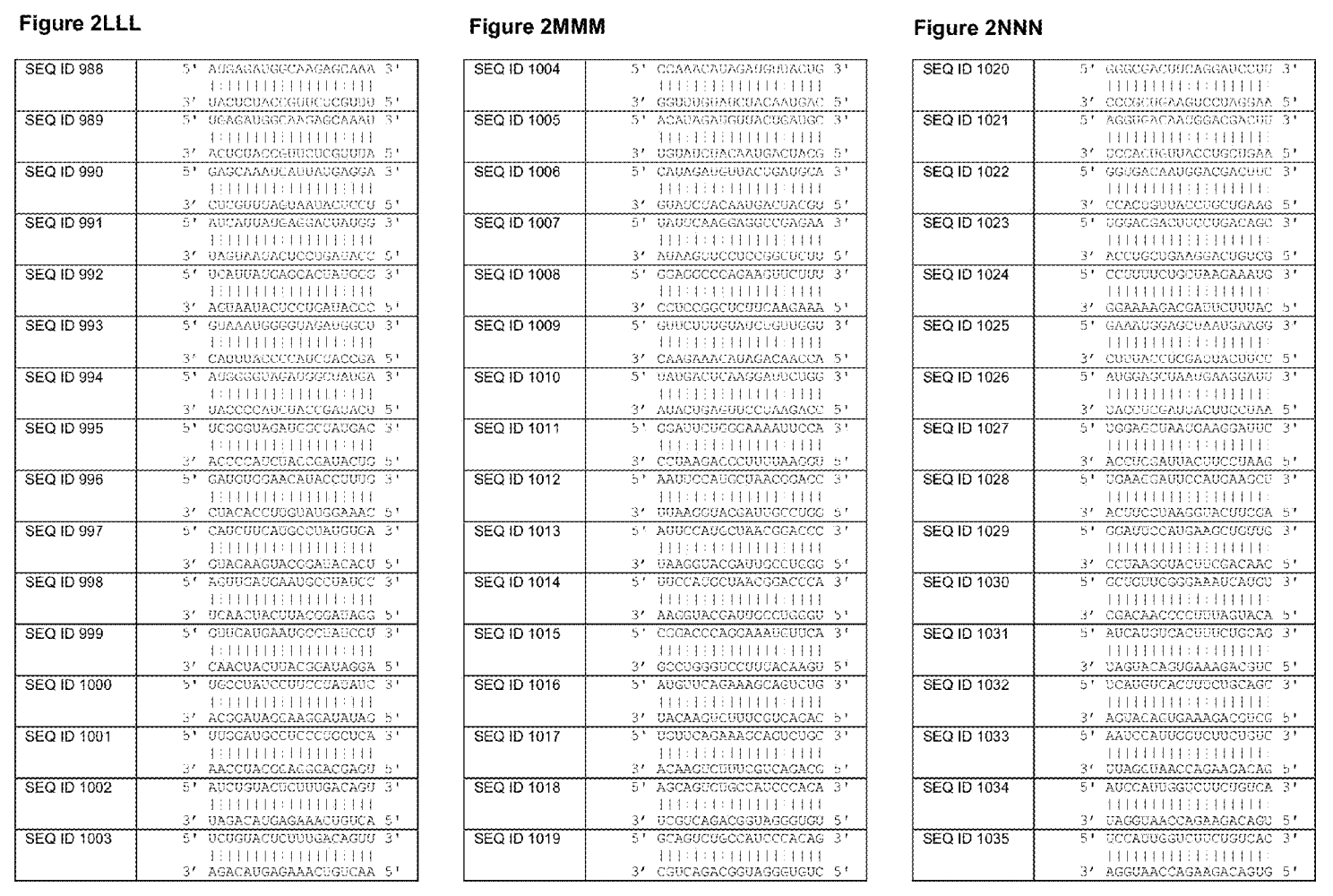

Figure 2LLL

| | |
|---|---|
| SEQ ID 988 | 5' AUGAGAUGGCAAGAGCAAA 3'<br>3' UACUCUACCGUUCUCGUUU 5' |
| SEQ ID 989 | 5' UGAGAUGGCAAGAGCAAAU 3'<br>3' ACUCUACCGUUCUCGUUUA 5' |
| SEQ ID 990 | 5' GAGCAAAUCAUUAUGAGGA 3'<br>3' CUCGUUUAGUAAUACUCCU 5' |
| SEQ ID 991 | 5' AUCAUUAUGAGGACUAUGG 3'<br>3' UAGUAAUACUCCUGAUACC 5' |
| SEQ ID 992 | 5' UCAUUAUCAGCACUAUGGG 3'<br>3' AGUAAUACUCCUGAUACCC 5' |
| SEQ ID 993 | 5' GUAAAUGGGGUAGAUGGCU 3'<br>3' CAUUUACCCCAUCUACCGA 5' |
| SEQ ID 994 | 5' AUGGGGUAGAUGGCUAUGA 3'<br>3' UACCCCAUCUACCGAUACU 5' |
| SEQ ID 995 | 5' UCGGGUAGAUCGCUAUGAC 3'<br>3' ACCCCAUCUACCGAUACUG 5' |
| SEQ ID 996 | 5' GAUGUGGAACAUACCUUUG 3'<br>3' CUACACCUUGUAUGGAAAC 5' |
| SEQ ID 997 | 5' CAUCUUCAUGCCUAUGUCA 3'<br>3' GUACAAGUACGGAUACACU 5' |
| SEQ ID 998 | 5' AGUUGAUCAAUGCCUAUCC 3'<br>3' UCAACUACUUACGGAUAGG 5' |
| SEQ ID 999 | 5' GUUGAUGAAUGCCUAUCCU 3'<br>3' CAACUACUUACGGAUAGGA 5' |
| SEQ ID 1000 | 5' UGCCUAUCCUUCCUAUAUC 3'<br>3' ACGGAUAGCAAGGAUAUAG 5' |
| SEQ ID 1001 | 5' UUGGAUGCCUCCCUGCUCA 3'<br>3' AACCUACGCAGGGACGAGU 5' |
| SEQ ID 1002 | 5' AUCUGUACUCUUUGACAGU 3'<br>3' UAGACAUGAGAAACUGUCA 5' |
| SEQ ID 1003 | 5' UCUGUACUCUUUGACAGUU 3'<br>3' AGACAUGAGAAACUGUCAA 5' |

Figure 2MMM

| | |
|---|---|
| SEQ ID 1004 | 5' CCAAACAUAGAUGUUACUG 3'<br>3' GGUUUGUAUCUACAAUGAC 5' |
| SEQ ID 1005 | 5' ACAUAGAUGUUACUGAUGC 3'<br>3' UGUAUCUACAAUGACUACG 5' |
| SEQ ID 1006 | 5' CAUAGAUGUUACUGAUGCA 3'<br>3' GUAUCUACAAUGACUACGU 5' |
| SEQ ID 1007 | 5' UAUUCAAGGAGGCCGAGAA 3'<br>3' AUAAGUUCCUCCGGCUCUU 5' |
| SEQ ID 1008 | 5' GGAGGCCCAGAAGUUCUUU 3'<br>3' CCUCCGGCUCUUCAAGAAA 5' |
| SEQ ID 1009 | 5' GUUCUUUGUAUCUGUUGGU 3'<br>3' CAAGAAACAUAGACAACCA 5' |
| SEQ ID 1010 | 5' UAUGACUCAAGGAUUCUGG 3'<br>3' AUACUGAGUUCCUAAGACC 5' |
| SEQ ID 1011 | 5' GGAUUCUGGCAAAAUUCCA 3'<br>3' CCUAAGACCCUUUUAAGGU 5' |
| SEQ ID 1012 | 5' AAUUCCAUGCUAACGGACC 3'<br>3' UUAAGGUACGAUUGCCUGG 5' |
| SEQ ID 1013 | 5' AUUCCAUGCUAACGGACCC 3'<br>3' UAAGGUACGAUUGCCUGGG 5' |
| SEQ ID 1014 | 5' UUCCAUGCUAACGGACCCA 3'<br>3' AAGGUACGAUUGCCUGGGU 5' |
| SEQ ID 1015 | 5' CGGACCCAGGAAAUGUUCA 3'<br>3' GCCUGGGUCCUUUACAAGU 5' |
| SEQ ID 1016 | 5' AUGUUCAGAAAGCAGUCUG 3'<br>3' UACAAGUCUUUCGUCAGAC 5' |
| SEQ ID 1017 | 5' UGUUCAGAAAGCAGUCUGC 3'<br>3' ACAAGUCUUUCGUCAGACG 5' |
| SEQ ID 1018 | 5' AGCAGUCUGCCAUCCCACA 3'<br>3' UCGUCAGACGGUAGGGUGU 5' |
| SEQ ID 1019 | 5' GCAGUCUGCCAUCCCACAG 3'<br>3' CGUCAGACGGUAGGGUGUC 5' |

Figure 2NNN

| | |
|---|---|
| SEQ ID 1020 | 5' GGGCGACUUCAGGAUCCUU 3'<br>3' CCCGCUGAAGUCCUAGGAA 5' |
| SEQ ID 1021 | 5' AGGUGACAAUGGACGACUU 3'<br>3' UCCACUGUUACCUGCUGAA 5' |
| SEQ ID 1022 | 5' GGUGACAAUGGACGACUUC 3'<br>3' CCACUGUUACCUGCUGAAG 5' |
| SEQ ID 1023 | 5' UGGACGACUUCCUGACAGC 3'<br>3' ACCUGCUGAAGGACUGUCG 5' |
| SEQ ID 1024 | 5' CCUUUUCUGCUAACAAAUG 3'<br>3' GGAAAAGACGAUUGUUUAC 5' |
| SEQ ID 1025 | 5' GAAAUGGAGCUAAUGAAGG 3'<br>3' CUUUACCUCGAUUACUUCC 5' |
| SEQ ID 1026 | 5' AUGGAGCUAAUGAAGGAUU 3'<br>3' UACCUCGAUUACUUCCUAA 5' |
| SEQ ID 1027 | 5' UGGAGCUAAUGAAGGAUUC 3'<br>3' ACCUCGAUUACUUCCUAAG 5' |
| SEQ ID 1028 | 5' UGAAGGAUUCCAUGAAGCU 3'<br>3' ACUUCCUAAGGUACUUCGA 5' |
| SEQ ID 1029 | 5' GGAUUCCAUGAAGCUGUUG 3'<br>3' CCUAAGGUACUUCGACAAC 5' |
| SEQ ID 1030 | 5' GCUGUUGGGGAAAUCAUGU 3'<br>3' CGACAACCCCUUUAGUACA 5' |
| SEQ ID 1031 | 5' AUCAUGUCACUUUCUGCAG 3'<br>3' UAGUACAGUGAAAGACGUC 5' |
| SEQ ID 1032 | 5' UCAUGUCACUUUCUGCAGC 3'<br>3' AGUACAGUGAAAGACGUCG 5' |
| SEQ ID 1033 | 5' AAUCCAUUGGUCUUCUGUC 3'<br>3' UUAGGUAACCAGAAGACAG 5' |
| SEQ ID 1034 | 5' AUCCAUUGGUCUUCUGUCA 3'<br>3' UAGGUAACCAGAAGACAGU 5' |
| SEQ ID 1035 | 5' UCCAUUGGUCUUCUGUCAC 3'<br>3' AGGUAACCAGAAGACAGUG 5' |

Figure 2OOO

| | |
|---|---|
| SEQ ID 1036 | 5' ACAGAAAUAAACUUCCUGC 3'<br>::|||||||||||||||||<br>3' UGUCUUUAUUUGAAGGACG 5' |
| SEQ ID 1037 | 5' CAGAAAUAAACUUCCUGCU 3'<br>::|||||||||||||||||<br>3' GUCUUUAUUUGAAGGACGA 5' |
| SEQ ID 1038 | 5' AUAAACUUCCUGCUCAAAC 3'<br>::|||||||||||||||||<br>3' UAUUUGAAGGACGAGUUUG 5' |
| SEQ ID 1039 | 5' UAAACUUCCUGCUCAAACA 3'<br>::|||||||||||||||||<br>3' AUUUGAAGGACGAGUUUGU 5' |
| SEQ ID 1040 | 5' ACUUCCUGCUCAAACAAGC 3'<br>::|||||||||||||||||<br>3' UGAAGGACGAGUUUGUUCG 5' |
| SEQ ID 1041 | 5' CUUCCUGCUCAAACAAGCA 3'<br>::|||||||||||||||||<br>3' GAAGGACGAGUUUGUUCGU 5' |
| SEQ ID 1042 | 5' ACAAGCACUCACGAUUGUU 3'<br>::|||||||||||||||||<br>3' UGUUCGUGAGUGCUAACAA 5' |
| SEQ ID 1043 | 5' CAAGCACUCACGAUUGUUG 3'<br>::|||||||||||||||||<br>3' GUUCGUGAGUGCUAACAAC 5' |
| SEQ ID 1044 | 5' GCACUCACGAUUGUUGGGA 3'<br>::|||||||||||||||||<br>3' CGUGAGUGCUAACAACCCU 5' |
| SEQ ID 1045 | 5' GUGGAGGUGGAUGGUCUUU 3'<br>::|||||||||||||||||<br>3' CACCUCCACCUACCAGAAA 5' |
| SEQ ID 1046 | 5' AGGGGAAAUUCCCAAAGAC 3'<br>::|||||||||||||||||<br>3' UCCCCUUUAAGGGUUUCUG 5' |
| SEQ ID 1047 | 5' GGGGAAAUUCCCAAAGACC 3'<br>::|||||||||||||||||<br>3' CCCCUUUAAGGGUUUCUGG 5' |
| SEQ ID 1048 | 5' AUUCCCAAAGACCAGUGGA 3'<br>::|||||||||||||||||<br>3' UAAGGGUUUCUGGUCACCU 5' |
| SEQ ID 1049 | 5' UUCCCAAAGACCAGUGGAU 3'<br>::|||||||||||||||||<br>3' AAGGGUUUCUGGUCACCUA 5' |
| SEQ ID 1050 | 5' AGACCAGUGGAUGAAAAAG 3'<br>::|||||||||||||||||<br>3' UCUGGUCACCUACUUUUUC 5' |
| SEQ ID 1051 | 5' GACCAGUGGAUGAAAAAGU 3'<br>::|||||||||||||||||<br>3' CUGGUCACCUACUUUUUCA 5' |

Figure 2PPP

| | |
|---|---|
| SEQ ID 1052 | 5' AAAGUGGUGGGAGAUGAAG 3'<br>||||||||||::::|||||<br>3' UUUCACCACCCUCUACUUC 5' |
| SEQ ID 1053 | 5' AAGUGGUGGGAGAUGAAGC 3'<br>||||||||||::::|||||<br>3' UUCACCACCCUCUACUUCG 5' |
| SEQ ID 1054 | 5' AGUGGUGGGAGAUGAAGCG 3'<br>||||||||||::::|||||<br>3' UCACCACCCUCUACUUCGC 5' |
| SEQ ID 1055 | 5' GUGGUGGGAGAUGAAGCGA 3'<br>||||||||||::::|||||<br>3' CACCACCCUCUACUUCGCU 5' |
| SEQ ID 1056 | 5' GCGAGAGAUAGUUGGGGUG 3'<br>||||||||||::::|||||<br>3' CGCUCUCUAUCAACCCCAC 5' |
| SEQ ID 1057 | 5' CCUGUGCCCCAUGAUGAAA 3'<br>||||||||||::::|||||<br>3' GGACACGGGGUACUACUUU 5' |
| SEQ ID 1058 | 5' ACAUACUGUGACCCCGCAU 3'<br>||||||||||::::|||||<br>3' UGUAUGACACUGGGGCGUA 5' |
| SEQ ID 1059 | 5' CAUACUGUGACCCCGCAUC 3'<br>||||||||||::::|||||<br>3' GUAUGACACUGGGGCGUAG 5' |
| SEQ ID 1060 | 5' CCACCCUUUACCAAUUCCA 3'<br>||||||||||::::|||||<br>3' CCUGGGAAAUGGUUAAGGU 5' |
| SEQ ID 1061 | 5' UUCCAGUUUCAAGAAGCAC 3'<br>||||||||||::::|||||<br>3' AAGGUCAAAGUUCUUCGUG 5' |
| SEQ ID 1062 | 5' GAAGCACUUUGUCAAGCAG 3'<br>||||||||||::::|||||<br>3' CUUCGUGAAACAGUUCGUC 5' |
| SEQ ID 1063 | 5' GCACUUUGUCAAGCAGCUA 3'<br>||||||||||::::|||||<br>3' CGUGAAACAGUUCGUCGAU 5' |
| SEQ ID 1064 | 5' GCAGCUAAACAUGAAGGCC 3'<br>||||||||||::::|||||<br>3' CGUCGAUUUGUACUUCCGG 5' |
| SEQ ID 1065 | 5' ACAUGAAGGCCCUCUGCAC 3'<br>||||||||||::::|||||<br>3' UGUACUUCCGGGAGACGUG 5' |
| SEQ ID 1066 | 5' CAUGAAGGCCCUCUCCACA 3'<br>||||||||||::::|||||<br>3' GUACUUCCGGGAGACGUGU 5' |
| SEQ ID 1067 | 5' GGCCCUCUGCACAAAUGUG 3'<br>||||||||||::::|||||<br>3' CCGGGAGACGUGUUUACAC 5' |

Figure 2QQQ

| | |
|---|---|
| SEQ ID 1068 | 5' AUGUGACAUCUCAAACUCU 3'<br>|||||||||::||||||||<br>3' UACACUGUAGAGUUUGAGA 5' |
| SEQ ID 1069 | 5' UGUGACAUCUCAAACUCUA 3'<br>|||||||||::||||||||<br>3' ACACUGUAGAGUUUGAGAU 5' |
| SEQ ID 1070 | 5' ACUCUACAGAACCUGGACA 3'<br>|||||||||::||||||||<br>3' UGAGAUGUCUUCGACCUGU 5' |
| SEQ ID 1071 | 5' CUCUACAGAAGCUGGACAG 3'<br>|||||||||::||||||||<br>3' GAGAUGUCUUCGACCUGUC 5' |
| SEQ ID 1072 | 5' GCUGGACAGAAACUGUUCA 3'<br>|||||||||::||||||||<br>3' CGACCUGUCUUUGACAAGU 5' |
| SEQ ID 1073 | 5' ACUGUUCAAUAUGCUGAGG 3'<br>|||||||||::||||||||<br>3' UGACAAGUUAUACGACUCC 5' |
| SEQ ID 1074 | 5' CUGUUCAAUAUGCUGAGGC 3'<br>|||||||||::||||||||<br>3' GACAAGUUAUACCACUCCG 5' |
| SEQ ID 1075 | 5' UAUGCUGAGGCUUGGAAAA 3'<br>|||||||||::||||||||<br>3' AUACGACUCCGAACCUUUU 5' |
| SEQ ID 1076 | 5' AAUCAGAACCCUGGACCCU 3'<br>|||||||||::||||||||<br>3' UUAGUCUUGGGACCUGGGA 5' |
| SEQ ID 1077 | 5' AUCAGAACCCUGGACCCUA 3'<br>|||||||||::||||||||<br>3' UAGUCUUGGGACCUGGGAU 5' |
| SEQ ID 1078 | 5' UCAGAACCCUGGACCCUAG 3'<br>|||||||||::||||||||<br>3' AGUCUUGGGACCUGGGAUC 5' |
| SEQ ID 1079 | 5' CCCUGGACCCUAGCAUUGG 3'<br>|||||||||::||||||||<br>3' GGGACCUGGGAUCGUAACC 5' |
| SEQ ID 1080 | 5' AAUGUUGUAGGAGCAAAGA 3'<br>|||||||||::||||||||<br>3' UUACAACAUCCUCGUUUCU 5' |
| SEQ ID 1081 | 5' AUGUUGUAGGACCAAAGAA 3'<br>|||||||||::||||||||<br>3' UACAACAUCCUCGUUUCUU 5' |
| SEQ ID 1082 | 5' UGUUGUAGGAGCAAAGAAC 3'<br>|||||||||::||||||||<br>3' ACAACAUCCUCGUUUCUUG 5' |
| SEQ ID 1083 | 5' AGAACAUGAAUGUAAGGCC 3'<br>|||||||||::||||||||<br>3' UCUUGUACUUACAUUCCGG 5' |

Figure 2RRR

<table>
<tr><td>SEQ ID 1084</td><td>5' GAACAUGAAUGUAAGGCCA 3'<br>:|||:|||:||||||||||<br>3' CUUGUACUUACAUUCCGGU 5'</td></tr>
<tr><td>SEQ ID 1085</td><td>5' CAUGAAUGUAAGGCCACUG 3'<br>:|||:|||:||||||||||<br>3' GUACUUACAUUCCGGUGAC 5'</td></tr>
<tr><td>SEQ ID 1086</td><td>5' UGUAAGGCCACUGCUCAAC 3'<br>:|||:|||:||||||||||<br>3' ACAUUCCGGUGACGAGUUG 5'</td></tr>
<tr><td>SEQ ID 1087</td><td>5' GGCCACUGCUCAACUACUU 3'<br>:|||:|||:||||||||||<br>3' CCGGUGACGAGUUGAUGAA 5'</td></tr>
<tr><td>SEQ ID 1088</td><td>5' CUACUUUGACCCCUUAUUU 3'<br>:|||:|||:||||||||||<br>3' GAUGAAACUCGGGAAUAAA 5'</td></tr>
<tr><td>SEQ ID 1089</td><td>5' AGACCAGAACAAGAAUUCU 3'<br>:|||:|||:||||||||||<br>3' UCUGGUCUUCUUCUUAACA 5'</td></tr>
<tr><td>SEQ ID 1090</td><td>5' GACCAGAACAAGAAUUCUU 3'<br>:|||:|||:||||||||||<br>3' CUGGUCUUGUUCUUAAGAA 5'</td></tr>
<tr><td>SEQ ID 1091</td><td>5' CAAGAAUUCUUUUCUGGGA 3'<br>:|||:|||:||||||||||<br>3' GUUCUUAAGAAAACACCCU 5'</td></tr>
<tr><td>SEQ ID 1092</td><td>5' GAAUUCUUUUGUGGGAUGG 3'<br>:|||:|||:||||||||||<br>3' CUUAAGAAAACACCCUACC 5'</td></tr>
<tr><td>SEQ ID 1093</td><td>5' UUCUUUUGUGGGAUGGAGU 3'<br>:|||:|||:||||||||||<br>3' AAGAAAACACCCUACCUCA 5'</td></tr>
<tr><td>SEQ ID 1094</td><td>5' AGCAUCAAAGUGACGAUAA 3'<br>:|||:|||:||||||||||<br>3' UCGUAGUUUCACUCCUAUU 5'</td></tr>
<tr><td>SEQ ID 1095</td><td>5' GCAUCAAAGUGAGGAUAAG 3'<br>:|||:|||:||||||||||<br>3' CGUAGUUUCACUCCUAUUC 5'</td></tr>
<tr><td>SEQ ID 1096</td><td>5' AGUGAGGAUAAGCCUAAAA 3'<br>:|||:|||:||||||||||<br>3' UCACUCCUAUUCGGAUUUU 5'</td></tr>
<tr><td>SEQ ID 1097</td><td>5' GUGAGGAUAAGCCUAAAAU 3'<br>:|||:|||:||||||||||<br>3' CACUCCUAUUCGGAUUUUA 5'</td></tr>
<tr><td>SEQ ID 1098</td><td>5' GCCUAAAAUCAGCUCUUGG 3'<br>:|||:|||:||||||||||<br>3' CGGAUUUUAGUCGAGAACC 5'</td></tr>
<tr><td>SEQ ID 1099</td><td>5' AAUCAGCUCUUGGAGAUAA 3'<br>:|||:|||:||||||||||<br>3' UUAGUCGAGAACCUCUAUU 5'</td></tr>
</table>

Figure 2SSS

<table>
<tr><td>SEQ ID 1100</td><td>5' AUCAGCUCUUGGAGAUAAA 3'<br>||:|||:|||:|||:|||:<br>3' UAGUCGAGAACCUCUAUUU 5'</td></tr>
<tr><td>SEQ ID 1101</td><td>5' UCAGCUCUUGGAGAUAAAG 3'<br>||:|||:|||:|||:|||:<br>3' AGUCGAGAACCUCUAUUUC 5'</td></tr>
<tr><td>SEQ ID 1102</td><td>5' AGCAUAUGAAUGGAACGAC 3'<br>||:|||:|||:|||:|||:<br>3' UCGUAUACUUACCUUGCUG 5'</td></tr>
<tr><td>SEQ ID 1103</td><td>5' GCAUAUGAAUGGAACGACA 3'<br>||:|||:|||:|||:|||:<br>3' CGUAUACUUACCUUGCUGU 5'</td></tr>
<tr><td>SEQ ID 1104</td><td>5' UGGAACGACAAUGAAAUGU 3'<br>||:|||:|||:|||:|||:<br>3' ACCUUGCUGUUACUUUACA 5'</td></tr>
<tr><td>SEQ ID 1105</td><td>5' CGACAAUGAAAUGUACCUG 3'<br>||:|||:|||:|||:|||:<br>3' GCUGUUACUUUACAUGGAC 5'</td></tr>
<tr><td>SEQ ID 1106</td><td>5' UGAAAUGUACCUGUUCCGA 3'<br>||:|||:|||:|||:|||:<br>3' ACUUUACAUGGACAAGGCU 5'</td></tr>
<tr><td>SEQ ID 1107</td><td>5' AUGUACCUGUUCCGAUCAU 3'<br>||:|||:|||:|||:|||:<br>3' UACAUGGACAAGGCUAGUA 5'</td></tr>
<tr><td>SEQ ID 1108</td><td>5' UGUACCUGUUCCGAUCAUC 3'<br>||:|||:|||:|||:|||:<br>3' ACAUGGACAAGGCUAGUAG 5'</td></tr>
<tr><td>SEQ ID 1109</td><td>5' UCAGAUGAUUCUUUUUGGG 3'<br>||:|||:|||:|||:|||:<br>3' AGUCUACUAAGAAAAACCC 5'</td></tr>
<tr><td>SEQ ID 1110</td><td>5' UUUGAAACCAAGAAUCUCC 3'<br>||:|||:|||:|||:|||:<br>3' AAACUUUGGUUCUUAGAGG 5'</td></tr>
<tr><td>SEQ ID 1111</td><td>5' UUUCUUUGUCACUGCACCU 3'<br>||:|||:|||:|||:|||:<br>3' AAAGAAACAGUGACGUGGA 5'</td></tr>
<tr><td>SEQ ID 1112</td><td>5' AUGUGUCUGAUAUCAUUCC 3'<br>||:|||:|||:|||:|||:<br>3' UACACAGACUAUAGUAAGG 5'</td></tr>
<tr><td>SEQ ID 1113</td><td>5' UGUGUCUGAUAUCAUUCCU 3'<br>||:|||:|||:|||:|||:<br>3' ACACAGACUAUAGUAAGGA 5'</td></tr>
<tr><td>SEQ ID 1114</td><td>5' CUGAAGUUGAAAAGGCCAU 3'<br>||:|||:|||:|||:|||:<br>3' GACUUCAACUUUUCCGGUA 5'</td></tr>
<tr><td>SEQ ID 1115</td><td>5' GUUGAAAAGGCCAUCAGGA 3'<br>||:|||:|||:|||:|||:<br>3' CAACUUUUCCGGUAGUCCU 5'</td></tr>
</table>

Figure 2TTT

<table>
<tr><td>SEQ ID 1116</td><td>5' AAGGCCAUCAGGAUGUCCC 3'<br>|||:||||||||:|||:||<br>3' UUCCGGUAGUCCUACAGGG 5'</td></tr>
<tr><td>SEQ ID 1117</td><td>5' AGGCCAUCAGGAUGUCCCG 3'<br>|||:||||||||:|||:||<br>3' UCCGGUAGUCCUACAGGGC 5'</td></tr>
<tr><td>SEQ ID 1118</td><td>5' UGAUGCUUUCCGUCUGAAU 3'<br>|||:||||||||:|||:||<br>3' ACUACGAAAGGCAGACUUA 5'</td></tr>
<tr><td>SEQ ID 1119</td><td>5' UGACAACAGCCUAGAGUUU 3'<br>|||:||||||||:|||:||<br>3' ACUGUUGUCGGAUCUCAAA 5'</td></tr>
<tr><td>SEQ ID 1120</td><td>5' CAGCCUAGAGUUUCUGGGG 3'<br>|||:||||||||:|||:||<br>3' GUCGGAUCUCAAAGACCCC 5'</td></tr>
<tr><td>SEQ ID 1121</td><td>5' CACUUGGACCUCCUAACCA 3'<br>|||:||||||||:|||:||<br>3' GUGAACCUGGAGGAUUGGU 5'</td></tr>
<tr><td>SEQ ID 1122</td><td>5' CCAGCCCCCUGUUUCCAUA 3'<br>|||:||||||||:|||:||<br>3' GGUCGGGGGACAAAGGUAU 5'</td></tr>
<tr><td>SEQ ID 1123</td><td>5' AAUAAAGCAAGAAGUGGAG 3'<br>|||:||||||||:|||:||<br>3' UUAUUUCGUUCUUCACCUC 5'</td></tr>
<tr><td>SEQ ID 1124</td><td>5' AUAAAGCAAGAAGUGGAGA 3'<br>|||:||||||||:|||:||<br>3' UAUUUCGUUCUUCACCUCU 5'</td></tr>
<tr><td>SEQ ID 1125</td><td>5' UAAAGCAAGAAGUGGAGAA 3'<br>|||:||||||||:|||:||<br>3' AUUUCGUUCUUCACCUCUU 5'</td></tr>
<tr><td>SEQ ID 1126</td><td>5' AGCAAGAAGUGGAGAAAAU 3'<br>|||:||||||||:|||:||<br>3' UCGUUCUUCACCUCUUUUA 5'</td></tr>
<tr><td>SEQ ID 1127</td><td>5' GCAAGAAGUGGAGAAAAUC 3'<br>|||:||||||||:|||:||<br>3' CGUUCUUCACCUCUUUUAG 5'</td></tr>
<tr><td>SEQ ID 1128</td><td>5' GAAGUGGAGAAAAUCCUUA 3'<br>|||:||||||||:|||:||<br>3' CUUCACCUCUUUUAGGAAU 5'</td></tr>
<tr><td>SEQ ID 1129</td><td>5' GUGGAGAAAAUCCUUAUGC 3'<br>|||:||||||||:|||:||<br>3' CACCUCUUUUAGGAAUACG 5'</td></tr>
<tr><td>SEQ ID 1130</td><td>5' AAUCCUUAUGCCUCCAUCG 3'<br>|||:||||||||:|||:||<br>3' UUAGGAAUACGGAGGUAGC 5'</td></tr>
<tr><td>SEQ ID 1131</td><td>5' AUCCUUAUGCCUCCAUCGA 3'<br>|||:||||||||:|||:||<br>3' UAGGAAUACGGAGGUAGCU 5'</td></tr>
</table>

Figure 2UUU

| | |
|---|---|
| SEQ ID 1132 | 5' UCCUUAUGCCUCCAUCGAU 3'<br>\|\|\|\|\|:\|\|\|\|\|\|:\|\|\|\|\|\|<br>3' AGGAAUACGGAGGUAGCUA 5' |
| SEQ ID 1133 | 5' AGGAGAAAAUAAUCCAGGA 3'<br>\|\|\|\|\|:\|\|\|\|\|\|:\|\|\|\|\|\|<br>3' UCCUCUUUUAUUAGGUCCU 5' |
| SEQ ID 1134 | 5' GCACAAAAUAAUCCAGGAU 3'<br>\|\|\|\|\|:\|\|\|\|\|\|:\|\|\|\|\|\|<br>3' CCUCUUUUAUUAGGUCCUA 5' |
| SEQ ID 1135 | 5' UAAUCCAGGAUUCCAAAAC 3'<br>\|\|\|\|\|:\|\|\|\|\|\|:\|\|\|\|\|\|<br>3' AUUAGGUCCUAAGGUUUUG 5' |
| SEQ ID 1136 | 5' UCCAGGAUUCCAAAACACU 3'<br>\|\|\|\|\|:\|\|\|\|\|\|:\|\|\|\|\|\|<br>3' AGGUCCUAAGCUUUUGUCA 5' |
| SEQ ID 1137 | 5' AACACUGAUGAUGUUCAGA 3'<br>\|\|\|\|\|:\|\|\|\|\|\|:\|\|\|\|\|\|<br>3' UUGUGACUACUACAAGUCU 5' |
| SEQ ID 1138 | 5' ACACUGAUGAUGUUCAGAC 3'<br>\|\|\|\|\|:\|\|\|\|\|\|:\|\|\|\|\|\|<br>3' UGUGACUACUACAAGUCUG 5' |
| SEQ ID 1139 | 5' CACUGAUGAUGUUCAGACC 3'<br>\|\|\|\|\|:\|\|\|\|\|\|:\|\|\|\|\|\|<br>3' GUGACUACUACAAGUCUGG 5' |

| | |
|---|---|
| REN | |
| SEQ ID 1140 | 5' GCAUGGAUGGAUGGAGAAG 3'<br>\|\|\|\|\|:\|\|\|\|\|\|:\|\|\|\|\|\|<br>3' CGUACCUACCUACCUCUUC 5' |
| SEQ ID 1141 | 5' ACGGAUCUUCCUCAAGAGA 3'<br>\|\|\|\|\|:\|\|\|\|\|\|:\|\|\|\|\|\|<br>3' UGCCUAGAAGGAGUUCUCU 5' |
| SEQ ID 1142 | 5' CGGAUCUUCCUCAAGAGAA 3'<br>\|\|\|\|\|:\|\|\|\|\|\|:\|\|\|\|\|\|<br>3' GCCUAGAAGGAGUUCUCUU 5' |
| SEQ ID 1143 | 5' GAGAAUGCCCUCAAUCCGA 3'<br>\|\|\|\|\|:\|\|\|\|\|\|:\|\|\|\|\|\|<br>3' CUCUUACGGGAGUUAGGCU 5' |
| SEQ ID 1144 | 5' UGCCCUCAAUCCGAGAAAG 3'<br>\|\|\|\|\|:\|\|\|\|\|\|:\|\|\|\|\|\|<br>3' ACGGGAGUUAGGCUCUUUC 5' |
| SEQ ID 1145 | 5' UCCGAGAAAGCCUGAAGGA 3'<br>\|\|\|\|\|:\|\|\|\|\|\|:\|\|\|\|\|\|<br>3' AGGCUCUUUCGGACUUCCU 5' |
| SEQ ID 1146 | 5' AGCCUGAAGGAACGAGGUG 3'<br>\|\|\|\|\|:\|\|\|\|\|\|:\|\|\|\|\|\|<br>3' UCGGACUUCCUUGCUCCAC 5' |

Figure 2VVV

| | |
|---|---|
| SEQ ID 1147 | 5' GCCUGAAGGAACGAGGUGU 3'<br>:\|\|\|\|\|\|:\|:\|\|\|\|\|\|:\|\|<br>3' CGGACUUCCUUGCUCCACA 5' |
| SEQ ID 1148 | 5' GGAACGAGGUGUGGACAUG 3'<br>:\|\|\|\|\|\|:\|:\|\|\|\|\|\|:\|\|<br>3' CCUUGCUCCACACCUGUAC 5' |
| SEQ ID 1149 | 5' CGAGGUGUGGACAUGGCCA 3'<br>:\|\|\|\|\|\|:\|:\|\|\|\|\|\|:\|\|<br>3' GCUCCACACCUGUACCGGU 5' |
| SEQ ID 1150 | 5' CCCAUGAAGAGGCUGACAC 3'<br>:\|\|\|\|\|\|:\|:\|\|\|\|\|\|:\|\|<br>3' GGGUACUUCUCCGACUGUG 5' |
| SEQ ID 1151 | 5' GAGGCUGACACUUGGCAAC 3'<br>:\|\|\|\|\|\|:\|:\|\|\|\|\|\|:\|\|<br>3' CUCCGACUGUGAACCGUUG 5' |
| SEQ ID 1152 | 5' CACCACCUCCUCCGUGAUC 3'<br>:\|\|\|\|\|\|:\|:\|\|\|\|\|\|:\|\|<br>3' GUGGUGGAGGAGGCACUAG 5' |
| SEQ ID 1153 | 5' CUACAUGGACACCCAGUAC 3'<br>:\|\|\|\|\|\|:\|:\|\|\|\|\|\|:\|\|<br>3' GAUGUACCUGUGGGUCAUG 5' |
| SEQ ID 1154 | 5' ACCUUCAAAGUCGUCUUUG 3'<br>:\|\|\|\|\|\|:\|:\|\|\|\|\|\|:\|\|<br>3' UGGAAGUUUCAGCAGAAAC 5' |
| SEQ ID 1155 | 5' CCUUCAAAGUCGUCUUUGA 3'<br>:\|\|\|\|\|\|:\|:\|\|\|\|\|\|:\|\|<br>3' GGAAGUUUCAGCAGAAACU 5' |
| SEQ ID 1156 | 5' AGUCGUCUUUGACACUGGU 3'<br>:\|\|\|\|\|\|:\|:\|\|\|\|\|\|:\|\|<br>3' UCAGCAGAAACUGUGACCA 5' |
| SEQ ID 1157 | 5' GUCGUCUUUGACACUGGUU 3'<br>:\|\|\|\|\|\|:\|:\|\|\|\|\|\|:\|\|<br>3' CAGCAGAAACUGUGACCAA 5' |
| SEQ ID 1158 | 5' UGUUUGGGUGCCCUCCUCC 3'<br>:\|\|\|\|\|\|:\|:\|\|\|\|\|\|:\|\|<br>3' ACAAACCCACGGGAGGAGG 5' |
| SEQ ID 1159 | 5' GUGCAGCCGUCUCUACACU 3'<br>:\|\|\|\|\|\|:\|:\|\|\|\|\|\|:\|\|<br>3' CACCUCGGCAGACAUCUGA 5' |
| SEQ ID 1160 | 5' GCUCUUCGAUGCUUCGGAU 3'<br>:\|\|\|\|\|\|:\|:\|\|\|\|\|\|:\|\|<br>3' CGAGAAGCUACGAAGCCUA 5' |
| SEQ ID 1161 | 5' GCACAAUGGAACAGAACUC 3'<br>:\|\|\|\|\|\|:\|:\|\|\|\|\|\|:\|\|<br>3' CGUGUUACCUUGUCUUGAG 5' |
| SEQ ID 1162 | 5' UGGAACAGAACUCACCCUC 3'<br>:\|\|\|\|\|\|:\|:\|\|\|\|\|\|:\|\|<br>3' ACCUUGUCUUGAGUGGGAG 5' |

Figure 2WWW

| | |
|---|---|
| SEQ ID 1163 | 5' CAGAACUCACCCUCCGCUA 3'<br>\|\|:\|:\|\|\|\|\|\|:\|:\|\|\|\|\|<br>3' GUCUUGAGUGGGAGGCGAU 5' |
| SEQ ID 1164 | 5' CUCACCCUCCGCUAUUCAA 3'<br>\|\|:\|:\|\|\|\|\|\|:\|:\|\|\|\|\|<br>3' GAGUGGGAGGCGAUAAGUU 5' |
| SEQ ID 1165 | 5' CACGGACAGUCACGCCCUU 3'<br>\|\|:\|:\|\|\|\|\|\|:\|:\|\|\|\|\|<br>3' GUCCCUGUCAGUCACCGAA 5' |
| SEQ ID 1166 | 5' UCACGGUGACACAGAUGUU 3'<br>\|\|:\|:\|\|\|\|\|\|:\|:\|\|\|\|\|<br>3' AGUGCCACUGUGUCUACAA 5' |
| SEQ ID 1167 | 5' CAGGCCAUUGGCAGGGUCA 3'<br>\|\|:\|:\|\|\|\|\|\|:\|:\|\|\|\|\|<br>3' GUCCGGUAACCGUCCCAGU 5' |
| SEQ ID 1168 | 5' CAUCAUCUCCCAAGGGGUG 3'<br>\|\|:\|:\|\|\|\|\|\|:\|:\|\|\|\|\|<br>3' GUAGUAGAGGGUUCCCCAC 5' |
| SEQ ID 1169 | 5' GGGGUGCUAAAAGAGGACG 3'<br>\|\|:\|:\|\|\|\|\|\|:\|:\|\|\|\|\|<br>3' CCCCACGAUUUUCUCCUGC 5' |
| SEQ ID 1170 | 5' AAGAGGACGUCUUCUCUUU 3'<br>\|\|:\|:\|\|\|\|\|\|:\|:\|\|\|\|\|<br>3' UUCUCCUGCAGAAGAGAAA 5' |
| SEQ ID 1171 | 5' AGAGGACGUCUUCUCUUUC 3'<br>\|\|:\|:\|\|\|\|\|\|:\|:\|\|\|\|\|<br>3' UCUCCUGCAGAAGAGAAAG 5' |
| SEQ ID 1172 | 5' GAGGACGUCUUCUCUUUCU 3'<br>\|\|:\|:\|\|\|\|\|\|:\|:\|\|\|\|\|<br>3' CUCCUGCAGAAGAGAAAGA 5' |
| SEQ ID 1173 | 5' CAGACAUUCCGACAAUUCC 3'<br>\|\|:\|:\|\|\|\|\|\|:\|:\|\|\|\|\|<br>3' GUCUGUAAGGCUGUUAAGG 5' |
| SEQ ID 1174 | 5' UUCCCAAUCGCUGGGAGGA 3'<br>\|\|:\|:\|\|\|\|\|\|:\|:\|\|\|\|\|<br>3' AAGGGUUAGCGACCCUCCU 5' |
| SEQ ID 1175 | 5' UCGCUGGGAGGACAGAUUG 3'<br>\|\|:\|:\|\|\|\|\|\|:\|:\|\|\|\|\|<br>3' AGCGACCCUCCUGUCUAAC 5' |
| SEQ ID 1176 | 5' GGGAAUUUCCACUAUAUCA 3'<br>\|\|:\|:\|\|\|\|\|\|:\|:\|\|\|\|\|<br>3' CCCUUAAAGGUGAUAUAGU 5' |
| SEQ ID 1177 | 5' UUUCCACUAUAUCAACCUC 3'<br>\|\|:\|:\|\|\|\|\|\|:\|:\|\|\|\|\|<br>3' AAAGGUGAUAUAGUUGGAG 5' |
| SEQ ID 1178 | 5' CCUCAUCAAGACUGGUGUC 3'<br>\|\|:\|:\|\|\|\|\|\|:\|:\|\|\|\|\|<br>3' GGAGUAGUUCUGACCACAG 5' |

Figure 2XXX

| | |
|---|---|
| SEQ ID 1179 | 5' GACUGGUGUCUGGCAGAUU 3'<br>:|||||:|||||:||||||<br>3' CUGACCACAGACCGUCUAA 5' |
| SEQ ID 1180 | 5' AUGAAGGGGGUGUCUGUGG 3'<br>:|||||:|||||:||||||<br>3' UACUUCCCCCACAGACACC 5' |
| SEQ ID 1181 | 5' UGAAGGGGGUGUCUGUGGG 3'<br>:|||||:|||||:||||||<br>3' ACUUCCCCCACAGACACCC 5' |
| SEQ ID 1182 | 5' GCUCAUGGAGGCCUUCGGA 3'<br>:|||||:|||||:||||||<br>3' CGAGUACCUCCGGAACCCU 5' |
| SEQ ID 1183 | 5' GAAGAGGCUGUUUGAUUAU 3'<br>:|||||:|||||:||||||<br>3' CUUCUCCGACAAACUAAUA 5' |
| SEQ ID 1184 | 5' GAGGCUGUUUGAUUAUGUC 3'<br>:|||||:|||||:||||||<br>3' CUCCGACAAACUAAUACAG 5' |
| SEQ ID 1185 | 5' GUGUAACGAGGCCCUACA 3'<br>:|||||:|||||:||||||<br>3' CACAUUGCUCCCGGGAUGU 5' |
| SEQ ID 1186 | 5' AGAAUACACGCUCACCAGC 3'<br>:|||||:|||||:||||||<br>3' UCUUAUGUGCGAGUGGUCG 5' |
| SEQ ID 1187 | 5' GAAUACACGCUCACCAGCG 3'<br>:|||||:|||||:||||||<br>3' CUUAUGUGCGAGUGGUCGC 5' |
| SEQ ID 1188 | 5' UCCUACAGUAGUAAAAAGC 3'<br>:|||||:|||||:||||||<br>3' AGGAUGUCAUCAUUUUUCG 5' |
| SEQ ID 1189 | 5' AAAGCUGUGCACACUGGCC 3'<br>:|||||:|||||:||||||<br>3' UUUCGACACGUGUGACCGG 5' |
| SEQ ID 1190 | 5' AAGCUGUGCACACUGGCCA 3'<br>:|||||:|||||:||||||<br>3' UUCGACACGUGUGACCGGU 5' |
| SEQ ID 1191 | 5' AGCUGUGCACACUGGCCAU 3'<br>:|||||:|||||:||||||<br>3' UCGACACGUGUGACCGGUA 5' |
| SEQ ID 1192 | 5' GCUGUGCACACUGGCCAUC 3'<br>:|||||:|||||:||||||<br>3' CGACACGUGUGACCGGUAG 5' |
| SEQ ID 1193 | 5' AGUUCUACACAGAGUUUGA 3'<br>:|||||:|||||:||||||<br>3' UCAAGAUGUGUCUCAAACU 5' |
| SEQ ID 1194 | 5' GUUCUACACAGAGUUUGAU 3'<br>:|||||:|||||:||||||<br>3' CAACAUGUGUCUCAAACUA 5' |

Figure 2YYY

| | |
|---|---|
| SEQ ID 1195 | 5' CAACCGCAUUGGCUUCGCC 3'<br>|||||:|||||:||:||||<br>3' GUUGGCGUAACCGAAGCGG 5' |
| SEQ ID 1196 | 5' CCGCAUUGGCUUCGCCUUG 3'<br>|||||:|||||:||:||||<br>3' GGCGUAACCGAAGCGGAAC 5' |

| COCH | |
|---|---|
| SEQ ID 1197 | 5' AGAGAAAGCAGAUGUCCUC 3'<br>|||||:|||||:||:||||<br>3' UCUCUUUCGUCUACAGGAG 5' |
| SEQ ID 1198 | 5' GAGAAAGCAGAUCUCCUCU 3'<br>|||||:|||||:||:||||<br>3' CUCUUUCGUCUACAGGAGA 5' |
| SEQ ID 1199 | 5' AGCAGAUGUCCUCUGCCCA 3'<br>|||||:|||||:||:||||<br>3' UCGUCUACAGGAGACGGGU 5' |
| SEQ ID 1200 | 5' GCAGAUGUCCUCUGCCCAG 3'<br>|||||:|||||:||:||||<br>3' CGUCUACAGGAGACGGGUC 5' |
| SEQ ID 1201 | 5' UUCUCUGUGUAUGGGAACA 3'<br>|||||:|||||:||:||||<br>3' AAGAGACACAUACCCUUGU 5' |
| SEQ ID 1202 | 5' UCAGCAACUCAGGGGGACC 3'<br>|||||:|||||:||:||||<br>3' AGUCGUUGAGUCCCCCUGG 5' |
| SEQ ID 1203 | 5' CUCAGGGGGACCUGUACGA 3'<br>|||||:|||||:||:||||<br>3' GAGUCCCCCUGGACAUGCU 5' |
| SEQ ID 1204 | 5' AACUAUUCCUCAGUAGAUG 3'<br>|||||:|||||:||:||||<br>3' UUGAUAAGGAGUCAUCUAC 5' |
| SEQ ID 1205 | 5' ACUAUUCCUCAGUAGAUGC 3'<br>|||||:|||||:||:||||<br>3' UGAUAAGGAGUCAUCUACG 5' |
| SEQ ID 1206 | 5' CUAUUCCUCAGUAGAUGCC 3'<br>|||||:|||||:||:||||<br>3' GAUAAGGAGUCAUCUACGG 5' |
| SEQ ID 1207 | 5' UGGCAUCCAGUCUCAAAUG 3'<br>|||||:|||||:||:||||<br>3' ACCGUAGGUCAGAGUUUAC 5' |
| SEQ ID 1208 | 5' AUGCUUUCUAGAUGGUCUG 3'<br>|||||:|||||:||:||||<br>3' UACGAAAGAUCUACCAGAC 5' |
| SEQ ID 1209 | 5' UGCUUUCUAGAUGGUCUGC 3'<br>|||||:|||||:||:||||<br>3' ACGAAAGAUCUACCAGACG 5' |

Figure 2ZZZ

| | |
|---|---|
| SEQ ID 1210 | 5' CUAAAGGCAAAAGUAGUAC 3'<br>|||||||||||||:|||||<br>3' GAUUUCCGUUUUCAUCAUG 5' |
| SEQ ID 1211 | 5' AGGCAAAAGUAGUACACAG 3'<br>|||||||||||||:|||||<br>3' UCCGUUUUCAUCAUGUGUC 5' |
| SEQ ID 1212 | 5' GGCAAAAGUAGUACACAGG 3'<br>|||||||||||||:|||||<br>3' CCGUUUUCAUCAUGUGUCC 5' |
| SEQ ID 1213 | 5' AAGUAGUACACAGGAGGCC 3'<br>|||||||||||||:|||||<br>3' UUCAUCAUGUGUCCUCCGG 5' |
| SEQ ID 1214 | 5' AGUAGUACACAGGAGGCCA 3'<br>|||||||||||||:|||||<br>3' UCAUCAUGUGUCCUCCGGU 5' |
| SEQ ID 1215 | 5' GUAGUACACAGGAGGCCAC 3'<br>|||||||||||||:|||||<br>3' CAUCAUGUGUCCUCCGGUG 5' |
| SEQ ID 1216 | 5' GCAGUGUCCACAGCACAUC 3'<br>|||||||||||||:|||||<br>3' CGUCACAGGUGUCGUGUAG 5' |
| SEQ ID 1217 | 5' CAGGUAAACGACUAAAGAA 3'<br>|||||||||||||:|||||<br>3' GUCCAUUUGCUGAUUUCUU 5' |
| SEQ ID 1218 | 5' ACGACUAAAGAAAACACCC 3'<br>|||||||||||||:|||||<br>3' UGCUGAUUUCUUUUGUGGG 5' |
| SEQ ID 1219 | 5' CGACUAAAGAAAACACCCG 3'<br>|||||||||||||:|||||<br>3' GCUGAUUUCUUUUGUGGGC 5' |
| SEQ ID 1220 | 5' AGAAAACACCCGAGAAGAA 3'<br>|||||||||||||:|||||<br>3' UCUUUUGUGGGCUCUUCUU 5' |
| SEQ ID 1221 | 5' GAAAACACCCGAGAAGAAA 3'<br>|||||||||||||:|||||<br>3' CUUUUGUGGGCUCUUCUUU 5' |
| SEQ ID 1222 | 5' AACACCCGAGAAGAAAACU 3'<br>|||||||||||||:|||||<br>3' UUGUGGGCUCUUCUUUUGA 5' |
| SEQ ID 1223 | 5' ACACCCGAGAAGAAAACUG 3'<br>|||||||||||||:|||||<br>3' UGUGGGCUCUUCUUUUGAC 5' |
| SEQ ID 1224 | 5' CACCCGAGAAGAAAACUGG 3'<br>|||||||||||||:|||||<br>3' GUGGGCUCUUCUUUUGACC 5' |
| SEQ ID 1225 | 5' GAUUGUAAAGCAGACAUUG 3'<br>|||||||||||||:|||||<br>3' CUAACAUUUCGUCUGUAAC 5' |

Figure 2AAAA

| | |
|---|---|
| SEQ ID 1226 | 5' AGCAGACAUUGCAUUUCUG 3'<br>\|:\|\|\|:\|\|\|\|:\|\|\|:\|\|\|\|<br>3' UCGUCUGUAACGUAAAGAC 5' |
| SEQ ID 1227 | 5' GCAGACAUUGCAUUUCUGA 3'<br>\|:\|\|\|:\|\|\|\|:\|\|\|:\|\|\|\|<br>3' CGUCUGUAACGUAAAGACU 5' |
| SEQ ID 1228 | 5' GCUUUAAUAUUGGGCAGCG 3'<br>\|:\|\|\|:\|\|\|\|:\|\|\|:\|\|\|\|<br>3' CGAAAUUAUAACCCGUCGC 5' |
| SEQ ID 1229 | 5' UAUUGGGCAGCGCCGAUUU 3'<br>\|:\|\|\|:\|\|\|\|:\|\|\|:\|\|\|\|<br>3' AUAACCCGUCGCGGCUAAA 5' |
| SEQ ID 1230 | 5' UUUUGUUGGAAAAGUGGCU 3'<br>\|:\|\|\|:\|\|\|\|:\|\|\|:\|\|\|\|<br>3' AAAACAACCUUUUCACCGA 5' |
| SEQ ID 1231 | 5' AAGUGGCUCUAAUGUUGGG 3'<br>\|:\|\|\|:\|\|\|\|:\|\|\|:\|\|\|\|<br>3' UUCACCGAGAUUACAACCC 5' |
| SEQ ID 1232 | 5' AGUGGCUCUAAUGUUGGGA 3'<br>\|:\|\|\|:\|\|\|\|:\|\|\|:\|\|\|\|<br>3' UCACCGAGAUUACAACCCU 5' |
| SEQ ID 1233 | 5' GUGGCUCUAAUGUUGGGAA 3'<br>\|:\|\|\|:\|\|\|\|:\|\|\|:\|\|\|\|<br>3' CACCGAGAUUACAACCCUU 5' |
| SEQ ID 1234 | 5' UGUUGGGAAUUGGAACAGA 3'<br>\|:\|\|\|:\|\|\|\|:\|\|\|:\|\|\|\|<br>3' ACAACCCUUAACCUUGUCU 5' |
| SEQ ID 1235 | 5' UUGGAACAGAAGGACCACA 3'<br>\|:\|\|\|:\|\|\|\|:\|\|\|:\|\|\|\|<br>3' AACCUUGUCUUCCUGGUGU 5' |
| SEQ ID 1236 | 5' CAGAAGGACCACAUGUGGG 3'<br>\|:\|\|\|:\|\|\|\|:\|\|\|:\|\|\|\|<br>3' GUCUUCCUGGUGUACACCC 5' |
| SEQ ID 1237 | 5' GGACCACAUGUGGGCCUUG 3'<br>\|:\|\|\|:\|\|\|\|:\|\|\|:\|\|\|\|<br>3' CCUGGUGUACACCCGGAAC 5' |
| SEQ ID 1238 | 5' GCCAGUGAACAUCCCAAAA 3'<br>\|:\|\|\|:\|\|\|\|:\|\|\|:\|\|\|\|<br>3' CGGUCACUUGUAGGGUUUU 5' |
| SEQ ID 1239 | 5' AACUUUACAUCAGCCAAAG 3'<br>\|:\|\|\|:\|\|\|\|:\|\|\|:\|\|\|\|<br>3' UUGAAAUGUAGUCGGUUUC 5' |
| SEQ ID 1240 | 5' ACUUUACAUCAGCCAAAGA 3'<br>\|:\|\|\|:\|\|\|\|:\|\|\|:\|\|\|\|<br>3' UGAAAUGUAGUCGGUUUCU 5' |
| SEQ ID 1241 | 5' CUUUACAUCAGCCAAAGAU 3'<br>\|:\|\|\|:\|\|\|\|:\|\|\|:\|\|\|\|<br>3' GAAAUGUAGUCGGUUUCUA 5' |

Figure 2BBBB

| | |
|---|---|
| SEQ ID 1242 | 5' AGGAACUAGGUUUCAGAGG 3'<br>\|\|\|\|:\|\|\|\|\|\|\|\|\|\|\|\|\|\|<br>3' UCCUUCAUCCAAAGUCUCC 5' |
| SEQ ID 1243 | 5' GGAAGUAGGUUUCACAGGG 3'<br>\|\|\|\|:\|\|\|\|\|\|\|\|\|\|\|\|\|\|<br>3' CCUUCAUCCAAAGUCUCCC 5' |
| SEQ ID 1244 | 5' GUAGGUUUCAGAGGGGGUA 3'<br>\|\|\|\|:\|\|\|\|\|\|\|\|\|\|\|\|\|\|<br>3' CAUCCAAAGUCUCCCCCAU 5' |
| SEQ ID 1245 | 5' UUCCAAUACAGGAAAAGCC 3'<br>\|\|\|\|:\|\|\|\|\|\|\|\|\|\|\|\|\|\|<br>3' AAGGUUAUGUCCUUUUCGG 5' |
| SEQ ID 1246 | 5' UACAGGAAAAGCCUUGAAG 3'<br>\|\|\|\|:\|\|\|\|\|\|\|\|\|\|\|\|\|\|<br>3' AUGUCCUUUUCGGAACUUC 5' |
| SEQ ID 1247 | 5' AAGCCUUGAAGCAUACUGC 3'<br>\|\|\|\|:\|\|\|\|\|\|\|\|\|\|\|\|\|\|<br>3' UUCGGAACUUCGUAUGACG 5' |
| SEQ ID 1248 | 5' AGCCUUGAAGCAUACUGCU 3'<br>\|\|\|\|:\|\|\|\|\|\|\|\|\|\|\|\|\|\|<br>3' UCGGAACUUCGUAUGACGA 5' |
| SEQ ID 1249 | 5' GCCUUGAAGCAUACUGCUC 3'<br>\|\|\|\|:\|\|\|\|\|\|\|\|\|\|\|\|\|\|<br>3' CGGAACUUCGUAUGACGAG 5' |
| SEQ ID 1250 | 5' GCAUACUGCUCAGAAAUUC 3'<br>\|\|\|\|:\|\|\|\|\|\|\|\|\|\|\|\|\|\|<br>3' CGUAUGACGAGUCUUUAAG 5' |
| SEQ ID 1251 | 5' AUUCUUCACGGUAGAUGCU 3'<br>\|\|\|\|:\|\|\|\|\|\|\|\|\|\|\|\|\|\|<br>3' UAAGAAGUGCCAUCUACGA 5' |
| SEQ ID 1252 | 5' UUCUUCACGGUAGAUGCUG 3'<br>\|\|\|\|:\|\|\|\|\|\|\|\|\|\|\|\|\|\|<br>3' AAGAAGUGCCAUCUACGAC 5' |
| SEQ ID 1253 | 5' GAAAACCGAUCCCCAAAGU 3'<br>\|\|\|\|:\|\|\|\|\|\|\|\|\|\|\|\|\|\|<br>3' CUUUUCCCUAGGGGUUUCA 5' |
| SEQ ID 1254 | 5' AAGGGAUCCCCAAAGUGGU 3'<br>\|\|\|\|:\|\|\|\|\|\|\|\|\|\|\|\|\|\|<br>3' UUCCCUAGGGGUUUCACCA 5' |
| SEQ ID 1255 | 5' AGGGAUCCCCAAAGUGGUG 3'<br>\|\|\|\|:\|\|\|\|\|\|\|\|\|\|\|\|\|\|<br>3' UCCCUAGGGGUUUCACCAC 5' |
| SEQ ID 1256 | 5' GGGAUCCCCAAAGUGGUGG 3'<br>\|\|\|\|:\|\|\|\|\|\|\|\|\|\|\|\|\|\|<br>3' CCCUAGGGGUUUCACCACC 5' |
| SEQ ID 1257 | 5' AGUGGUGGUGGUAUUUAUU 3'<br>\|\|\|\|:\|\|\|\|\|\|\|\|\|\|\|\|\|\|<br>3' UCACCACCACCAUAAAUAA 5' |

Figure 2CCCC

| | |
|---|---|
| SEQ ID 1258 | 5' GUGGUGGUGGUAUUUAUUG 3'<br>\|\|\|\|\|\|\|\|\|\|\|\|:\|\|\|\|:\|<br>3' CACCACCACCAUAAAUAAC 5' |
| SEQ ID 1259 | 5' GCACGCAUUGUGGCCAGAG 3'<br>\|\|\|\|\|\|\|\|\|\|\|\|:\|\|\|\|:\|<br>3' CGUGCGUAACACCGGUCUC 5' |
| SEQ ID 1260 | 5' GCCUAUCCCUGAAGAACUG 3'<br>\|\|\|\|\|\|\|\|\|\|\|\|:\|\|\|\|:\|<br>3' CGGAUAGGGACUUCUUGAC 5' |
| SEQ ID 1261 | 5' GAACUGGGGAUGGUUCAGG 3'<br>\|\|\|\|\|\|\|\|\|\|\|\|:\|\|\|\|:\|<br>3' CUUGACCCCUACCAAGUCC 5' |
| SEQ ID 1262 | 5' CUGGGGAUGGUUCAGGAUG 3'<br>\|\|\|\|\|\|\|\|\|\|\|\|:\|\|\|\|:\|<br>3' GACCCCUACCAAGUCCUAC 5' |
| SEQ ID 1263 | 5' GGCUGUCUGUCGGAAUAAU 3'<br>\|\|\|\|\|\|\|\|\|\|\|\|:\|\|\|\|:\|<br>3' CCGACAGACAGCCUUAUUA 5' |
| SEQ ID 1264 | 5' UAAUGGCUUCUUCUCUUAC 3'<br>\|\|\|\|\|\|\|\|\|\|\|\|:\|\|\|\|:\|<br>3' AUUACCGAAGAAGAGAAUG 5' |
| SEQ ID 1265 | 5' UGGCUUCUUCUCUUACCAC 3'<br>\|\|\|\|\|\|\|\|\|\|\|\|:\|\|\|\|:\|<br>3' ACCGAAGAAGAGAAUGGUG 5' |
| SEQ ID 1266 | 5' CUGGUUUGGCACCACAAAA 3'<br>\|\|\|\|\|\|\|\|\|\|\|\|:\|\|\|\|:\|<br>3' GACCAAACCGUGGUGUUUU 5' |
| SEQ ID 1267 | 5' AAUACGUAAAGCCUCUGGU 3'<br>\|\|\|\|\|\|\|\|\|\|\|\|:\|\|\|\|:\|<br>3' UUAUGCAUUUCGGAGACCA 5' |
| SEQ ID 1268 | 5' AUACGUAAAGCCUCUGGUA 3'<br>\|\|\|\|\|\|\|\|\|\|\|\|:\|\|\|\|:\|<br>3' UAUGCAUUUCGGAGACCAU 5' |
| SEQ ID 1269 | 5' UACCUAAACCCUCUGGUAC 3'<br>\|\|\|\|\|\|\|\|\|\|\|\|:\|\|\|\|:\|<br>3' AUGCAUUUCGGAGACCAUG 5' |
| SEQ ID 1270 | 5' AGCCUCUGGUACAGAAGCU 3'<br>\|\|\|\|\|\|\|\|\|\|\|\|:\|\|\|\|:\|<br>3' UCGGAGACCAUGUCUUCGA 5' |
| SEQ ID 1271 | 5' GCCUCUGGUACAGAAGCUG 3'<br>\|\|\|\|\|\|\|\|\|\|\|\|:\|\|\|\|:\|<br>3' CGGAGACCAUGUCUUCGAC 5' |
| SEQ ID 1272 | 5' GCUGUGCACUCAUGAACAA 3'<br>\|\|\|\|\|\|\|\|\|\|\|\|:\|\|\|\|:\|<br>3' CGACACGUGAGUACUUGUU 5' |
| SEQ ID 1273 | 5' CAAAUGAUGUGCAGCAAGA 3'<br>\|\|\|\|\|\|\|\|\|\|\|\|:\|\|\|\|:\|<br>3' GUUUACUACACGUCGUUCU 5' |

Figure 2DDDD

| | |
|---|---|
| SEQ ID 1274 | 5' AUGAUGUGCAGCAAGACCU 3'<br>\|\|\|\|:\|\|\|\|\|\|\|:\|\|:\|\|:<br>3' UACUACACGUCGUUCUGGA 5' |
| SEQ ID 1275 | 5' UGAUGUGCAGCAAGACCUG 3'<br>\|\|\|\|:\|\|\|\|\|\|\|:\|\|:\|\|:<br>3' ACUACACGUCGUUCUGGAC 5' |
| SEQ ID 1276 | 5' GACCUGUUAUAACUCAGUG 3'<br>\|\|\|\|:\|\|\|\|\|\|\|:\|\|:\|\|:<br>3' CUGGACAAUAUUGAGUCAC 5' |
| SEQ ID 1277 | 5' CUCAGUGAACAUUGCCUUU 3'<br>\|\|\|\|:\|\|\|\|\|\|\|:\|\|:\|\|:<br>3' GAGUCACUUGUAACGGAAA 5' |
| SEQ ID 1278 | 5' UUGAUGGCUCCAGCAGUGU 3'<br>\|\|\|\|:\|\|\|\|\|\|\|:\|\|:\|\|:<br>3' AACUACCGAGGUCGUCACA 5' |
| SEQ ID 1279 | 5' UUUCCGCCUCAUGCUUGAA 3'<br>\|\|\|\|:\|\|\|\|\|\|\|:\|\|:\|\|:<br>3' AAAGGCGGAGUACGAACUU 5' |
| SEQ ID 1280 | 5' UUUGUUUCCAACAUAGCCA 3'<br>\|\|\|\|:\|\|\|\|\|\|\|:\|\|:\|\|:<br>3' AAACAAAGGUUGUAUCGGU 5' |
| SEQ ID 1281 | 5' CAUAGCCAAGACUUUUGAA 3'<br>\|\|\|\|:\|\|\|\|\|\|\|:\|\|:\|\|:<br>3' GUAUCGGUUCUGAAAACUU 5' |
| SEQ ID 1282 | 5' GACUUUUGAAAUCUCGGAC 3'<br>\|\|\|\|:\|\|\|\|\|\|\|:\|\|:\|\|:<br>3' CUGAAAACUUUAGAGCCUG 5' |
| SEQ ID 1283 | 5' AUCUCGGACAUUGGUGCCA 3'<br>\|\|\|\|:\|\|\|\|\|\|\|:\|\|:\|\|:<br>3' UAGAGCCUGUAACCACGGU 5' |
| SEQ ID 1284 | 5' UCUCGGACAUUGGUGCCAA 3'<br>\|\|\|\|:\|\|\|\|\|\|\|:\|\|:\|\|:<br>3' AGAGCCUGUAACCACGGUU 5' |
| SEQ ID 1285 | 5' GAUAGCUGCUGUACAGUUU 3'<br>\|\|\|\|:\|\|\|\|\|\|\|:\|\|:\|\|:<br>3' CUAUCGACGACAUGUCAAA 5' |
| SEQ ID 1286 | 5' AGAGAAUGUCCUAGCUGUC 3'<br>\|\|\|\|:\|\|\|\|\|\|\|:\|\|:\|\|:<br>3' UCUCUUACAGGAUCGACAG 5' |
| SEQ ID 1287 | 5' GAGAAUGUCCUAGCUGUCA 3'<br>\|\|\|\|:\|\|\|\|\|\|\|:\|\|:\|\|:<br>3' CUCUUACAGGAUCGACAGU 5' |
| SEQ ID 1288 | 5' UGUCCUAGCUGUCAUCAGA 3'<br>\|\|\|\|:\|\|\|\|\|\|\|:\|\|:\|\|:<br>3' ACAGGAUCGACAGUAGUCU 5' |
| SEQ ID 1289 | 5' ACAUCCGCUAUAUGACUGG 3'<br>\|\|\|\|:\|\|\|\|\|\|\|:\|\|:\|\|:<br>3' UGUAGGCGAUAUACUGACC 5' |

Figure 2EEEE

| | |
|---|---|
| SEQ ID 1290 | 5' CAUCCGCUAUAUGAGUGGU 3'<br>:\|\|:\|\|\|\|\|\|\|\|\|:\|\|:\|\|<br>3' GUAGGCGAUAUACUCACCA 5' |
| SEQ ID 1291 | 5' CAGCUACUGGUGAUGCCAU 3'<br>:\|\|:\|\|\|\|\|\|\|\|\|:\|\|:\|\|<br>3' GUCGAUGACCACUACGGUA 5' |
| SEQ ID 1292 | 5' AUGUGUUUGGCCCUAUAAG 3'<br>:\|\|:\|\|\|\|\|\|\|\|\|:\|\|:\|\|<br>3' UACACAAACCGGGAUAUUC 5' |
| SEQ ID 1293 | 5' UGUGUUUGGCCCUAUAAGG 3'<br>:\|\|:\|\|\|\|\|\|\|\|\|:\|\|:\|\|<br>3' ACACAAACCGGGAUAUUCC 5' |
| SEQ ID 1294 | 5' GGGAGAGCCCCAACAAGAA 3'<br>:\|\|:\|\|\|\|\|\|\|\|\|:\|\|:\|\|<br>3' CCCUCUCGGGGUUGUUCUU 5' |
| SEQ ID 1295 | 5' GAACUUCCUAGUAAUUGUC 3'<br>:\|\|:\|\|\|\|\|\|\|\|\|:\|\|:\|\|<br>3' CUUGAAGGAUCAUUAACAG 5' |
| SEQ ID 1296 | 5' CUUCCUAGUAAUUGUCACA 3'<br>:\|\|:\|\|\|\|\|\|\|\|\|:\|\|:\|\|<br>3' GAAGGAUCAUUAACAGUGU 5' |
| SEQ ID 1297 | 5' UUGUCACAGAUGGGCAGUC 3'<br>:\|\|:\|\|\|\|\|\|\|\|\|:\|\|:\|\|<br>3' AACAGUGUCUACCCGUCAG 5' |
| SEQ ID 1298 | 5' UCACUAUCUUCUCUGUUGG 3'<br>:\|\|:\|\|\|\|\|\|\|\|\|:\|\|:\|\|<br>3' AGUGAUAGAAGAGACAACC 5' |
| SEQ ID 1299 | 5' AGAUAUGGCUUCUAAACCG 3'<br>:\|\|:\|\|\|\|\|\|\|\|\|:\|\|:\|\|<br>3' UCUAUACCGAAGAUUUGGC 5' |
| SEQ ID 1300 | 5' GAUAUGGCUUCUAAACCGA 3'<br>:\|\|:\|\|\|\|\|\|\|\|\|:\|\|:\|\|<br>3' CUAUACCGAAGAUUUGGCU 5' |
| SEQ ID 1301 | 5' ACCGAAGGAGUCUCAUGCU 3'<br>:\|\|:\|\|\|\|\|\|\|\|\|:\|\|:\|\|<br>3' UGGCUUCCUCAGAGUACGA 5' |
| SEQ ID 1302 | 5' CCGAAGGAGUCUCAUGCUU 3'<br>:\|\|:\|\|\|\|\|\|\|\|\|:\|\|:\|\|<br>3' GGCUUCCUCAGAGUACGAA 5' |
| SEQ ID 1303 | 5' GGAGUCUCAUGCUUUCUUC 3'<br>:\|\|:\|\|\|\|\|\|\|\|\|:\|\|:\|\|<br>3' CCUCAGAGUACGAAAGAAG 5' |
| SEQ ID 1304 | 5' GAGAGUUCACAGGAUUAGA 3'<br>:\|\|:\|\|\|\|\|\|\|\|\|:\|\|:\|\|<br>3' CUCUCAAGUGUCCUAAUCU 5' |
| SEQ ID 1305 | 5' CCAAUUGUUUCUGAUGUCA 3'<br>:\|\|:\|\|\|\|\|\|\|\|\|:\|\|:\|\|<br>3' GGUUAACAAAGACUACAGU 5' |

Figure 2FFFF

| | |
|---|---|
| SEQ ID 1306 | 5' UUGUUUCUGAUGUCAUCAG 3'<br>\|:\|\|:\|\|\|\|\|\|\|\|\|\|\|\|:\|<br>3' AACAAAGACUACAGUAGUC 5' |
| SEQ ID 1307 | 5' UCCCAGCAAUAAUGGUAAC 3'<br>\|:\|\|:\|\|\|\|\|\|\|\|\|\|\|\|:\|<br>3' AGGGUCGUUAUUACCAUUG 5' |

| | |
|---|---|
| **ATP1A1** | |
| SEQ ID 1308 | 5' GGCAAUGGACCUAUGAGCA 3'<br>\|:\|\|:\|\|\|\|\|\|\|\|\|\|\|\|:\|<br>3' CCGUUACCUGGAUACUCGU 5' |
| SEQ ID 1309 | 5' UGGACCUAUGAGCAGAGGA 3'<br>\|:\|\|:\|\|\|\|\|\|\|\|\|\|\|\|:\|<br>3' ACCUGGAUACUCGUCUCCU 5' |
| SEQ ID 1310 | 5' GGGGGUUGGACGUGAUAAG 3'<br>\|:\|\|:\|\|\|\|\|\|\|\|\|\|\|\|:\|<br>3' CCCCCAACCUGCACUAUUC 5' |
| SEQ ID 1311 | 5' GUAUGAGCCUGCAGCUGUU 3'<br>\|:\|\|:\|\|\|\|\|\|\|\|\|\|\|\|:\|<br>3' CAUACUCGGACGUCGACAA 5' |
| SEQ ID 1312 | 5' CAAGGUCAUAAAAAGGGCA 3'<br>\|:\|\|:\|\|\|\|\|\|\|\|\|\|\|\|:\|<br>3' GUUCCACUAUUUUUCCCGU 5' |
| SEQ ID 1313 | 5' GGUGAUAAAAAGGGCAAAA 3'<br>\|:\|\|:\|\|\|\|\|\|\|\|\|\|\|\|:\|<br>3' CCACUAUUUUUCCCGUUUU 5' |
| SEQ ID 1314 | 5' AAAGGGCAAAAAGGGCAAA 3'<br>\|:\|\|:\|\|\|\|\|\|\|\|\|\|\|\|:\|<br>3' UUUCCCGUUUUUCCCGUUU 5' |
| SEQ ID 1315 | 5' AAGGGCAAAAAGGGCAAAA 3'<br>\|:\|\|:\|\|\|\|\|\|\|\|\|\|\|\|:\|<br>3' UUCCCGUUUUUCCCGUUUU 5' |
| SEQ ID 1316 | 5' AGGGCAAAAAGGGCAAAAA 3'<br>\|:\|\|:\|\|\|\|\|\|\|\|\|\|\|\|:\|<br>3' UCCCGUUUUUCCCGUUUUU 5' |
| SEQ ID 1317 | 5' GGGCAAAAAGGGCAAAAAA 3'<br>\|:\|\|:\|\|\|\|\|\|\|\|\|\|\|\|:\|<br>3' CCCGUUUUUCCCGUUUUUU 5' |
| SEQ ID 1318 | 5' AAAGGGCAAAAAAGACAGG 3'<br>\|:\|\|:\|\|\|\|\|\|\|\|\|\|\|\|:\|<br>3' UUUCCCGUUUUUUCUGUCC 5' |
| SEQ ID 1319 | 5' AAGGGCAAAAAAGACAGGG 3'<br>\|:\|\|:\|\|\|\|\|\|\|\|\|\|\|\|:\|<br>3' UUCCCGUUUUUUCUGUCCC 5' |
| SEQ ID 1320 | 5' AGGGCAAAAAAGACAGGGA 3'<br>\|:\|\|:\|\|\|\|\|\|\|\|\|\|\|\|:\|<br>3' UCCCGUUUUUUCUGUCCCU 5' |

Figure 2GGGG

| | |
|---|---|
| SEQ ID 1321 | 5' GGGCAAAAAAGACAGGGAC 3'<br>\|\|:\|\|\|\|\|\|\|\|\|\|\|\|\|\|::<br>3' CCCGUUUUUUCUGUCCCUG 5' |
| SEQ ID 1322 | 5' AAAAGACAGGGACAUGGAU 3'<br>\|\|:\|\|\|\|\|\|\|\|\|\|\|\|\|\|::<br>3' UUUUCUGUCCCUGUACCUA 5' |
| SEQ ID 1323 | 5' AAAGACAGGGACAUGGAUG 3'<br>\|\|:\|\|\|\|\|\|\|\|\|\|\|\|\|\|::<br>3' UUUCUGUCCCUGUACCUAC 5' |
| SEQ ID 1324 | 5' AAGACAGGGACAUGGAUGA 3'<br>\|\|:\|\|\|\|\|\|\|\|\|\|\|\|\|\|::<br>3' UUCUGUCCCUGUACCUACU 5' |
| SEQ ID 1325 | 5' AGACAGGGACAUGCAUGAA 3'<br>\|\|:\|\|\|\|\|\|\|\|\|\|\|\|\|\|::<br>3' UCUGUCCCUGUACCUACUU 5' |
| SEQ ID 1326 | 5' GACAGGGACAUGGAUGAAC 3'<br>\|\|:\|\|\|\|\|\|\|\|\|\|\|\|\|\|::<br>3' CUGUCCCUGUACCUACUUG 5' |
| SEQ ID 1327 | 5' GAAGUUUCUAUGGAUGAUC 3'<br>\|\|:\|\|\|\|\|\|\|\|\|\|\|\|\|\|::<br>3' CUUCAAAGAUACCUACUAG 5' |
| SEQ ID 1328 | 5' ACUUAGCCUUGAUGAACUU 3'<br>\|\|:\|\|\|\|\|\|\|\|\|\|\|\|\|\|::<br>3' UGAAUCGGAACUACUUGAA 5' |
| SEQ ID 1329 | 5' CUUAGCCUUGAUGAACUUC 3'<br>\|\|:\|\|\|\|\|\|\|\|\|\|\|\|\|\|::<br>3' GAAUCGGAACUACUUGAAG 5' |
| SEQ ID 1330 | 5' AUAUGGAACAGACUUGAGC 3'<br>\|\|:\|\|\|\|\|\|\|\|\|\|\|\|\|\|::<br>3' UAUACCUUGUCUGAACUCG 5' |
| SEQ ID 1331 | 5' UAUGGAACAGACUUGAGCC 3'<br>\|\|:\|\|\|\|\|\|\|\|\|\|\|\|\|\|::<br>3' AUACCUUGUCUGAACUCGG 5' |
| SEQ ID 1332 | 5' CAGACUUGAGCCGGGAUU 3'<br>\|\|:\|\|\|\|\|\|\|\|\|\|\|\|\|\|::<br>3' GUCUGAACUCGGCCCCUAA 5' |
| SEQ ID 1333 | 5' CAUCUGCUCGUGCAGCUGA 3'<br>\|\|:\|\|\|\|\|\|\|\|\|\|\|\|\|\|::<br>3' GUAGACGAGCACGUCGACU 5' |
| SEQ ID 1334 | 5' UGGAUCAAGUUUUGUCGGC 3'<br>\|\|:\|\|\|\|\|\|\|\|\|\|\|\|\|\|::<br>3' ACCUAGUUCAAAACAGCCG 5' |
| SEQ ID 1335 | 5' GUUUUGUCGGCAGCUCUUU 3'<br>\|\|:\|\|\|\|\|\|\|\|\|\|\|\|\|\|::<br>3' CAAAACAGCCGUCCAGAAA 5' |
| SEQ ID 1336 | 5' UGUUACUGUGGAUUGGAGC 3'<br>\|\|:\|\|\|\|\|\|\|\|\|\|\|\|\|\|::<br>3' ACAAUGACACCUAACCUCG 5' |

Figure 2HHHH

| | |
|---|---|
| SEQ ID 1337 | 5' GCUGCUACAGAAGAGGAAC 3'<br>\|\|\|\|\|\|\|\|:\|\|\|\|:\|\|\|\|:<br>3' CGACGAUGUCUUCUCCUUG 5' |
| SEQ ID 1338 | 5' GAGGAACCUCAAAACGAUA 3'<br>\|\|\|\|\|\|\|\|:\|\|\|\|:\|\|\|\|:<br>3' CUCCUUGGAGUUUUGCUAU 5' |
| SEQ ID 1339 | 5' CCUCAAAACGAUAAUCUGU 3'<br>\|\|\|\|\|\|\|\|:\|\|\|\|:\|\|\|\|:<br>3' GGAGUUUUGCUAUUAGACA 5' |
| SEQ ID 1340 | 5' AACGAUAAUCUGUACCUGG 3'<br>\|\|\|\|\|\|\|\|:\|\|\|\|:\|\|\|\|:<br>3' UUGCUAUUAGACAUGGACC 5' |
| SEQ ID 1341 | 5' ACGAUAAUCUGUACCUGGG 3'<br>\|\|\|\|\|\|\|\|:\|\|\|\|:\|\|\|\|:<br>3' UGCUAUUAGACAUGGACCC 5' |
| SEQ ID 1342 | 5' CGAUAAUCUGUACCUGGGU 3'<br>\|\|\|\|\|\|\|\|:\|\|\|\|:\|\|\|\|:<br>3' GCUAUUAGACAUGGACCCA 5' |
| SEQ ID 1343 | 5' UCUGUACCUGGGUGUGGUG 3'<br>\|\|\|\|\|\|\|\|:\|\|\|\|:\|\|\|\|:<br>3' AGACAUGGACCCACACCAC 5' |
| SEQ ID 1344 | 5' UCAUAACUGGUUGCUUCUC 3'<br>\|\|\|\|\|\|\|\|:\|\|\|\|:\|\|\|\|:<br>3' AGUAUUGACCAACGAAGAG 5' |
| SEQ ID 1345 | 5' CUGGUUGCUUCUCCUACUA 3'<br>\|\|\|\|\|\|\|\|:\|\|\|\|:\|\|\|\|:<br>3' GACCAACGAAGAGGAUGAU 5' |
| SEQ ID 1346 | 5' GUUCAAAGAUCAUGGAAUC 3'<br>\|\|\|\|\|\|\|\|:\|\|\|\|:\|\|\|\|:<br>3' CAAGUUUCUAGUACCUUAG 5' |
| SEQ ID 1347 | 5' AGAUCAUGGAAUCCUUCAA 3'<br>\|\|\|\|\|\|\|\|:\|\|\|\|:\|\|\|\|:<br>3' UCUAGUACCUUAGGAAGUU 5' |
| SEQ ID 1348 | 5' GAUCAUGGAAUCCUUCAAA 3'<br>\|\|\|\|\|\|\|\|:\|\|\|\|:\|\|\|\|:<br>3' CUAGUACCUUAGGAAGUUU 5' |
| SEQ ID 1349 | 5' UCCUUCAAAAACAUGGUCC 3'<br>\|\|\|\|\|\|\|\|:\|\|\|\|:\|\|\|\|:<br>3' AGGAAGUUUUUGUACCAGG 5' |
| SEQ ID 1350 | 5' AAACAUGGUCCCUCAGCAA 3'<br>\|\|\|\|\|\|\|\|:\|\|\|\|:\|\|\|\|:<br>3' UUUGUACCAGGGAGUCGUU 5' |
| SEQ ID 1351 | 5' AACAUGGUCCCUCAGCAAG 3'<br>\|\|\|\|\|\|\|\|:\|\|\|\|:\|\|\|\|:<br>3' UUGUACCAGGGAGUCGUUC 5' |
| SEQ ID 1352 | 5' ACAUGGUCCCUCAGCAAGC 3'<br>\|\|\|\|\|\|\|\|:\|\|\|\|:\|\|\|\|:<br>3' UGUACCAGGGAGUCGUUCG 5' |

Figure 2IIII

| | |
|---|---|
| SEQ ID 1353 | 5' CAUGGUCCCUCAGCAAGCC 3'<br>\|\|\|\|\|\|\|\|\|\|\|\|\|:\|\|\|\|:<br>3' GUACCAGGGAGUCGUUCGG 5' |
| SEQ ID 1354 | 5' GCCCUUGUGAUUCGAAAUG 3'<br>\|\|\|\|\|\|\|\|\|\|\|\|\|:\|\|\|\|:<br>3' CGGGAACACUAAGCUUUAC 5' |
| SEQ ID 1355 | 5' AUGGUGAGAAAAUGAGCAU 3'<br>\|\|\|\|\|\|\|\|\|\|\|\|\|:\|\|\|\|:<br>3' UACCACUCUUUUACUCGUA 5' |
| SEQ ID 1356 | 5' UGGUGAGAAAAUGAGCAUA 3'<br>\|\|\|\|\|\|\|\|\|\|\|\|\|:\|\|\|\|:<br>3' ACCACUCUUUUACUCGUAU 5' |
| SEQ ID 1357 | 5' AAUGAGCAUAAAUGCGGAG 3'<br>\|\|\|\|\|\|\|\|\|\|\|\|\|:\|\|\|\|:<br>3' UUACUCGUAUUUACGCCUC 5' |
| SEQ ID 1358 | 5' AUGAGCAUAAAUGCGGAGG 3'<br>\|\|\|\|\|\|\|\|\|\|\|\|\|:\|\|\|\|:<br>3' UACUCGUAUUUACGCCUCC 5' |
| SEQ ID 1359 | 5' UGAGCAUAAAUGCGGAGGA 3'<br>\|\|\|\|\|\|\|\|\|\|\|\|\|:\|\|\|\|:<br>3' ACUCGUAUUUACGCCUCCU 5' |
| SEQ ID 1360 | 5' AUGCGGAGGAAGUUGUGGU 3'<br>\|\|\|\|\|\|\|\|\|\|\|\|\|:\|\|\|\|:<br>3' UACGCCUCCUUCAACACCA 5' |
| SEQ ID 1361 | 5' UGCGGAGGAAGUUGUGGUU 3'<br>\|\|\|\|\|\|\|\|\|\|\|\|\|:\|\|\|\|:<br>3' ACGCCUCCUUCAACACCAA 5' |
| SEQ ID 1362 | 5' GUUGUGGUUCGGGAUCUGG 3'<br>\|\|\|\|\|\|\|\|\|\|\|\|\|:\|\|\|\|:<br>3' CAACACCAACCCCUAGACC 5' |
| SEQ ID 1363 | 5' GUAAAAGGACGAGACCGAA 3'<br>\|\|\|\|\|\|\|\|\|\|\|\|\|:\|\|\|\|:<br>3' CAUUUUCCUCCUCUGGCUU 5' |
| SEQ ID 1364 | 5' AAGCAGGACACCGAAUUCC 3'<br>\|\|\|\|\|\|\|\|\|\|\|\|\|:\|\|\|\|:<br>3' UUCCUCCUCUGGCUUAAGG 5' |
| SEQ ID 1365 | 5' AGGAGGAGACCGAAUUCCU 3'<br>\|\|\|\|\|\|\|\|\|\|\|\|\|:\|\|\|\|:<br>3' UCCUCCUCUGGCUUAAGGA 5' |
| SEQ ID 1366 | 5' GGAGGAGACCGAAUUCCUG 3'<br>\|\|\|\|\|\|\|\|\|\|\|\|\|:\|\|\|\|:<br>3' CCUCCUCUGGCUUAAGGAC 5' |
| SEQ ID 1367 | 5' UUCCUGCUGACCUCAGAAU 3'<br>\|\|\|\|\|\|\|\|\|\|\|\|\|:\|\|\|\|:<br>3' AAGGACGACUGGAGUCUUA 5' |
| SEQ ID 1368 | 5' UCAUAUCUGCAAAUGGCUG 3'<br>\|\|\|\|\|\|\|\|\|\|\|\|\|:\|\|\|\|:<br>3' AGUAUAGACGUUUACCGAC 5' |

Figure 2JJJJ

| | |
|---|---|
| SEQ ID 1369 | 5' AUGGCUGCAAGGUGGAUAA 3'<br>\|\|\|\|:\|\|\|\|\|\|\|\|\|\|:\|:\|<br>3' UACCGACGUUCCACCUAUU 5' |
| SEQ ID 1370 | 5' UGGCUGCAAGGUGGAUAAC 3'<br>\|\|\|\|:\|\|\|\|\|\|\|\|\|\|:\|:\|<br>3' ACCGACGUUCCACCUAUUG 5' |
| SEQ ID 1371 | 5' GGUGGAUAACUCCUCGCUC 3'<br>\|\|\|\|:\|\|\|\|\|\|\|\|\|\|:\|:\|<br>3' CCACCUAUUGAGGAGCGAG 5' |
| SEQ ID 1372 | 5' CUCCUCGCUCACUGGUGAA 3'<br>\|\|\|\|:\|\|\|\|\|\|\|\|\|\|:\|:\|<br>3' GAGGAGCGAGUGACCACUU 5' |
| SEQ ID 1373 | 5' UCAGAACCCCAGACUAGGU 3'<br>\|\|\|\|:\|\|\|\|\|\|\|\|\|\|:\|:\|<br>3' AGUCUUGGGGUCUGAUCCA 5' |
| SEQ ID 1374 | 5' CCCCAGACUAGGUCUCCAG 3'<br>\|\|\|\|:\|\|\|\|\|\|\|\|\|\|:\|:\|<br>3' GGGGUCUGAUCCAGAGGUC 5' |
| SEQ ID 1375 | 5' AUGAAAACCCCCUGGAGAC 3'<br>\|\|\|\|:\|\|\|\|\|\|\|\|\|\|:\|:\|<br>3' UACUUUUGGGGGACCUCUG 5' |
| SEQ ID 1376 | 5' UGAAAACCCCCUGGAGACG 3'<br>\|\|\|\|:\|\|\|\|\|\|\|\|\|\|:\|:\|<br>3' ACUUUUGGGGGACCUCUGC 5' |
| SEQ ID 1377 | 5' AACCCCCUGGAGACGAGGA 3'<br>\|\|\|\|:\|\|\|\|\|\|\|\|\|\|:\|:\|<br>3' UUGGGGGACCUCUGCUCCU 5' |
| SEQ ID 1378 | 5' ACCCCCUGGAGACGAGGAA 3'<br>\|\|\|\|:\|\|\|\|\|\|\|\|\|\|:\|:\|<br>3' UGGGGGACCUCUGCUCCUU 5' |
| SEQ ID 1379 | 5' CAUUGCCUUCUUUUCAACC 3'<br>\|\|\|\|:\|\|\|\|\|\|\|\|\|\|:\|:\|<br>3' GUAACGGAAGAAAAGUUGG 5' |
| SEQ ID 1380 | 5' CCAAUUGUGUUGAAGGCAC 3'<br>\|\|\|\|:\|\|\|\|\|\|\|\|\|\|:\|:\|<br>3' GGUUAACACAACUUCCGUG 5' |
| SEQ ID 1381 | 5' UUGUGUUGAAGGCACCGCA 3'<br>\|\|\|\|:\|\|\|\|\|\|\|\|\|\|:\|:\|<br>3' AACACAACUUCCGUGGCGU 5' |
| SEQ ID 1382 | 5' GGCACCGCACGUGGUAUUG 3'<br>\|\|\|\|:\|\|\|\|\|\|\|\|\|\|:\|:\|<br>3' CCGUGGCGUGCACCAUAAC 5' |
| SEQ ID 1383 | 5' GAAUUGCCACACUUGCUUC 3'<br>\|\|\|\|:\|\|\|\|\|\|\|\|\|\|:\|:\|<br>3' CUUAACGGUGUGAACGAAG 5' |
| SEQ ID 1384 | 5' UUGCCACACUUGCUUCUGG 3'<br>\|\|\|\|:\|\|\|\|\|\|\|\|\|\|:\|:\|<br>3' AACGGUGUGAACGAAGACC 5' |

Figure 2KKKK

| | |
|---|---|
| SEQ ID 1385 | 5' UGUGCCGGAAGGUUUGCUG 3'<br>\|:\|\|\|:\|\|\|\|\|\|:\|\|\|:\|:<br>3' ACACGGCCUUCCAAACGAC 5' |
| SEQ ID 1386 | 5' GGUUUGCUGGCCACUGUCA 3'<br>\|:\|\|\|:\|\|\|\|\|\|:\|\|\|:\|:<br>3' CCAAACGACCGGUGACAGU 5' |
| SEQ ID 1387 | 5' ACGCAUGGCAAGGAAAAAC 3'<br>\|:\|\|\|:\|\|\|\|\|\|:\|\|\|:\|:<br>3' UGCGUACCGUUCCUUUUUG 5' |
| SEQ ID 1388 | 5' CGCAUGGCAAGGAAAAACU 3'<br>\|:\|\|\|:\|\|\|\|\|\|:\|\|\|:\|:<br>3' GCGUACCGUUCCUUUUUGA 5' |
| SEQ ID 1389 | 5' GGAAAAACUGCUUAGUGAA 3'<br>\|:\|\|\|:\|\|\|\|\|\|:\|\|\|:\|:<br>3' CCUUUUUGACGAAUCACUU 5' |
| SEQ ID 1390 | 5' AAACUGCUUAGUGAAGAAC 3'<br>\|:\|\|\|:\|\|\|\|\|\|:\|\|\|:\|:<br>3' UUUGACGAAUCACUUCUUG 5' |
| SEQ ID 1391 | 5' AACUGCUUAGUGAAGAACU 3'<br>\|:\|\|\|:\|\|\|\|\|\|:\|\|\|:\|:<br>3' UUGACGAAUCACUUCUUGA 5' |
| SEQ ID 1392 | 5' ACUGCUUAGUGAAGAACUU 3'<br>\|:\|\|\|:\|\|\|\|\|\|:\|\|\|:\|:<br>3' UGACGAAUCACUUCUUGAA 5' |
| SEQ ID 1393 | 5' CUGCUUAGUGAAGAACUUA 3'<br>\|:\|\|\|:\|\|\|\|\|\|:\|\|\|:\|:<br>3' GACGAAUCACUUCUUGAAU 5' |
| SEQ ID 1394 | 5' GAACUUAGAAGCUGUGGAG 3'<br>\|:\|\|\|:\|\|\|\|\|\|:\|\|\|:\|:<br>3' CUUGAAUCUUCGACACCUC 5' |
| SEQ ID 1395 | 5' CUUAGAAGCUGUGGAGACC 3'<br>\|:\|\|\|:\|\|\|\|\|\|:\|\|\|:\|:<br>3' GAAUCUUCGACACCUCUGG 5' |
| SEQ ID 1396 | 5' GCUGUGGAGACCUUGGGGU 3'<br>\|:\|\|\|:\|\|\|\|\|\|:\|\|\|:\|:<br>3' CGACACCUCUGGAACCCCA 5' |
| SEQ ID 1397 | 5' AACUGGAACUCUGACUCAG 3'<br>\|:\|\|\|:\|\|\|\|\|\|:\|\|\|:\|:<br>3' UUGACCUUGAGACUGAGUC 5' |
| SEQ ID 1398 | 5' ACUGGAACUCUGACUCAGA 3'<br>\|:\|\|\|:\|\|\|\|\|\|:\|\|\|:\|:<br>3' UGACCUUGAGACUGAGUCU 5' |
| SEQ ID 1399 | 5' CUGGAACUCUGACUCAGAA 3'<br>\|:\|\|\|:\|\|\|\|\|\|:\|\|\|:\|:<br>3' GACCUUGAGACUGAGUCUU 5' |
| SEQ ID 1400 | 5' CUCUGACUCAGAACCGGAU 3'<br>\|:\|\|\|:\|\|\|\|\|\|:\|\|\|:\|:<br>3' GAGACUGAGUCUUGGCCUA 5' |

Figure 2LLLL

| | |
|---|---|
| SEQ ID 1401 | 5' UCAAAUCCAUGAAGCUGAU 3'<br>\|\|:\|\|\|:\|:\|\|\|\|\|\|\|\|:\|<br>3' AGUUUAGGUACUUCGACUA 5' |
| SEQ ID 1402 | 5' AUCCAUGAAGCUGAUACGA 3'<br>\|\|:\|\|\|:\|:\|\|\|\|\|\|\|\|:\|<br>3' UAGGUACUUCGACUAUGCU 5' |
| SEQ ID 1403 | 5' UCCAUGAAGCUGAUACGAC 3'<br>\|\|:\|\|\|:\|:\|\|\|\|\|\|\|\|:\|<br>3' AGGUACUUCGACUAUGCUG 5' |
| SEQ ID 1404 | 5' GCUGAUACGACAGAGAAUC 3'<br>\|\|:\|\|\|:\|:\|\|\|\|\|\|\|\|:\|<br>3' CGACUAUGCUGUCUCUUAG 5' |
| SEQ ID 1405 | 5' UCAGAGUGGUGUCUCUUUU 3'<br>\|\|:\|\|\|:\|:\|\|\|\|\|\|\|\|:\|<br>3' AGUCUCACCACAGAGAAAA 5' |
| SEQ ID 1406 | 5' GACUUCAGCUACCUGGCUU 3'<br>\|\|:\|\|\|:\|:\|\|\|\|\|\|\|\|:\|<br>3' CUGAAGUCGAUGGACCGAA 5' |
| SEQ ID 1407 | 5' UUGCAGGUCUUUGUAACAG 3'<br>\|\|:\|\|\|:\|:\|\|\|\|\|\|\|\|:\|<br>3' AACGUCCAGAAACAUUGUC 5' |
| SEQ ID 1408 | 5' CAGGGCAGUGUUUCAGGCU 3'<br>\|\|:\|\|\|:\|:\|\|\|\|\|\|\|\|:\|<br>3' GUCCCGUCACAAAGUCCGA 5' |
| SEQ ID 1409 | 5' CCAGGAAAACCUACCUAUU 3'<br>\|\|:\|\|\|:\|:\|\|\|\|\|\|\|\|:\|<br>3' GGUCCUUUUGGAUGGAUAA 5' |
| SEQ ID 1410 | 5' AACCUACCUAUUCUUAAGC 3'<br>\|\|:\|\|\|:\|:\|\|\|\|\|\|\|\|:\|<br>3' UUGGAUGGAUAAGAAUUCG 5' |
| SEQ ID 1411 | 5' ACCUACCUAUUCUUAAGCG 3'<br>\|\|:\|\|\|:\|:\|\|\|\|\|\|\|\|:\|<br>3' UGGAUGGAUAAGAAUUCGC 5' |
| SEQ ID 1412 | 5' CCUACCUAUUCUUAAGCGG 3'<br>\|\|:\|\|\|:\|:\|\|\|\|\|\|\|\|:\|<br>3' GGAUGGAUAAGAAUUCGCC 5' |
| SEQ ID 1413 | 5' GCGGGCAGUUGCAGGAGAU 3'<br>\|\|:\|\|\|:\|:\|\|\|\|\|\|\|\|:\|<br>3' CGCCCGUCAACGUCCUCUA 5' |
| SEQ ID 1414 | 5' AGUGCAUAGAGCUGUGCUG 3'<br>\|\|:\|\|\|:\|:\|\|\|\|\|\|\|\|:\|<br>3' UCACGUAUCUCGACACGAC 5' |
| SEQ ID 1415 | 5' GUGCAUAGAGCUGUGCUGU 3'<br>\|\|:\|\|\|:\|:\|\|\|\|\|\|\|\|:\|<br>3' CACGUAUCUCGACACGACA 5' |
| SEQ ID 1416 | 5' GGAGAUGAGAGAAAGAUAC 3'<br>\|\|:\|\|\|:\|:\|\|\|\|\|\|\|\|:\|<br>3' CCUCUACUCUCUUUCUAUG 5' |

Figure 2:
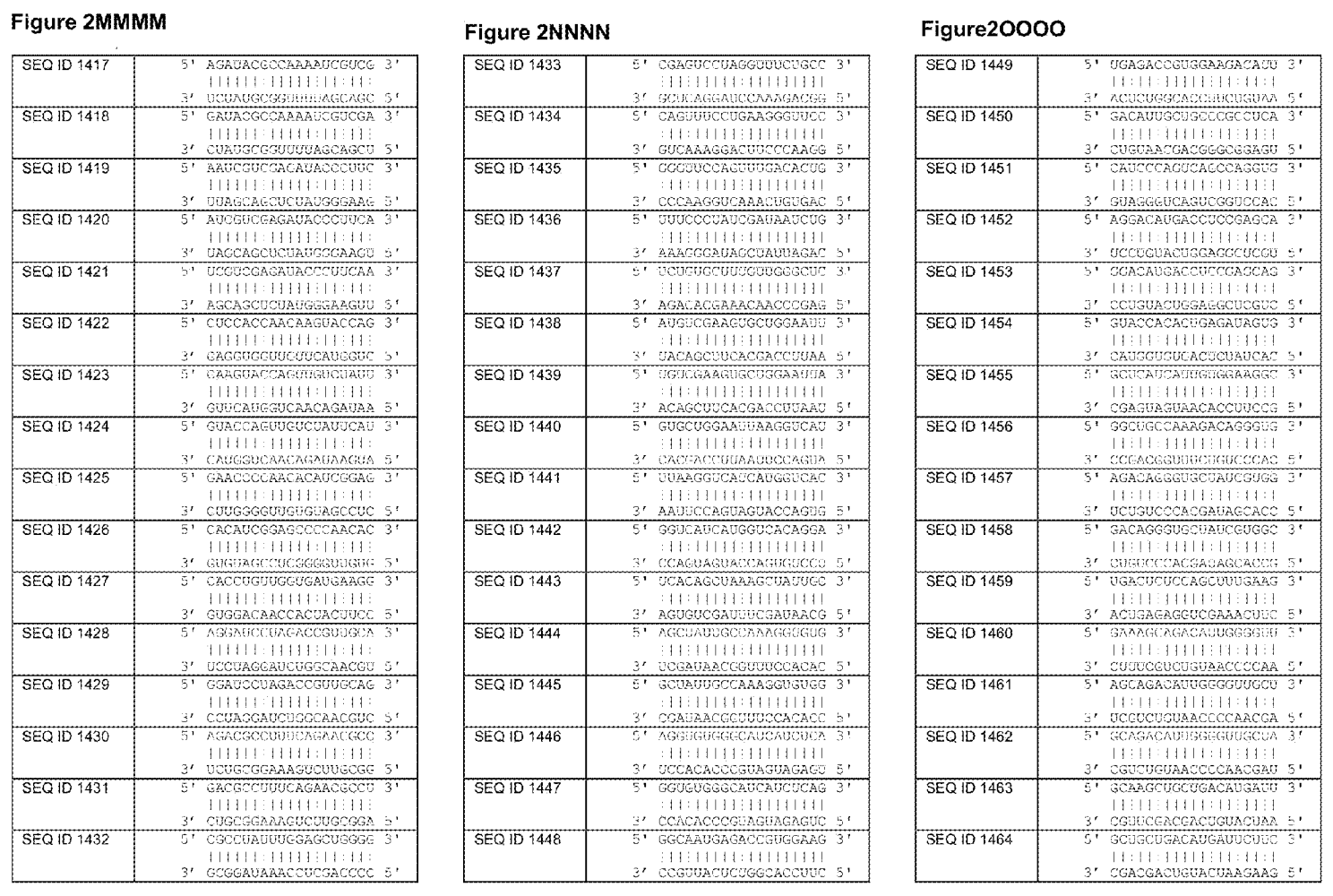

Figure 2MMMM

| | |
|---|---|
| SEQ ID 1417 | 5' AGAUACGCCAAAAUCGUCG 3'<br>3' UCUAUGCGGUUUUAGCAGC 5' |
| SEQ ID 1418 | 5' GAUACGCCAAAAUCGUCGA 3'<br>3' CUAUGCGGUUUUAGCAGCU 5' |
| SEQ ID 1419 | 5' AAUCGUCGACAUACCCUUC 3'<br>3' UUAGCAGCUCUAUGGGAAG 5' |
| SEQ ID 1420 | 5' AUCGUCGAGAUACCCUUCA 3'<br>3' UAGCAGCUCUAUGGGAAGU 5' |
| SEQ ID 1421 | 5' UCGUCGAGAUACCCUUCAA 3'<br>3' AGCAGCUCUAUGGGAAGUU 5' |
| SEQ ID 1422 | 5' CUCCACCAACAAGUACCAG 3'<br>3' GAGGUGGUUCUUCAUGGUC 5' |
| SEQ ID 1423 | 5' CAAGUACCAGUUGUCUAUU 3'<br>3' GUUCAUGGUCAACAGAUAA 5' |
| SEQ ID 1424 | 5' GUACCAGUUGUCUAUUCAU 3'<br>3' CAUGGUCAACAGAUAAGUA 5' |
| SEQ ID 1425 | 5' GAACCCCAACACAUCGGAG 3'<br>3' CUUGGGGUUGUGUAGCCUC 5' |
| SEQ ID 1426 | 5' CACAUCGGAGCCCCAACAC 3'<br>3' GUGUAGCCUCGGGGUUGUG 5' |
| SEQ ID 1427 | 5' CACCUGUUGGUGAUGAAGG 3'<br>3' GUGGACAACCACUACUUCC 5' |
| SEQ ID 1428 | 5' AGGAUCCUAGACCGUUGCA 3'<br>3' UCCUAGGAUCUGGCAACGU 5' |
| SEQ ID 1429 | 5' GGAUCCUAGACCGUUGCAG 3'<br>3' CCUAGGAUCUGGCAACGUC 5' |
| SEQ ID 1430 | 5' AGACGCCUUUCAGAACGCC 3'<br>3' UCUGCGGAAAGUCUUGCGG 5' |
| SEQ ID 1431 | 5' GACGCCUUUCAGAACGCCU 3'<br>3' CUGCGGAAAGUCUUGCGGA 5' |
| SEQ ID 1432 | 5' CGCCUAUUUGGAGCUGGGG 3'<br>3' GCGGAUAAACCUCGACCCC 5' |

Figure 2NNNN

| | |
|---|---|
| SEQ ID 1433 | 5' CGAGUCCUAGGUUUCUGCC 3'<br>3' GCUCAGGAUCCAAAGACGG 5' |
| SEQ ID 1434 | 5' CAGUUUCCUGAAGGGUUCC 3'<br>3' GUCAAAGGACUUCCCAAGG 5' |
| SEQ ID 1435 | 5' GGGUUCCACUUUGACACUG 3'<br>3' CCCAAGGUCAAACUGUGAC 5' |
| SEQ ID 1436 | 5' UUUCCCUAUCGAUAAUCUG 3'<br>3' AAAGGGAUAGCUAUUAGAC 5' |
| SEQ ID 1437 | 5' UCUGUGCUUUGUUGGGCUC 3'<br>3' AGACACGAAACAACCCGAG 5' |
| SEQ ID 1438 | 5' AUGUCGAAGUGCUGGAAUU 3'<br>3' UACAGCUUCACGACCUUAA 5' |
| SEQ ID 1439 | 5' UGUCGAAGUGCUGGAAUUA 3'<br>3' ACAGCUUCACGACCUUAAU 5' |
| SEQ ID 1440 | 5' GUGCUGGAAUUAAGGUCAU 3'<br>3' CACGACCUUAAUUCCAGUA 5' |
| SEQ ID 1441 | 5' UUAAGGUCAUCAUGGUCAC 3'<br>3' AAUUCCAGUAGUACCAGUG 5' |
| SEQ ID 1442 | 5' GGUCAUCAUGGUCACAGGA 3'<br>3' CCAGUAGUACCAGUGUCCU 5' |
| SEQ ID 1443 | 5' UCACAGCUAAAGCUAUUGC 3'<br>3' AGUGUCGAUUUCGAUAACG 5' |
| SEQ ID 1444 | 5' AGCUAUUGCCAAAGGUGUG 3'<br>3' UCGAUAACGGUUUCCACAC 5' |
| SEQ ID 1445 | 5' GCUAUUGCCAAAGGUGUGG 3'<br>3' CGAUAACGGUUUCCACACC 5' |
| SEQ ID 1446 | 5' AGGUGUGGGCAUCAUCUCA 3'<br>3' UCCACACCCGUAGUAGAGU 5' |
| SEQ ID 1447 | 5' GGUGUGGGCAUCAUCUCAG 3'<br>3' CCACACCCGUAGUAGAGUC 5' |
| SEQ ID 1448 | 5' GGCAAUGAGACCGUGGAAG 3'<br>3' CCGUUACUCUGGCACCUUC 5' |

Figure2OOOO

| | |
|---|---|
| SEQ ID 1449 | 5' UGAGACCGUGGAAGACAUU 3'<br>3' ACUCUGGCACCUUCUGUAA 5' |
| SEQ ID 1450 | 5' GACAUUGCUGCCCGCCUCA 3'<br>3' CUGUAACGACGGGCGGAGU 5' |
| SEQ ID 1451 | 5' CAUCCCAGUCAGCCAGGUG 3'<br>3' GUAGGGUCAGUCGGUCCAC 5' |
| SEQ ID 1452 | 5' AGGACAUGACCUCCGAGCA 3'<br>3' UCCUGUACUGGAGGCUCGU 5' |
| SEQ ID 1453 | 5' GGACAUGACCUCCGAGCAG 3'<br>3' CCUGUACUGGAGGCUCGUC 5' |
| SEQ ID 1454 | 5' GUACCACACUGAGAUAGUG 3'<br>3' CAUGGUGUCACUCUAUCAC 5' |
| SEQ ID 1455 | 5' GCUCAUCAUUGUGGAAGGC 3'<br>3' CGAGUAGUAACACCUUCCG 5' |
| SEQ ID 1456 | 5' GGCUGCCAAAGACAGGGUG 3'<br>3' CCGACGGUUUCUGUCCCAC 5' |
| SEQ ID 1457 | 5' AGACAGGGUGCUAUCGUGG 3'<br>3' UCUGUCCCACGAUAGCACC 5' |
| SEQ ID 1458 | 5' GACAGGGUGCUAUCGUGGC 3'<br>3' CUGUCCCACGAUAGCACCG 5' |
| SEQ ID 1459 | 5' UGACUCUCCAGCUUUGAAG 3'<br>3' ACUGAGAGGUCGAAACUUC 5' |
| SEQ ID 1460 | 5' GAAAGCAGACAUUGGGGUU 3'<br>3' CUUUCGUCUGUAACCCCAA 5' |
| SEQ ID 1461 | 5' AGCAGACAUUGGGGUUGCU 3'<br>3' UCGUCUGUAACCCCAACGA 5' |
| SEQ ID 1462 | 5' GCAGACAUUGGGGUUGCUA 3'<br>3' CGUCUGUAACCCCAACGAU 5' |
| SEQ ID 1463 | 5' GCAAGCUGCUGACAUGAUU 3'<br>3' CGUUCGACGACUGUACUAA 5' |
| SEQ ID 1464 | 5' GCUGCUGACAUGAUUCUUC 3'<br>3' CGACGACUGUACUAAGAAG 5' |

Figure 2PPPP

| | |
|---|---|
| SEQ ID 1465 | 5' CUUUGCCUCAAUUGUGACU 3'<br>\|\|:\|:\|:\|\|\|\|\|\|\|\|\|\|\|\|<br>3' GAAACGGAGUUAACACUGA 5' |
| SEQ ID 1466 | 5' UUGUGACUGGAGUAGAGGA 3'<br>\|\|:\|:\|:\|\|\|\|\|\|\|\|\|\|\|\|<br>3' AACACUGACCUCAUCUCCU 5' |
| SEQ ID 1467 | 5' GGUCGUCUGAUCUUUGAUA 3'<br>\|\|:\|:\|:\|\|\|\|\|\|\|\|\|\|\|\|<br>3' CCAGCAGACUAGAAACUAU 5' |
| SEQ ID 1468 | 5' CUUGAAGAAAUCCAUUGCU 3'<br>\|\|:\|:\|:\|\|\|\|\|\|\|\|\|\|\|\|<br>3' GAACUUCUUUAGGUAACGA 5' |
| SEQ ID 1469 | 5' GAAAUCCAUUGCUUAUACC 3'<br>\|\|:\|:\|:\|\|\|\|\|\|\|\|\|\|\|\|<br>3' CUUUAGGUAACGAAUAUGG 5' |
| SEQ ID 1470 | 5' CCAGUAACAUUCCCGAGAU 3'<br>\|\|:\|:\|:\|\|\|\|\|\|\|\|\|\|\|\|<br>3' GGUCAUUGUAAGGGCUCUA 5' |
| SEQ ID 1471 | 5' CAUUCCCGAGAUCACCCCG 3'<br>\|\|:\|:\|:\|\|\|\|\|\|\|\|\|\|\|\|<br>3' GUAAGGGCUCUAGUGGGGC 5' |
| SEQ ID 1472 | 5' ACAUUCCACUACCACUGGG 3'<br>\|\|:\|:\|:\|\|\|\|\|\|\|\|\|\|\|\|<br>3' UGUAAGGUGAUGGUGACCC 5' |
| SEQ ID 1473 | 5' CAUUCCACUACCACUGGGG 3'<br>\|\|:\|:\|:\|\|\|\|\|\|\|\|\|\|\|\|<br>3' GUAAGGUGAUGGUGACCCC 5' |
| SEQ ID 1474 | 5' GAGACAGCCCAGAAAUCCC 3'<br>\|\|:\|:\|:\|\|\|\|\|\|\|\|\|\|\|\|<br>3' CUCUGUCGGGUCUUUAGGG 5' |
| SEQ ID 1475 | 5' AUCCCAAAACAGACAAACU 3'<br>\|\|:\|:\|:\|\|\|\|\|\|\|\|\|\|\|\|<br>3' UAGGGUUUUGUCUGUUUGA 5' |
| SEQ ID 1476 | 5' UCCCAAAACAGACAAACUU 3'<br>\|\|:\|:\|:\|\|\|\|\|\|\|\|\|\|\|\|<br>3' AGGGUUUUGUCUGUUUGAA 5' |
| SEQ ID 1477 | 5' ACAGACAAACUUGUGAAUG 3'<br>\|\|:\|:\|:\|\|\|\|\|\|\|\|\|\|\|\|<br>3' UGUCUGUUUGAACACUUAC 5' |
| SEQ ID 1478 | 5' CAGACAAACUUGUCAAUGA 3'<br>\|\|:\|:\|:\|\|\|\|\|\|\|\|\|\|\|\|<br>3' GUCUGUUUGAACACUUACU 5' |
| SEQ ID 1479 | 5' ACUUGUGAAUGAGCGGCUG 3'<br>\|\|:\|:\|:\|\|\|\|\|\|\|\|\|\|\|\|<br>3' UGAACACUUACUCGCCGAC 5' |
| SEQ ID 1480 | 5' CUUGUGAAUGAGCGGCUGA 3'<br>\|\|:\|:\|:\|\|\|\|\|\|\|\|\|\|\|\|<br>3' GAACACUUACUCGCCGACU 5' |

Figure 2QQQQ

| | |
|---|---|
| SEQ ID 1481 | 5' UGAGCGGCUGAUCAGCAUG 3'<br>\|:\|\|\|\|\|\|\|\|\|:\|:\|\|\|\|\|\|<br>3' ACUCGCCGACUAGUCGUAC 5' |
| SEQ ID 1482 | 5' CGGCUUCCUCCCAAUUCAC 3'<br>\|:\|\|\|\|\|\|\|\|\|:\|:\|\|\|\|\|\|<br>3' GCCGAAGGAGGGUUAAGUG 5' |
| SEQ ID 1483 | 5' UUCACCUGUUGGGCCUCCG 3'<br>\|:\|\|\|\|\|\|\|\|\|:\|:\|\|\|\|\|\|<br>3' AAGUGGACAACCCGGAGGC 5' |
| SEQ ID 1484 | 5' CGAUGUGGAAGACAGCUAC 3'<br>\|:\|\|\|\|\|\|\|\|\|:\|:\|\|\|\|\|\|<br>3' GCUACACCUUCUGUCGAUG 5' |
| SEQ ID 1485 | 5' GACAGCUACGGGCAGCAGU 3'<br>\|:\|\|\|\|\|\|\|\|\|:\|:\|\|\|\|\|\|<br>3' CUGUCGAUGCCCGUCGUCA 5' |
| SEQ ID 1486 | 5' AAUCGUGGAGUUCACCUGC 3'<br>\|:\|\|\|\|\|\|\|\|\|:\|:\|\|\|\|\|\|<br>3' UUAGCACCUCAAGUGGACG 5' |
| SEQ ID 1487 | 5' AUCGUGGAGUUCACCUGCC 3'<br>\|:\|\|\|\|\|\|\|\|\|:\|:\|\|\|\|\|\|<br>3' UAGCACCUCAAGUGGACGG 5' |
| SEQ ID 1488 | 5' UCGUGGAGUUCACCUGCCA 3'<br>\|:\|\|\|\|\|\|\|\|\|:\|:\|\|\|\|\|\|<br>3' AGCACCUCAAGUGGACGGU 5' |
| SEQ ID 1489 | 5' GACCAGGAGGAAUUCGGUC 3'<br>\|:\|\|\|\|\|\|\|\|\|:\|:\|\|\|\|\|\|<br>3' CUGGUCCUCCUUAAGCCAG 5' |
| SEQ ID 1490 | 5' UUCGGUCUUCCAGCAGGGG 3'<br>\|:\|\|\|\|\|\|\|\|\|:\|:\|\|\|\|\|\|<br>3' AAGCCAGAAGGUCGUCCCC 5' |
| SEQ ID 1491 | 5' CAACAUCUUGAUAUUUGGC 3'<br>\|:\|\|\|\|\|\|\|\|\|:\|:\|\|\|\|\|\|<br>3' GUUGUAGAACUAUAAACCG 5' |
| SEQ ID 1492 | 5' GAUCUUGAUAUUUGGCCUC 3'<br>\|:\|\|\|\|\|\|\|\|\|:\|:\|\|\|\|\|\|<br>3' CUAGAACUAUAAACCGGAG 5' |
| SEQ ID 1493 | 5' GAGACAGCCCUGGCUGCUU 3'<br>\|:\|\|\|\|\|\|\|\|\|:\|:\|\|\|\|\|\|<br>3' CUCUGUCGGGACCGACGAA 5' |
| SEQ ID 1494 | 5' UGGGUGUUGCUCUUAGGAU 3'<br>\|:\|\|\|\|\|\|\|\|\|:\|:\|\|\|\|\|\|<br>3' ACCCACAACGAGAAUCCUA 5' |
| SEQ ID 1495 | 5' ACCUACCUGGUGGUUCUGU 3'<br>\|:\|\|\|\|\|\|\|\|\|:\|:\|\|\|\|\|\|<br>3' UGGAUGGACCACCAAGACA 5' |
| SEQ ID 1496 | 5' CCUACCUGGUGGUUCUGUG 3'<br>\|:\|\|\|\|\|\|\|\|\|:\|:\|\|\|\|\|\|<br>3' GGAUGGACCACCAAGACAC 5' |

Figure 2RRRR

| | |
|---|---|
| SEQ ID 1497 | 5' GUCAGAAAACUCAUCAUCA 3'<br>\|\|\|\|\|\|:\|\|\|\|\|\|:\|:\|\|\|<br>3' CAGUCUUUUGAGUAGUAGU 5' |
| SEQ ID 1498 | 5' AACUCAUCAUCAGGCGACG 3'<br>\|\|\|\|\|\|:\|\|\|\|\|\|:\|:\|\|\|<br>3' UUGAGUAGUAGUCCGCUGC 5' |
| SEQ ID 1499 | 5' ACUCAUCAUCAGGCGACGC 3'<br>\|\|\|\|\|\|:\|\|\|\|\|\|:\|:\|\|\|<br>3' UGAGUAGUAGUCCGCUGCG 5' |
| SEQ ID 1500 | 5' CUCAUCAUCAGGCGACGCC 3'<br>\|\|\|\|\|\|:\|\|\|\|\|\|:\|:\|\|\|<br>3' GAGUAGUAGUCCGCUGCGG 5' |
| **ATP1A2** | |
| SEQ ID 1501 | 5' UGGGGGCGGCAAGAAGAAA 3'<br>\|\|\|\|\|\|:\|\|\|\|\|\|:\|:\|\|\|<br>3' ACCCCCGCCGUUCUUCUUU 5' |
| SEQ ID 1502 | 5' GAAGAAACAGAAGGAGAAG 3'<br>\|\|\|\|\|\|:\|\|\|\|\|\|:\|:\|\|\|<br>3' CUUCUUUGUCUUCCUCUUC 5' |
| SEQ ID 1503 | 5' GAAACAGAAGGAGAAGGAA 3'<br>\|\|\|\|\|\|:\|\|\|\|\|\|:\|:\|\|\|<br>3' CUUUGUCUUCCUCUUCCUU 5' |
| SEQ ID 1504 | 5' ACAGAAGGAGAAGGAACUG 3'<br>\|\|\|\|\|\|:\|\|\|\|\|\|:\|:\|\|\|<br>3' UGUCUUCCUCUUCCUUGAC 5' |
| SEQ ID 1505 | 5' CAGAAGGAGAAGGAACUGG 3'<br>\|\|\|\|\|\|:\|\|\|\|\|\|:\|:\|\|\|<br>3' GUCUUCCUCUUCCUUGACC 5' |
| SEQ ID 1506 | 5' GGAGAAGGAACUGGAUGAG 3'<br>\|\|\|\|\|\|:\|\|\|\|\|\|:\|:\|\|\|<br>3' CCUCUUCCUUGACCUACUC 5' |
| SEQ ID 1507 | 5' GGAACUGGAUGAGCUGAAG 3'<br>\|\|\|\|\|\|:\|\|\|\|\|\|:\|:\|\|\|<br>3' CCUUGACCUACUCGACUUC 5' |
| SEQ ID 1508 | 5' CUGGAUGAGCUGAAGAAGG 3'<br>\|\|\|\|\|\|:\|\|\|\|\|\|:\|:\|\|\|<br>3' GACCUACUCGACUUCUUCC 5' |
| SEQ ID 1509 | 5' GAAGGAGGUGGCAAUGGAU 3'<br>\|\|\|\|\|\|:\|\|\|\|\|\|:\|:\|\|\|<br>3' CUUCCUCCACCGUUACCUA 5' |
| SEQ ID 1510 | 5' GGAGGUGGCAAUGGAUGAC 3'<br>\|\|\|\|\|\|:\|\|\|\|\|\|:\|:\|\|\|<br>3' CCUCCACCGUUACCUACUG 5' |
| SEQ ID 1511 | 5' UGGAUGACCACAAGCUGUC 3'<br>\|\|\|\|\|\|:\|\|\|\|\|\|:\|:\|\|\|<br>3' ACCUACUGGUGUUCGACAG 5' |

Figure 2SSSS

<table>
<tr><td>SEQ ID 1512</td><td>5' GCUGUCCUUGGAUGAGCUG 3'<br>||||||:||||||||||||<br>3' CGACAGGAACCUACUCGAC 5'</td></tr>
<tr><td>SEQ ID 1513</td><td>5' AUACCAAGUGGACCUGUCC 3'<br>||||||:||||||||||||<br>3' UAUGGUUCACCUGGACAGG 5'</td></tr>
<tr><td>SEQ ID 1514</td><td>5' UACCAAGUGGACCUGUCCA 3'<br>||||||:||||||||||||<br>3' AUGGUUCACCUGGACAGGU 5'</td></tr>
<tr><td>SEQ ID 1515</td><td>5' CCCCUGAGUGGGUCAAGUU 3'<br>||||||:||||||||||||<br>3' GGGGACUCACCCAGUUCAA 5'</td></tr>
<tr><td>SEQ ID 1516</td><td>5' GUUCUGCCGUCAGCUUUUC 3'<br>||||||:||||||||||||<br>3' CAAGACGGCAGUCGAAAAG 5'</td></tr>
<tr><td>SEQ ID 1517</td><td>5' CCAUCCAACGACAAUCUAU 3'<br>||||||:||||||||||||<br>3' GGUAGGUUGCUGUUAGAUA 5'</td></tr>
<tr><td>SEQ ID 1518</td><td>5' CGACAAUCUAUAUCUGGGU 3'<br>||||||:||||||||||||<br>3' GCUGUUAGAUAUAGACCCA 5'</td></tr>
<tr><td>SEQ ID 1519</td><td>5' UCUAUAUCUGGGUGUGGUG 3'<br>||||||:||||||||||||<br>3' AGAUAUAGACCCACACCAC 5'</td></tr>
<tr><td>SEQ ID 1520</td><td>5' GAGCUCCAAGAUCAUGGAU 3'<br>||||||:||||||||||||<br>3' CUCGAGGUUCUAGUACCUA 5'</td></tr>
<tr><td>SEQ ID 1521</td><td>5' GAUCAUGGAUUCCUUCAAG 3'<br>||||||:||||||||||||<br>3' CUAGUACCUAAGGAAGUUC 5'</td></tr>
<tr><td>SEQ ID 1522</td><td>5' GAACAUGGUACCUCAGCAA 3'<br>||||||:||||||||||||<br>3' CUUGUACCAUGGAGUCGUU 5'</td></tr>
<tr><td>SEQ ID 1523</td><td>5' CAUGGUACCUCAGCAAGCC 3'<br>||||||:||||||||||||<br>3' GUACCAUGGAGUCGUUCGG 5'</td></tr>
<tr><td>SEQ ID 1524</td><td>5' GAUGCAGAUCAACGCAGAG 3'<br>||||||:||||||||||||<br>3' CUACGUCUAGUUGCGUCUC 5'</td></tr>
<tr><td>SEQ ID 1525</td><td>5' CGCAGAGGAAGUGGUGGUG 3'<br>||||||:||||||||||||<br>3' GCGUCUCCUUCACCACCAC 5'</td></tr>
<tr><td>SEQ ID 1526</td><td>5' GGUGGAUAACUCAUCCUUA 3'<br>||||||:||||||||||||<br>3' CCACCUAUUGAGUAGGAAU 5'</td></tr>
<tr><td>SEQ ID 1527</td><td>5' CUCAUCCUUAACAGGAGAG 3'<br>||||||:||||||||||||<br>3' GAGUAGGAAUUGUCCUCUC 5'</td></tr>
</table>

Figure2TTTT

<table>
<tr><td>SEQ ID 1528</td><td>5' UAUCUGUUUCUUCUCCACC 3'<br>||||||||:|||:|||:||<br>3' AUAGACAAAGAAGAGGUGG 5'</td></tr>
<tr><td>SEQ ID 1529</td><td>5' CUGUGUUGAAGGCACUGCC 3'<br>||||||||:|||:|||:||<br>3' GACACAACUUCCGUGACGG 5'</td></tr>
<tr><td>SEQ ID 1530</td><td>5' UGGAGAUUCAACACUUCAU 3'<br>||||||||:|||:|||:||<br>3' ACCUCUAACUUGUGAAGUA 5'</td></tr>
<tr><td>SEQ ID 1531</td><td>5' CACUUCAUCCAGCUGAUCA 3'<br>||||||||:|||:|||:||<br>3' GUGAAGUAGGUCGACUAGU 5'</td></tr>
<tr><td>SEQ ID 1532</td><td>5' GCGCAUGGCACGCAAGAAC 3'<br>||||||||:|||:|||:||<br>3' CGCGUACCGUGCGUUCUUG 5'</td></tr>
<tr><td>SEQ ID 1533</td><td>5' GAACUGCCUGGUGAAGAAC 3'<br>||||||||:|||:|||:||<br>3' CUUGACGGACCACUUCUUG 5'</td></tr>
<tr><td>SEQ ID 1534</td><td>5' CUGCCUGGUGAAGAACCUG 3'<br>||||||||:|||:|||:||<br>3' GACGGACCACUUCUUGGAC 5'</td></tr>
<tr><td>SEQ ID 1535</td><td>5' CCAAAUCCAUGAGGCUGAC 3'<br>||||||||:|||:|||:||<br>3' GGUUUAGGUACUCCGACUG 5'</td></tr>
<tr><td>SEQ ID 1536</td><td>5' AUCCAUGAGGCUGACACCA 3'<br>||||||||:|||:|||:||<br>3' UAGGUACUCCGACUGUGGU 5'</td></tr>
<tr><td>SEQ ID 1537</td><td>5' UCCAUGAGGCUGACACCAC 3'<br>||||||||:|||:|||:||<br>3' AGGUACUCCGACUGUGGUG 5'</td></tr>
<tr><td>SEQ ID 1538</td><td>5' GAUCAGUCUGGGGCCACUU 3'<br>||||||||:|||:|||:||<br>3' CUAGUCAGACCCCGGUGAA 5'</td></tr>
<tr><td>SEQ ID 1539</td><td>5' ACGAUCCCCUACCUGGACG 3'<br>||||||||:|||:|||:||<br>3' UGCUAGGGGAUGCACCUGC 5'</td></tr>
<tr><td>SEQ ID 1540</td><td>5' UUGCUGGUCUCUCCAACCG 3'<br>||||||||:|||:|||:||<br>3' AACGACCAGAGACGUUGGC 5'</td></tr>
<tr><td>SEQ ID 1541</td><td>5' GGCAGGACAGGAGAACAUC 3'<br>||||||||:|||:|||:||<br>3' CCGUCCUGUCCUCUUGUAG 5'</td></tr>
<tr><td>SEQ ID 1542</td><td>5' CAUCUCCGUGUCUAAGCGG 3'<br>||||||||:|||:|||:||<br>3' GUAGAGGCACAGAUUCGCC 5'</td></tr>
<tr><td>SEQ ID 1543</td><td>5' GCGGGACACAGCUGGUGAU 3'<br>||||||||:|||:|||:||<br>3' CGCCCUGUGUCGACCACUA 5'</td></tr>
</table>

Figure 2UUUU

<table>
<tr><td>SEQ ID 1544</td><td>5' GUGCAUUGAGCUCUCCUGU 3'<br>|||||||:|||||||||||<br>3' CACGUAACUCGAGAGGACA 5'</td></tr>
<tr><td>SEQ ID 1545</td><td>5' AAUGAGAGACAGAAACCCC 3'<br>|||||||:|||||||||||<br>3' UUACUCUCUGUCUUUGGGG 5'</td></tr>
<tr><td>SEQ ID 1546</td><td>5' AUGAGAGACAGAAACCCCA 3'<br>|||||||:|||||||||||<br>3' UACUCUCUGUCUUUGGGGU 5'</td></tr>
<tr><td>SEQ ID 1547</td><td>5' UGAGAGACAGAAACCCCAA 3'<br>|||||||:|||||||||||<br>3' ACUCUCUGUCUUUGGGGUU 5'</td></tr>
<tr><td>SEQ ID 1548</td><td>5' ACCCCAAGGUGGCAGAGAU 3'<br>|||||||:|||||||||||<br>3' UGGGGUUCCACCGUCUCUA 5'</td></tr>
<tr><td>SEQ ID 1549</td><td>5' CCCCAAGGUGGCAGAGAUU 3'<br>|||||||:|||||||||||<br>3' GGGGUUCCACCGUCUCUAA 5'</td></tr>
<tr><td>SEQ ID 1550</td><td>5' GGUGGCAGAGAUUCCUUUC 3'<br>|||||||:|||||||||||<br>3' CCACCGUCUCUAAGGAAAG 5'</td></tr>
<tr><td>SEQ ID 1551</td><td>5' CUCUACCAACAAGUACCAC 3'<br>|||||||:|||||||||||<br>3' GAGAUGGUUGUUCAUGGUC 5'</td></tr>
<tr><td>SEQ ID 1552</td><td>5' CAAGUACCAGCUGUCUAUC 3'<br>|||||||:|||||||||||<br>3' GUUCAUGGUCGACAGAUAG 5'</td></tr>
<tr><td>SEQ ID 1553</td><td>5' GUACCAGCUGUCUAUCCAC 3'<br>|||||||:|||||||||||<br>3' CAUGGUCGACAGAUAGGUG 5'</td></tr>
<tr><td>SEQ ID 1554</td><td>5' GGACAUCCCGCUCCACAAG 3'<br>|||||||:|||||||||||<br>3' CCUGUAGGGCGAGGUGUUC 5'</td></tr>
<tr><td>SEQ ID 1555</td><td>5' GGAGAUGCAAGAUGCCUUU 3'<br>|||||||:|||||||||||<br>3' CCUCUACGUUCUACGGAAA 5'</td></tr>
<tr><td>SEQ ID 1556</td><td>5' GAUCCCUUUCAAAAUGCCU 3'<br>|||||||:|||||||||||<br>3' CUAGGGAAAGUUUUACGGA 5'</td></tr>
<tr><td>SEQ ID 1557</td><td>5' AAUGCCUACAUGGAGCUGG 3'<br>|||||||:|||||||||||<br>3' UUACGGAUGUACCUCGACC 5'</td></tr>
<tr><td>SEQ ID 1558</td><td>5' AUGCCUACAUGGAGCUGGG 3'<br>|||||||:|||||||||||<br>3' UACGGAUGUACCUCGACCC 5'</td></tr>
<tr><td>SEQ ID 1559</td><td>5' UGCCUACAUGGAGCUGGGG 3'<br>|||||||:|||||||||||<br>3' ACGGAUGUACCUCGACCCC 5'</td></tr>
</table>

Figure 2VVVV

<table>
<tr><td>SEQ ID 1560</td><td>5' CUGAAUCUGCCAUCUGGAA 3'<br>||:||||||||||||||:|<br>3' GACUUAGACGGUAGACCUU 5'</td></tr>
<tr><td>SEQ ID 1561</td><td>5' UCUGCCAUCUGGAAAGUUU 3'<br>||:||||||||||||||:|<br>3' AGACGGUAGACCUUUCAAA 5'</td></tr>
<tr><td>SEQ ID 1562</td><td>5' AGUUUCCUCGGGGCUUCAA 3'<br>||:||||||||||||||:|<br>3' UCAAAGGAGCCCCGAAGUU 5'</td></tr>
<tr><td>SEQ ID 1563</td><td>5' GUUUCCUCGGGGCUUCAAA 3'<br>||:||||||||||||||:|<br>3' CAAAGGAGCCCCGAAGUUU 5'</td></tr>
<tr><td>SEQ ID 1564</td><td>5' AUUCGACACGGAUGAGCUG 3'<br>||:||||||||||||||:|<br>3' UAAGCUGUGCCUACUCGAC 5'</td></tr>
<tr><td>SEQ ID 1565</td><td>5' UUCGACACGGAUGAGCUGA 3'<br>||:||||||||||||||:|<br>3' AAGCUGUGCCUACUCGACU 5'</td></tr>
<tr><td>SEQ ID 1566</td><td>5' CUUUCCCACGGAGAAGCUU 3'<br>||:||||||||||||||:|<br>3' GAAAGGGUGCCUCUUCGAA 5'</td></tr>
<tr><td>SEQ ID 1567</td><td>5' GCUUUGCUUUGUGGGGCUC 3'<br>||:||||||||||||||:|<br>3' CGAAACGAAACACCCCGAG 5'</td></tr>
<tr><td>SEQ ID 1568</td><td>5' GCGCAGGCAUCAAGGUGAU 3'<br>||:||||||||||||||:|<br>3' CGCGUCCGUAGUUCCACUA 5'</td></tr>
<tr><td>SEQ ID 1569</td><td>5' GGUGAUCAUGGUAACCGGG 3'<br>||:||||||||||||||:|<br>3' CCACUAGUACCAUUGGCCC 5'</td></tr>
<tr><td>SEQ ID 1570</td><td>5' CCGGGGAUCACCCUAUCAC 3'<br>||:||||||||||||||:|<br>3' GGCCCCUAGUGGGAUAGUG 5'</td></tr>
<tr><td>SEQ ID 1571</td><td>5' GGCCAUUGCCAAAGGCGUG 3'<br>||:||||||||||||||:|<br>3' CCGGUAACCGUUUCCGCAC 5'</td></tr>
<tr><td>SEQ ID 1572</td><td>5' AGGCGUGGGCAUCAUAUCA 3'<br>||:||||||||||||||:|<br>3' UCCGCACCCGUAGUAUAGU 5'</td></tr>
<tr><td>SEQ ID 1573</td><td>5' GGCGUGGGCAUCAUAUCAG 3'<br>||:||||||||||||||:|<br>3' CCGCACCCGUAGUAUAGUC 5'</td></tr>
<tr><td>SEQ ID 1574</td><td>5' CGAGACUGUGGAGGACAUU 3'<br>||:||||||||||||||:|<br>3' GCUCUGACACCUCCUGUAA 5'</td></tr>
<tr><td>SEQ ID 1575</td><td>5' CAUUCCCAUGAGUCAAGUC 3'<br>||:||||||||||||||:|<br>3' GUAAGGGUACUCAGUUCAG 5'</td></tr>
</table>

Figure 2WWWW

<table>
<tr><td>SEQ ID 1576</td><td>5' GUCAACCCCAGAGAAGCCA 3'<br>||||||||:||||:||||:<br>3' CAGUUGGGGUCUCUUCGGU 5'</td></tr>
<tr><td>SEQ ID 1577</td><td>5' CCCCAGAGAAGCCAAGGCA 3'<br>||||||||:||||:||||:<br>3' GGGGUCUCUUCGGUUCCGU 5'</td></tr>
<tr><td>SEQ ID 1578</td><td>5' GGACAUGACAUCGGAGCAG 3'<br>||||||||:||||:||||:<br>3' CCUGUACUGUAGCCUCGUC 5'</td></tr>
<tr><td>SEQ ID 1579</td><td>5' GAACCACACAGAGAUCGUC 3'<br>||||||||:||||:||||:<br>3' CUUGGUGUGUCUCUAGCAG 5'</td></tr>
<tr><td>SEQ ID 1580</td><td>5' CCACACAGAGAUCGUCUUU 3'<br>||||||||:||||:||||:<br>3' GGUGUGUCUCUAGCAGAAA 5'</td></tr>
<tr><td>SEQ ID 1581</td><td>5' CGUCUCCCCAGCAGAAGCU 3'<br>||||||||:||||:||||:<br>3' GCAGAGGGGUCGUCUUCGA 5'</td></tr>
<tr><td>SEQ ID 1582</td><td>5' GCUCAUCAUUGUGGAGGGA 3'<br>||||||||:||||:||||:<br>3' CGAGUAGUAACACCUCCCU 5'</td></tr>
<tr><td>SEQ ID 1583</td><td>5' CGACUCCCCUGCAUUGAAG 3'<br>||||||||:||||:||||:<br>3' GCUGAGGGGACGUAACUUC 5'</td></tr>
<tr><td>SEQ ID 1584</td><td>5' GAAGGCUGACAUUGCCAUU 3'<br>||||||||:||||:||||:<br>3' CUUCCGACUGUAACCGUAA 5'</td></tr>
<tr><td>SEQ ID 1585</td><td>5' GGCUGACAUUGGCAUUGCC 3'<br>||||||||:||||:||||:<br>3' CCGACUGUAACCGUAACGG 5'</td></tr>
<tr><td>SEQ ID 1586</td><td>5' GCAGGCAGCCGACAUGAUC 3'<br>||||||||:||||:||||:<br>3' CGUCCGUCGGCUGUACUAG 5'</td></tr>
<tr><td>SEQ ID 1587</td><td>5' CUUUGCCUCCAUCGUCACG 3'<br>||||||||:||||:||||:<br>3' GAAACGGAGGUAGCAGUGC 5'</td></tr>
<tr><td>SEQ ID 1588</td><td>5' CUUGAAGAAAUCCAUCGCC 3'<br>||||||||:||||:||||:<br>3' GAACUUCUUUAGGUAGCGG 5'</td></tr>
<tr><td>SEQ ID 1589</td><td>5' GAAAUCCAUCGCCUACACC 3'<br>||||||||:||||:||||:<br>3' CUUUAGGUAGCGGAUGUGG 5'</td></tr>
<tr><td>SEQ ID 1590</td><td>5' AUCCAUCGCCUACACCCUG 3'<br>||||||||:||||:||||:<br>3' UAGGUAGCGGAUGUGGGAC 5'</td></tr>
<tr><td>SEQ ID 1591</td><td>5' UCCAUCGCCUACACCCUGA 3'<br>||||||||:||||:||||:<br>3' AGGUAGCGGAUGUGGGACU 5'</td></tr>
</table>

Figure 2XXXX

<table>
<tr><td>SEQ ID 1592</td><td>5' ACUCCCAGACGGACAAGCU 3'<br>||||||||||||||||||:<br>3' UGAGGGUCUGCCUGUUCGA 5'</td></tr>
<tr><td>SEQ ID 1593</td><td>5' CUCCCAGACGGACAAGCUG 3'<br>||||||||||||||||||:<br>3' GAGGGUCUGCCUGUUCGAC 5'</td></tr>
<tr><td>SEQ ID 1594</td><td>5' GCUGGUGAAUGAGAGGCUC 3'<br>||||||||||||||||||:<br>3' CGACCACUUACUCUCCGAG 5'</td></tr>
<tr><td>SEQ ID 1595</td><td>5' UGAGAGGCUCAUCAGCAUG 3'<br>||||||||||||||||||:<br>3' ACUCUCCGAGUAGUCGUAC 5'</td></tr>
<tr><td>SEQ ID 1596</td><td>5' CGGUUUCCUGCCAUCACGG 3'<br>||||||||||||||||||:<br>3' GCCAAAGGACGGUAGUGCC 5'</td></tr>
<tr><td>SEQ ID 1597</td><td>5' UCCGCCUCGACUGGGAUGA 3'<br>||||||||||||||||||:<br>3' AGGCGGAGCUGACCCUACU 5'</td></tr>
<tr><td>SEQ ID 1598</td><td>5' UGAUCUGGAGGACAGCUAU 3'<br>||||||||||||||||||:<br>3' ACUAGACCUCCUGUCGAUA 5'</td></tr>
<tr><td>SEQ ID 1599</td><td>5' GGUCGUGGAGUUCACGUGC 3'<br>||||||||||||||||||:<br>3' CCACCACCUCAAGUGCACG 5'</td></tr>
<tr><td>SEQ ID 1600</td><td>5' CUCAGUCUUCCAGCAGGGC 3'<br>||||||||||||||||||:<br>3' GAGUCAGAAGGUCGUCCCG 5'</td></tr>
<tr><td>SEQ ID 1601</td><td>5' CAAGAUCCUGAUUUUUGGG 3'<br>||||||||||||||||||:<br>3' GUUCUAGGACUAAAAACCC 5'</td></tr>
<tr><td>SEQ ID 1602</td><td>5' GAUCCUGAUUUUUGGGCUC 3'<br>||||||||||||||||||:<br>3' CUAGGACUAAAAACCCGAG 5'</td></tr>
<tr><td>SEQ ID 1603</td><td>5' AGUCACCUGGUGGUUCUGC 3'<br>||||||||||||||||||:<br>3' UCAGUGGACCACCAAGACG 5'</td></tr>
<tr><td>SEQ ID 1604</td><td>5' GUCACCUGGUGGUUCUGCG 3'<br>||||||||||||||||||:<br>3' CAGUGGACCACCAAGACGC 5'</td></tr>
<tr><td>SEQ ID 1605</td><td>5' AGCUCAUCCUGCGGCGGUA 3'<br>||||||||||||||||||:<br>3' UCGAGUAGGACGCCGCCAU 5'</td></tr>
<tr><td>SEQ ID 1606</td><td>5' GCUCAUCCUGCGGCGGUAU 3'<br>||||||||||||||||||:<br>3' CGAGUAGGACGCCGCCAUA 5'</td></tr>
</table>

<table>
<tr><td>ATP1A3</td><td></td></tr>
</table>

Figure 2YYYY

| | |
|---|---|
| SEQ ID 1607 | 5' GAUGGGGGACAAGAAAGAU 3'<br>\|\|\|\|:\|\|:\|:\|\|\|\|:\|\|\|\|<br>3' CUACCCCCUGUUCUUUCUA 5' |
| SEQ ID 1608 | 5' GAAAGAUGACAAGGACUCA 3'<br>\|\|\|\|:\|\|:\|:\|\|\|\|:\|\|\|\|<br>3' CUUUCUACUGUUCCUGAGU 5' |
| SEQ ID 1609 | 5' AGAUGACAAGGACUCACCC 3'<br>\|\|\|\|:\|\|:\|:\|\|\|\|:\|\|\|\|<br>3' UCUACUGUUCCUGAGUGGG 5' |
| SEQ ID 1610 | 5' GAUGACAAGGACUCACCCA 3'<br>\|\|\|\|:\|\|:\|:\|\|\|\|:\|\|\|\|<br>3' CUACUGUUCCUGAGUGGGU 5' |
| SEQ ID 1611 | 5' GGACUCACCCAACAAGAAC 3'<br>\|\|\|\|:\|\|:\|:\|\|\|\|:\|\|\|\|<br>3' CCUGAGUGGGUUGUUCUUG 5' |
| SEQ ID 1612 | 5' GAAGAACAAGGGCAAGGAG 3'<br>\|\|\|\|:\|\|:\|:\|\|\|\|:\|\|\|\|<br>3' CUUCUUGUUCCCGUUCCUC 5' |
| SEQ ID 1613 | 5' GAACAAGGGCAAGGAGCGC 3'<br>\|\|\|\|:\|\|:\|:\|\|\|\|:\|\|\|\|<br>3' CUUGUUCCCGUUCCUCGCG 5' |
| SEQ ID 1614 | 5' GAAGGAGGUGGCUAUGACA 3'<br>\|\|\|\|:\|\|:\|:\|\|\|\|:\|\|\|\|<br>3' CUUCCUCCACCGAUACUGU 5' |
| SEQ ID 1615 | 5' GGAGGUGGCUAUGACAGAG 3'<br>\|\|\|\|:\|\|:\|:\|\|\|\|:\|\|\|\|<br>3' CCUCCACCGAUACUGUCUC 5' |
| SEQ ID 1616 | 5' GAUGUCAGUGGAAGAGGUC 3'<br>\|\|\|\|:\|\|:\|:\|\|\|\|:\|\|\|\|<br>3' CUACAGUCACCUUCUCCAG 5' |
| SEQ ID 1617 | 5' GAGGUCUGCCGGAAAUACA 3'<br>\|\|\|\|:\|\|:\|:\|\|\|\|:\|\|\|\|<br>3' CUCCAGACGGCCUUUAUGU 5' |
| SEQ ID 1618 | 5' AUACAACACAGACUGUGUG 3'<br>\|\|\|\|:\|\|:\|:\|\|\|\|:\|\|\|\|<br>3' UAUGUUGUGUCUGACACAC 5' |
| SEQ ID 1619 | 5' UACAACACAGACUGUGUGC 3'<br>\|\|\|\|:\|\|:\|:\|\|\|\|:\|\|\|\|<br>3' AUGUUGUGUCUGACACACG 5' |
| SEQ ID 1620 | 5' CACAGACUGUGUGCAGGGU 3'<br>\|\|\|\|:\|\|:\|:\|\|\|\|:\|\|\|\|<br>3' GUGUCUGACACACGUCCCA 5' |
| SEQ ID 1621 | 5' GUUUUGCCGGCAGCUCUUC 3'<br>\|\|\|\|:\|\|:\|:\|\|\|\|:\|\|\|\|<br>3' CAAAACGGCCGUCGAGAAG 5' |
| SEQ ID 1622 | 5' CCUGUACCUGGGCAUCGUG 3'<br>\|\|\|\|:\|\|:\|:\|\|\|\|:\|\|\|\|<br>3' GGACAUGGACCCGUAGCAC 5' |

Figure 2ZZZZ

| | |
|---|---|
| SEQ ID 1623 | 5' GAGCUCCAAGAUCAUGGAG 3'<br>\|\|\|\|\|\|:\|\|\|\|:\|\|\|\|:\|:<br>3' CUCGAGGUUCUAGUACCUC 5' |
| SEQ ID 1624 | 5' GAUCAUGGAGUCCUUCAAG 3'<br>\|\|\|\|\|\|:\|\|\|\|:\|\|\|\|:\|:<br>3' CUAGUACCUCAGGAAGUUC 5' |
| SEQ ID 1625 | 5' GAACAUGGUGCCCCAGCAA 3'<br>\|\|\|\|\|\|:\|\|\|\|:\|\|\|\|:\|:<br>3' CUUGUACCACGGGGUCGUU 5' |
| SEQ ID 1626 | 5' GGUGAGAAGAUGCAGGUGA 3'<br>\|\|\|\|\|\|:\|\|\|\|:\|\|\|\|:\|:<br>3' CCACUCUUCUACGUCCACU 5' |
| SEQ ID 1627 | 5' GAUGCAGGUGAACGCUGAG 3'<br>\|\|\|\|\|\|:\|\|\|\|:\|\|\|\|:\|:<br>3' CUACGUCCACUUGCGACUC 5' |
| SEQ ID 1628 | 5' GGUGGACAACUCCUCCCUG 3'<br>\|\|\|\|\|\|:\|\|\|\|:\|\|\|\|:\|:<br>3' CCACCUGUUGAGGAGGGAC 5' |
| SEQ ID 1629 | 5' CUCCUCCCUGACUGGCGAA 3'<br>\|\|\|\|\|\|:\|\|\|\|:\|\|\|\|:\|:<br>3' GAGGAGGGACUGACCGCUU 5' |
| SEQ ID 1630 | 5' CCCCUUGGAGACUCGGAAC 3'<br>\|\|\|\|\|\|:\|\|\|\|:\|\|\|\|:\|:<br>3' GGGGAACCUCUGAGCCUUG 5' |
| SEQ ID 1631 | 5' CAUCACCUUCUUUUCCACC 3'<br>\|\|\|\|\|\|:\|\|\|\|:\|\|\|\|:\|:<br>3' GUAGUGGAAGAAAAGGUGG 5' |
| SEQ ID 1632 | 5' CUGUGUGGAAGGCACGGCU 3'<br>\|\|\|\|\|\|:\|\|\|\|:\|\|\|\|:\|:<br>3' GACACACCUUCCGUGCCGA 5' |
| SEQ ID 1633 | 5' UGUCCCAGAGGGUCUGCUG 3'<br>\|\|\|\|\|\|:\|\|\|\|:\|\|\|\|:\|:<br>3' ACAGGGUCUCCCAGACGAC 5' |
| SEQ ID 1634 | 5' GAACUGCCUGGUGAAGAAC 3'<br>\|\|\|\|\|\|:\|\|\|\|:\|\|\|\|:\|:<br>3' CUUGACGGACCACUUCUUG 5' |
| SEQ ID 1635 | 5' CUGCCUGGUGAAGAACCUG 3'<br>\|\|\|\|\|\|:\|\|\|\|:\|\|\|\|:\|:<br>3' GACGGACCACUUCUUGGAC 5' |
| SEQ ID 1636 | 5' GAACCUGGAGGCUGUAGAA 3'<br>\|\|\|\|\|\|:\|\|\|\|:\|\|\|\|:\|:<br>3' CUUGGACCUCCGACAUCUU 5' |
| SEQ ID 1637 | 5' CCUGGAGGCUGUAGAAACC 3'<br>\|\|\|\|\|\|:\|\|\|\|:\|\|\|\|:\|:<br>3' GGACCUCCGACAUCUUUGG 5' |
| SEQ ID 1638 | 5' GACAGGGACCCUCACUCAG 3'<br>\|\|\|\|\|\|:\|\|\|\|:\|\|\|\|:\|:<br>3' CUGUCCCUGGGAGUGAGUC 5' |

Figure 2AAAAA

| | |
|---|---|
| SEQ ID 1639 | 5' CCAGAUCCACGAGGCUGAC 3'<br>\|:\|:\|\|\|\|\|:\|\|\|\|\|\|\|\|\|<br>3' GGUCUAGGUGCUCCGACUG 5' |
| SEQ ID 1640 | 5' GAGUUCGCACACCUGGGUG 3'<br>\|:\|:\|\|\|\|\|:\|\|\|\|\|\|\|\|\|<br>3' CUCAAGCGUGUGGACCCAC 5' |
| SEQ ID 1641 | 5' UCGCGCUGUCUUCAAGGGU 3'<br>\|:\|:\|\|\|\|\|:\|\|\|\|\|\|\|\|\|<br>3' AGCGCGACAGAAGUUCCCA 5' |
| SEQ ID 1642 | 5' GGGUGGUCAGGACAACAUC 3'<br>\|:\|:\|\|\|\|\|:\|\|\|\|\|\|\|\|\|<br>3' CCCACCAGUCCUGUUGUAG 5' |
| SEQ ID 1643 | 5' CAUCCCUGUGCUCAAGAGC 3'<br>\|:\|:\|\|\|\|\|:\|\|\|\|\|\|\|\|\|<br>3' GUAGGGACACGAGUUCUCC 5' |
| SEQ ID 1644 | 5' GAGGGAUGUGGCUGGGGAU 3'<br>\|:\|:\|\|\|\|\|:\|\|\|\|\|\|\|\|\|<br>3' CUCCCUACACCGACCCCUA 5' |
| SEQ ID 1645 | 5' GUGCAUCGAGCUGUCCUCU 3'<br>\|:\|:\|\|\|\|\|:\|\|\|\|\|\|\|\|\|<br>3' CACGUAGCUCGACAGGAGA 5' |
| SEQ ID 1646 | 5' GCUGAUGCGUGAACGCAAC 3'<br>\|:\|:\|\|\|\|\|:\|\|\|\|\|\|\|\|\|<br>3' CGACUACGCACUUGCGUUG 5' |
| SEQ ID 1647 | 5' CGCAACAAGAAAGUGGCUG 3'<br>\|:\|:\|\|\|\|\|:\|\|\|\|\|\|\|\|\|<br>3' GCGUUGUUCUUUCACCGAC 5' |
| SEQ ID 1648 | 5' CAAGAAAGUGGCUGAGAUU 3'<br>\|:\|:\|\|\|\|\|:\|\|\|\|\|\|\|\|\|<br>3' GUUCUUUCACCGACUCUAA 5' |
| SEQ ID 1649 | 5' GAAAGUGGCUGAGAUUCCC 3'<br>\|:\|:\|\|\|\|\|:\|\|\|\|\|\|\|\|\|<br>3' CUUUCACCGACUCUAAGGG 5' |
| SEQ ID 1650 | 5' AGUGGCUGAGAUUCCCUUC 3'<br>\|:\|:\|\|\|\|\|:\|\|\|\|\|\|\|\|\|<br>3' UCACCGACUCUAAGGGAAG 5' |
| SEQ ID 1651 | 5' GUGGCUGAGAUUCCCUUCA 3'<br>\|:\|:\|\|\|\|\|:\|\|\|\|\|\|\|\|\|<br>3' CACCGACUCUAAGGGAAGU 5' |
| SEQ ID 1652 | 5' UUCCACCAACAAAUACCAG 3'<br>\|:\|:\|\|\|\|\|:\|\|\|\|\|\|\|\|\|<br>3' AAGGUGGUUGUUUAUGGUC 5' |
| SEQ ID 1653 | 5' CAAAUACCAGCUCUCCAUC 3'<br>\|:\|:\|\|\|\|\|:\|\|\|\|\|\|\|\|\|<br>3' GUUUAUGGUCGAGAGGUAG 5' |
| SEQ ID 1654 | 5' AUACCAGCUCUCCAUCCAU 3'<br>\|:\|:\|\|\|\|\|:\|\|\|\|\|\|\|\|\|<br>3' UAUGGUCGAGAGGUAGGUA 5' |

Figure 2BBBBB

| | |
|---|---|
| SEQ ID 1655 | 5' UACCAGCUCUCCAUCCAUG 3'<br>\|\|\|:\|\|\|\|\|\|:\|\|\|:\|\|\|\|<br>3' AUGGUCGAGAGGUAGGUAC 5' |
| SEQ ID 1656 | 5' CGACAACCGAUACCUGCUG 3'<br>\|\|\|:\|\|\|\|\|\|:\|\|\|:\|\|\|\|<br>3' GCUGUUGGCUAUGGACGAC 5' |
| SEQ ID 1657 | 5' CCGAUACCUGCUGGUGAUG 3'<br>\|\|\|:\|\|\|\|\|\|:\|\|\|:\|\|\|\|<br>3' GGCUAUGGACGACCACUAC 5' |
| SEQ ID 1658 | 5' AUGAAGGAGGCCUUCCAGA 3'<br>\|\|\|:\|\|\|\|\|\|:\|\|\|:\|\|\|\|<br>3' UACUUCCUCCGGAAGGUCU 5' |
| SEQ ID 1659 | 5' UGAAGGAGGCCUUCCAGAA 3'<br>\|\|\|:\|\|\|\|\|\|:\|\|\|:\|\|\|\|<br>3' ACUUCCUCCGGAAGGUCUU 5' |
| SEQ ID 1660 | 5' GGAGGCCUUCCAGAAUGCC 3'<br>\|\|\|:\|\|\|\|\|\|:\|\|\|:\|\|\|\|<br>3' CCUCCGGAAGGUCUUACGG 5' |
| SEQ ID 1661 | 5' UGCCUACCUUGAGCUCGGU 3'<br>\|\|\|:\|\|\|\|\|\|:\|\|\|:\|\|\|\|<br>3' ACGGAUGGAACUCGAGCCA 5' |
| SEQ ID 1662 | 5' GGGCUUUGCCUUCGACUGU 3'<br>\|\|\|:\|\|\|\|\|\|:\|\|\|:\|\|\|\|<br>3' CCCGAAACGGAAGCUGACA 5' |
| SEQ ID 1663 | 5' CUUCACCACGGACAACCUC 3'<br>\|\|\|:\|\|\|\|\|\|:\|\|\|:\|\|\|\|<br>3' GAAGUGGUGCCUGUUGGAG 5' |
| SEQ ID 1664 | 5' CCUCUGCUUUGUGGGCCUC 3'<br>\|\|\|:\|\|\|\|\|\|:\|\|\|:\|\|\|\|<br>3' GGAGACGAAACACCCGGAG 5' |
| SEQ ID 1665 | 5' GGUCAUCAUGGUCACCGGC 3'<br>\|\|\|:\|\|\|\|\|\|:\|\|\|:\|\|\|\|<br>3' CCAGUAGUACCAGUGGCCG 5' |
| SEQ ID 1666 | 5' GGCCAUUGCCAAGGGUGUG 3'<br>\|\|\|:\|\|\|\|\|\|:\|\|\|:\|\|\|\|<br>3' CCGGUAACGGUUCCCACAC 5' |
| SEQ ID 1667 | 5' GGGUGUGGGCAUCAUCUCU 3'<br>\|\|\|:\|\|\|\|\|\|:\|\|\|:\|\|\|\|<br>3' CCCACACCCGUAGUAGAGA 5' |
| SEQ ID 1668 | 5' CGAGACUGUGGAGGACAUC 3'<br>\|\|\|:\|\|\|\|\|\|:\|\|\|:\|\|\|\|<br>3' GCUCUGACACCUCCUGUAG 5' |
| SEQ ID 1669 | 5' CAUUCCCGUCAGCCAGGUU 3'<br>\|\|\|:\|\|\|\|\|\|:\|\|\|:\|\|\|\|<br>3' GUAAGGGCAGUCGGUCCAA 5' |
| SEQ ID 1670 | 5' GGACUUCACCUCCGACCAA 3'<br>\|\|\|:\|\|\|\|\|\|:\|\|\|:\|\|\|\|<br>3' CCUGAAGUGGAGGCUGGUU 5' |

Figure 2CCCCC

| | |
|---|---|
| SEQ ID 1671 | 5' AUCGACGAGAUCCUGCAGA 3'<br>:\|\|\|\|\|\|\|\|\|\|:\|\|\|\|\|\|\|<br>3' UAGCUGCUCUAGGACGUCU 5' |
| SEQ ID 1672 | 5' UCGACGAGAUCCUGCAGAA 3'<br>:\|\|\|\|\|\|\|\|\|\|:\|\|\|\|\|\|\|<br>3' AGCUGCUCUAGGACGUCUU 5' |
| SEQ ID 1673 | 5' UCACACCGAGAUCGUCUUC 3'<br>:\|\|\|\|\|\|\|\|\|\|:\|\|\|\|\|\|\|<br>3' AGUGUGGCUCUAGCAGAAG 5' |
| SEQ ID 1674 | 5' GCUCAUCAUUGUGGAGGGC 3'<br>:\|\|\|\|\|\|\|\|\|\|:\|\|\|\|\|\|\|<br>3' CGAGUAGUAACACCUCCCG 5' |
| SEQ ID 1675 | 5' UUGUGGCUGUGACCGGGGA 3'<br>:\|\|\|\|\|\|\|\|\|\|:\|\|\|\|\|\|\|<br>3' AACACCGACACUGGCCCCU 5' |
| SEQ ID 1676 | 5' GAAGGCCGACAUUGGGGUG 3'<br>:\|\|\|\|\|\|\|\|\|\|:\|\|\|\|\|\|\|<br>3' CUUCCGGCUGUAACCCCAC 5' |
| SEQ ID 1677 | 5' GCAGGCAGCUGACAUGAUC 3'<br>:\|\|\|\|\|\|\|\|\|\|:\|\|\|\|\|\|\|<br>3' CGUCCGUCGACUGUACUAG 5' |
| SEQ ID 1678 | 5' CUUUGCCUCCAUCGUCACA 3'<br>:\|\|\|\|\|\|\|\|\|\|:\|\|\|\|\|\|\|<br>3' GAAACGGAGGUAGCAGUGU 5' |
| SEQ ID 1679 | 5' CCUAAAGAAGUCCAUUGCC 3'<br>:\|\|\|\|\|\|\|\|\|\|:\|\|\|\|\|\|\|<br>3' GGAUUUCUUCAGGUAACGG 5' |
| SEQ ID 1680 | 5' AGAAGUCCAUUGCCUACAC 3'<br>:\|\|\|\|\|\|\|\|\|\|:\|\|\|\|\|\|\|<br>3' UCUUCAGGUAACGGAUGUG 5' |
| SEQ ID 1681 | 5' GAAGUCCAUUGCCUACACC 3'<br>:\|\|\|\|\|\|\|\|\|\|:\|\|\|\|\|\|\|<br>3' CUUCAGGUAACGGAUGUGG 5' |
| SEQ ID 1682 | 5' GUCCAUUGCCUACACCCUG 3'<br>:\|\|\|\|\|\|\|\|\|\|:\|\|\|\|\|\|\|<br>3' CAGGUAACGGAUGUGGGAC 5' |
| SEQ ID 1683 | 5' UAUCCCGGAGAUCACGCCC 3'<br>:\|\|\|\|\|\|\|\|\|\|:\|\|\|\|\|\|\|<br>3' AUAGGGCCUCUAGUGCGGG 5' |
| SEQ ID 1684 | 5' AGCGACAUCAUGAAGAGAC 3'<br>:\|\|\|\|\|\|\|\|\|\|:\|\|\|\|\|\|\|<br>3' UCGCUGUAGUACUUCUCUG 5' |
| SEQ ID 1685 | 5' GCGACAUCAUGAAGAGACA 3'<br>:\|\|\|\|\|\|\|\|\|\|:\|\|\|\|\|\|\|<br>3' CGCUGUAGUACUUCUCUGU 5' |
| SEQ ID 1686 | 5' CCCGCGGACCGACAAAUUG 3'<br>:\|\|\|\|\|\|\|\|\|\|:\|\|\|\|\|\|\|<br>3' GGGCGCCUGCCUGUUUAAC 5' |

Figure 2DDDDD

| | |
|---|---|
| SEQ ID 1687 | 5' AUUGGUCAAUGAGAGACUC 3'<br>\|:\|:\|\|\|\|\|\|\|\|:\|:\|:\|:<br>3' UAACCAGUUACUCUCUGAG 5' |
| SEQ ID 1688 | 5' UUGGUCAAUGAGAGACUCA 3'<br>\|:\|:\|\|\|\|\|\|\|\|:\|:\|:\|:<br>3' AACCAGUUACUCUCUGAGU 5' |
| SEQ ID 1689 | 5' UGAGAGACUCAUCAGCAUG 3'<br>\|:\|:\|\|\|\|\|\|\|\|:\|:\|:\|:<br>3' ACUCUCUGAGUAGUCGUAC 5' |
| SEQ ID 1690 | 5' UGAUCCAGGCUCUCGGUGG 3'<br>\|:\|:\|\|\|\|\|\|\|\|:\|:\|:\|:<br>3' ACUAGGUCCGAGAGCCACC 5' |
| SEQ ID 1691 | 5' AAUGGCUUCUUGCCCGGCA 3'<br>\|:\|:\|\|\|\|\|\|\|\|:\|:\|:\|:<br>3' UUACCGAAGAACGGGCCGU 5' |
| SEQ ID 1692 | 5' AUGGCUUCUUGCCCGGCAA 3'<br>\|:\|:\|\|\|\|\|\|\|\|:\|:\|:\|:<br>3' UACCGAAGAACGGGCCGUU 5' |
| SEQ ID 1693 | 5' UGGCUUCUUGCCCGGCAAC 3'<br>\|:\|:\|\|\|\|\|\|\|\|:\|:\|:\|:<br>3' ACCGAAGAACGGGCCGUUG 5' |
| SEQ ID 1694 | 5' UGACCUGGAAGACAGUUAC 3'<br>\|:\|:\|\|\|\|\|\|\|\|:\|:\|:\|:<br>3' ACUGGACCUUCUGUCAAUG 5' |
| SEQ ID 1695 | 5' GACAGUUACGGGCAGCAGU 3'<br>\|:\|:\|\|\|\|\|\|\|\|:\|:\|:\|:<br>3' CUGUCAAUGCCCGUCGUCA 5' |
| SEQ ID 1696 | 5' GGUGGUGGAGUUCACCUGC 3'<br>\|:\|:\|\|\|\|\|\|\|\|:\|:\|:\|:<br>3' CCACCACCUCAAGUGGACG 5' |
| SEQ ID 1697 | 5' GAACAAGAUCCUGAUCUUC 3'<br>\|:\|:\|\|\|\|\|\|\|\|:\|:\|:\|:<br>3' CUUGUUCUAGGACUAGAAG 5' |
| SEQ ID 1698 | 5' CAAGAUCCUGAUCUUCGGG 3'<br>\|:\|:\|\|\|\|\|\|\|\|:\|:\|:\|:<br>3' GUUCUAGGACUAGAAGCCC 5' |
| SEQ ID 1699 | 5' GAUCCUGAUCUUCGGGCUG 3'<br>\|:\|:\|\|\|\|\|\|\|\|:\|:\|:\|:<br>3' CUAGGACUAGAAGCCCGAC 5' |
| SEQ ID 1700 | 5' GCCCAGCUGGUGGUUCUGU 3'<br>\|:\|:\|\|\|\|\|\|\|\|:\|:\|:\|:<br>3' CGGGUCGACCACCAAGACA 5' |
| SEQ ID 1701 | 5' AUCCGCAAACUCAUCCUGC 3'<br>\|:\|:\|\|\|\|\|\|\|\|:\|:\|:\|:<br>3' UAGGCGUUUGAGUAGGACG 5' |
| SEQ ID 1702 | 5' UCCGCAAACUCAUCCUGCG 3'<br>\|:\|:\|\|\|\|\|\|\|\|:\|:\|:\|:<br>3' AGGCGUUUGAGUAGGACGC 5' |

Figure 2EEEEE

<table>
<tr><td>SEQ ID 1703</td><td>5' ACUCAUCCUGCGCAGGAAC 3'<br>||||:||||:|||||:|||<br>3' UGAGUAGGACGCGUCCUUG 5'</td></tr>
<tr><td>SEQ ID 1704</td><td>5' CUCAUCCUGCGCAGGAACC 3'<br>||||:||||:|||||:|||<br>3' GAGUAGGACGCGUCCUUGG 5'</td></tr>
<tr><td>SEQ ID 1705</td><td>5' GGAAACCUACUACUGACCU 3'<br>||||:||||:|||||:|||<br>3' CCUUUGGAUGAUGACUGGA 5'</td></tr>
</table>

<table>
<tr><td>ATP1B1</td><td></td></tr>
<tr><td>SEQ ID 1706</td><td>5' AAAUUAAAUUUUAAGUGAC 3'<br>||||:||||:|||||:|||<br>3' UUUAAUUUAAAAUUCACUG 5'</td></tr>
<tr><td>SEQ ID 1707</td><td>5' AAUUAAAUUUUAAGUGACA 3'<br>||||:||||:|||||:|||<br>3' UUAAUUUAAAAUUCACUGU 5'</td></tr>
<tr><td>SEQ ID 1708</td><td>5' AUUAAAUUUUAAGUGACAC 3'<br>||||:||||:|||||:|||<br>3' UAAUUUAAAAUUCACUGUG 5'</td></tr>
<tr><td>SEQ ID 1709</td><td>5' UUAAAUUUUAAGUGACACU 3'<br>||||:||||:|||||:|||<br>3' AAUUUAAAAUUCACUGUGA 5'</td></tr>
<tr><td>SEQ ID 1710</td><td>5' GAAAUUCAUCUGGAACUCA 3'<br>||||:||||:|||||:|||<br>3' CUUUAAGUAGACCUUGAGU 5'</td></tr>
<tr><td>SEQ ID 1711</td><td>5' AUUCAUCUGGAACUCAGAG 3'<br>||||:||||:|||||:|||<br>3' UAAGUAGACCUUGAGUCUC 5'</td></tr>
<tr><td>SEQ ID 1712</td><td>5' UUCAUCUGGAACUCAGAGA 3'<br>||||:||||:|||||:|||<br>3' AAGUAGACCUUGAGUCUCU 5'</td></tr>
<tr><td>SEQ ID 1713</td><td>5' CUCAGAGAAGAAGGAGUUU 3'<br>||||:||||:|||||:|||<br>3' GAGUCUCUUCUUCCUCAAA 5'</td></tr>
<tr><td>SEQ ID 1714</td><td>5' CAAGGAGUUUCUGGGCAGG 3'<br>||||:||||:|||||:|||<br>3' CUUCCUCAAAGACCCGUCC 5'</td></tr>
<tr><td>SEQ ID 1715</td><td>5' GGAGUUUCUGGGCAGGACC 3'<br>||||:||||:|||||:|||<br>3' CCUCAAAGACCCGUCCUGG 5'</td></tr>
<tr><td>SEQ ID 1716</td><td>5' GAUCCUUCUAUUCUACGUA 3'<br>||||:||||:|||||:|||<br>3' CUAGGAAGAUAAGAUGCAU 5'</td></tr>
<tr><td>SEQ ID 1717</td><td>5' UAUUUUAUGGCUGCCUGGC 3'<br>||||:||||:|||||:|||<br>3' AUAAAAUACCGACGGACCG 5'</td></tr>
</table>

Figure 2FFFFF

<table>
<tr><td>SEQ ID 1718</td><td>5' CCAUCCAAGUGAUGCUGCU 3'<br>||||:||||::||||:|||<br>3' GGUAGGUUCACUACGACGA 5'</td></tr>
<tr><td>SEQ ID 1719</td><td>5' GUGAUGCUGCUCACCAUCA 3'<br>||||:||||::||||:|||<br>3' CACUACGACGAGUGGUAGU 5'</td></tr>
<tr><td>SEQ ID 1720</td><td>5' UUUAAGCCCACAUAUCAGG 3'<br>||||:||||::||||:|||<br>3' AAAUUCGGGUGUAUAGUCC 5'</td></tr>
<tr><td>SEQ ID 1721</td><td>5' GCCCACAUAUCAGGACCGA 3'<br>||||:||||::||||:|||<br>3' CGGGUGUAUAGUCCUGGCU 5'</td></tr>
<tr><td>SEQ ID 1722</td><td>5' CACAGAUUCCUCAGAUCCA 3'<br>||||:||||::||||:|||<br>3' GUGUCUAAGGAGUCUAGGU 5'</td></tr>
<tr><td>SEQ ID 1723</td><td>5' GACUGAAAUUUCCUUUCGU 3'<br>||||:||||::||||:|||<br>3' CUGACUUUAAAGGAAAGCA 5'</td></tr>
<tr><td>SEQ ID 1724</td><td>5' AUUUCCUUUCGUCCUAAUG 3'<br>||||:||||::||||:|||<br>3' UAAAGGAAAGCAGGAUUAC 5'</td></tr>
<tr><td>SEQ ID 1725</td><td>5' UUUCCUUUCGUCCUAAUGA 3'<br>||||:||||::||||:|||<br>3' AAAGGAAAGCAGGAUUACU 5'</td></tr>
<tr><td>SEQ ID 1726</td><td>5' UGAUCCAAGAGCUAUGAG 3'<br>||||:||||::||||:|||<br>3' ACUAGGUUCUCGAUACUC 5'</td></tr>
<tr><td>SEQ ID 1727</td><td>5' GAGCUAUGAGGCAUAUGUA 3'<br>||||:||||::||||:|||<br>3' CUCGAUACUCCGUAUACAU 5'</td></tr>
<tr><td>SEQ ID 1728</td><td>5' CAUAGUUAGGUUCCUGGAA 3'<br>||||:||||::||||:|||<br>3' GUAUCAAUCCAAGGACCUU 5'</td></tr>
<tr><td>SEQ ID 1729</td><td>5' AAGUACAAAGAUUCAGCCC 3'<br>||||:||||::||||:|||<br>3' UUCAUGUUUCUAAGUCGGG 5'</td></tr>
<tr><td>SEQ ID 1730</td><td>5' AGUACAAAGAUUCAGCCCA 3'<br>||||:||||::||||:|||<br>3' UCAUGUUUCUAAGUCGGGU 5'</td></tr>
<tr><td>SEQ ID 1731</td><td>5' GUACAAAGAUUCAGCCCAG 3'<br>||||:||||::||||:|||<br>3' CAUGUUUCUAAGUCGGGUC 5'</td></tr>
<tr><td>SEQ ID 1732</td><td>5' AGAUUCAGCCCAGAGGGAU 3'<br>||||:||||::||||:|||<br>3' UCUAAGUCGGGUCUCCCUA 5'</td></tr>
<tr><td>SEQ ID 1733</td><td>5' GAUUCAGCCCAGAGGGAUG 3'<br>||||:||||::||||:|||<br>3' CUAAGUCGGGUCUCCCUAC 5'</td></tr>
</table>

Figure 2GGGGG

<table>
<tr><td>SEQ ID 1734</td><td>5' GAUUGUGGCGAUGUGCCCA 3'<br>||||:||||::||||:|||<br>3' CUAACACCGCUACACGGGU 5'</td></tr>
<tr><td>SEQ ID 1735</td><td>5' CCGAAAGAACGAGGAGACU 3'<br>||||:||||::||||:|||<br>3' GGCUUUCUUGCUCCUCUGA 5'</td></tr>
<tr><td>SEQ ID 1736</td><td>5' AGAACGAGGAGACUUUAAU 3'<br>||||:||||::||||:|||<br>3' UCUUGCUCCUCUGAAAUUA 5'</td></tr>
<tr><td>SEQ ID 1737</td><td>5' GAACGAGGAGACUUUAAUC 3'<br>||||:||||::||||:|||<br>3' CUUGCUCCUCUGAAAUUAG 5'</td></tr>
<tr><td>SEQ ID 1738</td><td>5' CGAGGAGACUUUAAUCAUG 3'<br>||||:||||::||||:|||<br>3' GCUCCUCUGAAAUUAGUAC 5'</td></tr>
<tr><td>SEQ ID 1739</td><td>5' UCAUGAACGAGGAGAGCGA 3'<br>||||:||||::||||:|||<br>3' AGUACUUGCUCCUCUCGCU 5'</td></tr>
<tr><td>SEQ ID 1740</td><td>5' CGAGGAGAGCGAAAGGUCU 3'<br>||||:||||::||||:|||<br>3' GCUCCUCUCGCUUUCCAGA 5'</td></tr>
<tr><td>SEQ ID 1741</td><td>5' AGGUCUGCAGAUUCAAGCU 3'<br>||||:||||::||||:|||<br>3' UCCAGACGUCUAAGUUCGA 5'</td></tr>
<tr><td>SEQ ID 1742</td><td>5' GGUCUGCAGAUUCAAGCUU 3'<br>||||:||||::||||:|||<br>3' CCAGACGUCUAAGUUCGAA 5'</td></tr>
<tr><td>SEQ ID 1743</td><td>5' GCUUGAAUGGCUGGGAAAU 3'<br>||||:||||::||||:|||<br>3' CGAACUUACCGACCCUUUA 5'</td></tr>
<tr><td>SEQ ID 1744</td><td>5' UGGCUGGGAAAUUGCUCUG 3'<br>||||:||||::||||:|||<br>3' ACCGACCCUUUAACGAGAC 5'</td></tr>
<tr><td>SEQ ID 1745</td><td>5' UCAUGAAACUUAUGGCUAC 3'<br>||||:||||::||||:|||<br>3' AGUACUUUGAAUACCGAUG 5'</td></tr>
<tr><td>SEQ ID 1746</td><td>5' ACUUAUGGCUACAAAGAGG 3'<br>||||:||||::||||:|||<br>3' UGAAUACCGAUGUUUCUCC 5'</td></tr>
<tr><td>SEQ ID 1747</td><td>5' CUUAUGGCUACAAAGAGGG 3'<br>||||:||||::||||:|||<br>3' GAAUACCGAUGUUUCUCCC 5'</td></tr>
<tr><td>SEQ ID 1748</td><td>5' ACAGGGCAAACCGUGCAUU 3'<br>||||:||||::||||:|||<br>3' UGUCCCGUUUGGCACGUAA 5'</td></tr>
<tr><td>SEQ ID 1749</td><td>5' GAGGGCAAACCGUGCAUUA 3'<br>||||:||||::||||:|||<br>3' CUCCCGUUUGGCACGUAAU 5'</td></tr>
</table>

Figure 2HHHHH

| | |
|---|---|
| SEQ ID 1750 | 5' CCGUGCAUUAUUAUAAAGC 3'<br>\|\|\|\|:\|\|:\|:\|\|\|\|:\|\|\|\|<br>3' GGCACGUAAUAAUAUUUCG 5' |
| SEQ ID 1751 | 5' AGCUCAACCGAGUUCUAGG 3'<br>\|\|\|\|:\|\|:\|:\|\|\|\|:\|\|\|\|<br>3' UCGAGUUGGCUCAAGAUCC 5' |
| SEQ ID 1752 | 5' GCUCAACCGAGUUCUAGGC 3'<br>\|\|\|\|:\|\|:\|:\|\|\|\|:\|\|\|\|<br>3' CGAGUUGGCUCAAGAUCCG 5' |
| SEQ ID 1753 | 5' CCGAGUUCUAGGCUUCAAA 3'<br>\|\|\|\|:\|\|:\|:\|\|\|\|:\|\|\|\|<br>3' GGCUCAAGAUCCGAAGUUU 5' |
| SEQ ID 1754 | 5' ACCUAAGCCUCCCAAGAAU 3'<br>\|\|\|\|:\|\|:\|:\|\|\|\|:\|\|\|\|<br>3' UGGAUUCGGAGGGUUCUUA 5' |
| SEQ ID 1755 | 5' CCUAAGCCUCCCAAGAAUG 3'<br>\|\|\|\|:\|\|:\|:\|\|\|\|:\|\|\|\|<br>3' GGAUUCGGAGGGUUCUUAC 5' |
| SEQ ID 1756 | 5' GCCUCCCAAGAAUGAGUCC 3'<br>\|\|\|\|:\|\|:\|:\|\|\|\|:\|\|\|\|<br>3' CGGAGGGUUCUUACUCAGG 5' |
| SEQ ID 1757 | 5' GAAUGAGUCCUUGGAGACU 3'<br>\|\|\|\|:\|\|:\|:\|\|\|\|:\|\|\|\|<br>3' CUUACUCAGGAACCUCUGA 5' |
| SEQ ID 1758 | 5' UGAGUCCUUGGACACUUAC 3'<br>\|\|\|\|:\|\|:\|:\|\|\|\|:\|\|\|\|<br>3' ACUCAGGAACCUCUGAAUG 5' |
| SEQ ID 1759 | 5' GUAUAACCCAAAUGUCCUU 3'<br>\|\|\|\|:\|\|:\|:\|\|\|\|:\|\|\|\|<br>3' CAUAUUGGGUUUACAGGAA 5' |
| SEQ ID 1760 | 5' CCCAAAUGUCCUUCCCGUU 3'<br>\|\|\|\|:\|\|:\|:\|\|\|\|:\|\|\|\|<br>3' GGGUUUACAGGAAGGGCAA 5' |
| SEQ ID 1761 | 5' AUGUCCUUCCCGUUCAGUG 3'<br>\|\|\|\|:\|\|:\|:\|\|\|\|:\|\|\|\|<br>3' UACAGGAAGGGCAAGUCAC 5' |
| SEQ ID 1762 | 5' UGUCCUUCCCGUUCAGUGC 3'<br>\|\|\|\|:\|\|:\|:\|\|\|\|:\|\|\|\|<br>3' ACAGGAAGGGCAAGUCACG 5' |
| SEQ ID 1763 | 5' GCGAGAUGAAGAUAAGGAU 3'<br>\|\|\|\|:\|\|:\|:\|\|\|\|:\|\|\|\|<br>3' CGCUCUACUUCUAUUCCUA 5' |
| SEQ ID 1764 | 5' GGAUAAAGUUGGAAAUGUG 3'<br>\|\|\|\|:\|\|:\|:\|\|\|\|:\|\|\|\|<br>3' CCUAUUUCAACCUUUACAC 5' |
| SEQ ID 1765 | 5' AGUUGGAAAUGUGGAGUAU 3'<br>\|\|\|\|:\|\|:\|:\|\|\|\|:\|\|\|\|<br>3' UCAACCUUUACACCUCAUA 5' |

Figure 2IIIII

| | |
|---|---|
| SEQ ID 1766 | 5' GUUGGAAAUGUGGAGUAUU 3'<br>\|\|\|\|\|\|:\|\|\|\|:\|\|\|\|:\|:<br>3' CAACCUUUACACCUCAUAA 5' |
| SEQ ID 1767 | 5' AUGUGGAGUAUUUUGGACU 3'<br>\|\|\|\|\|\|:\|\|\|\|:\|\|\|\|:\|:<br>3' UACACCUCAUAAAACCUGA 5' |
| SEQ ID 1768 | 5' UGUGGAGUAUUUUGGACUG 3'<br>\|\|\|\|\|\|:\|\|\|\|:\|\|\|\|:\|:<br>3' ACACCUCAUAAAACCUGAC 5' |
| SEQ ID 1769 | 5' CUCCCCUGGUUUUCCUCUG 3'<br>\|\|\|\|\|\|:\|\|\|\|:\|\|\|\|:\|:<br>3' GAGGGGACCAAAAGGAGAC 5' |
| SEQ ID 1770 | 5' ACUCCUGCAGCCCAAAUAC 3'<br>\|\|\|\|\|\|:\|\|\|\|:\|\|\|\|:\|:<br>3' UGAGGACGUCGGGUUUAUG 5' |
| SEQ ID 1771 | 5' CUCCUGCAGCCCAAAUACC 3'<br>\|\|\|\|\|\|:\|\|\|\|:\|\|\|\|:\|:<br>3' GAGGACGUCGGGUUUAUGG 5' |
| SEQ ID 1772 | 5' AUACCUGCAGCCCCUGCUG 3'<br>\|\|\|\|\|\|:\|\|\|\|:\|\|\|\|:\|:<br>3' UAUGGACGUCGGGGACGAC 5' |
| SEQ ID 1773 | 5' UCUUACCAUGGACACUGAA 3'<br>\|\|\|\|\|\|:\|\|\|\|:\|\|\|\|:\|:<br>3' AGAAUGGUACCUGUGACUU 5' |
| SEQ ID 1774 | 5' AUUCGCAUAGAGUGUAAGG 3'<br>\|\|\|\|\|\|:\|\|\|\|:\|\|\|\|:\|:<br>3' UAAGCGUAUCUCACAUUCC 5' |
| SEQ ID 1775 | 5' UUCGCAUAGAGUGUAAGGC 3'<br>\|\|\|\|\|\|:\|\|\|\|:\|\|\|\|:\|:<br>3' AAGCGUAUCUCACAUUCCG 5' |
| SEQ ID 1776 | 5' GGCGUACGGUGAGAACAUU 3'<br>\|\|\|\|\|\|:\|\|\|\|:\|\|\|\|:\|:<br>3' CCGCAUGCCACUCUUGUAA 5' |
| SEQ ID 1777 | 5' CAUUGGGUACAGUGAGAAA 3'<br>\|\|\|\|\|\|:\|\|\|\|:\|\|\|\|:\|:<br>3' GUAACCCAUGUCACUCUUU 5' |
| SEQ ID 1778 | 5' AGACCGUUUUCAGGGACGU 3'<br>\|\|\|\|\|\|:\|\|\|\|:\|\|\|\|:\|:<br>3' UCUGGCAAAAGUCCCUGCA 5' |
| SEQ ID 1779 | 5' GACCGUUUUCAGGGACGUU 3'<br>\|\|\|\|\|\|:\|\|\|\|:\|\|\|\|:\|:<br>3' CUGGCAAAAGUCCCUGCAA 5' |
| SEQ ID 1780 | 5' UUGAAGUUAAGAGCUGAUC 3'<br>\|\|\|\|\|\|:\|\|\|\|:\|\|\|\|:\|:<br>3' AACUUCAAUUCUCGACUAG 5' |

| ATP1B2 | |
|---|---|

Figure 2JJJJJ

| | |
|---|---|
| SEQ ID 1781 | 5' GAUGGUCAUCCAGAAAGAG 3'<br>\|:\|:\|\|\|\|:\|\|\|\|\|\|\|\|\|\|<br>3' CUACCAGUAGGUCUUUCUC 5' |
| SEQ ID 1782 | 5' AGAGAAGAAGAGCUGCGGG 3'<br>\|:\|:\|\|\|\|:\|\|\|\|\|\|\|\|\|\|<br>3' UCUCUUCUUCUCGACGCCC 5' |
| SEQ ID 1783 | 5' GAGAAGAAGAGCUGCGGGC 3'<br>\|:\|:\|\|\|\|:\|\|\|\|\|\|\|\|\|\|<br>3' CUCUUCUUCUCGACGCCCG 5' |
| SEQ ID 1784 | 5' GGAGUUCGUGUGGAACCCG 3'<br>\|:\|:\|\|\|\|:\|\|\|\|\|\|\|\|\|\|<br>3' CCUCAAGCACACCUUGGGC 5' |
| SEQ ID 1785 | 5' CCCGAGGACGCACCAGUUU 3'<br>\|:\|:\|\|\|\|:\|\|\|\|\|\|\|\|\|\|<br>3' GGGCUCCUGCGUGGUCAAA 5' |
| SEQ ID 1786 | 5' GACUGAGAACCUUGAUGUC 3'<br>\|:\|:\|\|\|\|:\|\|\|\|\|\|\|\|\|\|<br>3' CUGACUCUUGGAACUACAG 5' |
| SEQ ID 1787 | 5' CCUUGAUGUCAUUGUCAAU 3'<br>\|:\|:\|\|\|\|:\|\|\|\|\|\|\|\|\|\|<br>3' GGAACUACAGUAACAGUUA 5' |
| SEQ ID 1788 | 5' UGUCAGUGACACUGAAAGC 3'<br>\|:\|:\|\|\|\|:\|\|\|\|\|\|\|\|\|\|<br>3' ACAGUCACUGUGACUUUCG 5' |
| SEQ ID 1789 | 5' AGCUGGGACCAGCAUGUUC 3'<br>\|:\|:\|\|\|\|:\|\|\|\|\|\|\|\|\|\|<br>3' UCGACCCUGGUCGUACAAG 5' |
| SEQ ID 1790 | 5' GCUGGGACCAGCAUGUUCA 3'<br>\|:\|:\|\|\|\|:\|\|\|\|\|\|\|\|\|\|<br>3' CGACCCUGGUCGUACAAGU 5' |
| SEQ ID 1791 | 5' GCUCAACAAGUUCUUGGAG 3'<br>\|:\|:\|\|\|\|:\|\|\|\|\|\|\|\|\|\|<br>3' CGAGUUGUUCAAGAACCUC 5' |
| SEQ ID 1792 | 5' CAAGUUCUUGGAGCCUUAC 3'<br>\|:\|:\|\|\|\|:\|\|\|\|\|\|\|\|\|\|<br>3' GUUCAAGAACCUCGGAAUG 5' |
| SEQ ID 1793 | 5' GUUCUUGGAGCCUUACAAC 3'<br>\|:\|:\|\|\|\|:\|\|\|\|\|\|\|\|\|\|<br>3' CAAGAACCUCGGAAUGUUG 5' |
| SEQ ID 1794 | 5' CGACUCUAUCCAAGCCCAA 3'<br>\|:\|:\|\|\|\|:\|\|\|\|\|\|\|\|\|\|<br>3' GCUGAGAUAGGUUCGGGUU 5' |
| SEQ ID 1795 | 5' GCCCAAAAGAAUGAUGUCU 3'<br>\|:\|:\|\|\|\|:\|\|\|\|\|\|\|\|\|\|<br>3' CGGGUUUUCUUACUACAGA 5' |
| SEQ ID 1796 | 5' AAGAAUGAUGUCUGCCGCC 3'<br>\|:\|:\|\|\|\|:\|\|\|\|\|\|\|\|\|\|<br>3' UUCUUACUACAGACGGCGG 5' |

Figure 2KKKKK

| | |
|---|---|
| SEQ ID 1797 | 5' AGAAUGAUGUCUGCCGCCC 3'<br>\|\|\|\|\|\|\|\|\|\|:\|\|:\|\|:\|\|<br>3' UCUUACUACAGACGGCGGG 5' |
| SEQ ID 1798 | 5' GAAUGAUGUCUGCCGCCCU 3'<br>\|\|\|\|\|\|\|\|\|\|:\|\|:\|\|:\|\|<br>3' CUUACUACAGACGGCGGGA 5' |
| SEQ ID 1799 | 5' CAGCCAGAUAAUGGAGUCC 3'<br>\|\|\|\|\|\|\|\|\|\|:\|\|:\|\|:\|\|<br>3' GUCGGUCUAUUACCUCAGG 5' |
| SEQ ID 1800 | 5' UGGAGUCCUCAACUACCCC 3'<br>\|\|\|\|\|\|\|\|\|\|:\|\|:\|\|:\|\|<br>3' ACCUCAGGAGUUGAUGGGG 5' |
| SEQ ID 1801 | 5' CUACCCCAAACGUGCCUGC 3'<br>\|\|\|\|\|\|\|\|\|\|:\|\|:\|\|:\|\|<br>3' GAUGGGGUUUGCACGGACG 5' |
| SEQ ID 1802 | 5' ACGUGCCUGCCAAUUCAAC 3'<br>\|\|\|\|\|\|\|\|\|\|:\|\|:\|\|:\|\|<br>3' UGCACGGACGGUUAAGUUG 5' |
| SEQ ID 1803 | 5' CGUGCCUGCCAAUUCAACC 3'<br>\|\|\|\|\|\|\|\|\|\|:\|\|:\|\|:\|\|<br>3' GCACGGACGGUUAAGUUGG 5' |
| SEQ ID 1804 | 5' UUCAACCGGACCCAGCUGG 3'<br>\|\|\|\|\|\|\|\|\|\|:\|\|:\|\|:\|\|<br>3' AAGUUGGCCUGGGUCGACC 5' |
| SEQ ID 1805 | 5' GAUGAACCGGGUCAUCAAC 3'<br>\|\|\|\|\|\|\|\|\|\|:\|\|:\|\|:\|\|<br>3' CUACUUGGCCCAGUAGUUG 5' |
| SEQ ID 1806 | 5' CCGGGUCAUCAACUUCUAU 3'<br>\|\|\|\|\|\|\|\|\|\|:\|\|:\|\|:\|\|<br>3' GGCCCAGUAGUUGAAGAUA 5' |
| SEQ ID 1807 | 5' CUUCUAUGCAGGAGCAAAC 3'<br>\|\|\|\|\|\|\|\|\|\|:\|\|:\|\|:\|\|<br>3' GAAGAUACGUCCUCGUUUG 5' |
| SEQ ID 1808 | 5' ACCAGAGCAUGAAUGUUAC 3'<br>\|\|\|\|\|\|\|\|\|\|:\|\|:\|\|:\|\|<br>3' UGGUCUCGUACUUACAAUG 5' |
| SEQ ID 1809 | 5' CCAGACCAUGAAUGUUACC 3'<br>\|\|\|\|\|\|\|\|\|\|:\|\|:\|\|:\|\|<br>3' GGUCUCGUACUUACAAUGG 5' |
| SEQ ID 1810 | 5' UGUUACCUGUGCUGGGAAG 3'<br>\|\|\|\|\|\|\|\|\|\|:\|\|:\|\|:\|\|<br>3' ACAAUGGACACGACCCUUC 5' |
| SEQ ID 1811 | 5' GCGAGAUGAAGAUGCUGAG 3'<br>\|\|\|\|\|\|\|\|\|\|:\|\|:\|\|:\|\|<br>3' CGCUCUACUUCUACGACUC 5' |
| SEQ ID 1812 | 5' GAUGCUGAGAAUCUCGGCA 3'<br>\|\|\|\|\|\|\|\|\|\|:\|\|:\|\|:\|\|<br>3' CUACGACUCUUAGAGCCGU 5' |

Figure 2LLLLL

| | |
|---|---|
| SEQ ID 1813 | 5' UCUCGGCAACUUCGUCAUG 3'<br>:\|\|\|\|\|:\|\|\|\|\|\|\|\|\|\|\|\|<br>3' AGAGCCGUUGAAGCAGUAC 5' |
| SEQ ID 1814 | 5' CUUCGUCAUGUUCCCCGCC 3'<br>:\|\|\|\|\|:\|\|\|\|\|\|\|\|\|\|\|\|<br>3' GAAGCAGUACAAGGGGCGG 5' |
| SEQ ID 1815 | 5' CGGCAACAUCGACCUCAUG 3'<br>:\|\|\|\|\|:\|\|\|\|\|\|\|\|\|\|\|\|<br>3' GCCGUUGUAGCUGGAGUAC 5' |
| SEQ ID 1816 | 5' CAUCGACCUCAUGUACUUC 3'<br>:\|\|\|\|\|:\|\|\|\|\|\|\|\|\|\|\|\|<br>3' GUAGCUGGAGUACAUGAAG 5' |
| SEQ ID 1817 | 5' AAAGUUCCACGUGAACUAC 3'<br>:\|\|\|\|\|:\|\|\|\|\|\|\|\|\|\|\|\|<br>3' UUUCAAGGUGCACUUGAUG 5' |
| SEQ ID 1818 | 5' AAGUUCCACGUGAACUACA 3'<br>:\|\|\|\|\|:\|\|\|\|\|\|\|\|\|\|\|\|<br>3' UUCAAGGUGCACUUGAUGU 5' |
| SEQ ID 1819 | 5' AGUUCCACGUGAACUACAC 3'<br>:\|\|\|\|\|:\|\|\|\|\|\|\|\|\|\|\|\|<br>3' UCAAGGUGCACUUGAUGUG 5' |
| SEQ ID 1820 | 5' GUUCCACGUGAACUACACA 3'<br>:\|\|\|\|\|:\|\|\|\|\|\|\|\|\|\|\|\|<br>3' CAAGGUGCACUUGAUGUGU 5' |
| SEQ ID 1821 | 5' CUACACACAGCCCCUGGUG 3'<br>:\|\|\|\|\|:\|\|\|\|\|\|\|\|\|\|\|\|<br>3' GAUGUGUGUCGGGGACCAC 5' |
| SEQ ID 1822 | 5' GUUCCUGAAUGUCACCCCC 3'<br>:\|\|\|\|\|:\|\|\|\|\|\|\|\|\|\|\|\|<br>3' CAAGGACUUACACUGGGGG 5' |
| SEQ ID 1823 | 5' UGUGACCCCCAACGUGGAG 3'<br>:\|\|\|\|\|:\|\|\|\|\|\|\|\|\|\|\|\|<br>3' ACACUGGGGGUUGCACCUC 5' |
| SEQ ID 1824 | 5' CGUGGAGGUGAAUGUAGAA 3'<br>:\|\|\|\|\|:\|\|\|\|\|\|\|\|\|\|\|\|<br>3' GCACCUCCACUUACAUCUU 5' |
| SEQ ID 1825 | 5' UGUAGAAUGUCGCAUCAAC 3'<br>:\|\|\|\|\|:\|\|\|\|\|\|\|\|\|\|\|\|<br>3' ACAUCUUACAGCGUAGUUG 5' |
| SEQ ID 1826 | 5' UGUCGCAUCAACGCCGCCA 3'<br>:\|\|\|\|\|:\|\|\|\|\|\|\|\|\|\|\|\|<br>3' ACAGCGUAGUUGCGGCGGU 5' |
| SEQ ID 1827 | 5' CAUCGCCACAGACGAUGAG 3'<br>:\|\|\|\|\|:\|\|\|\|\|\|\|\|\|\|\|\|<br>3' GUAGCGGUGUCUGCUACUC 5' |
| SEQ ID 1828 | 5' ACUCCGCAUCAACAAAACC 3'<br>:\|\|\|\|\|:\|\|\|\|\|\|\|\|\|\|\|\|<br>3' UGAGGCGUAGUUGUUUUGG 5' |

Figure 2MMMMM

| | |
|---|---|
| SEQ ID 1829 | 5' CUCCGCAUCAACAAAACCU 3'<br>\|\|\|:\|\|:\|\|:\|\|:\|\|:\|\|\|<br>3' GAGGCGUAGUUGUUUUGGA 5' |

Figure 3A

<table>
<tr><th>CA4</th><th></th></tr>
<tr><td>SEQ ID 5,<br>VTH, VTR VV</td><td>5' CAUCGUCACCACCAAGGCA 3'<br>|||||||||||||||||||<br>3' GUAGCAGUGGUGGUUCCGU 5'</td></tr>
<tr><td>SEQ ID 1834<br>(Hom. To SEQ<br>ID 14)<br>VTR</td><td>5' GCACGACUCGUGGAGAACA 3'<br>|||||||||||||||||||<br>3' CGUGCUGAGCACCUCUUGU 5'</td></tr>
<tr><td>SEQ ID 1835<br>(Hom. To SEQ<br>ID 43)<br>VTR</td><td>5' ACUCUACUAUGACCAGGAG 3'<br>|||||||||||||||||||<br>3' UGAGAUGAUACUGGUCCUC 5'</td></tr>
<tr><td>SEQ ID 44,<br>VTH</td><td>5' GGAACAGACAGUGAGCAUG 3'<br>|||||||||||||||||||<br>3' CCUUGUCUGUCACUCGUAC 5'</td></tr>
<tr><td>SEQ ID 45,<br>VTH</td><td>5' CAGACAGUGAGCAUGAAGG 3'<br>|||||||||||||||||||<br>3' GUCUGUCACUCGUACUUCC 5'</td></tr>
</table>

<table>
<tr><th>CA2</th><th></th></tr>
<tr><td>SEQ ID 54<br>VTH</td><td>5' CUUCCCUGAGGAUCCUCAA 3'<br>|||||||||||||||||||<br>3' GAAGGGACUCCUAGGAGUU 5'</td></tr>
<tr><td>SEQ ID 1836<br>(Hom. To<br>SEQ ID 64)<br>VTR</td><td>5' GUAUGCUGCAGAGCUUCAU 3'<br>|||||||||||||||||||<br>3' CAUACGACGUCUCGAAGUA 5'</td></tr>
<tr><td>SEQ ID 1837<br>(Hom. To<br>SEQ ID 65)<br>VTR</td><td>5' GUAUGCUGCAGAGCUUCAU 3'<br>|||||||||||||||||||<br>3' CAUACGACGUCUCGAAGUA 5'</td></tr>
<tr><td>SEQ ID 66<br>VTH</td><td>5' CUUCACUUGGUUCACUGGA 3'<br>|||||||||||||||||||<br>3' GAAGUGAACCAAGUGACCU 5'</td></tr>
<tr><td>SEQ ID 73<br>VTH</td><td>5' GGUUGGCAGCGCUAAACCG 3'<br>|||||||||||||||||||<br>3' CCAACCGUCGCGAUUUGGC 5'</td></tr>
<tr><td>SEQ ID 1838<br>(Hom. To<br>SEQ ID 73)<br>VTR, VV</td><td>5' GAUUGGCAGUGCUACACCA 3'<br>|||||||||||||||||||<br>3' CUAACCGUCACGAUGUGGU 5'</td></tr>
</table>

Figure 3B

<table>
<tr><td>SEQ ID 1830<br>VTR, VV</td><td>5' CACCAAGUACGGGGAUUUU 3'<br>|||||||||||||||:::|<br>3' GUGGUUCAUGCCCCUAAAA 5'</td></tr>
<tr><td>SEQ ID 1831<br>VTR, VV</td><td>5' GCCUGGACUACUGGACCUA 3'<br>|||||||||||||||:::|<br>3' CGGACCUGAUGACCUGGAU 5'</td></tr>
</table>

<table>
<tr><th>ADRB1</th><th></th></tr>
<tr><td>SEQ ID 1839<br>(Hom. To<br>SEQ ID 103)<br>VTR</td><td>5' GAAGAUCGACAGCUGUGAG 3'<br>|||||||||||||||:::|<br>3' CUUCUAGCUGUCGACACUC 5'</td></tr>
<tr><td>SEQ ID 105<br>VTR, VV</td><td>5' CGACCCCAAGUGCUGCGAC 3'<br>|||||||||||||||:::|<br>3' GCUGGGGUUCACGACGCUG 5'</td></tr>
<tr><td>SEQ ID 106<br>VV</td><td>5' CGUGGUGAAGGCCUUCCAC 3'<br>|||||||||||||||:::|<br>3' GCACCACUUCCGGAAGGUG 5'</td></tr>
<tr><td>SEQ ID 107<br>VTR, VV</td><td>5' CUCGGCCUUCAACCCCAUC 3'<br>|||||||||||||||:::|<br>3' GAGCCGGAAGUUGGGGUAG 5'</td></tr>
</table>

<table>
<tr><th>ADRB2</th><th></th></tr>
<tr><td>SEQ ID 1840<br>(Hom. To<br>SEQ ID 122)<br>VTR</td><td>5' GCCAUCAACUGCUACGCCA 3'<br>|||||||||||||||:::|<br>3' CGGUAGUUGACGAUGCGGU 5'</td></tr>
<tr><td>SEQ ID 125<br>VTH, VTR,<br>VV</td><td>5' CCAAGCCUAUGCCAUUGCC 3'<br>|||||||||||||||:::|<br>3' GGUUCGGAUACGGUAACGG 5'</td></tr>
<tr><td>SEQ ID 130<br>VTH</td><td>5' GAUUGACAAAUCUGAGGGC 3'<br>|||||||||||||||:::|<br>3' CUAACUGUUUAGACUCCCG 5'</td></tr>
<tr><td>SEQ ID 139<br>VTH</td><td>5' CAUUGUGCAUGUGAUCCAG 3'<br>|||||||||||||||:::|<br>3' GUAACACGUACACUAGGUC 5'</td></tr>
<tr><td>SEQ ID 1841<br>(Hom. To<br>SEQ ID 139)<br>VTR, VV</td><td>5' CAUCGUGCACGUGAUCCAG 3'<br>|||||||||||||||:::|<br>3' GUAGCACGUGCACUAGGUC 5'</td></tr>
<tr><td>SEQ ID 140<br>VTH</td><td>5' CCUCAUCCGUAAGGAAGUU 3'<br>|||||||||||||||:::|<br>3' GGAGUAGGCAUUCCUUCAA 5'</td></tr>
</table>

Figure 3C

<table>
<tr><th>ACHE</th><th></th></tr>
<tr><td>SEQ ID 161<br>VTH</td><td>5' CCUUCCAGAGUGUCUGCUA 3'<br>||||||||||:::||||||<br>3' GGAAGGUCUCACAGACGAU 5'</td></tr>
<tr><td>SEQ ID 1842<br>(Hom. To<br>SEQ ID 162)<br>VTR</td><td>5' UAUGUGGACACCCUAUACC 3'<br>||||||||||:::||||||<br>3' AUACACCUGUGGGACAUGG 5'</td></tr>
<tr><td>SEQ ID 1843<br>(Hom. To<br>SEQ ID 166)<br>VTR</td><td>5' CGACACAGAGCUGGUGGCC 3'<br>||||||||||:::||||||<br>3' GCUGUGUCUCGACCACCGG 5'</td></tr>
<tr><td>SEQ ID 1844<br>(Hom. To<br>SEQ ID 177)<br>VTR</td><td>5' GAGAGGAUCUUUGCCCAGA 3'<br>||||||||||:::||||||<br>3' CUCUCCUAGAAACGGGUCU 5'</td></tr>
<tr><td>SEQ ID 1845<br>(Hom. To<br>SEQ ID 185)<br>VTR</td><td>5' CUGCUCAGCGCCACCGACA 3'<br>||||||||||:::||||||<br>3' GACGAGUCGCGGUGGCUGU 5'</td></tr>
<tr><td>SEQ ID 189<br>VTH</td><td>5' CCGUGAGCUGAGCGAGGAC 3'<br>||||||||||:::||||||<br>3' GGCACUCGACUCGCUCCUG 5'</td></tr>
<tr><td>SEQ ID 1846<br>(Hom. To<br>189)<br>VTR, VV</td><td>5' CCGUGAGCUGAGCGAGGAC 3'<br>||||||||||:::||||||<br>3' GGCACUCGACUCGCUCCUG 5'</td></tr>
</table>

<table>
<tr><th>SELE</th><th></th></tr>
<tr><td>SEQ ID 1847<br>(Hom. To<br>SEQ ID 232)<br>VTR</td><td>5' CUAUUCUUGCAAGUGCUAC 3'<br>||||||||||:::||||||<br>3' GAUAAGAACGUUCACGAUG 5'</td></tr>
<tr><td>SEQ ID 1848<br>(Hom. To<br>SEQ ID 262)<br>VTR, VV</td><td>5' GCCAACUUGUAAAGCUGUG 3'<br>||||||||||:::||||||<br>3' CGGUUGAACAUUUCGACAC 5'</td></tr>
<tr><td>SEQ ID 1849<br>(Hom. To<br>286)<br>VTR</td><td>5' CUCGAGUGCACAUCUCAGG 3'<br>||||||||||:::||||||<br>3' GAGCUCACGUGUAGAGUCC 5'</td></tr>
</table>

Figure 3D

<table>
<tr><th>PTGS1</th><th></th></tr>
<tr><td>SEQ ID 1850<br>(Hom. To<br>SEQ ID 322)<br>VTR, VV</td><td>5' CGUGAGCUAUUACACGCGU 3'<br>||:||||:||||||||:||<br>3' GCACUCGAUAAUGUGCGCA 5'</td></tr>
<tr><td>SEQ ID 1851<br>(Hom. To<br>SEQ ID 353)<br>VTR</td><td>5' CCACCUCUACCACUGGCAU 3'<br>||:||||:||||||||:||<br>3' GGUGGAGAUGGUGACCGUA 5'</td></tr>
<tr><td>SEQ ID 1852<br>(Hom. To<br>SEQ ID 369)<br>VTR, VV</td><td>5' UCUCAUCAAGACAGCCACA 3'<br>||:||||:||||||||:||<br>3' AGAGUAGUUCUGUCGGUGU 5'</td></tr>
<tr><td>SEQ ID 371<br>VTH</td><td>5' GAAGCUGGUCUGCCUCAAC 3'<br>||:||||:||||||||:||<br>3' CUUCGACCAGACGGAGUUG 5'</td></tr>
</table>

<table>
<tr><th>PTGS2</th><th></th></tr>
<tr><td>SEQ ID 399<br>VTR</td><td>5' GCCUUCUCUAACCUCUCCU 3'<br>||:||||:||||||||:||<br>3' CGGAAGAGAUUGGAGAGGA 5'</td></tr>
<tr><td>SEQ ID 1853<br>(Hom. To<br>SEQ ID 421)<br>VTR</td><td>5' CAUAACAGAGUGUGCGAUG 3'<br>||:||||:||||||||:||<br>3' GUAUUGUCUCACACGCUAC 5'</td></tr>
<tr><td>SEQ ID 426<br>VV</td><td>5' GCAGGCUAAUACUGAUAGG 3'<br>||:||||:||||||||:||<br>3' CGUCCGAUUAUGACUAUCC 5'</td></tr>
<tr><td>SEQ ID 1854<br>(Hom. To<br>SEQ ID 477)<br>VTR</td><td>5' CACUGCCUCGAUUCAGUCC 3'<br>||:||||:||||||||:||<br>3' GUGACGGAGCUAAGUCAGG 5'</td></tr>
<tr><td>SEQ ID 1855<br>(Hom. To<br>SEQ ID 491)<br>VTR</td><td>5' CAUAACAGAGUGUGCGAUG 3'<br>||:||||:||||||||:||<br>3' GUAUUGUCUCACACGCUAC 5'</td></tr>
</table>

<table>
<tr><th>CA12</th><th></th></tr>
<tr><td>SEQ ID 522<br>VTR, VTH,<br>VV</td><td>5' AUCAUCAACAACUUCCGGC 3'<br>||:||||:||||||||:||<br>3' UACUAGUUGUUGAAGGCCG 5'</td></tr>
<tr><td>SEQ ID 523<br>VTH</td><td>5' UGAUCAACAACUUCCGGCA 3'<br>||:||||:||||||||:||<br>3' ACUAGUUGUUGAAGGCCGU 5'</td></tr>
</table>

Figure 3E

<table>
<tr><td>SEQ ID 1832<br>VTR</td><td>5' GUACAAAGGACAGAACGUG 3'<br>|||||||:||||:||||||<br>3' CAUGUUUCCUGUCUUGCAC 5'</td></tr>
</table>

<table>
<tr><th>ADRA1A</th><th></th></tr>
<tr><td>SEQ ID 1856<br>(Hom. To<br>SEQ ID 546)<br>VV</td><td>5' GACCGACAAAUCCGACUCG 3'<br>|||||||:||||:||||||<br>3' CUGGCUGUUUAGGCUGAGC 5'</td></tr>
</table>

<table>
<tr><th>ADRA1B</th><th></th></tr>
<tr><td>SEQ ID 1867<br>(Hom. To<br>SEQ ID 607)<br>VV</td><td>5' CAUCCUUGUCAUUCUGUCU 3'<br>|||||||:||||:||||||<br>3' GUAGGAACAGUAAGACAGA 5'</td></tr>
<tr><td>SEQ ID 1858<br>(Hom. To<br>SEQ ID 619)<br>VV</td><td>5' GAACUUUCAUGAGGACACC 3'<br>|||||||:||||:||||||<br>3' CUUGAAAGUACUCCUGUGG 5'</td></tr>
</table>

<table>
<tr><th>AGTR1</th><th></th></tr>
<tr><td>SEQ ID 1859<br>(Hom. To<br>SEQ ID 705)<br>VV</td><td>5' ACUCAAGACUGUGGCCAGU 3'<br>|||||||:||||:||||||<br>3' UGAGUUCUGACACCGGUCA 5'</td></tr>
</table>

<table>
<tr><th>AGTR2</th><th></th></tr>
<tr><td>SEQ ID 772<br>VV</td><td>5' AUCCCUGGCAAGCAUCUUA 3'<br>|||||||:||||:||||||<br>3' UAGGGACCGUUCGUAGAAU 5'</td></tr>
<tr><td>SEQ ID 774<br>VV</td><td>5' GCAUCUUAUAUAGUUCCCC 3'<br>|||||||:||||:||||||<br>3' CGUAGAAUAUAUCAAGGGG 5'</td></tr>
</table>

<table>
<tr><th>ACE1</th><th></th></tr>
<tr><td>SEQ ID 1860<br>(Hom. To<br>SEQ ID 866)<br>VV</td><td>5' CUGGAACUAUAACACCAAC 3'<br>|||||||:||||:||||||<br>3' GACCUUGAUAUUGUGGUUG 5'</td></tr>
</table>

Figure 3F

<table>
<tr><th>REN</th><th></th></tr>
<tr><td>SEQ ID 1861<br>(Hom. To<br>SEQ ID<br>1157)<br>VV</td><td>5' GUCAUCUUCGACACGGGUU 3'<br>|||:|||||||||||||:|<br>3' CAGUAGAAGCUGUGCCCAA 5'</td></tr>
</table>

<table>
<tr><th>COCH</th><th></th></tr>
<tr><td>SEQ ID 1862<br>(Hom. To<br>SEQ ID<br>1298)<br>VV</td><td>5' UCACCAUCUUCUCUGUUGG 3'<br>|||:|||||||||||||:|<br>3' AGUGGUAGAAGAGACAACC 5'</td></tr>
</table>

<table>
<tr><th>ATP1A1</th><th></th></tr>
<tr><td>SEQ ID 1399<br>VV</td><td>5' CUGGAACUCUGACUCAGAA 3'<br>|||:|||||||||||||:|<br>3' GACCUUGAGACUGAGUCUU 5'</td></tr>
</table>

<table>
<tr><th>ATP1B1</th><th></th></tr>
<tr><td>SEQ ID 1833<br>VV</td><td>5' GAAUGAUUCCUUGGAGUUU 3'<br>|||:|||||||||||||:|<br>3' CUUACUAAGGAACCUCAAA 5'</td></tr>
</table>

<table>
<tr><th>ATP1B2</th><th></th></tr>
<tr><td>SEQ ID 1820<br>VV</td><td>5' GUUCCACGUGAACUACACA 3'<br>||||:||||||||:||||:<br>3' CAAGGUGCACUUGAUGUGU 5'</td></tr>
</table>

METHODS AND COMPOSITIONS FOR THE TREATMENT OF EYE DISORDERS WITH INCREASED INTRAOCULAR PRESSURE

CROSS-REFERENCE TO RELATED APPLICATIONS

This application is a continuation of application U.S. Ser. No. 12/874,928, filed Sep. 2, 2010, now U.S. Pat. No. 8,389,490, which is a continuation of application U.S. Ser. No. 12/563,530, filed Sep. 21, 2009, now U.S. Pat. No. 7,902,169, which is a continuation of application U.S. Ser. No. 11/360,305, filed Feb. 22, 2006, now U.S. Pat. No. 7,592,325, which is a continuation-in-part of International Patent Application No. PCT/GB2005/050134, filed Aug. 23, 2005, which claims priority to British Application No. GB0503412.9, filed Feb. 18, 2005, and to British Application No. GB0418762.1, filed Aug. 23, 2004, the contents of each of which are incorporated by reference herein in their entirety.

1. FIELD OF THE INVENTION

The present invention relates to methods and compositions that decrease intraocular pressure (IOP) of the eye. The compositions of the invention comprise short interfering nucleic acid molecules (siNA) including, but not limited to, siRNA that decrease expression of genes associated with production or drainage of intraocular fluid. The compositions of the invention can be used in the preparation of a medicament for the treatment of an eye conditions displaying increased IOP such as glaucoma, infection, inflammation, uveitis, and diabetic retinopathy. The methods of the invention comprise the administration to a patient in need thereof an effective amount of one or more siNAs of the invention.

2. BACKGROUND OF THE INVENTION

Glaucoma is one of the leading causes of blindness. Approximately 15% of cases of blindness world-wide result from glaucoma. The most common type, primary open-angle glaucoma, has a prevalence of 1/200 in the general population over 40 years of age. Glaucoma has been simply defined as the process of ocular tissue destruction caused by a sustained elevation of the Intra Ocular Pressure (IOP) above its normal physiological limits. Although several etiologies may be involved in the glaucoma complex, an absolute determinant in therapy selection is the amount of primary and/or induced change in pressure within the iridocorneal angle.

Current therapies include medications or surgeries aimed at lowering this pressure, although the pathophysiological mechanisms by which elevated IOP leads to neuronal damage in glaucoma are unknown. Medical suppression of an elevated IOP can be attempted using four types of drugs: (1) the aqueous humor formation suppressors (such as carbonic anhydrase inhibitors, beta-adrenergic blocking agents, and alpha2-adrenoreceptor agonists); (2) miotics (such as parasympathomimetics, including cholinergics and anticholinesterase inhibitors); (3) uveoscleral outflow enhancers; and (4) hyperosmotic agents (that produce an osmotic pressure gradient across the blood/aqueous barrier within the cilliary epithelium). A fifth category of drugs, neuroprotection agents, is emerging as an important addition to medical therapy, including, for example, NOS inhibitors, excitatory amino acid antagonists, glutamate receptor antagonists, apoptosis inhibitors, and calcium channel blockers.

Reviews of various eye disorders and their treatments can be found in the following references: Bunce et al., 2005, Graefes Arch Clin Exp Ophthalmol.; 243(4):294; Costagliola et al., 2000, Exp Eye Res. 71(2):167; Costagliola et al., 1995, Eur J Ophthalmol., 5(1):19; Cullinane et al., 2002, Br J Ophthalmol., 86(6):676; Sakaguchi et al., 2002, Curr Eye Res. 24(5):325; Shah et al., 2000, J Cardiovasc Pharmacol., 36(2):169, and Wang et al., 2005, Exp Eye Res., 80(5):629.

RNA interference refers to the process of sequence-specific post-transcriptional gene silencing mediated by short interfering RNAs (siRNA). After the discovery of the phenomenon in plants in the early 1990s, Andy Fire and Craig Mello demonstrated that double-stranded RNA (dsRNA) specifically and selectively inhibited gene expression in an extremely efficient manner in *Caenorhabditis elegans* (Fire et al., 1998, Nature, 391:806). The sequence of the first strand (sense RNA) coincided with that of the corresponding region of the target messenger RNA (mRNA). The second strand (antisense RNA) was complementary to the mRNA. The resulting dsRNA turned out to be several orders of magnitude more efficient than the corresponding single-stranded RNA molecules (in particular, antisense RNA).

The process of RNAi begins when the enzyme, DICER, encounters dsRNA and chops it into pieces called small-interfering RNAs (siRNA). This protein belongs to the RNase III nuclease family. A complex of proteins gathers up these RNA remains and uses their code as a guide to search out and destroy any RNAs in the cell with a matching sequence, such as target mRNA (see Basher & Labouesse, 2000, Nat Cell Biol, 2000, 2(2):E31, and Akashi et al., 2001, Antisense Nucleic Acid Drug Dev, 11(6):359).

In attempting to utilize RNAi for gene knockdown, it was recognized that mammalian cells have developed various protective mechanisms against viral infections that could impede the use of this approach. Indeed, the presence of extremely low levels of viral dsRNA triggers an interferon response, resulting in a global non-specific suppression of translation, which in turn triggers apoptosis (Williams, 1997, Biochem Soc Trans, 25(2):509; Gil & Esteban, 2000, Apoptosis, 5(2):107-14).

In 2000 dsRNA was reported to specifically inhibit 3 genes in the mouse oocyte and early embryo. Translational arrest, and thus a PKR response, was not observed as the embryos continued to develop (Wianny & Zemicka-Goetz, 2000, Nat Cell Biol, 2(2):70). Research at Ribopharma AG (Kulmbach, Germany) demonstrated the functionality of RNAi in mammalian cells, using short (20-24 base pairs) dsRNA to switch off genes in human cells without initiating the acute-phase response. Similar experiments carried out by other research groups confirmed these results. (Elbashir et al., 2001, Genes Dev, 15(2):188; Caplen et al., 2001, Proc. Natl. Acad. Sci. USA, 98: 9742) Tested in a variety of normal and cancer human and mouse cell lines, it was determined that short hairpin RNAs (shRNA) can silence genes as efficiently as their siRNA counterparts (Paddison et al, 2002, Genes Dev, 16(8):948). Recently, another group of small RNAs (21-25 base pairs) was shown to mediate downregulation of gene expression. These RNAs, small temporally regulated RNAs (stRNA), regulate timing of gene expression during development in *Caenorhabditis elegans*. (for review see Banerjee & Slack, 2002 and Grosshans & Slack, 2002, J Cell Biol, 156 (1):17).

Scientists have used RNAi in several systems, including *Caenorhabditis elegans, Drosophila*, trypanosomes, and other invertebrates. Several groups have recently presented the specific suppression of protein biosynthesis in different mammalian cell lines (specifically in HeLa cells) demonstrating that RNAi is a broadly applicable method for gene silencing in vitro. Based on these results, RNAi has rapidly become a well-recognized tool for validating (identifying and assigning) gene function. RNAi employing short dsRNA oligonucleotides will yield an understanding of the function of genes that are only partially sequenced.

The preceding is a discussion of relevant art pertaining to RNAi. The discussion is provided only for understanding of the invention that follows, and is not an admission that any of the work described is prior art to the claimed invention.

3. SUMMARY OF THE INVENTION

The present invention relates to methods and compositions designed to decrease intraocular pressure (IOP) of the eye. The compositions of the invention can be used in the preparation of a medicament for the treatment of eye conditions displaying increased IOP such as, for example, glaucoma, infection, inflammation, uveitis, and diabetic retinopathy.

The compositions of the invention comprise short interfering nucleic acid molecules (siNA) that decrease or inhibit expression of genes associated with production or drainage of intraocular fluid. In one embodiment, siNAs of the invention decrease or inhibit expression of genes that are associated with production of intraocular fluid (e.g., aqueous humor). Examples of such genes that are targets of the invention include, but not limited to, Carbonic Anhydrases II, IV and XII; Adrenergic Receptors: beta 1 and 2 and alpha 1A, 1B and 1D; and ATPases: alpha 1, alpha 2, alpha 3, beta 1, beta 2. In another embodiment of the invention, siNAs of the invention decrease or inhibit expression of genes associated with drainage of intraocular fluid (e.g., aqueous humor). Examples of such genes that are targets of the invention include, but not limited to Acetylcholinesterase; Prostaglandin Endoperoxide Synthases 1 and 2; Selectin E; Angiotensin System: Angiotensin II, Angiotensin II Converting Enzymes (ACE I and ACE II), Angiotensin II Receptors (ATR1 and ATR2) and Renin; and Cochlin.

The present invention encompasses compositions and methods of use of short interfering nucleic acid (siNA) including, but not limited to, short interfering RNA (siRNA), double-stranded RNA (dsRNA), micro-RNA (miRNA), and short hairpin RNA (shRNA) molecules capable of mediating RNA interference (RNAi) against the target genes identified supra. In preferred embodiments, the siNA used in the methods of the invention are dsRNA. siNAs of the invention can be unmodified or chemically-modified.

The methods of the invention comprise the administration to a patient in need thereof of an effective amount of one or more siNAs of the invention. In embodiments where more than one type of siNA is administered, the siNAs can all be directed against the same or different target genes. In preferred embodiments, the methods of the invention provide a sustained decrease in IOP when compared with the duration of IOP decrease that results from administration of commercially available drugs (e.g., Xalatan, Trusopt, and Timoftol).

Methods of the invention also encompass administration of one or more siNAs of the invention in combination with one or more other therapeutics that decrease IOP including, but not limited to, commercially available drugs (e.g., Xalatan, Trusopt, and Timoftol).

4. BRIEF DESCRIPTION OF THE DRAWINGS

FIG. 1 shows the GenBank Accession Numbers corresponding to the selected human target genes.

FIGS. 2A-2Z, 2AA-2ZZ, 2AAA-2ZZZ, 2AAAA-2ZZZZ and 2AAAAA-2MMMMM show oligonucleotide sequences and their corresponding SEQ ID NOs. for siRNA molecules encompassed by the present invention. In FIGS. 2A-2Z, 2AA-2ZZ, 2AAA-2ZZZ, 2AAAA-2ZZZZ and 2AAAAA-2MMMMM, "CA4" indicates carbonic anhydrase IV, "CA2" indicates carbonic anhydrase II, "CA12" indicates carbonic anhydrase XII, "ADRB1" indicates adrenergic, beta-1-, receptor; "ADRB2" indicates adrenergic, beta-2-, receptor; "ACHE" indicates acetylcholinesterase; "SELE" indicates selectin E; "PTGS 1" indicates prostaglandin endoperoxide synthase 1; "PTGS2" indicates prostaglandin endoperoxide synthase 2; "ADRA1A" indicates adrenergic, alpha-1A-, receptor; "ADRA1B" indicates adrenergic, alpha-1B-, receptor; "ADRA1D" indicates adrenergic, alpha-1 D-, receptor; "AGT" indicates angiotensinogen; "AGTR1" indicates angiotensin II receptor, type 1; "AGTR2" indicates angiotensin II receptor, type 2; "ACE1" indicates angiotensin I converting enzyme 1; "ACE2" indicates angiotensin I converting enzyme 2; "REN" indicates renin; "COCH" indicates coagulation factor C homolog (cochlin); "ATP 1 A1" indicates ATPase, Na+/K+ transporting, alpha 1 polypeptide; "ATP1A2" indicates ATPase, Na+/K+ transporting, alpha 2 (+) polypeptide; "ATP1A3" indicates ATPase, Na+/K+ transporting, alpha 3 polypeptide; "ATP1B1" indicates ATPase, Na+/K+ transporting, beta 1 polypeptide; ATP1B2" indicates ATPase, Na+/K+ transporting, beta 2 polypeptide.

FIGS. 3A-3F show selected oligonucleotide sequences and their corresponding SEQ ID NOs. for siRNA molecules tested in vitro in human OMDC cells ("VTH"), in vitro in rabbit NPE cells ("VTR"), and/or in vivo ("VV") experiments. All sequences are human unless otherwise specified ("Hom. to" indicates a rabbit sequence that is homologous to the indicated human sequence). SEQ ID NOS:1830-1833 are rabbit sequences with no corresponding disclosed human sequence.

FIGS. 4A-4B show the effect of siRNA on gene expression in an in vitro system. RNA was prepared from cells treated with an siRNA molecule and analyzed by semi-quantitative PCR. Semi-quantitative gels demonstrating expression for (A) the adrenergic, beta-2-, receptor (siRNA were SEQ ID NOs: 122 in lane 1, 125 in lane 2, and 139 in lane 3) or (B) acetylcholinesterase (siRNA were SEQ ID NOS: 162 in lane 1 and 167 in lane 2) are shown. Lower panels show levels of beta actin in the cells as a control. Lanes are as follows: M=molecular weight marker, C=control cells, TC=transfection control cells, 1-3=the different siRNAs used to inhibit expression, NC=negative control. "30c" indicates 30 PCR cycles and "40c" indicates 40 PCR cycles.

Figure 5:
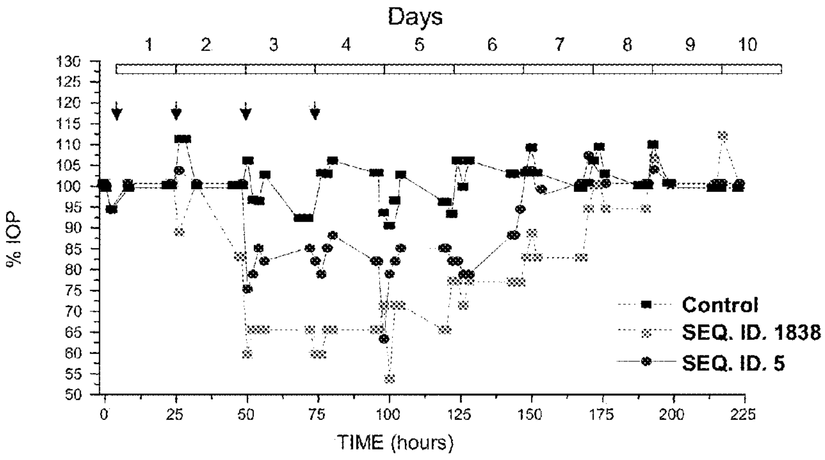

FIG. 5 shows the effect of inhibiting carbonic anhydrase II or carbonic anhydrase IV on IOP levels in rabbits in vivo. siRNA molecules targeting rabbit sequences for carbonic anhydrase II (SEQ ID NO:1838; homologous to SEQ ID NO: 73) and carbonic anhydrase IV (SEQ ID NO:5) were tested in an in vivo rabbit model. A 256 μg dose of the indicated siRNA was administered at time points indicated by an arrow. SEQ ID NO:73 decreased IOP by 25% while SEQ ID NO:5 decreased IOP by 16% over a saline control.

Figure 6:
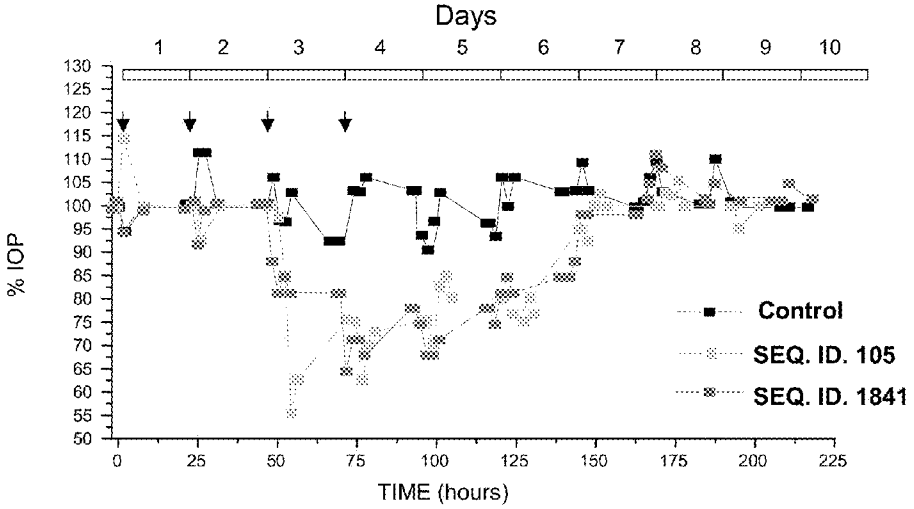

FIG. 6 shows the effect of inhibiting the adrenergic, beta-1-, receptor or the adrenergic, beta-2-, receptor on IOP levels in rabbits in vivo. siRNA molecules targeting rabbit sequences for the adrenergic, beta-1-, receptor (SEQ ID NO: 105) and the adrenergic, beta-2-, receptor (SEQ ID NO:1841; homologous to SEQ ID NO:139) were tested in an in vivo rabbit model. A 256 μg dose of the indicated siRNA was administered at time points indicated by an arrow. SEQ ID NO:105 decreased IOP by 25% while SEQ ID NO:139 decreased IOP by 22% over a saline control.

Figure 7:
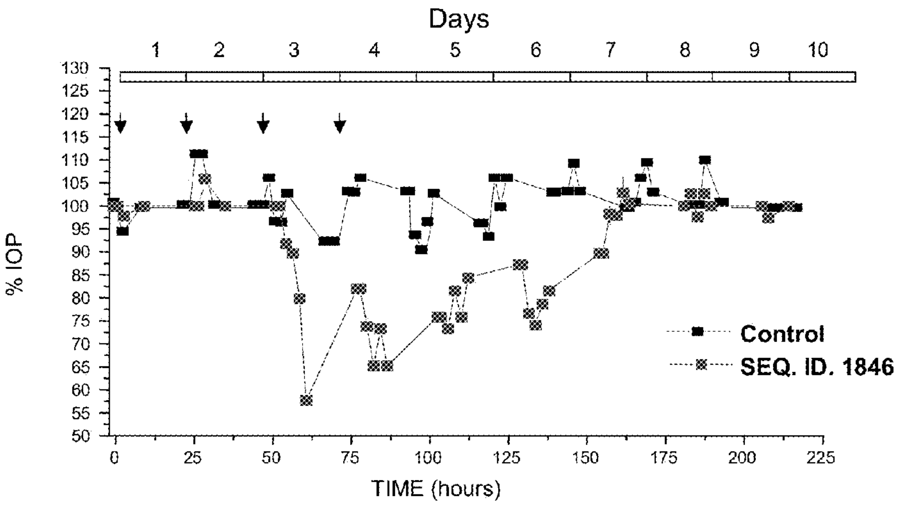

FIG. 7 shows the effect of inhibiting acetylcholinesterase on IOP levels in rabbits in vivo. A siRNA molecule targeting rabbit sequence for acetylcholinesterase (SEQ ID NO:1846; homologous to SEQ ID NO: 189) was tested in an in vivo rabbit model. A 256 μg dose of the siRNA was administered at time points indicated by an arrow. SEQ ID NO:189 decreased IOP by 25% over a saline control.

Figure 8:
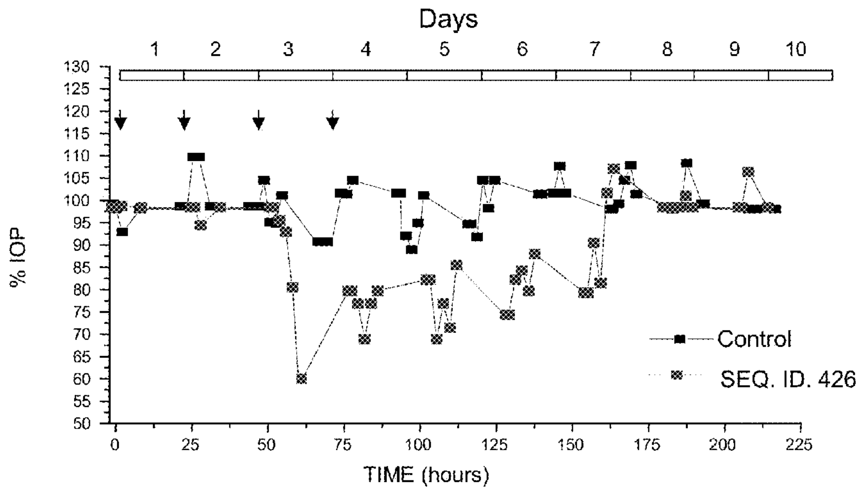
Figure 9A:
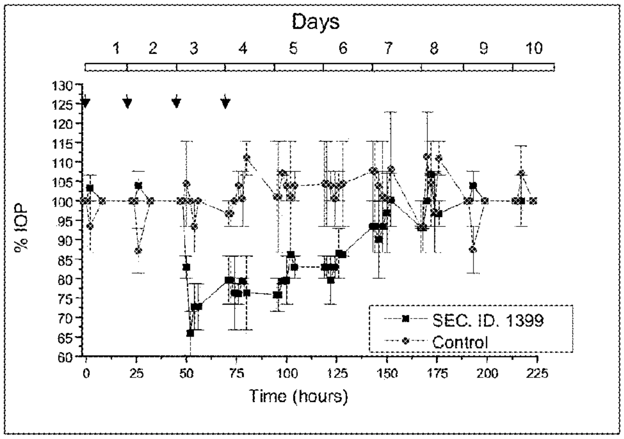
Figure 9B:
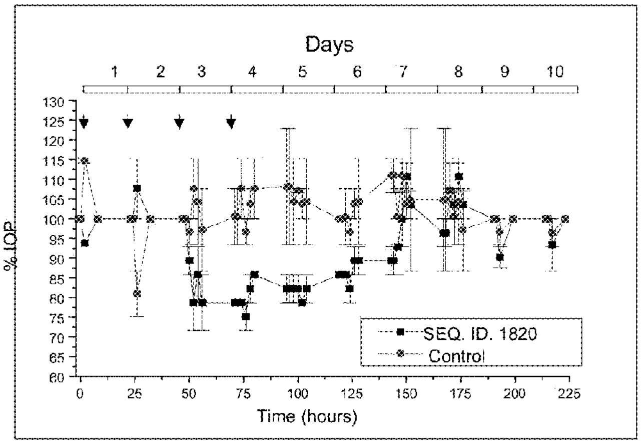
Figure 9C:
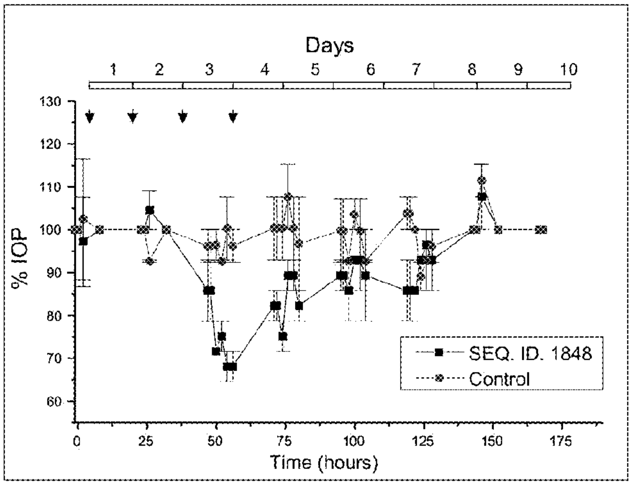
Figure 9D:
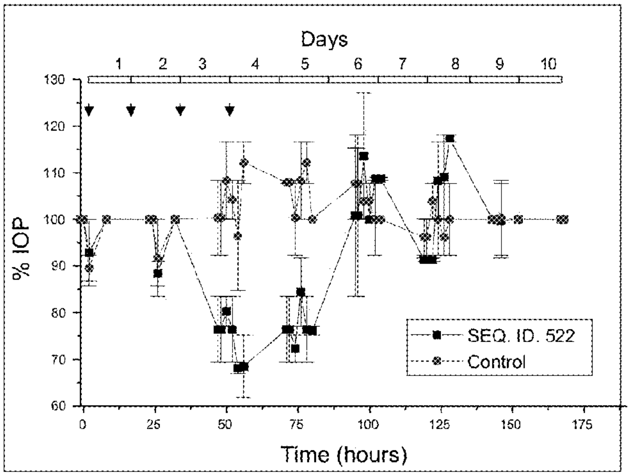

FIG. 8 shows the effect of inhibiting prostaglandin endoperoxide synthase 2 on IOP levels in rabbits in vivo. A siRNA molecule targeting rabbit sequence for a prostaglandin endoperoxide synthase 2 (SEQ ID NO: 426) was tested in an in vivo rabbit model. A 256 μg dose of the siRNA was administered at time points indicated by an arrow. SEQ ID NO:426 decreased IOP by 22% over a saline control.

FIGS. 9A-9D show the effect of inhibiting various molecules to decrease production or increase the drainage of intraocular fluid on IOP levels in rabbits in vivo. A siRNA molecule targeting either the human or rabbit sequence for the indicated target was tested in an in vivo rabbit model. A 256 μg dose of the siRNA was administered at time points indicated by an arrow. The targets were (A) ATPase, Na+/K+ transporting, alpha 1 polypeptide (SEQ ID NO: 1399), (B) ATPase, Na+/K+ transporting, beta 2 polypeptide (SEQ ID NO: 1820), (C) rabbit sequence of selectin E (SEQ ID NO:1848; homologous to SEQ ID NO: 262), (D) carbonic anhydrase XII (SEQ ID NO: 522). Effect of siRNAs are compared to saline controls.

Figure 10:
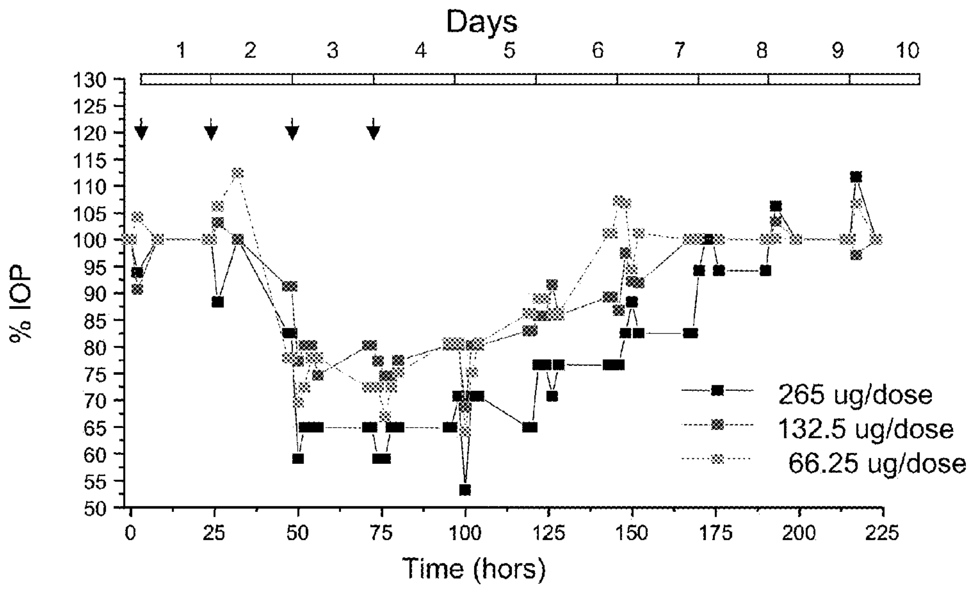

FIG. 10 shows the dose dependent effect of inhibiting carbonic anhydrase II on IOP levels in rabbits in vivo. A siRNA molecule targeting the rabbit sequence for a carbonic anhydrase II (SEQ ID NO:1838; homologous to SEQ ID NO:73) was tested in an in vivo rabbit model. Either a 256 μg dose, a 132.5 μg dose, or a 66.25 μg dose of the siRNA was administered at time points indicated by an arrow.

Figure 11:
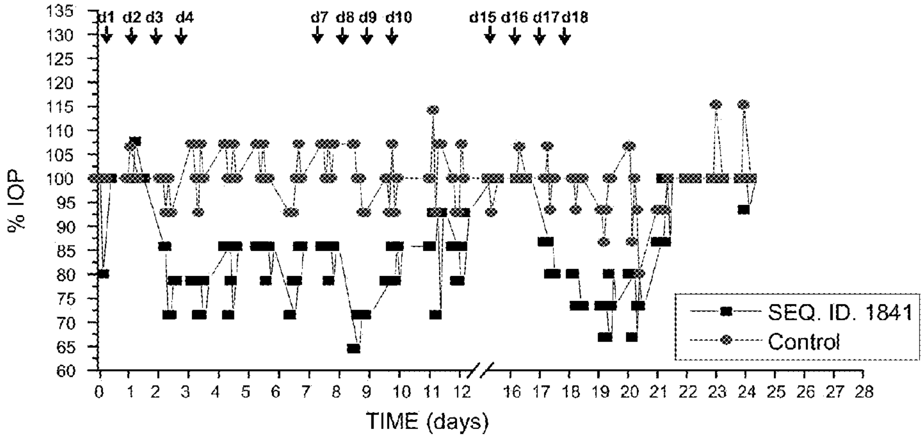

FIG. 11 shows the effect of inhibiting the adrenergic, beta-2-, receptor with consecutive applications of siRNA on IOP levels in rabbits in vivo. A siRNA molecule targeting the rabbit sequence for the adrenergic, beta-2-, receptor (SEQ ID NO:1841; homologous to SEQ ID NO: 139) was tested in an in vivo rabbit model. A 256 μg dose of the siRNA was administered at time points indicated by an arrow. Effect of siRNA is compared to a saline control.

Figure 12:
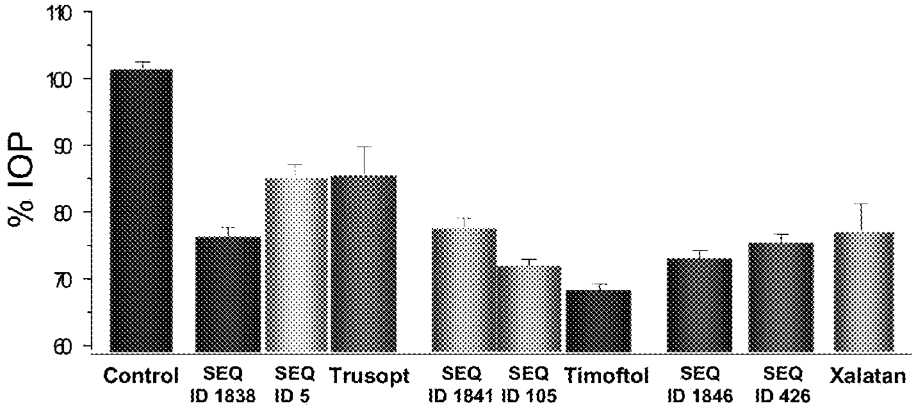

FIG. 12 shows the maximum decrease in IOP obtained in the rabbit in vivo model using the indicated siRNAs or commercially available drugs. siRNA molecules targeting the rabbit sequences for carbonic anhydrase II (SEQ ID NO:1838; homologous to SEQ ID NO: 73), carbonic anhydrase IV (SEQ ID NO: 5), the adrenergic, beta-2-, receptor (SEQ ID NO:1841; homologous to SEQ ID NO: 139), the adrenergic, beta-1-, receptor (SEQ ID NO: 105), acetylcholinesterase (SEQ ID NO:1846; homologous to SEQ ID NO:189), prostaglandin endoperoxide synthase 2 (SEQ ID NO:426) were administered in four doses of 256 μg each. The commercially available drugs Trusopt, Timoftol and Xalatan were administered in four doses of 8 mg, 1 mg, or 20 μg, respectively.

Figure 13:
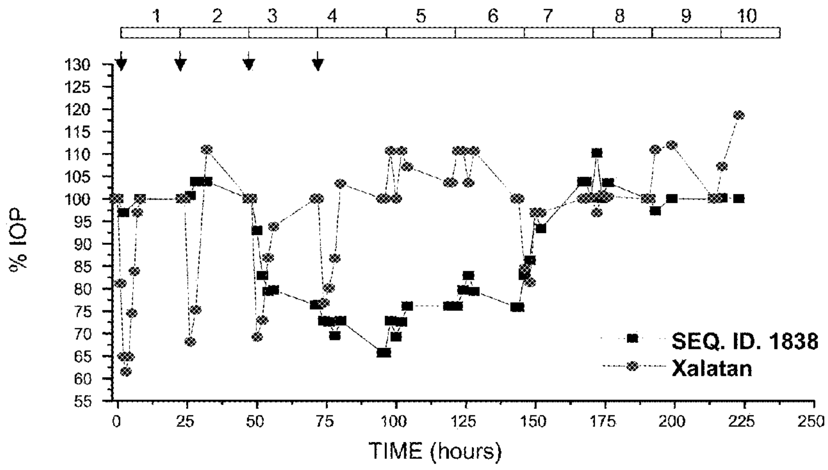

FIG. 13 shows a comparison of the effect of decreasing aqueous humor production with increasing drainage rate on IOP levels in rabbits in vivo. Aqueous humor production was decreased by inhibiting carbonic anhydrase II with siRNA and drainage rate was increased with the prostaglandin analog Xalatan. A 265 μg dose of either a siRNA molecule targeting the rabbit sequence for carbonic anhydrase II (SEQ ID NO:1838; homologous to SEQ ID NO: 73) or a 20 μg dose of the drug Xalatan were administered at time points indicated by an arrow to an in vivo rabbit model.

Figure 14:
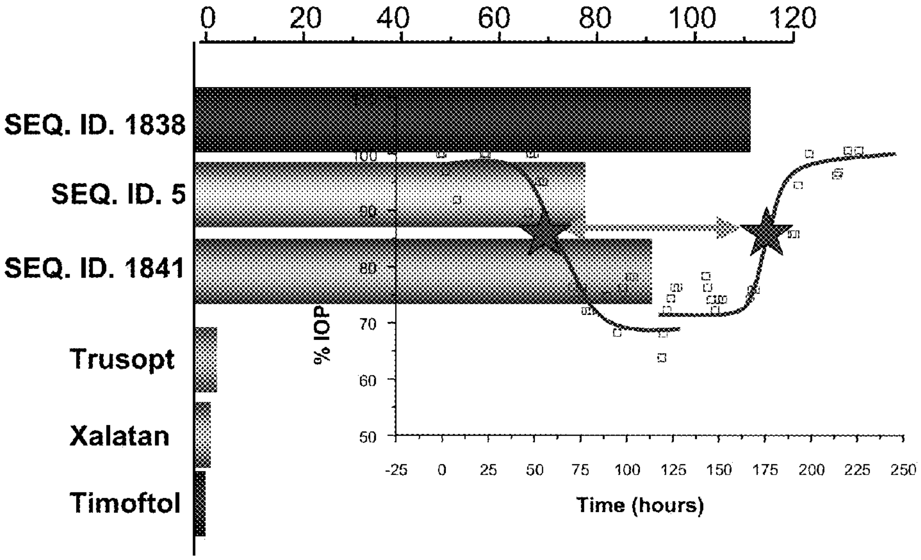

FIG. 14 shows a comparison in length of action of various siRNA treatments with commercially available drugs on IOP levels in rabbits in vivo. siRNA molecules targeting the rabbit sequences for carbonic anhydrase II (SEQ ID NO:1838; homologous to SEQ ID NO: 73), carbonic anhydrase IV (SEQ ID NO: 5), and the adrenergic, beta-2-, receptor (SEQ ID NO:1841; homologous to SEQ ID NO: 139) were administered in four doses of 256 μg each. The commercially available drugs Trusopt, Xalatan, and Timoftol were administered in four doses of 8 mg, 20 μg, or 1 mg, respectively.

5. DETAILED DESCRIPTION OF THE INVENTION

The present invention relates to methods and compositions that decrease intraocular pressure (IOP) of the eye. The compositions of the invention comprise short interfering nucleic acid molecules (siNA) that decrease expression of genes associated with production or drainage of intraocular fluid (e.g., aqueous humor). The compositions of the invention can be used in the preparation of a medicament for the treatment of an eye conditions displaying increased IOP such as glaucoma, infection, inflammation, uveitis, and diabetic retinopathy. The methods of the invention comprise the administration to a patient in need thereof an effective amount of one or more siNAs of the invention.

5.1 Design of siNAs siNAs of the invention are designed to modulate the activity by decreasing or inhibiting the expression of target genes that affect IOP. In one embodiment, a decrease in or inhibition of the target gene expression decreases the production of intraocular fluid (e.g., aqueous humor). Examples of such target genes are Carbonic Anhydrase H, Carbonic Anhydrase IV, Carbonic Anhydrase XII, Adrenergic Receptor beta 1, Adrenergic Receptor beta 2, Adrenergic Receptor alpha 1A, Adrenergic Receptor alpha 1B, Adrenergic Receptor alpha 1D, ATPase alpha 1, ATPase alpha 2, ATPase alpha 3, ATPase beta 1, and ATPase beta 2. In another embodiment, a decrease in or inhibition of the target gene expression increases the drainage of intraocular fluid (e.g., aqueous humor). Examples of such target genes are Acetylcholinesterase, Selectin E, Angiotensin II, Angiotensin II Converting Enzyme I, Angiotensin II Converting Enzyme II, Angiotensin II Receptor 1, Angiotensin 11 Receptor 2, Renin, Cochlin, Prostaglandin Endoperoxide Synthase 1, and Prostaglandin Endoperoxide Synthase 2. GenBank Accession numbers for preferred target genes are shown in FIG. 1.

A gene is "targeted" by a siNA according to the invention when, for example, the siNA molecule selectively decreases or inhibits the expression of the gene. The phrase "selectively decrease or inhibit" as used herein encompasses siNAs that affects expression of one gene as well those that effect the expression of more than one gene. In cases where an siNA affects expression of more than one gene, the gene that is targeted is effected at least two times, three times, four times, five times, ten times, twenty five times, fifty times, or one hundred times as much as any other gene. Alternatively, a siNA targets a gene when the siNA hybridizes under stringent conditions to the gene transcript. siNAs can be tested either in vitro or in vivo for the ability to target a gene.

A short fragment of the target gene sequence (e.g., 19-40 nucleotides in length) is chosen as the sequence of the siNA of the invention. In one embodiment, the siNA is a siRNA. In such embodiments, the short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, and 5) a sequence from the target gene mRNA that is unique to the target gene. The sequence fragment from the target gene mRNA may meet one or more of the criteria identified supra. In embodiments where a fragment of the target gene mRNA meets less than all of the criteria identified supra, the native sequence may be altered such that the siRNA conforms with more of the criteria than does the fragment of the target gene mRNA. In preferred embodiments, the siRNA has a G/C content below 60% and/or lacks repetitive sequences.

In some embodiments, each of the siNAs of the invention targets one gene. In one specific embodiment, the portion of the siNA that is complementary to the target region is perfectly complementary to the target region. In another specific embodiment, the portion of the siNA that is complementary to the target region is not perfectly complementary to the target region. siNA with insertions, deletions, and point mutations relative to the target sequence are also encompassed by the invention. Thus, sequence identity may calculated by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, or 99% sequence identity between the siNA and the portion of the target gene is preferred. Alternatively, the complementarity between the siNA and native RNA molecule may be defined functionally by hybridization. A siNA sequence of the invention is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing). A siNA sequence of the invention can also be defined functionally by its ability to decrease or inhibit the expression of a target gene. The ability of a siNA to effect gene expression can be determined empirically either in vivo or in vitro.

In addition to siNAs which specifically target only one gene, degenerate siNA sequences may be used to target homologous regions of multiple genes. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between homologous genes. In this approach, a single siNA can be used to inhibit expression of more than one gene instead of using more than one siNA molecule to target different genes.

Preferred siNA molecules of the invention are double stranded. In one embodiment, double stranded siNA molecules comprise blunt ends. In another embodiment, double stranded siNA molecules comprise overhanging nucleotides (e.g., 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g., other than phosphodiester bond).

In preferred embodiments, siNA compositions of the invention are any of SEQ ID NOS:1-1829. In an even more preferred embodiments, dsRNA compositions of the invention are any of SEQ ID NOS:1-1829 hybridized to its complement. The invention also encompasses siNAs that are 40 nucleotides or less and comprise a nucleotide sequence of any of SEQ ED NOS:1-1829 as well as dsRNA compositions that are 40 nucleotides or less and comprise a nucleotide sequence of any of SEQ ID NOS:1-1829 hybridized to its complement. In a specific embodiment, the siNA is 21-30 nucleotides and comprises any one of SEQ ID NOS:1-1829.

5.2 Synthesis of siNAs siNAs designed by methods described in Section 5.1 can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany), Ambion (USA) and Invitrogen (Scotland). Alternatively, siNA molecules of the invention can be expressed in cells by transfecting the cells with vectors containing the reverse complement siNA sequence under the control of a promoter. Once expressed, the siNA can be isolated from the cell using techniques well known in the art.

In embodiments where the siRNA is a dsRNA, an annealing step is necessary if single-stranded RNA molecules are obtained. Briefly, combine 30 μl of each RNA oligo 50 μM solution in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA); the two strands of the siRNA molecule may be connected by a linker region (e.g., a nucleotide linker or a non-nucleotide linker).

5.3 Chemical Modification of siNAs

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications WO031070744 and WO2005/045037 for an overview of types of modifications).

In one embodiment, modifications can be used to provide improved resistance to degradation or improved uptake. Examples of such modifications include phosphorothioate internucleotide linkages, 2'-0-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication WO2004/029212).

In another embodiment, modifications can be used to increase or decrease affinity for the complementary nucleotides in the target mRNA and/or in the complementary siNA strand (see generally International Publication WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides (see generally Elbashir et al., 2001, Genes Dev, 15:188).

5.4 Demonstration of Therapeutic Utility

The compositions and methods of the invention are preferably tested in vitro, and then in vivo, for the desired therapeutic activity prior to use in humans. For example, in vitro assays which can be used to determine whether administration of a specific therapeutic protocol is indicated, include in vitro cell culture assays in which a candidate siNA is administered to cells (e.g., rabbit non-pigmented cilliary epithelium cells (NPE), human cilliary epithelium cells (OMDC), or human embryonic kidney cells (HEK293)) in vitro and the effect of such protocol upon the cells is observed, e.g., decreased or inhibited expression of the target gene.

Compounds for use in therapy can be tested in suitable animal model systems prior to testing in humans, including but not limited to in rabbits, rats, mice, chicken, cows, monkeys, hamsters, etc. For example, the New Zealand rabbit is the preferred standard in experimental platforms designed to study IOP. It is easy to handle and it has a big eye, similar in size to the human organ. In addition, present equipment to measure IOP is not suited to use in animals with small eyes such as mice or rats. Finally, rabbits have an IOP (about or equal to 23 mm Hg) that can be reduced to 40% of its normal (or pre-drug) value (e.g., to about or equal to 9 mm Hg) using local commercial hypotensive medication. Thus, although it is possible to generate rabbit glaucoma models (for example, surgically blocking episclerotic veins or artificially occluding the trabecular meshwork), generally those in the field use normotensive rabbits.

5.5 Therapeutic Methods

The present invention encompasses methods for treating, preventing, or managing an eye disorder associated with increased IOP in a patient (e.g., a mammal, especially humans) comprising administering an effective amount of one or more siNAs of the invention. In a specific embodiment, the disorder to be treated, prevented, or managed is glaucoma. Any type of glaucoma that is associated with IOP can be treated with the methods of the present invention including, but not limited to, Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma, Post-Traumatic Glaucoma, Steroid-Induced Glaucoma, Sturge-Weber Syndrome Glaucoma, and Uveitis-Induced Glaucoma.

In preferred embodiments, the siNAs used in the therapeutic methods of the invention decrease or inhibit the expression of genes that effect IOP, for example, Carbonic Anhydrase II, Carbonic Anhydrase IV, Carbonic Anhydrase XII, Adrenergic Receptor beta 1, Adrenergic Receptor beta 2, Adrenergic Receptor alpha 1A, Adrenergic Receptor alpha 1B, Adrenergic Receptor alpha 1D, ATPase alpha 1, ATPase alpha 2, ATPase alpha 3, ATPase beta 1, and ATPase beta 2, Acetylcholinesterase, Selectin E, Angiotensin H, Angiotensin II Converting Enzyme I, Angiotensin II Converting Enzyme II, Angiotensin II Receptor 1, Angiotensin II Receptor 2, Renin, Cochlin, Prostaglandin Endoperoxide Synthase 1, and Prostaglandin Endoperoxide Synthase 2. In certain embodiments, one or more of the siNAs of the invention are selected from the group consisting of SEQ ID NOS:1-1829. In a specific preferred embodiment, the siNAs used in the therapeutic methods of the invention are dsRNA of any of SEQ ID NOS: 1-1829 hybridized to its complement. The invention also encompasses siNAs that are 40 nucleotides or less and comprise a nucleotide sequence of any of SEQ ID NOS:1-1829 as well as dsRNA compositions that are 40 nucleotides or less and comprise a nucleotide sequence of any of SEQ ID NOS: 1-1829 hybridized to its complement. In a specific embodiment, the siNA is 21-30 nucleotides and comprises any of SEQ ID NOS:1-1829.

In preferred embodiments, the methods of the invention provide a sustained decrease in IOP that lasts for longer than 8, 10, 12, or 14 hours, more preferably for several days (e.g., 2 days, 3 days, 4 days, or 5 days), after the last administration of siNA. In such embodiments, the effect (i.e., decreased IOP) of administered siNAs of the invention is longer lasting than the duration of IOP decrease that typically results from administration of presently commercially available drugs (e.g., Xalatan, Trusopt, and Timoftol). The siNAs of the invention that provide sustained IOP decreasing action can be administered in a regimen such that IOP is continually decreased without daily administration of the siNA. In a specific embodiment, a treatment regimen can include consecutive cycles of administration (e.g., one dose of siNA given daily for four days) and non-administration (e.g., 3 or 4 days with no treatment given) while still eliciting a continual decrease in IOP.

In one embodiment, a single type of siNA is administered in the therapeutic methods of the invention. In another embodiment, an siNA of the invention is administered in combination with another siNA of the invention and/or with one or more other non-siNA therapeutic agents useful in the treatment, prevention or management of an eye disorder associated with increased IOP. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

5.6 Dosage

As used herein, an "effective amount" refers to that amount of a siNA of the invention sufficient to treat or manage an eye disorder associated with increased IOP and, preferably, the amount sufficient to decrease IOP. For treatment of increased IOP in humans, it is preferred to reduce IOP so that IOP is between about 14 and 20 mm Hg. However, any reduction in IOP as compared to pretreatment IOP is advantageous (e.g., a decrease in IOP greater that 5%, 10%, 25%, 30%, 35%, 40%, 50%, or 60% of pretreatment IOP). A therapeutically effective amount may also refer to the amount of an siNA sufficient to delay or minimize the onset of an eye disorder associated with IOP. A therapeutically effective amount may also refer to the amount of the therapeutic agent that provides a therapeutic benefit in the treatment or management of an eye disorder associated with IOP. Further, a therapeutically effective amount with respect to an siNA of the invention means that amount of therapeutic agent alone, or in combination with other therapies, that provides a therapeutic benefit in the treatment or management of an eye disorder associated with IOP. Used in connection with an amount of an siRNA of the invention, the term can encompass an amount that improves overall therapy, reduces or avoids unwanted effects, or enhances the therapeutic efficacy of or synergies with another therapeutic agent. Treatment with siNA alone or in combination should result in an IOP of about 14 and 20 nun Hg. However, any decrease in IOP as compared to pretreatment IOP is advantageous (e.g., a decrease in IOP greater that 5%, 10%, 25%, 30%, 35%, 40%, 50%, or 60% of pretreatment IOP).

The effective amount of a composition of the invention can be determined by standard research techniques. For example, the dosage of the composition which will be effective in the treatment, prevention or management of the disorder can be determined by administering the composition to an animal model such as, e.g., the animal models disclosed herein or known to those skilled in the art. In addition, in vitro assays may optionally be employed to help identify optimal dosage ranges. Alternatively, the dosage may be determined for an individual by titrating the dose until an effective level is reached.

Selection of the preferred effective amount to be used in dosages can be determined (e.g., via clinical trials) by a skilled artisan based upon the consideration of several factors which will be known to one of ordinary skill in the art. Such factors include the disorder to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the disorder, and should be decided according to the judgment of the practitioner and each patient's circumstances. Effective doses may be extrapolated from dose-response curves derived from in vitro or animal model test systems.

When the siRNA is administered directly to the eye, generally an amount of between 0.3 mg/kg-20 mg/kg, 0.5 mg/kg-10 mg/kg, or 0.8 mg/kg-2 mg/kg body weight/day of siNA is administered. When the siRNA is administered intravenously, generally an amount of between 0.5 mg-20 mg, or 0.8 mg-10 mg, or 1.0 mg-2.0 mg/injection is administered.

5.7 Formulations and Routes of Administration

The siNAs of the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). Formulations comprising one or more siNAs for use in the methods of the invention may be in numerous forms, and may depend on the various factors specific for each patient (e.g., the type and severity of disorder, type of siNA administered, age, body weight, response, and the past medical history of the patient), the number and type of siNAs in the formulation, the form of the composition (e.g., in liquid, semi-liquid or solid form), the therapeutic regime (e.g. whether the therapeutic agent is administered over time as a slow infusion, a single bolus, once daily, several times a day or once every few days), and/or the route of administration (e.g., topical, oral, intravenous, intramuscular, intra-arterial, intramedullary, intrathecal, transdermal, subcutaneous, intraperitoneal, intranasal, enteral, or sublingual means).

These compositions can take the form of aqueous and non aqueous solutions, suspensions, emulsions, microemulsions, aqueous and non aqueous gels, creams, tablets, pills, capsules, powders, sustained-release formulations and the like. The siNAs of the invention can also be encapsulated in a delivery agent (including, but not limited to, liposomes, microspheres, microparticles, nanospheres, nanoparticles, biodegradable polymers, hydrogels, cyclodextrins poly (lactic-co-glycolic) acid (PLGA)) or complexed with polyethyleneimine and derivatives thereof (such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives).

Pharmaceutical carriers, vehicles, excipients, or diluents may be included in the compositions of the invention including, but not limited to, water, saline solutions, buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skim milk, glycerol, propylene, glycol, ethanol, biopolymers (e.g., carbopol, haluronic acid, polyacrylic acid, etc.), dextrose, permeation enhancers (e.g., fatty acids, fatty acid esters, fatty alcohols and amino acids), and hydrophilic polymers (e.g., polycarbophil and polyvinylpyrolidone) and the like. The composition, if desired, can also contain minor amounts of wetting or emulsifying agents, or pH buffering agents.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

Pharmaceutical compositions can be administered systemically or locally, e.g., near the intended site of action (i.e., the eye). Additionally, systemic administration is meant to encompass administration that can target to a particular area or tissue type of interest.

In preferred embodiments, the compositions of the invention are formulated in a solution or a gel for topical administration to the eye. In such embodiments, the formulations may be cationic emulsions and/or contain biopolymers including, but not limited to, poly(lactide-co-glycolide), carbopol, haluronic acid and polyacrylic acid.

The siNAs of the present invention can also be formulated in combination with other therapeutic compounds that decrease IOP (e.g., commercially available drugs).

Alternatively, the siNAs can be expressed directly in cells of interest (e.g., the eye, more particularly cells of the trabecular meshwork or pigmented cilliary epithelium cells) by transfecting the cells with vectors containing the reverse complement siNA sequence under the control of a promoter. For double stranded siNAs, cells can be transfected with one or more vectors expressing the reverse complement siNA sequence for each strand under the control of a promoter. The cell of interest will express the siNA directly without having to be administered a composition of the invention.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

6. EXAMPLES

6.1 Design of siRNAs

For each gene target, several siNA molecules were designed using proprietary software. The proprietary software used a number of criteria in choosing a sequence fragment of a gene as a candidate siRNA molecule including 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, and 5) a sequence from the target gene mRNA that is unique to the target gene.

Briefly, each of the target genes was introduced as a nucleotide sequence in a prediction program that takes into account all the variables described supra for the design of optimal oligonucleotides for use as siRNA. This program scanned any mRNA nucleotide sequence for regions susceptible to be targeted by siRNAs and thus were good candidates for use as the sequence of the siRNA molecule itself. The output of this analysis was a score of possible siRNA oligonucleotides. The highest scores were used to design double stranded RNA oligonucleotides (typically 19 bp long) that were typically made by chemical synthesis.

Target genes are listed with their GenBank Accession numbers in FIG. 1. siRNA molecules directed to the target genes are listed in FIGS. 2A-2Z, 2AA-2ZZ, 2AAA-2ZZZ, 2AAAA-2ZZZZ and 2AAAAA-2MMMMM. All siRNA molecules used in the experiments described infra were designed to have a 2 thymidine nucleotide 3' overhang. Some of the siRNA molecules were designed to target rabbit homologs of human target genes in preparation for in vivo assays in a rabbit model. Those siRNAs targeting rabbit genes are identified in FIGS. 3A-3F with "Hom. to" indicating the human siRNA that each is homologous to. Specifically, SEQ ID NOS:1834-1862 are rabbit homologs of human sequences. Four siRNAs tested, SEQ ID NOS:1830-1833, do not have a corresponding human homologous sequence.

6.2 In Vitro Assays

Cells (either NPE, OMDC, or HEK293 cells) were incubated with various siRNA molecules and assayed for expression of the native mRNA corresponding to the siRNA molecule. One day prior to transfection, $2-4\times10^5$ cells were seeded into each well of a 6 well plate in 3 ml of growth medium (DMEM, 10% serum, antibiotics and glutamine) and incubated under normal growth conditions (37° C. and 5% $CO_2$). Lipofectamine 2000 Reagent (Invitrogen Corporation, Carlsbad, Calif.) was used to transfect the cells with the siRNA molecules. The protocol supplied by the manufacturer was followed. Briefly, siRNA molecules were added to cells that were 30%-50% confluent to a final concentration of 100 nM. Prior to addition to the cells, the siRNA molecule was diluted in 250 μl DMEM and incubated at room temperature for 5 minutes. The siRNA was then mixed with 6 μl of Lipofectamine 2000 Reagent that also had been diluted in 250 μl DMEM and the mixture was incubated at room temperature for 20 minutes. The siRNA/Lipofectamine mixture was added to the cells drop-wise with 2 ml of fresh growth medium low in antibiotics. After swirling the plates to ensure uniform distribution of the transfection complexes, the cells were incubated under normal growth conditions for 24 hours. After incubation with either of the transfection complexes, the medium was removed and replaced with 3 ml of fresh complete growth medium. mRNA was collected from cells at 24, 48 and 72 hours post-transfection.

After transfection and incubation with a siRNA molecule, total RNA fractions were extracted from cells using protocols well known in the art. The effect of siRNAs on target gene expression was analyzed by real time PCR and semi-quantitative PCR according to standard protocols. Approximately 250 ng of total RNA was used for reverse transcription followed by PCR amplification with specific primers for the target gene in a reaction mixture containing SYBR Green I Dye (Applied Biosystems, Foster City, Calif.). Basic PCR conditions comprised an initial step of 30 minutes at 91° C., followed by 40 cycles of 5 s at 95° C., 10 s at 62° C. and 15 s at 72° C. Quantification of beta-actin mRNA was used as a control for data normalization.

Table 1 shows representative results of real time PCR experiments for some of the target genes. The values represent the mean of the percentage of siRNA interference of each gene expression once normalized with the control cells and their standard deviations. Compared to the control cells, the level of the different transcripts at both 24 and 48 h time points was significantly reduced after the siRNA treatment.

TABLE 1

| Target | siRNA used | % of gene transcript level in control cells 24 h | 48 h |
|---|---|---|---|
| CA2 | SEQ ID NO: 73 | 76.25 ± 12.60 | 84.57 ± 14.70 |
| | SEQ ID NO: 54 | 37.97 ± 9.78 | 61.45 ± 9.62 |
| | SEQ ID NO: 66 | 35.30 ± 9.73 | 51.14 ± 16.49 |
| PTGS1 | SEQ ID NO: 353 | 42.25 ± 13.76 | 42.68 ± 17.00 |
| | SEQ ID NO: 369 | 34.98 ± 14.33 | 26.30 ± 10.91 |
| PTGS2 | SEQ ID NO: 426 | 68.68 ± 12.48 | 70.17 ± 19.21 |
| | SEQ ID NO: 421 | 81.00 ± 13.54 | 66.85 + 18.67 |
| | SEQ ID NO: 477 | 75.45 ± 14.71 | 61.83 ± 16.96 |

FIGS. 4A and 4B show the effect of siRNA on gene expression for the adrenergic, beta-2-, receptor (FIG. 4A) and acetylcholinesterase (FIG. 4B). The siRNA molecules used for each were SEQ ID NOs: 122, 125, and 139 for the adrenergic, beta-2-, receptor (lanes 1-3 of FIG. 4A, respectively) and SEQ ID NOs: 162 and 167 for acetylcholinesterase (in lanes 1-2 of FIG. 4B, respectively). Lower panels show levels of beta actin in the cells as a control. "Control cells" were nontransfected NPE cells, "transfection control cells" were NPE cells transfected with an siRNA with a scrambled sequence, and "negative control cells" were a PCR control. Either 30 (indicated by "30c") or 40 (indicated by "40c") PCR cycles were run.

6.3 In Vivo Assays

Normotensive New Zealand White rabbits (males, 2-3 kg) were used in the in vivo assays. The animals were kept in individual cages with free access to food and water. Animals were submitted to artificial 12 hours light/darkness cycles to avoid uncontrolled circadian oscillations of IOP and all experiments were performed at the same time of day to control for any fluctuations in IOP due to circadian oscillations. Animal handling and treatment were carried out in accordance with the European Communities Council Directive (86/609/EEC) and the statement of the Association for Research in Vision and Ophthalmology on the Use of Animals in Ophthalmic and Vision Research. Each animal was used for only one experiment.

IOP measurements were done using a contact tonometer (TonoPen XL, Mentor, Norwell, Mass.) due to past success of measuring intraocular pressures within the range of 3 to 30 mm Hg in rabbits (Abrams et al., 1996, Invest Ophthalmol Vis Sci. 37:940-4). Measurements were performed by delicately applying the tonometer's sensor to the corneal surface of the animal. All measurements fell within the 3 to 30 mm Hg interval with the mean baseline value of intraocular pressure being 17.0±0.39 mm Hg for untreated animals (n=100). In order to avoid distress to the animal, rabbits were topically anesthetized (10 μl of oxibuprocaine/tetracaine, 0.4%/1%, in a saline solution (1/4 v:v)) prior to IOP measurement.

Commercially available drugs were typically administered to the animals by instilling a small volume (typically 40 μl) on the corneal surface. Contralateral eyes were treated with the vehicle alone and were used as controls in each experiment.

siRNA molecules or commercially available drugs were typically administered to the animals as follows. Doses of siRNA in saline solution (0.9% w/v) to a final volume of 40 μl were applied to the corneal surface of one eye each day during four consecutive days. The opposite eye was taken as a control and 40 μl of sterile saline (0.9% w/v) was instilled on it at the same time points. Commercially available drugs were typically administered to the animals by instilling a small volume (typically 40 μl) on the corneal surface. Contralateral eyes were treated with the vehicle alone and were used as controls in each experiment. The IOP was measured before each application and at 2 h, 4 h and 6 h following the instillation for 10 days.

The data are summarized in Table 2 where values represent the mean of the normalized maximum percentage of IOP reduction after siRNA treatment and their standard deviations. The decrease in IOP was statistically significant for all the treated targets. These results indicated that both siRNAs and commercial drugs reduced IOP levels around 20%, although siRNAs presented a more maintained effect. No secondary effects were observed in the animals during the experimental protocols.

TABLE 2

| Target | siRNA used | IOP Reduction (% of saline control) |
|---|---|---|
| CA2 | SEQ ID NO: 1838<br>(Hom. To SEQ ID NO: 73) | 24.84 ± 3.41 |
| CA4 | SEQ ID NO: 5 | 14.47 ± 5.00 |
| CA12 | SEQ ID NO: 522 | 24.30 ± 1.29 |
| ADRB1 | SEQ ID NO: 105 | 28.04 ± 2.98 |
| ADRB2 | SEQ ID NO: 1841<br>(Hom. To SEQ ID NO: 139) | 21.18 ± 1.88 |
| ADRAIA | SEQ ID NO: 1856<br>(Hom. To SEQ ID NO: 546) | 9.51 ± 1.04 |
| ADRAM | SEQ ID NO: 1858<br>(Hom. To SEQ ID NO: 619) | 17.48 ± 1.30 |
| ACHE | SEQ ID NO: 1846<br>(Hom. To SEQ ID NO: 189) | 25.25 ± 2.70 |
| PTGS1 | SEQ ID NO: 1850<br>(Hom. To SEQ ID NO: 322) | 14.62 ± 1.93 |
| PTGS2 | SEQ ID NO: 426 | 23.78 ± 2.27 |
| SELE | SEQ ID NO: 1848<br>(Hom. To SEQ ID NO: 262) | 21.80 ± 1.74 |
| ACE1 | SEQ ID NO: 1860<br>(Hom. To SEQ ID NO: 866) | 17.51 ± 1.28 |
| AGTR1 | SEQ ID NO: 1859<br>(Hom. To SEQ ID NO: 705) | 9.72 ± 1.35 |
| AGTR2 | SEQ ID NO: 774 | 11.22 ± 1.53 |
| ATP1A1 | SEQ ID NO: 1399 | 18.13 ± 1.39 |
| ATP1B2 | SEQ ID NO: 1820 | 16.32 ± 0.91 |
| Xalatan | — | 25.46 ± 5.24 |
| Trustop | — | 16.41 ± 2.38 |

i. "Hom. To" indicates that the siRNA used was the rabbit homolog of the indicated human sequence FIGS. 5-9 show time course experiments over 10 days for the indicated siRNAs using the in vivo rabbit model of IOP. The indicated siRNA was administered one time on each of days 1-4 of the experiment. Maximum responses (i.e., decrease in IOP) were generally observed on day 2 or 3 of the experiment and lasted for several days.

FIG. 10 shows the dose dependent effect of inhibiting carbonic anhydrase II on IOP levels in the in vivo rabbit model. Either a 265 μg, 132.5 μg, or 66.25 μg dose of the indicated siRNA was administered on each of days 1-4 of the ten day experiment. Although all levels of dose decreased IOP, there was a greater degree of decrease with increasing amounts of siRNA used.

FIG. 11 shows the effect of inhibiting the adrenergic, beta-2-, receptor with consecutive applications of siRNA on IOP levels in the in vivo rabbit model. The indicated siRNA was administered one time on each of days 1-4, 7-10, and 15-18 of the twenty eight day experiment. Decreased levels of IOP were maintained with administration schemes at 3 day intervals.

FIG. 12 shows a comparison of the maximum decrease in IOP in the in vivo rabbit model using the indicated siRNAs and commercially available drugs. For the siRNAs and drugs that decrease aqueous humor production, all of the siRNAs elicited a maximum decrease in IOP greater than that of Trusopt but less than that of Timoftol. For the siRNAs and drugs that increased drainage rate, all of the siRNAs elicited a maximum decrease in IOP greater than that of Xalatan.

FIG. 13 shows a time course experiment over 10 days for the indicated siRNA and drug using the in vivo rabbit model of IOP. The indicated siRNA or drug was administered one time on each of days 1-4 of the experiment. Maximum responses (i.e., decrease in IOP) were generally observed on day 2 or 3 of the experiment for the siRNA but were more immediate for the drug. Although the drug acted more quickly than siRNA in decreasing IOP, it only maintained an effect for about 8 hours whereas the effect of the siRNA lasted several days.

FIG. 14 shows a comparison in length of action of various siRNA treatments with commercially available drugs on IOP levels in the in vivo rabbit model. The indicated siRNA or drug was administered in four doses (one dose each on four consecutive days) and the IOP was measured four times a day during days 0-10. The $Effect_{50}$ represents the time interval between the moment when the IOP reaches a value which is 50% of the maximum decrease reached and the moment when the IOP level starts to recover to values higher than 50% of the maximum decrease value. All of the siRNAs tested decreased IOP for a longer period of time than any of the drugs.

What is claimed:

1. An isolated nucleic acid molecule consisting essentially of a double stranded, short interfering ribonucleic acid (siRNA) of 19 nucleotides in length, wherein the nucleotide sequence of one strand of the siRNA is the sequence as set forth in SEQ ID NO:139 or SEQ ID NO: 1841, which isolated siRNA specifically targets adrenergic beta receptor 2.

2. The isolated nucleic acid molecule according to claim 1, wherein the siRNA is short hairpin (shRNA).

3. The isolated nucleic acid molecule according to claim 1, wherein the siRNA comprises at least one modified oligonucleotide.

4. The isolated nucleic acid molecule according to claim 1, wherein the siRNA comprises at least one linkage between two nucleotides that is not a phosphodiester linkage.

5. The isolated nucleic acid molecule according to claim 1, wherein the nucleotide sequence of one strand of the siRNA is the sequence as set forth in SEQ ID NO: 139.

6. The isolated nucleic acid molecule according to claim 1, wherein the nucleotide sequence of one strand of the siRNA is the sequence as set forth in SEQ ID NO: 1841.

7. An isolated nucleic acid molecule consisting essentially of a double stranded, short interfering RNA (siRNA), wherein the nucleotide sequence of one strand of the siRNA is the sequence as set forth in SEQ ID NO: 139 or SEQ ID NO: 1841, which siRNA specifically targets adrenergic beta receptor 2 and has a dinucleotide 3' overhang.

8. The isolated nucleic acid molecule according to claim 7, wherein the nucleotide sequence of one strand of the siRNA is the sequence as set forth in SEQ ID NO: 139.

9. The isolated nucleic acid molecule according to claim 7, wherein the nucleotide sequence of one strand of the siRNA is the sequence as set forth in SEQ ID NO: 1841.

10. The isolated nucleic acid molecule according to claim 7, wherein the dinucleotide 3' overhang comprises thymidine (T) nucleotides.

11. The isolated nucleic acid molecule according to claim 7, wherein the siRNA is short hairpin (shRNA).

12. The isolated nucleic acid molecule according to claim 7, wherein the siRNA comprises at least one modified oligonucleotide.

13. The isolated nucleic acid molecule according to claim 7, wherein the siRNA comprises at least one linkage between two nucleotides that is not a phosphodiester linkage.

* * * * *

SEQUENCE LISTING

<160> NUMBER OF SEQ ID NOS: 1862

<210> SEQ ID NO 1
<211> LENGTH: 19
<212> TYPE: RNA
<213> ORGANISM: Homo sapiens

<400> SEQUENCE: 1
gccgaguccu ccaacuacc 19

<210> SEQ ID NO 2
<211> LENGTH: 19
<212> TYPE: RNA
<213> ORGANISM: Homo sapiens

<400> SEQUENCE: 2
cuaccccugc uuggugcca 19

<210> SEQ ID NO 3
<211> LENGTH: 19
<212> TYPE: RNA
<213> ORGANISM: Homo sapiens

<400> SEQUENCE: 3
guggggugga aacugccag 19

<210> SEQ ID NO 4
<211> LENGTH: 19
<212> TYPE: RNA
<213> ORGANISM: Homo sapiens

<400> SEQUENCE: 4
acugccagaa ggaccgcca 19

<210> SEQ ID NO 5
<211> LENGTH: 19
<212> TYPE: RNA
<213> ORGANISM: Homo sapiens

<400> SEQUENCE: 5
caucgucacc accaaggca 19

<210> SEQ ID NO 6
<211> LENGTH: 19
<212> TYPE: RNA
<213> ORGANISM: Homo sapiens

<400> SEQUENCE: 6
ggcaaaggug gacaaaaaa 19

-continued

<210> SEQ ID NO 7
<211> LENGTH: 19
<212> TYPE: RNA
<213> ORGANISM: Homo sapiens

<400> SEQUENCE: 7 aggugggacaa aaaacuggg 19

<210> SEQ ID NO 8
<211> LENGTH: 19
<212> TYPE: RNA
<213> ORGANISM: Homo sapiens

<400> SEQUENCE: 8
gguggacaaa aaacuggga 19

<210> SEQ ID NO 9
<211> LENGTH: 19
<212> TYPE: RNA
<213> ORGANISM: Homo sapiens

<400> SEQUENCE: 9
aaaacuggga cgcuucuuc 19

<210> SEQ ID NO 10
<211> LENGTH: 19
<212> TYPE: RNA
<213> ORGANISM: Homo sapiens

<400> SEQUENCE: 10
aaacugggac gcuucuucu 19

<210> SEQ ID NO 11
<211> LENGTH: 19
<212> TYPE: RNA
<213> ORGANISM: Homo sapiens

<400> SEQUENCE: 11
aacugggacg cuucuucuu 19

<210> SEQ ID NO 12
<211> LENGTH: 19
<212> TYPE: RNA
<213> ORGANISM: Homo sapiens

<400> SEQUENCE: 12
acugggacgc uucuucuuc 19

<210> SEQ ID NO 13
<211> LENGTH: 19
<212> TYPE: RNA
<213> ORGANISM: Homo sapiens

<400> SEQUENCE: 13
cugggacgcu ucuucuucu 19

<210> SEQ ID NO 14
<211> LENGTH: 19
<212> TYPE: RNA
<213> ORGANISM: Homo sapiens

<400> SEQUENCE: 14
gaagcaaacg uggacuguc 19

<210> SEQ ID NO 15
<211> LENGTH: 19
<212> TYPE: RNA
<213> ORGANISM: Homo sapiens

<400> SEQUENCE: 15
gcaaacgugg acuguccaa 19

<210> SEQ ID NO 16
<211> LENGTH: 19
<212> TYPE: RNA
<213> ORGANISM: Homo sapiens

<400> SEQUENCE: 16
acguggacug uccaaaaua 19

<210> SEQ ID NO 17
<211> LENGTH: 19
<212> TYPE: RNA
<213> ORGANISM: Homo sapiens

<400> SEQUENCE: 17
cguggacugu ccaaaauaa 19

<210> SEQ ID NO 18
<211> LENGTH: 19
<212> TYPE: RNA
<213> ORGANISM: Homo sapiens

<400> SEQUENCE: 18
aauaacgggc acucaguga 19

<210> SEQ ID NO 19
<211> LENGTH: 19
<212> TYPE: RNA
<213> ORGANISM: Homo sapiens

<400> SEQUENCE: 19
auaacgggca cucagugau 19

<210> SEQ ID NO 20
<211> LENGTH: 19
<212> TYPE: RNA
<213> ORGANISM: Homo sapiens

<400> SEQUENCE: 20
uaacgggcac ucagugaug 19

<210> SEQ ID NO 21
<211> LENGTH: 19
<212> TYPE: RNA
<213> ORGANISM: Homo sapiens

<400> SEQUENCE: 21
cgggcacuca gugaugaug 19

<210> SEQ ID NO 22
<211> LENGTH: 19
<212> TYPE: RNA
<213> ORGANISM: Homo sapiens

<400> SEQUENCE: 22
caaggccagc auuucugga 19

-continued

<210> SEQ ID NO 23
<211> LENGTH: 19
<212> TYPE: RNA
<213> ORGANISM: Homo sapiens

<400> SEQUENCE: 23
ggccagcauu ucuggagga 19

<210> SEQ ID NO 24
<211> LENGTH: 19
<212> TYPE: RNA
<213> ORGANISM: Homo sapiens

<400> SEQUENCE: 24
acaguugcac cugcacugg 19

<210> SEQ ID NO 25
<211> LENGTH: 19
<212> TYPE: RNA
<213> ORGANISM: Homo sapiens

<400> SEQUENCE: 25
caguugcacc ugcacuggu 19

<210> SEQ ID NO 26
<211> LENGTH: 19
<212> TYPE: RNA
<213> ORGANISM: Homo sapiens

<400> SEQUENCE: 26
agagaagggg acaucgagg 19

<210> SEQ ID NO 27
<211> LENGTH: 19
<212> TYPE: RNA
<213> ORGANISM: Homo sapiens

<400> SEQUENCE: 27
gagaagggga caucgagga 19

<210> SEQ ID NO 28
<211> LENGTH: 19
<212> TYPE: RNA
<213> ORGANISM: Homo sapiens

<400> SEQUENCE: 28
ggggacaucg aggaaugug 19

<210> SEQ ID NO 29
<211> LENGTH: 19
<212> TYPE: RNA
<213> ORGANISM: Homo sapiens

<400> SEQUENCE: 29
ugugaaagag gcccaggac 19

<210> SEQ ID NO 30
<211> LENGTH: 19
<212> TYPE: RNA
<213> ORGANISM: Homo sapiens

<400> SEQUENCE: 30
agaggcccag gacccugaa                                                                          19

<210> SEQ ID NO 31
<211> LENGTH: 19
<212> TYPE: RNA
<213> ORGANISM: Homo sapiens

<400> SEQUENCE: 31
gacgaaauug cggugcugg                                                                          19

<210> SEQ ID NO 32
<211> LENGTH: 19
<212> TYPE: RNA
<213> ORGANISM: Homo sapiens

<400> SEQUENCE: 32
auugcggugc uggccuuuc                                                                          19

<210> SEQ ID NO 33
<211> LENGTH: 19
<212> TYPE: RNA
<213> ORGANISM: Homo sapiens

<400> SEQUENCE: 33
uugcggugcu ggccuuucu                                                                          19

<210> SEQ ID NO 34
<211> LENGTH: 19
<212> TYPE: RNA
<213> ORGANISM: Homo sapiens

<400> SEQUENCE: 34
cccaggugaa cgagggcuu                                                                          19

<210> SEQ ID NO 35
<211> LENGTH: 19
<212> TYPE: RNA
<213> ORGANISM: Homo sapiens

<400> SEQUENCE: 35
uauccccaaa ccugagaug                                                                          19

<210> SEQ ID NO 36
<211> LENGTH: 19
<212> TYPE: RNA
<213> ORGANISM: Homo sapiens

<400> SEQUENCE: 36
accugagaug agcacuacg                                                                          19

<210> SEQ ID NO 37
<211> LENGTH: 19
<212> TYPE: RNA
<213> ORGANISM: Homo sapiens

<400> SEQUENCE: 37
ccugagauga gcacuacga                                                                          19

<210> SEQ ID NO 38
<211> LENGTH: 19
<212> TYPE: RNA
<213> ORGANISM: Homo sapiens

<400> SEQUENCE: 38
ggaggagaaa cugaggcac 19

<210> SEQ ID NO 39
<211> LENGTH: 19
<212> TYPE: RNA
<213> ORGANISM: Homo sapiens

<400> SEQUENCE: 39
acugaggcac uacuuccgc 19

<210> SEQ ID NO 40
<211> LENGTH: 19
<212> TYPE: RNA
<213> ORGANISM: Homo sapiens

<400> SEQUENCE: 40
cugaggcacu acuuccgcu 19

<210> SEQ ID NO 41
<211> LENGTH: 19
<212> TYPE: RNA
<213> ORGANISM: Homo sapiens

<400> SEQUENCE: 41
ggucgucugg acuguguuc 19

<210> SEQ ID NO 42
<211> LENGTH: 19
<212> TYPE: RNA
<213> ORGANISM: Homo sapiens

<400> SEQUENCE: 42
cagauccugg cauucucuc 19

<210> SEQ ID NO 43
<211> LENGTH: 19
<212> TYPE: RNA
<213> ORGANISM: Homo sapiens

<400> SEQUENCE: 43
gcuguacuac gacaaggaa 19

<210> SEQ ID NO 44
<211> LENGTH: 19
<212> TYPE: RNA
<213> ORGANISM: Homo sapiens

<400> SEQUENCE: 44
ggaacagaca gugagcaug 19

<210> SEQ ID NO 45
<211> LENGTH: 19
<212> TYPE: RNA
<213> ORGANISM: Homo sapiens

<400> SEQUENCE: 45
cagacaguga gcaugaagg 19

<210> SEQ ID NO 46
<211> LENGTH: 19
<212> TYPE: RNA
<213> ORGANISM: Homo sapiens

<400> SEQUENCE: 46
ggacaauguc aggccccug 19

<210> SEQ ID NO 47
<211> LENGTH: 19
<212> TYPE: RNA
<213> ORGANISM: Homo sapiens

<400> SEQUENCE: 47
acacaacgga ccugagcac 19

<210> SEQ ID NO 48
<211> LENGTH: 19
<212> TYPE: RNA
<213> ORGANISM: Homo sapiens

<400> SEQUENCE: 48
cacaacggac cugagcacu 19

<210> SEQ ID NO 49
<211> LENGTH: 19
<212> TYPE: RNA
<213> ORGANISM: Homo sapiens

<400> SEQUENCE: 49
cggaccugag cacuggcau 19

<210> SEQ ID NO 50
<211> LENGTH: 19
<212> TYPE: RNA
<213> ORGANISM: Homo sapiens

<400> SEQUENCE: 50
ggacuucccc auugccaag 19

<210> SEQ ID NO 51
<211> LENGTH: 19
<212> TYPE: RNA
<213> ORGANISM: Homo sapiens

<400> SEQUENCE: 51
guaugacccu ucccugaag 19

<210> SEQ ID NO 52
<211> LENGTH: 19
<212> TYPE: RNA
<213> ORGANISM: Homo sapiens

<400> SEQUENCE: 52
gccccugucu guuuccuau 19

<210> SEQ ID NO 53
<211> LENGTH: 19
<212> TYPE: RNA
<213> ORGANISM: Homo sapiens

<400> SEQUENCE: 53
gcaacuuccc ugaggaucc 19

<210> SEQ ID NO 54
<211> LENGTH: 19
<212> TYPE: RNA
<213> ORGANISM: Homo sapiens

<400> SEQUENCE: 54
cuucccugag gauccucaa 19

<210> SEQ ID NO 55
<211> LENGTH: 19
<212> TYPE: RNA
<213> ORGANISM: Homo sapiens

<400> SEQUENCE: 55
caauggucau gcuuucaac 19

<210> SEQ ID NO 56
<211> LENGTH: 19
<212> TYPE: RNA
<213> ORGANISM: Homo sapiens

<400> SEQUENCE: 56
uggucaugcu uucaacgug 19

<210> SEQ ID NO 57
<211> LENGTH: 19
<212> TYPE: RNA
<213> ORGANISM: Homo sapiens

<400> SEQUENCE: 57
cguggaguuu gaugacucu 19

<210> SEQ ID NO 58
<211> LENGTH: 19
<212> TYPE: RNA
<213> ORGANISM: Homo sapiens

<400> SEQUENCE: 58
agcagugcuc aagggagga 19

<210> SEQ ID NO 59
<211> LENGTH: 19
<212> TYPE: RNA
<213> ORGANISM: Homo sapiens

<400> SEQUENCE: 59
gcagugcuca agggaggac 19

<210> SEQ ID NO 60
<211> LENGTH: 19
<212> TYPE: RNA
<213> ORGANISM: Homo sapiens

<400> SEQUENCE: 60
gguucagagc auacugugg 19

<210> SEQ ID NO 61
<211> LENGTH: 19
<212> TYPE: RNA
<213> ORGANISM: Homo sapiens

<400> SEQUENCE: 61
aagaaauaug cugcagaac 19

<210> SEQ ID NO 62
<211> LENGTH: 19
<212> TYPE: RNA

<213> ORGANISM: Homo sapiens

<400> SEQUENCE: 62
agaaauaugc ugcagaacu 19

<210> SEQ ID NO 63
<211> LENGTH: 19
<212> TYPE: RNA
<213> ORGANISM: Homo sapiens

<400> SEQUENCE: 63
gaaauaugcu gcagaacuu 19

<210> SEQ ID NO 64
<211> LENGTH: 19
<212> TYPE: RNA
<213> ORGANISM: Homo sapiens

<400> SEQUENCE: 64
auaugcugca gaacuucac 19

<210> SEQ ID NO 65
<211> LENGTH: 19
<212> TYPE: RNA
<213> ORGANISM: Homo sapiens

<400> SEQUENCE: 65
uaugcugcag aacuucacu 19

<210> SEQ ID NO 66
<211> LENGTH: 19
<212> TYPE: RNA
<213> ORGANISM: Homo sapiens

<400> SEQUENCE: 66
cuucacuugg uucacugga 19

<210> SEQ ID NO 67
<211> LENGTH: 19
<212> TYPE: RNA
<213> ORGANISM: Homo sapiens

<400> SEQUENCE: 67
caccaaauau ggggauuuu 19

<210> SEQ ID NO 68
<211> LENGTH: 19
<212> TYPE: RNA
<213> ORGANISM: Homo sapiens

<400> SEQUENCE: 68
auauggggau uuugggaaa 19

<210> SEQ ID NO 69
<211> LENGTH: 19
<212> TYPE: RNA
<213> ORGANISM: Homo sapiens

<400> SEQUENCE: 69
uauggggauu uugggaaag 19

<210> SEQ ID NO 70
<211> LENGTH: 19

<212> TYPE: RNA
<213> ORGANISM: Homo sapiens

<400> SEQUENCE: 70
agcugugcag caaccugau 19

<210> SEQ ID NO 71
<211> LENGTH: 19
<212> TYPE: RNA
<213> ORGANISM: Homo sapiens

<400> SEQUENCE: 71
gcugugcagc aaccugaug 19

<210> SEQ ID NO 72
<211> LENGTH: 19
<212> TYPE: RNA
<213> ORGANISM: Homo sapiens

<400> SEQUENCE: 72
ccugauggac uggccguuc 19

<210> SEQ ID NO 73
<211> LENGTH: 19
<212> TYPE: RNA
<213> ORGANISM: Homo sapiens

<400> SEQUENCE: 73
gguuggcagc gcuaaaccg 19

<210> SEQ ID NO 74
<211> LENGTH: 19
<212> TYPE: RNA
<213> ORGANISM: Homo sapiens

<400> SEQUENCE: 74
accgggccuu cagaaaguu 19

<210> SEQ ID NO 75
<211> LENGTH: 19
<212> TYPE: RNA
<213> ORGANISM: Homo sapiens

<400> SEQUENCE: 75
ccgggccuuc agaaaguug 19

<210> SEQ ID NO 76
<211> LENGTH: 19
<212> TYPE: RNA
<213> ORGANISM: Homo sapiens

<400> SEQUENCE: 76
aguuguugau gugcuggau 19

<210> SEQ ID NO 77
<211> LENGTH: 19
<212> TYPE: RNA
<213> ORGANISM: Homo sapiens

<400> SEQUENCE: 77
guuguugaug ugcuggauu 19

<210> SEQ ID NO 78

<211> LENGTH: 19
<212> TYPE: RNA
<213> ORGANISM: Homo sapiens

<400> SEQUENCE: 78
aacaaagggc aagagugcu 19

<210> SEQ ID NO 79
<211> LENGTH: 19
<212> TYPE: RNA
<213> ORGANISM: Homo sapiens

<400> SEQUENCE: 79
acaaagggca agagugcug 19

<210> SEQ ID NO 80
<211> LENGTH: 19
<212> TYPE: RNA
<213> ORGANISM: Homo sapiens

<400> SEQUENCE: 80
caaagggcaa gagugcuga 19

<210> SEQ ID NO 81
<211> LENGTH: 19
<212> TYPE: RNA
<213> ORGANISM: Homo sapiens

<400> SEQUENCE: 81
agggcaagag ugcugacuu 19

<210> SEQ ID NO 82
<211> LENGTH: 19
<212> TYPE: RNA
<213> ORGANISM: Homo sapiens

<400> SEQUENCE: 82
gggcaagagu gcugacuuc 19

<210> SEQ ID NO 83
<211> LENGTH: 19
<212> TYPE: RNA
<213> ORGANISM: Homo sapiens

<400> SEQUENCE: 83
gagugcugac uucacuaac 19

<210> SEQ ID NO 84
<211> LENGTH: 19
<212> TYPE: RNA
<213> ORGANISM: Homo sapiens

<400> SEQUENCE: 84
gagugcugac uucacaaac 19

<210> SEQ ID NO 85
<211> LENGTH: 19
<212> TYPE: RNA
<213> ORGANISM: Homo sapiens

<400> SEQUENCE: 85
acuuugcagc ucguggccu 19

-continued

<210> SEQ ID NO 86
<211> LENGTH: 19
<212> TYPE: RNA
<213> ORGANISM: Homo sapiens

<400> SEQUENCE: 86
cuucgauccu cguggccuc 19

<210> SEQ ID NO 87
<211> LENGTH: 19
<212> TYPE: RNA
<213> ORGANISM: Homo sapiens

<400> SEQUENCE: 87
ucccuggauu acuggaccu 19

<210> SEQ ID NO 88
<211> LENGTH: 19
<212> TYPE: RNA
<213> ORGANISM: Homo sapiens

<400> SEQUENCE: 88
ugugugaccu ggauugugc 19

<210> SEQ ID NO 89
<211> LENGTH: 19
<212> TYPE: RNA
<213> ORGANISM: Homo sapiens

<400> SEQUENCE: 89
ggaacccauc agcgucagc 19

<210> SEQ ID NO 90
<211> LENGTH: 19
<212> TYPE: RNA
<213> ORGANISM: Homo sapiens

<400> SEQUENCE: 90
acuuaacuuc aauggggag 19

<210> SEQ ID NO 91
<211> LENGTH: 19
<212> TYPE: RNA
<213> ORGANISM: Homo sapiens

<400> SEQUENCE: 91
cuuaacuuca auggggagg 19

<210> SEQ ID NO 92
<211> LENGTH: 19
<212> TYPE: RNA
<213> ORGANISM: Homo sapiens

<400> SEQUENCE: 92
cuucaauggg gagggugaa 19

<210> SEQ ID NO 93
<211> LENGTH: 19
<212> TYPE: RNA
<213> ORGANISM: Homo sapiens

<400> SEQUENCE: 93
uggggagggu gaacccgaa 19

<210> SEQ ID NO 94
<211> LENGTH: 19
<212> TYPE: RNA
<213> ORGANISM: Homo sapiens

<400> SEQUENCE: 94
cccgaagaac ugauggugg 19

<210> SEQ ID NO 95
<211> LENGTH: 19
<212> TYPE: RNA
<213> ORGANISM: Homo sapiens

<400> SEQUENCE: 95
gaacugaugg uggacaacu 19

<210> SEQ ID NO 96
<211> LENGTH: 19
<212> TYPE: RNA
<213> ORGANISM: Homo sapiens

<400> SEQUENCE: 96
cugauggugg acaacuggc 19

<210> SEQ ID NO 97
<211> LENGTH: 19
<212> TYPE: RNA
<213> ORGANISM: Homo sapiens

<400> SEQUENCE: 97
gaacaggcaa aucaaagcu 19

<210> SEQ ID NO 98
<211> LENGTH: 19
<212> TYPE: RNA
<213> ORGANISM: Homo sapiens

<400> SEQUENCE: 98
caggcaaauc aaagcuucc 19

<210> SEQ ID NO 99
<211> LENGTH: 19
<212> TYPE: RNA
<213> ORGANISM: Homo sapiens

<400> SEQUENCE: 99
ugugcuggug aucguggcc 19

<210> SEQ ID NO 100
<211> LENGTH: 19
<212> TYPE: RNA
<213> ORGANISM: Homo sapiens

<400> SEQUENCE: 100
ccucuucauc augucccug 19

<210> SEQ ID NO 101
<211> LENGTH: 19
<212> TYPE: RNA
<213> ORGANISM: Homo sapiens

<400> SEQUENCE: 101
gugcugcgac uucgucacc 19

<210> SEQ ID NO 102
<211> LENGTH: 19
<212> TYPE: RNA
<213> ORGANISM: Homo sapiens

<400> SEQUENCE: 102
gcaggugaag aagaucgac 19

<210> SEQ ID NO 103
<211> LENGTH: 19
<212> TYPE: RNA
<213> ORGANISM: Homo sapiens

<400> SEQUENCE: 103
gaagaucgac agcugcgag 19

<210> SEQ ID NO 104
<211> LENGTH: 19
<212> TYPE: RNA
<213> ORGANISM: Homo sapiens

<400> SEQUENCE: 104
gacgcugggc aucaucaug 19

<210> SEQ ID NO 105
<211> LENGTH: 19
<212> TYPE: RNA
<213> ORGANISM: Homo sapiens

<400> SEQUENCE: 105
cgaccccaag ugcugcgac 19

<210> SEQ ID NO 106
<211> LENGTH: 19
<212> TYPE: RNA
<213> ORGANISM: Homo sapiens

<400> SEQUENCE: 106
cguggugaag gccuuccac 19

<210> SEQ ID NO 107
<211> LENGTH: 19
<212> TYPE: RNA
<213> ORGANISM: Homo sapiens

<400> SEQUENCE: 107
cucggccuuc aaccccauc 19

<210> SEQ ID NO 108
<211> LENGTH: 19
<212> TYPE: RNA
<213> ORGANISM: Homo sapiens

<400> SEQUENCE: 108
ccccaucauc uacugccgc 19

<210> SEQ ID NO 109
<211> LENGTH: 19
<212> TYPE: RNA
<213> ORGANISM: Homo sapiens

<400> SEQUENCE: 109

-continued gaagaucgac agcugugag 19

<210> SEQ ID NO 110
<211> LENGTH: 19
<212> TYPE: RNA
<213> ORGANISM: Homo sapiens

<400> SEQUENCE: 110
uagaagccau gcgccggac 19

<210> SEQ ID NO 111
<211> LENGTH: 19
<212> TYPE: RNA
<213> ORGANISM: Homo sapiens

<400> SEQUENCE: 111
ugugcugguc aucacagcc 19

<210> SEQ ID NO 112
<211> LENGTH: 19
<212> TYPE: RNA
<213> ORGANISM: Homo sapiens

<400> SEQUENCE: 112
guucgagcgu cugcagacg 19

<210> SEQ ID NO 113
<211> LENGTH: 19
<212> TYPE: RNA
<213> ORGANISM: Homo sapiens

<400> SEQUENCE: 113
cuacuucauc acuucacug 19

<210> SEQ ID NO 114
<211> LENGTH: 19
<212> TYPE: RNA
<213> ORGANISM: Homo sapiens

<400> SEQUENCE: 114
aauguggacu uuuggcaac 19

<210> SEQ ID NO 115
<211> LENGTH: 19
<212> TYPE: RNA
<213> ORGANISM: Homo sapiens

<400> SEQUENCE: 115
auguggacuu uuggcaacu 19

<210> SEQ ID NO 116
<211> LENGTH: 19
<212> TYPE: RNA
<213> ORGANISM: Homo sapiens

<400> SEQUENCE: 116
uguggacuuu uggcaacuu 19

<210> SEQ ID NO 117
<211> LENGTH: 19
<212> TYPE: RNA
<213> ORGANISM: Homo sapiens

<400> SEQUENCE: 117
cuucuggugc gaguuuugg 19

<210> SEQ ID NO 118
<211> LENGTH: 19
<212> TYPE: RNA
<213> ORGANISM: Homo sapiens

<400> SEQUENCE: 118
guaccagagc cugcugacc 19

<210> SEQ ID NO 119
<211> LENGTH: 19
<212> TYPE: RNA
<213> ORGANISM: Homo sapiens

<400> SEQUENCE: 119
gaauaaggcc cgggugauc 19

<210> SEQ ID NO 120
<211> LENGTH: 19
<212> TYPE: RNA
<213> ORGANISM: Homo sapiens

<400> SEQUENCE: 120
uaaggcccgg gugaucauu 19

<210> SEQ ID NO 121
<211> LENGTH: 19
<212> TYPE: RNA
<213> ORGANISM: Homo sapiens

<400> SEQUENCE: 121
ggcccgggug aucauucug 19

<210> SEQ ID NO 122
<211> LENGTH: 19
<212> TYPE: RNA
<213> ORGANISM: Homo sapiens

<400> SEQUENCE: 122
gccaucaacu gcuaugcca 19

<210> SEQ ID NO 123
<211> LENGTH: 19
<212> TYPE: RNA
<213> ORGANISM: Homo sapiens

<400> SEQUENCE: 123
cugcuaugcc aaugagacc 19

<210> SEQ ID NO 124
<211> LENGTH: 19
<212> TYPE: RNA
<213> ORGANISM: Homo sapiens

<400> SEQUENCE: 124
ugagaccugc ugugacuuc 19

<210> SEQ ID NO 125
<211> LENGTH: 19
<212> TYPE: RNA
<213> ORGANISM: Homo sapiens

<400> SEQUENCE: 125
ccaagccuau gccauugcc 19

<210> SEQ ID NO 126
<211> LENGTH: 19
<212> TYPE: RNA
<213> ORGANISM: Homo sapiens

<400> SEQUENCE: 126
gccuaugcca uugccucuu 19

<210> SEQ ID NO 127
<211> LENGTH: 19
<212> TYPE: RNA
<213> ORGANISM: Homo sapiens

<400> SEQUENCE: 127
aaggcagcuc cagaagauu 19

<210> SEQ ID NO 128
<211> LENGTH: 19
<212> TYPE: RNA
<213> ORGANISM: Homo sapiens

<400> SEQUENCE: 128
aggcagcucc agaagauug 19

<210> SEQ ID NO 129
<211> LENGTH: 19
<212> TYPE: RNA
<213> ORGANISM: Homo sapiens

<400> SEQUENCE: 129
ggcagcucca gaagauuga 19

<210> SEQ ID NO 130
<211> LENGTH: 19
<212> TYPE: RNA
<213> ORGANISM: Homo sapiens

<400> SEQUENCE: 130
gauugacaaa ucugagggc 19

<210> SEQ ID NO 131
<211> LENGTH: 19
<212> TYPE: RNA
<213> ORGANISM: Homo sapiens

<400> SEQUENCE: 131
aucugagggc cgcuuccau 19

<210> SEQ ID NO 132
<211> LENGTH: 19
<212> TYPE: RNA
<213> ORGANISM: Homo sapiens

<400> SEQUENCE: 132
ucugagggcc gcuuccaug 19

<210> SEQ ID NO 133
<211> LENGTH: 19
<212> TYPE: RNA
<213> ORGANISM: Homo sapiens

<400> SEQUENCE: 133
ccuuagccag guggagcag 19

<210> SEQ ID NO 134
<211> LENGTH: 19
<212> TYPE: RNA
<213> ORGANISM: Homo sapiens

<400> SEQUENCE: 134
guucugcuug aaggagcac 19

<210> SEQ ID NO 135
<211> LENGTH: 19
<212> TYPE: RNA
<213> ORGANISM: Homo sapiens

<400> SEQUENCE: 135
ggagcacaaa gcccucaag 19

<210> SEQ ID NO 136
<211> LENGTH: 19
<212> TYPE: RNA
<213> ORGANISM: Homo sapiens

<400> SEQUENCE: 136
agcccucaag acguuaggc 19

<210> SEQ ID NO 137
<211> LENGTH: 19
<212> TYPE: RNA
<213> ORGANISM: Homo sapiens

<400> SEQUENCE: 137
gcccucaaga cguuaggca 19

<210> SEQ ID NO 138
<211> LENGTH: 19
<212> TYPE: RNA
<213> ORGANISM: Homo sapiens

<400> SEQUENCE: 138
gacguuaggc aucaucaug 19

<210> SEQ ID NO 139
<211> LENGTH: 19
<212> TYPE: RNA
<213> ORGANISM: Homo sapiens

<400> SEQUENCE: 139
cauugugcau gugauccag 19

<210> SEQ ID NO 140
<211> LENGTH: 19
<212> TYPE: RNA
<213> ORGANISM: Homo sapiens

<400> SEQUENCE: 140
ccucauccgu aaggaaguu 19

<210> SEQ ID NO 141
<211> LENGTH: 19
<212> TYPE: RNA

<213> ORGANISM: Homo sapiens

<400> SEQUENCE: 141
ggaaguuuac auccuccua 19

<210> SEQ ID NO 142
<211> LENGTH: 19
<212> TYPE: RNA
<213> ORGANISM: Homo sapiens

<400> SEQUENCE: 142
auuggauagg cuaugucaa 19

<210> SEQ ID NO 143
<211> LENGTH: 19
<212> TYPE: RNA
<213> ORGANISM: Homo sapiens

<400> SEQUENCE: 143
uuggauaggc uaugucaau 19

<210> SEQ ID NO 144
<211> LENGTH: 19
<212> TYPE: RNA
<213> ORGANISM: Homo sapiens

<400> SEQUENCE: 144
uucugguuuc aauccccuu 19

<210> SEQ ID NO 145
<211> LENGTH: 19
<212> TYPE: RNA
<213> ORGANISM: Homo sapiens

<400> SEQUENCE: 145
uccccuuauc uacugccgg 19

<210> SEQ ID NO 146
<211> LENGTH: 19
<212> TYPE: RNA
<213> ORGANISM: Homo sapiens

<400> SEQUENCE: 146
ggccuauggg aauggcuac 19

<210> SEQ ID NO 147
<211> LENGTH: 19
<212> TYPE: RNA
<213> ORGANISM: Homo sapiens

<400> SEQUENCE: 147
uggcuacucc agcaacggc 19

<210> SEQ ID NO 148
<211> LENGTH: 19
<212> TYPE: RNA
<213> ORGANISM: Homo sapiens

<400> SEQUENCE: 148
cacaggggag cagagugga 19

<210> SEQ ID NO 149
<211> LENGTH: 19

<212> TYPE: RNA
<213> ORGANISM: Homo sapiens

<400> SEQUENCE: 149
gaaaauaaac ugcugugug 19

<210> SEQ ID NO 150
<211> LENGTH: 19
<212> TYPE: RNA
<213> ORGANISM: Homo sapiens

<400> SEQUENCE: 150
aauaaacugc ugugugaag 19

<210> SEQ ID NO 151
<211> LENGTH: 19
<212> TYPE: RNA
<213> ORGANISM: Homo sapiens

<400> SEQUENCE: 151
auaaacugcu gugugaaga 19

<210> SEQ ID NO 152
<211> LENGTH: 19
<212> TYPE: RNA
<213> ORGANISM: Homo sapiens

<400> SEQUENCE: 152
uaaacugcug ugugaagac 19

<210> SEQ ID NO 153
<211> LENGTH: 19
<212> TYPE: RNA
<213> ORGANISM: Homo sapiens

<400> SEQUENCE: 153
acugcugugu gaagaccuc 19

<210> SEQ ID NO 154
<211> LENGTH: 19
<212> TYPE: RNA
<213> ORGANISM: Homo sapiens

<400> SEQUENCE: 154
cugcugugug aagaccucc 19

<210> SEQ ID NO 155
<211> LENGTH: 19
<212> TYPE: RNA
<213> ORGANISM: Homo sapiens

<400> SEQUENCE: 155
gacuuugugg gccaucaag 19

<210> SEQ ID NO 156
<211> LENGTH: 19
<212> TYPE: RNA
<213> ORGANISM: Homo sapiens

<400> SEQUENCE: 156
gguacugugc cuagcgaua 19

<210> SEQ ID NO 157

<211> LENGTH: 19
<212> TYPE: RNA
<213> ORGANISM: Homo sapiens

<400> SEQUENCE: 157
cauugauuca caagggagg 19

<210> SEQ ID NO 158
<211> LENGTH: 19
<212> TYPE: RNA
<213> ORGANISM: Homo sapiens

<400> SEQUENCE: 158
gggaggaauu guaguacaa 19

<210> SEQ ID NO 159
<211> LENGTH: 19
<212> TYPE: RNA
<213> ORGANISM: Homo sapiens

<400> SEQUENCE: 159
gccaucaacu gcuacgcca 19

<210> SEQ ID NO 160
<211> LENGTH: 19
<212> TYPE: RNA
<213> ORGANISM: Homo sapiens

<400> SEQUENCE: 160
caucgugcac gugauccag 19

<210> SEQ ID NO 161
<211> LENGTH: 19
<212> TYPE: RNA
<213> ORGANISM: Homo sapiens

<400> SEQUENCE: 161
ccuuccagag ugucugcua 19

<210> SEQ ID NO 162
<211> LENGTH: 19
<212> TYPE: RNA
<213> ORGANISM: Homo sapiens

<400> SEQUENCE: 162
uauguggaca cccuauacc 19

<210> SEQ ID NO 163
<211> LENGTH: 19
<212> TYPE: RNA
<213> ORGANISM: Homo sapiens

<400> SEQUENCE: 163
cguguggaca ccauacccc 19

<210> SEQ ID NO 164
<211> LENGTH: 19
<212> TYPE: RNA
<213> ORGANISM: Homo sapiens

<400> SEQUENCE: 164
cuaccgggug ggagccuuu 19

<210> SEQ ID NO 165
<211> LENGTH: 19
<212> TYPE: RNA
<213> ORGANISM: Homo sapiens

<400> SEQUENCE: 165
ugugggucuc cuggaucag 19

<210> SEQ ID NO 166
<211> LENGTH: 19
<212> TYPE: RNA
<213> ORGANISM: Homo sapiens

<400> SEQUENCE: 166
ugacacagag cugguagcc 19

<210> SEQ ID NO 167
<211> LENGTH: 19
<212> TYPE: RNA
<213> ORGANISM: Homo sapiens

<400> SEQUENCE: 167
ccacgaaugg cacgugcug 19

<210> SEQ ID NO 168
<211> LENGTH: 19
<212> TYPE: RNA
<213> ORGANISM: Homo sapiens

<400> SEQUENCE: 168
uggcacgugc ugccucaag 19

<210> SEQ ID NO 169
<211> LENGTH: 19
<212> TYPE: RNA
<213> ORGANISM: Homo sapiens

<400> SEQUENCE: 169
gaaagcgucu uccgguucu 19

<210> SEQ ID NO 170
<211> LENGTH: 19
<212> TYPE: RNA
<213> ORGANISM: Homo sapiens

<400> SEQUENCE: 170
agcgucuucc gguucuccu 19

<210> SEQ ID NO 171
<211> LENGTH: 19
<212> TYPE: RNA
<213> ORGANISM: Homo sapiens

<400> SEQUENCE: 171
gcgucuuccg guucuccuu 19

<210> SEQ ID NO 172
<211> LENGTH: 19
<212> TYPE: RNA
<213> ORGANISM: Homo sapiens

<400> SEQUENCE: 172
ggaugagggc ucguauuuu 19

<210> SEQ ID NO 173
<211> LENGTH: 19
<212> TYPE: RNA
<213> ORGANISM: Homo sapiens

<400> SEQUENCE: 173
agacaacgag ucucucauc 19

<210> SEQ ID NO 174
<211> LENGTH: 19
<212> TYPE: RNA
<213> ORGANISM: Homo sapiens

<400> SEQUENCE: 174
gacaacgagu cucucauca 19

<210> SEQ ID NO 175
<211> LENGTH: 19
<212> TYPE: RNA
<213> ORGANISM: Homo sapiens

<400> SEQUENCE: 175
cgagucucuc aucagccgg 19

<210> SEQ ID NO 176
<211> LENGTH: 19
<212> TYPE: RNA
<213> ORGANISM: Homo sapiens

<400> SEQUENCE: 176
caccgugcuu ccacgcucu 19

<210> SEQ ID NO 177
<211> LENGTH: 19
<212> TYPE: RNA
<213> ORGANISM: Homo sapiens

<400> SEQUENCE: 177
acuacacggc agaggagaa 19

<210> SEQ ID NO 178
<211> LENGTH: 19
<212> TYPE: RNA
<213> ORGANISM: Homo sapiens

<400> SEQUENCE: 178
cuacacggca gaggagaaa 19

<210> SEQ ID NO 179
<211> LENGTH: 19
<212> TYPE: RNA
<213> ORGANISM: Homo sapiens

<400> SEQUENCE: 179
aaucuucgcc cagcgacug 19

<210> SEQ ID NO 180
<211> LENGTH: 19
<212> TYPE: RNA
<213> ORGANISM: Homo sapiens

<400> SEQUENCE: 180
aucuucgccc agcgacuga 19

-continued

<210> SEQ ID NO 181
<211> LENGTH: 19
<212> TYPE: RNA
<213> ORGANISM: Homo sapiens

<400> SEQUENCE: 181
ucuucgccca gcgacugau 19

<210> SEQ ID NO 182
<211> LENGTH: 19
<212> TYPE: RNA
<213> ORGANISM: Homo sapiens

<400> SEQUENCE: 182
cuuugcccgc acaggggau 19

<210> SEQ ID NO 183
<211> LENGTH: 19
<212> TYPE: RNA
<213> ORGANISM: Homo sapiens

<400> SEQUENCE: 183
ccgcuuccuc cccaaauug 19

<210> SEQ ID NO 184
<211> LENGTH: 19
<212> TYPE: RNA
<213> ORGANISM: Homo sapiens

<400> SEQUENCE: 184
auugcucagc gccaccgac 19

<210> SEQ ID NO 185
<211> LENGTH: 19
<212> TYPE: RNA
<213> ORGANISM: Homo sapiens

<400> SEQUENCE: 185
uugcucagcg ccaccgaca 19

<210> SEQ ID NO 186
<211> LENGTH: 19
<212> TYPE: RNA
<213> ORGANISM: Homo sapiens

<400> SEQUENCE: 186
gaaccaguuc gaccacuac 19

<210> SEQ ID NO 187
<211> LENGTH: 19
<212> TYPE: RNA
<213> ORGANISM: Homo sapiens

<400> SEQUENCE: 187
ccaguucgac cacuacagc 19

<210> SEQ ID NO 188
<211> LENGTH: 19
<212> TYPE: RNA
<213> ORGANISM: Homo sapiens

<400> SEQUENCE: 188
gcaggaucgc ugcucagac 19

<210> SEQ ID NO 189
<211> LENGTH: 19
<212> TYPE: RNA
<213> ORGANISM: Homo sapiens

<400> SEQUENCE: 189
ccgugagcug agcgaggac 19

<210> SEQ ID NO 190
<211> LENGTH: 19
<212> TYPE: RNA
<213> ORGANISM: Homo sapiens

<400> SEQUENCE: 190
gagaggaucu uugcccaga 19

<210> SEQ ID NO 191
<211> LENGTH: 19
<212> TYPE: RNA
<213> ORGANISM: Homo sapiens

<400> SEQUENCE: 191
agagagugga gccuggucu 19

<210> SEQ ID NO 192
<211> LENGTH: 19
<212> TYPE: RNA
<213> ORGANISM: Homo sapiens

<400> SEQUENCE: 192
gagaguggag ccuggucuu 19

<210> SEQ ID NO 193
<211> LENGTH: 19
<212> TYPE: RNA
<213> ORGANISM: Homo sapiens

<400> SEQUENCE: 193
caccuccacg gaagcuaug 19

<210> SEQ ID NO 194
<211> LENGTH: 19
<212> TYPE: RNA
<213> ORGANISM: Homo sapiens

<400> SEQUENCE: 194
gcuaugacuu augaugagg 19

<210> SEQ ID NO 195
<211> LENGTH: 19
<212> TYPE: RNA
<213> ORGANISM: Homo sapiens

<400> SEQUENCE: 195
agguacacac accugguug 19

<210> SEQ ID NO 196
<211> LENGTH: 19
<212> TYPE: RNA
<213> ORGANISM: Homo sapiens

<400> SEQUENCE: 196
gguacacaca ccugguugc 19

<210> SEQ ID NO 197
<211> LENGTH: 19
<212> TYPE: RNA
<213> ORGANISM: Homo sapiens

<400> SEQUENCE: 197
caaagaagag auugaguac 19

<210> SEQ ID NO 198
<211> LENGTH: 19
<212> TYPE: RNA
<213> ORGANISM: Homo sapiens

<400> SEQUENCE: 198
agaagagauu gaguaccua 19

<210> SEQ ID NO 199
<211> LENGTH: 19
<212> TYPE: RNA
<213> ORGANISM: Homo sapiens

<400> SEQUENCE: 199
gaagagauug aguaccuaa 19

<210> SEQ ID NO 200
<211> LENGTH: 19
<212> TYPE: RNA
<213> ORGANISM: Homo sapiens

<400> SEQUENCE: 200
gagauugagu accuaaacu 19

<210> SEQ ID NO 201
<211> LENGTH: 19
<212> TYPE: RNA
<213> ORGANISM: Homo sapiens

<400> SEQUENCE: 201
acuccauauu gagcuauuc 19

<210> SEQ ID NO 202
<211> LENGTH: 19
<212> TYPE: RNA
<213> ORGANISM: Homo sapiens

<400> SEQUENCE: 202
cuccauauug agcuauuca 19

<210> SEQ ID NO 203
<211> LENGTH: 19
<212> TYPE: RNA
<213> ORGANISM: Homo sapiens

<400> SEQUENCE: 203
aagucaacaa ugugugggu 19

<210> SEQ ID NO 204
<211> LENGTH: 19
<212> TYPE: RNA
<213> ORGANISM: Homo sapiens

<400> SEQUENCE: 204
agucaacaau gugugggguc 19

<210> SEQ ID NO 205
<211> LENGTH: 19
<212> TYPE: RNA
<213> ORGANISM: Homo sapiens

<400> SEQUENCE: 205
gucaacaaug ugugggucu 19

<210> SEQ ID NO 206
<211> LENGTH: 19
<212> TYPE: RNA
<213> ORGANISM: Homo sapiens

<400> SEQUENCE: 206
caaugugugg gucuggggua 19

<210> SEQ ID NO 207
<211> LENGTH: 19
<212> TYPE: RNA
<213> ORGANISM: Homo sapiens

<400> SEQUENCE: 207
uguguggguc uggguagga 19

<210> SEQ ID NO 208
<211> LENGTH: 19
<212> TYPE: RNA
<213> ORGANISM: Homo sapiens

<400> SEQUENCE: 208
cccagaaacc ucugacaga 19

<210> SEQ ID NO 209
<211> LENGTH: 19
<212> TYPE: RNA
<213> ORGANISM: Homo sapiens

<400> SEQUENCE: 209
accucugaca gaagaagcc 19

<210> SEQ ID NO 210
<211> LENGTH: 19
<212> TYPE: RNA
<213> ORGANISM: Homo sapiens

<400> SEQUENCE: 210
ccucugacag aagaagcca 19

<210> SEQ ID NO 211
<211> LENGTH: 19
<212> TYPE: RNA
<213> ORGANISM: Homo sapiens

<400> SEQUENCE: 211
gaagccaaga acugggcuc 19

<210> SEQ ID NO 212
<211> LENGTH: 19
<212> TYPE: RNA
<213> ORGANISM: Homo sapiens

<400> SEQUENCE: 212
gccaagaacu gggcuccag 19

<210> SEQ ID NO 213
<211> LENGTH: 19
<212> TYPE: RNA
<213> ORGANISM: Homo sapiens

<400> SEQUENCE: 213
gaacugggcu ccaggugaa 19

<210> SEQ ID NO 214
<211> LENGTH: 19
<212> TYPE: RNA
<213> ORGANISM: Homo sapiens

<400> SEQUENCE: 214
cccaacaaua ggcaaaaag 19

<210> SEQ ID NO 215
<211> LENGTH: 19
<212> TYPE: RNA
<213> ORGANISM: Homo sapiens

<400> SEQUENCE: 215
caauaggcaa aaagaugag 19

<210> SEQ ID NO 216
<211> LENGTH: 19
<212> TYPE: RNA
<213> ORGANISM: Homo sapiens

<400> SEQUENCE: 216
uaggcaaaaa gaugaggac 19

<210> SEQ ID NO 217
<211> LENGTH: 19
<212> TYPE: RNA
<213> ORGANISM: Homo sapiens

<400> SEQUENCE: 217
aaagaugagg acugcgugg 19

<210> SEQ ID NO 218
<211> LENGTH: 19
<212> TYPE: RNA
<213> ORGANISM: Homo sapiens

<400> SEQUENCE: 218
aagaugagga cugcgugga 19

<210> SEQ ID NO 219
<211> LENGTH: 19
<212> TYPE: RNA
<213> ORGANISM: Homo sapiens

<400> SEQUENCE: 219
agaugaggac ugcguggag 19

<210> SEQ ID NO 220
<211> LENGTH: 19
<212> TYPE: RNA

<213> ORGANISM: Homo sapiens

<400> SEQUENCE: 220
gaugaggacu gcguggaga 19

<210> SEQ ID NO 221
<211> LENGTH: 19
<212> TYPE: RNA
<213> ORGANISM: Homo sapiens

<400> SEQUENCE: 221
gagagaaaaa gaugugggc 19

<210> SEQ ID NO 222
<211> LENGTH: 19
<212> TYPE: RNA
<213> ORGANISM: Homo sapiens

<400> SEQUENCE: 222
aaagaugugg gcaugugga 19

<210> SEQ ID NO 223
<211> LENGTH: 19
<212> TYPE: RNA
<213> ORGANISM: Homo sapiens

<400> SEQUENCE: 223
aagaugaggg cauguggaa 19

<210> SEQ ID NO 224
<211> LENGTH: 19
<212> TYPE: RNA
<213> ORGANISM: Homo sapiens

<400> SEQUENCE: 224
agaugugggc auguggaau 19

<210> SEQ ID NO 225
<211> LENGTH: 19
<212> TYPE: RNA
<213> ORGANISM: Homo sapiens

<400> SEQUENCE: 225
gaugugggca uguggaaug 19

<210> SEQ ID NO 226
<211> LENGTH: 19
<212> TYPE: RNA
<213> ORGANISM: Homo sapiens

<400> SEQUENCE: 226
ugaugagagg ugcagcaag 19

<210> SEQ ID NO 227
<211> LENGTH: 19
<212> TYPE: RNA
<213> ORGANISM: Homo sapiens

<400> SEQUENCE: 227
gaagaagcuu gcccuaugc 19

<210> SEQ ID NO 228
<211> LENGTH: 19

<212> TYPE: RNA
<213> ORGANISM: Homo sapiens

<400> SEQUENCE: 228
gaagcuugcc cuaugcuac 19

<210> SEQ ID NO 229
<211> LENGTH: 19
<212> TYPE: RNA
<213> ORGANISM: Homo sapiens

<400> SEQUENCE: 229
gcuugcccua ugcuacaca 19

<210> SEQ ID NO 230
<211> LENGTH: 19
<212> TYPE: RNA
<213> ORGANISM: Homo sapiens

<400> SEQUENCE: 230
uacauccugc aguggccac 19

<210> SEQ ID NO 231
<211> LENGTH: 19
<212> TYPE: RNA
<213> ORGANISM: Homo sapiens

<400> SEQUENCE: 231
uguguagaga ccaucaaua 19

<210> SEQ ID NO 232
<211> LENGTH: 19
<212> TYPE: RNA
<213> ORGANISM: Homo sapiens

<400> SEQUENCE: 232
uuacacuugc aagugugac 19

<210> SEQ ID NO 233
<211> LENGTH: 19
<212> TYPE: RNA
<213> ORGANISM: Homo sapiens

<400> SEQUENCE: 233
gugugacccu ggcuucagu 19

<210> SEQ ID NO 234
<211> LENGTH: 19
<212> TYPE: RNA
<213> ORGANISM: Homo sapiens

<400> SEQUENCE: 234
gugugagcaa auugugaac 19

<210> SEQ ID NO 235
<211> LENGTH: 19
<212> TYPE: RNA
<213> ORGANISM: Homo sapiens

<400> SEQUENCE: 235
auugugaacu guacagccc 19

<210> SEQ ID NO 236

<211> LENGTH: 19
<212> TYPE: RNA
<213> ORGANISM: Homo sapiens

<400> SEQUENCE: 236
uugugaacug uacagcccu 19

<210> SEQ ID NO 237
<211> LENGTH: 19
<212> TYPE: RNA
<213> ORGANISM: Homo sapiens

<400> SEQUENCE: 237
cuguacagcc cuggaaucc 19

<210> SEQ ID NO 238
<211> LENGTH: 19
<212> TYPE: RNA
<213> ORGANISM: Homo sapiens

<400> SEQUENCE: 238
uccccugagc auggaagcc 19

<210> SEQ ID NO 239
<211> LENGTH: 19
<212> TYPE: RNA
<213> ORGANISM: Homo sapiens

<400> SEQUENCE: 239
gccugguuug cagucaccc 19

<210> SEQ ID NO 240
<211> LENGTH: 19
<212> TYPE: RNA
<213> ORGANISM: Homo sapiens

<400> SEQUENCE: 240
acuucagcua caauucuuc 19

<210> SEQ ID NO 241
<211> LENGTH: 19
<212> TYPE: RNA
<213> ORGANISM: Homo sapiens

<400> SEQUENCE: 241
cuucagcuac aauucuucc 19

<210> SEQ ID NO 242
<211> LENGTH: 19
<212> TYPE: RNA
<213> ORGANISM: Homo sapiens

<400> SEQUENCE: 242
uucuuccugc ucuaucagc 19

<210> SEQ ID NO 243
<211> LENGTH: 19
<212> TYPE: RNA
<213> ORGANISM: Homo sapiens

<400> SEQUENCE: 243
gcagcaugga gaccaugca 19

<210> SEQ ID NO 244
<211> LENGTH: 19
<212> TYPE: RNA
<213> ORGANISM: Homo sapiens

<400> SEQUENCE: 244
uggagugcuc cuauuccag 19

<210> SEQ ID NO 245
<211> LENGTH: 19
<212> TYPE: RNA
<213> ORGANISM: Homo sapiens

<400> SEQUENCE: 245
ugugguugag ugugaugcu 19

<210> SEQ ID NO 246
<211> LENGTH: 19
<212> TYPE: RNA
<213> ORGANISM: Homo sapiens

<400> SEQUENCE: 246
auccagccaa uggguucgu 19

<210> SEQ ID NO 247
<211> LENGTH: 19
<212> TYPE: RNA
<213> ORGANISM: Homo sapiens

<400> SEQUENCE: 247
uccagccaau ggguucgug 19

<210> SEQ ID NO 248
<211> LENGTH: 19
<212> TYPE: RNA
<213> ORGANISM: Homo sapiens

<400> SEQUENCE: 248
uggguucgug gaauguuuc 19

<210> SEQ ID NO 249
<211> LENGTH: 19
<212> TYPE: RNA
<213> ORGANISM: Homo sapiens

<400> SEQUENCE: 249
uguuuccaaa acccuggaa 19

<210> SEQ ID NO 250
<211> LENGTH: 19
<212> TYPE: RNA
<213> ORGANISM: Homo sapiens

<400> SEQUENCE: 250
aacccuggaa gcuucccau 19

<210> SEQ ID NO 251
<211> LENGTH: 19
<212> TYPE: RNA
<213> ORGANISM: Homo sapiens

<400> SEQUENCE: 251
acccuggaag cuucccaug 19

<210> SEQ ID NO 252
<211> LENGTH: 19
<212> TYPE: RNA
<213> ORGANISM: Homo sapiens

<400> SEQUENCE: 252
cccuggaagc uucccaugg 19

<210> SEQ ID NO 253
<211> LENGTH: 19
<212> TYPE: RNA
<213> ORGANISM: Homo sapiens

<400> SEQUENCE: 253
gcuucccaug gaacacaac 19

<210> SEQ ID NO 254
<211> LENGTH: 19
<212> TYPE: RNA
<213> ORGANISM: Homo sapiens

<400> SEQUENCE: 254
cacaaccugu acauuugac 19

<210> SEQ ID NO 255
<211> LENGTH: 19
<212> TYPE: RNA
<213> ORGANISM: Homo sapiens

<400> SEQUENCE: 255
ccuguacauu ugacuguga 19

<210> SEQ ID NO 256
<211> LENGTH: 19
<212> TYPE: RNA
<213> ORGANISM: Homo sapiens

<400> SEQUENCE: 256
gaaggauuug aacuaaugg 19

<210> SEQ ID NO 257
<211> LENGTH: 19
<212> TYPE: RNA
<213> ORGANISM: Homo sapiens

<400> SEQUENCE: 257
ggauuugaac uaaugggag 19

<210> SEQ ID NO 258
<211> LENGTH: 19
<212> TYPE: RNA
<213> ORGANISM: Homo sapiens

<400> SEQUENCE: 258
cuaaugggag cccagagcc 19

<210> SEQ ID NO 259
<211> LENGTH: 19
<212> TYPE: RNA
<213> ORGANISM: Homo sapiens

<400> SEQUENCE: 259
ugggagccca gagccuuca 19

<210> SEQ ID NO 260
<211> LENGTH: 19
<212> TYPE: RNA
<213> ORGANISM: Homo sapiens

<400> SEQUENCE: 260
uugggacaac gagaagcca 19

<210> SEQ ID NO 261
<211> LENGTH: 19
<212> TYPE: RNA
<213> ORGANISM: Homo sapiens

<400> SEQUENCE: 261
cgagaagcca acguguaaa 19

<210> SEQ ID NO 262
<211> LENGTH: 19
<212> TYPE: RNA
<213> ORGANISM: Homo sapiens

<400> SEQUENCE: 262
gccaacgugu aaagcugug 19

<210> SEQ ID NO 263
<211> LENGTH: 19
<212> TYPE: RNA
<213> ORGANISM: Homo sapiens

<400> SEQUENCE: 263
cguguaaagc ugugacaug 19

<210> SEQ ID NO 264
<211> LENGTH: 19
<212> TYPE: RNA
<213> ORGANISM: Homo sapiens

<400> SEQUENCE: 264
agcugugaca ugcagggcc 19

<210> SEQ ID NO 265
<211> LENGTH: 19
<212> TYPE: RNA
<213> ORGANISM: Homo sapiens

<400> SEQUENCE: 265
uggcucugug aggugcagc 19

<210> SEQ ID NO 266
<211> LENGTH: 19
<212> TYPE: RNA
<213> ORGANISM: Homo sapiens

<400> SEQUENCE: 266
aucauccugc aacuucacc 19

<210> SEQ ID NO 267
<211> LENGTH: 19
<212> TYPE: RNA
<213> ORGANISM: Homo sapiens

<400> SEQUENCE: 267
ucauccugca acuucaccu 19

<210> SEQ ID NO 268
<211> LENGTH: 19
<212> TYPE: RNA
<213> ORGANISM: Homo sapiens

<400> SEQUENCE: 268
cuucaccugu gaggaaggc 19

<210> SEQ ID NO 269
<211> LENGTH: 19
<212> TYPE: RNA
<213> ORGANISM: Homo sapiens

<400> SEQUENCE: 269
ggcuucaugu ugcagggac 19

<210> SEQ ID NO 270
<211> LENGTH: 19
<212> TYPE: RNA
<213> ORGANISM: Homo sapiens

<400> SEQUENCE: 270
ugcaccacuc aagggcagu 19

<210> SEQ ID NO 271
<211> LENGTH: 19
<212> TYPE: RNA
<213> ORGANISM: Homo sapiens

<400> SEQUENCE: 271
gggcagugga cacagcaaa 19

<210> SEQ ID NO 272
<211> LENGTH: 19
<212> TYPE: RNA
<213> ORGANISM: Homo sapiens

<400> SEQUENCE: 272
aucccaguuu gugaagcuu 19

<210> SEQ ID NO 273
<211> LENGTH: 19
<212> TYPE: RNA
<213> ORGANISM: Homo sapiens

<400> SEQUENCE: 273
ucccaguuug ugaagcuuu 19

<210> SEQ ID NO 274
<211> LENGTH: 19
<212> TYPE: RNA
<213> ORGANISM: Homo sapiens

<400> SEQUENCE: 274
gcuuuccagu gcacagccu 19

<210> SEQ ID NO 275
<211> LENGTH: 19
<212> TYPE: RNA
<213> ORGANISM: Homo sapiens

<400> SEQUENCE: 275
uugucuuccu agugcuucu 19

<210> SEQ ID NO 276
<211> LENGTH: 19
<212> TYPE: RNA
<213> ORGANISM: Homo sapiens

<400> SEQUENCE: 276
gggauccaaa aggcuccaa 19

<210> SEQ ID NO 277
<211> LENGTH: 19
<212> TYPE: RNA
<213> ORGANISM: Homo sapiens

<400> SEQUENCE: 277
aaggcuccaa uguggcccc 19

<210> SEQ ID NO 278
<211> LENGTH: 19
<212> TYPE: RNA
<213> ORGANISM: Homo sapiens

<400> SEQUENCE: 278
aggcuccaau guggcccca 19

<210> SEQ ID NO 279
<211> LENGTH: 19
<212> TYPE: RNA
<213> ORGANISM: Homo sapiens

<400> SEQUENCE: 279
cgagaagccc acaugugaa 19

<210> SEQ ID NO 280
<211> LENGTH: 19
<212> TYPE: RNA
<213> ORGANISM: Homo sapiens

<400> SEQUENCE: 280
gcccacaugu gaagcugug 19

<210> SEQ ID NO 281
<211> LENGTH: 19
<212> TYPE: RNA
<213> ORGANISM: Homo sapiens

<400> SEQUENCE: 281
gcugugagau gcgaugcug 19

<210> SEQ ID NO 282
<211> LENGTH: 19
<212> TYPE: RNA
<213> ORGANISM: Homo sapiens

<400> SEQUENCE: 282
ggguuuggug aggugugcu 19

<210> SEQ ID NO 283
<211> LENGTH: 19
<212> TYPE: RNA
<213> ORGANISM: Homo sapiens

<400> SEQUENCE: 283
uucaccuaca aguccucuu 19

<210> SEQ ID NO 284
<211> LENGTH: 19
<212> TYPE: RNA
<213> ORGANISM: Homo sapiens

<400> SEQUENCE: 284
guccucuugu gccuucagc 19

<210> SEQ ID NO 285
<211> LENGTH: 19
<212> TYPE: RNA
<213> ORGANISM: Homo sapiens

<400> SEQUENCE: 285
cucaacuuga gugcacauc 19

<210> SEQ ID NO 286
<211> LENGTH: 19
<212> TYPE: RNA
<213> ORGANISM: Homo sapiens

<400> SEQUENCE: 286
cuugagugca caucucagg 19

<210> SEQ ID NO 287
<211> LENGTH: 19
<212> TYPE: RNA
<213> ORGANISM: Homo sapiens

<400> SEQUENCE: 287
uggacagaag agguuccuu 19

<210> SEQ ID NO 288
<211> LENGTH: 19
<212> TYPE: RNA
<213> ORGANISM: Homo sapiens

<400> SEQUENCE: 288
gagguuccuu ccugccaag 19

<210> SEQ ID NO 289
<211> LENGTH: 19
<212> TYPE: RNA
<213> ORGANISM: Homo sapiens

<400> SEQUENCE: 289
gugguaaaau guucaagcc 19

<210> SEQ ID NO 290
<211> LENGTH: 19
<212> TYPE: RNA
<213> ORGANISM: Homo sapiens

<400> SEQUENCE: 290
aauguucaag ccuggcagu 19

<210> SEQ ID NO 291
<211> LENGTH: 19
<212> TYPE: RNA
<213> ORGANISM: Homo sapiens

<400> SEQUENCE: 291
auguucaagc cuggcaguu 19

<210> SEQ ID NO 292
<211> LENGTH: 19
<212> TYPE: RNA
<213> ORGANISM: Homo sapiens

<400> SEQUENCE: 292
uguucaagcc uggcaguuc 19

<210> SEQ ID NO 293
<211> LENGTH: 19
<212> TYPE: RNA
<213> ORGANISM: Homo sapiens

<400> SEQUENCE: 293
gccuggcagu uccgggaaa 19

<210> SEQ ID NO 294
<211> LENGTH: 19
<212> TYPE: RNA
<213> ORGANISM: Homo sapiens

<400> SEQUENCE: 294
agaucaacau gagcugcag 19

<210> SEQ ID NO 295
<211> LENGTH: 19
<212> TYPE: RNA
<213> ORGANISM: Homo sapiens

<400> SEQUENCE: 295
gaucaacaug agcugcagu 19

<210> SEQ ID NO 296
<211> LENGTH: 19
<212> TYPE: RNA
<213> ORGANISM: Homo sapiens

<400> SEQUENCE: 296
caugagcugc aguggggag 19

<210> SEQ ID NO 297
<211> LENGTH: 19
<212> TYPE: RNA
<213> ORGANISM: Homo sapiens

<400> SEQUENCE: 297
guucgccugu ccugaagga 19

<210> SEQ ID NO 298
<211> LENGTH: 19
<212> TYPE: RNA
<213> ORGANISM: Homo sapiens

<400> SEQUENCE: 298
ggauggacgc ucaauggcu 19

<210> SEQ ID NO 299
<211> LENGTH: 19
<212> TYPE: RNA

<213> ORGANISM: Homo sapiens

<400> SEQUENCE: 299
uggcucugca gcucggaca 19

<210> SEQ ID NO 300
<211> LENGTH: 19
<212> TYPE: RNA
<213> ORGANISM: Homo sapiens

<400> SEQUENCE: 300
gcucccacug aguccaaca 19

<210> SEQ ID NO 301
<211> LENGTH: 19
<212> TYPE: RNA
<213> ORGANISM: Homo sapiens

<400> SEQUENCE: 301
cauucccuug guagcugga 19

<210> SEQ ID NO 302
<211> LENGTH: 19
<212> TYPE: RNA
<213> ORGANISM: Homo sapiens

<400> SEQUENCE: 302
augcuuacgg aaagcaaag 19

<210> SEQ ID NO 303
<211> LENGTH: 19
<212> TYPE: RNA
<213> ORGANISM: Homo sapiens

<400> SEQUENCE: 303
ugcuuacgga aagcaaaga 19

<210> SEQ ID NO 304
<211> LENGTH: 19
<212> TYPE: RNA
<213> ORGANISM: Homo sapiens

<400> SEQUENCE: 304
gcaaagaaau uuguuccug 19

<210> SEQ ID NO 305
<211> LENGTH: 19
<212> TYPE: RNA
<213> ORGANISM: Homo sapiens

<400> SEQUENCE: 305
agaaauuugu uccugccag 19

<210> SEQ ID NO 306
<211> LENGTH: 19
<212> TYPE: RNA
<213> ORGANISM: Homo sapiens

<400> SEQUENCE: 306
gaaauuuguu ccugccagc 19

<210> SEQ ID NO 307
<211> LENGTH: 19

<212> TYPE: RNA
<213> ORGANISM: Homo sapiens

<400> SEQUENCE: 307
auuuguuccu gccagcagc 19

<210> SEQ ID NO 308
<211> LENGTH: 19
<212> TYPE: RNA
<213> ORGANISM: Homo sapiens

<400> SEQUENCE: 308
uuuguuccug ccagcagcu 19

<210> SEQ ID NO 309
<211> LENGTH: 19
<212> TYPE: RNA
<213> ORGANISM: Homo sapiens

<400> SEQUENCE: 309
agccuugaau cagacggaa 19

<210> SEQ ID NO 310
<211> LENGTH: 19
<212> TYPE: RNA
<213> ORGANISM: Homo sapiens

<400> SEQUENCE: 310
gccuugaauc agacggaag 19

<210> SEQ ID NO 311
<211> LENGTH: 19
<212> TYPE: RNA
<213> ORGANISM: Homo sapiens

<400> SEQUENCE: 311
ucagacggaa gcuaccaaa 19

<210> SEQ ID NO 312
<211> LENGTH: 19
<212> TYPE: RNA
<213> ORGANISM: Homo sapiens

<400> SEQUENCE: 312
gcuaccaaaa gccuucuua 19

<210> SEQ ID NO 313
<211> LENGTH: 19
<212> TYPE: RNA
<213> ORGANISM: Homo sapiens

<400> SEQUENCE: 313
aagccuucuu acauccuuu 19

<210> SEQ ID NO 314
<211> LENGTH: 19
<212> TYPE: RNA
<213> ORGANISM: Homo sapiens

<400> SEQUENCE: 314
agccuucuua cauccuuua 19

<210> SEQ ID NO 315

<211> LENGTH: 19
<212> TYPE: RNA
<213> ORGANISM: Homo sapiens

<400> SEQUENCE: 315
gccuucuuac auccuuuaa 19

<210> SEQ ID NO 316
<211> LENGTH: 19
<212> TYPE: RNA
<213> ORGANISM: Homo sapiens

<400> SEQUENCE: 316
agccuugaau cagauggaa 19

<210> SEQ ID NO 317
<211> LENGTH: 19
<212> TYPE: RNA
<213> ORGANISM: Homo sapiens

<400> SEQUENCE: 317
gccuugaauc agauggaag 19

<210> SEQ ID NO 318
<211> LENGTH: 19
<212> TYPE: RNA
<213> ORGANISM: Homo sapiens

<400> SEQUENCE: 318
ucagauggaa gcuaccaaa 19

<210> SEQ ID NO 319
<211> LENGTH: 19
<212> TYPE: RNA
<213> ORGANISM: Homo sapiens

<400> SEQUENCE: 319
ucccuguugu uacuaucca 19

<210> SEQ ID NO 320
<211> LENGTH: 19
<212> TYPE: RNA
<213> ORGANISM: Homo sapiens

<400> SEQUENCE: 320
ugccaccuuc auccgagag 19

<210> SEQ ID NO 321
<211> LENGTH: 19
<212> TYPE: RNA
<213> ORGANISM: Homo sapiens

<400> SEQUENCE: 321
cucagcacau gacuacauc 19

<210> SEQ ID NO 322
<211> LENGTH: 19
<212> TYPE: RNA
<213> ORGANISM: Homo sapiens

<400> SEQUENCE: 322
cgugagcuau uacacucgu 19

<210> SEQ ID NO 323
<211> LENGTH: 19
<212> TYPE: RNA
<213> ORGANISM: Homo sapiens

<400> SEQUENCE: 323
agauugcccc acacccaug 19

<210> SEQ ID NO 324
<211> LENGTH: 19
<212> TYPE: RNA
<213> ORGANISM: Homo sapiens

<400> SEQUENCE: 324
gauugcccca cacccaugg 19

<210> SEQ ID NO 325
<211> LENGTH: 19
<212> TYPE: RNA
<213> ORGANISM: Homo sapiens

<400> SEQUENCE: 325
ccaaagggaa gaagcaguu 19

<210> SEQ ID NO 326
<211> LENGTH: 19
<212> TYPE: RNA
<213> ORGANISM: Homo sapiens

<400> SEQUENCE: 326
agggaagaag caguugcca 19

<210> SEQ ID NO 327
<211> LENGTH: 19
<212> TYPE: RNA
<213> ORGANISM: Homo sapiens

<400> SEQUENCE: 327
gggaagaagc aguugccag 19

<210> SEQ ID NO 328
<211> LENGTH: 19
<212> TYPE: RNA
<213> ORGANISM: Homo sapiens

<400> SEQUENCE: 328
gaagcaguug ccagaugcc 19

<210> SEQ ID NO 329
<211> LENGTH: 19
<212> TYPE: RNA
<213> ORGANISM: Homo sapiens

<400> SEQUENCE: 329
gcaguugcca gaugcccag 19

<210> SEQ ID NO 330
<211> LENGTH: 19
<212> TYPE: RNA
<213> ORGANISM: Homo sapiens

<400> SEQUENCE: 330
guucauaccu gacccccaa 19

<210> SEQ ID NO 331
<211> LENGTH: 19
<212> TYPE: RNA
<213> ORGANISM: Homo sapiens

<400> SEQUENCE: 331
ggcaccaacc ucauguuug 19

<210> SEQ ID NO 332
<211> LENGTH: 19
<212> TYPE: RNA
<213> ORGANISM: Homo sapiens

<400> SEQUENCE: 332
ccucauguuu gccuucuuu 19

<210> SEQ ID NO 333
<211> LENGTH: 19
<212> TYPE: RNA
<213> ORGANISM: Homo sapiens

<400> SEQUENCE: 333
cacuucaccc accaguucu 19

<210> SEQ ID NO 334
<211> LENGTH: 19
<212> TYPE: RNA
<213> ORGANISM: Homo sapiens

<400> SEQUENCE: 334
aacuucuggc aagaugggu 19

<210> SEQ ID NO 335
<211> LENGTH: 19
<212> TYPE: RNA
<213> ORGANISM: Homo sapiens

<400> SEQUENCE: 335
acuucuggca agaugggu c 19

<210> SEQ ID NO 336
<211> LENGTH: 19
<212> TYPE: RNA
<213> ORGANISM: Homo sapiens

<400> SEQUENCE: 336
cuucuggcaa gauggguc c 19

<210> SEQ ID NO 337
<211> LENGTH: 19
<212> TYPE: RNA
<213> ORGANISM: Homo sapiens

<400> SEQUENCE: 337
gauggguccu ggcuucacc 19

<210> SEQ ID NO 338
<211> LENGTH: 19
<212> TYPE: RNA
<213> ORGANISM: Homo sapiens

<400> SEQUENCE: 338
ucuggagcgu caguaucaa 19

<210> SEQ ID NO 339
<211> LENGTH: 19
<212> TYPE: RNA
<213> ORGANISM: Homo sapiens

<400> SEQUENCE: 339
cugcggcucu uuaaggaug 19

<210> SEQ ID NO 340
<211> LENGTH: 19
<212> TYPE: RNA
<213> ORGANISM: Homo sapiens

<400> SEQUENCE: 340
ggaugggaaa cucaaguac 19

<210> SEQ ID NO 341
<211> LENGTH: 19
<212> TYPE: RNA
<213> ORGANISM: Homo sapiens

<400> SEQUENCE: 341
acucaaguac caggugcug 19

<210> SEQ ID NO 342
<211> LENGTH: 19
<212> TYPE: RNA
<213> ORGANISM: Homo sapiens

<400> SEQUENCE: 342
cucaaguacc aggugcugg 19

<210> SEQ ID NO 343
<211> LENGTH: 19
<212> TYPE: RNA
<213> ORGANISM: Homo sapiens

<400> SEQUENCE: 343
guaccaggug cuggaugga 19

<210> SEQ ID NO 344
<211> LENGTH: 19
<212> TYPE: RNA
<213> ORGANISM: Homo sapiens

<400> SEQUENCE: 344
auguacccgc ccucgguag 19

<210> SEQ ID NO 345
<211> LENGTH: 19
<212> TYPE: RNA
<213> ORGANISM: Homo sapiens

<400> SEQUENCE: 345
uguacccgcc cucgguaga 19

<210> SEQ ID NO 346
<211> LENGTH: 19
<212> TYPE: RNA
<213> ORGANISM: Homo sapiens

<400> SEQUENCE: 346
gaggcgccug uguugaugc 19

<210> SEQ ID NO 347
<211> LENGTH: 19
<212> TYPE: RNA
<213> ORGANISM: Homo sapiens

<400> SEQUENCE: 347
ccgugugugu gaccugcug 19

<210> SEQ ID NO 348
<211> LENGTH: 19
<212> TYPE: RNA
<213> ORGANISM: Homo sapiens

<400> SEQUENCE: 348
gauugucauc gaggaguac 19

<210> SEQ ID NO 349
<211> LENGTH: 19
<212> TYPE: RNA
<213> ORGANISM: Homo sapiens

<400> SEQUENCE: 349
auuugaccca gagcugcug 19

<210> SEQ ID NO 350
<211> LENGTH: 19
<212> TYPE: RNA
<213> ORGANISM: Homo sapiens

<400> SEQUENCE: 350
uuugacccag agcugcugu 19

<210> SEQ ID NO 351
<211> LENGTH: 19
<212> TYPE: RNA
<213> ORGANISM: Homo sapiens

<400> SEQUENCE: 351
uaccgcaacc gcauugcca 19

<210> SEQ ID NO 352
<211> LENGTH: 19
<212> TYPE: RNA
<213> ORGANISM: Homo sapiens

<400> SEQUENCE: 352
ccgcauugcc auggaguuc 19

<210> SEQ ID NO 353
<211> LENGTH: 19
<212> TYPE: RNA
<213> ORGANISM: Homo sapiens

<400> SEQUENCE: 353
ccaucucuac cacuggcac 19

<210> SEQ ID NO 354
<211> LENGTH: 19
<212> TYPE: RNA
<213> ORGANISM: Homo sapiens

<400> SEQUENCE: 354
caccuccaug uugguggac 19

<210> SEQ ID NO 355
<211> LENGTH: 19
<212> TYPE: RNA
<213> ORGANISM: Homo sapiens

<400> SEQUENCE: 355
cauggaccac cacauccug 19

<210> SEQ ID NO 356
<211> LENGTH: 19
<212> TYPE: RNA
<213> ORGANISM: Homo sapiens

<400> SEQUENCE: 356
ugaguaccgc aagagguuu 19

<210> SEQ ID NO 357
<211> LENGTH: 19
<212> TYPE: RNA
<213> ORGANISM: Homo sapiens

<400> SEQUENCE: 357
gagguuuggc augaaaccc 19

<210> SEQ ID NO 358
<211> LENGTH: 19
<212> TYPE: RNA
<213> ORGANISM: Homo sapiens

<400> SEQUENCE: 358
acccuacacc uccuuccag 19

<210> SEQ ID NO 359
<211> LENGTH: 19
<212> TYPE: RNA
<213> ORGANISM: Homo sapiens

<400> SEQUENCE: 359
cccuacaccu ccuuccagg 19

<210> SEQ ID NO 360
<211> LENGTH: 19
<212> TYPE: RNA
<213> ORGANISM: Homo sapiens

<400> SEQUENCE: 360
ggagauggca gcagaguug 19

<210> SEQ ID NO 361
<211> LENGTH: 19
<212> TYPE: RNA
<213> ORGANISM: Homo sapiens

<400> SEQUENCE: 361
uuguauggag acauugaug 19

<210> SEQ ID NO 362
<211> LENGTH: 19
<212> TYPE: RNA
<213> ORGANISM: Homo sapiens

<400> SEQUENCE: 362
aagugccauc caaacucua 19

<210> SEQ ID NO 363
<211> LENGTH: 19
<212> TYPE: RNA
<213> ORGANISM: Homo sapiens

<400> SEQUENCE: 363
agugccaucc aaacucuau 19

<210> SEQ ID NO 364
<211> LENGTH: 19
<212> TYPE: RNA
<213> ORGANISM: Homo sapiens

<400> SEQUENCE: 364
gugccaucca aacucuauc 19

<210> SEQ ID NO 365
<211> LENGTH: 19
<212> TYPE: RNA
<213> ORGANISM: Homo sapiens

<400> SEQUENCE: 365
acucuaucuu uggggagag 19

<210> SEQ ID NO 366
<211> LENGTH: 19
<212> TYPE: RNA
<213> ORGANISM: Homo sapiens

<400> SEQUENCE: 366
cucuaucuuu ggggagagu 19

<210> SEQ ID NO 367
<211> LENGTH: 19
<212> TYPE: RNA
<213> ORGANISM: Homo sapiens

<400> SEQUENCE: 367
gggucuccua gggaauccc 19

<210> SEQ ID NO 368
<211> LENGTH: 19
<212> TYPE: RNA
<213> ORGANISM: Homo sapiens

<400> SEQUENCE: 368
ucccaucugu ucuccggag 19

<210> SEQ ID NO 369
<211> LENGTH: 19
<212> TYPE: RNA
<213> ORGANISM: Homo sapiens

<400> SEQUENCE: 369
cauugucaag acggccaca 19

<210> SEQ ID NO 370
<211> LENGTH: 19
<212> TYPE: RNA
<213> ORGANISM: Homo sapiens

<400> SEQUENCE: 370
gacggccaca cugaagaag 19

<210> SEQ ID NO 371
<211> LENGTH: 19
<212> TYPE: RNA
<213> ORGANISM: Homo sapiens

<400> SEQUENCE: 371
gaagcugguc ugccucaac 19

<210> SEQ ID NO 372
<211> LENGTH: 19
<212> TYPE: RNA
<213> ORGANISM: Homo sapiens

<400> SEQUENCE: 372
gcuggucugc cucaacacc 19

<210> SEQ ID NO 373
<211> LENGTH: 19
<212> TYPE: RNA
<213> ORGANISM: Homo sapiens

<400> SEQUENCE: 373
caccaagacc ugucccuac 19

<210> SEQ ID NO 374
<211> LENGTH: 19
<212> TYPE: RNA
<213> ORGANISM: Homo sapiens

<400> SEQUENCE: 374
gaccuguccc uacguuucc 19

<210> SEQ ID NO 375
<211> LENGTH: 19
<212> TYPE: RNA
<213> ORGANISM: Homo sapiens

<400> SEQUENCE: 375
auccuugcug uucccaccc 19

<210> SEQ ID NO 376
<211> LENGTH: 19
<212> TYPE: RNA
<213> ORGANISM: Homo sapiens

<400> SEQUENCE: 376
uccuugcugu ucccaccca 19

<210> SEQ ID NO 377
<211> LENGTH: 19
<212> TYPE: RNA
<213> ORGANISM: Homo sapiens

<400> SEQUENCE: 377
aaccgaggug uauguauga 19

<210> SEQ ID NO 378
<211> LENGTH: 19
<212> TYPE: RNA

<213> ORGANISM: Homo sapiens

<400> SEQUENCE: 378
accgaggugu auguaugag 19

<210> SEQ ID NO 379
<211> LENGTH: 19
<212> TYPE: RNA
<213> ORGANISM: Homo sapiens

<400> SEQUENCE: 379
ccgaggugua uguaugagu 19

<210> SEQ ID NO 380
<211> LENGTH: 19
<212> TYPE: RNA
<213> ORGANISM: Homo sapiens

<400> SEQUENCE: 380
gugcgauugu acccggaca 19

<210> SEQ ID NO 381
<211> LENGTH: 19
<212> TYPE: RNA
<213> ORGANISM: Homo sapiens

<400> SEQUENCE: 381
aacugcucaa caccggaau 19

<210> SEQ ID NO 382
<211> LENGTH: 19
<212> TYPE: RNA
<213> ORGANISM: Homo sapiens

<400> SEQUENCE: 382
acugcucaac accggaauu 19

<210> SEQ ID NO 383
<211> LENGTH: 19
<212> TYPE: RNA
<213> ORGANISM: Homo sapiens

<400> SEQUENCE: 383
cugcucaaca ccggaauuu 19

<210> SEQ ID NO 384
<211> LENGTH: 19
<212> TYPE: RNA
<213> ORGANISM: Homo sapiens

<400> SEQUENCE: 384
caccggaauu uuugacaag 19

<210> SEQ ID NO 385
<211> LENGTH: 19
<212> TYPE: RNA
<213> ORGANISM: Homo sapiens

<400> SEQUENCE: 385
uuauuucuga aacccacuc 19

<210> SEQ ID NO 386
<211> LENGTH: 19

<212> TYPE: RNA
<213> ORGANISM: Homo sapiens

<400> SEQUENCE: 386
acccacucca aacacagug 19

<210> SEQ ID NO 387
<211> LENGTH: 19
<212> TYPE: RNA
<213> ORGANISM: Homo sapiens

<400> SEQUENCE: 387
cccacuccaa acacagugc 19

<210> SEQ ID NO 388
<211> LENGTH: 19
<212> TYPE: RNA
<213> ORGANISM: Homo sapiens

<400> SEQUENCE: 388
acacagugca cuacauacu 19

<210> SEQ ID NO 389
<211> LENGTH: 19
<212> TYPE: RNA
<213> ORGANISM: Homo sapiens

<400> SEQUENCE: 389
cacagugcac uacauacuu 19

<210> SEQ ID NO 390
<211> LENGTH: 19
<212> TYPE: RNA
<213> ORGANISM: Homo sapiens

<400> SEQUENCE: 390
gggauuuugg aacguugug 19

<210> SEQ ID NO 391
<211> LENGTH: 19
<212> TYPE: RNA
<213> ORGANISM: Homo sapiens

<400> SEQUENCE: 391
cguugugaau aacauuccc 19

<210> SEQ ID NO 392
<211> LENGTH: 19
<212> TYPE: RNA
<213> ORGANISM: Homo sapiens

<400> SEQUENCE: 392
uaacauuccc uuccuucga 19

<210> SEQ ID NO 393
<211> LENGTH: 19
<212> TYPE: RNA
<213> ORGANISM: Homo sapiens

<400> SEQUENCE: 393
cauucccuuc cuucgaaau 19

<210> SEQ ID NO 394

<211> LENGTH: 19
<212> TYPE: RNA
<213> ORGANISM: Homo sapiens

<400> SEQUENCE: 394
cuuacaaugc ugacuaugg 19

<210> SEQ ID NO 395
<211> LENGTH: 19
<212> TYPE: RNA
<213> ORGANISM: Homo sapiens

<400> SEQUENCE: 395
ugcugacuau ggcuacaaa 19

<210> SEQ ID NO 396
<211> LENGTH: 19
<212> TYPE: RNA
<213> ORGANISM: Homo sapiens

<400> SEQUENCE: 396
aagcugggaa gccuucucu 19

<210> SEQ ID NO 397
<211> LENGTH: 19
<212> TYPE: RNA
<213> ORGANISM: Homo sapiens

<400> SEQUENCE: 397
agcugggaag ccuucucua 19

<210> SEQ ID NO 398
<211> LENGTH: 19
<212> TYPE: RNA
<213> ORGANISM: Homo sapiens

<400> SEQUENCE: 398
gcugggaagc cuucucuaa 19

<210> SEQ ID NO 399
<211> LENGTH: 19
<212> TYPE: RNA
<213> ORGANISM: Homo sapiens

<400> SEQUENCE: 399
gccuucucua accucuccu 19

<210> SEQ ID NO 400
<211> LENGTH: 19
<212> TYPE: RNA
<213> ORGANISM: Homo sapiens

<400> SEQUENCE: 400
ccucuccuau uauacuaga 19

<210> SEQ ID NO 401
<211> LENGTH: 19
<212> TYPE: RNA
<213> ORGANISM: Homo sapiens

<400> SEQUENCE: 401
agguaaaaag cagcuuccu 19

<210> SEQ ID NO 402
<211> LENGTH: 19
<212> TYPE: RNA
<213> ORGANISM: Homo sapiens

<400> SEQUENCE: 402
gguaaaaagc agcuuccug 19

<210> SEQ ID NO 403
<211> LENGTH: 19
<212> TYPE: RNA
<213> ORGANISM: Homo sapiens

<400> SEQUENCE: 403
aaagcagcuu ccugauuca 19

<210> SEQ ID NO 404
<211> LENGTH: 19
<212> TYPE: RNA
<213> ORGANISM: Homo sapiens

<400> SEQUENCE: 404
aagcagcuuc cugauucaa 19

<210> SEQ ID NO 405
<211> LENGTH: 19
<212> TYPE: RNA
<213> ORGANISM: Homo sapiens

<400> SEQUENCE: 405
agcagcuucc ugauucaaa 19

<210> SEQ ID NO 406
<211> LENGTH: 19
<212> TYPE: RNA
<213> ORGANISM: Homo sapiens

<400> SEQUENCE: 406
gcagcuuccu gauucaaau 19

<210> SEQ ID NO 407
<211> LENGTH: 19
<212> TYPE: RNA
<213> ORGANISM: Homo sapiens

<400> SEQUENCE: 407
gaagaaaguu caucccuga 19

<210> SEQ ID NO 408
<211> LENGTH: 19
<212> TYPE: RNA
<213> ORGANISM: Homo sapiens

<400> SEQUENCE: 408
gaaaguucau cccugaucc 19

<210> SEQ ID NO 409
<211> LENGTH: 19
<212> TYPE: RNA
<213> ORGANISM: Homo sapiens

<400> SEQUENCE: 409
aguucauccc ugaucccca 19

<210> SEQ ID NO 410
<211> LENGTH: 19
<212> TYPE: RNA
<213> ORGANISM: Homo sapiens

<400> SEQUENCE: 410
guucaucccu gauccccag 19

<210> SEQ ID NO 411
<211> LENGTH: 19
<212> TYPE: RNA
<213> ORGANISM: Homo sapiens

<400> SEQUENCE: 411
gacagaucau aagcgaggg 19

<210> SEQ ID NO 412
<211> LENGTH: 19
<212> TYPE: RNA
<213> ORGANISM: Homo sapiens

<400> SEQUENCE: 412
acucuggcua gacagcgua 19

<210> SEQ ID NO 413
<211> LENGTH: 19
<212> TYPE: RNA
<213> ORGANISM: Homo sapiens

<400> SEQUENCE: 413
cucuggcuag acagcguaa 19

<210> SEQ ID NO 414
<211> LENGTH: 19
<212> TYPE: RNA
<213> ORGANISM: Homo sapiens

<400> SEQUENCE: 414
acugcgccuu uucaaggau 19

<210> SEQ ID NO 415
<211> LENGTH: 19
<212> TYPE: RNA
<213> ORGANISM: Homo sapiens

<400> SEQUENCE: 415
cugcgccuuu ucaaggaug 19

<210> SEQ ID NO 416
<211> LENGTH: 19
<212> TYPE: RNA
<213> ORGANISM: Homo sapiens

<400> SEQUENCE: 416
uugauggaga gauguaucc 19

<210> SEQ ID NO 417
<211> LENGTH: 19
<212> TYPE: RNA
<213> ORGANISM: Homo sapiens

<400> SEQUENCE: 417
agauacucag gcagagaug 19

<210> SEQ ID NO 418
<211> LENGTH: 19
<212> TYPE: RNA
<213> ORGANISM: Homo sapiens

<400> SEQUENCE: 418
gauacucagg cagagauga 19

<210> SEQ ID NO 419
<211> LENGTH: 19
<212> TYPE: RNA
<213> ORGANISM: Homo sapiens

<400> SEQUENCE: 419
gucccugagc aucuacggu 19

<210> SEQ ID NO 420
<211> LENGTH: 19
<212> TYPE: RNA
<213> ORGANISM: Homo sapiens

<400> SEQUENCE: 420
ucuggcugcg ggaacacaa 19

<210> SEQ ID NO 421
<211> LENGTH: 19
<212> TYPE: RNA
<213> ORGANISM: Homo sapiens

<400> SEQUENCE: 421
cacaacagag uaugcgaug 19

<210> SEQ ID NO 422
<211> LENGTH: 19
<212> TYPE: RNA
<213> ORGANISM: Homo sapiens

<400> SEQUENCE: 422
cagaguaugc gaugugcuu 19

<210> SEQ ID NO 423
<211> LENGTH: 19
<212> TYPE: RNA
<213> ORGANISM: Homo sapiens

<400> SEQUENCE: 423
acaggagcau ccugaaugg 19

<210> SEQ ID NO 424
<211> LENGTH: 19
<212> TYPE: RNA
<213> ORGANISM: Homo sapiens

<400> SEQUENCE: 424
caggagcauc cugaauggg 19

<210> SEQ ID NO 425
<211> LENGTH: 19
<212> TYPE: RNA
<213> ORGANISM: Homo sapiens

<400> SEQUENCE: 425
uggggugaug agcaguugu 19

<210> SEQ ID NO 426
<211> LENGTH: 19
<212> TYPE: RNA
<213> ORGANISM: Homo sapiens

<400> SEQUENCE: 426
gcaggcuaau acugauagg 19

<210> SEQ ID NO 427
<211> LENGTH: 19
<212> TYPE: RNA
<213> ORGANISM: Homo sapiens

<400> SEQUENCE: 427
uacugauagg agagacuau 19

<210> SEQ ID NO 428
<211> LENGTH: 19
<212> TYPE: RNA
<213> ORGANISM: Homo sapiens

<400> SEQUENCE: 428
gauuaugugc aacacuuga 19

<210> SEQ ID NO 429
<211> LENGTH: 19
<212> TYPE: RNA
<213> ORGANISM: Homo sapiens

<400> SEQUENCE: 429
cacuugagug gcuaucacu 19

<210> SEQ ID NO 430
<211> LENGTH: 19
<212> TYPE: RNA
<213> ORGANISM: Homo sapiens

<400> SEQUENCE: 430
acugaaauuu gacccagaa 19

<210> SEQ ID NO 431
<211> LENGTH: 19
<212> TYPE: RNA
<213> ORGANISM: Homo sapiens

<400> SEQUENCE: 431
cugaaauuug acccagaac 19

<210> SEQ ID NO 432
<211> LENGTH: 19
<212> TYPE: RNA
<213> ORGANISM: Homo sapiens

<400> SEQUENCE: 432
auuugaccca gaacuacuu 19

<210> SEQ ID NO 433
<211> LENGTH: 19
<212> TYPE: RNA
<213> ORGANISM: Homo sapiens

<400> SEQUENCE: 433
uuugacccag aacuacuuu 19

<210> SEQ ID NO 434
<211> LENGTH: 19
<212> TYPE: RNA
<213> ORGANISM: Homo sapiens

<400> SEQUENCE: 434
caaacaauuc caguaccaa 19

<210> SEQ ID NO 435
<211> LENGTH: 19
<212> TYPE: RNA
<213> ORGANISM: Homo sapiens

<400> SEQUENCE: 435
caauuccagu accaaaauc 19

<210> SEQ ID NO 436
<211> LENGTH: 19
<212> TYPE: RNA
<213> ORGANISM: Homo sapiens

<400> SEQUENCE: 436
uuccaguacc aaaaucgua 19

<210> SEQ ID NO 437
<211> LENGTH: 19
<212> TYPE: RNA
<213> ORGANISM: Homo sapiens

<400> SEQUENCE: 437
aaucguauug cugcugaau 19

<210> SEQ ID NO 438
<211> LENGTH: 19
<212> TYPE: RNA
<213> ORGANISM: Homo sapiens

<400> SEQUENCE: 438
aucguauugc ugcugaauu 19

<210> SEQ ID NO 439
<211> LENGTH: 19
<212> TYPE: RNA
<213> ORGANISM: Homo sapiens

<400> SEQUENCE: 439
ucguauugcu gcugaauuu 19

<210> SEQ ID NO 440
<211> LENGTH: 19
<212> TYPE: RNA
<213> ORGANISM: Homo sapiens

<400> SEQUENCE: 440
uuuaacaccc ucuaucacu 19

<210> SEQ ID NO 441
<211> LENGTH: 19
<212> TYPE: RNA
<213> ORGANISM: Homo sapiens

<400> SEQUENCE: 441
cacccucuau cacuggcau 19

<210> SEQ ID NO 442
<211> LENGTH: 19
<212> TYPE: RNA
<213> ORGANISM: Homo sapiens

<400> SEQUENCE: 442
caacucuaua uugcuggaa 19

<210> SEQ ID NO 443
<211> LENGTH: 19
<212> TYPE: RNA
<213> ORGANISM: Homo sapiens

<400> SEQUENCE: 443
cucuauauug cuggaacau 19

<210> SEQ ID NO 444
<211> LENGTH: 19
<212> TYPE: RNA
<213> ORGANISM: Homo sapiens

<400> SEQUENCE: 444
cauggaauua cccaguuug 19

<210> SEQ ID NO 445
<211> LENGTH: 19
<212> TYPE: RNA
<213> ORGANISM: Homo sapiens

<400> SEQUENCE: 445
uuacccaguu uguugaauc 19

<210> SEQ ID NO 446
<211> LENGTH: 19
<212> TYPE: RNA
<213> ORGANISM: Homo sapiens

<400> SEQUENCE: 446
ucauucacca ggcaaauug 19

<210> SEQ ID NO 447
<211> LENGTH: 19
<212> TYPE: RNA
<213> ORGANISM: Homo sapiens

<400> SEQUENCE: 447
auugcuggca ggguugcug 19

<210> SEQ ID NO 448
<211> LENGTH: 19
<212> TYPE: RNA
<213> ORGANISM: Homo sapiens

<400> SEQUENCE: 448
uugcuggcag gguugcugg 19

<210> SEQ ID NO 449
<211> LENGTH: 19
<212> TYPE: RNA
<213> ORGANISM: Homo sapiens

<400> SEQUENCE: 449
uguuccaccc gcaguacag 19

<210> SEQ ID NO 450
<211> LENGTH: 19
<212> TYPE: RNA
<213> ORGANISM: Homo sapiens

<400> SEQUENCE: 450
aguaucacag gcuuccauu 19

<210> SEQ ID NO 451
<211> LENGTH: 19
<212> TYPE: RNA
<213> ORGANISM: Homo sapiens

<400> SEQUENCE: 451
guaucacagg cuuccauug 19

<210> SEQ ID NO 452
<211> LENGTH: 19
<212> TYPE: RNA
<213> ORGANISM: Homo sapiens

<400> SEQUENCE: 452
ugaguaccgc aaacgcuuu 19

<210> SEQ ID NO 453
<211> LENGTH: 19
<212> TYPE: RNA
<213> ORGANISM: Homo sapiens

<400> SEQUENCE: 453
acgcuuuaug cugaagccc 19

<210> SEQ ID NO 454
<211> LENGTH: 19
<212> TYPE: RNA
<213> ORGANISM: Homo sapiens

<400> SEQUENCE: 454
cgcuuuaugc ugaagcccu 19

<210> SEQ ID NO 455
<211> LENGTH: 19
<212> TYPE: RNA
<213> ORGANISM: Homo sapiens

<400> SEQUENCE: 455
gcccuaugaa ucauuugaa 19

<210> SEQ ID NO 456
<211> LENGTH: 19
<212> TYPE: RNA
<213> ORGANISM: Homo sapiens

<400> SEQUENCE: 456
gaacuuacag gagaaaagg 19

<210> SEQ ID NO 457
<211> LENGTH: 19
<212> TYPE: RNA

<213> ORGANISM: Homo sapiens

<400> SEQUENCE: 457
cuuacaggag aaaaggaaa 19

<210> SEQ ID NO 458
<211> LENGTH: 19
<212> TYPE: RNA
<213> ORGANISM: Homo sapiens

<400> SEQUENCE: 458
aaggaaaugu cugcagagu 19

<210> SEQ ID NO 459
<211> LENGTH: 19
<212> TYPE: RNA
<213> ORGANISM: Homo sapiens

<400> SEQUENCE: 459
aggaaauguc ugcagaguu 19

<210> SEQ ID NO 460
<211> LENGTH: 19
<212> TYPE: RNA
<213> ORGANISM: Homo sapiens

<400> SEQUENCE: 460
ggaaaugucu gcagaguug 19

<210> SEQ ID NO 461
<211> LENGTH: 19
<212> TYPE: RNA
<213> ORGANISM: Homo sapiens

<400> SEQUENCE: 461
augucugcag aguuggaag 19

<210> SEQ ID NO 462
<211> LENGTH: 19
<212> TYPE: RNA
<213> ORGANISM: Homo sapiens

<400> SEQUENCE: 462
ugucugcaga guuggaagc 19

<210> SEQ ID NO 463
<211> LENGTH: 19
<212> TYPE: RNA
<213> ORGANISM: Homo sapiens

<400> SEQUENCE: 463
gcacucuaug gugacaucg 19

<210> SEQ ID NO 464
<211> LENGTH: 19
<212> TYPE: RNA
<213> ORGANISM: Homo sapiens

<400> SEQUENCE: 464
aagccucggc cagaugcca 19

<210> SEQ ID NO 465
<211> LENGTH: 19

-continued

<212> TYPE: RNA
<213> ORGANISM: Homo sapiens

<400> SEQUENCE: 465
agccucggcc agaugccau 19

<210> SEQ ID NO 466
<211> LENGTH: 19
<212> TYPE: RNA
<213> ORGANISM: Homo sapiens

<400> SEQUENCE: 466
accaugguag aaguuggag 19

<210> SEQ ID NO 467
<211> LENGTH: 19
<212> TYPE: RNA
<213> ORGANISM: Homo sapiens

<400> SEQUENCE: 467
ccaugguaga aguuggagc 19

<210> SEQ ID NO 468
<211> LENGTH: 19
<212> TYPE: RNA
<213> ORGANISM: Homo sapiens

<400> SEQUENCE: 468
guuggagcac cauucuccu 19

<210> SEQ ID NO 469
<211> LENGTH: 19
<212> TYPE: RNA
<213> ORGANISM: Homo sapiens

<400> SEQUENCE: 469
aggacuuaug gguaauguu 19

<210> SEQ ID NO 470
<211> LENGTH: 19
<212> TYPE: RNA
<213> ORGANISM: Homo sapiens

<400> SEQUENCE: 470
ggacuuaugg guaauguua 19

<210> SEQ ID NO 471
<211> LENGTH: 19
<212> TYPE: RNA
<213> ORGANISM: Homo sapiens

<400> SEQUENCE: 471
uguuauaugu ucuccugcc 19

<210> SEQ ID NO 472
<211> LENGTH: 19
<212> TYPE: RNA
<213> ORGANISM: Homo sapiens

<400> SEQUENCE: 472
gccaagcacu uuuggugga 19

<210> SEQ ID NO 473

-continued

<211> LENGTH: 19
<212> TYPE: RNA
<213> ORGANISM: Homo sapiens

<400> SEQUENCE: 473
gcacuuuugg uggagaagu 19

<210> SEQ ID NO 474
<211> LENGTH: 19
<212> TYPE: RNA
<213> ORGANISM: Homo sapiens

<400> SEQUENCE: 474
guggguuuuc aaaucauca 19

<210> SEQ ID NO 475
<211> LENGTH: 19
<212> TYPE: RNA
<213> ORGANISM: Homo sapiens

<400> SEQUENCE: 475
aucaucaaca cugccucaa 19

<210> SEQ ID NO 476
<211> LENGTH: 19
<212> TYPE: RNA
<213> ORGANISM: Homo sapiens

<400> SEQUENCE: 476
ucaucaacac ugccucaau 19

<210> SEQ ID NO 477
<211> LENGTH: 19
<212> TYPE: RNA
<213> ORGANISM: Homo sapiens

<400> SEQUENCE: 477
cacugccuca auucagucu 19

<210> SEQ ID NO 478
<211> LENGTH: 19
<212> TYPE: RNA
<213> ORGANISM: Homo sapiens

<400> SEQUENCE: 478
uucagucucu caucugcaa 19

<210> SEQ ID NO 479
<211> LENGTH: 19
<212> TYPE: RNA
<213> ORGANISM: Homo sapiens

<400> SEQUENCE: 479
uaacgugaag ggcuguccc 19

<210> SEQ ID NO 480
<211> LENGTH: 19
<212> TYPE: RNA
<213> ORGANISM: Homo sapiens

<400> SEQUENCE: 480
cgugaagggc ugucccuuu 19

```
<210> SEQ ID NO 481
<211> LENGTH: 19
<212> TYPE: RNA
<213> ORGANISM: Homo sapiens

<400> SEQUENCE: 481

gggcuguccc uuuacuuca                                                  19

<210> SEQ ID NO 482
<211> LENGTH: 19
<212> TYPE: RNA
<213> ORGANISM: Homo sapiens

<400> SEQUENCE: 482

aacagucacc aucaaugca                                                  19

<210> SEQ ID NO 483
<211> LENGTH: 19
<212> TYPE: RNA
<213> ORGANISM: Homo sapiens

<400> SEQUENCE: 483

acagucacca ucaaugcaa                                                  19

<210> SEQ ID NO 484
<211> LENGTH: 19
<212> TYPE: RNA
<213> ORGANISM: Homo sapiens

<400> SEQUENCE: 484

cagucaccau caaugcaag                                                  19

<210> SEQ ID NO 485
<211> LENGTH: 19
<212> TYPE: RNA
<213> ORGANISM: Homo sapiens

<400> SEQUENCE: 485

ugcaaguucu ucccgcucc                                                  19

<210> SEQ ID NO 486
<211> LENGTH: 19
<212> TYPE: RNA
<213> ORGANISM: Homo sapiens

<400> SEQUENCE: 486

guucuucccg cuccggacu                                                  19

<210> SEQ ID NO 487
<211> LENGTH: 19
<212> TYPE: RNA
<213> ORGANISM: Homo sapiens

<400> SEQUENCE: 487

ucccacagua cuacuaaaa                                                  19

<210> SEQ ID NO 488
<211> LENGTH: 19
<212> TYPE: RNA
<213> ORGANISM: Homo sapiens

<400> SEQUENCE: 488

aagaacguuc gacugaacu                                                  19
```

```
<210> SEQ ID NO 489
<211> LENGTH: 19
<212> TYPE: RNA
<213> ORGANISM: Homo sapiens

<400> SEQUENCE: 489

agaacguucg acugaacug                                                19

<210> SEQ ID NO 490
<211> LENGTH: 19
<212> TYPE: RNA
<213> ORGANISM: Homo sapiens

<400> SEQUENCE: 490

gaacguucga cugaacugu                                                19

<210> SEQ ID NO 491
<211> LENGTH: 19
<212> TYPE: RNA
<213> ORGANISM: Homo sapiens

<400> SEQUENCE: 491

cacaacagag uaugcgacg                                                19

<210> SEQ ID NO 492
<211> LENGTH: 19
<212> TYPE: RNA
<213> ORGANISM: Homo sapiens

<400> SEQUENCE: 492

aggaacagcc uuccagccc                                                19

<210> SEQ ID NO 493
<211> LENGTH: 19
<212> TYPE: RNA
<213> ORGANISM: Homo sapiens

<400> SEQUENCE: 493

cgguuccaag uggacuuau                                                19

<210> SEQ ID NO 494
<211> LENGTH: 19
<212> TYPE: RNA
<213> ORGANISM: Homo sapiens

<400> SEQUENCE: 494

guggacuuau uuugguccu                                                19

<210> SEQ ID NO 495
<211> LENGTH: 19
<212> TYPE: RNA
<213> ORGANISM: Homo sapiens

<400> SEQUENCE: 495

uagcuggucc aagaaguac                                                19

<210> SEQ ID NO 496
<211> LENGTH: 19
<212> TYPE: RNA
<213> ORGANISM: Homo sapiens

<400> SEQUENCE: 496

gaaguacccg ucguguggg                                                19
```

<210> SEQ ID NO 497
<211> LENGTH: 19
<212> TYPE: RNA
<213> ORGANISM: Homo sapiens

<400> SEQUENCE: 497
ggcuacaauc ugucugcca 19

<210> SEQ ID NO 498
<211> LENGTH: 19
<212> TYPE: RNA
<213> ORGANISM: Homo sapiens

<400> SEQUENCE: 498
ucugucugcc aacaagcag 19

<210> SEQ ID NO 499
<211> LENGTH: 19
<212> TYPE: RNA
<213> ORGANISM: Homo sapiens

<400> SEQUENCE: 499
caagcaguuu cuccugacc 19

<210> SEQ ID NO 500
<211> LENGTH: 19
<212> TYPE: RNA
<213> ORGANISM: Homo sapiens

<400> SEQUENCE: 500
gcaguuucuc cugaccaac 19

<210> SEQ ID NO 501
<211> LENGTH: 19
<212> TYPE: RNA
<213> ORGANISM: Homo sapiens

<400> SEQUENCE: 501
caauggccau ucagugaag 19

<210> SEQ ID NO 502
<211> LENGTH: 19
<212> TYPE: RNA
<213> ORGANISM: Homo sapiens

<400> SEQUENCE: 502
uggccauuca gugaagcug 19

<210> SEQ ID NO 503
<211> LENGTH: 19
<212> TYPE: RNA
<213> ORGANISM: Homo sapiens

<400> SEQUENCE: 503
cucagaccuu uauccugac 19

<210> SEQ ID NO 504
<211> LENGTH: 19
<212> TYPE: RNA
<213> ORGANISM: Homo sapiens

<400> SEQUENCE: 504
caagucagaa ggccucgcu 19

<210> SEQ ID NO 505
<211> LENGTH: 19
<212> TYPE: RNA
<213> ORGANISM: Homo sapiens

<400> SEQUENCE: 505
gucagaaggc cucgcuguc 19

<210> SEQ ID NO 506
<211> LENGTH: 19
<212> TYPE: RNA
<213> ORGANISM: Homo sapiens

<400> SEQUENCE: 506
uccguccuau gacaagauc 19

<210> SEQ ID NO 507
<211> LENGTH: 19
<212> TYPE: RNA
<213> ORGANISM: Homo sapiens

<400> SEQUENCE: 507
gaucuucagu caccuucaa 19

<210> SEQ ID NO 508
<211> LENGTH: 19
<212> TYPE: RNA
<213> ORGANISM: Homo sapiens

<400> SEQUENCE: 508
cauguaaagu acaaaggcc 19

<210> SEQ ID NO 509
<211> LENGTH: 19
<212> TYPE: RNA
<213> ORGANISM: Homo sapiens

<400> SEQUENCE: 509
aguacaaagg ccaggaagc 19

<210> SEQ ID NO 510
<211> LENGTH: 19
<212> TYPE: RNA
<213> ORGANISM: Homo sapiens

<400> SEQUENCE: 510
guacaaaggc caggaagca 19

<210> SEQ ID NO 511
<211> LENGTH: 19
<212> TYPE: RNA
<213> ORGANISM: Homo sapiens

<400> SEQUENCE: 511
aggccaggaa gcauucguc 19

<210> SEQ ID NO 512
<211> LENGTH: 19
<212> TYPE: RNA
<213> ORGANISM: Homo sapiens

<400> SEQUENCE: 512
ggccaggaag cauucgucc 19

<210> SEQ ID NO 513
<211> LENGTH: 19
<212> TYPE: RNA
<213> ORGANISM: Homo sapiens

<400> SEQUENCE: 513
gcauucgucc cgggauuca 19

<210> SEQ ID NO 514
<211> LENGTH: 19
<212> TYPE: RNA
<213> ORGANISM: Homo sapiens

<400> SEQUENCE: 514
cauugaagag cugcuuccg 19

<210> SEQ ID NO 515
<211> LENGTH: 19
<212> TYPE: RNA
<213> ORGANISM: Homo sapiens

<400> SEQUENCE: 515
gagcugcuuc cggagagga 19

<210> SEQ ID NO 516
<211> LENGTH: 19
<212> TYPE: RNA
<213> ORGANISM: Homo sapiens

<400> SEQUENCE: 516
uauuaccgcu accgggggu 19

<210> SEQ ID NO 517
<211> LENGTH: 19
<212> TYPE: RNA
<213> ORGANISM: Homo sapiens

<400> SEQUENCE: 517
ccccacugug cucuggaca 19

<210> SEQ ID NO 518
<211> LENGTH: 19
<212> TYPE: RNA
<213> ORGANISM: Homo sapiens

<400> SEQUENCE: 518
accccgugca aauuuccca 19

<210> SEQ ID NO 519
<211> LENGTH: 19
<212> TYPE: RNA
<213> ORGANISM: Homo sapiens

<400> SEQUENCE: 519
ccccgugcaa auuucccag 19

<210> SEQ ID NO 520
<211> LENGTH: 19
<212> TYPE: RNA
<213> ORGANISM: Homo sapiens

<400> SEQUENCE: 520
auuucccagg agcagcugc 19

<210> SEQ ID NO 521
<211> LENGTH: 19
<212> TYPE: RNA
<213> ORGANISM: Homo sapiens

<400> SEQUENCE: 521
uuucccagga gcagcugcu 19

<210> SEQ ID NO 522
<211> LENGTH: 19
<212> TYPE: RNA
<213> ORGANISM: Homo sapiens

<400> SEQUENCE: 522
augaucaaca acuuccggc 19

<210> SEQ ID NO 523
<211> LENGTH: 19
<212> TYPE: RNA
<213> ORGANISM: Homo sapiens

<400> SEQUENCE: 523
ugaucaacaa cuuccggca 19

<210> SEQ ID NO 524
<211> LENGTH: 19
<212> TYPE: RNA
<213> ORGANISM: Homo sapiens

<400> SEQUENCE: 524
caacuuccgg cagguccag 19

<210> SEQ ID NO 525
<211> LENGTH: 19
<212> TYPE: RNA
<213> ORGANISM: Homo sapiens

<400> SEQUENCE: 525
cuuccggcag guccagaag 19

<210> SEQ ID NO 526
<211> LENGTH: 19
<212> TYPE: RNA
<213> ORGANISM: Homo sapiens

<400> SEQUENCE: 526
guucgaugag aggcuggua 19

<210> SEQ ID NO 527
<211> LENGTH: 19
<212> TYPE: RNA
<213> ORGANISM: Homo sapiens

<400> SEQUENCE: 527
gugcaagucu guacugcgg 19

<210> SEQ ID NO 528
<211> LENGTH: 19
<212> TYPE: RNA
<213> ORGANISM: Homo sapiens

<400> SEQUENCE: 528
gucuguacug cggcaggac 19

<210> SEQ ID NO 529
<211> LENGTH: 19
<212> TYPE: RNA
<213> ORGANISM: Homo sapiens

<400> SEQUENCE: 529
ggaagaguau caaaaaagg 19

<210> SEQ ID NO 530
<211> LENGTH: 19
<212> TYPE: RNA
<213> ORGANISM: Homo sapiens

<400> SEQUENCE: 530
aaaaggugau aacaaggga 19

<210> SEQ ID NO 531
<211> LENGTH: 19
<212> TYPE: RNA
<213> ORGANISM: Homo sapiens

<400> SEQUENCE: 531
aaaggugaua acaagggag 19

<210> SEQ ID NO 532
<211> LENGTH: 19
<212> TYPE: RNA
<213> ORGANISM: Homo sapiens

<400> SEQUENCE: 532
aaggugauaa caagggagu 19

<210> SEQ ID NO 533
<211> LENGTH: 19
<212> TYPE: RNA
<213> ORGANISM: Homo sapiens

<400> SEQUENCE: 533
aggugauaac aagggaguc 19

<210> SEQ ID NO 534
<211> LENGTH: 19
<212> TYPE: RNA
<213> ORGANISM: Homo sapiens

<400> SEQUENCE: 534
ggugauaaca agggaguca 19

<210> SEQ ID NO 535
<211> LENGTH: 19
<212> TYPE: RNA
<213> ORGANISM: Homo sapiens

<400> SEQUENCE: 535
caagggaguc auuuacaag 19

<210> SEQ ID NO 536
<211> LENGTH: 19
<212> TYPE: RNA

-continued

<213> ORGANISM: Homo sapiens

<400> SEQUENCE: 536
gggagucauu uacaagcca 19

<210> SEQ ID NO 537
<211> LENGTH: 19
<212> TYPE: RNA
<213> ORGANISM: Homo sapiens

<400> SEQUENCE: 537
gccagccacc aagauggag 19

<210> SEQ ID NO 538
<211> LENGTH: 19
<212> TYPE: RNA
<213> ORGANISM: Homo sapiens

<400> SEQUENCE: 538
gauggagacu gaggcccac 19

<210> SEQ ID NO 539
<211> LENGTH: 19
<212> TYPE: RNA
<213> ORGANISM: Homo sapiens

<400> SEQUENCE: 539
augcuuccga cagcuccaa 19

<210> SEQ ID NO 540
<211> LENGTH: 19
<212> TYPE: RNA
<213> ORGANISM: Homo sapiens

<400> SEQUENCE: 540
ugcuuccgac agcuccaac 19

<210> SEQ ID NO 541
<211> LENGTH: 19
<212> TYPE: RNA
<213> ORGANISM: Homo sapiens

<400> SEQUENCE: 541
cauuuccaag gccauucug 19

<210> SEQ ID NO 542
<211> LENGTH: 19
<212> TYPE: RNA
<213> ORGANISM: Homo sapiens

<400> SEQUENCE: 542
cauccuagug auccucucc 19

<210> SEQ ID NO 543
<211> LENGTH: 19
<212> TYPE: RNA
<213> ORGANISM: Homo sapiens

<400> SEQUENCE: 543
caucugggcg gcaguggau 19

<210> SEQ ID NO 544
<211> LENGTH: 19

<212> TYPE: RNA
<213> ORGANISM: Homo sapiens

<400> SEQUENCE: 544
ccaucgucac ccagaggag 19

<210> SEQ ID NO 545
<211> LENGTH: 19
<212> TYPE: RNA
<213> ORGANISM: Homo sapiens

<400> SEQUENCE: 545
gucuggccuc aagaccgac 19

<210> SEQ ID NO 546
<211> LENGTH: 19
<212> TYPE: RNA
<213> ORGANISM: Homo sapiens

<400> SEQUENCE: 546
gaccgacaag ucggacucg 19

<210> SEQ ID NO 547
<211> LENGTH: 19
<212> TYPE: RNA
<213> ORGANISM: Homo sapiens

<400> SEQUENCE: 547
gucggacucg gagcaagug 19

<210> SEQ ID NO 548
<211> LENGTH: 19
<212> TYPE: RNA
<213> ORGANISM: Homo sapiens

<400> SEQUENCE: 548
gugacgcucc gcauccauc 19

<210> SEQ ID NO 549
<211> LENGTH: 19
<212> TYPE: RNA
<213> ORGANISM: Homo sapiens

<400> SEQUENCE: 549
gaccaagacg cacuucuca 19

<210> SEQ ID NO 550
<211> LENGTH: 19
<212> TYPE: RNA
<213> ORGANISM: Homo sapiens

<400> SEQUENCE: 550
gacgcacuuc ucagugagg 19

<210> SEQ ID NO 551
<211> LENGTH: 19
<212> TYPE: RNA
<213> ORGANISM: Homo sapiens

<400> SEQUENCE: 551
guucucccgg gagaagaaa 19

<210> SEQ ID NO 552

<211> LENGTH: 19
<212> TYPE: RNA
<213> ORGANISM: Homo sapiens

<400> SEQUENCE: 552
gaaagcggcc aaaacgcug 19

<210> SEQ ID NO 553
<211> LENGTH: 19
<212> TYPE: RNA
<213> ORGANISM: Homo sapiens

<400> SEQUENCE: 553
aacgcugggc aucgugguc 19

<210> SEQ ID NO 554
<211> LENGTH: 19
<212> TYPE: RNA
<213> ORGANISM: Homo sapiens

<400> SEQUENCE: 554
gcccucugaa acaguuuuu 19

<210> SEQ ID NO 555
<211> LENGTH: 19
<212> TYPE: RNA
<213> ORGANISM: Homo sapiens

<400> SEQUENCE: 555
aauaguauuu uggcucgga 19

<210> SEQ ID NO 556
<211> LENGTH: 19
<212> TYPE: RNA
<213> ORGANISM: Homo sapiens

<400> SEQUENCE: 556
auaguauuuu ggcucggau 19

<210> SEQ ID NO 557
<211> LENGTH: 19
<212> TYPE: RNA
<213> ORGANISM: Homo sapiens

<400> SEQUENCE: 557
uaguauuuug gcucggaua 19

<210> SEQ ID NO 558
<211> LENGTH: 19
<212> TYPE: RNA
<213> ORGANISM: Homo sapiens

<400> SEQUENCE: 558
acagcugcau caaccccau 19

<210> SEQ ID NO 559
<211> LENGTH: 19
<212> TYPE: RNA
<213> ORGANISM: Homo sapiens

<400> SEQUENCE: 559
cagcugcauc aaccccauc 19

<210> SEQ ID NO 560
<211> LENGTH: 19
<212> TYPE: RNA
<213> ORGANISM: Homo sapiens

<400> SEQUENCE: 560
ccccaucaua uacccaugc 19

<210> SEQ ID NO 561
<211> LENGTH: 19
<212> TYPE: RNA
<213> ORGANISM: Homo sapiens

<400> SEQUENCE: 561
gaguucaaaa aggccuuuc 19

<210> SEQ ID NO 562
<211> LENGTH: 19
<212> TYPE: RNA
<213> ORGANISM: Homo sapiens

<400> SEQUENCE: 562
aaaggccuuu cagaauguc 19

<210> SEQ ID NO 563
<211> LENGTH: 19
<212> TYPE: RNA
<213> ORGANISM: Homo sapiens

<400> SEQUENCE: 563
aaggccuuuc agaaugucu 19

<210> SEQ ID NO 564
<211> LENGTH: 19
<212> TYPE: RNA
<213> ORGANISM: Homo sapiens

<400> SEQUENCE: 564
aggccuuuca gaaugucuu 19

<210> SEQ ID NO 565
<211> LENGTH: 19
<212> TYPE: RNA
<213> ORGANISM: Homo sapiens

<400> SEQUENCE: 565
ggccuuucag aaugucuug 19

<210> SEQ ID NO 566
<211> LENGTH: 19
<212> TYPE: RNA
<213> ORGANISM: Homo sapiens

<400> SEQUENCE: 566
ugucuugaga auccagugu 19

<210> SEQ ID NO 567
<211> LENGTH: 19
<212> TYPE: RNA
<213> ORGANISM: Homo sapiens

<400> SEQUENCE: 567
uccagugucu cugcagaaa 19

<210> SEQ ID NO 568
<211> LENGTH: 19
<212> TYPE: RNA
<213> ORGANISM: Homo sapiens

<400> SEQUENCE: 568
uccagugucu ccgcagaaa 19

<210> SEQ ID NO 569
<211> LENGTH: 19
<212> TYPE: RNA
<213> ORGANISM: Homo sapiens

<400> SEQUENCE: 569
agcagucuuc caaacaugc 19

<210> SEQ ID NO 570
<211> LENGTH: 19
<212> TYPE: RNA
<213> ORGANISM: Homo sapiens

<400> SEQUENCE: 570
gcagucuucc aaacaugcc 19

<210> SEQ ID NO 571
<211> LENGTH: 19
<212> TYPE: RNA
<213> ORGANISM: Homo sapiens

<400> SEQUENCE: 571
acaugcccug ggcuacacc 19

<210> SEQ ID NO 572
<211> LENGTH: 19
<212> TYPE: RNA
<213> ORGANISM: Homo sapiens

<400> SEQUENCE: 572
gggcaacaca aggacaugg 19

<210> SEQ ID NO 573
<211> LENGTH: 19
<212> TYPE: RNA
<213> ORGANISM: Homo sapiens

<400> SEQUENCE: 573
cacaaggaca uggugcgca 19

<210> SEQ ID NO 574
<211> LENGTH: 19
<212> TYPE: RNA
<213> ORGANISM: Homo sapiens

<400> SEQUENCE: 574
gagagaccuu cuacaggau 19

<210> SEQ ID NO 575
<211> LENGTH: 19
<212> TYPE: RNA
<213> ORGANISM: Homo sapiens

<400> SEQUENCE: 575
gacggauggc guuugugaa 19

<210> SEQ ID NO 576
<211> LENGTH: 19
<212> TYPE: RNA
<213> ORGANISM: Homo sapiens

<400> SEQUENCE: 576
auuuuucucu uccaugccc 19

<210> SEQ ID NO 577
<211> LENGTH: 19
<212> TYPE: RNA
<213> ORGANISM: Homo sapiens

<400> SEQUENCE: 577
uuuuucucuu ccaugcccc 19

<210> SEQ ID NO 578
<211> LENGTH: 19
<212> TYPE: RNA
<213> ORGANISM: Homo sapiens

<400> SEQUENCE: 578
agaccaaucc uccuguacc 19

<210> SEQ ID NO 579
<211> LENGTH: 19
<212> TYPE: RNA
<213> ORGANISM: Homo sapiens

<400> SEQUENCE: 579
gaccaauccu ccuguacca 19

<210> SEQ ID NO 580
<211> LENGTH: 19
<212> TYPE: RNA
<213> ORGANISM: Homo sapiens

<400> SEQUENCE: 580
uccuccugua ccacagccc 19

<210> SEQ ID NO 581
<211> LENGTH: 19
<212> TYPE: RNA
<213> ORGANISM: Homo sapiens

<400> SEQUENCE: 581
gucucgcucu gucaccagg 19

<210> SEQ ID NO 582
<211> LENGTH: 19
<212> TYPE: RNA
<213> ORGANISM: Homo sapiens

<400> SEQUENCE: 582
gagauucucc ugccucagc 19

<210> SEQ ID NO 583
<211> LENGTH: 19
<212> TYPE: RNA
<213> ORGANISM: Homo sapiens

<400> SEQUENCE: 583
gaauugcaga gagcauauc 19

<210> SEQ ID NO 584
<211> LENGTH: 19
<212> TYPE: RNA
<213> ORGANISM: Homo sapiens

<400> SEQUENCE: 584
uugcagagag cauaucaag 19

<210> SEQ ID NO 585
<211> LENGTH: 19
<212> TYPE: RNA
<213> ORGANISM: Homo sapiens

<400> SEQUENCE: 585
uuuuaugaug ccaccgugg 19

<210> SEQ ID NO 586
<211> LENGTH: 19
<212> TYPE: RNA
<213> ORGANISM: Homo sapiens

<400> SEQUENCE: 586
agggucuaga augcugauc 19

<210> SEQ ID NO 587
<211> LENGTH: 19
<212> TYPE: RNA
<213> ORGANISM: Homo sapiens

<400> SEQUENCE: 587
gggucuagaa ugcugaucu 19

<210> SEQ ID NO 588
<211> LENGTH: 19
<212> TYPE: RNA
<213> ORGANISM: Homo sapiens

<400> SEQUENCE: 588
guaaaagcuu uuuggaggu 19

<210> SEQ ID NO 589
<211> LENGTH: 19
<212> TYPE: RNA
<213> ORGANISM: Homo sapiens

<400> SEQUENCE: 589
aagcuuuuug gaggucugc 19

<210> SEQ ID NO 590
<211> LENGTH: 19
<212> TYPE: RNA
<213> ORGANISM: Homo sapiens

<400> SEQUENCE: 590
agcuuuuugg aggucugcu 19

<210> SEQ ID NO 591
<211> LENGTH: 19
<212> TYPE: RNA
<213> ORGANISM: Homo sapiens

<400> SEQUENCE: 591
gcuuuuugga ggucugcug 19

<210> SEQ ID NO 592
<211> LENGTH: 19
<212> TYPE: RNA
<213> ORGANISM: Homo sapiens

<400> SEQUENCE: 592
cccccagccu ugacaagaa 19

<210> SEQ ID NO 593
<211> LENGTH: 19
<212> TYPE: RNA
<213> ORGANISM: Homo sapiens

<400> SEQUENCE: 593
gaaccaucaa guuccaacc 19

<210> SEQ ID NO 594
<211> LENGTH: 19
<212> TYPE: RNA
<213> ORGANISM: Homo sapiens

<400> SEQUENCE: 594
ccaucaaguu ccaaccauu 19

<210> SEQ ID NO 595
<211> LENGTH: 19
<212> TYPE: RNA
<213> ORGANISM: Homo sapiens

<400> SEQUENCE: 595
guuccaacca uuaaggucc 19

<210> SEQ ID NO 596
<211> LENGTH: 19
<212> TYPE: RNA
<213> ORGANISM: Homo sapiens

<400> SEQUENCE: 596
ccauuaaggu ccacaccau 19

<210> SEQ ID NO 597
<211> LENGTH: 19
<212> TYPE: RNA
<213> ORGANISM: Homo sapiens

<400> SEQUENCE: 597
gguccacacc aucucccuc 19

<210> SEQ ID NO 598
<211> LENGTH: 19
<212> TYPE: RNA
<213> ORGANISM: Homo sapiens

<400> SEQUENCE: 598
cggggaggaa gucuaggac 19

<210> SEQ ID NO 599
<211> LENGTH: 19
<212> TYPE: RNA
<213> ORGANISM: Homo sapiens

<400> SEQUENCE: 599
gaugaauccc gaccuggac 19

<210> SEQ ID NO 600
<211> LENGTH: 19
<212> TYPE: RNA
<213> ORGANISM: Homo sapiens

<400> SEQUENCE: 600
cacaucagca ccugcccac 19

<210> SEQ ID NO 601
<211> LENGTH: 19
<212> TYPE: RNA
<213> ORGANISM: Homo sapiens

<400> SEQUENCE: 601
aaaugccaac uucacuggc 19

<210> SEQ ID NO 602
<211> LENGTH: 19
<212> TYPE: RNA
<213> ORGANISM: Homo sapiens

<400> SEQUENCE: 602
aaugccaacu ucacuggcc 19

<210> SEQ ID NO 603
<211> LENGTH: 19
<212> TYPE: RNA
<213> ORGANISM: Homo sapiens

<400> SEQUENCE: 603
augccaacuu cacuggccc 19

<210> SEQ ID NO 604
<211> LENGTH: 19
<212> TYPE: RNA
<213> ORGANISM: Homo sapiens

<400> SEQUENCE: 604
ugccaacuuc acuggcccc 19

<210> SEQ ID NO 605
<211> LENGTH: 19
<212> TYPE: RNA
<213> ORGANISM: Homo sapiens

<400> SEQUENCE: 605
cuucacuggc cccaaccag 19

<210> SEQ ID NO 606
<211> LENGTH: 19
<212> TYPE: RNA
<213> ORGANISM: Homo sapiens

<400> SEQUENCE: 606
ccagaccucg agcaacucc 19

<210> SEQ ID NO 607
<211> LENGTH: 19
<212> TYPE: RNA
<213> ORGANISM: Homo sapiens

<400> SEQUENCE: 607
cauccuaguc aucuugucu 19

<210> SEQ ID NO 608
<211> LENGTH: 19
<212> TYPE: RNA
<213> ORGANISM: Homo sapiens

<400> SEQUENCE: 608
cuacuucauu gucaaccug 19

<210> SEQ ID NO 609
<211> LENGTH: 19
<212> TYPE: RNA
<213> ORGANISM: Homo sapiens

<400> SEQUENCE: 609
cgaugacaag gagugcggg 19

<210> SEQ ID NO 610
<211> LENGTH: 19
<212> TYPE: RNA
<213> ORGANISM: Homo sapiens

<400> SEQUENCE: 610
gaacccuucu augcccucu 19

<210> SEQ ID NO 611
<211> LENGTH: 19
<212> TYPE: RNA
<213> ORGANISM: Homo sapiens

<400> SEQUENCE: 611
cccuucuaug cccucuucu 19

<210> SEQ ID NO 612
<211> LENGTH: 19
<212> TYPE: RNA
<213> ORGANISM: Homo sapiens

<400> SEQUENCE: 612
gagaaccacc aagaaccua 19

<210> SEQ ID NO 613
<211> LENGTH: 19
<212> TYPE: RNA
<213> ORGANISM: Homo sapiens

<400> SEQUENCE: 613
ccaccaagaa ccuagaggc 19

<210> SEQ ID NO 614
<211> LENGTH: 19
<212> TYPE: RNA
<213> ORGANISM: Homo sapiens

<400> SEQUENCE: 614
gaaccuagag gcaggaguc 19

<210> SEQ ID NO 615
<211> LENGTH: 19
<212> TYPE: RNA

<213> ORGANISM: Homo sapiens

<400> SEQUENCE: 615
ccuagaggca ggagucaug 19

<210> SEQ ID NO 616
<211> LENGTH: 19
<212> TYPE: RNA
<213> ORGANISM: Homo sapiens

<400> SEQUENCE: 616
ggagaugucc aacuccaag 19

<210> SEQ ID NO 617
<211> LENGTH: 19
<212> TYPE: RNA
<213> ORGANISM: Homo sapiens

<400> SEQUENCE: 617
cuccaaggag cugacccug 19

<210> SEQ ID NO 618
<211> LENGTH: 19
<212> TYPE: RNA
<213> ORGANISM: Homo sapiens

<400> SEQUENCE: 618
ggagcugacc cugaggauc 19

<210> SEQ ID NO 619
<211> LENGTH: 19
<212> TYPE: RNA
<213> ORGANISM: Homo sapiens

<400> SEQUENCE: 619
gaacuuucac gaggacacc 19

<210> SEQ ID NO 620
<211> LENGTH: 19
<212> TYPE: RNA
<213> ORGANISM: Homo sapiens

<400> SEQUENCE: 620
cuuucacgag gacacccuu 19

<210> SEQ ID NO 621
<211> LENGTH: 19
<212> TYPE: RNA
<213> ORGANISM: Homo sapiens

<400> SEQUENCE: 621
ccccaggagu uccauagcu 19

<210> SEQ ID NO 622
<211> LENGTH: 19
<212> TYPE: RNA
<213> ORGANISM: Homo sapiens

<400> SEQUENCE: 622
acuuuuuaag uucuccagg 19

<210> SEQ ID NO 623
<211> LENGTH: 19

<212> TYPE: RNA
<213> ORGANISM: Homo sapiens

<400> SEQUENCE: 623
cuuuuuaagu ucuccaggg 19

<210> SEQ ID NO 624
<211> LENGTH: 19
<212> TYPE: RNA
<213> ORGANISM: Homo sapiens

<400> SEQUENCE: 624
guucuccagg gaaaagaaa 19

<210> SEQ ID NO 625
<211> LENGTH: 19
<212> TYPE: RNA
<213> ORGANISM: Homo sapiens

<400> SEQUENCE: 625
aagaaagcag cuaagacgu 19

<210> SEQ ID NO 626
<211> LENGTH: 19
<212> TYPE: RNA
<213> ORGANISM: Homo sapiens

<400> SEQUENCE: 626
agaaagcagc uaagacguu 19

<210> SEQ ID NO 627
<211> LENGTH: 19
<212> TYPE: RNA
<213> ORGANISM: Homo sapiens

<400> SEQUENCE: 627
gaaagcagcu aagacguug 19

<210> SEQ ID NO 628
<211> LENGTH: 19
<212> TYPE: RNA
<213> ORGANISM: Homo sapiens

<400> SEQUENCE: 628
agcagcuaag acguugggc 19

<210> SEQ ID NO 629
<211> LENGTH: 19
<212> TYPE: RNA
<213> ORGANISM: Homo sapiens

<400> SEQUENCE: 629
gcagcuaaga cguugggca 19

<210> SEQ ID NO 630
<211> LENGTH: 19
<212> TYPE: RNA
<213> ORGANISM: Homo sapiens

<400> SEQUENCE: 630
gacguugggc auugugguc 19

<210> SEQ ID NO 631

<211> LENGTH: 19
<212> TYPE: RNA
<213> ORGANISM: Homo sapiens

<400> SEQUENCE: 631
cagcugccuc aaccccauc 19

<210> SEQ ID NO 632
<211> LENGTH: 19
<212> TYPE: RNA
<213> ORGANISM: Homo sapiens

<400> SEQUENCE: 632
ccccaucauc uacccaugc 19

<210> SEQ ID NO 633
<211> LENGTH: 19
<212> TYPE: RNA
<213> ORGANISM: Homo sapiens

<400> SEQUENCE: 633
ggaguucaag cgcgcuuuc 19

<210> SEQ ID NO 634
<211> LENGTH: 19
<212> TYPE: RNA
<213> ORGANISM: Homo sapiens

<400> SEQUENCE: 634
aagcaacaug ccccuggcg 19

<210> SEQ ID NO 635
<211> LENGTH: 19
<212> TYPE: RNA
<213> ORGANISM: Homo sapiens

<400> SEQUENCE: 635
ccugcuuguc auccucuca 19

<210> SEQ ID NO 636
<211> LENGTH: 19
<212> TYPE: RNA
<213> ORGANISM: Homo sapiens

<400> SEQUENCE: 636
cuauuucauc gugaaccug 19

<210> SEQ ID NO 637
<211> LENGTH: 19
<212> TYPE: RNA
<213> ORGANISM: Homo sapiens

<400> SEQUENCE: 637
guacccagcc aucaugacc 19

<210> SEQ ID NO 638
<211> LENGTH: 19
<212> TYPE: RNA
<213> ORGANISM: Homo sapiens

<400> SEQUENCE: 638
guucucccgu gagaagaaa 19

<210> SEQ ID NO 639
<211> LENGTH: 19
<212> TYPE: RNA
<213> ORGANISM: Homo sapiens

<400> SEQUENCE: 639
gaaagcggcc aagacucug 19

<210> SEQ ID NO 640
<211> LENGTH: 19
<212> TYPE: RNA
<213> ORGANISM: Homo sapiens

<400> SEQUENCE: 640
gacucuggcc aucgucgug 19

<210> SEQ ID NO 641
<211> LENGTH: 19
<212> TYPE: RNA
<213> ORGANISM: Homo sapiens

<400> SEQUENCE: 641
ggucaucuuc uggcucggc 19

<210> SEQ ID NO 642
<211> LENGTH: 19
<212> TYPE: RNA
<213> ORGANISM: Homo sapiens

<400> SEQUENCE: 642
cccgcucauc uaccccugu 19

<210> SEQ ID NO 643
<211> LENGTH: 19
<212> TYPE: RNA
<213> ORGANISM: Homo sapiens

<400> SEQUENCE: 643
agucuccagc cugucgcac 19

<210> SEQ ID NO 644
<211> LENGTH: 19
<212> TYPE: RNA
<213> ORGANISM: Homo sapiens

<400> SEQUENCE: 644
gucuccagcc ugucgcaca 19

<210> SEQ ID NO 645
<211> LENGTH: 19
<212> TYPE: RNA
<213> ORGANISM: Homo sapiens

<400> SEQUENCE: 645
uuggccgacu acagcaacc 19

<210> SEQ ID NO 646
<211> LENGTH: 19
<212> TYPE: RNA
<213> ORGANISM: Homo sapiens

<400> SEQUENCE: 646
ccuacgggag accgauauu 19

<210> SEQ ID NO 647
<211> LENGTH: 19
<212> TYPE: RNA
<213> ORGANISM: Homo sapiens

<400> SEQUENCE: 647
ugagaguacc ugugagcag 19

<210> SEQ ID NO 648
<211> LENGTH: 19
<212> TYPE: RNA
<213> ORGANISM: Homo sapiens

<400> SEQUENCE: 648
ugccgggaag cccaaagac 19

<210> SEQ ID NO 649
<211> LENGTH: 19
<212> TYPE: RNA
<213> ORGANISM: Homo sapiens

<400> SEQUENCE: 649
gcccaaagac cccaccuuc 19

<210> SEQ ID NO 650
<211> LENGTH: 19
<212> TYPE: RNA
<213> ORGANISM: Homo sapiens

<400> SEQUENCE: 650
agaccccacc uucauaccu 19

<210> SEQ ID NO 651
<211> LENGTH: 19
<212> TYPE: RNA
<213> ORGANISM: Homo sapiens

<400> SEQUENCE: 651
gaccccaccu ucauaccug 19

<210> SEQ ID NO 652
<211> LENGTH: 19
<212> TYPE: RNA
<213> ORGANISM: Homo sapiens

<400> SEQUENCE: 652
uucaggccaa gacaucccc 19

<210> SEQ ID NO 653
<211> LENGTH: 19
<212> TYPE: RNA
<213> ORGANISM: Homo sapiens

<400> SEQUENCE: 653 gacaucccu guggaugaa 19

<210> SEQ ID NO 654
<211> LENGTH: 19
<212> TYPE: RNA
<213> ORGANISM: Homo sapiens

<400> SEQUENCE: 654
aaggcccuac aggaccagc 19

<210> SEQ ID NO 655
<211> LENGTH: 19
<212> TYPE: RNA
<213> ORGANISM: Homo sapiens

<400> SEQUENCE: 655
aggcccuaca ggaccagcu 19

<210> SEQ ID NO 656
<211> LENGTH: 19
<212> TYPE: RNA
<213> ORGANISM: Homo sapiens

<400> SEQUENCE: 656
aacuugacac cgaagacaa 19

<210> SEQ ID NO 657
<211> LENGTH: 19
<212> TYPE: RNA
<213> ORGANISM: Homo sapiens

<400> SEQUENCE: 657
acuugacacc gaagacaag 19

<210> SEQ ID NO 658
<211> LENGTH: 19
<212> TYPE: RNA
<213> ORGANISM: Homo sapiens

<400> SEQUENCE: 658
cuugacaccg aagacaagu 19

<210> SEQ ID NO 659
<211> LENGTH: 19
<212> TYPE: RNA
<213> ORGANISM: Homo sapiens

<400> SEQUENCE: 659
gacaaguuga gggccgcaa 19

<210> SEQ ID NO 660
<211> LENGTH: 19
<212> TYPE: RNA
<213> ORGANISM: Homo sapiens

<400> SEQUENCE: 660
guugagggcc gcaaugguc 19

<210> SEQ ID NO 661
<211> LENGTH: 19
<212> TYPE: RNA
<213> ORGANISM: Homo sapiens

<400> SEQUENCE: 661
uggucgggau gcuggccaa 19

<210> SEQ ID NO 662
<211> LENGTH: 19
<212> TYPE: RNA
<213> ORGANISM: Homo sapiens

<400> SEQUENCE: 662
cuucuugggc uuccguaua 19

<210> SEQ ID NO 663
<211> LENGTH: 19
<212> TYPE: RNA
<213> ORGANISM: Homo sapiens

<400> SEQUENCE: 663
cggcugucuu uggcacccu 19

<210> SEQ ID NO 664
<211> LENGTH: 19
<212> TYPE: RNA
<213> ORGANISM: Homo sapiens

<400> SEQUENCE: 664
uccugggugu uccuuggaa 19

<210> SEQ ID NO 665
<211> LENGTH: 19
<212> TYPE: RNA
<213> ORGANISM: Homo sapiens

<400> SEQUENCE: 665
ggacaagaac ugcaccucc 19

<210> SEQ ID NO 666
<211> LENGTH: 19
<212> TYPE: RNA
<213> ORGANISM: Homo sapiens

<400> SEQUENCE: 666
cuggauguug cugcugaga 19

<210> SEQ ID NO 667
<211> LENGTH: 19
<212> TYPE: RNA
<213> ORGANISM: Homo sapiens

<400> SEQUENCE: 667
gauugacagg uucaugcag 19

<210> SEQ ID NO 668
<211> LENGTH: 19
<212> TYPE: RNA
<213> ORGANISM: Homo sapiens

<400> SEQUENCE: 668
gacuggcugc ucccugaug 19

<210> SEQ ID NO 669
<211> LENGTH: 19
<212> TYPE: RNA
<213> ORGANISM: Homo sapiens

<400> SEQUENCE: 669
caccuacguc cacuuccaa 19

<210> SEQ ID NO 670
<211> LENGTH: 19
<212> TYPE: RNA
<213> ORGANISM: Homo sapiens

<400> SEQUENCE: 670
gggaagauga agggcuucu 19

<210> SEQ ID NO 671
<211> LENGTH: 19
<212> TYPE: RNA
<213> ORGANISM: Homo sapiens

<400> SEQUENCE: 671
gaugaagggc uucucccug 19

<210> SEQ ID NO 672
<211> LENGTH: 19
<212> TYPE: RNA
<213> ORGANISM: Homo sapiens

<400> SEQUENCE: 672
cagcaccuca gugucuguu 19

<210> SEQ ID NO 673
<211> LENGTH: 19
<212> TYPE: RNA
<213> ORGANISM: Homo sapiens

<400> SEQUENCE: 673
cuucucggug acucaagug 19

<210> SEQ ID NO 674
<211> LENGTH: 19
<212> TYPE: RNA
<213> ORGANISM: Homo sapiens

<400> SEQUENCE: 674
gugcccuuca cugagagcg 19

<210> SEQ ID NO 675
<211> LENGTH: 19
<212> TYPE: RNA
<213> ORGANISM: Homo sapiens

<400> SEQUENCE: 675
gguggagggu cucacuuuc 19

<210> SEQ ID NO 676
<211> LENGTH: 19
<212> TYPE: RNA
<213> ORGANISM: Homo sapiens

<400> SEQUENCE: 676
aacucccuca acuggauga 19

<210> SEQ ID NO 677
<211> LENGTH: 19
<212> TYPE: RNA
<213> ORGANISM: Homo sapiens

<400> SEQUENCE: 677
acucccucaa cuggaugaa 19

<210> SEQ ID NO 678
<211> LENGTH: 19
<212> TYPE: RNA
<213> ORGANISM: Homo sapiens

```
<400> SEQUENCE: 678

cucccucaac uggaugaag                                                19

<210> SEQ ID NO 679
<211> LENGTH: 19
<212> TYPE: RNA
<213> ORGANISM: Homo sapiens

<400> SEQUENCE: 679

cuggaugaag aaacugucu                                                19

<210> SEQ ID NO 680
<211> LENGTH: 19
<212> TYPE: RNA
<213> ORGANISM: Homo sapiens

<400> SEQUENCE: 680

gaaacugucu ccccggacc                                                19

<210> SEQ ID NO 681
<211> LENGTH: 19
<212> TYPE: RNA
<213> ORGANISM: Homo sapiens

<400> SEQUENCE: 681

acugucuccc cggaccauc                                                19

<210> SEQ ID NO 682
<211> LENGTH: 19
<212> TYPE: RNA
<213> ORGANISM: Homo sapiens

<400> SEQUENCE: 682

cuggugcugc aaggaucuu                                                19

<210> SEQ ID NO 683
<211> LENGTH: 19
<212> TYPE: RNA
<213> ORGANISM: Homo sapiens

<400> SEQUENCE: 683

ggaucuuaug accugcagg                                                19

<210> SEQ ID NO 684
<211> LENGTH: 19
<212> TYPE: RNA
<213> ORGANISM: Homo sapiens

<400> SEQUENCE: 684

ccugcaaaaa uugagcaau                                                19

<210> SEQ ID NO 685
<211> LENGTH: 19
<212> TYPE: RNA
<213> ORGANISM: Homo sapiens

<400> SEQUENCE: 685

aaauugagca augaccgca                                                19

<210> SEQ ID NO 686
<211> LENGTH: 19
<212> TYPE: RNA
<213> ORGANISM: Homo sapiens
```

<400> SEQUENCE: 686
aauugagcaa ugaccgcau 19

<210> SEQ ID NO 687
<211> LENGTH: 19
<212> TYPE: RNA
<213> ORGANISM: Homo sapiens

<400> SEQUENCE: 687
auugagcaau gaccgcauc 19

<210> SEQ ID NO 688
<211> LENGTH: 19
<212> TYPE: RNA
<213> ORGANISM: Homo sapiens

<400> SEQUENCE: 688
uugagcaaug accgcauca 19

<210> SEQ ID NO 689
<211> LENGTH: 19
<212> TYPE: RNA
<213> ORGANISM: Homo sapiens

<400> SEQUENCE: 689
gcggaugaga gagagccca 19

<210> SEQ ID NO 690
<211> LENGTH: 19
<212> TYPE: RNA
<213> ORGANISM: Homo sapiens

<400> SEQUENCE: 690
cagcuuaaca agccugagg 19

<210> SEQ ID NO 691
<211> LENGTH: 19
<212> TYPE: RNA
<213> ORGANISM: Homo sapiens

<400> SEQUENCE: 691
caagccugag gucuuggag 19

<210> SEQ ID NO 692
<211> LENGTH: 19
<212> TYPE: RNA
<213> ORGANISM: Homo sapiens

<400> SEQUENCE: 692
gccugagguc uuggaggug 19

<210> SEQ ID NO 693
<211> LENGTH: 19
<212> TYPE: RNA
<213> ORGANISM: Homo sapiens

<400> SEQUENCE: 693
ccgcccauuc cuguuugcu 19

<210> SEQ ID NO 694
<211> LENGTH: 19
<212> TYPE: RNA

-continued

```
<213> ORGANISM: Homo sapiens

<400> SEQUENCE: 694

cccgcugagc acagcauga                                              19

<210> SEQ ID NO 695
<211> LENGTH: 19
<212> TYPE: RNA
<213> ORGANISM: Homo sapiens

<400> SEQUENCE: 695

cucuucuacu gaagauggu                                              19

<210> SEQ ID NO 696
<211> LENGTH: 19
<212> TYPE: RNA
<213> ORGANISM: Homo sapiens

<400> SEQUENCE: 696

agaauccaag augauuguc                                              19

<210> SEQ ID NO 697
<211> LENGTH: 19
<212> TYPE: RNA
<213> ORGANISM: Homo sapiens

<400> SEQUENCE: 697

gaauccaaga ugauugucc                                              19

<210> SEQ ID NO 698
<211> LENGTH: 19
<212> TYPE: RNA
<213> ORGANISM: Homo sapiens

<400> SEQUENCE: 698

uccaagauga uugucccaa                                              19

<210> SEQ ID NO 699
<211> LENGTH: 19
<212> TYPE: RNA
<213> ORGANISM: Homo sapiens

<400> SEQUENCE: 699

gaugauuguc ccaaagcug                                              19

<210> SEQ ID NO 700
<211> LENGTH: 19
<212> TYPE: RNA
<213> ORGANISM: Homo sapiens

<400> SEQUENCE: 700

agcuggaagg cauaauuac                                              19

<210> SEQ ID NO 701
<211> LENGTH: 19
<212> TYPE: RNA
<213> ORGANISM: Homo sapiens

<400> SEQUENCE: 701

gcuggaaggc auaauuaca                                              19

<210> SEQ ID NO 702
<211> LENGTH: 19
```

<212> TYPE: RNA
<213> ORGANISM: Homo sapiens

<400> SEQUENCE: 702
uauuuggaaa cagcuuggu 19

<210> SEQ ID NO 703
<211> LENGTH: 19
<212> TYPE: RNA
<213> ORGANISM: Homo sapiens

<400> SEQUENCE: 703
acagcuuggu ggugauagu 19

<210> SEQ ID NO 704
<211> LENGTH: 19
<212> TYPE: RNA
<213> ORGANISM: Homo sapiens

<400> SEQUENCE: 704
cagcuuggug gugauaguc 19

<210> SEQ ID NO 705
<211> LENGTH: 19
<212> TYPE: RNA
<213> ORGANISM: Homo sapiens

<400> SEQUENCE: 705
gcugaagacu guggccagu 19

<210> SEQ ID NO 706
<211> LENGTH: 19
<212> TYPE: RNA
<213> ORGANISM: Homo sapiens

<400> SEQUENCE: 706
gacuguggcc aguguuuuu 19

<210> SEQ ID NO 707
<211> LENGTH: 19
<212> TYPE: RNA
<213> ORGANISM: Homo sapiens

<400> SEQUENCE: 707
uuuagcacug gcugacuua 19

<210> SEQ ID NO 708
<211> LENGTH: 19
<212> TYPE: RNA
<213> ORGANISM: Homo sapiens

<400> SEQUENCE: 708
uaccgcuggc ccuuuggca 19

<210> SEQ ID NO 709
<211> LENGTH: 19
<212> TYPE: RNA
<213> ORGANISM: Homo sapiens

<400> SEQUENCE: 709
gauugcuuca gccagcguc 19

<210> SEQ ID NO 710

<211> LENGTH: 19
<212> TYPE: RNA
<213> ORGANISM: Homo sapiens

<400> SEQUENCE: 710
ccuguacgcu aguguguuu 19

<210> SEQ ID NO 711
<211> LENGTH: 19
<212> TYPE: RNA
<213> ORGANISM: Homo sapiens

<400> SEQUENCE: 711
ugaagucccg ccuucgacg 19

<210> SEQ ID NO 712
<211> LENGTH: 19
<212> TYPE: RNA
<213> ORGANISM: Homo sapiens

<400> SEQUENCE: 712
ugcuuguagc caaagucac 19

<210> SEQ ID NO 713
<211> LENGTH: 19
<212> TYPE: RNA
<213> ORGANISM: Homo sapiens

<400> SEQUENCE: 713
agucaccugc aucaucauu 19

<210> SEQ ID NO 714
<211> LENGTH: 19
<212> TYPE: RNA
<213> ORGANISM: Homo sapiens

<400> SEQUENCE: 714
gucaccugca ucaucauuu 19

<210> SEQ ID NO 715
<211> LENGTH: 19
<212> TYPE: RNA
<213> ORGANISM: Homo sapiens

<400> SEQUENCE: 715
aauucaaccc uuccgauag 19

<210> SEQ ID NO 716
<211> LENGTH: 19
<212> TYPE: RNA
<213> ORGANISM: Homo sapiens

<400> SEQUENCE: 716
auucaacccu uccgauagg 19

<210> SEQ ID NO 717
<211> LENGTH: 19
<212> TYPE: RNA
<213> ORGANISM: Homo sapiens

<400> SEQUENCE: 717
uucaacccuu ccgauaggg 19

<210> SEQ ID NO 718
<211> LENGTH: 19
<212> TYPE: RNA
<213> ORGANISM: Homo sapiens

<400> SEQUENCE: 718
aaauauacug gguuuccug 19

<210> SEQ ID NO 719
<211> LENGTH: 19
<212> TYPE: RNA
<213> ORGANISM: Homo sapiens

<400> SEQUENCE: 719
aauauacugg guuuccugu 19

<210> SEQ ID NO 720
<211> LENGTH: 19
<212> TYPE: RNA
<213> ORGANISM: Homo sapiens

<400> SEQUENCE: 720
auauacuggg uuuccuguu 19

<210> SEQ ID NO 721
<211> LENGTH: 19
<212> TYPE: RNA
<213> ORGANISM: Homo sapiens

<400> SEQUENCE: 721
uauacugggu uuccuguuu 19

<210> SEQ ID NO 722
<211> LENGTH: 19
<212> TYPE: RNA
<213> ORGANISM: Homo sapiens

<400> SEQUENCE: 722
ggcccuaaag aaggcuuau 19

<210> SEQ ID NO 723
<211> LENGTH: 19
<212> TYPE: RNA
<213> ORGANISM: Homo sapiens

<400> SEQUENCE: 723
gaaggcuuau gaaauucag 19

<210> SEQ ID NO 724
<211> LENGTH: 19
<212> TYPE: RNA
<213> ORGANISM: Homo sapiens

<400> SEQUENCE: 724
ggcuuaugaa auucagaag 19

<210> SEQ ID NO 725
<211> LENGTH: 19
<212> TYPE: RNA
<213> ORGANISM: Homo sapiens

<400> SEQUENCE: 725
uucagaagaa caaaccaag 19

<210> SEQ ID NO 726
<211> LENGTH: 19
<212> TYPE: RNA
<213> ORGANISM: Homo sapiens

<400> SEQUENCE: 726
cuaggcauca uacgugacu 19

<210> SEQ ID NO 727
<211> LENGTH: 19
<212> TYPE: RNA
<213> ORGANISM: Homo sapiens

<400> SEQUENCE: 727
uugcagauau uguggacac 19

<210> SEQ ID NO 728
<211> LENGTH: 19
<212> TYPE: RNA
<213> ORGANISM: Homo sapiens

<400> SEQUENCE: 728
caauugccug aauccucuu 19

<210> SEQ ID NO 729
<211> LENGTH: 19
<212> TYPE: RNA
<213> ORGANISM: Homo sapiens

<400> SEQUENCE: 729
uugccugaau ccucuuuuu 19

<210> SEQ ID NO 730
<211> LENGTH: 19
<212> TYPE: RNA
<213> ORGANISM: Homo sapiens

<400> SEQUENCE: 730
agauauuuuc uccagcuuc 19

<210> SEQ ID NO 731
<211> LENGTH: 19
<212> TYPE: RNA
<213> ORGANISM: Homo sapiens

<400> SEQUENCE: 731
gauauuuucu ccagcuucu 19

<210> SEQ ID NO 732
<211> LENGTH: 19
<212> TYPE: RNA
<213> ORGANISM: Homo sapiens

<400> SEQUENCE: 732
aauauauucc cccaaaagc 19

<210> SEQ ID NO 733
<211> LENGTH: 19
<212> TYPE: RNA
<213> ORGANISM: Homo sapiens

<400> SEQUENCE: 733
auauauuccc ccaaaagcc 19

<210> SEQ ID NO 734
<211> LENGTH: 19
<212> TYPE: RNA
<213> ORGANISM: Homo sapiens

<400> SEQUENCE: 734
uauauucccc caaaagcca 19

<210> SEQ ID NO 735
<211> LENGTH: 19
<212> TYPE: RNA
<213> ORGANISM: Homo sapiens

<400> SEQUENCE: 735
aagccaaauc ccacucaaa 19

<210> SEQ ID NO 736
<211> LENGTH: 19
<212> TYPE: RNA
<213> ORGANISM: Homo sapiens

<400> SEQUENCE: 736
agccaaaucc cacucaaac 19

<210> SEQ ID NO 737
<211> LENGTH: 19
<212> TYPE: RNA
<213> ORGANISM: Homo sapiens

<400> SEQUENCE: 737
gccaaauccc acucaaacc 19

<210> SEQ ID NO 738
<211> LENGTH: 19
<212> TYPE: RNA
<213> ORGANISM: Homo sapiens

<400> SEQUENCE: 738
aucccacuca aaccuuuca 19

<210> SEQ ID NO 739
<211> LENGTH: 19
<212> TYPE: RNA
<213> ORGANISM: Homo sapiens

<400> SEQUENCE: 739
ucccacucaa accuuucaa 19

<210> SEQ ID NO 740
<211> LENGTH: 19
<212> TYPE: RNA
<213> ORGANISM: Homo sapiens

<400> SEQUENCE: 740
ccuuucaaca aaaaugagc 19

<210> SEQ ID NO 741
<211> LENGTH: 19
<212> TYPE: RNA
<213> ORGANISM: Homo sapiens

<400> SEQUENCE: 741

-continued caaaaaugag cacgcuuuc 19

<210> SEQ ID NO 742
<211> LENGTH: 19
<212> TYPE: RNA
<213> ORGANISM: Homo sapiens

<400> SEQUENCE: 742
aaaugagcac gcuuuccua 19

<210> SEQ ID NO 743
<211> LENGTH: 19
<212> TYPE: RNA
<213> ORGANISM: Homo sapiens

<400> SEQUENCE: 743
aaugagcacg cuuuccuac 19

<210> SEQ ID NO 744
<211> LENGTH: 19
<212> TYPE: RNA
<213> ORGANISM: Homo sapiens

<400> SEQUENCE: 744
augagcacgc uuuccuacc 19

<210> SEQ ID NO 745
<211> LENGTH: 19
<212> TYPE: RNA
<213> ORGANISM: Homo sapiens

<400> SEQUENCE: 745
ugagcacgcu uuccuaccg 19

<210> SEQ ID NO 746
<211> LENGTH: 19
<212> TYPE: RNA
<213> ORGANISM: Homo sapiens

<400> SEQUENCE: 746
uguaagcuca uccaccaag 19

<210> SEQ ID NO 747
<211> LENGTH: 19
<212> TYPE: RNA
<213> ORGANISM: Homo sapiens

<400> SEQUENCE: 747
gcucauccac caagaagcc 19

<210> SEQ ID NO 748
<211> LENGTH: 19
<212> TYPE: RNA
<213> ORGANISM: Homo sapiens

<400> SEQUENCE: 748
gaagccugca ccauguuuu 19

<210> SEQ ID NO 749
<211> LENGTH: 19
<212> TYPE: RNA
<213> ORGANISM: Homo sapiens

<400> SEQUENCE: 749
gccugcacca uguuuugag 19

<210> SEQ ID NO 750
<211> LENGTH: 19
<212> TYPE: RNA
<213> ORGANISM: Homo sapiens

<400> SEQUENCE: 750
uaugaagggc aacuccacc 19

<210> SEQ ID NO 751
<211> LENGTH: 19
<212> TYPE: RNA
<213> ORGANISM: Homo sapiens

<400> SEQUENCE: 751
cuccacccuu gccacuacu 19

<210> SEQ ID NO 752
<211> LENGTH: 19
<212> TYPE: RNA
<213> ORGANISM: Homo sapiens

<400> SEQUENCE: 752
aaacauuacc agcggucuu 19

<210> SEQ ID NO 753
<211> LENGTH: 19
<212> TYPE: RNA
<213> ORGANISM: Homo sapiens

<400> SEQUENCE: 753
aacauuacca gcggucuuc 19

<210> SEQ ID NO 754
<211> LENGTH: 19
<212> TYPE: RNA
<213> ORGANISM: Homo sapiens

<400> SEQUENCE: 754
acauuaccag cggucuuca 19

<210> SEQ ID NO 755
<211> LENGTH: 19
<212> TYPE: RNA
<213> ORGANISM: Homo sapiens

<400> SEQUENCE: 755
cauuaccagc ggucuucac 19

<210> SEQ ID NO 756
<211> LENGTH: 19
<212> TYPE: RNA
<213> ORGANISM: Homo sapiens

<400> SEQUENCE: 756
caucucuggc aacaaugag 19

<210> SEQ ID NO 757
<211> LENGTH: 19
<212> TYPE: RNA
<213> ORGANISM: Homo sapiens

<400> SEQUENCE: 757
caaugagucu accuugaac 19

<210> SEQ ID NO 758
<211> LENGTH: 19
<212> TYPE: RNA
<213> ORGANISM: Homo sapiens

<400> SEQUENCE: 758
ugagucuacc uugaacugu 19

<210> SEQ ID NO 759
<211> LENGTH: 19
<212> TYPE: RNA
<213> ORGANISM: Homo sapiens

<400> SEQUENCE: 759
cuguucacag aaaccauca 19

<210> SEQ ID NO 760
<211> LENGTH: 19
<212> TYPE: RNA
<213> ORGANISM: Homo sapiens

<400> SEQUENCE: 760
ccaucagaua agcauuuag 19

<210> SEQ ID NO 761
<211> LENGTH: 19
<212> TYPE: RNA
<213> ORGANISM: Homo sapiens

<400> SEQUENCE: 761
gcauuuagau gcaauuccu 19

<210> SEQ ID NO 762
<211> LENGTH: 19
<212> TYPE: RNA
<213> ORGANISM: Homo sapiens

<400> SEQUENCE: 762
uauugucgug guuacacug 19

<210> SEQ ID NO 763
<211> LENGTH: 19
<212> TYPE: RNA
<213> ORGANISM: Homo sapiens

<400> SEQUENCE: 763 aagggguccua aaaagguuu 19

<210> SEQ ID NO 764
<211> LENGTH: 19
<212> TYPE: RNA
<213> ORGANISM: Homo sapiens

<400> SEQUENCE: 764
aggguccuaa aaagguuuc 19

<210> SEQ ID NO 765
<211> LENGTH: 19
<212> TYPE: RNA
<213> ORGANISM: Homo sapiens

```
<400> SEQUENCE: 765

ggguccuaaa aagguuucu                                                  19

<210> SEQ ID NO 766
<211> LENGTH: 19
<212> TYPE: RNA
<213> ORGANISM: Homo sapiens

<400> SEQUENCE: 766

gguuucuagc auauacauc                                                  19

<210> SEQ ID NO 767
<211> LENGTH: 19
<212> TYPE: RNA
<213> ORGANISM: Homo sapiens

<400> SEQUENCE: 767

ccucgcugug gcugauuua                                                  19

<210> SEQ ID NO 768
<211> LENGTH: 19
<212> TYPE: RNA
<213> ORGANISM: Homo sapiens

<400> SEQUENCE: 768

ucugucaucu accccuuuc                                                  19

<210> SEQ ID NO 769
<211> LENGTH: 19
<212> TYPE: RNA
<213> ORGANISM: Homo sapiens

<400> SEQUENCE: 769

agaagaaauc ccuggcaag                                                  19

<210> SEQ ID NO 770
<211> LENGTH: 19
<212> TYPE: RNA
<213> ORGANISM: Homo sapiens

<400> SEQUENCE: 770

gaagaaaucc cuggcaagc                                                  19

<210> SEQ ID NO 771
<211> LENGTH: 19
<212> TYPE: RNA
<213> ORGANISM: Homo sapiens

<400> SEQUENCE: 771

gaaaucccug gcaagcauc                                                  19

<210> SEQ ID NO 772
<211> LENGTH: 19
<212> TYPE: RNA
<213> ORGANISM: Homo sapiens

<400> SEQUENCE: 772

aucccuggca agcaucuua                                                  19

<210> SEQ ID NO 773
<211> LENGTH: 19
<212> TYPE: RNA
```

<213> ORGANISM: Homo sapiens

<400> SEQUENCE: 773
ucccuggcaa gcaucuuau 19

<210> SEQ ID NO 774
<211> LENGTH: 19
<212> TYPE: RNA
<213> ORGANISM: Homo sapiens

<400> SEQUENCE: 774
gcaucuuaua uaguucccc 19

<210> SEQ ID NO 775
<211> LENGTH: 19
<212> TYPE: RNA
<213> ORGANISM: Homo sapiens

<400> SEQUENCE: 775
ccauugaaua cuuaggagu 19

<210> SEQ ID NO 776
<211> LENGTH: 19
<212> TYPE: RNA
<213> ORGANISM: Homo sapiens

<400> SEQUENCE: 776
uacuuaggag ugaaugcuu 19

<210> SEQ ID NO 777
<211> LENGTH: 19
<212> TYPE: RNA
<213> ORGANISM: Homo sapiens

<400> SEQUENCE: 777
ugcuugcauu auggcuuuc 19

<210> SEQ ID NO 778
<211> LENGTH: 19
<212> TYPE: RNA
<213> ORGANISM: Homo sapiens

<400> SEQUENCE: 778
auaugcccaa uggucagcu 19

<210> SEQ ID NO 779
<211> LENGTH: 19
<212> TYPE: RNA
<213> ORGANISM: Homo sapiens

<400> SEQUENCE: 779
uaugcccaau ggucagcug 19

<210> SEQ ID NO 780
<211> LENGTH: 19
<212> TYPE: RNA
<213> ORGANISM: Homo sapiens

<400> SEQUENCE: 780
uggucagcug ggauugccu 19

<210> SEQ ID NO 781
<211> LENGTH: 19

<212> TYPE: RNA
<213> ORGANISM: Homo sapiens

<400> SEQUENCE: 781
aacacuuacu gaagacgaa 19

<210> SEQ ID NO 782
<211> LENGTH: 19
<212> TYPE: RNA
<213> ORGANISM: Homo sapiens

<400> SEQUENCE: 782
acacuuacug aagacgaau 19

<210> SEQ ID NO 783
<211> LENGTH: 19
<212> TYPE: RNA
<213> ORGANISM: Homo sapiens

<400> SEQUENCE: 783
cacuuacuga agacgaaua 19

<210> SEQ ID NO 784
<211> LENGTH: 19
<212> TYPE: RNA
<213> ORGANISM: Homo sapiens

<400> SEQUENCE: 784
gacgaauagc uaugggaag 19

<210> SEQ ID NO 785
<211> LENGTH: 19
<212> TYPE: RNA
<213> ORGANISM: Homo sapiens

<400> SEQUENCE: 785
uagcuauggg aagaacagg 19

<210> SEQ ID NO 786
<211> LENGTH: 19
<212> TYPE: RNA
<213> ORGANISM: Homo sapiens

<400> SEQUENCE: 786
gaacaggaua acccgugac 19

<210> SEQ ID NO 787
<211> LENGTH: 19
<212> TYPE: RNA
<213> ORGANISM: Homo sapiens

<400> SEQUENCE: 787
caggauaacc cgugaccaa 19

<210> SEQ ID NO 788
<211> LENGTH: 19
<212> TYPE: RNA
<213> ORGANISM: Homo sapiens

<400> SEQUENCE: 788
cccgugacca aguccugaa 19

<210> SEQ ID NO 789

<211> LENGTH: 19
<212> TYPE: RNA
<213> ORGANISM: Homo sapiens

<400> SEQUENCE: 789
guccugaaga uggcagcug 19

<210> SEQ ID NO 790
<211> LENGTH: 19
<212> TYPE: RNA
<213> ORGANISM: Homo sapiens

<400> SEQUENCE: 790
gauggcagcu gcuguuguu 19

<210> SEQ ID NO 791
<211> LENGTH: 19
<212> TYPE: RNA
<213> ORGANISM: Homo sapiens

<400> SEQUENCE: 791
uagcugcgaa guuauagca 19

<210> SEQ ID NO 792
<211> LENGTH: 19
<212> TYPE: RNA
<213> ORGANISM: Homo sapiens

<400> SEQUENCE: 792
guuauagcag ucauugacc 19

<210> SEQ ID NO 793
<211> LENGTH: 19
<212> TYPE: RNA
<213> ORGANISM: Homo sapiens

<400> SEQUENCE: 793
cagcugcguu aauccguuu 19

<210> SEQ ID NO 794
<211> LENGTH: 19
<212> TYPE: RNA
<213> ORGANISM: Homo sapiens

<400> SEQUENCE: 794
accgguucca acagaagcu 19

<210> SEQ ID NO 795
<211> LENGTH: 19
<212> TYPE: RNA
<213> ORGANISM: Homo sapiens

<400> SEQUENCE: 795
ccgguuccaa cagaagcuc 19

<210> SEQ ID NO 796
<211> LENGTH: 19
<212> TYPE: RNA
<213> ORGANISM: Homo sapiens

<400> SEQUENCE: 796
cagaagcucc gcagugugu 19

<210> SEQ ID NO 797
<211> LENGTH: 19
<212> TYPE: RNA
<213> ORGANISM: Homo sapiens

<400> SEQUENCE: 797
gcuccgcagu guguuuagg 19

<210> SEQ ID NO 798
<211> LENGTH: 19
<212> TYPE: RNA
<213> ORGANISM: Homo sapiens

<400> SEQUENCE: 798
uuacuuggcu ccaagggaa 19

<210> SEQ ID NO 799
<211> LENGTH: 19
<212> TYPE: RNA
<213> ORGANISM: Homo sapiens

<400> SEQUENCE: 799
gggaaaagag agaguaugu 19

<210> SEQ ID NO 800
<211> LENGTH: 19
<212> TYPE: RNA
<213> ORGANISM: Homo sapiens

<400> SEQUENCE: 800
aagagagagu augucuugc 19

<210> SEQ ID NO 801
<211> LENGTH: 19
<212> TYPE: RNA
<213> ORGANISM: Homo sapiens

<400> SEQUENCE: 801
agagagagua ugucuugcc 19

<210> SEQ ID NO 802
<211> LENGTH: 19
<212> TYPE: RNA
<213> ORGANISM: Homo sapiens

<400> SEQUENCE: 802
gagagaguau gucuugccg 19

<210> SEQ ID NO 803
<211> LENGTH: 19
<212> TYPE: RNA
<213> ORGANISM: Homo sapiens

<400> SEQUENCE: 803
aagcaguucu cuuagagaa 19

<210> SEQ ID NO 804
<211> LENGTH: 19
<212> TYPE: RNA
<213> ORGANISM: Homo sapiens

<400> SEQUENCE: 804
agcaguucuc uuagagaaa 19

<210> SEQ ID NO 805
<211> LENGTH: 19
<212> TYPE: RNA
<213> ORGANISM: Homo sapiens

<400> SEQUENCE: 805
gcaguucucu uagagaaau 19

<210> SEQ ID NO 806
<211> LENGTH: 19
<212> TYPE: RNA
<213> ORGANISM: Homo sapiens

<400> SEQUENCE: 806
auggagaccu uugugucuu 19

<210> SEQ ID NO 807
<211> LENGTH: 19
<212> TYPE: RNA
<213> ORGANISM: Homo sapiens

<400> SEQUENCE: 807
uggagaccuu ugugucuua 19

<210> SEQ ID NO 808
<211> LENGTH: 19
<212> TYPE: RNA
<213> ORGANISM: Homo sapiens

<400> SEQUENCE: 808
cuuuucugcu gacgaggcc 19

<210> SEQ ID NO 809
<211> LENGTH: 19
<212> TYPE: RNA
<213> ORGANISM: Homo sapiens

<400> SEQUENCE: 809
caggugcugu uccagagcg 19

<210> SEQ ID NO 810
<211> LENGTH: 19
<212> TYPE: RNA
<213> ORGANISM: Homo sapiens

<400> SEQUENCE: 810
caucaccgcg gagaaugca 19

<210> SEQ ID NO 811
<211> LENGTH: 19
<212> TYPE: RNA
<213> ORGANISM: Homo sapiens

<400> SEQUENCE: 811
ugcaaggcgc caggaggaa 19

<210> SEQ ID NO 812
<211> LENGTH: 19
<212> TYPE: RNA
<213> ORGANISM: Homo sapiens

<400> SEQUENCE: 812
ggccaaggag cuguaugaa 19

<210> SEQ ID NO 813
<211> LENGTH: 19
<212> TYPE: RNA
<213> ORGANISM: Homo sapiens

<400> SEQUENCE: 813
ggagcuguau gaaccgauc 19

<210> SEQ ID NO 814
<211> LENGTH: 19
<212> TYPE: RNA
<213> ORGANISM: Homo sapiens

<400> SEQUENCE: 814
ccgaucuggc agaacuuca 19

<210> SEQ ID NO 815
<211> LENGTH: 19
<212> TYPE: RNA
<213> ORGANISM: Homo sapiens

<400> SEQUENCE: 815
cgcccugcua agcaacaug 19

<210> SEQ ID NO 816
<211> LENGTH: 19
<212> TYPE: RNA
<213> ORGANISM: Homo sapiens

<400> SEQUENCE: 816
gcaacaugag caggaucua 19

<210> SEQ ID NO 817
<211> LENGTH: 19
<212> TYPE: RNA
<213> ORGANISM: Homo sapiens

<400> SEQUENCE: 817
caugagcagg aucuacucc 19

<210> SEQ ID NO 818
<211> LENGTH: 19
<212> TYPE: RNA
<213> ORGANISM: Homo sapiens

<400> SEQUENCE: 818
ggucugccuc cccaacaag 19

<210> SEQ ID NO 819
<211> LENGTH: 19
<212> TYPE: RNA
<213> ORGANISM: Homo sapiens

<400> SEQUENCE: 819
caagacugcc accugcugg 19

<210> SEQ ID NO 820
<211> LENGTH: 19
<212> TYPE: RNA
<213> ORGANISM: Homo sapiens

<400> SEQUENCE: 820
cauccuggcu uccucgcga 19

<210> SEQ ID NO 821
<211> LENGTH: 19
<212> TYPE: RNA
<213> ORGANISM: Homo sapiens

<400> SEQUENCE: 821
gcuacgccau gcuccuguu 19

<210> SEQ ID NO 822
<211> LENGTH: 19
<212> TYPE: RNA
<213> ORGANISM: Homo sapiens

<400> SEQUENCE: 822
accgcuguac gaggauuuc 19

<210> SEQ ID NO 823
<211> LENGTH: 19
<212> TYPE: RNA
<213> ORGANISM: Homo sapiens

<400> SEQUENCE: 823
ccgcuguacg aggauuuca 19

<210> SEQ ID NO 824
<211> LENGTH: 19
<212> TYPE: RNA
<213> ORGANISM: Homo sapiens

<400> SEQUENCE: 824
ugaagccuac aagcaggac 19

<210> SEQ ID NO 825
<211> LENGTH: 19
<212> TYPE: RNA
<213> ORGANISM: Homo sapiens

<400> SEQUENCE: 825
gccuacaagc aggacggcu 19

<210> SEQ ID NO 826
<211> LENGTH: 19
<212> TYPE: RNA
<213> ORGANISM: Homo sapiens

<400> SEQUENCE: 826
gcaggacggc uucacagac 19

<210> SEQ ID NO 827
<211> LENGTH: 19
<212> TYPE: RNA
<213> ORGANISM: Homo sapiens

<400> SEQUENCE: 827
caccucuacc aacagcuag 19

<210> SEQ ID NO 828
<211> LENGTH: 19
<212> TYPE: RNA
<213> ORGANISM: Homo sapiens

<400> SEQUENCE: 828
cagcuagagc cccucuacc 19

<210> SEQ ID NO 829
<211> LENGTH: 19
<212> TYPE: RNA
<213> ORGANISM: Homo sapiens

<400> SEQUENCE: 829
aacaucuacg acauggugg 19

<210> SEQ ID NO 830
<211> LENGTH: 19
<212> TYPE: RNA
<213> ORGANISM: Homo sapiens

<400> SEQUENCE: 830
acaucuacga caugguggu 19

<210> SEQ ID NO 831
<211> LENGTH: 19
<212> TYPE: RNA
<213> ORGANISM: Homo sapiens

<400> SEQUENCE: 831
caucuacgac augguggug 19

<210> SEQ ID NO 832
<211> LENGTH: 19
<212> TYPE: RNA
<213> ORGANISM: Homo sapiens

<400> SEQUENCE: 832
gcccaaccuc gaugucacc 19

<210> SEQ ID NO 833
<211> LENGTH: 19
<212> TYPE: RNA
<213> ORGANISM: Homo sapiens

<400> SEQUENCE: 833
ccucgauguc accaguacu 19

<210> SEQ ID NO 834
<211> LENGTH: 19
<212> TYPE: RNA
<213> ORGANISM: Homo sapiens

<400> SEQUENCE: 834
gggucgaugc uggagaagc 19

<210> SEQ ID NO 835
<211> LENGTH: 19
<212> TYPE: RNA
<213> ORGANISM: Homo sapiens

<400> SEQUENCE: 835
caggaaagac uucaggauc 19

<210> SEQ ID NO 836
<211> LENGTH: 19
<212> TYPE: RNA
<213> ORGANISM: Homo sapiens

<400> SEQUENCE: 836
agacuucagg aucaagcag 19

<210> SEQ ID NO 837
<211> LENGTH: 19
<212> TYPE: RNA
<213> ORGANISM: Homo sapiens

<400> SEQUENCE: 837
gacuucagga ucaagcagu 19

<210> SEQ ID NO 838
<211> LENGTH: 19
<212> TYPE: RNA
<213> ORGANISM: Homo sapiens

<400> SEQUENCE: 838
caucugcaca aaaucggcc 19

<210> SEQ ID NO 839
<211> LENGTH: 19
<212> TYPE: RNA
<213> ORGANISM: Homo sapiens

<400> SEQUENCE: 839
aaucggccug cuggaccgu 19

<210> SEQ ID NO 840
<211> LENGTH: 19
<212> TYPE: RNA
<213> ORGANISM: Homo sapiens

<400> SEQUENCE: 840
ugacacggaa agugacauc 19

<210> SEQ ID NO 841
<211> LENGTH: 19
<212> TYPE: RNA
<213> ORGANISM: Homo sapiens

<400> SEQUENCE: 841
agugacauca auuacuugc 19

<210> SEQ ID NO 842
<211> LENGTH: 19
<212> TYPE: RNA
<213> ORGANISM: Homo sapiens

<400> SEQUENCE: 842
gugacaucaa uuacuugcu 19

<210> SEQ ID NO 843
<211> LENGTH: 19
<212> TYPE: RNA
<213> ORGANISM: Homo sapiens

<400> SEQUENCE: 843
auggcacugg aaaaaauug 19

<210> SEQ ID NO 844
<211> LENGTH: 19
<212> TYPE: RNA
<213> ORGANISM: Homo sapiens

<400> SEQUENCE: 844
uggcacugga aaaaauugc 19

<210> SEQ ID NO 845
<211> LENGTH: 19
<212> TYPE: RNA
<213> ORGANISM: Homo sapiens

<400> SEQUENCE: 845
aaaauugccu uccugcccu 19

<210> SEQ ID NO 846
<211> LENGTH: 19
<212> TYPE: RNA
<213> ORGANISM: Homo sapiens

<400> SEQUENCE: 846
aaauugccuu ccugcccuu 19

<210> SEQ ID NO 847
<211> LENGTH: 19
<212> TYPE: RNA
<213> ORGANISM: Homo sapiens

<400> SEQUENCE: 847
aauugccuuc cugcccuuu 19

<210> SEQ ID NO 848
<211> LENGTH: 19
<212> TYPE: RNA
<213> ORGANISM: Homo sapiens

<400> SEQUENCE: 848
auugccuucc ugcccuuug 19

<210> SEQ ID NO 849
<211> LENGTH: 19
<212> TYPE: RNA
<213> ORGANISM: Homo sapiens

<400> SEQUENCE: 849
uugccuuccu gcccuuugg 19

<210> SEQ ID NO 850
<211> LENGTH: 19
<212> TYPE: RNA
<213> ORGANISM: Homo sapiens

<400> SEQUENCE: 850
cuucgacugg ugguaucuu 19

<210> SEQ ID NO 851
<211> LENGTH: 19
<212> TYPE: RNA
<213> ORGANISM: Homo sapiens

<400> SEQUENCE: 851
ccaaguauca ggggaucug 19

<210> SEQ ID NO 852
<211> LENGTH: 19
<212> TYPE: RNA

```
<213> ORGANISM: Homo sapiens

<400> SEQUENCE: 852

guaucagggg aucuguccu                                                   19

<210> SEQ ID NO 853
<211> LENGTH: 19
<212> TYPE: RNA
<213> ORGANISM: Homo sapiens

<400> SEQUENCE: 853

acgaaaccca cuuugaugc                                                   19

<210> SEQ ID NO 854
<211> LENGTH: 19
<212> TYPE: RNA
<213> ORGANISM: Homo sapiens

<400> SEQUENCE: 854

cgaaacccac uuugaugcu                                                   19

<210> SEQ ID NO 855
<211> LENGTH: 19
<212> TYPE: RNA
<213> ORGANISM: Homo sapiens

<400> SEQUENCE: 855

acccacuuug augcuggag                                                   19

<210> SEQ ID NO 856
<211> LENGTH: 19
<212> TYPE: RNA
<213> ORGANISM: Homo sapiens

<400> SEQUENCE: 856

cccacuuuga ugcuggagc                                                   19

<210> SEQ ID NO 857
<211> LENGTH: 19
<212> TYPE: RNA
<213> ORGANISM: Homo sapiens

<400> SEQUENCE: 857

guuucauguu ccaaaugug                                                   19

<210> SEQ ID NO 858
<211> LENGTH: 19
<212> TYPE: RNA
<213> ORGANISM: Homo sapiens

<400> SEQUENCE: 858

augugacacc auacaucag                                                   19

<210> SEQ ID NO 859
<211> LENGTH: 19
<212> TYPE: RNA
<213> ORGANISM: Homo sapiens

<400> SEQUENCE: 859

ugugacacca uacaucagg                                                   19

<210> SEQ ID NO 860
<211> LENGTH: 19
```

<212> TYPE: RNA
<213> ORGANISM: Homo sapiens

<400> SEQUENCE: 860
ggacaugguc ggcuuagau 19

<210> SEQ ID NO 861
<211> LENGTH: 19
<212> TYPE: RNA
<213> ORGANISM: Homo sapiens

<400> SEQUENCE: 861
guacuuccag ccagucacc 19

<210> SEQ ID NO 862
<211> LENGTH: 19
<212> TYPE: RNA
<213> ORGANISM: Homo sapiens

<400> SEQUENCE: 862
cuacccggag ggcauagac 19

<210> SEQ ID NO 863
<211> LENGTH: 19
<212> TYPE: RNA
<213> ORGANISM: Homo sapiens

<400> SEQUENCE: 863
guuuguggag gaauaugac 19

<210> SEQ ID NO 864
<211> LENGTH: 19
<212> TYPE: RNA
<213> ORGANISM: Homo sapiens

<400> SEQUENCE: 864
uaugaccgga caucccagg 19

<210> SEQ ID NO 865
<211> LENGTH: 19
<212> TYPE: RNA
<213> ORGANISM: Homo sapiens

<400> SEQUENCE: 865
cgaguaugcc gaggccaac 19

<210> SEQ ID NO 866
<211> LENGTH: 19
<212> TYPE: RNA
<213> ORGANISM: Homo sapiens

<400> SEQUENCE: 866
cuggaacuac aacaccaac 19

<210> SEQ ID NO 867
<211> LENGTH: 19
<212> TYPE: RNA
<213> ORGANISM: Homo sapiens

<400> SEQUENCE: 867
cuacaacacc aacaucacc 19

<210> SEQ ID NO 868

<211> LENGTH: 19
<212> TYPE: RNA
<213> ORGANISM: Homo sapiens

<400> SEQUENCE: 868
caccaacauc accacagag 19

<210> SEQ ID NO 869
<211> LENGTH: 19
<212> TYPE: RNA
<213> ORGANISM: Homo sapiens

<400> SEQUENCE: 869
caucaccaca gagaccagc 19

<210> SEQ ID NO 870
<211> LENGTH: 19
<212> TYPE: RNA
<213> ORGANISM: Homo sapiens

<400> SEQUENCE: 870
gauucugcug cagaagaac 19

<210> SEQ ID NO 871
<211> LENGTH: 19
<212> TYPE: RNA
<213> ORGANISM: Homo sapiens

<400> SEQUENCE: 871
gaacaugcaa auagccaac 19

<210> SEQ ID NO 872
<211> LENGTH: 19
<212> TYPE: RNA
<213> ORGANISM: Homo sapiens

<400> SEQUENCE: 872
caugcaaaua gccaaccac 19

<210> SEQ ID NO 873
<211> LENGTH: 19
<212> TYPE: RNA
<213> ORGANISM: Homo sapiens

<400> SEQUENCE: 873
auagccaacc acacccuga 19

<210> SEQ ID NO 874
<211> LENGTH: 19
<212> TYPE: RNA
<213> ORGANISM: Homo sapiens

<400> SEQUENCE: 874
uagccaacca cacccugaa 19

<210> SEQ ID NO 875
<211> LENGTH: 19
<212> TYPE: RNA
<213> ORGANISM: Homo sapiens

<400> SEQUENCE: 875
ccacacccug aaguacggc 19

<210> SEQ ID NO 876
<211> LENGTH: 19
<212> TYPE: RNA
<213> ORGANISM: Homo sapiens

<400> SEQUENCE: 876
guuugaugug aaccaguug 19

<210> SEQ ID NO 877
<211> LENGTH: 19
<212> TYPE: RNA
<213> ORGANISM: Homo sapiens

<400> SEQUENCE: 877
ccaguugcag aacaccacu 19

<210> SEQ ID NO 878
<211> LENGTH: 19
<212> TYPE: RNA
<213> ORGANISM: Homo sapiens

<400> SEQUENCE: 878
caccacuauc aagcggauc 19

<210> SEQ ID NO 879
<211> LENGTH: 19
<212> TYPE: RNA
<213> ORGANISM: Homo sapiens

<400> SEQUENCE: 879
gcggaucaua aagaagguu 19

<210> SEQ ID NO 880
<211> LENGTH: 19
<212> TYPE: RNA
<213> ORGANISM: Homo sapiens

<400> SEQUENCE: 880
agaagguuca ggaccuaga 19

<210> SEQ ID NO 881
<211> LENGTH: 19
<212> TYPE: RNA
<213> ORGANISM: Homo sapiens

<400> SEQUENCE: 881
gaagguucag gaccuagaa 19

<210> SEQ ID NO 882
<211> LENGTH: 19
<212> TYPE: RNA
<213> ORGANISM: Homo sapiens

<400> SEQUENCE: 882
gguucaggac cuagaacgg 19

<210> SEQ ID NO 883
<211> LENGTH: 19
<212> TYPE: RNA
<213> ORGANISM: Homo sapiens

<400> SEQUENCE: 883
caagauccug uuggauaug 19

<210> SEQ ID NO 884
<211> LENGTH: 19
<212> TYPE: RNA
<213> ORGANISM: Homo sapiens

<400> SEQUENCE: 884
gauccuguug gauauggaa 19

<210> SEQ ID NO 885
<211> LENGTH: 19
<212> TYPE: RNA
<213> ORGANISM: Homo sapiens

<400> SEQUENCE: 885
accaccuaca gcguggcca 19

<210> SEQ ID NO 886
<211> LENGTH: 19
<212> TYPE: RNA
<213> ORGANISM: Homo sapiens

<400> SEQUENCE: 886
auaugaagac cuguuaugg 19

<210> SEQ ID NO 887
<211> LENGTH: 19
<212> TYPE: RNA
<213> ORGANISM: Homo sapiens

<400> SEQUENCE: 887
uaugaagacc uguuauggg 19

<210> SEQ ID NO 888
<211> LENGTH: 19
<212> TYPE: RNA
<213> ORGANISM: Homo sapiens

<400> SEQUENCE: 888
gaccuguuau gggcauggg 19

<210> SEQ ID NO 889
<211> LENGTH: 19
<212> TYPE: RNA
<213> ORGANISM: Homo sapiens

<400> SEQUENCE: 889
auacguggaa cucaucaac 19

<210> SEQ ID NO 890
<211> LENGTH: 19
<212> TYPE: RNA
<213> ORGANISM: Homo sapiens

<400> SEQUENCE: 890
uacguggaac ucaucaacc 19

<210> SEQ ID NO 891
<211> LENGTH: 19
<212> TYPE: RNA
<213> ORGANISM: Homo sapiens

<400> SEQUENCE: 891
cucaucaacc aggcugccc 19

<210> SEQ ID NO 892
<211> LENGTH: 19
<212> TYPE: RNA
<213> ORGANISM: Homo sapiens

<400> SEQUENCE: 892
uggcuaugua gaugcaggg 19

<210> SEQ ID NO 893
<211> LENGTH: 19
<212> TYPE: RNA
<213> ORGANISM: Homo sapiens

<400> SEQUENCE: 893
caucuaugac uugguggug 19

<210> SEQ ID NO 894
<211> LENGTH: 19
<212> TYPE: RNA
<213> ORGANISM: Homo sapiens

<400> SEQUENCE: 894
ggaggcugau gauuucuuc 19

<210> SEQ ID NO 895
<211> LENGTH: 19
<212> TYPE: RNA
<213> ORGANISM: Homo sapiens

<400> SEQUENCE: 895
caagucgaug cuggagaag 19

<210> SEQ ID NO 896
<211> LENGTH: 19
<212> TYPE: RNA
<213> ORGANISM: Homo sapiens

<400> SEQUENCE: 896
gucgaugcug gagaagcca 19

<210> SEQ ID NO 897
<211> LENGTH: 19
<212> TYPE: RNA
<213> ORGANISM: Homo sapiens

<400> SEQUENCE: 897
cggcaaggac uuccggauc 19

<210> SEQ ID NO 898
<211> LENGTH: 19
<212> TYPE: RNA
<213> ORGANISM: Homo sapiens

<400> SEQUENCE: 898
ggacuuccgg aucaagcag 19

<210> SEQ ID NO 899
<211> LENGTH: 19
<212> TYPE: RNA
<213> ORGANISM: Homo sapiens

<400> SEQUENCE: 899
gcagugcacc accgugaac 19

<210> SEQ ID NO 900
<211> LENGTH: 19
<212> TYPE: RNA
<213> ORGANISM: Homo sapiens

<400> SEQUENCE: 900
cuuggaggac cugguggug 19

<210> SEQ ID NO 901
<211> LENGTH: 19
<212> TYPE: RNA
<213> ORGANISM: Homo sapiens

<400> SEQUENCE: 901
augggccaca uccaguauu 19

<210> SEQ ID NO 902
<211> LENGTH: 19
<212> TYPE: RNA
<213> ORGANISM: Homo sapiens

<400> SEQUENCE: 902
ugggccacau ccaguauuu 19

<210> SEQ ID NO 903
<211> LENGTH: 19
<212> TYPE: RNA
<213> ORGANISM: Homo sapiens

<400> SEQUENCE: 903
agacuuaccu guggccuug 19

<210> SEQ ID NO 904
<211> LENGTH: 19
<212> TYPE: RNA
<213> ORGANISM: Homo sapiens

<400> SEQUENCE: 904
gacuuaccug uggccuuga 19

<210> SEQ ID NO 905
<211> LENGTH: 19
<212> TYPE: RNA
<213> ORGANISM: Homo sapiens

<400> SEQUENCE: 905
gcaccugcac agucucaac 19

<210> SEQ ID NO 906
<211> LENGTH: 19
<212> TYPE: RNA
<213> ORGANISM: Homo sapiens

<400> SEQUENCE: 906
ccugcugagc agugagggu 19

<210> SEQ ID NO 907
<211> LENGTH: 19
<212> TYPE: RNA
<213> ORGANISM: Homo sapiens

<400> SEQUENCE: 907
cuuucugaug aagauggcc 19

<210> SEQ ID NO 908
<211> LENGTH: 19
<212> TYPE: RNA
<213> ORGANISM: Homo sapiens

<400> SEQUENCE: 908
gauggcccuu gacaagauc 19

<210> SEQ ID NO 909
<211> LENGTH: 19
<212> TYPE: RNA
<213> ORGANISM: Homo sapiens

<400> SEQUENCE: 909
gaucgccuuu auccccuuc 19

<210> SEQ ID NO 910
<211> LENGTH: 19
<212> TYPE: RNA
<213> ORGANISM: Homo sapiens

<400> SEQUENCE: 910
gcaucaccaa ggagaacua 19

<210> SEQ ID NO 911
<211> LENGTH: 19
<212> TYPE: RNA
<213> ORGANISM: Homo sapiens

<400> SEQUENCE: 911
ggagaacuau aaccaggag 19

<210> SEQ ID NO 912
<211> LENGTH: 19
<212> TYPE: RNA
<213> ORGANISM: Homo sapiens

<400> SEQUENCE: 912
cuauaaccag gaguggugg 19

<210> SEQ ID NO 913
<211> LENGTH: 19
<212> TYPE: RNA
<213> ORGANISM: Homo sapiens

<400> SEQUENCE: 913
ggugacuuug acccagggg 19

<210> SEQ ID NO 914
<211> LENGTH: 19
<212> TYPE: RNA
<213> ORGANISM: Homo sapiens

<400> SEQUENCE: 914
guuccacauu ccuucuagc 19

<210> SEQ ID NO 915
<211> LENGTH: 19
<212> TYPE: RNA
<213> ORGANISM: Homo sapiens

<400> SEQUENCE: 915
gugugacauc uaccagucc 19

<210> SEQ ID NO 916
<211> LENGTH: 19
<212> TYPE: RNA
<213> ORGANISM: Homo sapiens

<400> SEQUENCE: 916
gccaugcagc ugaucacgg 19

<210> SEQ ID NO 917
<211> LENGTH: 19
<212> TYPE: RNA
<213> ORGANISM: Homo sapiens

<400> SEQUENCE: 917
cgagcugcau ggggagaag 19

<210> SEQ ID NO 918
<211> LENGTH: 19
<212> TYPE: RNA
<213> ORGANISM: Homo sapiens

<400> SEQUENCE: 918
caggugacag ucacccaug 19

<210> SEQ ID NO 919
<211> LENGTH: 19
<212> TYPE: RNA
<213> ORGANISM: Homo sapiens

<400> SEQUENCE: 919
gcagccaggc aacaaccag 19

<210> SEQ ID NO 920
<211> LENGTH: 19
<212> TYPE: RNA
<213> ORGANISM: Homo sapiens

<400> SEQUENCE: 920
caaccagcag ccagacaac 19

<210> SEQ ID NO 921
<211> LENGTH: 19
<212> TYPE: RNA
<213> ORGANISM: Homo sapiens

<400> SEQUENCE: 921
ccagcagcca gacaaccac 19

<210> SEQ ID NO 922
<211> LENGTH: 19
<212> TYPE: RNA
<213> ORGANISM: Homo sapiens

<400> SEQUENCE: 922
accuggugac ugaugaggc 19

<210> SEQ ID NO 923
<211> LENGTH: 19
<212> TYPE: RNA
<213> ORGANISM: Homo sapiens

<400> SEQUENCE: 923
ccuggugacu gaugaggcu 19

<210> SEQ ID NO 924
<211> LENGTH: 19
<212> TYPE: RNA
<213> ORGANISM: Homo sapiens

<400> SEQUENCE: 924
cuggacgccg aacuccgau 19

<210> SEQ ID NO 925
<211> LENGTH: 19
<212> TYPE: RNA
<213> ORGANISM: Homo sapiens

<400> SEQUENCE: 925
cuccgaugac uucuacaau 19

<210> SEQ ID NO 926
<211> LENGTH: 19
<212> TYPE: RNA
<213> ORGANISM: Homo sapiens

<400> SEQUENCE: 926
ugagaccgag accaagauc 19

<210> SEQ ID NO 927
<211> LENGTH: 19
<212> TYPE: RNA
<213> ORGANISM: Homo sapiens

<400> SEQUENCE: 927
gaucuuccug caguuuuau 19

<210> SEQ ID NO 928
<211> LENGTH: 19
<212> TYPE: RNA
<213> ORGANISM: Homo sapiens

<400> SEQUENCE: 928
acagggauuu gggaccaug 19

<210> SEQ ID NO 929
<211> LENGTH: 19
<212> TYPE: RNA
<213> ORGANISM: Homo sapiens

<400> SEQUENCE: 929
cagggauuug ggaccaugg 19

<210> SEQ ID NO 930
<211> LENGTH: 19
<212> TYPE: RNA
<213> ORGANISM: Homo sapiens

<400> SEQUENCE: 930
gcaagaggaa caagggaag 19

<210> SEQ ID NO 931
<211> LENGTH: 19
<212> TYPE: RNA

<213> ORGANISM: Homo sapiens

<400> SEQUENCE: 931
gaggaacaag ggaagcccc 19

<210> SEQ ID NO 932
<211> LENGTH: 19
<212> TYPE: RNA
<213> ORGANISM: Homo sapiens

<400> SEQUENCE: 932
caagggaagc cccagugua 19

<210> SEQ ID NO 933
<211> LENGTH: 19
<212> TYPE: RNA
<213> ORGANISM: Homo sapiens

<400> SEQUENCE: 933
gggaagcccc aguguacau 19

<210> SEQ ID NO 934
<211> LENGTH: 19
<212> TYPE: RNA
<213> ORGANISM: Homo sapiens

<400> SEQUENCE: 934
gccccagugu acaugucaa 19

<210> SEQ ID NO 935
<211> LENGTH: 19
<212> TYPE: RNA
<213> ORGANISM: Homo sapiens

<400> SEQUENCE: 935
agagggcugc aagcucugg 19

<210> SEQ ID NO 936
<211> LENGTH: 19
<212> TYPE: RNA
<213> ORGANISM: Homo sapiens

<400> SEQUENCE: 936
gcccuaaacu uccuccagc 19

<210> SEQ ID NO 937
<211> LENGTH: 19
<212> TYPE: RNA
<213> ORGANISM: Homo sapiens

<400> SEQUENCE: 937
acuuccucca gcugcacaa 19

<210> SEQ ID NO 938
<211> LENGTH: 19
<212> TYPE: RNA
<213> ORGANISM: Homo sapiens

<400> SEQUENCE: 938
cuuccuccag cugcacaag 19

<210> SEQ ID NO 939
<211> LENGTH: 19

<212> TYPE: RNA
<213> ORGANISM: Homo sapiens

<400> SEQUENCE: 939
ggacauggag aggucccag 19

<210> SEQ ID NO 940
<211> LENGTH: 19
<212> TYPE: RNA
<213> ORGANISM: Homo sapiens

<400> SEQUENCE: 940
gcucuuccug gcuccuucu 19

<210> SEQ ID NO 941
<211> LENGTH: 19
<212> TYPE: RNA
<213> ORGANISM: Homo sapiens

<400> SEQUENCE: 941
cugcugcuca guccaccau 19

<210> SEQ ID NO 942
<211> LENGTH: 19
<212> TYPE: RNA
<213> ORGANISM: Homo sapiens

<400> SEQUENCE: 942
caggccaaga cauuuuugg 19

<210> SEQ ID NO 943
<211> LENGTH: 19
<212> TYPE: RNA
<213> ORGANISM: Homo sapiens

<400> SEQUENCE: 943
guuuaaccac gaagccgaa 19

<210> SEQ ID NO 944
<211> LENGTH: 19
<212> TYPE: RNA
<213> ORGANISM: Homo sapiens

<400> SEQUENCE: 944
ccacgaagcc gaagaccug 19

<210> SEQ ID NO 945
<211> LENGTH: 19
<212> TYPE: RNA
<213> ORGANISM: Homo sapiens

<400> SEQUENCE: 945
gccgaagacc uguucuauc 19

<210> SEQ ID NO 946
<211> LENGTH: 19
<212> TYPE: RNA
<213> ORGANISM: Homo sapiens

<400> SEQUENCE: 946
gaccuguucu aucaaaguu 19

<210> SEQ ID NO 947

<211> LENGTH: 19
<212> TYPE: RNA
<213> ORGANISM: Homo sapiens

<400> SEQUENCE: 947
aguucacuug cuucuugga 19

<210> SEQ ID NO 948
<211> LENGTH: 19
<212> TYPE: RNA
<213> ORGANISM: Homo sapiens

<400> SEQUENCE: 948
guucacuugc uucuuggaa 19

<210> SEQ ID NO 949
<211> LENGTH: 19
<212> TYPE: RNA
<213> ORGANISM: Homo sapiens

<400> SEQUENCE: 949
caccaauauu acugaagag 19

<210> SEQ ID NO 950
<211> LENGTH: 19
<212> TYPE: RNA
<213> ORGANISM: Homo sapiens

<400> SEQUENCE: 950
gagaaugucc aaaacauga 19

<210> SEQ ID NO 951
<211> LENGTH: 19
<212> TYPE: RNA
<213> ORGANISM: Homo sapiens

<400> SEQUENCE: 951
aacaugaaua augcugggg 19

<210> SEQ ID NO 952
<211> LENGTH: 19
<212> TYPE: RNA
<213> ORGANISM: Homo sapiens

<400> SEQUENCE: 952
acaugaauaa ugcugggga 19

<210> SEQ ID NO 953
<211> LENGTH: 19
<212> TYPE: RNA
<213> ORGANISM: Homo sapiens

<400> SEQUENCE: 953
caugaauaau gcuggggac 19

<210> SEQ ID NO 954
<211> LENGTH: 19
<212> TYPE: RNA
<213> ORGANISM: Homo sapiens

<400> SEQUENCE: 954
uaaugcuggg gacaaaugg 19

<210> SEQ ID NO 955
<211> LENGTH: 19
<212> TYPE: RNA
<213> ORGANISM: Homo sapiens

<400> SEQUENCE: 955
ugcuggggac aaaugggucu 19

<210> SEQ ID NO 956
<211> LENGTH: 19
<212> TYPE: RNA
<213> ORGANISM: Homo sapiens

<400> SEQUENCE: 956
auggucugcc uuuuuaaag 19

<210> SEQ ID NO 957
<211> LENGTH: 19
<212> TYPE: RNA
<213> ORGANISM: Homo sapiens

<400> SEQUENCE: 957
uggucugccu uuuuaaagg 19

<210> SEQ ID NO 958
<211> LENGTH: 19
<212> TYPE: RNA
<213> ORGANISM: Homo sapiens

<400> SEQUENCE: 958
aggaacaguc cacacuugc 19

<210> SEQ ID NO 959
<211> LENGTH: 19
<212> TYPE: RNA
<213> ORGANISM: Homo sapiens

<400> SEQUENCE: 959
ggaacagucc acacuugcc 19

<210> SEQ ID NO 960
<211> LENGTH: 19
<212> TYPE: RNA
<213> ORGANISM: Homo sapiens

<400> SEQUENCE: 960
caguccacac uugcccaaa 19

<210> SEQ ID NO 961
<211> LENGTH: 19
<212> TYPE: RNA
<213> ORGANISM: Homo sapiens

<400> SEQUENCE: 961
gaaauucaga aucucacag 19

<210> SEQ ID NO 962
<211> LENGTH: 19
<212> TYPE: RNA
<213> ORGANISM: Homo sapiens

<400> SEQUENCE: 962
auucagaauc ucacaguca 19

<210> SEQ ID NO 963
<211> LENGTH: 19
<212> TYPE: RNA
<213> ORGANISM: Homo sapiens

<400> SEQUENCE: 963
uucagaaucu cacagucaa 19

<210> SEQ ID NO 964
<211> LENGTH: 19
<212> TYPE: RNA
<213> ORGANISM: Homo sapiens

<400> SEQUENCE: 964
ucucacaguc aagcuucag 19

<210> SEQ ID NO 965
<211> LENGTH: 19
<212> TYPE: RNA
<213> ORGANISM: Homo sapiens

<400> SEQUENCE: 965
gcuucagcug caggcucuu 19

<210> SEQ ID NO 966
<211> LENGTH: 19
<212> TYPE: RNA
<213> ORGANISM: Homo sapiens

<400> SEQUENCE: 966
aaugggucuu cagugcucu 19

<210> SEQ ID NO 967
<211> LENGTH: 19
<212> TYPE: RNA
<213> ORGANISM: Homo sapiens

<400> SEQUENCE: 967
augggucuuc agugcucuc 19

<210> SEQ ID NO 968
<211> LENGTH: 19
<212> TYPE: RNA
<213> ORGANISM: Homo sapiens

<400> SEQUENCE: 968
ugggucuuca gugcucuca 19

<210> SEQ ID NO 969
<211> LENGTH: 19
<212> TYPE: RNA
<213> ORGANISM: Homo sapiens

<400> SEQUENCE: 969
gacaagagca aacgguuga 19

<210> SEQ ID NO 970
<211> LENGTH: 19
<212> TYPE: RNA
<213> ORGANISM: Homo sapiens

<400> SEQUENCE: 970
gagcaaacgg uugaacaca 19

<210> SEQ ID NO 971
<211> LENGTH: 19
<212> TYPE: RNA
<213> ORGANISM: Homo sapiens

<400> SEQUENCE: 971
acgguugaac acaauucua 19

<210> SEQ ID NO 972
<211> LENGTH: 19
<212> TYPE: RNA
<213> ORGANISM: Homo sapiens

<400> SEQUENCE: 972
cgguugaaca caauucuaa 19

<210> SEQ ID NO 973
<211> LENGTH: 19
<212> TYPE: RNA
<213> ORGANISM: Homo sapiens

<400> SEQUENCE: 973
auacaaugag caccaucua 19

<210> SEQ ID NO 974
<211> LENGTH: 19
<212> TYPE: RNA
<213> ORGANISM: Homo sapiens

<400> SEQUENCE: 974
uacaaugagc accaucuac 19

<210> SEQ ID NO 975
<211> LENGTH: 19
<212> TYPE: RNA
<213> ORGANISM: Homo sapiens

<400> SEQUENCE: 975
ugagcaccau cuacaguac 19

<210> SEQ ID NO 976
<211> LENGTH: 19
<212> TYPE: RNA
<213> ORGANISM: Homo sapiens

<400> SEQUENCE: 976
guuuguaacc cagauaauc 19

<210> SEQ ID NO 977
<211> LENGTH: 19
<212> TYPE: RNA
<213> ORGANISM: Homo sapiens

<400> SEQUENCE: 977
cccagauaau ccacaagaa 19

<210> SEQ ID NO 978
<211> LENGTH: 19
<212> TYPE: RNA
<213> ORGANISM: Homo sapiens

<400> SEQUENCE: 978
ugcuuauuac uugaaccag 19

<210> SEQ ID NO 979
<211> LENGTH: 19
<212> TYPE: RNA
<213> ORGANISM: Homo sapiens

<400> SEQUENCE: 979
uggcaaacag uuuagacua 19

<210> SEQ ID NO 980
<211> LENGTH: 19
<212> TYPE: RNA
<213> ORGANISM: Homo sapiens

<400> SEQUENCE: 980
caguuuagac uacaaugag 19

<210> SEQ ID NO 981
<211> LENGTH: 19
<212> TYPE: RNA
<213> ORGANISM: Homo sapiens

<400> SEQUENCE: 981
ugagaggcuc ugggcuugg 19

<210> SEQ ID NO 982
<211> LENGTH: 19
<212> TYPE: RNA
<213> ORGANISM: Homo sapiens

<400> SEQUENCE: 982
agcuggagau cugaggucg 19

<210> SEQ ID NO 983
<211> LENGTH: 19
<212> TYPE: RNA
<213> ORGANISM: Homo sapiens

<400> SEQUENCE: 983
gcuggagauc ugaggucgg 19

<210> SEQ ID NO 984
<211> LENGTH: 19
<212> TYPE: RNA
<213> ORGANISM: Homo sapiens

<400> SEQUENCE: 984
gcagcugagg ccauuauau 19

<210> SEQ ID NO 985
<211> LENGTH: 19
<212> TYPE: RNA
<213> ORGANISM: Homo sapiens

<400> SEQUENCE: 985
gaguaugugg ucuugaaaa 19

<210> SEQ ID NO 986
<211> LENGTH: 19
<212> TYPE: RNA
<213> ORGANISM: Homo sapiens

<400> SEQUENCE: 986
aaaugagaug gcaagagca 19

<210> SEQ ID NO 987
<211> LENGTH: 19
<212> TYPE: RNA
<213> ORGANISM: Homo sapiens

<400> SEQUENCE: 987
aaugagaugg caagagcaa 19

<210> SEQ ID NO 988
<211> LENGTH: 19
<212> TYPE: RNA
<213> ORGANISM: Homo sapiens

<400> SEQUENCE: 988
augagauggc aagagcaaa 19

<210> SEQ ID NO 989
<211> LENGTH: 19
<212> TYPE: RNA
<213> ORGANISM: Homo sapiens

<400> SEQUENCE: 989
ugagauggca agagcaaau 19

<210> SEQ ID NO 990
<211> LENGTH: 19
<212> TYPE: RNA
<213> ORGANISM: Homo sapiens

<400> SEQUENCE: 990
gagcaaauca uuaugagga 19

<210> SEQ ID NO 991
<211> LENGTH: 19
<212> TYPE: RNA
<213> ORGANISM: Homo sapiens

<400> SEQUENCE: 991
aucauuauga ggacuaugg 19

<210> SEQ ID NO 992
<211> LENGTH: 19
<212> TYPE: RNA
<213> ORGANISM: Homo sapiens

<400> SEQUENCE: 992
ucauuaugag gacuauggg 19

<210> SEQ ID NO 993
<211> LENGTH: 19
<212> TYPE: RNA
<213> ORGANISM: Homo sapiens

<400> SEQUENCE: 993
guaaaugggg uagauggcu 19

<210> SEQ ID NO 994
<211> LENGTH: 19
<212> TYPE: RNA
<213> ORGANISM: Homo sapiens

<400> SEQUENCE: 994 auggguaga uggcuauga                                              19

<210> SEQ ID NO 995
<211> LENGTH: 19
<212> TYPE: RNA
<213> ORGANISM: Homo sapiens

<400> SEQUENCE: 995
ugggguagau ggcuaugac                                             19

<210> SEQ ID NO 996
<211> LENGTH: 19
<212> TYPE: RNA
<213> ORGANISM: Homo sapiens

<400> SEQUENCE: 996
gauguggaac auaccuuug                                             19

<210> SEQ ID NO 997
<211> LENGTH: 19
<212> TYPE: RNA
<213> ORGANISM: Homo sapiens

<400> SEQUENCE: 997
caucuucaug ccuauguga                                             19

<210> SEQ ID NO 998
<211> LENGTH: 19
<212> TYPE: RNA
<213> ORGANISM: Homo sapiens

<400> SEQUENCE: 998
aguugaugaa ugccuaucc                                             19

<210> SEQ ID NO 999
<211> LENGTH: 19
<212> TYPE: RNA
<213> ORGANISM: Homo sapiens

<400> SEQUENCE: 999
guugaugaau gccuauccu                                             19

<210> SEQ ID NO 1000
<211> LENGTH: 19
<212> TYPE: RNA
<213> ORGANISM: Homo sapiens

<400> SEQUENCE: 1000
ugccuauccu uccuauauc                                             19

<210> SEQ ID NO 1001
<211> LENGTH: 19
<212> TYPE: RNA
<213> ORGANISM: Homo sapiens

<400> SEQUENCE: 1001
uuggaugccu cccugcuca                                             19

<210> SEQ ID NO 1002
<211> LENGTH: 19
<212> TYPE: RNA
<213> ORGANISM: Homo sapiens

<400> SEQUENCE: 1002
aucuguacuc uuugacagu 19

<210> SEQ ID NO 1003
<211> LENGTH: 19
<212> TYPE: RNA
<213> ORGANISM: Homo sapiens

<400> SEQUENCE: 1003
ucuguacucu uugacaguu 19

<210> SEQ ID NO 1004
<211> LENGTH: 19
<212> TYPE: RNA
<213> ORGANISM: Homo sapiens

<400> SEQUENCE: 1004
ccaaacauag auguuacug 19

<210> SEQ ID NO 1005
<211> LENGTH: 19
<212> TYPE: RNA
<213> ORGANISM: Homo sapiens

<400> SEQUENCE: 1005
acauagaugu uacugaugc 19

<210> SEQ ID NO 1006
<211> LENGTH: 19
<212> TYPE: RNA
<213> ORGANISM: Homo sapiens

<400> SEQUENCE: 1006
cauagauguu acugaugca 19

<210> SEQ ID NO 1007
<211> LENGTH: 19
<212> TYPE: RNA
<213> ORGANISM: Homo sapiens

<400> SEQUENCE: 1007
uauucaagga ggccgagaa 19

<210> SEQ ID NO 1008
<211> LENGTH: 19
<212> TYPE: RNA
<213> ORGANISM: Homo sapiens

<400> SEQUENCE: 1008
ggaggccgag aaguucuuu 19

<210> SEQ ID NO 1009
<211> LENGTH: 19
<212> TYPE: RNA
<213> ORGANISM: Homo sapiens

<400> SEQUENCE: 1009
guucuuugua ucuguuggu 19

<210> SEQ ID NO 1010
<211> LENGTH: 19
<212> TYPE: RNA

<213> ORGANISM: Homo sapiens

<400> SEQUENCE: 1010
uaugacucaa ggauucugg 19

<210> SEQ ID NO 1011
<211> LENGTH: 19
<212> TYPE: RNA
<213> ORGANISM: Homo sapiens

<400> SEQUENCE: 1011
ggauucuggg aaaauucca 19

<210> SEQ ID NO 1012
<211> LENGTH: 19
<212> TYPE: RNA
<213> ORGANISM: Homo sapiens

<400> SEQUENCE: 1012
aauuccaugc uaacggacc 19

<210> SEQ ID NO 1013
<211> LENGTH: 19
<212> TYPE: RNA
<213> ORGANISM: Homo sapiens

<400> SEQUENCE: 1013
auuccaugcu aacggaccc 19

<210> SEQ ID NO 1014
<211> LENGTH: 19
<212> TYPE: RNA
<213> ORGANISM: Homo sapiens

<400> SEQUENCE: 1014
uuccaugcua acggaccca 19

<210> SEQ ID NO 1015
<211> LENGTH: 19
<212> TYPE: RNA
<213> ORGANISM: Homo sapiens

<400> SEQUENCE: 1015
cggacccagg aaauguuca 19

<210> SEQ ID NO 1016
<211> LENGTH: 19
<212> TYPE: RNA
<213> ORGANISM: Homo sapiens

<400> SEQUENCE: 1016
auguucagaa agcagucug 19

<210> SEQ ID NO 1017
<211> LENGTH: 19
<212> TYPE: RNA
<213> ORGANISM: Homo sapiens

<400> SEQUENCE: 1017
uguucagaaa gcagucugc 19

<210> SEQ ID NO 1018
<211> LENGTH: 19

<212> TYPE: RNA
<213> ORGANISM: Homo sapiens

<400> SEQUENCE: 1018
agcagucugc caucccaca 19

<210> SEQ ID NO 1019
<211> LENGTH: 19
<212> TYPE: RNA
<213> ORGANISM: Homo sapiens

<400> SEQUENCE: 1019
gcagucugcc aucccacag 19

<210> SEQ ID NO 1020
<211> LENGTH: 19
<212> TYPE: RNA
<213> ORGANISM: Homo sapiens

<400> SEQUENCE: 1020
gggcgacuuc aggauccuu 19

<210> SEQ ID NO 1021
<211> LENGTH: 19
<212> TYPE: RNA
<213> ORGANISM: Homo sapiens

<400> SEQUENCE: 1021
aggugacaau ggacgacuu 19

<210> SEQ ID NO 1022
<211> LENGTH: 19
<212> TYPE: RNA
<213> ORGANISM: Homo sapiens

<400> SEQUENCE: 1022
ggugacaaug gacgacuuc 19

<210> SEQ ID NO 1023
<211> LENGTH: 19
<212> TYPE: RNA
<213> ORGANISM: Homo sapiens

<400> SEQUENCE: 1023
uggacgacuu ccugacagc 19

<210> SEQ ID NO 1024
<211> LENGTH: 19
<212> TYPE: RNA
<213> ORGANISM: Homo sapiens

<400> SEQUENCE: 1024
ccuuuucugc uaagaaaug 19

<210> SEQ ID NO 1025
<211> LENGTH: 19
<212> TYPE: RNA
<213> ORGANISM: Homo sapiens

<400> SEQUENCE: 1025
gaaauggagc uaaugaagg 19

<210> SEQ ID NO 1026

<211> LENGTH: 19
<212> TYPE: RNA
<213> ORGANISM: Homo sapiens

<400> SEQUENCE: 1026
auggagcuaa ugaaggauu 19

<210> SEQ ID NO 1027
<211> LENGTH: 19
<212> TYPE: RNA
<213> ORGANISM: Homo sapiens

<400> SEQUENCE: 1027
uggagcuaau gaaggauuc 19

<210> SEQ ID NO 1028
<211> LENGTH: 19
<212> TYPE: RNA
<213> ORGANISM: Homo sapiens

<400> SEQUENCE: 1028
ugaaggauuc caugaagcu 19

<210> SEQ ID NO 1029
<211> LENGTH: 19
<212> TYPE: RNA
<213> ORGANISM: Homo sapiens

<400> SEQUENCE: 1029
ggauuccaug aagcuguug 19

<210> SEQ ID NO 1030
<211> LENGTH: 19
<212> TYPE: RNA
<213> ORGANISM: Homo sapiens

<400> SEQUENCE: 1030
gcuguugggg aaaucaugu 19

<210> SEQ ID NO 1031
<211> LENGTH: 19
<212> TYPE: RNA
<213> ORGANISM: Homo sapiens

<400> SEQUENCE: 1031
aucaugucac uuucugcag 19

<210> SEQ ID NO 1032
<211> LENGTH: 19
<212> TYPE: RNA
<213> ORGANISM: Homo sapiens

<400> SEQUENCE: 1032
ucaugucacu uucugcagc 19

<210> SEQ ID NO 1033
<211> LENGTH: 19
<212> TYPE: RNA
<213> ORGANISM: Homo sapiens

<400> SEQUENCE: 1033
aauccauugg ucuucuguc 19

<210> SEQ ID NO 1034
<211> LENGTH: 19
<212> TYPE: RNA
<213> ORGANISM: Homo sapiens

<400> SEQUENCE: 1034
auccauuggu cuucuguca 19

<210> SEQ ID NO 1035
<211> LENGTH: 19
<212> TYPE: RNA
<213> ORGANISM: Homo sapiens

<400> SEQUENCE: 1035
uccauugguc uucugucac 19

<210> SEQ ID NO 1036
<211> LENGTH: 19
<212> TYPE: RNA
<213> ORGANISM: Homo sapiens

<400> SEQUENCE: 1036
acagaaauaa acuuccugc 19

<210> SEQ ID NO 1037
<211> LENGTH: 19
<212> TYPE: RNA
<213> ORGANISM: Homo sapiens

<400> SEQUENCE: 1037
cagaaauaaa cuuccugcu 19

<210> SEQ ID NO 1038
<211> LENGTH: 19
<212> TYPE: RNA
<213> ORGANISM: Homo sapiens

<400> SEQUENCE: 1038
auaaacuucc ugcucaaac 19

<210> SEQ ID NO 1039
<211> LENGTH: 19
<212> TYPE: RNA
<213> ORGANISM: Homo sapiens

<400> SEQUENCE: 1039
uaaacuuccu gcucaaaca 19

<210> SEQ ID NO 1040
<211> LENGTH: 19
<212> TYPE: RNA
<213> ORGANISM: Homo sapiens

<400> SEQUENCE: 1040
acuuccugcu caaacaagc 19

<210> SEQ ID NO 1041
<211> LENGTH: 19
<212> TYPE: RNA
<213> ORGANISM: Homo sapiens

<400> SEQUENCE: 1041
cuuccugcuc aaacaagca 19

<210> SEQ ID NO 1042
<211> LENGTH: 19
<212> TYPE: RNA
<213> ORGANISM: Homo sapiens

<400> SEQUENCE: 1042
acaagcacuc acgauuguu 19

<210> SEQ ID NO 1043
<211> LENGTH: 19
<212> TYPE: RNA
<213> ORGANISM: Homo sapiens

<400> SEQUENCE: 1043
caagcacuca cgauuguug 19

<210> SEQ ID NO 1044
<211> LENGTH: 19
<212> TYPE: RNA
<213> ORGANISM: Homo sapiens

<400> SEQUENCE: 1044
gcacucacga uuguuggga 19

<210> SEQ ID NO 1045
<211> LENGTH: 19
<212> TYPE: RNA
<213> ORGANISM: Homo sapiens

<400> SEQUENCE: 1045
guggaggugg auggucuuu 19

<210> SEQ ID NO 1046
<211> LENGTH: 19
<212> TYPE: RNA
<213> ORGANISM: Homo sapiens

<400> SEQUENCE: 1046
aggggaaauu cccaaagac 19

<210> SEQ ID NO 1047
<211> LENGTH: 19
<212> TYPE: RNA
<213> ORGANISM: Homo sapiens

<400> SEQUENCE: 1047
ggggaaauuc ccaaagacc 19

<210> SEQ ID NO 1048
<211> LENGTH: 19
<212> TYPE: RNA
<213> ORGANISM: Homo sapiens

<400> SEQUENCE: 1048
auucccaaag accagugga 19

<210> SEQ ID NO 1049
<211> LENGTH: 19
<212> TYPE: RNA
<213> ORGANISM: Homo sapiens

<400> SEQUENCE: 1049
uucccaaaga ccaguggau 19

<210> SEQ ID NO 1050
<211> LENGTH: 19
<212> TYPE: RNA
<213> ORGANISM: Homo sapiens

<400> SEQUENCE: 1050
agaccagugg augaaaaag 19

<210> SEQ ID NO 1051
<211> LENGTH: 19
<212> TYPE: RNA
<213> ORGANISM: Homo sapiens

<400> SEQUENCE: 1051
gaccagugga ugaaaaagu 19

<210> SEQ ID NO 1052
<211> LENGTH: 19
<212> TYPE: RNA
<213> ORGANISM: Homo sapiens

<400> SEQUENCE: 1052
aaaguggugg gagaugaag 19

<210> SEQ ID NO 1053
<211> LENGTH: 19
<212> TYPE: RNA
<213> ORGANISM: Homo sapiens

<400> SEQUENCE: 1053 aaguggoggg agaugaagc 19

<210> SEQ ID NO 1054
<211> LENGTH: 19
<212> TYPE: RNA
<213> ORGANISM: Homo sapiens

<400> SEQUENCE: 1054
agugguggga gaugaagcg 19

<210> SEQ ID NO 1055
<211> LENGTH: 19
<212> TYPE: RNA
<213> ORGANISM: Homo sapiens

<400> SEQUENCE: 1055
guggugggag augaagcga 19

<210> SEQ ID NO 1056
<211> LENGTH: 19
<212> TYPE: RNA
<213> ORGANISM: Homo sapiens

<400> SEQUENCE: 1056
gcgagagaua guuggggug 19

<210> SEQ ID NO 1057
<211> LENGTH: 19
<212> TYPE: RNA
<213> ORGANISM: Homo sapiens

<400> SEQUENCE: 1057
ccugugcccc augaugaaa 19

<210> SEQ ID NO 1058
<211> LENGTH: 19
<212> TYPE: RNA
<213> ORGANISM: Homo sapiens

<400> SEQUENCE: 1058
acauacugug accccgcau 19

<210> SEQ ID NO 1059
<211> LENGTH: 19
<212> TYPE: RNA
<213> ORGANISM: Homo sapiens

<400> SEQUENCE: 1059
cauacuguga ccccgcauc 19

<210> SEQ ID NO 1060
<211> LENGTH: 19
<212> TYPE: RNA
<213> ORGANISM: Homo sapiens

<400> SEQUENCE: 1060
ggacccuuua ccaauucca 19

<210> SEQ ID NO 1061
<211> LENGTH: 19
<212> TYPE: RNA
<213> ORGANISM: Homo sapiens

<400> SEQUENCE: 1061
uuccaguuuc aagaagcac 19

<210> SEQ ID NO 1062
<211> LENGTH: 19
<212> TYPE: RNA
<213> ORGANISM: Homo sapiens

<400> SEQUENCE: 1062
gaagcacuuu gucaagcag 19

<210> SEQ ID NO 1063
<211> LENGTH: 19
<212> TYPE: RNA
<213> ORGANISM: Homo sapiens

<400> SEQUENCE: 1063
gcacuuuguc aagcagcua 19

<210> SEQ ID NO 1064
<211> LENGTH: 19
<212> TYPE: RNA
<213> ORGANISM: Homo sapiens

<400> SEQUENCE: 1064
gcagcuaaac augaaggcc 19

<210> SEQ ID NO 1065
<211> LENGTH: 19
<212> TYPE: RNA
<213> ORGANISM: Homo sapiens

<400> SEQUENCE: 1065
acaugaaggc ccucugcac 19

<210> SEQ ID NO 1066
<211> LENGTH: 19
<212> TYPE: RNA
<213> ORGANISM: Homo sapiens

<400> SEQUENCE: 1066
caugaaggcc cucugcaca 19

<210> SEQ ID NO 1067
<211> LENGTH: 19
<212> TYPE: RNA
<213> ORGANISM: Homo sapiens

<400> SEQUENCE: 1067
ggcccucugc acaaaugug 19

<210> SEQ ID NO 1068
<211> LENGTH: 19
<212> TYPE: RNA
<213> ORGANISM: Homo sapiens

<400> SEQUENCE: 1068
augugacauc ucaaacucu 19

<210> SEQ ID NO 1069
<211> LENGTH: 19
<212> TYPE: RNA
<213> ORGANISM: Homo sapiens

<400> SEQUENCE: 1069
ugugacaucu caaacucua 19

<210> SEQ ID NO 1070
<211> LENGTH: 19
<212> TYPE: RNA
<213> ORGANISM: Homo sapiens

<400> SEQUENCE: 1070
acucuacaga agcuggaca 19

<210> SEQ ID NO 1071
<211> LENGTH: 19
<212> TYPE: RNA
<213> ORGANISM: Homo sapiens

<400> SEQUENCE: 1071
cucuacagaa gcuggacag 19

<210> SEQ ID NO 1072
<211> LENGTH: 19
<212> TYPE: RNA
<213> ORGANISM: Homo sapiens

<400> SEQUENCE: 1072
gcuggacaga aacuguuca 19

<210> SEQ ID NO 1073
<211> LENGTH: 19
<212> TYPE: RNA
<213> ORGANISM: Homo sapiens

<400> SEQUENCE: 1073
acuguucaau augcugagg 19

<210> SEQ ID NO 1074
<211> LENGTH: 19
<212> TYPE: RNA
<213> ORGANISM: Homo sapiens

<400> SEQUENCE: 1074
cuguucaaua ugcugaggc 19

<210> SEQ ID NO 1075
<211> LENGTH: 19
<212> TYPE: RNA
<213> ORGANISM: Homo sapiens

<400> SEQUENCE: 1075
uaugcugagg cuuggaaaa 19

<210> SEQ ID NO 1076
<211> LENGTH: 19
<212> TYPE: RNA
<213> ORGANISM: Homo sapiens

<400> SEQUENCE: 1076
aaucagaacc cuggacccu 19

<210> SEQ ID NO 1077
<211> LENGTH: 19
<212> TYPE: RNA
<213> ORGANISM: Homo sapiens

<400> SEQUENCE: 1077
aucagaaccc uggacccua 19

<210> SEQ ID NO 1078
<211> LENGTH: 19
<212> TYPE: RNA
<213> ORGANISM: Homo sapiens

<400> SEQUENCE: 1078
ucagaacccu ggacccuag 19

<210> SEQ ID NO 1079
<211> LENGTH: 19
<212> TYPE: RNA
<213> ORGANISM: Homo sapiens

<400> SEQUENCE: 1079
cccuggaccc uagcauugg 19

<210> SEQ ID NO 1080
<211> LENGTH: 19
<212> TYPE: RNA
<213> ORGANISM: Homo sapiens

<400> SEQUENCE: 1080
aauguuguag gagcaaaga 19

<210> SEQ ID NO 1081
<211> LENGTH: 19
<212> TYPE: RNA
<213> ORGANISM: Homo sapiens

<400> SEQUENCE: 1081
auguuguagg agcaaagaa 19

<210> SEQ ID NO 1082
<211> LENGTH: 19
<212> TYPE: RNA
<213> ORGANISM: Homo sapiens

<400> SEQUENCE: 1082
uguuguagga gcaaagaac 19

<210> SEQ ID NO 1083
<211> LENGTH: 19
<212> TYPE: RNA
<213> ORGANISM: Homo sapiens

<400> SEQUENCE: 1083
agaacaugaa uguaaggcc 19

<210> SEQ ID NO 1084
<211> LENGTH: 19
<212> TYPE: RNA
<213> ORGANISM: Homo sapiens

<400> SEQUENCE: 1084
gaacaugaau guaaggcca 19

<210> SEQ ID NO 1085
<211> LENGTH: 19
<212> TYPE: RNA
<213> ORGANISM: Homo sapiens

<400> SEQUENCE: 1085
caugaaugua aggccacug 19

<210> SEQ ID NO 1086
<211> LENGTH: 19
<212> TYPE: RNA
<213> ORGANISM: Homo sapiens

<400> SEQUENCE: 1086
uguaaggcca cugcucaac 19

<210> SEQ ID NO 1087
<211> LENGTH: 19
<212> TYPE: RNA
<213> ORGANISM: Homo sapiens

<400> SEQUENCE: 1087
ggccacugcu caacuacuu 19

<210> SEQ ID NO 1088
<211> LENGTH: 19
<212> TYPE: RNA
<213> ORGANISM: Homo sapiens

<400> SEQUENCE: 1088
cuacuuugag cccuuauuu 19

<210> SEQ ID NO 1089
<211> LENGTH: 19
<212> TYPE: RNA

<213> ORGANISM: Homo sapiens

<400> SEQUENCE: 1089
agaccagaac aagaauucu 19

<210> SEQ ID NO 1090
<211> LENGTH: 19
<212> TYPE: RNA
<213> ORGANISM: Homo sapiens

<400> SEQUENCE: 1090
gaccagaaca agaauucuu 19

<210> SEQ ID NO 1091
<211> LENGTH: 19
<212> TYPE: RNA
<213> ORGANISM: Homo sapiens

<400> SEQUENCE: 1091
caagaauucu uuuguggga 19

<210> SEQ ID NO 1092
<211> LENGTH: 19
<212> TYPE: RNA
<213> ORGANISM: Homo sapiens

<400> SEQUENCE: 1092
gaauucuuuu gugggaugg 19

<210> SEQ ID NO 1093
<211> LENGTH: 19
<212> TYPE: RNA
<213> ORGANISM: Homo sapiens

<400> SEQUENCE: 1093
uucuuuugug ggauggagu 19

<210> SEQ ID NO 1094
<211> LENGTH: 19
<212> TYPE: RNA
<213> ORGANISM: Homo sapiens

<400> SEQUENCE: 1094
agcaucaaag ugaggauaa 19

<210> SEQ ID NO 1095
<211> LENGTH: 19
<212> TYPE: RNA
<213> ORGANISM: Homo sapiens

<400> SEQUENCE: 1095
gcaucaaagu gaggauaag 19

<210> SEQ ID NO 1096
<211> LENGTH: 19
<212> TYPE: RNA
<213> ORGANISM: Homo sapiens

<400> SEQUENCE: 1096
agugaggaua agccuaaaa 19

<210> SEQ ID NO 1097
<211> LENGTH: 19

<212> TYPE: RNA
<213> ORGANISM: Homo sapiens

<400> SEQUENCE: 1097
gugaggauaa gccuaaaau 19

<210> SEQ ID NO 1098
<211> LENGTH: 19
<212> TYPE: RNA
<213> ORGANISM: Homo sapiens

<400> SEQUENCE: 1098
gccuaaaauc agcucuugg 19

<210> SEQ ID NO 1099
<211> LENGTH: 19
<212> TYPE: RNA
<213> ORGANISM: Homo sapiens

<400> SEQUENCE: 1099
aaucagcucu uggagauaa 19

<210> SEQ ID NO 1100
<211> LENGTH: 19
<212> TYPE: RNA
<213> ORGANISM: Homo sapiens

<400> SEQUENCE: 1100
aucagcucuu ggagauaaa 19

<210> SEQ ID NO 1101
<211> LENGTH: 19
<212> TYPE: RNA
<213> ORGANISM: Homo sapiens

<400> SEQUENCE: 1101
ucagcucuug gagauaaag 19

<210> SEQ ID NO 1102
<211> LENGTH: 19
<212> TYPE: RNA
<213> ORGANISM: Homo sapiens

<400> SEQUENCE: 1102
agcauaugaa uggaacgac 19

<210> SEQ ID NO 1103
<211> LENGTH: 19
<212> TYPE: RNA
<213> ORGANISM: Homo sapiens

<400> SEQUENCE: 1103
gcauaugaau ggaacgaca 19

<210> SEQ ID NO 1104
<211> LENGTH: 19
<212> TYPE: RNA
<213> ORGANISM: Homo sapiens

<400> SEQUENCE: 1104
uggaacgaca augaaaugu 19

<210> SEQ ID NO 1105

<211> LENGTH: 19
<212> TYPE: RNA
<213> ORGANISM: Homo sapiens

<400> SEQUENCE: 1105
cgacaaugaa auguaccug 19

<210> SEQ ID NO 1106
<211> LENGTH: 19
<212> TYPE: RNA
<213> ORGANISM: Homo sapiens

<400> SEQUENCE: 1106
ugaaauguac cuguuccga 19

<210> SEQ ID NO 1107
<211> LENGTH: 19
<212> TYPE: RNA
<213> ORGANISM: Homo sapiens

<400> SEQUENCE: 1107
auguaccugu uccgaucau 19

<210> SEQ ID NO 1108
<211> LENGTH: 19
<212> TYPE: RNA
<213> ORGANISM: Homo sapiens

<400> SEQUENCE: 1108
uguaccuguu ccgaucauc 19

<210> SEQ ID NO 1109
<211> LENGTH: 19
<212> TYPE: RNA
<213> ORGANISM: Homo sapiens

<400> SEQUENCE: 1109
ucagaugauu cuuuuuggg 19

<210> SEQ ID NO 1110
<211> LENGTH: 19
<212> TYPE: RNA
<213> ORGANISM: Homo sapiens

<400> SEQUENCE: 1110
uuugaaacca agaaucucc 19

<210> SEQ ID NO 1111
<211> LENGTH: 19
<212> TYPE: RNA
<213> ORGANISM: Homo sapiens

<400> SEQUENCE: 1111
uuucuuuguc acugcaccu 19

<210> SEQ ID NO 1112
<211> LENGTH: 19
<212> TYPE: RNA
<213> ORGANISM: Homo sapiens

<400> SEQUENCE: 1112
augugucuga uaucauucc 19

```
<210> SEQ ID NO 1113
<211> LENGTH: 19
<212> TYPE: RNA
<213> ORGANISM: Homo sapiens

<400> SEQUENCE: 1113

ugugucugau aucauuccu                                                 19

<210> SEQ ID NO 1114
<211> LENGTH: 19
<212> TYPE: RNA
<213> ORGANISM: Homo sapiens

<400> SEQUENCE: 1114

cugaaguuga aaaggccau                                                 19

<210> SEQ ID NO 1115
<211> LENGTH: 19
<212> TYPE: RNA
<213> ORGANISM: Homo sapiens

<400> SEQUENCE: 1115

guugaaaagg ccaucagga                                                 19

<210> SEQ ID NO 1116
<211> LENGTH: 19
<212> TYPE: RNA
<213> ORGANISM: Homo sapiens

<400> SEQUENCE: 1116

aaggccauca ggauguccc                                                 19

<210> SEQ ID NO 1117
<211> LENGTH: 19
<212> TYPE: RNA
<213> ORGANISM: Homo sapiens

<400> SEQUENCE: 1117

aggccaucag gaugucccg                                                 19

<210> SEQ ID NO 1118
<211> LENGTH: 19
<212> TYPE: RNA
<213> ORGANISM: Homo sapiens

<400> SEQUENCE: 1118

ugaugcuuuc cgucugaau                                                 19

<210> SEQ ID NO 1119
<211> LENGTH: 19
<212> TYPE: RNA
<213> ORGANISM: Homo sapiens

<400> SEQUENCE: 1119

ugacaacagc cuagaguuu                                                 19

<210> SEQ ID NO 1120
<211> LENGTH: 19
<212> TYPE: RNA
<213> ORGANISM: Homo sapiens

<400> SEQUENCE: 1120

cagccuagag uuucugggg                                                 19
```

<210> SEQ ID NO 1121
<211> LENGTH: 19
<212> TYPE: RNA
<213> ORGANISM: Homo sapiens

<400> SEQUENCE: 1121
cacuuggacc uccuaacca 19

<210> SEQ ID NO 1122
<211> LENGTH: 19
<212> TYPE: RNA
<213> ORGANISM: Homo sapiens

<400> SEQUENCE: 1122
ccagcccccu guuuccaua 19

<210> SEQ ID NO 1123
<211> LENGTH: 19
<212> TYPE: RNA
<213> ORGANISM: Homo sapiens

<400> SEQUENCE: 1123
aauaaagcaa gaaguggag 19

<210> SEQ ID NO 1124
<211> LENGTH: 19
<212> TYPE: RNA
<213> ORGANISM: Homo sapiens

<400> SEQUENCE: 1124
auaaagcaag aaguggaga 19

<210> SEQ ID NO 1125
<211> LENGTH: 19
<212> TYPE: RNA
<213> ORGANISM: Homo sapiens

<400> SEQUENCE: 1125
uaaagcaaga aguggagaa 19

<210> SEQ ID NO 1126
<211> LENGTH: 19
<212> TYPE: RNA
<213> ORGANISM: Homo sapiens

<400> SEQUENCE: 1126
agcaagaagu ggagaaaau 19

<210> SEQ ID NO 1127
<211> LENGTH: 19
<212> TYPE: RNA
<213> ORGANISM: Homo sapiens

<400> SEQUENCE: 1127
gcaagaagug gagaaaauc 19

<210> SEQ ID NO 1128
<211> LENGTH: 19
<212> TYPE: RNA
<213> ORGANISM: Homo sapiens

<400> SEQUENCE: 1128
gaaguggaga aaauccuua 19

<210> SEQ ID NO 1129
<211> LENGTH: 19
<212> TYPE: RNA
<213> ORGANISM: Homo sapiens

<400> SEQUENCE: 1129
guggagaaaa uccuuaugc 19

<210> SEQ ID NO 1130
<211> LENGTH: 19
<212> TYPE: RNA
<213> ORGANISM: Homo sapiens

<400> SEQUENCE: 1130
aauccuuaug ccuccaucg 19

<210> SEQ ID NO 1131
<211> LENGTH: 19
<212> TYPE: RNA
<213> ORGANISM: Homo sapiens

<400> SEQUENCE: 1131
auccuuaugc cuccaucga 19

<210> SEQ ID NO 1132
<211> LENGTH: 19
<212> TYPE: RNA
<213> ORGANISM: Homo sapiens

<400> SEQUENCE: 1132
uccuuaugcc uccaucgau 19

<210> SEQ ID NO 1133
<211> LENGTH: 19
<212> TYPE: RNA
<213> ORGANISM: Homo sapiens

<400> SEQUENCE: 1133
aggagaaaau aauccagga 19

<210> SEQ ID NO 1134
<211> LENGTH: 19
<212> TYPE: RNA
<213> ORGANISM: Homo sapiens

<400> SEQUENCE: 1134
ggagaaaaua auccaggau 19

<210> SEQ ID NO 1135
<211> LENGTH: 19
<212> TYPE: RNA
<213> ORGANISM: Homo sapiens

<400> SEQUENCE: 1135
uaauccagga uuccaaaac 19

<210> SEQ ID NO 1136
<211> LENGTH: 19
<212> TYPE: RNA
<213> ORGANISM: Homo sapiens

<400> SEQUENCE: 1136
uccaggauuc caaaacacu 19

<210> SEQ ID NO 1137
<211> LENGTH: 19
<212> TYPE: RNA
<213> ORGANISM: Homo sapiens

<400> SEQUENCE: 1137
aacacugaug auguucaga 19

<210> SEQ ID NO 1138
<211> LENGTH: 19
<212> TYPE: RNA
<213> ORGANISM: Homo sapiens

<400> SEQUENCE: 1138
acacugauga uguucagac 19

<210> SEQ ID NO 1139
<211> LENGTH: 19
<212> TYPE: RNA
<213> ORGANISM: Homo sapiens

<400> SEQUENCE: 1139
cacugaugau guucagacc 19

<210> SEQ ID NO 1140
<211> LENGTH: 19
<212> TYPE: RNA
<213> ORGANISM: Homo sapiens

<400> SEQUENCE: 1140
gcauggaugg auggagaag 19

<210> SEQ ID NO 1141
<211> LENGTH: 19
<212> TYPE: RNA
<213> ORGANISM: Homo sapiens

<400> SEQUENCE: 1141
acggaucuuc cucaagaga 19

<210> SEQ ID NO 1142
<211> LENGTH: 19
<212> TYPE: RNA
<213> ORGANISM: Homo sapiens

<400> SEQUENCE: 1142
cggaucuucc ucaagagaa 19

<210> SEQ ID NO 1143
<211> LENGTH: 19
<212> TYPE: RNA
<213> ORGANISM: Homo sapiens

<400> SEQUENCE: 1143
gagaaugccc ucaauccga 19

<210> SEQ ID NO 1144
<211> LENGTH: 19
<212> TYPE: RNA
<213> ORGANISM: Homo sapiens

<400> SEQUENCE: 1144
ugcccucaau ccgagaaag 19

<210> SEQ ID NO 1145
<211> LENGTH: 19
<212> TYPE: RNA
<213> ORGANISM: Homo sapiens

<400> SEQUENCE: 1145
uccgagaaag ccugaagga 19

<210> SEQ ID NO 1146
<211> LENGTH: 19
<212> TYPE: RNA
<213> ORGANISM: Homo sapiens

<400> SEQUENCE: 1146
agccugaagg aacgaggug 19

<210> SEQ ID NO 1147
<211> LENGTH: 19
<212> TYPE: RNA
<213> ORGANISM: Homo sapiens

<400> SEQUENCE: 1147
gccugaagga acgaggugu 19

<210> SEQ ID NO 1148
<211> LENGTH: 19
<212> TYPE: RNA
<213> ORGANISM: Homo sapiens

<400> SEQUENCE: 1148
ggaacgaggu guggacaug 19

<210> SEQ ID NO 1149
<211> LENGTH: 19
<212> TYPE: RNA
<213> ORGANISM: Homo sapiens

<400> SEQUENCE: 1149
cgaggugugg acauggcca 19

<210> SEQ ID NO 1150
<211> LENGTH: 19
<212> TYPE: RNA
<213> ORGANISM: Homo sapiens

<400> SEQUENCE: 1150
cccaugaaga ggcugacac 19

<210> SEQ ID NO 1151
<211> LENGTH: 19
<212> TYPE: RNA
<213> ORGANISM: Homo sapiens

<400> SEQUENCE: 1151
gaggcugaca cuuggcaac 19

<210> SEQ ID NO 1152
<211> LENGTH: 19
<212> TYPE: RNA
<213> ORGANISM: Homo sapiens

<400> SEQUENCE: 1152
caccaccucc uccgugauc 19

<210> SEQ ID NO 1153
<211> LENGTH: 19
<212> TYPE: RNA
<213> ORGANISM: Homo sapiens

<400> SEQUENCE: 1153
cuacauggac acccaguac 19

<210> SEQ ID NO 1154
<211> LENGTH: 19
<212> TYPE: RNA
<213> ORGANISM: Homo sapiens

<400> SEQUENCE: 1154
accuucaaag ucgucuuug 19

<210> SEQ ID NO 1155
<211> LENGTH: 19
<212> TYPE: RNA
<213> ORGANISM: Homo sapiens

<400> SEQUENCE: 1155
ccuucaaagu cgucuuuga 19

<210> SEQ ID NO 1156
<211> LENGTH: 19
<212> TYPE: RNA
<213> ORGANISM: Homo sapiens

<400> SEQUENCE: 1156
agucgucuuu gacacuggu 19

<210> SEQ ID NO 1157
<211> LENGTH: 19
<212> TYPE: RNA
<213> ORGANISM: Homo sapiens

<400> SEQUENCE: 1157
gucgucuuug acacugguu 19

<210> SEQ ID NO 1158
<211> LENGTH: 19
<212> TYPE: RNA
<213> ORGANISM: Homo sapiens

<400> SEQUENCE: 1158
uguuugggug cccuccucc 19

<210> SEQ ID NO 1159
<211> LENGTH: 19
<212> TYPE: RNA
<213> ORGANISM: Homo sapiens

<400> SEQUENCE: 1159
gugcagccgu cucuacacu 19

<210> SEQ ID NO 1160
<211> LENGTH: 19
<212> TYPE: RNA
<213> ORGANISM: Homo sapiens

<400> SEQUENCE: 1160
gcucuucgau gcuucggau 19

<210> SEQ ID NO 1161
<211> LENGTH: 19
<212> TYPE: RNA
<213> ORGANISM: Homo sapiens

<400> SEQUENCE: 1161
gcacaaugga acagaacuc 19

<210> SEQ ID NO 1162
<211> LENGTH: 19
<212> TYPE: RNA
<213> ORGANISM: Homo sapiens

<400> SEQUENCE: 1162
uggaacagaa cucacccuc 19

<210> SEQ ID NO 1163
<211> LENGTH: 19
<212> TYPE: RNA
<213> ORGANISM: Homo sapiens

<400> SEQUENCE: 1163
cagaacucac ccuccgcua 19

<210> SEQ ID NO 1164
<211> LENGTH: 19
<212> TYPE: RNA
<213> ORGANISM: Homo sapiens

<400> SEQUENCE: 1164
cucacccucc gcuauucaa 19

<210> SEQ ID NO 1165
<211> LENGTH: 19
<212> TYPE: RNA
<213> ORGANISM: Homo sapiens

<400> SEQUENCE: 1165
cagggacagu caguggcuu 19

<210> SEQ ID NO 1166
<211> LENGTH: 19
<212> TYPE: RNA
<213> ORGANISM: Homo sapiens

<400> SEQUENCE: 1166
ucacggugac acagauguu 19

<210> SEQ ID NO 1167
<211> LENGTH: 19
<212> TYPE: RNA
<213> ORGANISM: Homo sapiens

<400> SEQUENCE: 1167
caggccauug gcaggguca 19

<210> SEQ ID NO 1168
<211> LENGTH: 19
<212> TYPE: RNA

<213> ORGANISM: Homo sapiens

<400> SEQUENCE: 1168
caucaucucc caaggggug 19

<210> SEQ ID NO 1169
<211> LENGTH: 19
<212> TYPE: RNA
<213> ORGANISM: Homo sapiens

<400> SEQUENCE: 1169
ggggugcuaa aagaggacg 19

<210> SEQ ID NO 1170
<211> LENGTH: 19
<212> TYPE: RNA
<213> ORGANISM: Homo sapiens

<400> SEQUENCE: 1170
aagaggacgu cuucucuuu 19

<210> SEQ ID NO 1171
<211> LENGTH: 19
<212> TYPE: RNA
<213> ORGANISM: Homo sapiens

<400> SEQUENCE: 1171
agaggacguc uucucuuuc 19

<210> SEQ ID NO 1172
<211> LENGTH: 19
<212> TYPE: RNA
<213> ORGANISM: Homo sapiens

<400> SEQUENCE: 1172
gaggacgucu ucucuuucu 19

<210> SEQ ID NO 1173
<211> LENGTH: 19
<212> TYPE: RNA
<213> ORGANISM: Homo sapiens

<400> SEQUENCE: 1173
cagagauucc gagaauucc 19

<210> SEQ ID NO 1174
<211> LENGTH: 19
<212> TYPE: RNA
<213> ORGANISM: Homo sapiens

<400> SEQUENCE: 1174
uucccaaucg cugggagga 19

<210> SEQ ID NO 1175
<211> LENGTH: 19
<212> TYPE: RNA
<213> ORGANISM: Homo sapiens

<400> SEQUENCE: 1175
ucgcugggag gacagauug 19

<210> SEQ ID NO 1176
<211> LENGTH: 19

```
<212> TYPE: RNA
<213> ORGANISM: Homo sapiens

<400> SEQUENCE: 1176

gggaauuucc acuauauca                                               19

<210> SEQ ID NO 1177
<211> LENGTH: 19
<212> TYPE: RNA
<213> ORGANISM: Homo sapiens

<400> SEQUENCE: 1177

uuuccacuau aucaaccuc                                               19

<210> SEQ ID NO 1178
<211> LENGTH: 19
<212> TYPE: RNA
<213> ORGANISM: Homo sapiens

<400> SEQUENCE: 1178

ccucaucaag acugguguc                                               19

<210> SEQ ID NO 1179
<211> LENGTH: 19
<212> TYPE: RNA
<213> ORGANISM: Homo sapiens

<400> SEQUENCE: 1179

gacugguguc uggcagauu                                               19

<210> SEQ ID NO 1180
<211> LENGTH: 19
<212> TYPE: RNA
<213> ORGANISM: Homo sapiens

<400> SEQUENCE: 1180

augaaggggg ugucugugg                                               19

<210> SEQ ID NO 1181
<211> LENGTH: 19
<212> TYPE: RNA
<213> ORGANISM: Homo sapiens

<400> SEQUENCE: 1181

ugaaggggu gucuguggg                                                19

<210> SEQ ID NO 1182
<211> LENGTH: 19
<212> TYPE: RNA
<213> ORGANISM: Homo sapiens

<400> SEQUENCE: 1182

gcucauggag gccuuggga                                               19

<210> SEQ ID NO 1183
<211> LENGTH: 19
<212> TYPE: RNA
<213> ORGANISM: Homo sapiens

<400> SEQUENCE: 1183

gaagaggcug uuugauuau                                               19

<210> SEQ ID NO 1184
```

<211> LENGTH: 19
<212> TYPE: RNA
<213> ORGANISM: Homo sapiens

<400> SEQUENCE: 1184
gaggcuguuu gauuauguc 19

<210> SEQ ID NO 1185
<211> LENGTH: 19
<212> TYPE: RNA
<213> ORGANISM: Homo sapiens

<400> SEQUENCE: 1185
guguaacgag ggcccuaca 19

<210> SEQ ID NO 1186
<211> LENGTH: 19
<212> TYPE: RNA
<213> ORGANISM: Homo sapiens

<400> SEQUENCE: 1186
agaauacacg cucaccagc 19

<210> SEQ ID NO 1187
<211> LENGTH: 19
<212> TYPE: RNA
<213> ORGANISM: Homo sapiens

<400> SEQUENCE: 1187
gaauacacgc ucaccagcg 19

<210> SEQ ID NO 1188
<211> LENGTH: 19
<212> TYPE: RNA
<213> ORGANISM: Homo sapiens

<400> SEQUENCE: 1188
uccuacagua guaaaaagc 19

<210> SEQ ID NO 1189
<211> LENGTH: 19
<212> TYPE: RNA
<213> ORGANISM: Homo sapiens

<400> SEQUENCE: 1189
aaagcugugc acacuggcc 19

<210> SEQ ID NO 1190
<211> LENGTH: 19
<212> TYPE: RNA
<213> ORGANISM: Homo sapiens

<400> SEQUENCE: 1190
aagcugugca cacuggcca 19

<210> SEQ ID NO 1191
<211> LENGTH: 19
<212> TYPE: RNA
<213> ORGANISM: Homo sapiens

<400> SEQUENCE: 1191
agcugugcac acuggccau 19

<210> SEQ ID NO 1192
<211> LENGTH: 19
<212> TYPE: RNA
<213> ORGANISM: Homo sapiens

<400> SEQUENCE: 1192
gcugugcaca cuggccauc 19

<210> SEQ ID NO 1193
<211> LENGTH: 19
<212> TYPE: RNA
<213> ORGANISM: Homo sapiens

<400> SEQUENCE: 1193
aguucuacac agaguuuga 19

<210> SEQ ID NO 1194
<211> LENGTH: 19
<212> TYPE: RNA
<213> ORGANISM: Homo sapiens

<400> SEQUENCE: 1194
guucuacaca gaguuugau 19

<210> SEQ ID NO 1195
<211> LENGTH: 19
<212> TYPE: RNA
<213> ORGANISM: Homo sapiens

<400> SEQUENCE: 1195
caaccgcauu ggcuucgcc 19

<210> SEQ ID NO 1196
<211> LENGTH: 19
<212> TYPE: RNA
<213> ORGANISM: Homo sapiens

<400> SEQUENCE: 1196
ccgcauuggc uucgccuug 19

<210> SEQ ID NO 1197
<211> LENGTH: 19
<212> TYPE: RNA
<213> ORGANISM: Homo sapiens

<400> SEQUENCE: 1197
agagaaagca gauguccuc 19

<210> SEQ ID NO 1198
<211> LENGTH: 19
<212> TYPE: RNA
<213> ORGANISM: Homo sapiens

<400> SEQUENCE: 1198
gagaaagcag auguccucu 19

<210> SEQ ID NO 1199
<211> LENGTH: 19
<212> TYPE: RNA
<213> ORGANISM: Homo sapiens

<400> SEQUENCE: 1199
agcagauguc cucugccca 19

<210> SEQ ID NO 1200
<211> LENGTH: 19
<212> TYPE: RNA
<213> ORGANISM: Homo sapiens

<400> SEQUENCE: 1200
gcagauguuc ucugcccag 19

<210> SEQ ID NO 1201
<211> LENGTH: 19
<212> TYPE: RNA
<213> ORGANISM: Homo sapiens

<400> SEQUENCE: 1201
uucucugugu augggaaca 19

<210> SEQ ID NO 1202
<211> LENGTH: 19
<212> TYPE: RNA
<213> ORGANISM: Homo sapiens

<400> SEQUENCE: 1202
ucagcaacuc agggggacc 19

<210> SEQ ID NO 1203
<211> LENGTH: 19
<212> TYPE: RNA
<213> ORGANISM: Homo sapiens

<400> SEQUENCE: 1203
cucaggggga ccuguacga 19

<210> SEQ ID NO 1204
<211> LENGTH: 19
<212> TYPE: RNA
<213> ORGANISM: Homo sapiens

<400> SEQUENCE: 1204
aacuauuccu caguagaug 19

<210> SEQ ID NO 1205
<211> LENGTH: 19
<212> TYPE: RNA
<213> ORGANISM: Homo sapiens

<400> SEQUENCE: 1205
acuauuccuc aguagaugc 19

<210> SEQ ID NO 1206
<211> LENGTH: 19
<212> TYPE: RNA
<213> ORGANISM: Homo sapiens

<400> SEQUENCE: 1206
cuauuccuca guagaugcc 19

<210> SEQ ID NO 1207
<211> LENGTH: 19
<212> TYPE: RNA
<213> ORGANISM: Homo sapiens

<400> SEQUENCE: 1207
uggcauccag ucucaaaug 19

<210> SEQ ID NO 1208
<211> LENGTH: 19
<212> TYPE: RNA
<213> ORGANISM: Homo sapiens

<400> SEQUENCE: 1208
augcuuucua gauggucug 19

<210> SEQ ID NO 1209
<211> LENGTH: 19
<212> TYPE: RNA
<213> ORGANISM: Homo sapiens

<400> SEQUENCE: 1209
ugcuuucuag auggucugc 19

<210> SEQ ID NO 1210
<211> LENGTH: 19
<212> TYPE: RNA
<213> ORGANISM: Homo sapiens

<400> SEQUENCE: 1210
cuaaaggcaa aaguaguac 19

<210> SEQ ID NO 1211
<211> LENGTH: 19
<212> TYPE: RNA
<213> ORGANISM: Homo sapiens

<400> SEQUENCE: 1211
aggcaaaagu aguacacag 19

<210> SEQ ID NO 1212
<211> LENGTH: 19
<212> TYPE: RNA
<213> ORGANISM: Homo sapiens

<400> SEQUENCE: 1212
ggcaaaagua guacacagg 19

<210> SEQ ID NO 1213
<211> LENGTH: 19
<212> TYPE: RNA
<213> ORGANISM: Homo sapiens

<400> SEQUENCE: 1213
aaguaguaca caggaggcc 19

<210> SEQ ID NO 1214
<211> LENGTH: 19
<212> TYPE: RNA
<213> ORGANISM: Homo sapiens

<400> SEQUENCE: 1214
aguaguacac aggaggcca 19

<210> SEQ ID NO 1215
<211> LENGTH: 19
<212> TYPE: RNA
<213> ORGANISM: Homo sapiens

<400> SEQUENCE: 1215
guaguacaca ggaggccac 19

<210> SEQ ID NO 1216
<211> LENGTH: 19
<212> TYPE: RNA
<213> ORGANISM: Homo sapiens

<400> SEQUENCE: 1216
gcagugucca cagcacauc 19

<210> SEQ ID NO 1217
<211> LENGTH: 19
<212> TYPE: RNA
<213> ORGANISM: Homo sapiens

<400> SEQUENCE: 1217
cagguaaacg acuaaagaa 19

<210> SEQ ID NO 1218
<211> LENGTH: 19
<212> TYPE: RNA
<213> ORGANISM: Homo sapiens

<400> SEQUENCE: 1218
acgacuaaag aaaacaccc 19

<210> SEQ ID NO 1219
<211> LENGTH: 19
<212> TYPE: RNA
<213> ORGANISM: Homo sapiens

<400> SEQUENCE: 1219
cgacuaaaga aaacacccg 19

<210> SEQ ID NO 1220
<211> LENGTH: 19
<212> TYPE: RNA
<213> ORGANISM: Homo sapiens

<400> SEQUENCE: 1220
agaaaacacc cgagaagaa 19

<210> SEQ ID NO 1221
<211> LENGTH: 19
<212> TYPE: RNA
<213> ORGANISM: Homo sapiens

<400> SEQUENCE: 1221
gaaaacaccc gagaagaaa 19

<210> SEQ ID NO 1222
<211> LENGTH: 19
<212> TYPE: RNA
<213> ORGANISM: Homo sapiens

<400> SEQUENCE: 1222
aacacccgag aagaaaacu 19

<210> SEQ ID NO 1223
<211> LENGTH: 19
<212> TYPE: RNA
<213> ORGANISM: Homo sapiens

<400> SEQUENCE: 1223
acacccgaga agaaaacug 19

<210> SEQ ID NO 1224
<211> LENGTH: 19
<212> TYPE: RNA
<213> ORGANISM: Homo sapiens

<400> SEQUENCE: 1224
cacccgagaa gaaaacugg 19

<210> SEQ ID NO 1225
<211> LENGTH: 19
<212> TYPE: RNA
<213> ORGANISM: Homo sapiens

<400> SEQUENCE: 1225
gauuguaaag cagacauug 19

<210> SEQ ID NO 1226
<211> LENGTH: 19
<212> TYPE: RNA
<213> ORGANISM: Homo sapiens

<400> SEQUENCE: 1226
agcagacauu gcauuucug 19

<210> SEQ ID NO 1227
<211> LENGTH: 19
<212> TYPE: RNA
<213> ORGANISM: Homo sapiens

<400> SEQUENCE: 1227
gcagacauug cauuucuga 19

<210> SEQ ID NO 1228
<211> LENGTH: 19
<212> TYPE: RNA
<213> ORGANISM: Homo sapiens

<400> SEQUENCE: 1228
gcuuuaauau ugggcagcg 19

<210> SEQ ID NO 1229
<211> LENGTH: 19
<212> TYPE: RNA
<213> ORGANISM: Homo sapiens

<400> SEQUENCE: 1229
uauugggcag cgccgauuu 19

<210> SEQ ID NO 1230
<211> LENGTH: 19
<212> TYPE: RNA
<213> ORGANISM: Homo sapiens

<400> SEQUENCE: 1230
uuuuguugga aaaguggcu 19

<210> SEQ ID NO 1231
<211> LENGTH: 19
<212> TYPE: RNA
<213> ORGANISM: Homo sapiens

<400> SEQUENCE: 1231
aaguggcucu aauguuggg 19

<210> SEQ ID NO 1232
<211> LENGTH: 19
<212> TYPE: RNA
<213> ORGANISM: Homo sapiens

<400> SEQUENCE: 1232
aguggcucua auguuggga 19

<210> SEQ ID NO 1233
<211> LENGTH: 19
<212> TYPE: RNA
<213> ORGANISM: Homo sapiens

<400> SEQUENCE: 1233
guggcucuaa uguugggaa 19

<210> SEQ ID NO 1234
<211> LENGTH: 19
<212> TYPE: RNA
<213> ORGANISM: Homo sapiens

<400> SEQUENCE: 1234
uguugggaau uggaacaga 19

<210> SEQ ID NO 1235
<211> LENGTH: 19
<212> TYPE: RNA
<213> ORGANISM: Homo sapiens

<400> SEQUENCE: 1235
uuggaacaga aggaccaca 19

<210> SEQ ID NO 1236
<211> LENGTH: 19
<212> TYPE: RNA
<213> ORGANISM: Homo sapiens

<400> SEQUENCE: 1236
cagaaggacc acauguggg 19

<210> SEQ ID NO 1237
<211> LENGTH: 19
<212> TYPE: RNA
<213> ORGANISM: Homo sapiens

<400> SEQUENCE: 1237
ggaccacaug ugggccuug 19

<210> SEQ ID NO 1238
<211> LENGTH: 19
<212> TYPE: RNA
<213> ORGANISM: Homo sapiens

<400> SEQUENCE: 1238
gccagugaac aucccaaaa 19

<210> SEQ ID NO 1239
<211> LENGTH: 19
<212> TYPE: RNA
<213> ORGANISM: Homo sapiens

<400> SEQUENCE: 1239
aacuuuacau cagccaaag 19

<210> SEQ ID NO 1240
<211> LENGTH: 19
<212> TYPE: RNA
<213> ORGANISM: Homo sapiens

<400> SEQUENCE: 1240
acuuuacauc agccaaaga 19

<210> SEQ ID NO 1241
<211> LENGTH: 19
<212> TYPE: RNA
<213> ORGANISM: Homo sapiens

<400> SEQUENCE: 1241
cuuuacauca gccaaagau 19

<210> SEQ ID NO 1242
<211> LENGTH: 19
<212> TYPE: RNA
<213> ORGANISM: Homo sapiens

<400> SEQUENCE: 1242
aggaaguagg uuucagagg 19

<210> SEQ ID NO 1243
<211> LENGTH: 19
<212> TYPE: RNA
<213> ORGANISM: Homo sapiens

<400> SEQUENCE: 1243
ggaaguaggu uucagaggg 19

<210> SEQ ID NO 1244
<211> LENGTH: 19
<212> TYPE: RNA
<213> ORGANISM: Homo sapiens

<400> SEQUENCE: 1244
guagguuuca gagggggua 19

<210> SEQ ID NO 1245
<211> LENGTH: 19
<212> TYPE: RNA
<213> ORGANISM: Homo sapiens

<400> SEQUENCE: 1245
uuccaauaca ggaaaagcc 19

<210> SEQ ID NO 1246
<211> LENGTH: 19
<212> TYPE: RNA
<213> ORGANISM: Homo sapiens

<400> SEQUENCE: 1246
uacaggaaaa gccuugaag 19

<210> SEQ ID NO 1247
<211> LENGTH: 19
<212> TYPE: RNA

<213> ORGANISM: Homo sapiens

<400> SEQUENCE: 1247
aagccuugaa gcauacugc 19

<210> SEQ ID NO 1248
<211> LENGTH: 19
<212> TYPE: RNA
<213> ORGANISM: Homo sapiens

<400> SEQUENCE: 1248
agccuugaag cauacugcu 19

<210> SEQ ID NO 1249
<211> LENGTH: 19
<212> TYPE: RNA
<213> ORGANISM: Homo sapiens

<400> SEQUENCE: 1249
gccuugaagc auacugcuc 19

<210> SEQ ID NO 1250
<211> LENGTH: 19
<212> TYPE: RNA
<213> ORGANISM: Homo sapiens

<400> SEQUENCE: 1250
gcauacugcu cagaaauuc 19

<210> SEQ ID NO 1251
<211> LENGTH: 19
<212> TYPE: RNA
<213> ORGANISM: Homo sapiens

<400> SEQUENCE: 1251
auucuucacg guagaugcu 19

<210> SEQ ID NO 1252
<211> LENGTH: 19
<212> TYPE: RNA
<213> ORGANISM: Homo sapiens

<400> SEQUENCE: 1252
uucuucacgg uagaugcug 19

<210> SEQ ID NO 1253
<211> LENGTH: 19
<212> TYPE: RNA
<213> ORGANISM: Homo sapiens

<400> SEQUENCE: 1253
gaaaagggau ccccaaagu 19

<210> SEQ ID NO 1254
<211> LENGTH: 19
<212> TYPE: RNA
<213> ORGANISM: Homo sapiens

<400> SEQUENCE: 1254
aagggauccc caaaguggu 19

<210> SEQ ID NO 1255
<211> LENGTH: 19

<212> TYPE: RNA
<213> ORGANISM: Homo sapiens

<400> SEQUENCE: 1255
agggaucccc aaaguggug 19

<210> SEQ ID NO 1256
<211> LENGTH: 19
<212> TYPE: RNA
<213> ORGANISM: Homo sapiens

<400> SEQUENCE: 1256
gggaucccca aagugguggg 19

<210> SEQ ID NO 1257
<211> LENGTH: 19
<212> TYPE: RNA
<213> ORGANISM: Homo sapiens

<400> SEQUENCE: 1257 aguggugug guauuuauu 19

<210> SEQ ID NO 1258
<211> LENGTH: 19
<212> TYPE: RNA
<213> ORGANISM: Homo sapiens

<400> SEQUENCE: 1258
gugguggugg uauuuauug 19

<210> SEQ ID NO 1259
<211> LENGTH: 19
<212> TYPE: RNA
<213> ORGANISM: Homo sapiens

<400> SEQUENCE: 1259
gcaggcauug uggccagag 19

<210> SEQ ID NO 1260
<211> LENGTH: 19
<212> TYPE: RNA
<213> ORGANISM: Homo sapiens

<400> SEQUENCE: 1260
gccuaucccu gaagaacug 19

<210> SEQ ID NO 1261
<211> LENGTH: 19
<212> TYPE: RNA
<213> ORGANISM: Homo sapiens

<400> SEQUENCE: 1261
gaacugggga ugguucagg 19

<210> SEQ ID NO 1262
<211> LENGTH: 19
<212> TYPE: RNA
<213> ORGANISM: Homo sapiens

<400> SEQUENCE: 1262
cuggggaugg uucaggaug 19

<210> SEQ ID NO 1263

<211> LENGTH: 19
<212> TYPE: RNA
<213> ORGANISM: Homo sapiens

<400> SEQUENCE: 1263
ggcugucugu cggaauaau 19

<210> SEQ ID NO 1264
<211> LENGTH: 19
<212> TYPE: RNA
<213> ORGANISM: Homo sapiens

<400> SEQUENCE: 1264
uaauggcuuc uucucuuac 19

<210> SEQ ID NO 1265
<211> LENGTH: 19
<212> TYPE: RNA
<213> ORGANISM: Homo sapiens

<400> SEQUENCE: 1265
uggcuucuuc ucuuaccac 19

<210> SEQ ID NO 1266
<211> LENGTH: 19
<212> TYPE: RNA
<213> ORGANISM: Homo sapiens

<400> SEQUENCE: 1266
cugguuuggc accacaaaa 19

<210> SEQ ID NO 1267
<211> LENGTH: 19
<212> TYPE: RNA
<213> ORGANISM: Homo sapiens

<400> SEQUENCE: 1267
aauacguaaa gccucuggu 19

<210> SEQ ID NO 1268
<211> LENGTH: 19
<212> TYPE: RNA
<213> ORGANISM: Homo sapiens

<400> SEQUENCE: 1268
auacguaaag ccucuggua 19

<210> SEQ ID NO 1269
<211> LENGTH: 19
<212> TYPE: RNA
<213> ORGANISM: Homo sapiens

<400> SEQUENCE: 1269
uacguaaagc cucugguac 19

<210> SEQ ID NO 1270
<211> LENGTH: 19
<212> TYPE: RNA
<213> ORGANISM: Homo sapiens

<400> SEQUENCE: 1270
agccucuggu acagaagcu 19

<210> SEQ ID NO 1271
<211> LENGTH: 19
<212> TYPE: RNA
<213> ORGANISM: Homo sapiens

<400> SEQUENCE: 1271
gccucuggua cagaagcug 19

<210> SEQ ID NO 1272
<211> LENGTH: 19
<212> TYPE: RNA
<213> ORGANISM: Homo sapiens

<400> SEQUENCE: 1272
gcugugcacu caugaacaa 19

<210> SEQ ID NO 1273
<211> LENGTH: 19
<212> TYPE: RNA
<213> ORGANISM: Homo sapiens

<400> SEQUENCE: 1273
caaaugaugu gcagcaaga 19

<210> SEQ ID NO 1274
<211> LENGTH: 19
<212> TYPE: RNA
<213> ORGANISM: Homo sapiens

<400> SEQUENCE: 1274
augaugugca gcaagaccu 19

<210> SEQ ID NO 1275
<211> LENGTH: 19
<212> TYPE: RNA
<213> ORGANISM: Homo sapiens

<400> SEQUENCE: 1275
ugaugugcag caagaccug 19

<210> SEQ ID NO 1276
<211> LENGTH: 19
<212> TYPE: RNA
<213> ORGANISM: Homo sapiens

<400> SEQUENCE: 1276
gaccuguuau aacucagug 19

<210> SEQ ID NO 1277
<211> LENGTH: 19
<212> TYPE: RNA
<213> ORGANISM: Homo sapiens

<400> SEQUENCE: 1277
cucagugaac auugccuuu 19

<210> SEQ ID NO 1278
<211> LENGTH: 19
<212> TYPE: RNA
<213> ORGANISM: Homo sapiens

<400> SEQUENCE: 1278
uugauggcuc cagcagugu 19

<210> SEQ ID NO 1279
<211> LENGTH: 19
<212> TYPE: RNA
<213> ORGANISM: Homo sapiens

<400> SEQUENCE: 1279
uuuccgccuc augcuugaa 19

<210> SEQ ID NO 1280
<211> LENGTH: 19
<212> TYPE: RNA
<213> ORGANISM: Homo sapiens

<400> SEQUENCE: 1280
uuuguuucca acauagcca 19

<210> SEQ ID NO 1281
<211> LENGTH: 19
<212> TYPE: RNA
<213> ORGANISM: Homo sapiens

<400> SEQUENCE: 1281
cauagccaag acuuuugaa 19

<210> SEQ ID NO 1282
<211> LENGTH: 19
<212> TYPE: RNA
<213> ORGANISM: Homo sapiens

<400> SEQUENCE: 1282
gacuuuugaa aucucggac 19

<210> SEQ ID NO 1283
<211> LENGTH: 19
<212> TYPE: RNA
<213> ORGANISM: Homo sapiens

<400> SEQUENCE: 1283
aucucggaca uuggugcca 19

<210> SEQ ID NO 1284
<211> LENGTH: 19
<212> TYPE: RNA
<213> ORGANISM: Homo sapiens

<400> SEQUENCE: 1284
ucucggacau uggugccaa 19

<210> SEQ ID NO 1285
<211> LENGTH: 19
<212> TYPE: RNA
<213> ORGANISM: Homo sapiens

<400> SEQUENCE: 1285
gauagcugcu guacaguuu 19

<210> SEQ ID NO 1286
<211> LENGTH: 19
<212> TYPE: RNA
<213> ORGANISM: Homo sapiens

<400> SEQUENCE: 1286
agagaauguc cuagcuguc 19

```
<210> SEQ ID NO 1287
<211> LENGTH: 19
<212> TYPE: RNA
<213> ORGANISM: Homo sapiens

<400> SEQUENCE: 1287

gagaaugucc uagcuguca                                                    19

<210> SEQ ID NO 1288
<211> LENGTH: 19
<212> TYPE: RNA
<213> ORGANISM: Homo sapiens

<400> SEQUENCE: 1288

uguccuagcu gucaucaga                                                    19

<210> SEQ ID NO 1289
<211> LENGTH: 19
<212> TYPE: RNA
<213> ORGANISM: Homo sapiens

<400> SEQUENCE: 1289

acauccgcua uaugagugg                                                    19

<210> SEQ ID NO 1290
<211> LENGTH: 19
<212> TYPE: RNA
<213> ORGANISM: Homo sapiens

<400> SEQUENCE: 1290

cauccgcuau augaguggu                                                    19

<210> SEQ ID NO 1291
<211> LENGTH: 19
<212> TYPE: RNA
<213> ORGANISM: Homo sapiens

<400> SEQUENCE: 1291

cagcuacugg ugaugccau                                                    19

<210> SEQ ID NO 1292
<211> LENGTH: 19
<212> TYPE: RNA
<213> ORGANISM: Homo sapiens

<400> SEQUENCE: 1292

auguguuugg cccuauaag                                                    19

<210> SEQ ID NO 1293
<211> LENGTH: 19
<212> TYPE: RNA
<213> ORGANISM: Homo sapiens

<400> SEQUENCE: 1293

uguguuuggc ccuauaagg                                                    19

<210> SEQ ID NO 1294
<211> LENGTH: 19
<212> TYPE: RNA
<213> ORGANISM: Homo sapiens

<400> SEQUENCE: 1294
```

gggagagccc caacaagaa 19

<210> SEQ ID NO 1295
<211> LENGTH: 19
<212> TYPE: RNA
<213> ORGANISM: Homo sapiens

<400> SEQUENCE: 1295
gaacuuccua guaauuguc 19

<210> SEQ ID NO 1296
<211> LENGTH: 19
<212> TYPE: RNA
<213> ORGANISM: Homo sapiens

<400> SEQUENCE: 1296
cuuccuagua auugucaca 19

<210> SEQ ID NO 1297
<211> LENGTH: 19
<212> TYPE: RNA
<213> ORGANISM: Homo sapiens

<400> SEQUENCE: 1297
uugucacaga ugggcaguc 19

<210> SEQ ID NO 1298
<211> LENGTH: 19
<212> TYPE: RNA
<213> ORGANISM: Homo sapiens

<400> SEQUENCE: 1298
ucacuaucuu cucuguugg 19

<210> SEQ ID NO 1299
<211> LENGTH: 19
<212> TYPE: RNA
<213> ORGANISM: Homo sapiens

<400> SEQUENCE: 1299
agauauggcu ucuaaaccg 19

<210> SEQ ID NO 1300
<211> LENGTH: 19
<212> TYPE: RNA
<213> ORGANISM: Homo sapiens

<400> SEQUENCE: 1300
gauauggcuu cuaaaccga 19

<210> SEQ ID NO 1301
<211> LENGTH: 19
<212> TYPE: RNA
<213> ORGANISM: Homo sapiens

<400> SEQUENCE: 1301
accgaaggag ucucaugcu 19

<210> SEQ ID NO 1302
<211> LENGTH: 19
<212> TYPE: RNA
<213> ORGANISM: Homo sapiens

<400> SEQUENCE: 1302
ccgaaggagu cucaugcuu 19

<210> SEQ ID NO 1303
<211> LENGTH: 19
<212> TYPE: RNA
<213> ORGANISM: Homo sapiens

<400> SEQUENCE: 1303
ggagucucau gcuuucuuc 19

<210> SEQ ID NO 1304
<211> LENGTH: 19
<212> TYPE: RNA
<213> ORGANISM: Homo sapiens

<400> SEQUENCE: 1304
gagaguucac aggauuaga 19

<210> SEQ ID NO 1305
<211> LENGTH: 19
<212> TYPE: RNA
<213> ORGANISM: Homo sapiens

<400> SEQUENCE: 1305
ccaauuguuu cugauguca 19

<210> SEQ ID NO 1306
<211> LENGTH: 19
<212> TYPE: RNA
<213> ORGANISM: Homo sapiens

<400> SEQUENCE: 1306
uuguuucuga ugucaucag 19

<210> SEQ ID NO 1307
<211> LENGTH: 19
<212> TYPE: RNA
<213> ORGANISM: Homo sapiens

<400> SEQUENCE: 1307
ucccagcaau aaugguaac 19

<210> SEQ ID NO 1308
<211> LENGTH: 19
<212> TYPE: RNA
<213> ORGANISM: Homo sapiens

<400> SEQUENCE: 1308
ggcaauggac cuaugagca 19

<210> SEQ ID NO 1309
<211> LENGTH: 19
<212> TYPE: RNA
<213> ORGANISM: Homo sapiens

<400> SEQUENCE: 1309
uggaccuaug agcagagga 19

<210> SEQ ID NO 1310
<211> LENGTH: 19
<212> TYPE: RNA
<213> ORGANISM: Homo sapiens

<400> SEQUENCE: 1310 gggggguugga cgugauaag 19

<210> SEQ ID NO 1311
<211> LENGTH: 19
<212> TYPE: RNA
<213> ORGANISM: Homo sapiens

<400> SEQUENCE: 1311
guaugagccu gcagcuguu 19

<210> SEQ ID NO 1312
<211> LENGTH: 19
<212> TYPE: RNA
<213> ORGANISM: Homo sapiens

<400> SEQUENCE: 1312
caaggugaua aaaagggca 19

<210> SEQ ID NO 1313
<211> LENGTH: 19
<212> TYPE: RNA
<213> ORGANISM: Homo sapiens

<400> SEQUENCE: 1313
ggugauaaaa agggcaaaa 19

<210> SEQ ID NO 1314
<211> LENGTH: 19
<212> TYPE: RNA
<213> ORGANISM: Homo sapiens

<400> SEQUENCE: 1314
aaagggcaaa aagggcaaa 19

<210> SEQ ID NO 1315
<211> LENGTH: 19
<212> TYPE: RNA
<213> ORGANISM: Homo sapiens

<400> SEQUENCE: 1315
aagggcaaaa agggcaaaa 19

<210> SEQ ID NO 1316
<211> LENGTH: 19
<212> TYPE: RNA
<213> ORGANISM: Homo sapiens

<400> SEQUENCE: 1316
agggcaaaaa gggcaaaaa 19

<210> SEQ ID NO 1317
<211> LENGTH: 19
<212> TYPE: RNA
<213> ORGANISM: Homo sapiens

<400> SEQUENCE: 1317
gggcaaaaag ggcaaaaaa 19

<210> SEQ ID NO 1318
<211> LENGTH: 19
<212> TYPE: RNA
<213> ORGANISM: Homo sapiens

<400> SEQUENCE: 1318
aaagggcaaa aaagacagg 19

<210> SEQ ID NO 1319
<211> LENGTH: 19
<212> TYPE: RNA
<213> ORGANISM: Homo sapiens

<400> SEQUENCE: 1319
aagggcaaaa aagacaggg 19

<210> SEQ ID NO 1320
<211> LENGTH: 19
<212> TYPE: RNA
<213> ORGANISM: Homo sapiens

<400> SEQUENCE: 1320
agggcaaaaa agacaggga 19

<210> SEQ ID NO 1321
<211> LENGTH: 19
<212> TYPE: RNA
<213> ORGANISM: Homo sapiens

<400> SEQUENCE: 1321
gggcaaaaaa gacagggac 19

<210> SEQ ID NO 1322
<211> LENGTH: 19
<212> TYPE: RNA
<213> ORGANISM: Homo sapiens

<400> SEQUENCE: 1322
aaaagacagg gacauggau 19

<210> SEQ ID NO 1323
<211> LENGTH: 19
<212> TYPE: RNA
<213> ORGANISM: Homo sapiens

<400> SEQUENCE: 1323
aaagacaggg acauggaug 19

<210> SEQ ID NO 1324
<211> LENGTH: 19
<212> TYPE: RNA
<213> ORGANISM: Homo sapiens

<400> SEQUENCE: 1324
aagacaggga cauggauga 19

<210> SEQ ID NO 1325
<211> LENGTH: 19
<212> TYPE: RNA
<213> ORGANISM: Homo sapiens

<400> SEQUENCE: 1325
agacagggac auggaugaa 19

<210> SEQ ID NO 1326
<211> LENGTH: 19
<212> TYPE: RNA

<213> ORGANISM: Homo sapiens

<400> SEQUENCE: 1326
gacagggaca uggaugaac 19

<210> SEQ ID NO 1327
<211> LENGTH: 19
<212> TYPE: RNA
<213> ORGANISM: Homo sapiens

<400> SEQUENCE: 1327
gaaguuucua uggaugauc 19

<210> SEQ ID NO 1328
<211> LENGTH: 19
<212> TYPE: RNA
<213> ORGANISM: Homo sapiens

<400> SEQUENCE: 1328
acuuagccuu gaugaacuu 19

<210> SEQ ID NO 1329
<211> LENGTH: 19
<212> TYPE: RNA
<213> ORGANISM: Homo sapiens

<400> SEQUENCE: 1329
cuuagccuug augaacuuc 19

<210> SEQ ID NO 1330
<211> LENGTH: 19
<212> TYPE: RNA
<213> ORGANISM: Homo sapiens

<400> SEQUENCE: 1330
auauggaaca gacuugagc 19

<210> SEQ ID NO 1331
<211> LENGTH: 19
<212> TYPE: RNA
<213> ORGANISM: Homo sapiens

<400> SEQUENCE: 1331
uauggaacag acuugagcc 19

<210> SEQ ID NO 1332
<211> LENGTH: 19
<212> TYPE: RNA
<213> ORGANISM: Homo sapiens

<400> SEQUENCE: 1332
cagacuugag ccggggauu 19

<210> SEQ ID NO 1333
<211> LENGTH: 19
<212> TYPE: RNA
<213> ORGANISM: Homo sapiens

<400> SEQUENCE: 1333
caucugcucg ugcagcuga 19

<210> SEQ ID NO 1334
<211> LENGTH: 19

<212> TYPE: RNA
<213> ORGANISM: Homo sapiens

<400> SEQUENCE: 1334
uggaucaagu uuugucggc 19

<210> SEQ ID NO 1335
<211> LENGTH: 19
<212> TYPE: RNA
<213> ORGANISM: Homo sapiens

<400> SEQUENCE: 1335
guuuugucgg cagcucuuu 19

<210> SEQ ID NO 1336
<211> LENGTH: 19
<212> TYPE: RNA
<213> ORGANISM: Homo sapiens

<400> SEQUENCE: 1336
uguuacugug gauuggagc 19

<210> SEQ ID NO 1337
<211> LENGTH: 19
<212> TYPE: RNA
<213> ORGANISM: Homo sapiens

<400> SEQUENCE: 1337
gcugcuacag aagaggaac 19

<210> SEQ ID NO 1338
<211> LENGTH: 19
<212> TYPE: RNA
<213> ORGANISM: Homo sapiens

<400> SEQUENCE: 1338
gaggaaccuc aaaacgaua 19

<210> SEQ ID NO 1339
<211> LENGTH: 19
<212> TYPE: RNA
<213> ORGANISM: Homo sapiens

<400> SEQUENCE: 1339
ccucaaaacg auaaucugu 19

<210> SEQ ID NO 1340
<211> LENGTH: 19
<212> TYPE: RNA
<213> ORGANISM: Homo sapiens

<400> SEQUENCE: 1340
aacgauaauc uguaccugg 19

<210> SEQ ID NO 1341
<211> LENGTH: 19
<212> TYPE: RNA
<213> ORGANISM: Homo sapiens

<400> SEQUENCE: 1341
acgauaaucu guaccuggg 19

<210> SEQ ID NO 1342

<211> LENGTH: 19
<212> TYPE: RNA
<213> ORGANISM: Homo sapiens

<400> SEQUENCE: 1342
cgauaaucug uaccugggu 19

<210> SEQ ID NO 1343
<211> LENGTH: 19
<212> TYPE: RNA
<213> ORGANISM: Homo sapiens

<400> SEQUENCE: 1343
ucuguaccug ggugguggug 19

<210> SEQ ID NO 1344
<211> LENGTH: 19
<212> TYPE: RNA
<213> ORGANISM: Homo sapiens

<400> SEQUENCE: 1344
ucauaacugg uugcuucuc 19

<210> SEQ ID NO 1345
<211> LENGTH: 19
<212> TYPE: RNA
<213> ORGANISM: Homo sapiens

<400> SEQUENCE: 1345
cugguugcuu cuccuacua 19

<210> SEQ ID NO 1346
<211> LENGTH: 19
<212> TYPE: RNA
<213> ORGANISM: Homo sapiens

<400> SEQUENCE: 1346
guucaaagau cauggaauc 19

<210> SEQ ID NO 1347
<211> LENGTH: 19
<212> TYPE: RNA
<213> ORGANISM: Homo sapiens

<400> SEQUENCE: 1347
agaucaugga auccuucaa 19

<210> SEQ ID NO 1348
<211> LENGTH: 19
<212> TYPE: RNA
<213> ORGANISM: Homo sapiens

<400> SEQUENCE: 1348
gaucauggaa uccuucaaa 19

<210> SEQ ID NO 1349
<211> LENGTH: 19
<212> TYPE: RNA
<213> ORGANISM: Homo sapiens

<400> SEQUENCE: 1349
uccuucaaaa acauggucc 19

```
<210> SEQ ID NO 1350
<211> LENGTH: 19
<212> TYPE: RNA
<213> ORGANISM: Homo sapiens

<400> SEQUENCE: 1350

aaacaugguc ccucagcaa                                                    19

<210> SEQ ID NO 1351
<211> LENGTH: 19
<212> TYPE: RNA
<213> ORGANISM: Homo sapiens

<400> SEQUENCE: 1351

aacauggucc cucagcaag                                                    19

<210> SEQ ID NO 1352
<211> LENGTH: 19
<212> TYPE: RNA
<213> ORGANISM: Homo sapiens

<400> SEQUENCE: 1352

acauggcccc ucagcaagc                                                    19

<210> SEQ ID NO 1353
<211> LENGTH: 19
<212> TYPE: RNA
<213> ORGANISM: Homo sapiens

<400> SEQUENCE: 1353

cauggucccu cagcaagcc                                                    19

<210> SEQ ID NO 1354
<211> LENGTH: 19
<212> TYPE: RNA
<213> ORGANISM: Homo sapiens

<400> SEQUENCE: 1354

gcccuuguga uucgaaaug                                                    19

<210> SEQ ID NO 1355
<211> LENGTH: 19
<212> TYPE: RNA
<213> ORGANISM: Homo sapiens

<400> SEQUENCE: 1355

auggugagaa aaugagcau                                                    19

<210> SEQ ID NO 1356
<211> LENGTH: 19
<212> TYPE: RNA
<213> ORGANISM: Homo sapiens

<400> SEQUENCE: 1356

uggugagaaa augagcaua                                                    19

<210> SEQ ID NO 1357
<211> LENGTH: 19
<212> TYPE: RNA
<213> ORGANISM: Homo sapiens

<400> SEQUENCE: 1357

aaugagcaua aaugcggag                                                    19
```

<210> SEQ ID NO 1358
<211> LENGTH: 19
<212> TYPE: RNA
<213> ORGANISM: Homo sapiens

<400> SEQUENCE: 1358
augagcauaa augcggagg 19

<210> SEQ ID NO 1359
<211> LENGTH: 19
<212> TYPE: RNA
<213> ORGANISM: Homo sapiens

<400> SEQUENCE: 1359
ugagcauaaa ugcggagga 19

<210> SEQ ID NO 1360
<211> LENGTH: 19
<212> TYPE: RNA
<213> ORGANISM: Homo sapiens

<400> SEQUENCE: 1360
augcggagga aguuguggu 19

<210> SEQ ID NO 1361
<211> LENGTH: 19
<212> TYPE: RNA
<213> ORGANISM: Homo sapiens

<400> SEQUENCE: 1361
ugcggaggaa guugugguu 19

<210> SEQ ID NO 1362
<211> LENGTH: 19
<212> TYPE: RNA
<213> ORGANISM: Homo sapiens

<400> SEQUENCE: 1362
guugugguug gggaucugg 19

<210> SEQ ID NO 1363
<211> LENGTH: 19
<212> TYPE: RNA
<213> ORGANISM: Homo sapiens

<400> SEQUENCE: 1363
guaaaaggag gagaccgaa 19

<210> SEQ ID NO 1364
<211> LENGTH: 19
<212> TYPE: RNA
<213> ORGANISM: Homo sapiens

<400> SEQUENCE: 1364
aaggaggaga ccgaauucc 19

<210> SEQ ID NO 1365
<211> LENGTH: 19
<212> TYPE: RNA
<213> ORGANISM: Homo sapiens

<400> SEQUENCE: 1365
aggaggagac cgaauuccu 19

<210> SEQ ID NO 1366
<211> LENGTH: 19
<212> TYPE: RNA
<213> ORGANISM: Homo sapiens

<400> SEQUENCE: 1366
ggaggagacc gaauuccug 19

<210> SEQ ID NO 1367
<211> LENGTH: 19
<212> TYPE: RNA
<213> ORGANISM: Homo sapiens

<400> SEQUENCE: 1367
uuccugcuga ccucagaau 19

<210> SEQ ID NO 1368
<211> LENGTH: 19
<212> TYPE: RNA
<213> ORGANISM: Homo sapiens

<400> SEQUENCE: 1368
ucauaucugc aaauggcug 19

<210> SEQ ID NO 1369
<211> LENGTH: 19
<212> TYPE: RNA
<213> ORGANISM: Homo sapiens

<400> SEQUENCE: 1369
auggcugcaa gguggauaa 19

<210> SEQ ID NO 1370
<211> LENGTH: 19
<212> TYPE: RNA
<213> ORGANISM: Homo sapiens

<400> SEQUENCE: 1370
uggcugcaag guggauaac 19

<210> SEQ ID NO 1371
<211> LENGTH: 19
<212> TYPE: RNA
<213> ORGANISM: Homo sapiens

<400> SEQUENCE: 1371
gguggauaac uccucgcuc 19

<210> SEQ ID NO 1372
<211> LENGTH: 19
<212> TYPE: RNA
<213> ORGANISM: Homo sapiens

<400> SEQUENCE: 1372
cuccucgcuc acuggugaa 19

<210> SEQ ID NO 1373
<211> LENGTH: 19
<212> TYPE: RNA
<213> ORGANISM: Homo sapiens

<400> SEQUENCE: 1373
ucagaacccc agacuaggu 19

<210> SEQ ID NO 1374
<211> LENGTH: 19
<212> TYPE: RNA
<213> ORGANISM: Homo sapiens

<400> SEQUENCE: 1374
ccccagacua ggucuccag 19

<210> SEQ ID NO 1375
<211> LENGTH: 19
<212> TYPE: RNA
<213> ORGANISM: Homo sapiens

<400> SEQUENCE: 1375
augaaaaccc ccuggagac 19

<210> SEQ ID NO 1376
<211> LENGTH: 19
<212> TYPE: RNA
<213> ORGANISM: Homo sapiens

<400> SEQUENCE: 1376
ugaaaacccc cuggagacg 19

<210> SEQ ID NO 1377
<211> LENGTH: 19
<212> TYPE: RNA
<213> ORGANISM: Homo sapiens

<400> SEQUENCE: 1377
aacccccugg agacgagga 19

<210> SEQ ID NO 1378
<211> LENGTH: 19
<212> TYPE: RNA
<213> ORGANISM: Homo sapiens

<400> SEQUENCE: 1378
acccccugga gacgaggaa 19

<210> SEQ ID NO 1379
<211> LENGTH: 19
<212> TYPE: RNA
<213> ORGANISM: Homo sapiens

<400> SEQUENCE: 1379
cauugccuuc uuuucaacc 19

<210> SEQ ID NO 1380
<211> LENGTH: 19
<212> TYPE: RNA
<213> ORGANISM: Homo sapiens

<400> SEQUENCE: 1380
ccaauugugu ugaaggcac 19

<210> SEQ ID NO 1381
<211> LENGTH: 19
<212> TYPE: RNA
<213> ORGANISM: Homo sapiens

<400> SEQUENCE: 1381
uuguguugaa ggcaccgca 19

<210> SEQ ID NO 1382
<211> LENGTH: 19
<212> TYPE: RNA
<213> ORGANISM: Homo sapiens

<400> SEQUENCE: 1382
ggcaccgcac gugguauug 19

<210> SEQ ID NO 1383
<211> LENGTH: 19
<212> TYPE: RNA
<213> ORGANISM: Homo sapiens

<400> SEQUENCE: 1383
gaauugccac acuugcuuc 19

<210> SEQ ID NO 1384
<211> LENGTH: 19
<212> TYPE: RNA
<213> ORGANISM: Homo sapiens

<400> SEQUENCE: 1384
uugccacacu ugcuucugg 19

<210> SEQ ID NO 1385
<211> LENGTH: 19
<212> TYPE: RNA
<213> ORGANISM: Homo sapiens

<400> SEQUENCE: 1385
ugugccggaa gguuugcug 19

<210> SEQ ID NO 1386
<211> LENGTH: 19
<212> TYPE: RNA
<213> ORGANISM: Homo sapiens

<400> SEQUENCE: 1386
gguuugcugg ccacuguca 19

<210> SEQ ID NO 1387
<211> LENGTH: 19
<212> TYPE: RNA
<213> ORGANISM: Homo sapiens

<400> SEQUENCE: 1387
acgcauggca aggaaaaac 19

<210> SEQ ID NO 1388
<211> LENGTH: 19
<212> TYPE: RNA
<213> ORGANISM: Homo sapiens

<400> SEQUENCE: 1388
cgcauggcaa ggaaaaacu 19

<210> SEQ ID NO 1389
<211> LENGTH: 19
<212> TYPE: RNA
<213> ORGANISM: Homo sapiens

<400> SEQUENCE: 1389
ggaaaaacug cuuagugaa 19

<210> SEQ ID NO 1390
<211> LENGTH: 19
<212> TYPE: RNA
<213> ORGANISM: Homo sapiens

<400> SEQUENCE: 1390
aaacugcuua gugaagaac 19

<210> SEQ ID NO 1391
<211> LENGTH: 19
<212> TYPE: RNA
<213> ORGANISM: Homo sapiens

<400> SEQUENCE: 1391
aacugcuuag ugaagaacu 19

<210> SEQ ID NO 1392
<211> LENGTH: 19
<212> TYPE: RNA
<213> ORGANISM: Homo sapiens

<400> SEQUENCE: 1392
acugcuuagu gaagaacuu 19

<210> SEQ ID NO 1393
<211> LENGTH: 19
<212> TYPE: RNA
<213> ORGANISM: Homo sapiens

<400> SEQUENCE: 1393
cugcuuagug aagaacuua 19

<210> SEQ ID NO 1394
<211> LENGTH: 19
<212> TYPE: RNA
<213> ORGANISM: Homo sapiens

<400> SEQUENCE: 1394
gaacuuagaa gcuguggag 19

<210> SEQ ID NO 1395
<211> LENGTH: 19
<212> TYPE: RNA
<213> ORGANISM: Homo sapiens

<400> SEQUENCE: 1395
cuuagaagcu guggagacc 19

<210> SEQ ID NO 1396
<211> LENGTH: 19
<212> TYPE: RNA
<213> ORGANISM: Homo sapiens

<400> SEQUENCE: 1396
gcuguggaga ccuuggggu 19

<210> SEQ ID NO 1397
<211> LENGTH: 19
<212> TYPE: RNA
<213> ORGANISM: Homo sapiens

<400> SEQUENCE: 1397
aacuggaacu cugacucag 19

<210> SEQ ID NO 1398
<211> LENGTH: 19
<212> TYPE: RNA
<213> ORGANISM: Homo sapiens

<400> SEQUENCE: 1398
acuggaacuc ugacucaga 19

<210> SEQ ID NO 1399
<211> LENGTH: 19
<212> TYPE: RNA
<213> ORGANISM: Homo sapiens

<400> SEQUENCE: 1399
cuggaacucu gacucagaa 19

<210> SEQ ID NO 1400
<211> LENGTH: 19
<212> TYPE: RNA
<213> ORGANISM: Homo sapiens

<400> SEQUENCE: 1400
cucugacuca gaaccggau 19

<210> SEQ ID NO 1401
<211> LENGTH: 19
<212> TYPE: RNA
<213> ORGANISM: Homo sapiens

<400> SEQUENCE: 1401
ucaaauccau gaagcugau 19

<210> SEQ ID NO 1402
<211> LENGTH: 19
<212> TYPE: RNA
<213> ORGANISM: Homo sapiens

<400> SEQUENCE: 1402
auccaugaag cugauacga 19

<210> SEQ ID NO 1403
<211> LENGTH: 19
<212> TYPE: RNA
<213> ORGANISM: Homo sapiens

<400> SEQUENCE: 1403
uccaugaagc ugauacgac 19

<210> SEQ ID NO 1404
<211> LENGTH: 19
<212> TYPE: RNA
<213> ORGANISM: Homo sapiens

<400> SEQUENCE: 1404
gcugauacga cagagaauc 19

<210> SEQ ID NO 1405
<211> LENGTH: 19
<212> TYPE: RNA

<213> ORGANISM: Homo sapiens

<400> SEQUENCE: 1405
ucagaguggu gucucuuuu 19

<210> SEQ ID NO 1406
<211> LENGTH: 19
<212> TYPE: RNA
<213> ORGANISM: Homo sapiens

<400> SEQUENCE: 1406
gacuucagcu accuggcuu 19

<210> SEQ ID NO 1407
<211> LENGTH: 19
<212> TYPE: RNA
<213> ORGANISM: Homo sapiens

<400> SEQUENCE: 1407
uugcaggucu uuguaacag 19

<210> SEQ ID NO 1408
<211> LENGTH: 19
<212> TYPE: RNA
<213> ORGANISM: Homo sapiens

<400> SEQUENCE: 1408
cagggcagug uuucaggcu 19

<210> SEQ ID NO 1409
<211> LENGTH: 19
<212> TYPE: RNA
<213> ORGANISM: Homo sapiens

<400> SEQUENCE: 1409
ccaggaaaac cuaccuauu 19

<210> SEQ ID NO 1410
<211> LENGTH: 19
<212> TYPE: RNA
<213> ORGANISM: Homo sapiens

<400> SEQUENCE: 1410
aaccuaccua uucuuaagc 19

<210> SEQ ID NO 1411
<211> LENGTH: 19
<212> TYPE: RNA
<213> ORGANISM: Homo sapiens

<400> SEQUENCE: 1411
accuaccuau ucuuaagcg 19

<210> SEQ ID NO 1412
<211> LENGTH: 19
<212> TYPE: RNA
<213> ORGANISM: Homo sapiens

<400> SEQUENCE: 1412
ccuaccuauu cuuaagcgg 19

<210> SEQ ID NO 1413
<211> LENGTH: 19

<212> TYPE: RNA
<213> ORGANISM: Homo sapiens

<400> SEQUENCE: 1413
gcgggcaguu gcaggagau 19

<210> SEQ ID NO 1414
<211> LENGTH: 19
<212> TYPE: RNA
<213> ORGANISM: Homo sapiens

<400> SEQUENCE: 1414
agugcauaga gcugugcug 19

<210> SEQ ID NO 1415
<211> LENGTH: 19
<212> TYPE: RNA
<213> ORGANISM: Homo sapiens

<400> SEQUENCE: 1415
gugcauagag cugugcugu 19

<210> SEQ ID NO 1416
<211> LENGTH: 19
<212> TYPE: RNA
<213> ORGANISM: Homo sapiens

<400> SEQUENCE: 1416
ggagaugaga gaaagauac 19

<210> SEQ ID NO 1417
<211> LENGTH: 19
<212> TYPE: RNA
<213> ORGANISM: Homo sapiens

<400> SEQUENCE: 1417
agauacgcca aaaucgucg 19

<210> SEQ ID NO 1418
<211> LENGTH: 19
<212> TYPE: RNA
<213> ORGANISM: Homo sapiens

<400> SEQUENCE: 1418
gauacgccaa aaucgucga 19

<210> SEQ ID NO 1419
<211> LENGTH: 19
<212> TYPE: RNA
<213> ORGANISM: Homo sapiens

<400> SEQUENCE: 1419
aaucgucgag auacccuuc 19

<210> SEQ ID NO 1420
<211> LENGTH: 19
<212> TYPE: RNA
<213> ORGANISM: Homo sapiens

<400> SEQUENCE: 1420
aucgucgaga uacccuuca 19

<210> SEQ ID NO 1421

<211> LENGTH: 19
<212> TYPE: RNA
<213> ORGANISM: Homo sapiens

<400> SEQUENCE: 1421
ucgucgagau acccuucaa 19

<210> SEQ ID NO 1422
<211> LENGTH: 19
<212> TYPE: RNA
<213> ORGANISM: Homo sapiens

<400> SEQUENCE: 1422
cuccaccaac aaguaccag 19

<210> SEQ ID NO 1423
<211> LENGTH: 19
<212> TYPE: RNA
<213> ORGANISM: Homo sapiens

<400> SEQUENCE: 1423
caaguaccag uugucuauu 19

<210> SEQ ID NO 1424
<211> LENGTH: 19
<212> TYPE: RNA
<213> ORGANISM: Homo sapiens

<400> SEQUENCE: 1424
guaccaguug ucuauucau 19

<210> SEQ ID NO 1425
<211> LENGTH: 19
<212> TYPE: RNA
<213> ORGANISM: Homo sapiens

<400> SEQUENCE: 1425
gaaccccaac acaucggag 19

<210> SEQ ID NO 1426
<211> LENGTH: 19
<212> TYPE: RNA
<213> ORGANISM: Homo sapiens

<400> SEQUENCE: 1426
cacaucggag ccccaacac 19

<210> SEQ ID NO 1427
<211> LENGTH: 19
<212> TYPE: RNA
<213> ORGANISM: Homo sapiens

<400> SEQUENCE: 1427
caccuguugg ugaugaagg 19

<210> SEQ ID NO 1428
<211> LENGTH: 19
<212> TYPE: RNA
<213> ORGANISM: Homo sapiens

<400> SEQUENCE: 1428
aggauccuag accguugca 19

<210> SEQ ID NO 1429
<211> LENGTH: 19
<212> TYPE: RNA
<213> ORGANISM: Homo sapiens

<400> SEQUENCE: 1429
ggauccuaga ccguugcag 19

<210> SEQ ID NO 1430
<211> LENGTH: 19
<212> TYPE: RNA
<213> ORGANISM: Homo sapiens

<400> SEQUENCE: 1430
agacgccuuu cagaacgcc 19

<210> SEQ ID NO 1431
<211> LENGTH: 19
<212> TYPE: RNA
<213> ORGANISM: Homo sapiens

<400> SEQUENCE: 1431
gacgccuuuc agaacgccu 19

<210> SEQ ID NO 1432
<211> LENGTH: 19
<212> TYPE: RNA
<213> ORGANISM: Homo sapiens

<400> SEQUENCE: 1432
cgccuauuug gagcugggg 19

<210> SEQ ID NO 1433
<211> LENGTH: 19
<212> TYPE: RNA
<213> ORGANISM: Homo sapiens

<400> SEQUENCE: 1433
cgaguccuag guuucugcc 19

<210> SEQ ID NO 1434
<211> LENGTH: 19
<212> TYPE: RNA
<213> ORGANISM: Homo sapiens

<400> SEQUENCE: 1434
caguuuccug aaggguucc 19

<210> SEQ ID NO 1435
<211> LENGTH: 19
<212> TYPE: RNA
<213> ORGANISM: Homo sapiens

<400> SEQUENCE: 1435
ggguuccagu uugacacug 19

<210> SEQ ID NO 1436
<211> LENGTH: 19
<212> TYPE: RNA
<213> ORGANISM: Homo sapiens

<400> SEQUENCE: 1436
uuucccuauc gauaaucug 19

<210> SEQ ID NO 1437
<211> LENGTH: 19
<212> TYPE: RNA
<213> ORGANISM: Homo sapiens

<400> SEQUENCE: 1437
ucugugcuuu guugggcuc 19

<210> SEQ ID NO 1438
<211> LENGTH: 19
<212> TYPE: RNA
<213> ORGANISM: Homo sapiens

<400> SEQUENCE: 1438
augucgaagu gcuggaauu 19

<210> SEQ ID NO 1439
<211> LENGTH: 19
<212> TYPE: RNA
<213> ORGANISM: Homo sapiens

<400> SEQUENCE: 1439
ugucgaagug cuggaauua 19

<210> SEQ ID NO 1440
<211> LENGTH: 19
<212> TYPE: RNA
<213> ORGANISM: Homo sapiens

<400> SEQUENCE: 1440
gugcuggaau uaaggucau 19

<210> SEQ ID NO 1441
<211> LENGTH: 19
<212> TYPE: RNA
<213> ORGANISM: Homo sapiens

<400> SEQUENCE: 1441
uuaaggucau cauggucac 19

<210> SEQ ID NO 1442
<211> LENGTH: 19
<212> TYPE: RNA
<213> ORGANISM: Homo sapiens

<400> SEQUENCE: 1442
ggucaucaug gucacagga 19

<210> SEQ ID NO 1443
<211> LENGTH: 19
<212> TYPE: RNA
<213> ORGANISM: Homo sapiens

<400> SEQUENCE: 1443
ucacagcuaa agcuauugc 19

<210> SEQ ID NO 1444
<211> LENGTH: 19
<212> TYPE: RNA
<213> ORGANISM: Homo sapiens

<400> SEQUENCE: 1444
agcuauugcc aaaggugug 19

<210> SEQ ID NO 1445
<211> LENGTH: 19
<212> TYPE: RNA
<213> ORGANISM: Homo sapiens

<400> SEQUENCE: 1445
gcuauugcca aaggugugg 19

<210> SEQ ID NO 1446
<211> LENGTH: 19
<212> TYPE: RNA
<213> ORGANISM: Homo sapiens

<400> SEQUENCE: 1446
aggugugggc aucaucuca 19

<210> SEQ ID NO 1447
<211> LENGTH: 19
<212> TYPE: RNA
<213> ORGANISM: Homo sapiens

<400> SEQUENCE: 1447
ggugugggca ucaucucag 19

<210> SEQ ID NO 1448
<211> LENGTH: 19
<212> TYPE: RNA
<213> ORGANISM: Homo sapiens

<400> SEQUENCE: 1448
ggcaaugaga ccguggaag 19

<210> SEQ ID NO 1449
<211> LENGTH: 19
<212> TYPE: RNA
<213> ORGANISM: Homo sapiens

<400> SEQUENCE: 1449
ugagaccgug gaagacauu 19

<210> SEQ ID NO 1450
<211> LENGTH: 19
<212> TYPE: RNA
<213> ORGANISM: Homo sapiens

<400> SEQUENCE: 1450
gacauugcug cccgccuca 19

<210> SEQ ID NO 1451
<211> LENGTH: 19
<212> TYPE: RNA
<213> ORGANISM: Homo sapiens

<400> SEQUENCE: 1451
caucccaguc agccaggug 19

<210> SEQ ID NO 1452
<211> LENGTH: 19
<212> TYPE: RNA
<213> ORGANISM: Homo sapiens

<400> SEQUENCE: 1452
aggacaugac cuccgagca 19

<210> SEQ ID NO 1453
<211> LENGTH: 19
<212> TYPE: RNA
<213> ORGANISM: Homo sapiens

<400> SEQUENCE: 1453
ggacaugacc uccgagcag 19

<210> SEQ ID NO 1454
<211> LENGTH: 19
<212> TYPE: RNA
<213> ORGANISM: Homo sapiens

<400> SEQUENCE: 1454
guaccacacu gagauagug 19

<210> SEQ ID NO 1455
<211> LENGTH: 19
<212> TYPE: RNA
<213> ORGANISM: Homo sapiens

<400> SEQUENCE: 1455
gcucaucauu guggaaggc 19

<210> SEQ ID NO 1456
<211> LENGTH: 19
<212> TYPE: RNA
<213> ORGANISM: Homo sapiens

<400> SEQUENCE: 1456
ggcugccaaa gacagggug 19

<210> SEQ ID NO 1457
<211> LENGTH: 19
<212> TYPE: RNA
<213> ORGANISM: Homo sapiens

<400> SEQUENCE: 1457
agacagggug cuaucgugg 19

<210> SEQ ID NO 1458
<211> LENGTH: 19
<212> TYPE: RNA
<213> ORGANISM: Homo sapiens

<400> SEQUENCE: 1458
gacagggugc uaucguggc 19

<210> SEQ ID NO 1459
<211> LENGTH: 19
<212> TYPE: RNA
<213> ORGANISM: Homo sapiens

<400> SEQUENCE: 1459
ugacucucca gcuuugaag 19

<210> SEQ ID NO 1460
<211> LENGTH: 19
<212> TYPE: RNA
<213> ORGANISM: Homo sapiens

<400> SEQUENCE: 1460
gaaagcagac auuggggüu 19

<210> SEQ ID NO 1461
<211> LENGTH: 19
<212> TYPE: RNA
<213> ORGANISM: Homo sapiens

<400> SEQUENCE: 1461
agcagacauu gggguugcu 19

<210> SEQ ID NO 1462
<211> LENGTH: 19
<212> TYPE: RNA
<213> ORGANISM: Homo sapiens

<400> SEQUENCE: 1462
gcagacauug ggguugcua 19

<210> SEQ ID NO 1463
<211> LENGTH: 19
<212> TYPE: RNA
<213> ORGANISM: Homo sapiens

<400> SEQUENCE: 1463
gcaagcugcu gacaugauu 19

<210> SEQ ID NO 1464
<211> LENGTH: 19
<212> TYPE: RNA
<213> ORGANISM: Homo sapiens

<400> SEQUENCE: 1464
gcugcugaca ugauucuuc 19

<210> SEQ ID NO 1465
<211> LENGTH: 19
<212> TYPE: RNA
<213> ORGANISM: Homo sapiens

<400> SEQUENCE: 1465
cuuugccuca auugugacu 19

<210> SEQ ID NO 1466
<211> LENGTH: 19
<212> TYPE: RNA
<213> ORGANISM: Homo sapiens

<400> SEQUENCE: 1466
uugugacugg aguagagga 19

<210> SEQ ID NO 1467
<211> LENGTH: 19
<212> TYPE: RNA
<213> ORGANISM: Homo sapiens

<400> SEQUENCE: 1467
ggucgucuga ucuuugaua 19

<210> SEQ ID NO 1468
<211> LENGTH: 19
<212> TYPE: RNA
<213> ORGANISM: Homo sapiens

<400> SEQUENCE: 1468
cuugaagaaa uccauugcu 19

<210> SEQ ID NO 1469
<211> LENGTH: 19
<212> TYPE: RNA
<213> ORGANISM: Homo sapiens

<400> SEQUENCE: 1469
gaaauccauu gcuuauacc 19

<210> SEQ ID NO 1470
<211> LENGTH: 19
<212> TYPE: RNA
<213> ORGANISM: Homo sapiens

<400> SEQUENCE: 1470
ccaguaacau ucccgagau 19

<210> SEQ ID NO 1471
<211> LENGTH: 19
<212> TYPE: RNA
<213> ORGANISM: Homo sapiens

<400> SEQUENCE: 1471
cauucccgag aucaccccg 19

<210> SEQ ID NO 1472
<211> LENGTH: 19
<212> TYPE: RNA
<213> ORGANISM: Homo sapiens

<400> SEQUENCE: 1472
acauuccacu accacuggg 19

<210> SEQ ID NO 1473
<211> LENGTH: 19
<212> TYPE: RNA
<213> ORGANISM: Homo sapiens

<400> SEQUENCE: 1473
cauuccacua ccacugggg 19

<210> SEQ ID NO 1474
<211> LENGTH: 19
<212> TYPE: RNA
<213> ORGANISM: Homo sapiens

<400> SEQUENCE: 1474
gagacagccc agaaauccc 19

<210> SEQ ID NO 1475
<211> LENGTH: 19
<212> TYPE: RNA
<213> ORGANISM: Homo sapiens

<400> SEQUENCE: 1475
aucccaaaac agacaaacu 19

<210> SEQ ID NO 1476
<211> LENGTH: 19
<212> TYPE: RNA
<213> ORGANISM: Homo sapiens

<400> SEQUENCE: 1476
ucccaaaaca gacaaacuu 19

<210> SEQ ID NO 1477
<211> LENGTH: 19
<212> TYPE: RNA
<213> ORGANISM: Homo sapiens

<400> SEQUENCE: 1477
acagacaaac uugugaaug 19

<210> SEQ ID NO 1478
<211> LENGTH: 19
<212> TYPE: RNA
<213> ORGANISM: Homo sapiens

<400> SEQUENCE: 1478
cagacaaacu ugugaauga 19

<210> SEQ ID NO 1479
<211> LENGTH: 19
<212> TYPE: RNA
<213> ORGANISM: Homo sapiens

<400> SEQUENCE: 1479
acuugugaau gagcggcug 19

<210> SEQ ID NO 1480
<211> LENGTH: 19
<212> TYPE: RNA
<213> ORGANISM: Homo sapiens

<400> SEQUENCE: 1480
cuugugaaug agcggcuga 19

<210> SEQ ID NO 1481
<211> LENGTH: 19
<212> TYPE: RNA
<213> ORGANISM: Homo sapiens

<400> SEQUENCE: 1481
ugagcggcug aucagcaug 19

<210> SEQ ID NO 1482
<211> LENGTH: 19
<212> TYPE: RNA
<213> ORGANISM: Homo sapiens

<400> SEQUENCE: 1482
cggcuuccuc ccaauucac 19

<210> SEQ ID NO 1483
<211> LENGTH: 19
<212> TYPE: RNA
<213> ORGANISM: Homo sapiens

<400> SEQUENCE: 1483
uucaccuguu gggccuccg 19

<210> SEQ ID NO 1484
<211> LENGTH: 19
<212> TYPE: RNA

<213> ORGANISM: Homo sapiens

<400> SEQUENCE: 1484
cgauguggaa gacagcuac 19

<210> SEQ ID NO 1485
<211> LENGTH: 19
<212> TYPE: RNA
<213> ORGANISM: Homo sapiens

<400> SEQUENCE: 1485
gacagcuacg ggcagcagu 19

<210> SEQ ID NO 1486
<211> LENGTH: 19
<212> TYPE: RNA
<213> ORGANISM: Homo sapiens

<400> SEQUENCE: 1486
aaucguggag uucaccugc 19

<210> SEQ ID NO 1487
<211> LENGTH: 19
<212> TYPE: RNA
<213> ORGANISM: Homo sapiens

<400> SEQUENCE: 1487
aucguggagu ucaccugcc 19

<210> SEQ ID NO 1488
<211> LENGTH: 19
<212> TYPE: RNA
<213> ORGANISM: Homo sapiens

<400> SEQUENCE: 1488
ucguggaguu caccugcca 19

<210> SEQ ID NO 1489
<211> LENGTH: 19
<212> TYPE: RNA
<213> ORGANISM: Homo sapiens

<400> SEQUENCE: 1489
gaccaggagg aauucgguc 19

<210> SEQ ID NO 1490
<211> LENGTH: 19
<212> TYPE: RNA
<213> ORGANISM: Homo sapiens

<400> SEQUENCE: 1490
uucggucuuc cagcagggg 19

<210> SEQ ID NO 1491
<211> LENGTH: 19
<212> TYPE: RNA
<213> ORGANISM: Homo sapiens

<400> SEQUENCE: 1491
caagaucuug auauuuggc 19

<210> SEQ ID NO 1492
<211> LENGTH: 19

```
<212> TYPE: RNA
<213> ORGANISM: Homo sapiens

<400> SEQUENCE: 1492

gaucuugaua uuuggccuc                                                19

<210> SEQ ID NO 1493
<211> LENGTH: 19
<212> TYPE: RNA
<213> ORGANISM: Homo sapiens

<400> SEQUENCE: 1493

gagacagccc uggcugcuu                                                19

<210> SEQ ID NO 1494
<211> LENGTH: 19
<212> TYPE: RNA
<213> ORGANISM: Homo sapiens

<400> SEQUENCE: 1494

uggguguugc ucuuaggau                                                19

<210> SEQ ID NO 1495
<211> LENGTH: 19
<212> TYPE: RNA
<213> ORGANISM: Homo sapiens

<400> SEQUENCE: 1495

accuaccugg ugguucugu                                                19

<210> SEQ ID NO 1496
<211> LENGTH: 19
<212> TYPE: RNA
<213> ORGANISM: Homo sapiens

<400> SEQUENCE: 1496

ccuaccuggu gguucugug                                                19

<210> SEQ ID NO 1497
<211> LENGTH: 19
<212> TYPE: RNA
<213> ORGANISM: Homo sapiens

<400> SEQUENCE: 1497

gucagaaaac ucaucauca                                                19

<210> SEQ ID NO 1498
<211> LENGTH: 19
<212> TYPE: RNA
<213> ORGANISM: Homo sapiens

<400> SEQUENCE: 1498

aacucaucau caggcgacg                                                19

<210> SEQ ID NO 1499
<211> LENGTH: 19
<212> TYPE: RNA
<213> ORGANISM: Homo sapiens

<400> SEQUENCE: 1499

acucaucauc aggcgacgc                                                19

<210> SEQ ID NO 1500
```

<211> LENGTH: 19
<212> TYPE: RNA
<213> ORGANISM: Homo sapiens

<400> SEQUENCE: 1500
cucaucauca ggcgacgcc 19

<210> SEQ ID NO 1501
<211> LENGTH: 19
<212> TYPE: RNA
<213> ORGANISM: Homo sapiens

<400> SEQUENCE: 1501
ugggggcggc aagaagaaa 19

<210> SEQ ID NO 1502
<211> LENGTH: 19
<212> TYPE: RNA
<213> ORGANISM: Homo sapiens

<400> SEQUENCE: 1502
gaagaaacag aaggagaag 19

<210> SEQ ID NO 1503
<211> LENGTH: 19
<212> TYPE: RNA
<213> ORGANISM: Homo sapiens

<400> SEQUENCE: 1503
gaaacagaag gagaaggaa 19

<210> SEQ ID NO 1504
<211> LENGTH: 19
<212> TYPE: RNA
<213> ORGANISM: Homo sapiens

<400> SEQUENCE: 1504
acagaaggag aaggaacug 19

<210> SEQ ID NO 1505
<211> LENGTH: 19
<212> TYPE: RNA
<213> ORGANISM: Homo sapiens

<400> SEQUENCE: 1505
cagaaggaga aggaacugg 19

<210> SEQ ID NO 1506
<211> LENGTH: 19
<212> TYPE: RNA
<213> ORGANISM: Homo sapiens

<400> SEQUENCE: 1506
ggagaaggaa cuggaugag 19

<210> SEQ ID NO 1507
<211> LENGTH: 19
<212> TYPE: RNA
<213> ORGANISM: Homo sapiens

<400> SEQUENCE: 1507
ggaacuggau gagcugaag 19

<210> SEQ ID NO 1508
<211> LENGTH: 19
<212> TYPE: RNA
<213> ORGANISM: Homo sapiens

<400> SEQUENCE: 1508
cuggaugagc ugaagaagg 19

<210> SEQ ID NO 1509
<211> LENGTH: 19
<212> TYPE: RNA
<213> ORGANISM: Homo sapiens

<400> SEQUENCE: 1509
gaaggaggug gcaauggau 19

<210> SEQ ID NO 1510
<211> LENGTH: 19
<212> TYPE: RNA
<213> ORGANISM: Homo sapiens

<400> SEQUENCE: 1510
ggagguggca auggaugac 19

<210> SEQ ID NO 1511
<211> LENGTH: 19
<212> TYPE: RNA
<213> ORGANISM: Homo sapiens

<400> SEQUENCE: 1511
uggaugacca caagcuguc 19

<210> SEQ ID NO 1512
<211> LENGTH: 19
<212> TYPE: RNA
<213> ORGANISM: Homo sapiens

<400> SEQUENCE: 1512
gcuguccuug gaugagcug 19

<210> SEQ ID NO 1513
<211> LENGTH: 19
<212> TYPE: RNA
<213> ORGANISM: Homo sapiens

<400> SEQUENCE: 1513
auaccaagug gaccugucc 19

<210> SEQ ID NO 1514
<211> LENGTH: 19
<212> TYPE: RNA
<213> ORGANISM: Homo sapiens

<400> SEQUENCE: 1514
uaccaagugg accugucca 19

<210> SEQ ID NO 1515
<211> LENGTH: 19
<212> TYPE: RNA
<213> ORGANISM: Homo sapiens

<400> SEQUENCE: 1515
ccccugagug ggucaaguu 19

```
<210> SEQ ID NO 1516
<211> LENGTH: 19
<212> TYPE: RNA
<213> ORGANISM: Homo sapiens

<400> SEQUENCE: 1516

guucugccgu cagcuuuuc                                                19

<210> SEQ ID NO 1517
<211> LENGTH: 19
<212> TYPE: RNA
<213> ORGANISM: Homo sapiens

<400> SEQUENCE: 1517

ccauccaacg acaaucuau                                                19

<210> SEQ ID NO 1518
<211> LENGTH: 19
<212> TYPE: RNA
<213> ORGANISM: Homo sapiens

<400> SEQUENCE: 1518

cgacaaucua uaucugggu                                                19

<210> SEQ ID NO 1519
<211> LENGTH: 19
<212> TYPE: RNA
<213> ORGANISM: Homo sapiens

<400> SEQUENCE: 1519

ucuauaucug gguguggug                                                19

<210> SEQ ID NO 1520
<211> LENGTH: 19
<212> TYPE: RNA
<213> ORGANISM: Homo sapiens

<400> SEQUENCE: 1520

gagcuccaag aucauggau                                                19

<210> SEQ ID NO 1521
<211> LENGTH: 19
<212> TYPE: RNA
<213> ORGANISM: Homo sapiens

<400> SEQUENCE: 1521

gaucauggau uccuucaag                                                19

<210> SEQ ID NO 1522
<211> LENGTH: 19
<212> TYPE: RNA
<213> ORGANISM: Homo sapiens

<400> SEQUENCE: 1522

gaacauggua ccucagcaa                                                19

<210> SEQ ID NO 1523
<211> LENGTH: 19
<212> TYPE: RNA
<213> ORGANISM: Homo sapiens

<400> SEQUENCE: 1523

caugguaccu cagcaagcc                                                19
```

<210> SEQ ID NO 1524
<211> LENGTH: 19
<212> TYPE: RNA
<213> ORGANISM: Homo sapiens

<400> SEQUENCE: 1524
gaugcagauc aacgcagag 19

<210> SEQ ID NO 1525
<211> LENGTH: 19
<212> TYPE: RNA
<213> ORGANISM: Homo sapiens

<400> SEQUENCE: 1525
cgcagaggaa gugguggug 19

<210> SEQ ID NO 1526
<211> LENGTH: 19
<212> TYPE: RNA
<213> ORGANISM: Homo sapiens

<400> SEQUENCE: 1526
gguggauaac ucauccuua 19

<210> SEQ ID NO 1527
<211> LENGTH: 19
<212> TYPE: RNA
<213> ORGANISM: Homo sapiens

<400> SEQUENCE: 1527
cucauccuua acaggagag 19

<210> SEQ ID NO 1528
<211> LENGTH: 19
<212> TYPE: RNA
<213> ORGANISM: Homo sapiens

<400> SEQUENCE: 1528
uaucuguuuc uucuccacc 19

<210> SEQ ID NO 1529
<211> LENGTH: 19
<212> TYPE: RNA
<213> ORGANISM: Homo sapiens

<400> SEQUENCE: 1529
cuguguugaa ggcacugcc 19

<210> SEQ ID NO 1530
<211> LENGTH: 19
<212> TYPE: RNA
<213> ORGANISM: Homo sapiens

<400> SEQUENCE: 1530
uggagauuga acacuucau 19

<210> SEQ ID NO 1531
<211> LENGTH: 19
<212> TYPE: RNA
<213> ORGANISM: Homo sapiens

<400> SEQUENCE: 1531
cacuucaucc agcugauca 19

<210> SEQ ID NO 1532
<211> LENGTH: 19
<212> TYPE: RNA
<213> ORGANISM: Homo sapiens

<400> SEQUENCE: 1532
gcgcauggca cggaagaac 19

<210> SEQ ID NO 1533
<211> LENGTH: 19
<212> TYPE: RNA
<213> ORGANISM: Homo sapiens

<400> SEQUENCE: 1533
gaacugccug gugaagaac 19

<210> SEQ ID NO 1534
<211> LENGTH: 19
<212> TYPE: RNA
<213> ORGANISM: Homo sapiens

<400> SEQUENCE: 1534
cugccuggug aagaaccug 19

<210> SEQ ID NO 1535
<211> LENGTH: 19
<212> TYPE: RNA
<213> ORGANISM: Homo sapiens

<400> SEQUENCE: 1535
ccaaauccau gaggcugac 19

<210> SEQ ID NO 1536
<211> LENGTH: 19
<212> TYPE: RNA
<213> ORGANISM: Homo sapiens

<400> SEQUENCE: 1536
auccaugagg cugacacca 19

<210> SEQ ID NO 1537
<211> LENGTH: 19
<212> TYPE: RNA
<213> ORGANISM: Homo sapiens

<400> SEQUENCE: 1537
uccaugaggc ugacaccac 19

<210> SEQ ID NO 1538
<211> LENGTH: 19
<212> TYPE: RNA
<213> ORGANISM: Homo sapiens

<400> SEQUENCE: 1538
gaucagucug gggccacuu 19

<210> SEQ ID NO 1539
<211> LENGTH: 19
<212> TYPE: RNA
<213> ORGANISM: Homo sapiens

<400> SEQUENCE: 1539
acgauccccu acguggacg 19

<210> SEQ ID NO 1540
<211> LENGTH: 19
<212> TYPE: RNA
<213> ORGANISM: Homo sapiens

<400> SEQUENCE: 1540
uugcuggucu cugcaaccg 19

<210> SEQ ID NO 1541
<211> LENGTH: 19
<212> TYPE: RNA
<213> ORGANISM: Homo sapiens

<400> SEQUENCE: 1541
ggcaggacag gagaacauc 19

<210> SEQ ID NO 1542
<211> LENGTH: 19
<212> TYPE: RNA
<213> ORGANISM: Homo sapiens

<400> SEQUENCE: 1542
caucuccgug ucuaagcgg 19

<210> SEQ ID NO 1543
<211> LENGTH: 19
<212> TYPE: RNA
<213> ORGANISM: Homo sapiens

<400> SEQUENCE: 1543
gcgggacaca gcuggugau 19

<210> SEQ ID NO 1544
<211> LENGTH: 19
<212> TYPE: RNA
<213> ORGANISM: Homo sapiens

<400> SEQUENCE: 1544
gugcauugag cucuccugu 19

<210> SEQ ID NO 1545
<211> LENGTH: 19
<212> TYPE: RNA
<213> ORGANISM: Homo sapiens

<400> SEQUENCE: 1545
aaugagagac agaaacccc 19

<210> SEQ ID NO 1546
<211> LENGTH: 19
<212> TYPE: RNA
<213> ORGANISM: Homo sapiens

<400> SEQUENCE: 1546
augagagaca gaaacccca 19

<210> SEQ ID NO 1547
<211> LENGTH: 19
<212> TYPE: RNA
<213> ORGANISM: Homo sapiens

<400> SEQUENCE: 1547
ugagagacag aaaccccaa 19

<210> SEQ ID NO 1548
<211> LENGTH: 19
<212> TYPE: RNA
<213> ORGANISM: Homo sapiens

<400> SEQUENCE: 1548
accccaaggu ggcagagau 19

<210> SEQ ID NO 1549
<211> LENGTH: 19
<212> TYPE: RNA
<213> ORGANISM: Homo sapiens

<400> SEQUENCE: 1549
ccccaaggug gcagagauu 19

<210> SEQ ID NO 1550
<211> LENGTH: 19
<212> TYPE: RNA
<213> ORGANISM: Homo sapiens

<400> SEQUENCE: 1550
gguggcagag auuccuuuc 19

<210> SEQ ID NO 1551
<211> LENGTH: 19
<212> TYPE: RNA
<213> ORGANISM: Homo sapiens

<400> SEQUENCE: 1551
cucuaccaac aaguaccag 19

<210> SEQ ID NO 1552
<211> LENGTH: 19
<212> TYPE: RNA
<213> ORGANISM: Homo sapiens

<400> SEQUENCE: 1552
caaguaccag cugucuauc 19

<210> SEQ ID NO 1553
<211> LENGTH: 19
<212> TYPE: RNA
<213> ORGANISM: Homo sapiens

<400> SEQUENCE: 1553
guaccagcug ucuauccac 19

<210> SEQ ID NO 1554
<211> LENGTH: 19
<212> TYPE: RNA
<213> ORGANISM: Homo sapiens

<400> SEQUENCE: 1554
ggagaucccg cucgacaag 19

<210> SEQ ID NO 1555
<211> LENGTH: 19
<212> TYPE: RNA
<213> ORGANISM: Homo sapiens

<400> SEQUENCE: 1555
ggagaugcaa gaugccuuu 19

<210> SEQ ID NO 1556
<211> LENGTH: 19
<212> TYPE: RNA
<213> ORGANISM: Homo sapiens

<400> SEQUENCE: 1556
gaugccuuuc aaaaugccu 19

<210> SEQ ID NO 1557
<211> LENGTH: 19
<212> TYPE: RNA
<213> ORGANISM: Homo sapiens

<400> SEQUENCE: 1557
aaugccuaca uggagcugg 19

<210> SEQ ID NO 1558
<211> LENGTH: 19
<212> TYPE: RNA
<213> ORGANISM: Homo sapiens

<400> SEQUENCE: 1558
augccuacau ggagcuggg 19

<210> SEQ ID NO 1559
<211> LENGTH: 19
<212> TYPE: RNA
<213> ORGANISM: Homo sapiens

<400> SEQUENCE: 1559
ugccuacaug gagcugggg 19

<210> SEQ ID NO 1560
<211> LENGTH: 19
<212> TYPE: RNA
<213> ORGANISM: Homo sapiens

<400> SEQUENCE: 1560
cugaaucugc caucuggaa 19

<210> SEQ ID NO 1561
<211> LENGTH: 19
<212> TYPE: RNA
<213> ORGANISM: Homo sapiens

<400> SEQUENCE: 1561
ucugccaucu ggaaaguuu 19

<210> SEQ ID NO 1562
<211> LENGTH: 19
<212> TYPE: RNA
<213> ORGANISM: Homo sapiens

<400> SEQUENCE: 1562
aguuuccucg gggcuucaa 19

<210> SEQ ID NO 1563
<211> LENGTH: 19
<212> TYPE: RNA

<213> ORGANISM: Homo sapiens

<400> SEQUENCE: 1563
guuuccucgg ggcuucaaa 19

<210> SEQ ID NO 1564
<211> LENGTH: 19
<212> TYPE: RNA
<213> ORGANISM: Homo sapiens

<400> SEQUENCE: 1564
auucgacacg gaugagcug 19

<210> SEQ ID NO 1565
<211> LENGTH: 19
<212> TYPE: RNA
<213> ORGANISM: Homo sapiens

<400> SEQUENCE: 1565
uucgacacgg augagcuga 19

<210> SEQ ID NO 1566
<211> LENGTH: 19
<212> TYPE: RNA
<213> ORGANISM: Homo sapiens

<400> SEQUENCE: 1566
cuuucccacg gagaagcuu 19

<210> SEQ ID NO 1567
<211> LENGTH: 19
<212> TYPE: RNA
<213> ORGANISM: Homo sapiens

<400> SEQUENCE: 1567
gcuuugcuuu guggggcuc 19

<210> SEQ ID NO 1568
<211> LENGTH: 19
<212> TYPE: RNA
<213> ORGANISM: Homo sapiens

<400> SEQUENCE: 1568
gcgcaggcau caaggugau 19

<210> SEQ ID NO 1569
<211> LENGTH: 19
<212> TYPE: RNA
<213> ORGANISM: Homo sapiens

<400> SEQUENCE: 1569
ggugaucaug guaaccggg 19

<210> SEQ ID NO 1570
<211> LENGTH: 19
<212> TYPE: RNA
<213> ORGANISM: Homo sapiens

<400> SEQUENCE: 1570
ccggggauca cccuaucac 19

<210> SEQ ID NO 1571
<211> LENGTH: 19

<212> TYPE: RNA
<213> ORGANISM: Homo sapiens

<400> SEQUENCE: 1571
ggccauugcc aaaggcgug 19

<210> SEQ ID NO 1572
<211> LENGTH: 19
<212> TYPE: RNA
<213> ORGANISM: Homo sapiens

<400> SEQUENCE: 1572
aggcgugggc aucauauca 19

<210> SEQ ID NO 1573
<211> LENGTH: 19
<212> TYPE: RNA
<213> ORGANISM: Homo sapiens

<400> SEQUENCE: 1573
ggcgugggca ucauaucag 19

<210> SEQ ID NO 1574
<211> LENGTH: 19
<212> TYPE: RNA
<213> ORGANISM: Homo sapiens

<400> SEQUENCE: 1574
cgagacugug gaggacauu 19

<210> SEQ ID NO 1575
<211> LENGTH: 19
<212> TYPE: RNA
<213> ORGANISM: Homo sapiens

<400> SEQUENCE: 1575
cauucccaug agucaaguc 19

<210> SEQ ID NO 1576
<211> LENGTH: 19
<212> TYPE: RNA
<213> ORGANISM: Homo sapiens

<400> SEQUENCE: 1576
gucaacccca gagaagcca 19

<210> SEQ ID NO 1577
<211> LENGTH: 19
<212> TYPE: RNA
<213> ORGANISM: Homo sapiens

<400> SEQUENCE: 1577
ccccagagaa gccaaggca 19

<210> SEQ ID NO 1578
<211> LENGTH: 19
<212> TYPE: RNA
<213> ORGANISM: Homo sapiens

<400> SEQUENCE: 1578
ggacaugaca ucggagcag 19

<210> SEQ ID NO 1579

<211> LENGTH: 19
<212> TYPE: RNA
<213> ORGANISM: Homo sapiens

<400> SEQUENCE: 1579
gaaccacaca gagaucguc 19

<210> SEQ ID NO 1580
<211> LENGTH: 19
<212> TYPE: RNA
<213> ORGANISM: Homo sapiens

<400> SEQUENCE: 1580
ccacacagag aucgucuuu 19

<210> SEQ ID NO 1581
<211> LENGTH: 19
<212> TYPE: RNA
<213> ORGANISM: Homo sapiens

<400> SEQUENCE: 1581
cgucucccca gcagaagcu 19

<210> SEQ ID NO 1582
<211> LENGTH: 19
<212> TYPE: RNA
<213> ORGANISM: Homo sapiens

<400> SEQUENCE: 1582
gcucaucauu guggaggga 19

<210> SEQ ID NO 1583
<211> LENGTH: 19
<212> TYPE: RNA
<213> ORGANISM: Homo sapiens

<400> SEQUENCE: 1583
cgacuccccu gcauugaag 19

<210> SEQ ID NO 1584
<211> LENGTH: 19
<212> TYPE: RNA
<213> ORGANISM: Homo sapiens

<400> SEQUENCE: 1584
gaaggcugac auuggcauu 19

<210> SEQ ID NO 1585
<211> LENGTH: 19
<212> TYPE: RNA
<213> ORGANISM: Homo sapiens

<400> SEQUENCE: 1585
ggcugacauu ggcauugcc 19

<210> SEQ ID NO 1586
<211> LENGTH: 19
<212> TYPE: RNA
<213> ORGANISM: Homo sapiens

<400> SEQUENCE: 1586
gcaggcagcc gacaugauc 19

<210> SEQ ID NO 1587
<211> LENGTH: 19
<212> TYPE: RNA
<213> ORGANISM: Homo sapiens

<400> SEQUENCE: 1587
cuuugccucc aucgucacg 19

<210> SEQ ID NO 1588
<211> LENGTH: 19
<212> TYPE: RNA
<213> ORGANISM: Homo sapiens

<400> SEQUENCE: 1588
cuugaagaaa uccaucgcc 19

<210> SEQ ID NO 1589
<211> LENGTH: 19
<212> TYPE: RNA
<213> ORGANISM: Homo sapiens

<400> SEQUENCE: 1589
gaaauccauc gccuacacc 19

<210> SEQ ID NO 1590
<211> LENGTH: 19
<212> TYPE: RNA
<213> ORGANISM: Homo sapiens

<400> SEQUENCE: 1590
auccaucgcc uacacccug 19

<210> SEQ ID NO 1591
<211> LENGTH: 19
<212> TYPE: RNA
<213> ORGANISM: Homo sapiens

<400> SEQUENCE: 1591
uccaucgccu acacccuga 19

<210> SEQ ID NO 1592
<211> LENGTH: 19
<212> TYPE: RNA
<213> ORGANISM: Homo sapiens

<400> SEQUENCE: 1592
acucccagac ggacaagcu 19

<210> SEQ ID NO 1593
<211> LENGTH: 19
<212> TYPE: RNA
<213> ORGANISM: Homo sapiens

<400> SEQUENCE: 1593
cucccagacg gacaagcug 19

<210> SEQ ID NO 1594
<211> LENGTH: 19
<212> TYPE: RNA
<213> ORGANISM: Homo sapiens

<400> SEQUENCE: 1594
gcuggugaau gagaggcuc 19

<210> SEQ ID NO 1595
<211> LENGTH: 19
<212> TYPE: RNA
<213> ORGANISM: Homo sapiens

<400> SEQUENCE: 1595
ugagaggcuc aucagcaug 19

<210> SEQ ID NO 1596
<211> LENGTH: 19
<212> TYPE: RNA
<213> ORGANISM: Homo sapiens

<400> SEQUENCE: 1596
cgguuuccug ccaucacgg 19

<210> SEQ ID NO 1597
<211> LENGTH: 19
<212> TYPE: RNA
<213> ORGANISM: Homo sapiens

<400> SEQUENCE: 1597
uccgccucga cugggauga 19

<210> SEQ ID NO 1598
<211> LENGTH: 19
<212> TYPE: RNA
<213> ORGANISM: Homo sapiens

<400> SEQUENCE: 1598
ugaucuggag gacagcuau 19

<210> SEQ ID NO 1599
<211> LENGTH: 19
<212> TYPE: RNA
<213> ORGANISM: Homo sapiens

<400> SEQUENCE: 1599
ggugguggag uucacgugc 19

<210> SEQ ID NO 1600
<211> LENGTH: 19
<212> TYPE: RNA
<213> ORGANISM: Homo sapiens

<400> SEQUENCE: 1600
cucagucuuc cagcagggc 19

<210> SEQ ID NO 1601
<211> LENGTH: 19
<212> TYPE: RNA
<213> ORGANISM: Homo sapiens

<400> SEQUENCE: 1601
caagauccug auuuuuggg 19

<210> SEQ ID NO 1602
<211> LENGTH: 19
<212> TYPE: RNA
<213> ORGANISM: Homo sapiens

<400> SEQUENCE: 1602
gauccugauu uuugggcuc 19

<210> SEQ ID NO 1603
<211> LENGTH: 19
<212> TYPE: RNA
<213> ORGANISM: Homo sapiens

<400> SEQUENCE: 1603
agucaccugg ugguucugc 19

<210> SEQ ID NO 1604
<211> LENGTH: 19
<212> TYPE: RNA
<213> ORGANISM: Homo sapiens

<400> SEQUENCE: 1604
gucaccuggu gguucugcg 19

<210> SEQ ID NO 1605
<211> LENGTH: 19
<212> TYPE: RNA
<213> ORGANISM: Homo sapiens

<400> SEQUENCE: 1605
agcucauccu gcggcggua 19

<210> SEQ ID NO 1606
<211> LENGTH: 19
<212> TYPE: RNA
<213> ORGANISM: Homo sapiens

<400> SEQUENCE: 1606
gcucauccug cggcgguau 19

<210> SEQ ID NO 1607
<211> LENGTH: 19
<212> TYPE: RNA
<213> ORGANISM: Homo sapiens

<400> SEQUENCE: 1607
gaugggggac aagaaagau 19

<210> SEQ ID NO 1608
<211> LENGTH: 19
<212> TYPE: RNA
<213> ORGANISM: Homo sapiens

<400> SEQUENCE: 1608
gaaagaugac aaggacuca 19

<210> SEQ ID NO 1609
<211> LENGTH: 19
<212> TYPE: RNA
<213> ORGANISM: Homo sapiens

<400> SEQUENCE: 1609
agaugacaag gacucaccc 19

<210> SEQ ID NO 1610
<211> LENGTH: 19
<212> TYPE: RNA
<213> ORGANISM: Homo sapiens

<400> SEQUENCE: 1610
gaugacaagg acucaccca 19

<210> SEQ ID NO 1611
<211> LENGTH: 19
<212> TYPE: RNA
<213> ORGANISM: Homo sapiens

<400> SEQUENCE: 1611
ggacucaccc aagaagaac 19

<210> SEQ ID NO 1612
<211> LENGTH: 19
<212> TYPE: RNA
<213> ORGANISM: Homo sapiens

<400> SEQUENCE: 1612
gaagaacaag ggcaaggag 19

<210> SEQ ID NO 1613
<211> LENGTH: 19
<212> TYPE: RNA
<213> ORGANISM: Homo sapiens

<400> SEQUENCE: 1613
gaacaagggc aaggagcgc 19

<210> SEQ ID NO 1614
<211> LENGTH: 19
<212> TYPE: RNA
<213> ORGANISM: Homo sapiens

<400> SEQUENCE: 1614
gaaggaggug gcuaugaca 19

<210> SEQ ID NO 1615
<211> LENGTH: 19
<212> TYPE: RNA
<213> ORGANISM: Homo sapiens

<400> SEQUENCE: 1615
ggagguggcu augacagag 19

<210> SEQ ID NO 1616
<211> LENGTH: 19
<212> TYPE: RNA
<213> ORGANISM: Homo sapiens

<400> SEQUENCE: 1616
gaugucagug gaagagguc 19

<210> SEQ ID NO 1617
<211> LENGTH: 19
<212> TYPE: RNA
<213> ORGANISM: Homo sapiens

<400> SEQUENCE: 1617
gaggucugcc ggaaauaca 19

<210> SEQ ID NO 1618
<211> LENGTH: 19
<212> TYPE: RNA
<213> ORGANISM: Homo sapiens

<400> SEQUENCE: 1618
auacaacaca gacugugug 19

<210> SEQ ID NO 1619
<211> LENGTH: 19
<212> TYPE: RNA
<213> ORGANISM: Homo sapiens

<400> SEQUENCE: 1619
uacaacacag acugugugc 19

<210> SEQ ID NO 1620
<211> LENGTH: 19
<212> TYPE: RNA
<213> ORGANISM: Homo sapiens

<400> SEQUENCE: 1620
cacagacugu gugcagggu 19

<210> SEQ ID NO 1621
<211> LENGTH: 19
<212> TYPE: RNA
<213> ORGANISM: Homo sapiens

<400> SEQUENCE: 1621
guuuugccgg cagcucuuc 19

<210> SEQ ID NO 1622
<211> LENGTH: 19
<212> TYPE: RNA
<213> ORGANISM: Homo sapiens

<400> SEQUENCE: 1622
ccuguaccug ggcaucgug 19

<210> SEQ ID NO 1623
<211> LENGTH: 19
<212> TYPE: RNA
<213> ORGANISM: Homo sapiens

<400> SEQUENCE: 1623
gagcuccaag aucauggag 19

<210> SEQ ID NO 1624
<211> LENGTH: 19
<212> TYPE: RNA
<213> ORGANISM: Homo sapiens

<400> SEQUENCE: 1624
gaucauggag uccuucaag 19

<210> SEQ ID NO 1625
<211> LENGTH: 19
<212> TYPE: RNA
<213> ORGANISM: Homo sapiens

<400> SEQUENCE: 1625
gaacauggug ccccagcaa 19

<210> SEQ ID NO 1626
<211> LENGTH: 19
<212> TYPE: RNA
<213> ORGANISM: Homo sapiens

<400> SEQUENCE: 1626
ggugagaaga ugcagguga 19

<210> SEQ ID NO 1627
<211> LENGTH: 19
<212> TYPE: RNA
<213> ORGANISM: Homo sapiens

<400> SEQUENCE: 1627
gaugcaggug aacgcugag 19

<210> SEQ ID NO 1628
<211> LENGTH: 19
<212> TYPE: RNA
<213> ORGANISM: Homo sapiens

<400> SEQUENCE: 1628
gguggacaac uccucccug 19

<210> SEQ ID NO 1629
<211> LENGTH: 19
<212> TYPE: RNA
<213> ORGANISM: Homo sapiens

<400> SEQUENCE: 1629
cuccucccug acuggcgaa 19

<210> SEQ ID NO 1630
<211> LENGTH: 19
<212> TYPE: RNA
<213> ORGANISM: Homo sapiens

<400> SEQUENCE: 1630
ccccuuggag acucggaac 19

<210> SEQ ID NO 1631
<211> LENGTH: 19
<212> TYPE: RNA
<213> ORGANISM: Homo sapiens

<400> SEQUENCE: 1631
caucaccuuc uuuuccacc 19

<210> SEQ ID NO 1632
<211> LENGTH: 19
<212> TYPE: RNA
<213> ORGANISM: Homo sapiens

<400> SEQUENCE: 1632
cuguguggaa ggcacggcu 19

<210> SEQ ID NO 1633
<211> LENGTH: 19
<212> TYPE: RNA
<213> ORGANISM: Homo sapiens

<400> SEQUENCE: 1633
ugucccagag ggucugcug 19

<210> SEQ ID NO 1634
<211> LENGTH: 19
<212> TYPE: RNA
<213> ORGANISM: Homo sapiens

<400> SEQUENCE: 1634
gaacugccug gugaagaac 19

<210> SEQ ID NO 1635
<211> LENGTH: 19
<212> TYPE: RNA
<213> ORGANISM: Homo sapiens

<400> SEQUENCE: 1635
cugccuggug aagaaccug 19

<210> SEQ ID NO 1636
<211> LENGTH: 19
<212> TYPE: RNA
<213> ORGANISM: Homo sapiens

<400> SEQUENCE: 1636
gaaccuggag gcuguagaa 19

<210> SEQ ID NO 1637
<211> LENGTH: 19
<212> TYPE: RNA
<213> ORGANISM: Homo sapiens

<400> SEQUENCE: 1637
ccuggaggcu guagaaacc 19

<210> SEQ ID NO 1638
<211> LENGTH: 19
<212> TYPE: RNA
<213> ORGANISM: Homo sapiens

<400> SEQUENCE: 1638
gacagggacc cucacucag 19

<210> SEQ ID NO 1639
<211> LENGTH: 19
<212> TYPE: RNA
<213> ORGANISM: Homo sapiens

<400> SEQUENCE: 1639
ccagauccac gaggcugac 19

<210> SEQ ID NO 1640
<211> LENGTH: 19
<212> TYPE: RNA
<213> ORGANISM: Homo sapiens

<400> SEQUENCE: 1640
gaguucgcac accugggug 19

<210> SEQ ID NO 1641
<211> LENGTH: 19
<212> TYPE: RNA
<213> ORGANISM: Homo sapiens

<400> SEQUENCE: 1641
ucgcgcuguc uucaagggu 19

<210> SEQ ID NO 1642
<211> LENGTH: 19
<212> TYPE: RNA

<213> ORGANISM: Homo sapiens

<400> SEQUENCE: 1642
ggguggucag gacaacauc 19

<210> SEQ ID NO 1643
<211> LENGTH: 19
<212> TYPE: RNA
<213> ORGANISM: Homo sapiens

<400> SEQUENCE: 1643
caucccugug cucaagagg 19

<210> SEQ ID NO 1644
<211> LENGTH: 19
<212> TYPE: RNA
<213> ORGANISM: Homo sapiens

<400> SEQUENCE: 1644
gagggaugug gcuggggau 19

<210> SEQ ID NO 1645
<211> LENGTH: 19
<212> TYPE: RNA
<213> ORGANISM: Homo sapiens

<400> SEQUENCE: 1645
gugcaucgag cuguccucu 19

<210> SEQ ID NO 1646
<211> LENGTH: 19
<212> TYPE: RNA
<213> ORGANISM: Homo sapiens

<400> SEQUENCE: 1646
gcugaugcgu gaacgcaac 19

<210> SEQ ID NO 1647
<211> LENGTH: 19
<212> TYPE: RNA
<213> ORGANISM: Homo sapiens

<400> SEQUENCE: 1647
cgcaacaaga aaguggcug 19

<210> SEQ ID NO 1648
<211> LENGTH: 19
<212> TYPE: RNA
<213> ORGANISM: Homo sapiens

<400> SEQUENCE: 1648
caagaaagug gcugagauu 19

<210> SEQ ID NO 1649
<211> LENGTH: 19
<212> TYPE: RNA
<213> ORGANISM: Homo sapiens

<400> SEQUENCE: 1649
gaaaguggcu gagauuccc 19

<210> SEQ ID NO 1650
<211> LENGTH: 19

<212> TYPE: RNA
<213> ORGANISM: Homo sapiens

<400> SEQUENCE: 1650
aguggcugag auucccuuc 19

<210> SEQ ID NO 1651
<211> LENGTH: 19
<212> TYPE: RNA
<213> ORGANISM: Homo sapiens

<400> SEQUENCE: 1651
guggcugaga uucccuuca 19

<210> SEQ ID NO 1652
<211> LENGTH: 19
<212> TYPE: RNA
<213> ORGANISM: Homo sapiens

<400> SEQUENCE: 1652
uuccaccaac aaauaccag 19

<210> SEQ ID NO 1653
<211> LENGTH: 19
<212> TYPE: RNA
<213> ORGANISM: Homo sapiens

<400> SEQUENCE: 1653
caaauaccag cucuccauc 19

<210> SEQ ID NO 1654
<211> LENGTH: 19
<212> TYPE: RNA
<213> ORGANISM: Homo sapiens

<400> SEQUENCE: 1654
auaccagcuc uccauccau 19

<210> SEQ ID NO 1655
<211> LENGTH: 19
<212> TYPE: RNA
<213> ORGANISM: Homo sapiens

<400> SEQUENCE: 1655
uaccagcucu ccauccaug 19

<210> SEQ ID NO 1656
<211> LENGTH: 19
<212> TYPE: RNA
<213> ORGANISM: Homo sapiens

<400> SEQUENCE: 1656
cgacaaccga uaccugcug 19

<210> SEQ ID NO 1657
<211> LENGTH: 19
<212> TYPE: RNA
<213> ORGANISM: Homo sapiens

<400> SEQUENCE: 1657
ccgauaccug cuggugaug 19

<210> SEQ ID NO 1658

<211> LENGTH: 19
<212> TYPE: RNA
<213> ORGANISM: Homo sapiens

<400> SEQUENCE: 1658
augaaggagg ccuuccaga 19

<210> SEQ ID NO 1659
<211> LENGTH: 19
<212> TYPE: RNA
<213> ORGANISM: Homo sapiens

<400> SEQUENCE: 1659
ugaaggaggc cuuccagaa 19

<210> SEQ ID NO 1660
<211> LENGTH: 19
<212> TYPE: RNA
<213> ORGANISM: Homo sapiens

<400> SEQUENCE: 1660
ggaggccuuc cagaaugcc 19

<210> SEQ ID NO 1661
<211> LENGTH: 19
<212> TYPE: RNA
<213> ORGANISM: Homo sapiens

<400> SEQUENCE: 1661
ugccuaccuu gagcucggu 19

<210> SEQ ID NO 1662
<211> LENGTH: 19
<212> TYPE: RNA
<213> ORGANISM: Homo sapiens

<400> SEQUENCE: 1662
gggcuuugcc uucgacugu 19

<210> SEQ ID NO 1663
<211> LENGTH: 19
<212> TYPE: RNA
<213> ORGANISM: Homo sapiens

<400> SEQUENCE: 1663
cuucaccacg gacaaccuc 19

<210> SEQ ID NO 1664
<211> LENGTH: 19
<212> TYPE: RNA
<213> ORGANISM: Homo sapiens

<400> SEQUENCE: 1664
ccucugcuuu gugggccuc 19

<210> SEQ ID NO 1665
<211> LENGTH: 19
<212> TYPE: RNA
<213> ORGANISM: Homo sapiens

<400> SEQUENCE: 1665
ggucaucaug gucaccggc 19

<210> SEQ ID NO 1666
<211> LENGTH: 19
<212> TYPE: RNA
<213> ORGANISM: Homo sapiens

<400> SEQUENCE: 1666
ggccauugcc aagggugug 19

<210> SEQ ID NO 1667
<211> LENGTH: 19
<212> TYPE: RNA
<213> ORGANISM: Homo sapiens

<400> SEQUENCE: 1667
gggugugggc aucaucucu 19

<210> SEQ ID NO 1668
<211> LENGTH: 19
<212> TYPE: RNA
<213> ORGANISM: Homo sapiens

<400> SEQUENCE: 1668
cgagacugug gaggacauc 19

<210> SEQ ID NO 1669
<211> LENGTH: 19
<212> TYPE: RNA
<213> ORGANISM: Homo sapiens

<400> SEQUENCE: 1669
cauucccguc agccagguu 19

<210> SEQ ID NO 1670
<211> LENGTH: 19
<212> TYPE: RNA
<213> ORGANISM: Homo sapiens

<400> SEQUENCE: 1670
ggacuucacc uccgagcaa 19

<210> SEQ ID NO 1671
<211> LENGTH: 19
<212> TYPE: RNA
<213> ORGANISM: Homo sapiens

<400> SEQUENCE: 1671
aucgacgaga uccugcaga 19

<210> SEQ ID NO 1672
<211> LENGTH: 19
<212> TYPE: RNA
<213> ORGANISM: Homo sapiens

<400> SEQUENCE: 1672
ucgacgagau ccugcagaa 19

<210> SEQ ID NO 1673
<211> LENGTH: 19
<212> TYPE: RNA
<213> ORGANISM: Homo sapiens

<400> SEQUENCE: 1673
ucacaccgag aucgucuuc 19

<210> SEQ ID NO 1674
<211> LENGTH: 19
<212> TYPE: RNA
<213> ORGANISM: Homo sapiens

<400> SEQUENCE: 1674
gcucaucauu guggagggc 19

<210> SEQ ID NO 1675
<211> LENGTH: 19
<212> TYPE: RNA
<213> ORGANISM: Homo sapiens

<400> SEQUENCE: 1675
uuguggcugu gaccgggga 19

<210> SEQ ID NO 1676
<211> LENGTH: 19
<212> TYPE: RNA
<213> ORGANISM: Homo sapiens

<400> SEQUENCE: 1676
gaaggccgac auuggggug 19

<210> SEQ ID NO 1677
<211> LENGTH: 19
<212> TYPE: RNA
<213> ORGANISM: Homo sapiens

<400> SEQUENCE: 1677
gcaggcagcu gacaugauc 19

<210> SEQ ID NO 1678
<211> LENGTH: 19
<212> TYPE: RNA
<213> ORGANISM: Homo sapiens

<400> SEQUENCE: 1678
cuuugccucc aucgucaca 19

<210> SEQ ID NO 1679
<211> LENGTH: 19
<212> TYPE: RNA
<213> ORGANISM: Homo sapiens

<400> SEQUENCE: 1679
ccuaaagaag uccauugcc 19

<210> SEQ ID NO 1680
<211> LENGTH: 19
<212> TYPE: RNA
<213> ORGANISM: Homo sapiens

<400> SEQUENCE: 1680
agaaguccau ugccuacac 19

<210> SEQ ID NO 1681
<211> LENGTH: 19
<212> TYPE: RNA
<213> ORGANISM: Homo sapiens

<400> SEQUENCE: 1681
gaaguccauu gccuacacc 19

<210> SEQ ID NO 1682
<211> LENGTH: 19
<212> TYPE: RNA
<213> ORGANISM: Homo sapiens

<400> SEQUENCE: 1682
guccauugcc uacacccug 19

<210> SEQ ID NO 1683
<211> LENGTH: 19
<212> TYPE: RNA
<213> ORGANISM: Homo sapiens

<400> SEQUENCE: 1683
uaucccggag aucacgccc 19

<210> SEQ ID NO 1684
<211> LENGTH: 19
<212> TYPE: RNA
<213> ORGANISM: Homo sapiens

<400> SEQUENCE: 1684
agcgacauca ugaagagac 19

<210> SEQ ID NO 1685
<211> LENGTH: 19
<212> TYPE: RNA
<213> ORGANISM: Homo sapiens

<400> SEQUENCE: 1685
gcgacaucau gaagagaca 19

<210> SEQ ID NO 1686
<211> LENGTH: 19
<212> TYPE: RNA
<213> ORGANISM: Homo sapiens

<400> SEQUENCE: 1686
cccgcggacg gacaaauug 19

<210> SEQ ID NO 1687
<211> LENGTH: 19
<212> TYPE: RNA
<213> ORGANISM: Homo sapiens

<400> SEQUENCE: 1687
auuggucaau gagagacuc 19

<210> SEQ ID NO 1688
<211> LENGTH: 19
<212> TYPE: RNA
<213> ORGANISM: Homo sapiens

<400> SEQUENCE: 1688
uuggucaaug agagacuca 19

<210> SEQ ID NO 1689
<211> LENGTH: 19
<212> TYPE: RNA
<213> ORGANISM: Homo sapiens

<400> SEQUENCE: 1689
ugagagacuc aucagcaug 19

<210> SEQ ID NO 1690
<211> LENGTH: 19
<212> TYPE: RNA
<213> ORGANISM: Homo sapiens

<400> SEQUENCE: 1690
ugauccaggc ucucggugg 19

<210> SEQ ID NO 1691
<211> LENGTH: 19
<212> TYPE: RNA
<213> ORGANISM: Homo sapiens

<400> SEQUENCE: 1691
aauggcuucu ugcccggca 19

<210> SEQ ID NO 1692
<211> LENGTH: 19
<212> TYPE: RNA
<213> ORGANISM: Homo sapiens

<400> SEQUENCE: 1692
auggcuucuu gcccggcaa 19

<210> SEQ ID NO 1693
<211> LENGTH: 19
<212> TYPE: RNA
<213> ORGANISM: Homo sapiens

<400> SEQUENCE: 1693
uggcuucuug cccggcaac 19

<210> SEQ ID NO 1694
<211> LENGTH: 19
<212> TYPE: RNA
<213> ORGANISM: Homo sapiens

<400> SEQUENCE: 1694
ugaccuggaa gacaguuac 19

<210> SEQ ID NO 1695
<211> LENGTH: 19
<212> TYPE: RNA
<213> ORGANISM: Homo sapiens

<400> SEQUENCE: 1695
gacaguuacg ggcagcagu 19

<210> SEQ ID NO 1696
<211> LENGTH: 19
<212> TYPE: RNA
<213> ORGANISM: Homo sapiens

<400> SEQUENCE: 1696
ggugguggag uucaccugc 19

<210> SEQ ID NO 1697
<211> LENGTH: 19
<212> TYPE: RNA
<213> ORGANISM: Homo sapiens

<400> SEQUENCE: 1697
gaacaagauc cugaucuuc 19

<210> SEQ ID NO 1698
<211> LENGTH: 19
<212> TYPE: RNA
<213> ORGANISM: Homo sapiens

<400> SEQUENCE: 1698
caagauccug aucuucggg 19

<210> SEQ ID NO 1699
<211> LENGTH: 19
<212> TYPE: RNA
<213> ORGANISM: Homo sapiens

<400> SEQUENCE: 1699
gauccugauc uucgggcug 19

<210> SEQ ID NO 1700
<211> LENGTH: 19
<212> TYPE: RNA
<213> ORGANISM: Homo sapiens

<400> SEQUENCE: 1700
gcccagcugg ugguucugu 19

<210> SEQ ID NO 1701
<211> LENGTH: 19
<212> TYPE: RNA
<213> ORGANISM: Homo sapiens

<400> SEQUENCE: 1701
auccgcaaac ucauccugc 19

<210> SEQ ID NO 1702
<211> LENGTH: 19
<212> TYPE: RNA
<213> ORGANISM: Homo sapiens

<400> SEQUENCE: 1702
uccgcaaacu cauccugcg 19

<210> SEQ ID NO 1703
<211> LENGTH: 19
<212> TYPE: RNA
<213> ORGANISM: Homo sapiens

<400> SEQUENCE: 1703
acucauccug cgcaggaac 19

<210> SEQ ID NO 1704
<211> LENGTH: 19
<212> TYPE: RNA
<213> ORGANISM: Homo sapiens

<400> SEQUENCE: 1704
cucauccugc gcaggaacc 19

<210> SEQ ID NO 1705
<211> LENGTH: 19
<212> TYPE: RNA
<213> ORGANISM: Homo sapiens

<400> SEQUENCE: 1705
ggaaaccuac uacugaccu 19

<210> SEQ ID NO 1706
<211> LENGTH: 19
<212> TYPE: RNA
<213> ORGANISM: Homo sapiens

<400> SEQUENCE: 1706
aaauuaaauu uuaagugac 19

<210> SEQ ID NO 1707
<211> LENGTH: 19
<212> TYPE: RNA
<213> ORGANISM: Homo sapiens

<400> SEQUENCE: 1707
aauuaaauuu uaagugaca 19

<210> SEQ ID NO 1708
<211> LENGTH: 19
<212> TYPE: RNA
<213> ORGANISM: Homo sapiens

<400> SEQUENCE: 1708
auuaaauuuu aagugacac 19

<210> SEQ ID NO 1709
<211> LENGTH: 19
<212> TYPE: RNA
<213> ORGANISM: Homo sapiens

<400> SEQUENCE: 1709
uuaaauuuua agugacacu 19

<210> SEQ ID NO 1710
<211> LENGTH: 19
<212> TYPE: RNA
<213> ORGANISM: Homo sapiens

<400> SEQUENCE: 1710
gaaauucauc uggaacuca 19

<210> SEQ ID NO 1711
<211> LENGTH: 19
<212> TYPE: RNA
<213> ORGANISM: Homo sapiens

<400> SEQUENCE: 1711
auucaucugg aacucagag 19

<210> SEQ ID NO 1712
<211> LENGTH: 19
<212> TYPE: RNA
<213> ORGANISM: Homo sapiens

<400> SEQUENCE: 1712
uucaucugga acucagaga 19

<210> SEQ ID NO 1713
<211> LENGTH: 19
<212> TYPE: RNA
<213> ORGANISM: Homo sapiens

<400> SEQUENCE: 1713
cucagagaag aaggaguuu 19

<210> SEQ ID NO 1714
<211> LENGTH: 19
<212> TYPE: RNA
<213> ORGANISM: Homo sapiens

<400> SEQUENCE: 1714
gaaggaguuu cugggcagg 19

<210> SEQ ID NO 1715
<211> LENGTH: 19
<212> TYPE: RNA
<213> ORGANISM: Homo sapiens

<400> SEQUENCE: 1715
ggaguuucug ggcaggacc 19

<210> SEQ ID NO 1716
<211> LENGTH: 19
<212> TYPE: RNA
<213> ORGANISM: Homo sapiens

<400> SEQUENCE: 1716
gauccuucua uucuacgua 19

<210> SEQ ID NO 1717
<211> LENGTH: 19
<212> TYPE: RNA
<213> ORGANISM: Homo sapiens

<400> SEQUENCE: 1717
uauuuuaugg cugccuggc 19

<210> SEQ ID NO 1718
<211> LENGTH: 19
<212> TYPE: RNA
<213> ORGANISM: Homo sapiens

<400> SEQUENCE: 1718
ccauccaagu gaugcugcu 19

<210> SEQ ID NO 1719
<211> LENGTH: 19
<212> TYPE: RNA
<213> ORGANISM: Homo sapiens

<400> SEQUENCE: 1719
gugaugcugc ucaccauca 19

<210> SEQ ID NO 1720
<211> LENGTH: 19
<212> TYPE: RNA
<213> ORGANISM: Homo sapiens

<400> SEQUENCE: 1720
uuuaagccca cauaucagg 19

<210> SEQ ID NO 1721
<211> LENGTH: 19
<212> TYPE: RNA

<213> ORGANISM: Homo sapiens

<400> SEQUENCE: 1721
gcccacauau caggaccga 19

<210> SEQ ID NO 1722
<211> LENGTH: 19
<212> TYPE: RNA
<213> ORGANISM: Homo sapiens

<400> SEQUENCE: 1722
cacagauucc ucagaucca 19

<210> SEQ ID NO 1723
<211> LENGTH: 19
<212> TYPE: RNA
<213> ORGANISM: Homo sapiens

<400> SEQUENCE: 1723
gacugaaauu uccuuucgu 19

<210> SEQ ID NO 1724
<211> LENGTH: 19
<212> TYPE: RNA
<213> ORGANISM: Homo sapiens

<400> SEQUENCE: 1724
auuuccuuuc guccuaaug 19

<210> SEQ ID NO 1725
<211> LENGTH: 19
<212> TYPE: RNA
<213> ORGANISM: Homo sapiens

<400> SEQUENCE: 1725
uuuccuuucg uccuaauga 19

<210> SEQ ID NO 1726
<211> LENGTH: 19
<212> TYPE: RNA
<213> ORGANISM: Homo sapiens

<400> SEQUENCE: 1726
ugaucccaag agcuaugag 19

<210> SEQ ID NO 1727
<211> LENGTH: 19
<212> TYPE: RNA
<213> ORGANISM: Homo sapiens

<400> SEQUENCE: 1727
gagcuaugag gcauaugua 19

<210> SEQ ID NO 1728
<211> LENGTH: 19
<212> TYPE: RNA
<213> ORGANISM: Homo sapiens

<400> SEQUENCE: 1728
cauaguuagg uuccuggaa 19

<210> SEQ ID NO 1729
<211> LENGTH: 19

<212> TYPE: RNA
<213> ORGANISM: Homo sapiens

<400> SEQUENCE: 1729
aaguacaaag auucagccc 19

<210> SEQ ID NO 1730
<211> LENGTH: 19
<212> TYPE: RNA
<213> ORGANISM: Homo sapiens

<400> SEQUENCE: 1730
aguacaaaga uucagccca 19

<210> SEQ ID NO 1731
<211> LENGTH: 19
<212> TYPE: RNA
<213> ORGANISM: Homo sapiens

<400> SEQUENCE: 1731
guacaaagau ucagcccag 19

<210> SEQ ID NO 1732
<211> LENGTH: 19
<212> TYPE: RNA
<213> ORGANISM: Homo sapiens

<400> SEQUENCE: 1732
agauucagcc cagagggau 19

<210> SEQ ID NO 1733
<211> LENGTH: 19
<212> TYPE: RNA
<213> ORGANISM: Homo sapiens

<400> SEQUENCE: 1733
gauucagccc agagggaug 19

<210> SEQ ID NO 1734
<211> LENGTH: 19
<212> TYPE: RNA
<213> ORGANISM: Homo sapiens

<400> SEQUENCE: 1734
gauuguggcg augugccca 19

<210> SEQ ID NO 1735
<211> LENGTH: 19
<212> TYPE: RNA
<213> ORGANISM: Homo sapiens

<400> SEQUENCE: 1735
ccgaaagaac gaggagacu 19

<210> SEQ ID NO 1736
<211> LENGTH: 19
<212> TYPE: RNA
<213> ORGANISM: Homo sapiens

<400> SEQUENCE: 1736
agaacgagga gacuuuaau 19

<210> SEQ ID NO 1737

<211> LENGTH: 19
<212> TYPE: RNA
<213> ORGANISM: Homo sapiens

<400> SEQUENCE: 1737
gaacgaggag acuuuaauc 19

<210> SEQ ID NO 1738
<211> LENGTH: 19
<212> TYPE: RNA
<213> ORGANISM: Homo sapiens

<400> SEQUENCE: 1738
cgaggagacu uuaaucaug 19

<210> SEQ ID NO 1739
<211> LENGTH: 19
<212> TYPE: RNA
<213> ORGANISM: Homo sapiens

<400> SEQUENCE: 1739
ucaugaacga ggagagcga 19

<210> SEQ ID NO 1740
<211> LENGTH: 19
<212> TYPE: RNA
<213> ORGANISM: Homo sapiens

<400> SEQUENCE: 1740
cgaggagagc gaaaggucu 19

<210> SEQ ID NO 1741
<211> LENGTH: 19
<212> TYPE: RNA
<213> ORGANISM: Homo sapiens

<400> SEQUENCE: 1741
aggucugcag auucaagcu 19

<210> SEQ ID NO 1742
<211> LENGTH: 19
<212> TYPE: RNA
<213> ORGANISM: Homo sapiens

<400> SEQUENCE: 1742
ggucugcaga uucaagcuu 19

<210> SEQ ID NO 1743
<211> LENGTH: 19
<212> TYPE: RNA
<213> ORGANISM: Homo sapiens

<400> SEQUENCE: 1743
gcuugaaugg cugggaaau 19

<210> SEQ ID NO 1744
<211> LENGTH: 19
<212> TYPE: RNA
<213> ORGANISM: Homo sapiens

<400> SEQUENCE: 1744
uggcugggaa auugcucug 19

<210> SEQ ID NO 1745
<211> LENGTH: 19
<212> TYPE: RNA
<213> ORGANISM: Homo sapiens

<400> SEQUENCE: 1745
ugaugaaacu uauggcuac 19

<210> SEQ ID NO 1746
<211> LENGTH: 19
<212> TYPE: RNA
<213> ORGANISM: Homo sapiens

<400> SEQUENCE: 1746
acuuauggcu acaaagagg 19

<210> SEQ ID NO 1747
<211> LENGTH: 19
<212> TYPE: RNA
<213> ORGANISM: Homo sapiens

<400> SEQUENCE: 1747
cuuauggcua caaagaggg 19

<210> SEQ ID NO 1748
<211> LENGTH: 19
<212> TYPE: RNA
<213> ORGANISM: Homo sapiens

<400> SEQUENCE: 1748
agagggcaaa ccgugcauu 19

<210> SEQ ID NO 1749
<211> LENGTH: 19
<212> TYPE: RNA
<213> ORGANISM: Homo sapiens

<400> SEQUENCE: 1749
gagggcaaac cgugcauua 19

<210> SEQ ID NO 1750
<211> LENGTH: 19
<212> TYPE: RNA
<213> ORGANISM: Homo sapiens

<400> SEQUENCE: 1750
ccgugcauua uuauaaagc 19

<210> SEQ ID NO 1751
<211> LENGTH: 19
<212> TYPE: RNA
<213> ORGANISM: Homo sapiens

<400> SEQUENCE: 1751
agcucaaccg aguucuagg 19

<210> SEQ ID NO 1752
<211> LENGTH: 19
<212> TYPE: RNA
<213> ORGANISM: Homo sapiens

<400> SEQUENCE: 1752
gcucaaccga guucuaggc 19

<210> SEQ ID NO 1753
<211> LENGTH: 19
<212> TYPE: RNA
<213> ORGANISM: Homo sapiens

<400> SEQUENCE: 1753
ccgaguucua ggcuucaaa 19

<210> SEQ ID NO 1754
<211> LENGTH: 19
<212> TYPE: RNA
<213> ORGANISM: Homo sapiens

<400> SEQUENCE: 1754
accuaagccu cccaagaau 19

<210> SEQ ID NO 1755
<211> LENGTH: 19
<212> TYPE: RNA
<213> ORGANISM: Homo sapiens

<400> SEQUENCE: 1755
ccuaagccuc ccaagaaug 19

<210> SEQ ID NO 1756
<211> LENGTH: 19
<212> TYPE: RNA
<213> ORGANISM: Homo sapiens

<400> SEQUENCE: 1756
gccucccaag aaugagucc 19

<210> SEQ ID NO 1757
<211> LENGTH: 19
<212> TYPE: RNA
<213> ORGANISM: Homo sapiens

<400> SEQUENCE: 1757
gaaugagucc uuggagacu 19

<210> SEQ ID NO 1758
<211> LENGTH: 19
<212> TYPE: RNA
<213> ORGANISM: Homo sapiens

<400> SEQUENCE: 1758
ugaguccuug gagacuuac 19

<210> SEQ ID NO 1759
<211> LENGTH: 19
<212> TYPE: RNA
<213> ORGANISM: Homo sapiens

<400> SEQUENCE: 1759
guauaaccca aauguccuu 19

<210> SEQ ID NO 1760
<211> LENGTH: 19
<212> TYPE: RNA
<213> ORGANISM: Homo sapiens

<400> SEQUENCE: 1760
cccaaauguc cuucccguu 19

<210> SEQ ID NO 1761
<211> LENGTH: 19
<212> TYPE: RNA
<213> ORGANISM: Homo sapiens

<400> SEQUENCE: 1761
auguccuucc cguucagug 19

<210> SEQ ID NO 1762
<211> LENGTH: 19
<212> TYPE: RNA
<213> ORGANISM: Homo sapiens

<400> SEQUENCE: 1762
uguccuuccc guucagugc 19

<210> SEQ ID NO 1763
<211> LENGTH: 19
<212> TYPE: RNA
<213> ORGANISM: Homo sapiens

<400> SEQUENCE: 1763
gcgagaugaa gauaaggau 19

<210> SEQ ID NO 1764
<211> LENGTH: 19
<212> TYPE: RNA
<213> ORGANISM: Homo sapiens

<400> SEQUENCE: 1764
ggauaaaguu ggaaaugug 19

<210> SEQ ID NO 1765
<211> LENGTH: 19
<212> TYPE: RNA
<213> ORGANISM: Homo sapiens

<400> SEQUENCE: 1765
aguuggaaau guggaguau 19

<210> SEQ ID NO 1766
<211> LENGTH: 19
<212> TYPE: RNA
<213> ORGANISM: Homo sapiens

<400> SEQUENCE: 1766
guuggaaaug uggaguauu 19

<210> SEQ ID NO 1767
<211> LENGTH: 19
<212> TYPE: RNA
<213> ORGANISM: Homo sapiens

<400> SEQUENCE: 1767
auguggagua uuuuggacu 19

<210> SEQ ID NO 1768
<211> LENGTH: 19
<212> TYPE: RNA
<213> ORGANISM: Homo sapiens

<400> SEQUENCE: 1768
uguggaguau uuuggacug 19

<210> SEQ ID NO 1769
<211> LENGTH: 19
<212> TYPE: RNA
<213> ORGANISM: Homo sapiens

<400> SEQUENCE: 1769
cuccccuggu uuuccucug 19

<210> SEQ ID NO 1770
<211> LENGTH: 19
<212> TYPE: RNA
<213> ORGANISM: Homo sapiens

<400> SEQUENCE: 1770
acuccugcag cccaaauac 19

<210> SEQ ID NO 1771
<211> LENGTH: 19
<212> TYPE: RNA
<213> ORGANISM: Homo sapiens

<400> SEQUENCE: 1771
cuccugcagc ccaaauacc 19

<210> SEQ ID NO 1772
<211> LENGTH: 19
<212> TYPE: RNA
<213> ORGANISM: Homo sapiens

<400> SEQUENCE: 1772
auaccugcag ccccugcug 19

<210> SEQ ID NO 1773
<211> LENGTH: 19
<212> TYPE: RNA
<213> ORGANISM: Homo sapiens

<400> SEQUENCE: 1773
ucuuaccaug gacacugaa 19

<210> SEQ ID NO 1774
<211> LENGTH: 19
<212> TYPE: RNA
<213> ORGANISM: Homo sapiens

<400> SEQUENCE: 1774
auucgcauag aguguaagg 19

<210> SEQ ID NO 1775
<211> LENGTH: 19
<212> TYPE: RNA
<213> ORGANISM: Homo sapiens

<400> SEQUENCE: 1775
uucgcauaga guguaaggc 19

<210> SEQ ID NO 1776
<211> LENGTH: 19
<212> TYPE: RNA
<213> ORGANISM: Homo sapiens

<400> SEQUENCE: 1776
ggcguacggu gagaacauu 19

<210> SEQ ID NO 1777
<211> LENGTH: 19
<212> TYPE: RNA
<213> ORGANISM: Homo sapiens

<400> SEQUENCE: 1777
cauuggguac agugagaaa 19

<210> SEQ ID NO 1778
<211> LENGTH: 19
<212> TYPE: RNA
<213> ORGANISM: Homo sapiens

<400> SEQUENCE: 1778
agaccguuuu cagggacgu 19

<210> SEQ ID NO 1779
<211> LENGTH: 19
<212> TYPE: RNA
<213> ORGANISM: Homo sapiens

<400> SEQUENCE: 1779
gaccguuuuc agggacguu 19

<210> SEQ ID NO 1780
<211> LENGTH: 19
<212> TYPE: RNA
<213> ORGANISM: Homo sapiens

<400> SEQUENCE: 1780
uugaaguuaa gagcugauc 19

<210> SEQ ID NO 1781
<211> LENGTH: 19
<212> TYPE: RNA
<213> ORGANISM: Homo sapiens

<400> SEQUENCE: 1781
gauggucauc cagaaagag 19

<210> SEQ ID NO 1782
<211> LENGTH: 19
<212> TYPE: RNA
<213> ORGANISM: Homo sapiens

<400> SEQUENCE: 1782
agagaagaag agcugcggg 19

<210> SEQ ID NO 1783
<211> LENGTH: 19
<212> TYPE: RNA
<213> ORGANISM: Homo sapiens

<400> SEQUENCE: 1783
gagaagaaga gcugcgggc 19

<210> SEQ ID NO 1784
<211> LENGTH: 19
<212> TYPE: RNA
<213> ORGANISM: Homo sapiens

<400> SEQUENCE: 1784
ggaguucgug uggaacccg 19

<210> SEQ ID NO 1785
<211> LENGTH: 19
<212> TYPE: RNA
<213> ORGANISM: Homo sapiens

<400> SEQUENCE: 1785
cccgaggacg caccaguuu 19

<210> SEQ ID NO 1786
<211> LENGTH: 19
<212> TYPE: RNA
<213> ORGANISM: Homo sapiens

<400> SEQUENCE: 1786
gacugagaac cuugauguc 19

<210> SEQ ID NO 1787
<211> LENGTH: 19
<212> TYPE: RNA
<213> ORGANISM: Homo sapiens

<400> SEQUENCE: 1787
ccuugauguc auugucaau 19

<210> SEQ ID NO 1788
<211> LENGTH: 19
<212> TYPE: RNA
<213> ORGANISM: Homo sapiens

<400> SEQUENCE: 1788
ugucagugac acugaaagc 19

<210> SEQ ID NO 1789
<211> LENGTH: 19
<212> TYPE: RNA
<213> ORGANISM: Homo sapiens

<400> SEQUENCE: 1789
agcugggacc agcauguuc 19

<210> SEQ ID NO 1790
<211> LENGTH: 19
<212> TYPE: RNA
<213> ORGANISM: Homo sapiens

<400> SEQUENCE: 1790
gcugggacca gcauguuca 19

<210> SEQ ID NO 1791
<211> LENGTH: 19
<212> TYPE: RNA
<213> ORGANISM: Homo sapiens

<400> SEQUENCE: 1791
gcucaacaag uucuuggag 19

<210> SEQ ID NO 1792
<211> LENGTH: 19
<212> TYPE: RNA
<213> ORGANISM: Homo sapiens

<400> SEQUENCE: 1792
caaguucuug gagccuuac 19

<210> SEQ ID NO 1793
<211> LENGTH: 19
<212> TYPE: RNA
<213> ORGANISM: Homo sapiens

<400> SEQUENCE: 1793
guucuuggag ccuuacaac 19

<210> SEQ ID NO 1794
<211> LENGTH: 19
<212> TYPE: RNA
<213> ORGANISM: Homo sapiens

<400> SEQUENCE: 1794
cgacucuauc caagcccaa 19

<210> SEQ ID NO 1795
<211> LENGTH: 19
<212> TYPE: RNA
<213> ORGANISM: Homo sapiens

<400> SEQUENCE: 1795
gcccaaaaga augaugucu 19

<210> SEQ ID NO 1796
<211> LENGTH: 19
<212> TYPE: RNA
<213> ORGANISM: Homo sapiens

<400> SEQUENCE: 1796
aagaaugaug ucugccgcc 19

<210> SEQ ID NO 1797
<211> LENGTH: 19
<212> TYPE: RNA
<213> ORGANISM: Homo sapiens

<400> SEQUENCE: 1797
agaaugaugu cugccgccc 19

<210> SEQ ID NO 1798
<211> LENGTH: 19
<212> TYPE: RNA
<213> ORGANISM: Homo sapiens

<400> SEQUENCE: 1798
gaaugauguc ugccgcccu 19

<210> SEQ ID NO 1799
<211> LENGTH: 19
<212> TYPE: RNA
<213> ORGANISM: Homo sapiens

<400> SEQUENCE: 1799
cagccagaua auggagucc 19

<210> SEQ ID NO 1800
<211> LENGTH: 19
<212> TYPE: RNA

<213> ORGANISM: Homo sapiens

<400> SEQUENCE: 1800
uggaguccuc aacuacccc 19

<210> SEQ ID NO 1801
<211> LENGTH: 19
<212> TYPE: RNA
<213> ORGANISM: Homo sapiens

<400> SEQUENCE: 1801
cuaccccaaa cgugccugc 19

<210> SEQ ID NO 1802
<211> LENGTH: 19
<212> TYPE: RNA
<213> ORGANISM: Homo sapiens

<400> SEQUENCE: 1802
acgugccugc caauucaac 19

<210> SEQ ID NO 1803
<211> LENGTH: 19
<212> TYPE: RNA
<213> ORGANISM: Homo sapiens

<400> SEQUENCE: 1803
cgugccugcc aauucaacc 19

<210> SEQ ID NO 1804
<211> LENGTH: 19
<212> TYPE: RNA
<213> ORGANISM: Homo sapiens

<400> SEQUENCE: 1804
uucaaccgga cccagcugg 19

<210> SEQ ID NO 1805
<211> LENGTH: 19
<212> TYPE: RNA
<213> ORGANISM: Homo sapiens

<400> SEQUENCE: 1805
gaugaaccgg gucaucaac 19

<210> SEQ ID NO 1806
<211> LENGTH: 19
<212> TYPE: RNA
<213> ORGANISM: Homo sapiens

<400> SEQUENCE: 1806
ccgggucauc aacuucuau 19

<210> SEQ ID NO 1807
<211> LENGTH: 19
<212> TYPE: RNA
<213> ORGANISM: Homo sapiens

<400> SEQUENCE: 1807
cuucuaugca ggagcaaac 19

<210> SEQ ID NO 1808
<211> LENGTH: 19

<212> TYPE: RNA
<213> ORGANISM: Homo sapiens

<400> SEQUENCE: 1808
accagagcau gaauguuac 19

<210> SEQ ID NO 1809
<211> LENGTH: 19
<212> TYPE: RNA
<213> ORGANISM: Homo sapiens

<400> SEQUENCE: 1809
ccagagcaug aauguuacc 19

<210> SEQ ID NO 1810
<211> LENGTH: 19
<212> TYPE: RNA
<213> ORGANISM: Homo sapiens

<400> SEQUENCE: 1810
uguuaccugu gcugggaag 19

<210> SEQ ID NO 1811
<211> LENGTH: 19
<212> TYPE: RNA
<213> ORGANISM: Homo sapiens

<400> SEQUENCE: 1811
gcgagaugaa gaugcugag 19

<210> SEQ ID NO 1812
<211> LENGTH: 19
<212> TYPE: RNA
<213> ORGANISM: Homo sapiens

<400> SEQUENCE: 1812
gaugcugaga aucucggca 19

<210> SEQ ID NO 1813
<211> LENGTH: 19
<212> TYPE: RNA
<213> ORGANISM: Homo sapiens

<400> SEQUENCE: 1813
ucucggcaac uucgucaug 19

<210> SEQ ID NO 1814
<211> LENGTH: 19
<212> TYPE: RNA
<213> ORGANISM: Homo sapiens

<400> SEQUENCE: 1814
cuucgucaug uuccccgcc 19

<210> SEQ ID NO 1815
<211> LENGTH: 19
<212> TYPE: RNA
<213> ORGANISM: Homo sapiens

<400> SEQUENCE: 1815
cggcaacauc gaccucaug 19

<210> SEQ ID NO 1816

<211> LENGTH: 19
<212> TYPE: RNA
<213> ORGANISM: Homo sapiens

<400> SEQUENCE: 1816
caucgaccuc auguacuuc 19

<210> SEQ ID NO 1817
<211> LENGTH: 19
<212> TYPE: RNA
<213> ORGANISM: Homo sapiens

<400> SEQUENCE: 1817
aaaguuccac gugaacuac 19

<210> SEQ ID NO 1818
<211> LENGTH: 19
<212> TYPE: RNA
<213> ORGANISM: Homo sapiens

<400> SEQUENCE: 1818
aaguuccacg ugaacuaca 19

<210> SEQ ID NO 1819
<211> LENGTH: 19
<212> TYPE: RNA
<213> ORGANISM: Homo sapiens

<400> SEQUENCE: 1819
aguuccacgu gaacuacac 19

<210> SEQ ID NO 1820
<211> LENGTH: 19
<212> TYPE: RNA
<213> ORGANISM: Homo sapiens

<400> SEQUENCE: 1820
guuccacgug aacuacaca 19

<210> SEQ ID NO 1821
<211> LENGTH: 19
<212> TYPE: RNA
<213> ORGANISM: Homo sapiens

<400> SEQUENCE: 1821
cuacacacag ccccuggug 19

<210> SEQ ID NO 1822
<211> LENGTH: 19
<212> TYPE: RNA
<213> ORGANISM: Homo sapiens

<400> SEQUENCE: 1822
guuccugaau gugaccccc 19

<210> SEQ ID NO 1823
<211> LENGTH: 19
<212> TYPE: RNA
<213> ORGANISM: Homo sapiens

<400> SEQUENCE: 1823
ugugaccccc aacguggag 19

<210> SEQ ID NO 1824
<211> LENGTH: 19
<212> TYPE: RNA
<213> ORGANISM: Homo sapiens

<400> SEQUENCE: 1824
cguggaggug aauguagaa 19

<210> SEQ ID NO 1825
<211> LENGTH: 19
<212> TYPE: RNA
<213> ORGANISM: Homo sapiens

<400> SEQUENCE: 1825
uguagaaugu cgcaucaac 19

<210> SEQ ID NO 1826
<211> LENGTH: 19
<212> TYPE: RNA
<213> ORGANISM: Homo sapiens

<400> SEQUENCE: 1826
ugucgcauca acgccgcca 19

<210> SEQ ID NO 1827
<211> LENGTH: 19
<212> TYPE: RNA
<213> ORGANISM: Homo sapiens

<400> SEQUENCE: 1827
caucgccaca gacgaugag 19

<210> SEQ ID NO 1828
<211> LENGTH: 19
<212> TYPE: RNA
<213> ORGANISM: Homo sapiens

<400> SEQUENCE: 1828
acuccgcauc aacaaaacc 19

<210> SEQ ID NO 1829
<211> LENGTH: 19
<212> TYPE: RNA
<213> ORGANISM: Homo sapiens

<400> SEQUENCE: 1829
cuccgcauca acaaaaccu 19

<210> SEQ ID NO 1830
<211> LENGTH: 19
<212> TYPE: RNA
<213> ORGANISM: Oryctolagus sp.

<400> SEQUENCE: 1830
caccaaguac ggggauuuu 19

<210> SEQ ID NO 1831
<211> LENGTH: 19
<212> TYPE: RNA
<213> ORGANISM: Oryctolagus sp.

<400> SEQUENCE: 1831
gccuggacua cuggaccua 19

<210> SEQ ID NO 1832
<211> LENGTH: 19
<212> TYPE: RNA
<213> ORGANISM: Oryctolagus sp.

<400> SEQUENCE: 1832
guacaaagga cagaacgug 19

<210> SEQ ID NO 1833
<211> LENGTH: 19
<212> TYPE: RNA
<213> ORGANISM: Oryctolagus sp.

<400> SEQUENCE: 1833
gaaugauucc uuggaguuu 19

<210> SEQ ID NO 1834
<211> LENGTH: 19
<212> TYPE: RNA
<213> ORGANISM: Oryctolagus sp.

<400> SEQUENCE: 1834
gcacgacucg uggagaaca 19

<210> SEQ ID NO 1835
<211> LENGTH: 19
<212> TYPE: RNA
<213> ORGANISM: Oryctolagus sp.

<400> SEQUENCE: 1835
acucuacuau gaccaggag 19

<210> SEQ ID NO 1836
<211> LENGTH: 19
<212> TYPE: RNA
<213> ORGANISM: Oryctolagus sp.

<400> SEQUENCE: 1836
guaugcugca gagcuucau 19

<210> SEQ ID NO 1837
<211> LENGTH: 19
<212> TYPE: RNA
<213> ORGANISM: Oryctolagus sp.

<400> SEQUENCE: 1837
guaugcugca gagcuucau 19

<210> SEQ ID NO 1838
<211> LENGTH: 19
<212> TYPE: RNA
<213> ORGANISM: Oryctolagus sp.

<400> SEQUENCE: 1838
gauuggcagu gcuacacca 19

<210> SEQ ID NO 1839
<211> LENGTH: 19
<212> TYPE: RNA
<213> ORGANISM: Oryctolagus sp.

<400> SEQUENCE: 1839
gaagaucgac agcugugag 19

<210> SEQ ID NO 1840
<211> LENGTH: 19
<212> TYPE: RNA
<213> ORGANISM: Oryctolagus sp.

<400> SEQUENCE: 1840
gccaucaacu gcuacgcca 19

<210> SEQ ID NO 1841
<211> LENGTH: 19
<212> TYPE: RNA
<213> ORGANISM: Oryctolagus sp.

<400> SEQUENCE: 1841
caucgugcac gugauccag 19

<210> SEQ ID NO 1842
<211> LENGTH: 19
<212> TYPE: RNA
<213> ORGANISM: Oryctolagus sp.

<400> SEQUENCE: 1842
uauguggaca cccuguacc 19

<210> SEQ ID NO 1843
<211> LENGTH: 19
<212> TYPE: RNA
<213> ORGANISM: Oryctolagus sp.

<400> SEQUENCE: 1843
cgacacagag cugguggcc 19

<210> SEQ ID NO 1844
<211> LENGTH: 19
<212> TYPE: RNA
<213> ORGANISM: Oryctolagus sp.

<400> SEQUENCE: 1844
gagaggaucu uugcccaga 19

<210> SEQ ID NO 1845
<211> LENGTH: 19
<212> TYPE: RNA
<213> ORGANISM: Oryctolagus sp.

<400> SEQUENCE: 1845
cugcucagcg ccaccgaca 19

<210> SEQ ID NO 1846
<211> LENGTH: 19
<212> TYPE: RNA
<213> ORGANISM: Oryctolagus sp.

<400> SEQUENCE: 1846
ccgugagcug agugaggac 19

<210> SEQ ID NO 1847
<211> LENGTH: 19
<212> TYPE: RNA
<213> ORGANISM: Oryctolagus sp.

<400> SEQUENCE: 1847

-continued cuauucuugc aagugcuac 19

<210> SEQ ID NO 1848
<211> LENGTH: 19
<212> TYPE: RNA
<213> ORGANISM: Oryctolagus sp.

<400> SEQUENCE: 1848
gccaacuugu aaagcugug 19

<210> SEQ ID NO 1849
<211> LENGTH: 19
<212> TYPE: RNA
<213> ORGANISM: Oryctolagus sp.

<400> SEQUENCE: 1849
cucgagugca caucucagg 19

<210> SEQ ID NO 1850
<211> LENGTH: 19
<212> TYPE: RNA
<213> ORGANISM: Oryctolagus sp.

<400> SEQUENCE: 1850
cgugagcuau uacacgcgu 19

<210> SEQ ID NO 1851
<211> LENGTH: 19
<212> TYPE: RNA
<213> ORGANISM: Oryctolagus sp.

<400> SEQUENCE: 1851
ccaccucuac cacuggcau 19

<210> SEQ ID NO 1852
<211> LENGTH: 19
<212> TYPE: RNA
<213> ORGANISM: Oryctolagus sp.

<400> SEQUENCE: 1852
ucucaucaag acagccaca 19

<210> SEQ ID NO 1853
<211> LENGTH: 19
<212> TYPE: RNA
<213> ORGANISM: Oryctolagus sp.

<400> SEQUENCE: 1853
cauaacagag ugugcgaug 19

<210> SEQ ID NO 1854
<211> LENGTH: 19
<212> TYPE: RNA
<213> ORGANISM: Oryctolagus sp.

<400> SEQUENCE: 1854
cacugccucg auucagucc 19

<210> SEQ ID NO 1855
<211> LENGTH: 19
<212> TYPE: RNA
<213> ORGANISM: Oryctolagus sp.

<400> SEQUENCE: 1855
cauaacagag ugugcgaug 19

<210> SEQ ID NO 1856
<211> LENGTH: 19
<212> TYPE: RNA
<213> ORGANISM: Oryctolagus sp.

<400> SEQUENCE: 1856
gaccgacaaa uccgacucg 19

<210> SEQ ID NO 1857
<211> LENGTH: 19
<212> TYPE: RNA
<213> ORGANISM: Oryctolagus sp.

<400> SEQUENCE: 1857
cauccuuguc auucugucu 19

<210> SEQ ID NO 1858
<211> LENGTH: 19
<212> TYPE: RNA
<213> ORGANISM: Oryctolagus sp.

<400> SEQUENCE: 1858
gaacuuucau gaggacacc 19

<210> SEQ ID NO 1859
<211> LENGTH: 19
<212> TYPE: RNA
<213> ORGANISM: Oryctolagus sp.

<400> SEQUENCE: 1859
acucaagacu guggccagu 19

<210> SEQ ID NO 1860
<211> LENGTH: 19
<212> TYPE: RNA
<213> ORGANISM: Oryctolagus sp.

<400> SEQUENCE: 1860
cuggaacuau aacaccaac 19

<210> SEQ ID NO 1861
<211> LENGTH: 19
<212> TYPE: RNA
<213> ORGANISM: Oryctolagus sp.

<400> SEQUENCE: 1861
gucaucuucg acacggguu 19

<210> SEQ ID NO 1862
<211> LENGTH: 19
<212> TYPE: RNA
<213> ORGANISM: Oryctolagus sp.

<400> SEQUENCE: 1862
ucaccaucuu cucuguugg 19